(12) United States Patent
Cassayre et al.

(10) Patent No.: US 9,078,444 B2
(45) Date of Patent: Jul. 14, 2015

(54) ISOTHIAZOLINE DERIVATIVES AS INSECTICIDAL COMPOUNDS

(75) Inventors: Jerome Yves Cassayre, Stein (CH); Myriem El Qacemi, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/344,123

(22) PCT Filed: Aug. 27, 2012

(86) PCT No.: PCT/EP2012/066579
§ 371 (c)(1),
(2), (4) Date: Mar. 11, 2014

(87) PCT Pub. No.: WO2013/037626
PCT Pub. Date: Mar. 21, 2013

(65) Prior Publication Data
US 2014/0378415 A1   Dec. 25, 2014

(30) Foreign Application Priority Data

Sep. 13, 2011 (EP) .................................. 11181057
Jul. 5, 2012 (EP) .................................. 12175166

(51) Int. Cl.
| | |
|---|---|
| *C07D 275/02* | (2006.01) |
| *C07D 417/12* | (2006.01) |
| *A01N 43/90* | (2006.01) |
| *C07D 331/04* | (2006.01) |
| *C07D 417/10* | (2006.01) |
| *C07D 249/08* | (2006.01) |
| *C07D 291/04* | (2006.01) |
| *C07C 323/22* | (2006.01) |
| *C07C 323/56* | (2006.01) |
| *C07C 327/22* | (2006.01) |
| *C07C 327/32* | (2006.01) |
| *A01N 43/80* | (2006.01) |
| *A01N 43/00* | (2006.01) |
| *A01N 51/00* | (2006.01) |

(52) U.S. Cl.
CPC ................ *A01N 43/90* (2013.01); *A01N 43/00* (2013.01); *A01N 43/80* (2013.01); *A01N 51/00* (2013.01); *C07C 323/22* (2013.01); *C07C 323/56* (2013.01); *C07C 327/22* (2013.01); *C07C 327/32* (2013.01); *C07D 249/08* (2013.01); *C07D 275/02* (2013.01); *C07D 291/04* (2013.01); *C07D 331/04* (2013.01); *C07D 417/10* (2013.01); *C07D 417/12* (2013.01)

(58) Field of Classification Search
USPC .......................................................... 548/206
See application file for complete search history.

(56) References Cited

FOREIGN PATENT DOCUMENTS

| | | |
|---|---|---|
| EP | 1731512 A1 | 12/2006 |
| GB | 2481118 A | 12/2011 |
| WO | 2007123855 | 11/2007 |
| WO | 2009112275 | 9/2009 |

OTHER PUBLICATIONS

International Search Report dated Oct. 8, 2012 for International Patent Application No. PCT/EP2012/066579.

*Primary Examiner* — Laura L. Stockton
(74) *Attorney, Agent, or Firm* — Brian D. McAlhaney

(57) ABSTRACT

The present invention provides compounds of formula (I) wherein P is P0, heterocyclyl or heterocyclyl substituted by one to five Z formula (II); $Y^1, Y^2, Y^3$ and $Y^4$ are independently of each other C—H, C—$R^5$, or nitrogen; G1 is oxygen or sulfur; $X^4$ is $C_1$-$C_8$ haloalkyl; $R^4$ is aryl or aryl substituted by one to five $R^9$, or heteroaryl or heteroaryl substituted by one to five $R^9$; and $R^1, R^2, R^4, R^5, R^9$ and Z are as defined in the claims. The invention also provides compositions comprising the compounds of formula (I), intermediates useful in the preparation of compounds of formula (I) and methods of using the compounds of formula (I) to control insects, acarines, nematodes or molluscs.

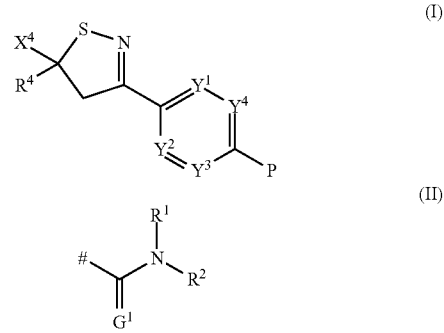

14 Claims, No Drawings

ISOTHIAZOLINE DERIVATIVES AS INSECTICIDAL COMPOUNDS

RELATED APPLICATION INFORMATION

This application is a 371 of International Application No. PCT/EP2012/066579, filed 27 Aug. 2012, which claims priority to EP Patent Application No. 12175166.3, filed 05 Jul. 2012, and EP Patent Application No. 11181057.8 filed 13 Sep. 2011.

The present invention relates to certain isothiazoline derivatives, to processes and intermediates for preparing these derivatives, to insecticidal, acaricidal, nematicidal and molluscicidal compositions comprising these derivatives and to methods of using these derivatives to control insect, acarine, nematode and mollusc pests.

Certain isoxazoline derivatives with insecticidal properties are disclosed, for example, in EP 1,731,512. However there is a continuing need to find new biologically active compounds as well as new biologically active compounds displaying superior properties for use as agrochemical active ingredients, for example greater biological activity, different spectrum of activity, increased safety profile, or increased biodegradability.

It has now surprisingly been found that certain isothiazoline derivatives have highly potent insecticidal properties and show significantly improved bio-degradability compared to the corresponding isoxazoline analogues.

The present invention provides compounds of formula (I)

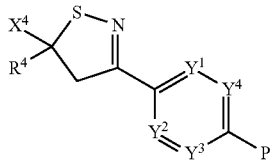

(I)

wherein

P is P0, heterocyclyl or heterocyclyl substituted by one to five Z;

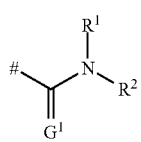

(P0)

$Y^1$, $Y^2$, $Y^3$ and $Y^4$ are independently of each other C—H, C—$R^5$, or nitrogen;

$G^1$ is oxygen or sulfur;

$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;

$R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl-N($R^{20}$)— or aryl-N($R^{20}$)— wherein the aryl moiety is substituted by one to five $R^8$, heterocyclyl-N($R^{20}$)— or heterocyclyl-N($R^{20}$)— wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, $C_1$-$C_8$alkylaminocarbonyl-, $C_1$-$C_8$haloalkylaminocarbonyl, $C_3$-$C_8$cycloalkyl-aminocarbonyl, $C_1$-$C_6$alkyl-O—N=CH—, $C_1$-$C_6$haloalkyl-O—N=CH—;

or $R^1$ and $R^2$ together represent group A

(A)

$G^2$ is O($R^{13}$), N($R^{14}$)($R^{15}$) or S($R^{16}$);

$G^3$ is N($R^{17}$)($R^{18}$) or S($R^{19}$);

$X^4$ is $C_1$-$C_8$haloalkyl;

$R^4$ is aryl or aryl substituted by one to five $R^9$, or heteroaryl or heteroaryl substituted by one to five $R^9$;

each $R^5$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-; or two $R^5$ on adjacent carbon atoms together form a —CH=CH—CH=CH— bridge;

each $R^6$ is independently halogen, cyano, nitro, hydroxy, amino, $C_1$-$C_8$alkylamino, ($C_1$-$C_8$alkyl)$_2$amino, $C_1$-$C_8$alkylcarbonylamino, $C_1$-$C_8$haloalkylcarbonylamino, $C_1$-$C_8$alkoxy-, $C_1$-$C_8$haloalkoxy-, aryloxy or aryloxy substituted by one to five $R^{10}$, aryloxy-$C_1$-$C_4$alkylene or aryloxy-$C_1$-$C_4$alkylene wherein the aryl moiety is substituted by one to five $R^{10}$, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, aryl-$C_1$-$C_4$alkylthio or aryl-$C_1$-$C_4$alkylthio wherein the aryl moiety is substituted by one to five $R^{10}$;

each $R^7$ is independently halogen, $C_1$-$C_8$alkyl, $C_1$-$C_8$alkenyl, $C_1$-$C_8$alkynyl, $C_1$-$C_8$alkyl-O—N=, $C_1$-$C_8$haloalkyl-O—N=; $C_1$-$C_8$alkoxy, $C_1$-$C_8$akoxycarbonyl;

each $R^8$ is independently halogen, cyano, nitro, oxo, $C_1$-$C_8$alkyl, $C_1$-$C_8$haloalkyl, $C_1$-$C_8$cyanoalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkylene, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylaminosulfonyl, ($C_1$-$C_8$alkyl)$_2$aminosulfonyl-, $C_1$-$C_8$alkylcarbonyl-, $C_1$-$C_8$alkoxycarbonyl-, aryl or aryl substituted by one to five $R^{10}$, heterocyclyl or heterocyclyl substituted by one to five $R^{10}$, aryl-$C_1$-$C_4$alkylene or aryl-$C_1$-$C_4$alkylene wherein the aryl moiety is substituted by one to five $R^{10}$, heterocyclyl-$C_1$-$C_4$alkylene or heterocyclyl-$C_1$-$C_4$alkylene wherein the heterocyclyl moiety is substituted by one to five $R^{10}$, aryloxy or aryloxy substituted by one to five $R^{10}$, aryloxy-$C_1$-$C_4$alkylene or aryloxy-$C_1$-$C_4$alkylene wherein the aryl moiety is substituted by one to five $R^{10}$;

each $R^9$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{10}$, or heterocyclyl or heterocyclyl substituted by one to five $R^{10}$;

each $R^{10}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-;

each Z is independently halogen, $C_1$-$C_{12}$alkyl or $C_1$-$C_{12}$alkyl substituted by one to five $R^6$, nitro, $C_1$-$C_{12}$alkoxy or $C_1$-$C_{12}$alkoxy substituted by one to five $R^6$, cyano, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, hydroxyl or thiol;

$R^{13}$, $R^{16}$ and $R^{19}$ are independently $C_1$-$C_4$ alkyl;

$R^{14}$, $R^{15}$, $R^{17}$, and $R^{18}$ are independently hydrogen or $C_1$-$C_4$ alkyl;

$R^{20}$ is hydrogen or $C_1$-$C_4$ alkyl;

or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds. The invention also covers N-oxides and salts. The compounds of the invention may contain one or more additional asymmetric carbon atoms and may exist as enantiomers (or as pairs of diastereoisomers) or as mixtures of such.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, —CH$_2$—, —CH$_2$—CH$_2$—, —CH(CH$_3$)—, —CH$_2$—CH$_2$—CH$_2$—, —CH(CH$_3$)—CH$_2$—, or —CH(CH$_2$CH$_3$)—. The alkylene groups are preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl- or haloalkylsulfonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene-) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene-) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. 1.2.4 triazoyl), furanyl, thiophenyl, oxazolyl, isoxazolyl, oxadiazolyl, thiazolyl, isothiazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkylene-) are defined to include heteroaryl groups and in addition their unsaturated or partially unsaturated analogues. Examples of monocyclic groups include isoxazolyl, thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Preferred values of P, $Y^1$, $Y^2$, $Y^3$, $Y^4$, $G^1$, Z, $R^1$, $R^2$, $X^4$, $R^4$, $R^5$, $R^6$, $R^7$, $R^8$, $R^9$ and $R^{10}$ are, in any combination, as set out below.

Preferably, P is P0, or a heterocycle selected from H1 to H9.

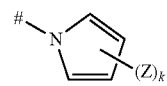

H1

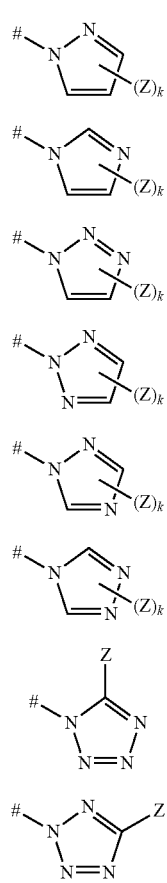

H2

H3

H4

H5

H6

H7

H8

H9 k is 0, 1 or 2.

When P is a heterocycle, P is preferably H2 or H6.

More preferably P is P0.

In one group of compounds P is P0. In another group of compounds P is a heterocycle, preferably selected form H1 to H9, more preferably H2 or H6.

Preferably no more than two of $Y^1$, $Y^2$, $Y^3$ and $Y^4$ are nitrogen, more preferably no more than one of $Y^1$, $Y^2$, $Y^3$ and $Y^4$ is nitrogen.

Preferably $Y^1$ is C—H or C—$R^5$, most preferably $Y^1$ is C—H.

Preferably $Y^2$ is C—H or C—$R^5$, most preferably $Y^2$ is C—H.

Preferably $Y^3$ is C—H or C—$R^5$, most preferably $Y^3$ is C—H.

Preferably $Y^4$ is C—H or C—$R^5$, most preferably $Y^4$ is C—$R^5$.

In one preferred group of compounds $Y^1$ is C—$R^{5b}$, C—H or nitrogen, $Y^2$ and $Y^3$ are independently C—H or nitrogen and $Y^4$ is C—$R^5$; wherein no more than two of $Y^1$, $Y^2$ and $Y^3$ are nitrogen and wherein $Y^2$ and $Y^3$ are not both nitrogen, and wherein $R^{5b}$ when present forms a —CH═CH—CH═CH— bridge with $R^5$.

In another preferred group of compounds $Y^1$ is C—H, $Y^2$ is C—H or nitrogen, $Y^3$ is C—H or nitrogen and $Y^4$ is C—$R^5$, wherein $Y^2$ and $Y^3$ are not both nitrogen.

In another preferred group of compounds $Y^1$ is C—H, $Y^2$ is C—H, $Y^3$ is C—H and $Y^4$ is C—$R^5$.

Preferably $G^1$ is oxygen.

Preferably $R^1$ is hydrogen, methyl, ethyl, methylcarbonyl-, or methoxycarbonyl-, more preferably hydrogen, methyl or ethyl, most preferably hydrogen.

Preferably, $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1

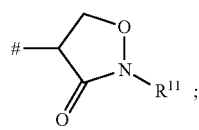

(C1)

wherein $R^{11}$ is hydrogen, methyl, ethyl, propyl, isopropyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, benzyl, benzyl substituted by one to three $R^{12}$, or $R^{11}$ is pyridyl-methyl- or pyridyl-methyl-substituted by one to three $R^{12}$; and each $R^{12}$ is independently fluoro, chloro, bromo, trifluoromethyl, trifluoromethoxy, cyano or methoxy.

More preferably $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1 wherein each aryl group is a phenyl group and each heterocyclyl group is independently selected from pyridyl, pyridazinyl, pyrimidinyl, pyrazinyl, pyrrolyl, pyrazolyl, imidazolyl, triazolyl, tetrahydrothiophenyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxo-thietanyl, dioxo-thietanyl, pyrrolidinyl, tetrahydrofuranyl, [1,3]dioxolanyl, piperidinyl, piperazinyl, [1,4]dioxanyl, and morpholinyl, 2,3-dihydro-benzofuranyl, benzo[1,3]dioxolanyl, and 2,3-dihydro-benzo[1,4]dioxinyl.

More preferably $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1, wherein each aryl group is a phenyl group and each heterocyclyl group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl.

More preferably still $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1, wherein each aryl group is a phenyl group and each heterocyclyl group is selected from pyridyl, tetrahydrofuranyl, imidazolyl, pyrazolyl, pyrrolyl, thiazolyl, oxetanyl, thietanyl, oxo-thietanyl and dioxo-thietanyl.

More preferably still $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, phenyl-$C_1$-$C_4$alkylene- or phenyl-$C_1$-$C_4$alkylene- wherein the phenyl moiety is substituted by one to five $R^8$, pyridyl-$C_1$-$C_4$alkylene- or pyridyl-$C_1$-$C_4$alkylene- wherein the pyridyl moiety is substituted by one to four $R^8$, tetrahydrofuranyl-$C_1$-$C_4$alkylene- or tetrahydrofuranyl-$C_1$-$C_4$alkylene- wherein the tetrahydrofuranyl moiety is substituted by one to five $R^8$, imidazolyl-$C_1$-$C_4$alkylene- or imidazolyl-$C_1$-$C_4$alkylene- wherein the imidazolyl moiety is substituted by one to three $R^8$, pyrazolyl-$C_1$-$C_4$alkylene- or pyryazolyl-$C_1$-$C_4$alkylene- wherein the pyrazolyl moiety is substituted by one to three $R^8$, pyrrolyl-$C_1$-$C_4$alkylene- or pyrrolyl-$C_1$-$C_4$alkylene- wherein the pyrrolyl moiety is substituted by one to four $R^8$, thiazolyl-$C_1$-$C_4$alkylene- or thiazolyl-$C_1$-$C_4$alkylene- wherein the thiazolyl moiety is substituted by one to four $R^8$, oxetanyl-$C_1$-$C_4$ alkylene or oxetanyl-$C_1$-$C_4$ alkylene wherein the oxetanyl moiety is substituted by one to five $R^8$, thietanyl-$C_1$-$C_4$ alkylene or thietanyl-$C_1$-$C_4$ alkylene wherein the thietanyl moiety is substituted by one to five $R^8$, oxo-thietanyl-$C_1$-$C_4$ alkylene or oxo-thietanyl-$C_1$-$C_4$ alkylene wherein the oxo-thietanyl moiety is substituted by one to five $R^8$, dioxo-thietanyl-$C_1$-$C_4$ alkylene or dioxo-thietanyl-$C_1$-$C_4$ alkylene wherein the dioxo-thietanyl moiety is substituted by one to five $R^8$, oxetanyl or oxetanyl substituted by one to five $R^8$, thietanyl or thietanyl substituted by one to five $R^8$, oxo-thietanyl or oxo-thietanyl substituted by one to five $R^8$, dioxo-thietanyl or dioxo-thietanyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1.

Even more preferably $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, phenyl-$C_1$-$C_4$alkylene- or phenyl-$C_1$-$C_4$alkylene- wherein the phenyl moiety is substituted by one to five $R^8$, pyridyl-$C_1$-$C_4$alkylene- or pyridyl-$C_1$-$C_4$alkylene- wherein the pyridyl moiety is substituted by one to four $R^8$, oxetanyl or oxetanyl substituted by one to five $R^8$, thietanyl-$C_1$-$C_4$ alkylene or thietanyl-$C_1$-$C_4$ alkylene wherein the thietanyl moiety is substituted by one to five $R^8$, oxo-thietanyl-$C_1$-$C_4$ alkylene or oxo-thietanyl-$C_1$-$C_4$ alkylene wherein the oxo-thietanyl moiety is substituted by one to five $R^8$, dioxo-thietanyl-$C_1$-$C_4$ alkylene or dioxo-thietanyl-$C_1$-$C_4$ alkylene wherein the dioxo-thietanyl moiety is substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, or group C1.

Yet even more preferably $R^2$ is $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two groups independently selected from fluoro and methyl, phenyl-$C_1$-$C_4$alkylene- or phenyl-$C_1$-$C_4$alkylene- wherein the phenyl moiety is substituted by one to five $R^8$, pyridyl-$C_1$-$C_4$alkylene- or pyridyl-$C_1$-$C_4$alkylene- wherein the pyridyl moiety is substituted by one to four $R^8$, thietanyl, oxo-thietanyl, dioxo-thietanyl, $C_1$-$C_8$alkylaminocarbonyl-methylene, $C_1$-$C_8$haloalkylaminocarbonyl-methylene, $C_3$-$C_8$cycloalkyl-aminocarbonyl-methylene, or group C1.

A group of preferred compounds are those wherein $R^2$ is $C_1$-$C_6$alkyl or $C_1$-$C_6$alkyl substituted by one to five $R^6$, for example ethyl-, butyl-, but-2-yl-, 3-bromo-propyl-, 2,2,2-trifluoro-ethyl-, 3,3,3-trifluoro-propyl-, 2-methoxy-ethyl-, and 1-methoxy-prop-2-yl-.

A group of preferred compounds are those wherein $R^2$ is $C_3$-$C_8$cycloalkyl or $C_3$-$C_8$cycloalkyl substituted by one to five $R^7$, for example cyclobutyl-, 2-fluoro-cyclopropyl and 2-methyl-cyclohex-1-yl-.

A group of preferred compounds are those wherein $R^2$ is aryl-$C_1$-$C_2$alkylene- or aryl-$C_1$-$C_2$alkylene- wherein the aryl moiety is substituted by one to five $R^8$, for example phenyl-methyl-, 1-phenyl-eth-1-yl-, 2-phenyl-eth-1-yl-, (3-chloro-phenyl)-methyl-, (2-fluoro-phenyl)-methyl-, (4-methoxy-phenyl)-methyl-, (2-trifluoromethyl-phenyl)-methyl-, and (2-trifluoromethoxy-phenyl)-methyl-.

A group of preferred compounds are those wherein $R^2$ is heterocyclyl-$C_1$-$C_2$alkylene- or heterocyclyl-$C_1$-$C_2$alkylene- wherein the heterocyclyl moiety is substituted by one to five $R^8$, for example (pyrid-2-yl)-methyl-, (pyrid-3-yl)-methyl-, (2-chloro-pyrid-5-yl)-methyl-, (1-methyl-1H-imidazol-4-yl)-methyl-, (furan-2-yl)-methyl-, 2-(thiophen-2'-yl)-eth-1-yl-, 2-(indol-3'-yl)-eth-1-yl-, (1H-benzimidazol-2-yl)-methyl-, (oxetan-2-yl)-methyl-, (tetrahydrofuran-2-yl)-methyl-, 2-([1',3']dioxolan-2'-yl)-eth-1-yl-, 2-(morpholin-4'-yl)-eth-1-yl-, 2-(benzo[1',3']dioxol-5'-yl)-eth-1-yl-, (2,3-dihydro-benzo[1,4]dioxin-6-yl)-methyl-, thietan-2-yl-methyl-, 1-oxo-thietan-2-yl-methyl-, 1,1-dioxo-thietan-2-yl-methyl-, thietan-3-yl-methyl-, 1-oxo-thietan-3-yl-methyl-, 1,1-dioxo-thietan-3-yl-methyl-, thietan-3-yl-ethyl-, 1-oxo-thietan-3-yl-ethyl-, and 1,1-dioxo-thietan-3-yl-ethyl-, preferably thietan-2-yl-methyl-, 1-oxo-thietan-2-yl-methyl-, 1,1-dioxo-thietan-2-yl-methyl-, thietane-3-yl-methyl-, 1-oxo-thietan-3-yl-methyl-, 1,1-dioxo-thietan-3-yl-methyl-, thietan-3-yl-ethyl-, 1-oxo-thietan-3-yl-ethyl-, and 1,1-dioxo-thietan-3-yl-ethyl-.

A group of preferred compounds are those wherein $R^2$ is heterocyclyl-$C_1$-$C_2$alkylene- or heterocyclyl-$C_1$-$C_2$alkylene- wherein the heterocyclyl moiety is substituted by one to five $R^8$ in which the heterocyclyl group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl, preferably the heterocyclyl group is selected from thietanyl, oxo-thietanyl and dioxo-thietanyl.

A group of preferred compounds are those wherein $R^2$ is heteroaryl-$C_1$-$C_2$alkylene- or heteroaryl-$C_1$-$C_2$alkylene- wherein the heteroaryl moiety is substituted by one to five $R^8$.

A group of preferred compounds are those wherein $R^2$ is aryl or aryl substituted by one to five $R^8$, for example 2-chloro-phenyl-, 3-fluoro-phenyl-, 2-methyl-phenyl-, 2-chloro-6-methyl-phenyl-, 2-trifluoromethyl-phenyl-, and 2,4-dimethoxy-phenyl-.

A group of preferred compounds are those wherein $R^2$ is heterocyclyl or heterocyclyl substituted by one to five $R^8$, for example 3-methyl-pyrid-2-yl-, 1,3-dimethyl-1H-pyrazol-5-yl-, 4-methyl-thiazol-2-yl-, 5-methyl-thiadiazol-2-yl-, quinolin-2-yl-, quinolin-5-yl-, benzothiazol-6-yl-, 4-methyl-benzothiazol-2-yl-, thietan-3-yl-, 1-oxo-thietan-3-yl-, 1,1-dioxo-thietan-3-yl-, and 3-methyl-thietan-3-yl-, more preferably $R^2$ is oxetanyl, thietanyl, oxo-thietanyl or dioxo-thietanyl each optionally substituted by one to five $R^8$, most preferably $R^2$ is thietanyl, oxo-thietanyl or dioxo-thietanyl each optionally substituted by one to five $R^8$. It is particularly preferred that the oxetanyl, thietanyl, oxo-thietanyl or dioxo-thietanyl ring is linked via the 3-position.

A group of preferred compounds are those wherein $R^2$ is heterocyclyl- or heterocyclyl substituted by one to five $R^8$ in which the heterocyclyl group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl, preferably the heterocyclyl group is selected from thietanyl, oxo-thietanyl and dioxo-thietanyl.

A group of preferred compounds are those wherein $R^2$ is $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, more preferably $C_1$-$C_4$alkylaminocarbonyl-$C_1$-$C_4$ alkylene, $C_1$-$C_4$haloalkylaminocarbonyl-$C_1$-$C_4$ alkylene, or $C_3$-$C_6$cycloalkyl-aminocarbonyl-$C_1$-$C_4$ alkylene, most preferably $C_1$-$C_4$alkylaminocarbonyl-$C_1$-$C_2$ alkylene or $C_1$-$C_4$haloalkylaminocarbonyl-$C_1$-$C_2$ alkylene.

A group of preferred compounds are those wherein $R^1$ and $R^2$ together represent group A

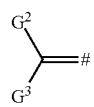

(A)

wherein $G^2$ and $G^3$ are as defined above, for example group A1, A2, A3 or A4

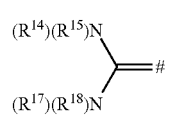

(A1)

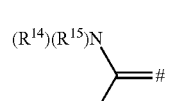

(A2)

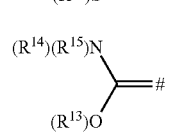

(A3)

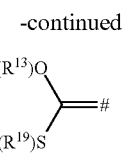

(A4)

wherein $R^{13}$, $R^{14}$, $R^{15}$, $R^{16}$, $R^{17}$, $R^{18}$ and $R^{19}$ are as defined above.

$R^{13}$, $R^{17}$, $R^{18}$ and $R^{19}$ are preferably $C_1$-$C_4$alkyl, more preferably methyl or ethyl/$R^{14}$ and $R^{15}$ are preferably hydrogen.

A group of preferred compounds are those wherein $R^2$ is group C1.

A group of preferred compounds are those wherein $R^2$ is group C2.

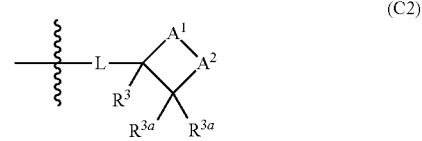

(C2)

wherein L is a bond, methylene or ethylene; one of $A^1$ and $A^2$ is S, SO or $SO_2$ and the other is —C($R^{3a}$)$R^{3a}$—; $R^3$ is hydrogen or methyl; each $R^{3a}$ is independently hydrogen or methyl; and preferably L is a bond, preferably $R^3$ and each $R^{3a}$ is hydrogen; preferably $A^1$ is —C($R^4$)$R^4$—, more preferably —$CH_2$—; preferably $A^2$ is S, SO or $SO_2$.

In one group of compounds P is selected from P0 and P1 to P44 and $R^2$ is group C1 or C2

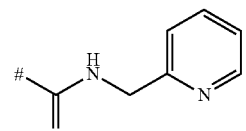

P1

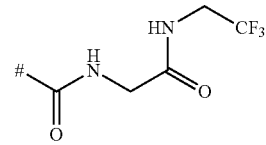

P2

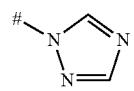

P3

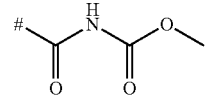

P4

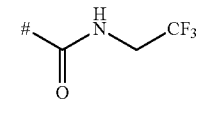

P5

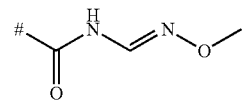

P6

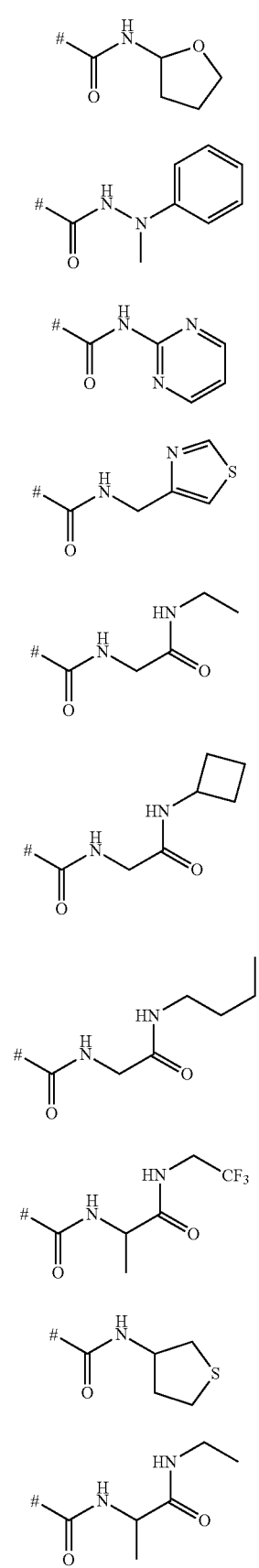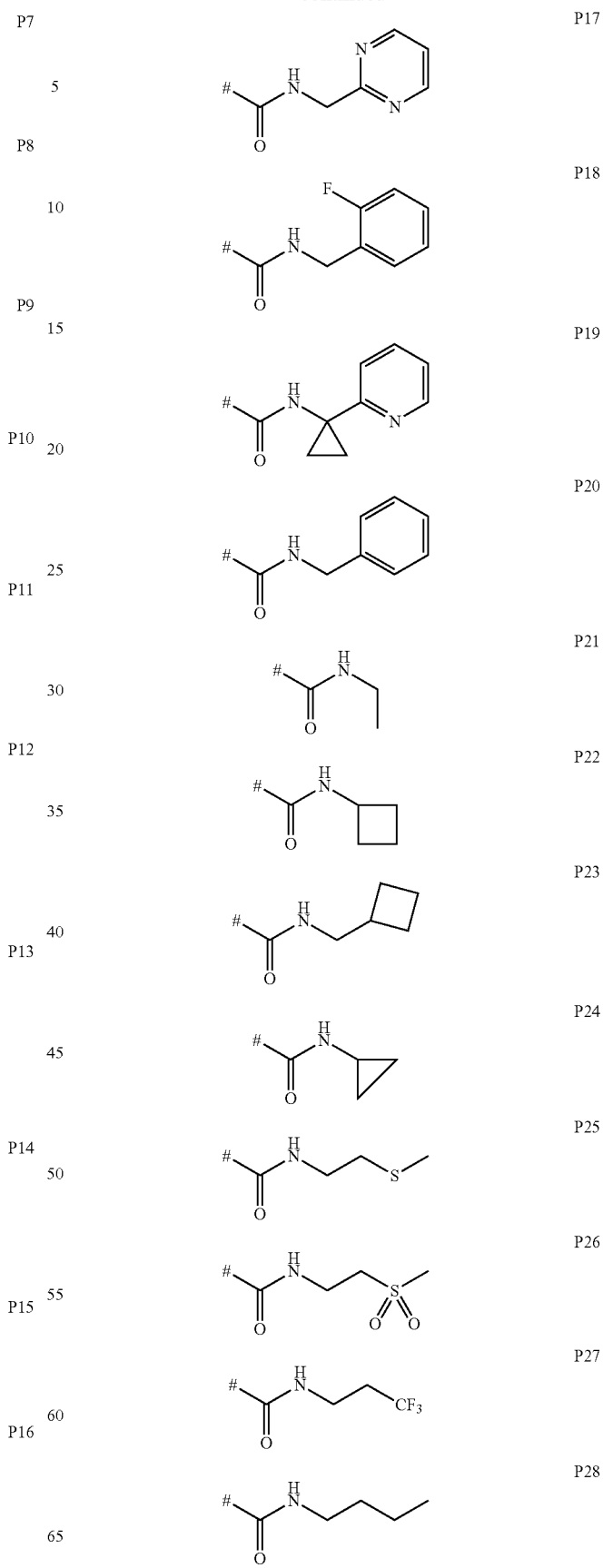

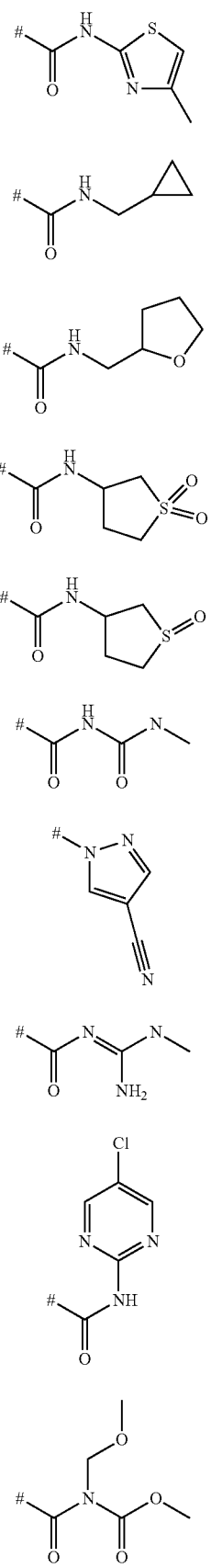
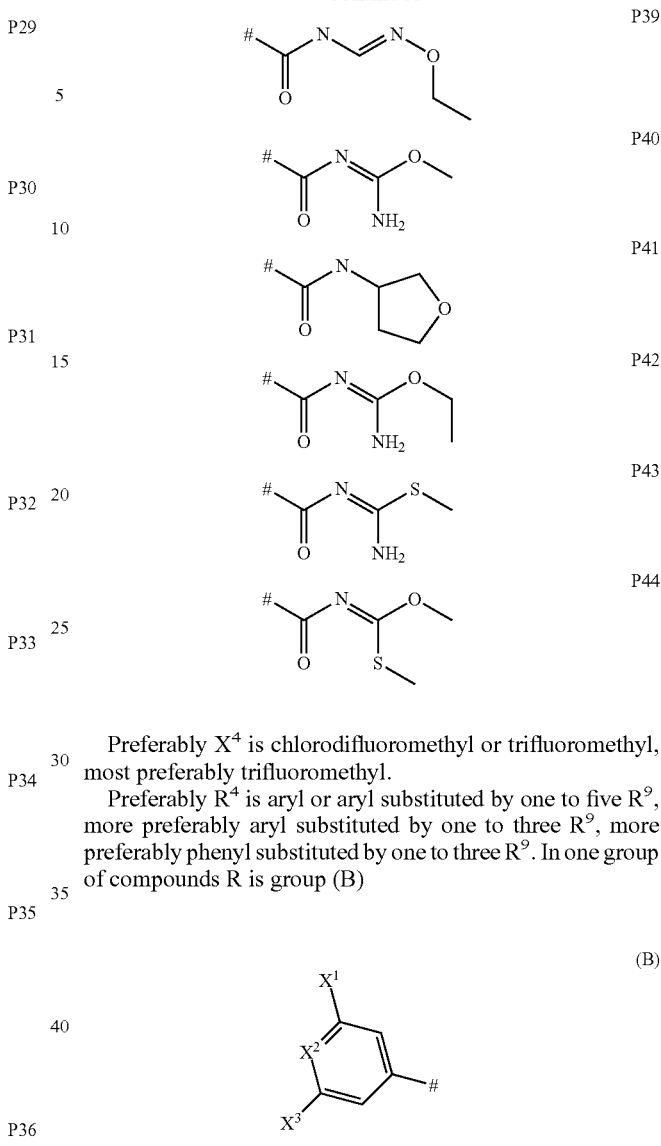

Preferably $X^4$ is chlorodifluoromethyl or trifluoromethyl, most preferably trifluoromethyl.

Preferably $R^4$ is aryl or aryl substituted by one to five $R^9$, more preferably aryl substituted by one to three $R^9$, more preferably phenyl substituted by one to three $R^9$. In one group of compounds R is group (B)

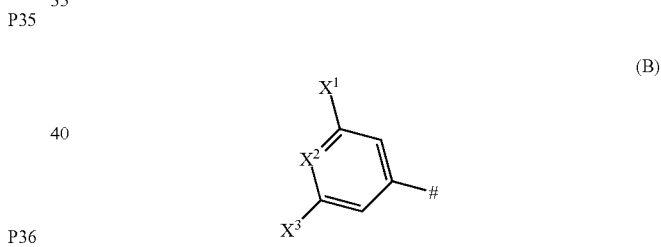

wherein $X^2$ is C—$X^6$ or nitrogen (preferably C—$X^6$); $X^1$, $X^3$ and $X^6$ are independently hydrogen, halogen or trihalomethyl, e.g. wherein at least two of $X^1$, $X^3$ and $X^6$ are not hydrogen; even more preferably $R^4$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-, even more preferably 3,5-dichloro-phenyl, 3,5-dichloro-4-fluorophenyl-, 3,4,5-trichlorophenyl-, 3,5-bis(trifluoromethyl)phenyl-, most preferably $R^4$ is 3,5-dichloro-phenyl.

In one group of compounds $R^4$ is 3,5-dichloro-phenyl. In one group of compounds $R^4$ is 3,5-dichloro-4-fluorophenyl-. In one group of compounds $R^4$ is 3,4,5-trichlorophenyl-. In one group of compounds $R^4$ is 3,5-bis(trifluoromethyl)phenyl.

Preferably each $R^5$ is independently halogen, cyano, nitro, $NH_2$, $C_1$-$C_8$alkyl, $C_1$-$C_8$haloalkyl, $C_3$-$C_5$cycloalkyl, $C_3$-$C_5$halocycloalkyl, $C_1$-$C_8$alkenyl, $C_1$-$C_8$haloalkenyl, $C_1$-$C_8$alkoxy-, or $C_1$-$C_8$haloalkoxy-, preferably halogen, cyano, nitro, $NH_2$, $C_1$-$C_2$alkyl, $C_1$-$C_2$haloalkyl, $C_3$-$C_5$cycloalkyl, $C_3$-$C_5$halocycloalkyl, $C_1$-$C_2$alkoxy, $C_1$-$C_2$haloalkoxy; more preferably chloro, bromo, fluoro, trifluoromethyl, methyl, ethyl, methoxy, nitro, trifluoromethoxy, cyano, cyclopropyl, even more preferably $R^5$ is chloro, bromo, fluoro, methyl or trifluoromethyl, most preferably methyl.

In one group of compounds $R^5$ is chloro. In one group of compounds $R^5$ is bromo. In one group of compounds $R^5$ is methyl. In one group of compounds $R^5$ is halogen.

Preferably each $R^6$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-, more preferably each $R^6$ is independently halogen, cyano, nitro, hydroxy, $C_1$-$C_8$alkoxy-, $C_1$-$C_8$haloalkoxy-, mercapto, $C_1$-$C_8$alkylthio-, $C_1$-$C_8$haloalkylthio-, more preferably bromo, chloro, fluoro, methoxy, or methylthio, most preferably chloro, fluoro, or methoxy.

Preferably each $R^7$ is independently halogen or $C_1$-$C_8$alkyl, more preferably each $R^7$ is independently chloro, fluoro or methyl, most preferably fluoro or methyl.

Preferably each $R^8$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{10}$, or heterocyclyl or heterocyclyl substituted by one to five $R^{10}$, more preferably each $R^8$ is independently halogen, cyano, nitro, $C_1$-$C_8$alkyl, $C_1$-$C_8$haloalkyl, $C_1$-$C_8$alkoxy-, $C_1$-$C_8$haloalkoxy-, more preferably bromo, chloro, fluoro, cyano, nitro, methyl, ethyl, trifluoromethyl, methoxy, difluoromethoxy, or trifluoromethoxy, most preferably bromo, chloro, fluoro, cyano or methyl.

Preferably each $R^9$ is independently halogen, $C_1$-$C_8$alkyl, $C_1$-$C_8$haloalkyl, $C_1$-$C_8$alkoxy-, $C_1$-$C_8$haloalkoxy-, $C_1$-$C_8$alkylthio-, or $C_1$-$C_8$haloalkylthio-, more preferably bromo, chloro, fluoro, trifluoromethyl, methoxy, or methylthio, most preferably bromo or chloro.

Preferably each $R^{10}$ is independently bromo, chloro, fluoro, cyano, nitro, methyl, ethyl, trifluoromethyl, methoxy, difluoromethoxy, or trifluoromethoxy, more preferably bromo, chloro, fluoro, nitro, or methyl, most preferably chloro, fluoro, or methyl.

Preferably $R^{11}$ is methyl, ethyl or trifluoroethyl.

Preferably each Z is independently halogen, cyano, $C_1$-$C_4$alkyl, $C_1$-$C_4$haloalkyl, $C_1$-$C_4$alkoxy, or $C_1$-$C_4$haloalkoxy, more preferably each Z is independently hydrogen, halogen, methyl, halomethyl, methoxy or halomethoxy.

In one embodiment E1 the present invention provides compounds of formula (Ia-1)

(Ia-1)

wherein $G^1$, $R^1$, $R^2$, $X^4$, $R^4$ and $R^5$ are as defined for compounds of formula (I); or a salt or N-oxide thereof. The preferences for $G^1$, $R^1$, $R^2$, $X^4$, $R^4$ and $R^5$ are the same as the preferences set out for the corresponding substituents of compounds of the formula (I).

In one embodiment E2 the present invention provides compounds of formula (Ia-2)

(Ia-2)

wherein $G^1$, $R^1$, $R^2$, $X^4$, and $R^4$ are as defined for compounds of formula (I); or a salt or N-oxide thereof. The preferences for $G^1$, $R^1$, $R^2$, $X^4$ and $R^4$ are the same as the preferences set out for the corresponding substituents of compounds of the formula (I).

In a further embodiment E3 the present invention provides compounds of formula (Ia-3)

(Ia-3)

wherein $G^1$, $R^1$, $R^2$, $X^4$, and $R^4$ are as defined for compounds of formula (I); or a salt or N-oxide thereof. The preferences for $G^1$, $R^1$, $R^2$, $X^4$ and $R^4$ are the same as the preferences set out for the corresponding substituents of compounds of the formula (I).

In a further embodiment E4 the present invention provides compounds of formula (Ib-1)

(Ib-1)

wherein $X^4$, $R^4$ and $R^5$ are as defined for compounds of formula (I) and Het is selected from H1 to H9 as defined for compounds of formula (I); or a salt or N-oxide thereof. The preferences for $X^4$, $R^4$, $R^5$, and Het are the same as the preferences set out for the corresponding substituents of compounds of the formula (I).

In a further embodiment E5 the present invention provides compounds of formula (Ib-2)

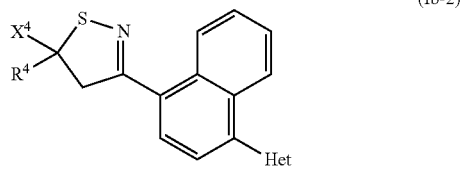

(Ib-2)

wherein $X^4$ and $R^4$ are as defined for compounds of formula (I) and Het is selected from H1 to H9 as defined for compounds of formula (I); or a salt or N-oxide thereof. The preferences for $X^4$, $R^4$ and Het are the same as the preferences set out for the corresponding substituents of compounds of the formula (I).

In a further embodiment E6 the present invention provides compounds of formula (Ib-3)

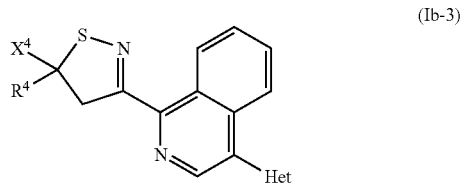

(Ib-3)

wherein $X^4$ and $R^4$ are as defined for compounds of formula (I) and Het is selected from H1 to H9 as defined for compounds of formula (I); or a salt or N-oxide thereof. The preferences for $X^4$, $R^4$ and Het are the same as the preferences set out for the corresponding substituents of compounds of the formula (I).

In a further embodiment E7 the present invention provides compounds of formula (Ic)

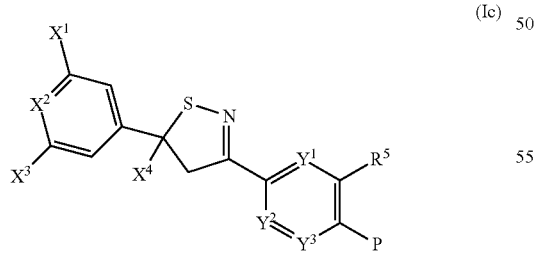

(Ic)

wherein
P is as defined for compounds of formula I including preferred definitions thereof;
$Y^1$ is C—$R^{5b}$, CH or nitrogen;
$Y^2$ and $Y^3$ are independently CH or nitrogen;
wherein no more than two of $Y^1$, $Y^2$ and $Y^3$ are nitrogen and wherein $Y^2$ and $Y^3$ are not both nitrogen;

$R^5$ is hydrogen, halogen, cyano, nitro, $NH_2$, $C_1$-$C_2$alkyl, $C_1$-$C_2$haloalkyl, $C_3$-$C_5$cycloalkyl, $C_3$-$C_5$halocycloalkyl, $C_1$-$C_2$alkoxy, $C_1$-$C_2$haloalkoxy;

$R^{5b}$ when present together with $R^5$ forms a —CH=CH—CH=CH— bridge;

$X^2$ is C—$X^6$ or nitrogen;

$X^1$, $X^3$ and $X^6$ are independently hydrogen, halogen or trihalomethyl, wherein at least two of $X^1$, $X^3$ and $X^6$ are not hydrogen;

$X^4$ is trifluoromethyl, difluoromethyl or chlorodifluoromethyl.

In a further embodiment E8 the present invention provides compounds of formula (Ic) wherein $R^4$, $X^1$, $X^2$, $X^3$, $X^4$ and $X^6$ are as defined for the compounds of formula Ic and P is selected from P0 and P1 to P44; $G^1$ is oxygen; $R^1$ is hydrogen; $R^2$ is A1 or A2; L is a bond, methylene or ethylene; one of $A^1$ and $A^2$ is S, SO or $SO_2$ and the other is —C($R^{3a}$)$R^{3a}$—; $R^3$ is hydrogen or methyl; each $R^{3a}$ is independently hydrogen or methyl; $R^{11}$ is hydrogen, methyl, ethyl, propyl, isopropyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, benzyl, benzyl substituted by one to three $R^{12}$, or $R^{11}$ is pyridyl-methyl- or pyridyl-methyl-substituted by one to three $R^{12}$; each $R^{12}$ is independently fluoro, chloro, bromo, trifluoromethyl, trifluoromethoxy, cyano or methoxy.

In a further embodiment E9 the present invention provides compounds of formula (Ic) wherein P is selected from P0 and P1 to P44; $G^1$ is oxygen; $R^1$ is hydrogen; $R^2$ is A1 or A2; $R^3$ and $R^{3a}$ are hydrogen; $R^5$ is chloro, bromo, fluoro, methyl, trifluoromethyl; $R^{11}$ is methyl, ethyl or trifluoroethyl; L is a bond; $A^1$ is —$CH_2$—; $A^2$ is S, SO or $SO_2$; $Y^1$ is CH, $Y^2$ is CH, and $Y^3$ is CH; $X^1$, $X^3$ and $X^6$ are independently hydrogen, halogen or trifluoromethyl, wherein at least two of $X^1$, $X^3$ and $X^6$ are not hydrogen; $X^2$ is C—$X^6$; $X^4$ is trifluoromethyl, or chlorodifluoromethyl.

Certain intermediates are novel and as such form further aspects of the invention.

One group of novel intermediates are compounds of formula (Int-I)

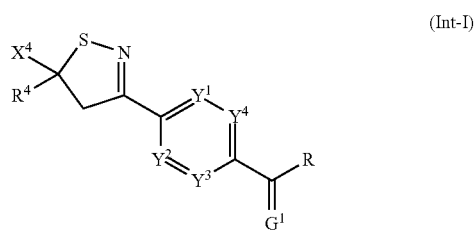

(Int-I)

wherein $X^4$, $R^4$, $Y^1$, $Y^2$, $Y^3$ and $Y^4$ are as defined for a compound of formula (I), $G^1$ is oxygen, and R is hydroxy, $C_1$-$C_{15}$alkoxy or halogen, such as bromo, chloro or fluoro; or a salt or N-oxide thereof. The preferences for $X^4$, $R^4$, $Y^1$, $Y^2$, $Y^3$ and $Y^4$ are the same as the preferences set out for the corresponding substituents of a compound of formula (I). Preferably R is hydroxy, $C_1$-$C_6$alkoxy or chloro.

A further group of novel intermediates are compounds of formula (Int-II)

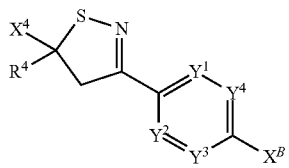
(Int-II)

wherein $X^4$, $R^4$, $Y^1$, $Y^2$, $Y^3$ and $Y^4$ are as defined for a compound of formula (I), and $X^B$ is a leaving group such as halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. $X^B$ is $-N_2^+$ $Cl^-$, $-N_2^+$ $BF_4^-$, $-N_2^+$ $Br^-$, $-N_2^+$ $PF_6^-$), phosphonate esters (e.g. $-OP(O)(OR)_2$, wherein R is methyl or ethyl), preferably bromo, iodo, chloro, trifluoromethylsulfoxy, p-toluenesulfoxy, diazonium chloride; or a salt or N-oxide thereof. The preferences for $X^4$, $R^4$, $Y^1$, $Y^2$, $Y^3$ and $Y^4$ are the same as the preferences set out for the corresponding substituents of a compound of formula (I).

A further group of novel intermediates are compounds of formula (Int-III)

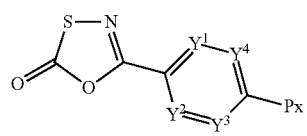
(Int-III)

wherein $Y^1$, $Y^2$, $Y^3$ and $Y^4$ are as defined for compounds of formula (I), Px is P as defined above, a leaving group, such as halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. $X^B$ is $-N_2^+$ $Cl^-$, $-N_2^+$ $BF_4^-$, $-N_2^+$ $Br^-$, $-N_2^+$ $PF_6^-$), phosphonate esters (e.g. $-OP(O)(OR)_2$, wherein R is methyl or ethyl), preferably bromo, iodo, chloro, trifluoromethylsulfoxy, p-toluenesulfoxy, diazonium chloride, or C(O)R wherein R is halogen, OH or $C_1$-$C_{15}$alkoxy, or a salt or N-oxide thereof. The preferences for $Y^1$, $Y^2$, $Y^3$ and $Y^4$ and the preferences at position Px when Px is P or heterocycle are the same as the preferences set out for the corresponding substituents of a compound of formula (I).

A group of compounds of formula (Int-III) are compounds of formula (Int-IV)

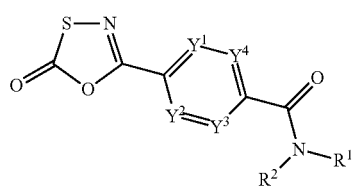
(Int-IV)

wherein $Y^1$, $Y^2$, $Y^3$, $Y^4$, $R^1$ and $R^2$ are as defined for compounds of formula (I). The preferences for $Y^1$, $Y^2$, $Y^3$, $Y^4$, $R^1$ and $R^2$ are the same as the preferences set out for the corresponding substituents of a compound of formula (I).

Another group of compounds of formula (Int-III) are compounds of formula (Int-V)

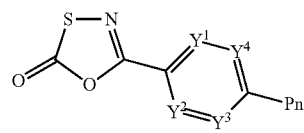
(Int-V)

wherein $Y^1$, $Y^2$, $Y^3$ and $Y^4$ are as defined for the compounds of formula (I), and Pn is a heterocyclyl or heteocyclyl substituted by one to five Z, as defined for substituent P of compounds of formula I. The preferences for $Y^1$, $Y^2$, $Y^3$ and $Y^4$ and Pn are the same as the preferences set out for the corresponding substituents of a compound of formula (I).

A further group of novel intermediates are compounds of formula (Int-VI)

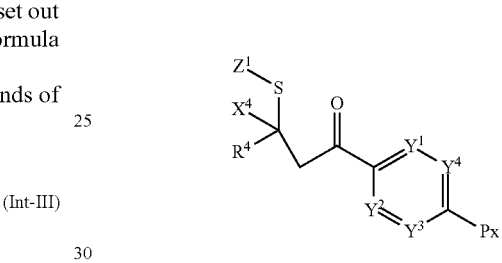
(Int-VI)

wherein $X^4$, $R^4$, $Y^1$, $Y^2$, $Y^3$ and $Y^4$ are as defined for the compounds of formula (I), and Px is as defined for the compound of formula (Int-III), $Z^1$ is hydrogen, halogen, cyano, $C_1$-$C_8$alkyl, optionally substituted aryl-$C_1$-$C_4$alkylene-, $C_1$-$C_8$alkylcarbonyl-, optionally substituted arylsulfonyl- or optionally substituted arylthio-, or a salt or N-oxide thereof. The preferences for $X^4$, $R^4$, $Y^1$, $Y^2$, $Y^3$ and $Y^4$ are the same as the preferences set out for the corresponding substituents of a compound of formula (I). $Z^1$ is preferably hydrogen, benzyl, halogen (preferably chloro) or cyano. Aryl is preferably phenyl and is preferably optionally substituted by one or more groups selected from halogen, cyano, $C_1$-$C_4$alkyl, $C_1$-$C_4$ haloalkyl, $C_1$-$C_4$alkoxy or $C_1$-$C_4$haloalkoxy.

A further group of novel intermediates are compounds of formula (Int-VII)

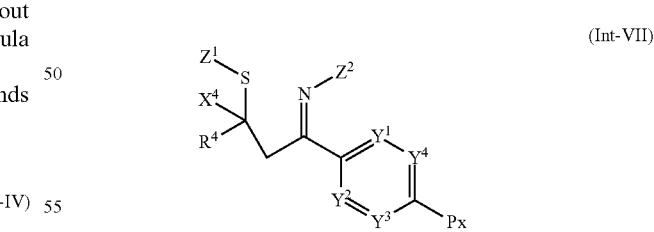
(Int-VII)

wherein $X^4$, $R^4$, $Y^1$, $Y^2$, $Y^3$ and $Y^4$ are as defined for the compounds of formula (I), and Px is as defined for the compound of formula (Int-III), $Z^1$ is hydrogen, halogen, cyano, $C_1$-$C_8$alkyl, optionally substituted aryl-$C_1$-$C_4$alkylene-, $C_1$-$C_8$alkylcarbonyl-, optionally substituted arylsulfonyl- or optionally substituted arylthio- and $Z^2$ is hydrogen or hydroxyl or $C_1$-$C_8$alkoxy- or $C_1$-$C_8$alkylsulfonyloxy- or arylsulfonyloxy- or aryl-$C_1$-$C_4$alkylene- or aryl. The preferences for $X^4$, $R^4$, $Y^1$, $Y^2$, $Y^3$ and $Y^4$ are the same as the preferences set out for the corresponding substituents of a compound of formula (I). $Z^1$ is preferably hydrogen, benzyl, halogen (preferably chloro) or cyano. Aryl is preferably phenyl and is preferably optionally substituted by one or more groups selected from halogen, cyano, $C_1$-$C_4$alkyl, $C_1$-$C_4$ haloalkyl, $C_1$-$C_4$alkoxy or $C_1$-$C_4$haloalkoxy.

A further group of novel intermediates are compounds of formula (Int-VIII)

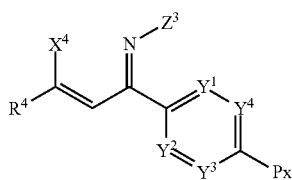
(Int-VIII)

wherein $X^4$, $R^4$, $Y^1$, $Y^2$, $Y^3$ and $Y^4$ are as defined for the compounds of formula (I), and Px is as defined for the compound of formula (Int-III), and $Z^3$ is thiol or optionally substituted aryl-$C_1$-$C_8$alkylsulfinyl-. The preferences for $X^4$, $R^4$, $Y^1$, $Y^2$, $Y^3$ and $Y^4$ are the same as the preferences set out for the corresponding substituents of a compound of formula (I). Aryl is preferably phenyl and is preferably optionally substituted by one or more groups selected from halogen, cyano, $C_1$-$C_4$alkyl, $C_1$-$C_4$ haloalkyl, $C_1$-$C_4$alkoxy or $C_1$-$C_4$haloalkoxy.

Compounds of formula I include at least one chiral centre and may exist as compounds of formula I* or compounds of formula I**.

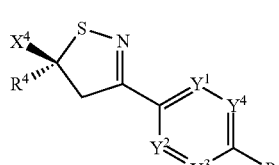
(I*)

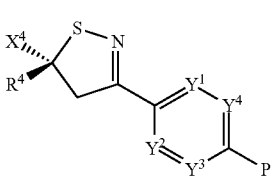
(I**)

Generally compounds of formula I** are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I** compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixture of formula I*, the molar proportion of the compound of formula I* compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula I** are preferred. Each compound disclosed in Tables 1P-120P and Tables 1Q to 240Q represents a disclosure of a compound according to the compound of formula I*, and a disclosure according to the compound of formula I**.

TABLE G

| Group number | $R^2$ |
| --- | --- |
| G.001 | ethyl- |
| G.002 | butyl- |
| G.003 | but-2-yl- |
| G.004 | 3-bromo-propyl- |
| G.005 | 2,2,2-trifluoro-ethyl- |
| G.006 | 3,3,3-trifluoro-propyl- |
| G.007 | 2-methoxy-ethyl- |
| G.008 | 1-methoxy-prop-2-yl- |
| G.009 | cyclobutyl- |
| G.010 | 2-methyl-cyclohex-1-yl- |
| G.011 | phenyl-methyl- |
| G.012 | 1-phenyl-eth-1-yl- |
| G.013 | 2-phenyl-eth-1-yl- |
| G.014 | (3-chloro-phenyl)-methyl- |
| G.015 | (2-fluoro-phenyl)-methyl- |
| G.016 | (4-methoxy-phenyl)-methyl- |
| G.017 | (2-trifluoromethyl-phenyl)-methyl- |
| G.018 | (2-trifluoromethoxy-phenyl)-methyl- |
| G.019 | (pyrid-2-yl)-methyl- |
| G.020 | (pyrid-3-yl)-methyl- |
| G.021 | (2-chloro-pyrid-5-yl)-methyl- |
| G.022 | (1-methyl-1H-imidazol-4-yl)-methyl- |
| G.023 | (furan-2-yl)-methyl- |
| G.024 | 2-(thiophen-2'-yl)-eth-1-yl- |
| G.025 | 2-(indol-3'-yl)-eth-1-yl- |
| G.026 | (1H-benzimidazol-2-yl)-methyl- |
| G.027 | (oxetan-2-yl)-methyl- |
| G.028 | (tetrahydrofuran-2-yl)-methyl- |
| G.029 | 2-([1',3']dioxolan-2'-yl)-eth-1-yl- |
| G.030 | 2-(morpholin-4'-yl)-eth-1-yl- |
| G.031 | 2-(benzo[1',3']dioxol-5'-yl)-eth-1-yl- |
| G.032 | (2,3-dihydro-benzo[1,4]dioxin-6-yl)-methyl- |
| G.033 | 2-chloro-phenyl- |
| G.034 | 3-fluoro-phenyl- |
| G.035 | 2-methyl-phenyl- |
| G.036 | 2-chloro-6-methyl-phenyl- |
| G.037 | 2-trifluoromethyl-phenyl- |
| G.038 | 2,4-dimethoxy-phenyl- |
| G.039 | 3-methyl-pyrid-2-yl- |
| G.040 | 1,3-dimethyl-1H-pyrazol-5-yl- |
| G.041 | 4-methyl-thiazol-2-yl- |
| G.042 | 5-methyl-thiadiazol-2-yl- |
| G.043 | quinolin-2-yl- |
| G.044 | quinolin-5-yl- |
| G.045 | benzothiazol-6-yl- |
| G.046 | 4-methyl-benzothiazol-2-yl- |
| G.047 | thietan-3-yl- |
| G.048 | 1-oxo-thietan-3-yl- |
| G.049 | 1,1-dioxo-thietan-3-yl- |
| G.050 | 3-methyl-thietan-3-yl- |
| G.051 | N-(2,2,2-Trifluoro-ethyl)-acetamide-2-yl |
| G.052 | thietan-2-yl-methyl- |
| G.053 | 1-oxo-thietan-2-yl-methyl- |
| G.054 | 1,1-dioxo-thietan-2-yl-methyl- |
| G.055 | thietan-3-yl-methyl- |
| G.056 | 1-oxo-thietan-3-yl-methyl- |
| G.057 | 1,1-dioxo-thietan-3-yl-methyl- |
| G.058 | thietan-3-yl-ethyl- |
| G.059 | 1-oxo-thietan-3-yl-ethyl- |
| G.060 | 1,1-dioxo-thietan-3-yl-ethyl- |
| G.061 | 2-fluoro-cyclopropyl |
| G.062 | n-Butyl |
| G.063 | 2-Methoxy-1-methyl-ethyl |
| G.064 | 1-Oxo-thietan-3-yl |
| G.065 | 2-ethyl-isoxazolidin-3-one-4-yl |
| G.066 | Dihydro-thiophen-2-one-3-yl |
| G.067 | 6-Ethoxycarbonyl-cyclohex-3-enyl |
| G.068 | 2-Benzylsulfanyl-ethyl |
| G.069 | 4-Methanesulfonyl-benzyl |
| G.070 | N',N'-Dimethylamino-ethyl |
| G.071 | sec-Butyl |
| G.072 | Butan-1-ol-2-yl |
| G.073 | 2,2-Difluoro-ethyl |

TABLE G-continued

| Group number | R² |
|---|---|
| G.074 | Ethynyl-cyclohexyl |
| G.075 | 2-Morpholin-4-yl-ethyl |
| G.076 | 3-Pyrrolidin-1-yl-propyl |
| G.077 | 3-Piperidin-1-yl-propyl |
| G.078 | [3-(4-Chloro-phenyl)-isoxazol-5-yl]-methyl |
| G.079 | Phenethyl |
| G.080 | 1,2,2,6,6-Pentamethyl-piperidin-4-yl |
| G.081 | 2-Phenoxy-ethyl |
| G.082 | 3-Chloro-benzyl |
| G.083 | 2-Acetylamino-ethyl |
| G.084 | 4-Pyrazol-1-yl-benzyl |
| G.085 | 2-Methylsulfanyl-ethyl |
| G.086 | 2-Piperidin-1-yl-benzyl |
| G.087 | 4-Phenoxy-benzyl |
| G.088 | (6-Chloro-pyridin-3-yl)-methyl |
| G.089 | 1-Benzyl-pyrrolidin-3-yl |
| G.090 | 2-(4-Benzyl-piperazin-1-yl)-ethyl |
| G.091 | Furan-2-yl-methyl |
| G.092 | 1H-Indazol-5-yl |
| G.093 | 4-Pyrrol-1-yl-phenyl |
| G.094 | 4-Piperidin-1-yl-phenyl |
| G.095 | 2-Methylsulfanyl-phenyl |
| G.096 | 4-Methyl-2-oxo-2H-chromen-7-yl |
| G.097 | 4-Dimethylsulfamoyl-phenyl |
| G.098 | 2,5-Dimethyl-2H-pyrazol-3-yl |
| G.099 | 5-Methylsulfanyl-1H-[1,2,4]triazol-3-yl |
| G.100 | 4-Hydroxy-6-methyl-pyrimidin-2-yl |
| G.101 | Quinolin-2-yl |
| G.102 | 5-Methyl-3-phenyl-isoxazol-4-yl |
| G.103 | 9H-Purin-6-yl |
| G.104 | 5-Acetyl-4-methyl-thiazol-2-yl |
| G.105 | 4-Methyl-benzothiazol-2-yl |
| G.106 | 5-Methyl-[1,3,4]thiadiazol-2-yl |
| G.107 | 4,6-Dimethyl-2H-pyrazolo[3,4-b]pyridin-3-yl |
| G.108 | 3-(2,2,2-Trifluoro-ethoxyimino)-cyclobutyl |
| G.109 | 2-Thietan-3-yl-ethyl |
| G.110 | 2-(1,1-Dioxo-thietan-3-yl)-ethyl |
| G.111 | 3-Oxo-2-(2,2,2-trifluoro-ethyl)-isoxazolidin-4-yl |
| G.112 | (structure: =N-OMe oxime methyl group) |
| G.113 | (structure: =N-OEt oxime methyl group) |
| G.114 | 2-(2,2,2-trifluoro-ethyl)-isoxazolidin-3-one-4-yl |
| G.115 | 2-(2,2-Difluoro-ethyl)-isoxazolidin-3-one-4-yl |
| G.116 | 2-(2-Fluoro-ethyl)-isoxazolidin-3-one-4-yl |

TABLE P

| | X1, X2, X3 | X4 | R5 | Y1, Y2, Y3 |
|---|---|---|---|---|
| P.0001 | X¹ is chloro, X² is CH, X³ is chloro | chlorodifluoromethyl | bromo | Y¹ is CH, Y² is CH, Y³ is CH |
| P.0002 | X¹ is chloro, X² is CH, X³ is chloro | chlorodifluoromethyl | chloro | Y¹ is CH, Y² is CH, Y³ is CH |
| P.0003 | X¹ is chloro, X² is CH, X³ is chloro | chlorodifluoromethyl | cyano | Y¹ is CH, Y² is CH, Y³ is CH |
| P.0004 | X¹ is chloro, X² is CH, X³ is chloro | chlorodifluoromethyl | cyclopropyl | Y¹ is CH, Y² is CH, Y³ is CH |
| P.0005 | X¹ is chloro, X² is CH, X³ is chloro | chlorodifluoromethyl | ethyl | Y¹ is CH, Y² is CH, Y³ is CH |
| P.0006 | X¹ is chloro, X² is CH, X³ is chloro | chlorodifluoromethyl | fluoro | Y¹ is CH, Y² is CH, Y³ is CH |
| P.0007 | X¹ is chloro, X² is CH, X³ is chloro | chlorodifluoromethyl | hydrogen | Y¹ is CH, Y² is CH, Y³ is CH |
| P.0008 | X¹ is chloro, X² is CH, X³ is chloro | chlorodifluoromethyl | methoxy | Y¹ is CH, Y² is CH, Y³ is CH |
| P.0009 | X¹ is chloro, X² is CH, X³ is chloro | chlorodifluoromethyl | methyl | Y¹ is CH, Y² is CH, Y³ is CH |
| P.0010 | X¹ is chloro, X² is CH, X³ is chloro | chlorodifluoromethyl | nitro | Y¹ is CH, Y² is CH, Y³ is CH |
| P.0011 | X¹ is chloro, X² is CH, X³ is chloro | chlorodifluoromethyl | trifluoromethoxy | Y¹ is CH, Y² is CH, Y³ is CH |
| P.0012 | X¹ is chloro, X² is CH, X³ is chloro | chlorodifluoromethyl | trifluoromethyl | Y¹ is CH, Y² is CH, Y³ is CH |
| P.0013 | X¹ is chloro, X² is CH, X³ is chloro | difluoromethyl | bromo | Y¹ is CH, Y² is CH, Y³ is CH |
| P.0014 | X¹ is chloro, X² is CH, X³ is chloro | difluoromethyl | chloro | Y¹ is CH, Y² is CH, Y³ is CH |
| P.0015 | X¹ is chloro, X² is CH, X³ is chloro | difluoromethyl | cyano | Y¹ is CH, Y² is CH, Y³ is CH |
| P.0016 | X¹ is chloro, X² is CH, X³ is chloro | difluoromethyl | cyclopropyl | Y¹ is CH, Y² is CH, Y³ is CH |
| P.0017 | X¹ is chloro, X² is CH, X³ is chloro | difluoromethyl | ethyl | Y¹ is CH, Y² is CH, Y³ is CH |
| P.0018 | X¹ is chloro, X² is CH, X³ is chloro | difluoromethyl | fluoro | Y¹ is CH, Y² is CH, Y³ is CH |
| P.0019 | X¹ is chloro, X² is CH, X³ is chloro | difluoromethyl | hydrogen | Y¹ is CH, Y² is CH, Y³ is CH |
| P.0020 | X¹ is chloro, X² is CH, X³ is chloro | difluoromethyl | methoxy | Y¹ is CH, Y² is CH, Y³ is CH |
| P.0021 | X¹ is chloro, X² is CH, X³ is chloro | difluoromethyl | methyl | Y¹ is CH, Y² is CH, Y³ is CH |

TABLE P-continued

| | X1, X2, X3 | X4 | R5 | Y1, Y2, Y3 |
|---|---|---|---|---|
| P.0022 | $X^1$ is chloro, $X^2$ is CH, $X^3$ is chloro | difluoromethyl | nitro | $Y^1$ is CH, $Y^2$ is CH, $Y^3$ is CH |
| P.0023 | $X^1$ is chloro, $X^2$ is CH, $X^3$ is chloro | difluoromethyl | trifluoromethoxy | $Y^1$ is CH, $Y^2$ is CH, $Y^3$ is CH |
| P.0024 | $X^1$ is chloro, $X^2$ is CH, $X^3$ is chloro | difluoromethyl | trifluoromethyl | $Y^1$ is CH, $Y^2$ is CH, $Y^3$ is CH |
| P.0025 | $X^1$ is chloro, $X^2$ is CH, $X^3$ is chloro | trifluoromethyl | bromo | $Y^1$ is CH, $Y^2$ is CH, $Y^3$ is CH |
| P.0026 | $X^1$ is chloro, $X^2$ is CH, $X^3$ is chloro | trifluoromethyl | chloro | $Y^1$ is CH, $Y^2$ is CH, $Y^3$ is CH |
| P.0027 | $X^1$ is chloro, $X^2$ is CH, $X^3$ is chloro | trifluoromethyl | cyano | $Y^1$ is CH, $Y^2$ is CH, $Y^3$ is CH |
| P.0028 | $X^1$ is chloro, $X^2$ is CH, $X^3$ is chloro | trifluoromethyl | cyclopropyl | $Y^1$ is CH, $Y^2$ is CH, $Y^3$ is CH |
| P.0029 | $X^1$ is chloro, $X^2$ is CH, $X^3$ is chloro | trifluoromethyl | ethyl | $Y^1$ is CH, $Y^2$ is CH, $Y^3$ is CH |
| P.0030 | $X^1$ is chloro, $X^2$ is CH, $X^3$ is chloro | trifluoromethyl | fluoro | $Y^1$ is CH, $Y^2$ is CH, $Y^3$ is CH |
| P.0031 | $X^1$ is chloro, $X^2$ is CH, $X^3$ is chloro | trifluoromethyl | hydrogen | $Y^1$ is CH, $Y^2$ is CH, $Y^3$ is CH |
| P.0032 | $X^1$ is chloro, $X^2$ is CH, $X^3$ is chloro | trifluoromethyl | methoxy | $Y^1$ is CH, $Y^2$ is CH, $Y^3$ is CH |
| P.0033 | $X^1$ is chloro, $X^2$ is CH, $X^3$ is chloro | trifluoromethyl | methyl | $Y^1$ is CH, $Y^2$ is CH, $Y^3$ is CH |
| P.0034 | $X^1$ is chloro, $X^2$ is CH, $X^3$ is chloro | trifluoromethyl | nitro | $Y^1$ is CH, $Y^2$ is CH, $Y^3$ is CH |
| P.0035 | $X^1$ is chloro, $X^2$ is CH, $X^3$ is chloro | trifluoromethyl | trifluoromethoxy | $Y^1$ is CH, $Y^2$ is CH, $Y^3$ is CH |
| P.0036 | $X^1$ is chloro, $X^2$ is CH, $X^3$ is chloro | trifluoromethyl | trifluoromethyl | $Y^1$ is CH, $Y^2$ is CH, $Y^3$ is CH |
| P.0037 | $X^1$ is chloro, $X^2$ is C—F, $X^3$ is hydrogen | chlorodifluoromethyl | bromo | $Y^1$ is CH, $Y^2$ is CH, $Y^3$ is CH |
| P.0038 | $X^1$ is chloro, $X^2$ is C—F, $X^3$ is hydrogen | chlorodifluoromethyl | chloro | $Y^1$ is CH, $Y^2$ is CH, $Y^3$ is CH |
| P.0039 | $X^1$ is chloro, $X^2$ is C—F, $X^3$ is hydrogen | chlorodifluoromethyl | cyano | $Y^1$ is CH, $Y^2$ is CH, $Y^3$ is CH |
| P.0040 | $X^1$ is chloro, $X^2$ is C—F, $X^3$ is hydrogen | chlorodifluoromethyl | cyclopropyl | $Y^1$ is CH, $Y^2$ is CH, $Y^3$ is CH |
| P.0041 | $X^1$ is chloro, $X^2$ is C—F, $X^3$ is hydrogen | chlorodifluoromethyl | ethyl | $Y^1$ is CH, $Y^2$ is CH, $Y^3$ is CH |
| P.0042 | $X^1$ is chloro, $X^2$ is C—F, $X^3$ is hydrogen | chlorodifluoromethyl | fluoro | $Y^1$ is CH, $Y^2$ is CH, $Y^3$ is CH |
| P.0043 | $X^1$ is chloro, $X^2$ is C—F, $X^3$ is hydrogen | chlorodifluoromethyl | hydrogen | $Y^1$ is CH, $Y^2$ is CH, $Y^3$ is CH |
| P.0044 | $X^1$ is chloro, $X^2$ is C—F, $X^3$ is hydrogen | chlorodifluoromethyl | methoxy | $Y^1$ is CH, $Y^2$ is CH, $Y^3$ is CH |
| P.0045 | $X^1$ is chloro, $X^2$ is C—F, $X^3$ is hydrogen | chlorodifluoromethyl | methyl | $Y^1$ is CH, $Y^2$ is CH, $Y^3$ is CH |
| P.0046 | $X^1$ is chloro, $X^2$ is C—F, $X^3$ is hydrogen | chlorodifluoromethyl | nitro | $Y^1$ is CH, $Y^2$ is CH, $Y^3$ is CH |
| P.0047 | $X^1$ is chloro, $X^2$ is C—F, $X^3$ is hydrogen | chlorodifluoromethyl | trifluoromethoxy | $Y^1$ is CH, $Y^2$ is CH, $Y^3$ is CH |
| P.0048 | $X^1$ is chloro, $X^2$ is C—F, $X^3$ is hydrogen | chlorodifluoromethyl | trifluoromethyl | $Y^1$ is CH, $Y^2$ is CH, $Y^3$ is CH |
| P.0049 | $X^1$ is chloro, $X^2$ is C—F, $X^3$ is hydrogen | difluoromethyl | bromo | $Y^1$ is CH, $Y^2$ is CH, $Y^3$ is CH |
| P.0050 | $X^1$ is chloro, $X^2$ is C—F, $X^3$ is hydrogen | difluoromethyl | chloro | $Y^1$ is CH, $Y^2$ is CH, $Y^3$ is CH |
| P.0051 | $X^1$ is chloro, $X^2$ is C—F, $X^3$ is hydrogen | difluoromethyl | cyano | $Y^1$ is CH, $Y^2$ is CH, $Y^3$ is CH |
| P.0052 | $X^1$ is chloro, $X^2$ is C—F, $X^3$ is hydrogen | difluoromethyl | cyclopropyl | $Y^1$ is CH, $Y^2$ is CH, $Y^3$ is CH |
| P.0053 | $X^1$ is chloro, $X^2$ is C—F, $X^3$ is hydrogen | difluoromethyl | ethyl | $Y^1$ is CH, $Y^2$ is CH, $Y^3$ is CH |
| P.0054 | $X^1$ is chloro, $X^2$ is C—F, $X^3$ is hydrogen | difluoromethyl | fluoro | $Y^1$ is CH, $Y^2$ is CH, $Y^3$ is CH |
| P.0055 | $X^1$ is chloro, $X^2$ is C—F, $X^3$ is hydrogen | difluoromethyl | hydrogen | $Y^1$ is CH, $Y^2$ is CH, $Y^3$ is CH |
| P.0056 | $X^1$ is chloro, $X^2$ is C—F, $X^3$ is hydrogen | difluoromethyl | methoxy | $Y^1$ is CH, $Y^2$ is CH, $Y^3$ is CH |
| P.0057 | $X^1$ is chloro, $X^2$ is C—F, $X^3$ is hydrogen | difluoromethyl | methyl | $Y^1$ is CH, $Y^2$ is CH, $Y^3$ is CH |
| P.0058 | $X^1$ is chloro, $X^2$ is C—F, $X^3$ is hydrogen | difluoromethyl | nitro | $Y^1$ is CH, $Y^2$ is CH, $Y^3$ is CH |
| P.0059 | $X^1$ is chloro, $X^2$ is C—F, $X^3$ is hydrogen | difluoromethyl | trifluoromethoxy | $Y^1$ is CH, $Y^2$ is CH, $Y^3$ is CH |
| P.0060 | $X^1$ is chloro, $X^2$ is C—F, $X^3$ is hydrogen | difluoromethyl | trifluoromethyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0061 | $X^1$ is chloro, $X^2$ is C—F, $X^3$ is hydrogen | trifluoromethyl | bromo | $Y^1$ is CH, $Y^2$ is CH, $Y^3$ is CH |
| P.0062 | $X^1$ is chloro, $X^2$ is C—F, $X^3$ is hydrogen | trifluoromethyl | chloro | $Y^1$ is CH, $Y^2$ is CH, $Y^3$ is CH |
| P.0063 | $X^1$ is chloro, $X^2$ is C—F, $X^3$ is hydrogen | trifluoromethyl | cyano | $Y^1$ is CH, $Y^2$ is CH, $Y^3$ is CH |
| P.0064 | $X^1$ is chloro, $X^2$ is C—F, $X^3$ is hydrogen | trifluoromethyl | cyclopropyl | $Y^1$ is CH, $Y^2$ is CH, $Y^3$ is CH |
| P.0065 | $X^1$ is chloro, $X^2$ is C—F, $X^3$ is hydrogen | trifluoromethyl | ethyl | $Y^1$ is CH, $Y^2$ is CH, $Y^3$ is CH |
| P.0066 | $X^1$ is chloro, $X^2$ is C—F, $X^3$ is hydrogen | trifluoromethyl | fluoro | $Y^1$ is CH, $Y^2$ is CH, $Y^3$ is CH |
| P.0067 | $X^1$ is chloro, $X^2$ is C—F, $X^3$ is hydrogen | trifluoromethyl | hydrogen | $Y^1$ is CH, $Y^2$ is CH, $Y^3$ is CH |
| P.0068 | $X^1$ is chloro, $X^2$ is C—F, $X^3$ is hydrogen | trifluoromethyl | methoxy | $Y^1$ is CH, $Y^2$ is CH, $Y^3$ is CH |
| P.0069 | $X^1$ is chloro, $X^2$ is C—F, $X^3$ is hydrogen | trifluoromethyl | methyl | $Y^1$ is CH, $Y^2$ is CH, $Y^3$ is CH |
| P.0070 | $X^1$ is chloro, $X^2$ is C—F, $X^3$ is hydrogen | trifluoromethyl | nitro | $Y^1$ is CH, $Y^2$ is CH, $Y^3$ is CH |
| P.0071 | $X^1$ is chloro, $X^2$ is C—F, $X^3$ is hydrogen | trifluoromethyl | trifluoromethoxy | $Y^1$ is CH, $Y^2$ is CH, $Y^3$ is CH |
| P.0072 | $X^1$ is chloro, $X^2$ is C—F, $X^3$ is hydrogen | trifluoromethyl | trifluoromethyl | $Y^1$ is CH, $Y^2$ is CH, $Y^3$ is CH |
| P.0073 | $X^1$ is fluoro, $X^2$ is C—Cl, $X^3$ is hydrogen | chlorodifluoromethyl | bromo | $Y^1$ is CH, $Y^2$ is CH, $Y^3$ is CH |
| P.0074 | $X^1$ is fluoro, $X^2$ is C—Cl, $X^3$ is hydrogen | chlorodifluoromethyl | chloro | $Y^1$ is CH, $Y^2$ is CH, $Y^3$ is CH |
| P.0075 | $X^1$ is fluoro, $X^2$ is C—Cl, $X^3$ is hydrogen | chlorodifluoromethyl | cyano | $Y^1$ is CH, $Y^2$ is CH, $Y^3$ is CH |
| P.0076 | $X^1$ is fluoro, $X^2$ is C—Cl, $X^3$ is hydrogen | chlorodifluoromethyl | cyclopropyl | $Y^1$ is CH, $Y^2$ is CH, $Y^3$ is CH |
| P.0077 | $X^1$ is fluoro, $X^2$ is C—Cl, $X^3$ is hydrogen | chlorodifluoromethyl | ethyl | $Y^1$ is CH, $Y^2$ is CH, $Y^3$ is CH |
| P.0078 | $X^1$ is fluoro, $X^2$ is C—Cl, $X^3$ is hydrogen | chlorodifluoromethyl | fluoro | $Y^1$ is CH, $Y^2$ is CH, $Y^3$ is CH |
| P.0079 | $X^1$ is fluoro, $X^2$ is C—Cl, $X^3$ is hydrogen | chlorodifluoromethyl | hydrogen | $Y^1$ is CH, $Y^2$ is CH, $Y^3$ is CH |
| P.0080 | $X^1$ is fluoro, $X^2$ is C—Cl, $X^3$ is hydrogen | chlorodifluoromethyl | methoxy | $Y^1$ is CH, $Y^2$ is CH, $Y^3$ is CH |
| P.0081 | $X^1$ is fluoro, $X^2$ is C—Cl, $X^3$ is hydrogen | chlorodifluoromethyl | methyl | $Y^1$ is CH, $Y^2$ is CH, $Y^3$ is CH |
| P.0082 | $X^1$ is fluoro, $X^2$ is C—Cl, $X^3$ is hydrogen | chlorodifluoromethyl | nitro | $Y^1$ is CH, $Y^2$ is CH, $Y^3$ is CH |
| P.0083 | $X^1$ is fluoro, $X^2$ is C—Cl, $X^3$ is hydrogen | chlorodifluoromethyl | trifluoromethoxy | $Y^1$ is CH, $Y^2$ is CH, $Y^3$ is CH |
| P.0084 | $X^1$ is fluoro, $X^2$ is C—Cl, $X^3$ is hydrogen | chlorodifluoromethyl | trifluoromethyl | $Y^1$ is CH, $Y^2$ is CH, $Y^3$ is CH |
| P.0085 | $X^1$ is fluoro, $X^2$ is C—Cl, $X^3$ is hydrogen | difluoromethyl | bromo | $Y^1$ is CH, $Y^2$ is CH, $Y^3$ is CH |
| P.0086 | $X^1$ is fluoro, $X^2$ is C—Cl, $X^3$ is hydrogen | difluoromethyl | chloro | $Y^1$ is CH, $Y^2$ is CH, $Y^3$ is CH |
| P.0087 | $X^1$ is fluoro, $X^2$ is C—Cl, $X^3$ is hydrogen | difluoromethyl | cyano | $Y^1$ is CH, $Y^2$ is CH, $Y^3$ is CH |
| P.0088 | $X^1$ is fluoro, $X^2$ is C—Cl, $X^3$ is hydrogen | difluoromethyl | cyclopropyl | $Y^1$ is CH, $Y^2$ is CH, $Y^3$ is CH |
| P.0089 | $X^1$ is fluoro, $X^2$ is C—Cl, $X^3$ is hydrogen | difluoromethyl | ethyl | $Y^1$ is CH, $Y^2$ is CH, $Y^3$ is CH |
| P.0090 | $X^1$ is fluoro, $X^2$ is C—Cl, $X^3$ is hydrogen | difluoromethyl | fluoro | $Y^1$ is CH, $Y^2$ is CH, $Y^3$ is CH |
| P.0091 | $X^1$ is fluoro, $X^2$ is C—Cl, $X^3$ is hydrogen | difluoromethyl | hydrogen | $Y^1$ is CH, $Y^2$ is CH, $Y^3$ is CH |
| P.0092 | $X^1$ is fluoro, $X^2$ is C—Cl, $X^3$ is hydrogen | difluoromethyl | methoxy | $Y^1$ is CH, $Y^2$ is CH, $Y^3$ is CH |
| P.0093 | $X^1$ is fluoro, $X^2$ is C—Cl, $X^3$ is hydrogen | difluoromethyl | methyl | $Y^1$ is CH, $Y^2$ is CH, $Y^3$ is CH |
| P.0094 | $X^1$ is fluoro, $X^2$ is C—Cl, $X^3$ is hydrogen | difluoromethyl | nitro | $Y^1$ is CH, $Y^2$ is CH, $Y^3$ is CH |
| P.0095 | $X^1$ is fluoro, $X^2$ is C—Cl, $X^3$ is hydrogen | difluoromethyl | trifluoromethoxy | $Y^1$ is CH, $Y^2$ is CH, $Y^3$ is CH |
| P.0096 | $X^1$ is fluoro, $X^2$ is C—Cl, $X^3$ is hydrogen | difluoromethyl | trifluoromethyl | $Y^1$ is CH, $Y^2$ is CH, $Y^3$ is CH |
| P.0097 | $X^1$ is fluoro, $X^2$ is C—Cl, $X^3$ is hydrogen | trifluoromethyl | bromo | $Y^1$ is CH, $Y^2$ is CH, $Y^3$ is CH |
| P.0098 | $X^1$ is fluoro, $X^2$ is C—Cl, $X^3$ is hydrogen | trifluoromethyl | chloro | $Y^1$ is CH, $Y^2$ is CH, $Y^3$ is CH |
| P.0099 | $X^1$ is fluoro, $X^2$ is C—Cl, $X^3$ is hydrogen | trifluoromethyl | cyano | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0100 | $X^1$ is fluoro, $X^2$ is C—Cl, $X^3$ is hydrogen | trifluoromethyl | cyclopropyl | $Y^1$ is CH, $Y^2$ is CH, $Y^3$ is CH |
| P.0101 | $X^1$ is fluoro, $X^2$ is C—Cl, $X^3$ is hydrogen | trifluoromethyl | ethyl | $Y^1$ is CH, $Y^2$ is CH, $Y^3$ is CH |
| P.0102 | $X^1$ is fluoro, $X^2$ is C—Cl, $X^3$ is hydrogen | trifluoromethyl | fluoro | $Y^1$ is CH, $Y^2$ is CH, $Y^3$ is CH |
| P.0103 | $X^1$ is fluoro, $X^2$ is C—Cl, $X^3$ is hydrogen | trifluoromethyl | hydrogen | $Y^1$ is CH, $Y^2$ is CH, $Y^3$ is CH |
| P.0104 | $X^1$ is fluoro, $X^2$ is C—Cl, $X^3$ is hydrogen | trifluoromethyl | methoxy | $Y^1$ is CH, $Y^2$ is CH, $Y^3$ is CH |
| P.0105 | $X^1$ is fluoro, $X^2$ is C—Cl, $X^3$ is hydrogen | trifluoromethyl | methyl | $Y^1$ is CH, $Y^2$ is CH, $Y^3$ is CH |
| P.0106 | $X^1$ is fluoro, $X^2$ is C—Cl, $X^3$ is hydrogen | trifluoromethyl | nitro | $Y^1$ is CH, $Y^2$ is CH, $Y^3$ is CH |
| P.0107 | $X^1$ is fluoro, $X^2$ is C—Cl, $X^3$ is hydrogen | trifluoromethyl | trifluoromethoxy | $Y^1$ is CH, $Y^2$ is CH, $Y^3$ is CH |
| P.0108 | $X^1$ is fluoro, $X^2$ is C—Cl, $X^3$ is hydrogen | trifluoromethyl | trifluoromethyl | $Y^1$ is CH, $Y^2$ is CH, $Y^3$ is CH |
| P.0109 | $X^1$ is chloro, $X^2$ is C—Cl, $X^3$ is hydrogen | chlorodifluoromethyl | bromo | $Y^1$ is CH, $Y^2$ is CH, $Y^3$ is CH |
| P.0110 | $X^1$ is chloro, $X^2$ is C—Cl, $X^3$ is hydrogen | chlorodifluoromethyl | chloro | $Y^1$ is CH, $Y^2$ is CH, $Y^3$ is CH |
| P.0111 | $X^1$ is chloro, $X^2$ is C—Cl, $X^3$ is hydrogen | chlorodifluoromethyl | cyano | $Y^1$ is CH, $Y^2$ is CH, $Y^3$ is CH |
| P.0112 | $X^1$ is chloro, $X^2$ is C—Cl, $X^3$ is hydrogen | chlorodifluoromethyl | cyclopropyl | $Y^1$ is CH, $Y^2$ is CH, $Y^3$ is CH |
| P.0113 | $X^1$ is chloro, $X^2$ is C—Cl, $X^3$ is hydrogen | chlorodifluoromethyl | ethyl | $Y^1$ is CH, $Y^2$ is CH, $Y^3$ is CH |
| P.0114 | $X^1$ is chloro, $X^2$ is C—Cl, $X^3$ is hydrogen | chlorodifluoromethyl | fluoro | $Y^1$ is CH, $Y^2$ is CH, $Y^3$ is CH |
| P.0115 | $X^1$ is chloro, $X^2$ is C—Cl, $X^3$ is hydrogen | chlorodifluoromethyl | hydrogen | $Y^1$ is CH, $Y^2$ is CH, $Y^3$ is CH |
| P.0116 | $X^1$ is chloro, $X^2$ is C—Cl, $X^3$ is hydrogen | chlorodifluoromethyl | methoxy | $Y^1$ is CH, $Y^2$ is CH, $Y^3$ is CH |
| P.0117 | $X^1$ is chloro, $X^2$ is C—Cl, $X^3$ is hydrogen | chlorodifluoromethyl | methyl | $Y^1$ is CH, $Y^2$ is CH, $Y^3$ is CH |
| P.0118 | $X^1$ is chloro, $X^2$ is C—Cl, $X^3$ is hydrogen | chlorodifluoromethyl | nitro | $Y^1$ is CH, $Y^2$ is CH, $Y^3$ is CH |
| P.0119 | $X^1$ is chloro, $X^2$ is C—Cl, $X^3$ is hydrogen | chlorodifluoromethyl | trifluoromethoxy | $Y^1$ is CH, $Y^2$ is CH, $Y^3$ is CH |
| P.0120 | $X^1$ is chloro, $X^2$ is C—Cl, $X^3$ is hydrogen | chlorodifluoromethyl | trifluoromethyl | $Y^1$ is CH, $Y^2$ is CH, $Y^3$ is CH |
| P.0121 | $X^1$ is chloro, $X^2$ is C—Cl, $X^3$ is hydrogen | difluoromethyl | bromo | $Y^1$ is CH, $Y^2$ is CH, $Y^3$ is CH |
| P.0122 | $X^1$ is chloro, $X^2$ is C—Cl, $X^3$ is hydrogen | difluoromethyl | chloro | $Y^1$ is CH, $Y^2$ is CH, $Y^3$ is CH |
| P.0123 | $X^1$ is chloro, $X^2$ is C—Cl, $X^3$ is hydrogen | difluoromethyl | cyano | $Y^1$ is CH, $Y^2$ is CH, $Y^3$ is CH |
| P.0124 | $X^1$ is chloro, $X^2$ is C—Cl, $X^3$ is hydrogen | difluoromethyl | cyclopropyl | $Y^1$ is CH, $Y^2$ is CH, $Y^3$ is CH |
| P.0125 | $X^1$ is chloro, $X^2$ is C—Cl, $X^3$ is hydrogen | difluoromethyl | ethyl | $Y^1$ is CH, $Y^2$ is CH, $Y^3$ is CH |
| P.0126 | $X^1$ is chloro, $X^2$ is C—Cl, $X^3$ is hydrogen | difluoromethyl | fluoro | $Y^1$ is CH, $Y^2$ is CH, $Y^3$ is CH |
| P.0127 | $X^1$ is chloro, $X^2$ is C—Cl, $X^3$ is hydrogen | difluoromethyl | hydrogen | $Y^1$ is CH, $Y^2$ is CH, $Y^3$ is CH |
| P.0128 | $X^1$ is chloro, $X^2$ is C—Cl, $X^3$ is hydrogen | difluoromethyl | methoxy | $Y^1$ is CH, $Y^2$ is CH, $Y^3$ is CH |
| P.0129 | $X^1$ is chloro, $X^2$ is C—Cl, $X^3$ is hydrogen | difluoromethyl | methyl | $Y^1$ is CH, $Y^2$ is CH, $Y^3$ is CH |
| P.0130 | $X^1$ is chloro, $X^2$ is C—Cl, $X^3$ is hydrogen | difluoromethyl | nitro | $Y^1$ is CH, $Y^2$ is CH, $Y^3$ is CH |
| P.0131 | $X^1$ is chloro, $X^2$ is C—Cl, $X^3$ is hydrogen | difluoromethyl | trifluoromethoxy | $Y^1$ is CH, $Y^2$ is CH, $Y^3$ is CH |
| P.0132 | $X^1$ is chloro, $X^2$ is C—Cl, $X^3$ is hydrogen | difluoromethyl | trifluoromethyl | $Y^1$ is CH, $Y^2$ is CH, $Y^3$ is CH |
| P.0133 | $X^1$ is chloro, $X^2$ is C—Cl, $X^3$ is hydrogen | trifluoromethyl | bromo | $Y^1$ is CH, $Y^2$ is CH, $Y^3$ is CH |
| P.0134 | $X^1$ is chloro, $X^2$ is C—Cl, $X^3$ is hydrogen | trifluoromethyl | chloro | $Y^1$ is CH, $Y^2$ is CH, $Y^3$ is CH |
| P.0135 | $X^1$ is chloro, $X^2$ is C—Cl, $X^3$ is hydrogen | trifluoromethyl | cyano | $Y^1$ is CH, $Y^2$ is CH, $Y^3$ is CH |
| P.0136 | $X^1$ is chloro, $X^2$ is C—Cl, $X^3$ is hydrogen | trifluoromethyl | cyclopropyl | $Y^1$ is CH, $Y^2$ is CH, $Y^3$ is CH |
| P.0137 | $X^1$ is chloro, $X^2$ is C—Cl, $X^3$ is hydrogen | trifluoromethyl | ethyl | $Y^1$ is CH, $Y^2$ is CH, $Y^3$ is CH |
| P.0138 | $X^1$ is chloro, $X^2$ is C—Cl, $X^3$ is hydrogen | trifluoromethyl | fluoro | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0139 | $X^1$ is chloro, $X^2$ is C—Cl, $X^3$ is hydrogen | trifluoromethyl | hydrogen | $Y^1$ is CH, $Y^2$ is CH, $Y^3$ is CH |
| P.0140 | $X^1$ is chloro, $X^2$ is C—Cl, $X^3$ is hydrogen | trifluoromethyl | methoxy | $Y^1$ is CH, $Y^2$ is CH, $Y^3$ is CH |
| P.0141 | $X^1$ is chloro, $X^2$ is C—Cl, $X^3$ is hydrogen | trifluoromethyl | methyl | $Y^1$ is CH, $Y^2$ is CH, $Y^3$ is CH |
| P.0142 | $X^1$ is chloro, $X^2$ is C—Cl, $X^3$ is hydrogen | trifluoromethyl | nitro | $Y^1$ is CH, $Y^2$ is CH, $Y^3$ is CH |
| P.0143 | $X^1$ is chloro, $X^2$ is C—Cl, $X^3$ is hydrogen | trifluoromethyl | trifluoromethoxy | $Y^1$ is CH, $Y^2$ is CH, $Y^3$ is CH |
| P.0144 | $X^1$ is chloro, $X^2$ is C—Cl, $X^3$ is hydrogen | trifluoromethyl | trifluoromethyl | $Y^1$ is CH, $Y^2$ is CH, $Y^3$ is CH |
| P.0145 | $X^1$ is chloro, $X^2$ is C—Br, $X^3$ is chloro | chlorodifluoromethyl | bromo | $Y^1$ is CH, $Y^2$ is CH, $Y^3$ is CH |
| P.0146 | $X^1$ is chloro, $X^2$ is C—Br, $X^3$ is chloro | chlorodifluoromethyl | chloro | $Y^1$ is CH, $Y^2$ is CH, $Y^3$ is CH |
| P.0147 | $X^1$ is chloro, $X^2$ is C—Br, $X^3$ is chloro | chlorodifluoromethyl | cyano | $Y^1$ is CH, $Y^2$ is CH, $Y^3$ is CH |
| P.0148 | $X^1$ is chloro, $X^2$ is C—Br, $X^3$ is chloro | chlorodifluoromethyl | cyclopropyl | $Y^1$ is CH, $Y^2$ is CH, $Y^3$ is CH |
| P.0149 | $X^1$ is chloro, $X^2$ is C—Br, $X^3$ is chloro | chlorodifluoromethyl | ethyl | $Y^1$ is CH, $Y^2$ is CH, $Y^3$ is CH |
| P.0150 | $X^1$ is chloro, $X^2$ is C—Br, $X^3$ is chloro | chlorodifluoromethyl | fluoro | $Y^1$ is CH, $Y^2$ is CH, $Y^3$ is CH |
| P.0151 | $X^1$ is chloro, $X^2$ is C—Br, $X^3$ is chloro | chlorodifluoromethyl | hydrogen | $Y^1$ is CH, $Y^2$ is CH, $Y^3$ is CH |
| P.0152 | $X^1$ is chloro, $X^2$ is C—Br, $X^3$ is chloro | chlorodifluoromethyl | methoxy | $Y^1$ is CH, $Y^2$ is CH, $Y^3$ is CH |
| P.0153 | $X^1$ is chloro, $X^2$ is C—Br, $X^3$ is chloro | chlorodifluoromethyl | methyl | $Y^1$ is CH, $Y^2$ is CH, $Y^3$ is CH |
| P.0154 | $X^1$ is chloro, $X^2$ is C—Br, $X^3$ is chloro | chlorodifluoromethyl | nitro | $Y^1$ is CH, $Y^2$ is CH, $Y^3$ is CH |
| P.0155 | $X^1$ is chloro, $X^2$ is C—Br, $X^3$ is chloro | chlorodifluoromethyl | trifluoromethoxy | $Y^1$ is CH, $Y^2$ is CH, $Y^3$ is CH |
| P.0156 | $X^1$ is chloro, $X^2$ is C—Br, $X^3$ is chloro | chlorodifluoromethyl | trifluoromethyl | $Y^1$ is CH, $Y^2$ is CH, $Y^3$ is CH |
| P.0157 | $X^1$ is chloro, $X^2$ is C—Br, $X^3$ is chloro | difluoromethyl | bromo | $Y^1$ is CH, $Y^2$ is CH, $Y^3$ is CH |
| P.0158 | $X^1$ is chloro, $X^2$ is C—Br, $X^3$ is chloro | difluoromethyl | chloro | $Y^1$ is CH, $Y^2$ is CH, $Y^3$ is CH |
| P.0159 | $X^1$ is chloro, $X^2$ is C—Br, $X^3$ is chloro | difluoromethyl | cyano | $Y^1$ is CH, $Y^2$ is CH, $Y^3$ is CH |
| P.0160 | $X^1$ is chloro, $X^2$ is C—Br, $X^3$ is chloro | difluoromethyl | cyclopropyl | $Y^1$ is CH, $Y^2$ is CH, $Y^3$ is CH |
| P.0161 | $X^1$ is chloro, $X^2$ is C—Br, $X^3$ is chloro | difluoromethyl | ethyl | $Y^1$ is CH, $Y^2$ is CH, $Y^3$ is CH |
| P.0162 | $X^1$ is chloro, $X^2$ is C—Br, $X^3$ is chloro | difluoromethyl | fluoro | $Y^1$ is CH, $Y^2$ is CH, $Y^3$ is CH |
| P.0163 | $X^1$ is chloro, $X^2$ is C—Br, $X^3$ is chloro | difluoromethyl | hydrogen | $Y^1$ is CH, $Y^2$ is CH, $Y^3$ is CH |
| P.0164 | $X^1$ is chloro, $X^2$ is C—Br, $X^3$ is chloro | difluoromethyl | methoxy | $Y^1$ is CH, $Y^2$ is CH, $Y^3$ is CH |
| P.0165 | $X^1$ is chloro, $X^2$ is C—Br, $X^3$ is chloro | difluoromethyl | methyl | $Y^1$ is CH, $Y^2$ is CH, $Y^3$ is CH |
| P.0166 | $X^1$ is chloro, $X^2$ is C—Br, $X^3$ is chloro | difluoromethyl | nitro | $Y^1$ is CH, $Y^2$ is CH, $Y^3$ is CH |
| P.0167 | $X^1$ is chloro, $X^2$ is C—Br, $X^3$ is chloro | difluoromethyl | trifluoromethoxy | $Y^1$ is CH, $Y^2$ is CH, $Y^3$ is CH |
| P.0168 | $X^1$ is chloro, $X^2$ is C—Br, $X^3$ is chloro | difluoromethyl | trifluoromethyl | $Y^1$ is CH, $Y^2$ is CH, $Y^3$ is CH |
| P.0169 | $X^1$ is chloro, $X^2$ is C—Br, $X^3$ is chloro | trifluoromethyl | bromo | $Y^1$ is CH, $Y^2$ is CH, $Y^3$ is CH |
| P.0170 | $X^1$ is chloro, $X^2$ is C—Br, $X^3$ is chloro | trifluoromethyl | chloro | $Y^1$ is CH, $Y^2$ is CH, $Y^3$ is CH |
| P.0171 | $X^1$ is chloro, $X^2$ is C—Br, $X^3$ is chloro | trifluoromethyl | cyano | $Y^1$ is CH, $Y^2$ is CH, $Y^3$ is CH |
| P.0172 | $X^1$ is chloro, $X^2$ is C—Br, $X^3$ is chloro | trifluoromethyl | cyclopropyl | $Y^1$ is CH, $Y^2$ is CH, $Y^3$ is CH |
| P.0173 | $X^1$ is chloro, $X^2$ is C—Br, $X^3$ is chloro | trifluoromethyl | ethyl | $Y^1$ is CH, $Y^2$ is CH, $Y^3$ is CH |
| P.0174 | $X^1$ is chloro, $X^2$ is C—Br, $X^3$ is chloro | trifluoromethyl | fluoro | $Y^1$ is CH, $Y^2$ is CH, $Y^3$ is CH |
| P.0175 | $X^1$ is chloro, $X^2$ is C—Br, $X^3$ is chloro | trifluoromethyl | hydrogen | $Y^1$ is CH, $Y^2$ is CH, $Y^3$ is CH |
| P.0176 | $X^1$ is chloro, $X^2$ is C—Br, $X^3$ is chloro | trifluoromethyl | methoxy | $Y^1$ is CH, $Y^2$ is CH, $Y^3$ is CH |
| P.0177 | $X^1$ is chloro, $X^2$ is C—Br, $X^3$ is chloro | trifluoromethyl | methyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0178 | $X^1$ is chloro, $X^2$ is C—Br, $X^3$ is chloro | trifluoromethyl | nitro | $Y^1$ is CH, $Y^2$ is CH, $Y^3$ is CH |
| P.0179 | $X^1$ is chloro, $X^2$ is C—Br, $X^3$ is chloro | trifluoromethyl | trifluoromethoxy | $Y^1$ is CH, $Y^2$ is CH, $Y^3$ is CH |
| P.0180 | $X^1$ is chloro, $X^2$ is C—Br, $X^3$ is chloro | trifluoromethyl | trifluoromethyl | $Y^1$ is CH, $Y^2$ is CH, $Y^3$ is CH |
| P.0181 | $X^1$ is chloro, $X^2$ is C—F, $X^3$ is chloro | chlorodifluoromethyl | bromo | $Y^1$ is CH, $Y^2$ is CH, $Y^3$ is CH |
| P.0182 | $X^1$ is chloro, $X^2$ is C—F, $X^3$ is chloro | chlorodifluoromethyl | chloro | $Y^1$ is CH, $Y^2$ is CH, $Y^3$ is CH |
| P.0183 | $X^1$ is chloro, $X^2$ is C—F, $X^3$ is chloro | chlorodifluoromethyl | cyano | $Y^1$ is CH, $Y^2$ is CH, $Y^3$ is CH |
| P.0184 | $X^1$ is chloro, $X^2$ is C—F, $X^3$ is chloro | chlorodifluoromethyl | cyclopropyl | $Y^1$ is CH, $Y^2$ is CH, $Y^3$ is CH |
| P.0185 | $X^1$ is chloro, $X^2$ is C—F, $X^3$ is chloro | chlorodifluoromethyl | ethyl | $Y^1$ is CH, $Y^2$ is CH, $Y^3$ is CH |
| P.0186 | $X^1$ is chloro, $X^2$ is C—F, $X^3$ is chloro | chlorodifluoromethyl | fluoro | $Y^1$ is CH, $Y^2$ is CH, $Y^3$ is CH |
| P.0187 | $X^1$ is chloro, $X^2$ is C—F, $X^3$ is chloro | chlorodifluoromethyl | hydrogen | $Y^1$ is CH, $Y^2$ is CH, $Y^3$ is CH |
| P.0188 | $X^1$ is chloro, $X^2$ is C—F, $X^3$ is chloro | chlorodifluoromethyl | methoxy | $Y^1$ is CH, $Y^2$ is CH, $Y^3$ is CH |
| P.0189 | $X^1$ is chloro, $X^2$ is C—F, $X^3$ is chloro | chlorodifluoromethyl | methyl | $Y^1$ is CH, $Y^2$ is CH, $Y^3$ is CH |
| P.0190 | $X^1$ is chloro, $X^2$ is C—F, $X^3$ is chloro | chlorodifluoromethyl | nitro | $Y^1$ is CH, $Y^2$ is CH, $Y^3$ is CH |
| P.0191 | $X^1$ is chloro, $X^2$ is C—F, $X^3$ is chloro | chlorodifluoromethyl | trifluoromethoxy | $Y^1$ is CH, $Y^2$ is CH, $Y^3$ is CH |
| P.0192 | $X^1$ is chloro, $X^2$ is C—F, $X^3$ is chloro | chlorodifluoromethyl | trifluoromethyl | $Y^1$ is CH, $Y^2$ is CH, $Y^3$ is CH |
| P.0193 | $X^1$ is chloro, $X^2$ is C—F, $X^3$ is chloro | difluoromethyl | bromo | $Y^1$ is CH, $Y^2$ is CH, $Y^3$ is CH |
| P.0194 | $X^1$ is chloro, $X^2$ is C—F, $X^3$ is chloro | difluoromethyl | chloro | $Y^1$ is CH, $Y^2$ is CH, $Y^3$ is CH |
| P.0195 | $X^1$ is chloro, $X^2$ is C—F, $X^3$ is chloro | difluoromethyl | cyano | $Y^1$ is CH, $Y^2$ is CH, $Y^3$ is CH |
| P.0196 | $X^1$ is chloro, $X^2$ is C—F, $X^3$ is chloro | difluoromethyl | cyclopropyl | $Y^1$ is CH, $Y^2$ is CH, $Y^3$ is CH |
| P.0197 | $X^1$ is chloro, $X^2$ is C—F, $X^3$ is chloro | difluoromethyl | ethyl | $Y^1$ is CH, $Y^2$ is CH, $Y^3$ is CH |
| P.0198 | $X^1$ is chloro, $X^2$ is C—F, $X^3$ is chloro | difluoromethyl | fluoro | $Y^1$ is CH, $Y^2$ is CH, $Y^3$ is CH |
| P.0199 | $X^1$ is chloro, $X^2$ is C—F, $X^3$ is chloro | difluoromethyl | hydrogen | $Y^1$ is CH, $Y^2$ is CH, $Y^3$ is CH |
| P.0200 | $X^1$ is chloro, $X^2$ is C—F, $X^3$ is chloro | difluoromethyl | methoxy | $Y^1$ is CH, $Y^2$ is CH, $Y^3$ is CH |
| P.0201 | $X^1$ is chloro, $X^2$ is C—F, $X^3$ is chloro | difluoromethyl | methyl | $Y^1$ is CH, $Y^2$ is CH, $Y^3$ is CH |
| P.0202 | $X^1$ is chloro, $X^2$ is C—F, $X^3$ is chloro | difluoromethyl | nitro | $Y^1$ is CH, $Y^2$ is CH, $Y^3$ is CH |
| P.0203 | $X^1$ is chloro, $X^2$ is C—F, $X^3$ is chloro | difluoromethyl | trifluoromethoxy | $Y^1$ is CH, $Y^2$ is CH, $Y^3$ is CH |
| P.0204 | $X^1$ is chloro, $X^2$ is C—F, $X^3$ is chloro | difluoromethyl | trifluoromethyl | $Y^1$ is CH, $Y^2$ is CH, $Y^3$ is CH |
| P.0205 | $X^1$ is chloro, $X^2$ is C—F, $X^3$ is chloro | trifluoromethyl | bromo | $Y^1$ is CH, $Y^2$ is CH, $Y^3$ is CH |
| P.0206 | $X^1$ is chloro, $X^2$ is C—F, $X^3$ is chloro | trifluoromethyl | chloro | $Y^1$ is CH, $Y^2$ is CH, $Y^3$ is CH |
| P.0207 | $X^1$ is chloro, $X^2$ is C—F, $X^3$ is chloro | trifluoromethyl | cyano | $Y^1$ is CH, $Y^2$ is CH, $Y^3$ is CH |
| P.0208 | $X^1$ is chloro, $X^2$ is C—F, $X^3$ is chloro | trifluoromethyl | cyclopropyl | $Y^1$ is CH, $Y^2$ is CH, $Y^3$ is CH |
| P.0209 | $X^1$ is chloro, $X^2$ is C—F, $X^3$ is chloro | trifluoromethyl | ethyl | $Y^1$ is CH, $Y^2$ is CH, $Y^3$ is CH |
| P.0210 | $X^1$ is chloro, $X^2$ is C—F, $X^3$ is chloro | trifluoromethyl | fluoro | $Y^1$ is CH, $Y^2$ is CH, $Y^3$ is CH |
| P.0211 | $X^1$ is chloro, $X^2$ is C—F, $X^3$ is chloro | trifluoromethyl | hydrogen | $Y^1$ is CH, $Y^2$ is CH, $Y^3$ is CH |
| P.0212 | $X^1$ is chloro, $X^2$ is C—F, $X^3$ is chloro | trifluoromethyl | methoxy | $Y^1$ is CH, $Y^2$ is CH, $Y^3$ is CH |
| P.0213 | $X^1$ is chloro, $X^2$ is C—F, $X^3$ is chloro | trifluoromethyl | methyl | $Y^1$ is CH, $Y^2$ is CH, $Y^3$ is CH |
| P.0214 | $X^1$ is chloro, $X^2$ is C—F, $X^3$ is chloro | trifluoromethyl | nitro | $Y^1$ is CH, $Y^2$ is CH, $Y^3$ is CH |
| P.0215 | $X^1$ is chloro, $X^2$ is C—F, $X^3$ is chloro | trifluoromethyl | trifluoromethoxy | $Y^1$ is CH, $Y^2$ is CH, $Y^3$ is CH |
| P.0216 | $X^1$ is chloro, $X^2$ is C—F, $X^3$ is chloro | trifluoromethyl | trifluoromethyl | $Y^1$ is CH, $Y^2$ is CH, $Y^3$ is CH |

TABLE P-continued

|  | X1, X2, X3 | X4 | R5 | Y1, Y2, Y3 |
| --- | --- | --- | --- | --- |
| P.0217 | $X^1$ is chloro, $X^2$ is C—Cl, $X^3$ is chloro | chlorodifluoromethyl | bromo | $Y^1$ is CH, $Y^2$ is CH, $Y^3$ is CH |
| P.0218 | $X^1$ is chloro, $X^2$ is C—Cl, $X^3$ is chloro | chlorodifluoromethyl | chloro | $Y^1$ is CH, $Y^2$ is CH, $Y^3$ is CH |
| P.0219 | $X^1$ is chloro, $X^2$ is C—Cl, $X^3$ is chloro | chlorodifluoromethyl | cyano | $Y^1$ is CH, $Y^2$ is CH, $Y^3$ is CH |
| P.0220 | $X^1$ is chloro, $X^2$ is C—Cl, $X^3$ is chloro | chlorodifluoromethyl | cyclopropyl | $Y^1$ is CH, $Y^2$ is CH, $Y^3$ is CH |
| P.0221 | $X^1$ is chloro, $X^2$ is C—Cl, $X^3$ is chloro | chlorodifluoromethyl | ethyl | $Y^1$ is CH, $Y^2$ is CH, $Y^3$ is CH |
| P.0222 | $X^1$ is chloro, $X^2$ is C—Cl, $X^3$ is chloro | chlorodifluoromethyl | fluoro | $Y^1$ is CH, $Y^2$ is CH, $Y^3$ is CH |
| P.0223 | $X^1$ is chloro, $X^2$ is C—Cl, $X^3$ is chloro | chlorodifluoromethyl | hydrogen | $Y^1$ is CH, $Y^2$ is CH, $Y^3$ is CH |
| P.0224 | $X^1$ is chloro, $X^2$ is C—Cl, $X^3$ is chloro | chlorodifluoromethyl | methoxy | $Y^1$ is CH, $Y^2$ is CH, $Y^3$ is CH |
| P.0225 | $X^1$ is chloro, $X^2$ is C—Cl, $X^3$ is chloro | chlorodifluoromethyl | methyl | $Y^1$ is CH, $Y^2$ is CH, $Y^3$ is CH |
| P.0226 | $X^1$ is chloro, $X^2$ is C—Cl, $X^3$ is chloro | chlorodifluoromethyl | nitro | $Y^1$ is CH, $Y^2$ is CH, $Y^3$ is CH |
| P.0227 | $X^1$ is chloro, $X^2$ is C—Cl, $X^3$ is chloro | chlorodifluoromethyl | trifluoromethoxy | $Y^1$ is CH, $Y^2$ is CH, $Y^3$ is CH |
| P.0228 | $X^1$ is chloro, $X^2$ is C—Cl, $X^3$ is chloro | chlorodifluoromethyl | trifluoromethyl | $Y^1$ is CH, $Y^2$ is CH, $Y^3$ is CH |
| P.0229 | $X^1$ is chloro, $X^2$ is C—Cl, $X^3$ is chloro | difluoromethyl | bromo | $Y^1$ is CH, $Y^2$ is CH, $Y^3$ is CH |
| P.0230 | $X^1$ is chloro, $X^2$ is C—Cl, $X^3$ is chloro | difluoromethyl | chloro | $Y^1$ is CH, $Y^2$ is CH, $Y^3$ is CH |
| P.0231 | $X^1$ is chloro, $X^2$ is C—Cl, $X^3$ is chloro | difluoromethyl | cyano | $Y^1$ is CH, $Y^2$ is CH, $Y^3$ is CH |
| P.0232 | $X^1$ is chloro, $X^2$ is C—Cl, $X^3$ is chloro | difluoromethyl | cyclopropyl | $Y^1$ is CH, $Y^2$ is CH, $Y^3$ is CH |
| P.0233 | $X^1$ is chloro, $X^2$ is C—Cl, $X^3$ is chloro | difluoromethyl | ethyl | $Y^1$ is CH, $Y^2$ is CH, $Y^3$ is CH |
| P.0234 | $X^1$ is chloro, $X^2$ is C—Cl, $X^3$ is chloro | difluoromethyl | fluoro | $Y^1$ is CH, $Y^2$ is CH, $Y^3$ is CH |
| P.0235 | $X^1$ is chloro, $X^2$ is C—Cl, $X^3$ is chloro | difluoromethyl | hydrogen | $Y^1$ is CH, $Y^2$ is CH, $Y^3$ is CH |
| P.0236 | $X^1$ is chloro, $X^2$ is C—Cl, $X^3$ is chloro | difluoromethyl | methoxy | $Y^1$ is CH, $Y^2$ is CH, $Y^3$ is CH |
| P.0237 | $X^1$ is chloro, $X^2$ is C—Cl, $X^3$ is chloro | difluoromethyl | methyl | $Y^1$ is CH, $Y^2$ is CH, $Y^3$ is CH |
| P.0238 | $X^1$ is chloro, $X^2$ is C—Cl, $X^3$ is chloro | difluoromethyl | nitro | $Y^1$ is CH, $Y^2$ is CH, $Y^3$ is CH |
| P.0239 | $X^1$ is chloro, $X^2$ is C—Cl, $X^3$ is chloro | difluoromethyl | trifluoromethoxy | $Y^1$ is CH, $Y^2$ is CH, $Y^3$ is CH |
| P.0240 | $X^1$ is chloro, $X^2$ is C—Cl, $X^3$ is chloro | difluoromethyl | trifluoromethyl | $Y^1$ is CH, $Y^2$ is CH, $Y^3$ is CH |
| P.0241 | $X^1$ is chloro, $X^2$ is C—Cl, $X^3$ is chloro | trifluoromethyl | bromo | $Y^1$ is CH, $Y^2$ is CH, $Y^3$ is CH |
| P.0242 | $X^1$ is chloro, $X^2$ is C—Cl, $X^3$ is chloro | trifluoromethyl | chloro | $Y^1$ is CH, $Y^2$ is CH, $Y^3$ is CH |
| P.0243 | $X^1$ is chloro, $X^2$ is C—Cl, $X^3$ is chloro | trifluoromethyl | cyano | $Y^1$ is CH, $Y^2$ is CH, $Y^3$ is CH |
| P.0244 | $X^1$ is chloro, $X^2$ is C—Cl, $X^3$ is chloro | trifluoromethyl | cyclopropyl | $Y^1$ is CH, $Y^2$ is CH, $Y^3$ is CH |
| P.0245 | $X^1$ is chloro, $X^2$ is C—Cl, $X^3$ is chloro | trifluoromethyl | ethyl | $Y^1$ is CH, $Y^2$ is CH, $Y^3$ is CH |
| P.0246 | $X^1$ is chloro, $X^2$ is C—Cl, $X^3$ is chloro | trifluoromethyl | fluoro | $Y^1$ is CH, $Y^2$ is CH, $Y^3$ is CH |
| P.0247 | $X^1$ is chloro, $X^2$ is C—Cl, $X^3$ is chloro | trifluoromethyl | hydrogen | $Y^1$ is CH, $Y^2$ is CH, $Y^3$ is CH |
| P.0248 | $X^1$ is chloro, $X^2$ is C—Cl, $X^3$ is chloro | trifluoromethyl | methoxy | $Y^1$ is CH, $Y^2$ is CH, $Y^3$ is CH |
| P.0249 | $X^1$ is chloro, $X^2$ is C—Cl, $X^3$ is chloro | trifluoromethyl | methyl | $Y^1$ is CH, $Y^2$ is CH, $Y^3$ is CH |
| P.0250 | $X^1$ is chloro, $X^2$ is C—Cl, $X^3$ is chloro | trifluoromethyl | nitro | $Y^1$ is CH, $Y^2$ is CH, $Y^3$ is CH |
| P.0251 | $X^1$ is chloro, $X^2$ is C—Cl, $X^3$ is chloro | trifluoromethyl | trifluoromethoxy | $Y^1$ is CH, $Y^2$ is CH, $Y^3$ is CH |
| P.0252 | $X^1$ is chloro, $X^2$ is C—Cl, $X^3$ is chloro | trifluoromethyl | trifluoromethyl | $Y^1$ is CH, $Y^2$ is CH, $Y^3$ is CH |
| P.0253 | $X^1$ is chloro, $X^2$ is C—I, $X^3$ is chloro | chlorodifluoromethyl | bromo | $Y^1$ is CH, $Y^2$ is CH, $Y^3$ is CH |
| P.0254 | $X^1$ is chloro, $X^2$ is C—I, $X^3$ is chloro | chlorodifluoromethyl | chloro | $Y^1$ is CH, $Y^2$ is CH, $Y^3$ is CH |
| P.0255 | $X^1$ is chloro, $X^2$ is C—I, $X^3$ is chloro | chlorodifluoromethyl | cyano | $Y^1$ is CH, $Y^2$ is CH, $Y^3$ is CH |

TABLE P-continued

|  | X1, X2, X3 | X4 | R5 | Y1, Y2, Y3 |
|---|---|---|---|---|
| P.0256 | $X^1$ is chloro, $X^2$ is C—I, $X^3$ is chloro | chlorodifluoromethyl | cyclopropyl | $Y^1$ is CH, $Y^2$ is CH, $Y^3$ is CH |
| P.0257 | $X^1$ is chloro, $X^2$ is C—I, $X^3$ is chloro | chlorodifluoromethyl | ethyl | $Y^1$ is CH, $Y^2$ is CH, $Y^3$ is CH |
| P.0258 | $X^1$ is chloro, $X^2$ is C—I, $X^3$ is chloro | chlorodifluoromethyl | fluoro | $Y^1$ is CH, $Y^2$ is CH, $Y^3$ is CH |
| P.0259 | $X^1$ is chloro, $X^2$ is C—I, $X^3$ is chloro | chlorodifluoromethyl | hydrogen | $Y^1$ is CH, $Y^2$ is CH, $Y^3$ is CH |
| P.0260 | $X^1$ is chloro, $X^2$ is C—I, $X^3$ is chloro | chlorodifluoromethyl | methoxy | $Y^1$ is CH, $Y^2$ is CH, $Y^3$ is CH |
| P.0261 | $X^1$ is chloro, $X^2$ is C—I, $X^3$ is chloro | chlorodifluoromethyl | methyl | $Y^1$ is CH, $Y^2$ is CH, $Y^3$ is CH |
| P.0262 | $X^1$ is chloro, $X^2$ is C—I, $X^3$ is chloro | chlorodifluoromethyl | nitro | $Y^1$ is CH, $Y^2$ is CH, $Y^3$ is CH |
| P.0263 | $X^1$ is chloro, $X^2$ is C—I, $X^3$ is chloro | chlorodifluoromethyl | trifluoromethoxy | $Y^1$ is CH, $Y^2$ is CH, $Y^3$ is CH |
| P.0264 | $X^1$ is chloro, $X^2$ is C—I, $X^3$ is chloro | chlorodifluoromethyl | trifluoromethyl | $Y^1$ is CH, $Y^2$ is CH, $Y^3$ is CH |
| P.0265 | $X^1$ is chloro, $X^2$ is C—I, $X^3$ is chloro | difluoromethyl | bromo | $Y^1$ is CH, $Y^2$ is CH, $Y^3$ is CH |
| P.0266 | $X^1$ is chloro, $X^2$ is C—I, $X^3$ is chloro | difluoromethyl | chloro | $Y^1$ is CH, $Y^2$ is CH, $Y^3$ is CH |
| P.0267 | $X^1$ is chloro, $X^2$ is C—I, $X^3$ is chloro | difluoromethyl | cyano | $Y^1$ is CH, $Y^2$ is CH, $Y^3$ is CH |
| P.0268 | $X^1$ is chloro, $X^2$ is C—I, $X^3$ is chloro | difluoromethyl | cyclopropyl | $Y^1$ is CH, $Y^2$ is CH, $Y^3$ is CH |
| P.0269 | $X^1$ is chloro, $X^2$ is C—I, $X^3$ is chloro | difluoromethyl | ethyl | $Y^1$ is CH, $Y^2$ is CH, $Y^3$ is CH |
| P.0270 | $X^1$ is chloro, $X^2$ is C—I, $X^3$ is chloro | difluoromethyl | fluoro | $Y^1$ is CH, $Y^2$ is CH, $Y^3$ is CH |
| P.0271 | $X^1$ is chloro, $X^2$ is C—I, $X^3$ is chloro | difluoromethyl | hydrogen | $Y^1$ is CH, $Y^2$ is CH, $Y^3$ is CH |
| P.0272 | $X^1$ is chloro, $X^2$ is C—I, $X^3$ is chloro | difluoromethyl | methoxy | $Y^1$ is CH, $Y^2$ is CH, $Y^3$ is CH |
| P.0273 | $X^1$ is chloro, $X^2$ is C—I, $X^3$ is chloro | difluoromethyl | methyl | $Y^1$ is CH, $Y^2$ is CH, $Y^3$ is CH |
| P.0274 | $X^1$ is chloro, $X^2$ is C—I, $X^3$ is chloro | difluoromethyl | nitro | $Y^1$ is CH, $Y^2$ is CH, $Y^3$ is CH |
| P.0275 | $X^1$ is chloro, $X^2$ is C—I, $X^3$ is chloro | difluoromethyl | trifluoromethoxy | $Y^1$ is CH, $Y^2$ is CH, $Y^3$ is CH |
| P.0276 | $X^1$ is chloro, $X^2$ is C—I, $X^3$ is chloro | difluoromethyl | trifluoromethyl | $Y^1$ is CH, $Y^2$ is CH, $Y^3$ is CH |
| P.0277 | $X^1$ is chloro, $X^2$ is C—I, $X^3$ is chloro | trifluoromethyl | bromo | $Y^1$ is CH, $Y^2$ is CH, $Y^3$ is CH |
| P.0278 | $X^1$ is chloro, $X^2$ is C—I, $X^3$ is chloro | trifluoromethyl | chloro | $Y^1$ is CH, $Y^2$ is CH, $Y^3$ is CH |
| P.0279 | $X^1$ is chloro, $X^2$ is C—I, $X^3$ is chloro | trifluoromethyl | cyano | $Y^1$ is CH, $Y^2$ is CH, $Y^3$ is CH |
| P.0280 | $X^1$ is chloro, $X^2$ is C—I, $X^3$ is chloro | trifluoromethyl | cyclopropyl | $Y^1$ is CH, $Y^2$ is CH, $Y^3$ is CH |
| P.0281 | $X^1$ is chloro, $X^2$ is C—I, $X^3$ is chloro | trifluoromethyl | ethyl | $Y^1$ is CH, $Y^2$ is CH, $Y^3$ is CH |
| P.0282 | $X^1$ is chloro, $X^2$ is C—I, $X^3$ is chloro | trifluoromethyl | fluoro | $Y^1$ is CH, $Y^2$ is CH, $Y^3$ is CH |
| P.0283 | $X^1$ is chloro, $X^2$ is C—I, $X^3$ is chloro | trifluoromethyl | hydrogen | $Y^1$ is CH, $Y^2$ is CH, $Y^3$ is CH |
| P.0284 | $X^1$ is chloro, $X^2$ is C—I, $X^3$ is chloro | trifluoromethyl | methoxy | $Y^1$ is CH, $Y^2$ is CH, $Y^3$ is CH |
| P.0285 | $X^1$ is chloro, $X^2$ is C—I, $X^3$ is chloro | trifluoromethyl | methyl | $Y^1$ is CH, $Y^2$ is CH, $Y^3$ is CH |
| P.0286 | $X^1$ is chloro, $X^2$ is C—I, $X^3$ is chloro | trifluoromethyl | nitro | $Y^1$ is CH, $Y^2$ is CH, $Y^3$ is CH |
| P.0287 | $X^1$ is chloro, $X^2$ is C—I, $X^3$ is chloro | trifluoromethyl | trifluoromethoxy | $Y^1$ is CH, $Y^2$ is CH, $Y^3$ is CH |
| P.0288 | $X^1$ is chloro, $X^2$ is C—I, $X^3$ is chloro | trifluoromethyl | trifluoromethyl | $Y^1$ is CH, $Y^2$ is CH, $Y^3$ is CH |
| P.0289 | $X^1$ is fluoro, $X^2$ is C—F, $X^3$ is fluoro | chlorodifluoromethyl | bromo | $Y^1$ is CH, $Y^2$ is CH, $Y^3$ is CH |
| P.0290 | $X^1$ is fluoro, $X^2$ is C—F, $X^3$ is fluoro | chlorodifluoromethyl | chloro | $Y^1$ is CH, $Y^2$ is CH, $Y^3$ is CH |
| P.0291 | $X^1$ is fluoro, $X^2$ is C—F, $X^3$ is fluoro | chlorodifluoromethyl | cyano | $Y^1$ is CH, $Y^2$ is CH, $Y^3$ is CH |
| P.0292 | $X^1$ is fluoro, $X^2$ is C—F, $X^3$ is fluoro | chlorodifluoromethyl | cyclopropyl | $Y^1$ is CH, $Y^2$ is CH, $Y^3$ is CH |
| P.0293 | $X^1$ is fluoro, $X^2$ is C—F, $X^3$ is fluoro | chlorodifluoromethyl | ethyl | $Y^1$ is CH, $Y^2$ is CH, $Y^3$ is CH |
| P.0294 | $X^1$ is fluoro, $X^2$ is C—F, $X^3$ is fluoro | chlorodifluoromethyl | fluoro | $Y^1$ is CH, $Y^2$ is CH, $Y^3$ is CH |

TABLE P-continued

|  | X1, X2, X3 | X4 | R5 | Y1, Y2, Y3 |
|---|---|---|---|---|
| P.0295 | $X^1$ is fluoro, $X^2$ is C—F, $X^3$ is fluoro | chlorodifluoromethyl | hydrogen | $Y^1$ is CH, $Y^2$ is CH, $Y^3$ is CH |
| P.0296 | $X^1$ is fluoro, $X^2$ is C—F, $X^3$ is fluoro | chlorodifluoromethyl | methoxy | $Y^1$ is CH, $Y^2$ is CH, $Y^3$ is CH |
| P.0297 | $X^1$ is fluoro, $X^2$ is C—F, $X^3$ is fluoro | chlorodifluoromethyl | methyl | $Y^1$ is CH, $Y^2$ is CH, $Y^3$ is CH |
| P.0298 | $X^1$ is fluoro, $X^2$ is C—F, $X^3$ is fluoro | chlorodifluoromethyl | nitro | $Y^1$ is CH, $Y^2$ is CH, $Y^3$ is CH |
| P.0299 | $X^1$ is fluoro, $X^2$ is C—F, $X^3$ is fluoro | chlorodifluoromethyl | trifluoromethoxy | $Y^1$ is CH, $Y^2$ is CH, $Y^3$ is CH |
| P.0300 | $X^1$ is fluoro, $X^2$ is C—F, $X^3$ is fluoro | chlorodifluoromethyl | trifluoromethyl | $Y^1$ is CH, $Y^2$ is CH, $Y^3$ is CH |
| P.0301 | $X^1$ is fluoro, $X^2$ is C—F, $X^3$ is fluoro | difluoromethyl | bromo | $Y^1$ is CH, $Y^2$ is CH, $Y^3$ is CH |
| P.0302 | $X^1$ is fluoro, $X^2$ is C—F, $X^3$ is fluoro | difluoromethyl | chloro | $Y^1$ is CH, $Y^2$ is CH, $Y^3$ is CH |
| P.0303 | $X^1$ is fluoro, $X^2$ is C—F, $X^3$ is fluoro | difluoromethyl | cyano | $Y^1$ is CH, $Y^2$ is CH, $Y^3$ is CH |
| P.0304 | $X^1$ is fluoro, $X^2$ is C—F, $X^3$ is fluoro | difluoromethyl | cyclopropyl | $Y^1$ is CH, $Y^2$ is CH, $Y^3$ is CH |
| P.0305 | $X^1$ is fluoro, $X^2$ is C—F, $X^3$ is fluoro | difluoromethyl | ethyl | $Y^1$ is CH, $Y^2$ is CH, $Y^3$ is CH |
| P.0306 | $X^1$ is fluoro, $X^2$ is C—F, $X^3$ is fluoro | difluoromethyl | fluoro | $Y^1$ is CH, $Y^2$ is CH, $Y^3$ is CH |
| P.0307 | $X^1$ is fluoro, $X^2$ is C—F, $X^3$ is fluoro | difluoromethyl | hydrogen | $Y^1$ is CH, $Y^2$ is CH, $Y^3$ is CH |
| P.0308 | $X^1$ is fluoro, $X^2$ is C—F, $X^3$ is fluoro | difluoromethyl | methoxy | $Y^1$ is CH, $Y^2$ is CH, $Y^3$ is CH |
| P.0309 | $X^1$ is fluoro, $X^2$ is C—F, $X^3$ is fluoro | difluoromethyl | methyl | $Y^1$ is CH, $Y^2$ is CH, $Y^3$ is CH |
| P.0310 | $X^1$ is fluoro, $X^2$ is C—F, $X^3$ is fluoro | difluoromethyl | nitro | $Y^1$ is CH, $Y^2$ is CH, $Y^3$ is CH |
| P.0311 | $X^1$ is fluoro, $X^2$ is C—F, $X^3$ is fluoro | difluoromethyl | trifluoromethoxy | $Y^1$ is CH, $Y^2$ is CH, $Y^3$ is CH |
| P.0312 | $X^1$ is fluoro, $X^2$ is C—F, $X^3$ is fluoro | difluoromethyl | trifluoromethyl | $Y^1$ is CH, $Y^2$ is CH, $Y^3$ is CH |
| P.0313 | $X^1$ is fluoro, $X^2$ is C—F, $X^3$ is fluoro | trifluoromethyl | bromo | $Y^1$ is CH, $Y^2$ is CH, $Y^3$ is CH |
| P.0314 | $X^1$ is fluoro, $X^2$ is C—F, $X^3$ is fluoro | trifluoromethyl | chloro | $Y^1$ is CH, $Y^2$ is CH, $Y^3$ is CH |
| P.0315 | $X^1$ is fluoro, $X^2$ is C—F, $X^3$ is fluoro | trifluoromethyl | cyano | $Y^1$ is CH, $Y^2$ is CH, $Y^3$ is CH |
| P.0316 | $X^1$ is fluoro, $X^2$ is C—F, $X^3$ is fluoro | trifluoromethyl | cyclopropyl | $Y^1$ is CH, $Y^2$ is CH, $Y^3$ is CH |
| P.0317 | $X^1$ is fluoro, $X^2$ is C—F, $X^3$ is fluoro | trifluoromethyl | ethyl | $Y^1$ is CH, $Y^2$ is CH, $Y^3$ is CH |
| P.0318 | $X^1$ is fluoro, $X^2$ is C—F, $X^3$ is fluoro | trifluoromethyl | fluoro | $Y^1$ is CH, $Y^2$ is CH, $Y^3$ is CH |
| P.0319 | $X^1$ is fluoro, $X^2$ is C—F, $X^3$ is fluoro | trifluoromethyl | hydrogen | $Y^1$ is CH, $Y^2$ is CH, $Y^3$ is CH |
| P.0320 | $X^1$ is fluoro, $X^2$ is C—F, $X^3$ is fluoro | trifluoromethyl | methoxy | $Y^1$ is CH, $Y^2$ is CH, $Y^3$ is CH |
| P.0321 | $X^1$ is fluoro, $X^2$ is C—F, $X^3$ is fluoro | trifluoromethyl | methyl | $Y^1$ is CH, $Y^2$ is CH, $Y^3$ is CH |
| P.0322 | $X^1$ is fluoro, $X^2$ is C—F, $X^3$ is fluoro | trifluoromethyl | nitro | $Y^1$ is CH, $Y^2$ is CH, $Y^3$ is CH |
| P.0323 | $X^1$ is fluoro, $X^2$ is C—F, $X^3$ is fluoro | trifluoromethyl | trifluoromethoxy | $Y^1$ is CH, $Y^2$ is CH, $Y^3$ is CH |
| P.0324 | $X^1$ is fluoro, $X^2$ is C—F, $X^3$ is fluoro | trifluoromethyl | trifluoromethyl | $Y^1$ is CH, $Y^2$ is CH, $Y^3$ is CH |
| P.0325 | $X^1$ is chloro, $X^2$ is CH, $X^3$ is bromo | chlorodifluoromethyl | bromo | $Y^1$ is CH, $Y^2$ is CH, $Y^3$ is CH |
| P.0326 | $X^1$ is chloro, $X^2$ is CH, $X^3$ is bromo | chlorodifluoromethyl | chloro | $Y^1$ is CH, $Y^2$ is CH, $Y^3$ is CH |
| P.0327 | $X^1$ is chloro, $X^2$ is CH, $X^3$ is bromo | chlorodifluoromethyl | cyano | $Y^1$ is CH, $Y^2$ is CH, $Y^3$ is CH |
| P.0328 | $X^1$ is chloro, $X^2$ is CH, $X^3$ is bromo | chlorodifluoromethyl | cyclopropyl | $Y^1$ is CH, $Y^2$ is CH, $Y^3$ is CH |
| P.0329 | $X^1$ is chloro, $X^2$ is CH, $X^3$ is bromo | chlorodifluoromethyl | ethyl | $Y^1$ is CH, $Y^2$ is CH, $Y^3$ is CH |
| P.0330 | $X^1$ is chloro, $X^2$ is CH, $X^3$ is bromo | chlorodifluoromethyl | fluoro | $Y^1$ is CH, $Y^2$ is CH, $Y^3$ is CH |
| P.0331 | $X^1$ is chloro, $X^2$ is CH, $X^3$ is bromo | chlorodifluoromethyl | hydrogen | $Y^1$ is CH, $Y^2$ is CH, $Y^3$ is CH |
| P.0332 | $X^1$ is chloro, $X^2$ is CH, $X^3$ is bromo | chlorodifluoromethyl | methoxy | $Y^1$ is CH, $Y^2$ is CH, $Y^3$ is CH |
| P.0333 | $X^1$ is chloro, $X^2$ is CH, $X^3$ is bromo | chlorodifluoromethyl | methyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0334 | $X^1$ is chloro, $X^2$ is CH, $X^3$ is bromo | chlorodifluoromethyl | nitro | $Y^1$ is CH, $Y^2$ is CH, $Y^3$ is CH |
| P.0335 | $X^1$ is chloro, $X^2$ is CH, $X^3$ is bromo | chlorodifluoromethyl | trifluoromethoxy | $Y^1$ is CH, $Y^2$ is CH, $Y^3$ is CH |
| P.0336 | $X^1$ is chloro, $X^2$ is CH, $X^3$ is bromo | chlorodifluoromethyl | trifluoromethyl | $Y^1$ is CH, $Y^2$ is CH, $Y^3$ is CH |
| P.0337 | $X^1$ is chloro, $X^2$ is CH, $X^3$ is bromo | difluoromethyl | bromo | $Y^1$ is CH, $Y^2$ is CH, $Y^3$ is CH |
| P.0338 | $X^1$ is chloro, $X^2$ is CH, $X^3$ is bromo | difluoromethyl | chloro | $Y^1$ is CH, $Y^2$ is CH, $Y^3$ is CH |
| P.0339 | $X^1$ is chloro, $X^2$ is CH, $X^3$ is bromo | difluoromethyl | cyano | $Y^1$ is CH, $Y^2$ is CH, $Y^3$ is CH |
| P.0340 | $X^1$ is chloro, $X^2$ is CH, $X^3$ is bromo | difluoromethyl | cyclopropyl | $Y^1$ is CH, $Y^2$ is CH, $Y^3$ is CH |
| P.0341 | $X^1$ is chloro, $X^2$ is CH, $X^3$ is bromo | difluoromethyl | ethyl | $Y^1$ is CH, $Y^2$ is CH, $Y^3$ is CH |
| P.0342 | $X^1$ is chloro, $X^2$ is CH, $X^3$ is bromo | difluoromethyl | fluoro | $Y^1$ is CH, $Y^2$ is CH, $Y^3$ is CH |
| P.0343 | $X^1$ is chloro, $X^2$ is CH, $X^3$ is bromo | difluoromethyl | hydrogen | $Y^1$ is CH, $Y^2$ is CH, $Y^3$ is CH |
| P.0344 | $X^1$ is chloro, $X^2$ is CH, $X^3$ is bromo | difluoromethyl | methoxy | $Y^1$ is CH, $Y^2$ is CH, $Y^3$ is CH |
| P.0345 | $X^1$ is chloro, $X^2$ is CH, $X^3$ is bromo | difluoromethyl | methyl | $Y^1$ is CH, $Y^2$ is CH, $Y^3$ is CH |
| P.0346 | $X^1$ is chloro, $X^2$ is CH, $X^3$ is bromo | difluoromethyl | nitro | $Y^1$ is CH, $Y^2$ is CH, $Y^3$ is CH |
| P.0347 | $X^1$ is chloro, $X^2$ is CH, $X^3$ is bromo | difluoromethyl | trifluoromethoxy | $Y^1$ is CH, $Y^2$ is CH, $Y^3$ is CH |
| P.0348 | $X^1$ is chloro, $X^2$ is CH, $X^3$ is bromo | difluoromethyl | trifluoromethyl | $Y^1$ is CH, $Y^2$ is CH, $Y^3$ is CH |
| P.0349 | $X^1$ is chloro, $X^2$ is CH, $X^3$ is bromo | trifluoromethyl | bromo | $Y^1$ is CH, $Y^2$ is CH, $Y^3$ is CH |
| P.0350 | $X^1$ is chloro, $X^2$ is CH, $X^3$ is bromo | trifluoromethyl | chloro | $Y^1$ is CH, $Y^2$ is CH, $Y^3$ is CH |
| P.0351 | $X^1$ is chloro, $X^2$ is CH, $X^3$ is bromo | trifluoromethyl | cyano | $Y^1$ is CH, $Y^2$ is CH, $Y^3$ is CH |
| P.0352 | $X^1$ is chloro, $X^2$ is CH, $X^3$ is bromo | trifluoromethyl | cyclopropyl | $Y^1$ is CH, $Y^2$ is CH, $Y^3$ is CH |
| P.0353 | $X^1$ is chloro, $X^2$ is CH, $X^3$ is bromo | trifluoromethyl | ethyl | $Y^1$ is CH, $Y^2$ is CH, $Y^3$ is CH |
| P.0354 | $X^1$ is chloro, $X^2$ is CH, $X^3$ is bromo | trifluoromethyl | fluoro | $Y^1$ is CH, $Y^2$ is CH, $Y^3$ is CH |
| P.0355 | $X^1$ is chloro, $X^2$ is CH, $X^3$ is bromo | trifluoromethyl | hydrogen | $Y^1$ is CH, $Y^2$ is CH, $Y^3$ is CH |
| P.0356 | $X^1$ is chloro, $X^2$ is CH, $X^3$ is bromo | trifluoromethyl | methoxy | $Y^1$ is CH, $Y^2$ is CH, $Y^3$ is CH |
| P.0357 | $X^1$ is chloro, $X^2$ is CH, $X^3$ is bromo | trifluoromethyl | methyl | $Y^1$ is CH, $Y^2$ is CH, $Y^3$ is CH |
| P.0358 | $X^1$ is chloro, $X^2$ is CH, $X^3$ is bromo | trifluoromethyl | nitro | $Y^1$ is CH, $Y^2$ is CH, $Y^3$ is CH |
| P.0359 | $X^1$ is chloro, $X^2$ is CH, $X^3$ is bromo | trifluoromethyl | trifluoromethoxy | $Y^1$ is CH, $Y^2$ is CH, $Y^3$ is CH |
| P.0360 | $X^1$ is chloro, $X^2$ is CH, $X^3$ is bromo | trifluoromethyl | trifluoromethyl | $Y^1$ is CH, $Y^2$ is CH, $Y^3$ is CH |
| P.0361 | $X^1$ is chloro, $X^2$ is CH, $X^3$ is bromo | chlorodifluoromethyl | bromo | $Y^1$ is CH, $Y^2$ is CH, $Y^3$ is CH |
| P.0362 | $X^1$ is chloro, $X^2$ is CH, $X^3$ is bromo | chlorodifluoromethyl | chloro | $Y^1$ is CH, $Y^2$ is CH, $Y^3$ is CH |
| P.0363 | $X^1$ is chloro, $X^2$ is CH, $X^3$ is bromo | chlorodifluoromethyl | cyano | $Y^1$ is CH, $Y^2$ is CH, $Y^3$ is CH |
| P.0364 | $X^1$ is chloro, $X^2$ is CH, $X^3$ is bromo | chlorodifluoromethyl | cyclopropyl | $Y^1$ is CH, $Y^2$ is CH, $Y^3$ is CH |
| P.0365 | $X^1$ is chloro, $X^2$ is CH, $X^3$ is bromo | chlorodifluoromethyl | ethyl | $Y^1$ is CH, $Y^2$ is CH, $Y^3$ is CH |
| P.0366 | $X^1$ is chloro, $X^2$ is CH, $X^3$ is bromo | chlorodifluoromethyl | fluoro | $Y^1$ is CH, $Y^2$ is CH, $Y^3$ is CH |
| P.0367 | $X^1$ is chloro, $X^2$ is CH, $X^3$ is bromo | chlorodifluoromethyl | hydrogen | $Y^1$ is CH, $Y^2$ is CH, $Y^3$ is CH |
| P.0368 | $X^1$ is chloro, $X^2$ is CH, $X^3$ is bromo | chlorodifluoromethyl | methoxy | $Y^1$ is CH, $Y^2$ is CH, $Y^3$ is CH |
| P.0369 | $X^1$ is chloro, $X^2$ is CH, $X^3$ is bromo | chlorodifluoromethyl | methyl | $Y^1$ is CH, $Y^2$ is CH, $Y^3$ is CH |
| P.0370 | $X^1$ is chloro, $X^2$ is CH, $X^3$ is bromo | chlorodifluoromethyl | nitro | $Y^1$ is CH, $Y^2$ is CH, $Y^3$ is CH |
| P.0371 | $X^1$ is chloro, $X^2$ is CH, $X^3$ is bromo | chlorodifluoromethyl | trifluoromethoxy | $Y^1$ is CH, $Y^2$ is CH, $Y^3$ is CH |
| P.0372 | $X^1$ is chloro, $X^2$ is CH, $X^3$ is bromo | chlorodifluoromethyl | trifluoromethyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0373 | $X^1$ is chloro, $X^2$ is CH, $X^3$ is bromo | difluoromethyl | bromo | $Y^1$ is CH, $Y^2$ is CH, $Y^3$ is CH |
| P.0374 | $X^1$ is chloro, $X^2$ is CH, $X^3$ is bromo | difluoromethyl | chloro | $Y^1$ is CH, $Y^2$ is CH, $Y^3$ is CH |
| P.0375 | $X^1$ is chloro, $X^2$ is CH, $X^3$ is bromo | difluoromethyl | cyano | $Y^1$ is CH, $Y^2$ is CH, $Y^3$ is CH |
| P.0376 | $X^1$ is chloro, $X^2$ is CH, $X^3$ is bromo | difluoromethyl | cyclopropyl | $Y^1$ is CH, $Y^2$ is CH, $Y^3$ is CH |
| P.0377 | $X^1$ is chloro, $X^2$ is CH, $X^3$ is bromo | difluoromethyl | ethyl | $Y^1$ is CH, $Y^2$ is CH, $Y^3$ is CH |
| P.0378 | $X^1$ is chloro, $X^2$ is CH, $X^3$ is bromo | difluoromethyl | fluoro | $Y^1$ is CH, $Y^2$ is CH, $Y^3$ is CH |
| P.0379 | $X^1$ is chloro, $X^2$ is CH, $X^3$ is bromo | difluoromethyl | hydrogen | $Y^1$ is CH, $Y^2$ is CH, $Y^3$ is CH |
| P.0380 | $X^1$ is chloro, $X^2$ is CH, $X^3$ is bromo | difluoromethyl | methoxy | $Y^1$ is CH, $Y^2$ is CH, $Y^3$ is CH |
| P.0381 | $X^1$ is chloro, $X^2$ is CH, $X^3$ is bromo | difluoromethyl | methyl | $Y^1$ is CH, $Y^2$ is CH, $Y^3$ is CH |
| P.0382 | $X^1$ is chloro, $X^2$ is CH, $X^3$ is bromo | difluoromethyl | nitro | $Y^1$ is CH, $Y^2$ is CH, $Y^3$ is CH |
| P.0383 | $X^1$ is chloro, $X^2$ is CH, $X^3$ is bromo | difluoromethyl | trifluoromethoxy | $Y^1$ is CH, $Y^2$ is CH, $Y^3$ is CH |
| P.0384 | $X^1$ is chloro, $X^2$ is CH, $X^3$ is bromo | difluoromethyl | trifluoromethyl | $Y^1$ is CH, $Y^2$ is CH, $Y^3$ is CH |
| P.0385 | $X^1$ is chloro, $X^2$ is CH, $X^3$ is bromo | trifluoromethyl | bromo | $Y^1$ is CH, $Y^2$ is CH, $Y^3$ is CH |
| P.0386 | $X^1$ is chloro, $X^2$ is CH, $X^3$ is bromo | trifluoromethyl | chloro | $Y^1$ is CH, $Y^2$ is CH, $Y^3$ is CH |
| P.0387 | $X^1$ is chloro, $X^2$ is CH, $X^3$ is bromo | trifluoromethyl | cyano | $Y^1$ is CH, $Y^2$ is CH, $Y^3$ is CH |
| P.0388 | $X^1$ is chloro, $X^2$ is CH, $X^3$ is bromo | trifluoromethyl | cyclopropyl | $Y^1$ is CH, $Y^2$ is CH, $Y^3$ is CH |
| P.0389 | $X^1$ is chloro, $X^2$ is CH, $X^3$ is bromo | trifluoromethyl | ethyl | $Y^1$ is CH, $Y^2$ is CH, $Y^3$ is CH |
| P.0390 | $X^1$ is chloro, $X^2$ is CH, $X^3$ is bromo | trifluoromethyl | fluoro | $Y^1$ is CH, $Y^2$ is CH, $Y^3$ is CH |
| P.0391 | $X^1$ is chloro, $X^2$ is CH, $X^3$ is bromo | trifluoromethyl | hydrogen | $Y^1$ is CH, $Y^2$ is CH, $Y^3$ is CH |
| P.0392 | $X^1$ is chloro, $X^2$ is CH, $X^3$ is bromo | trifluoromethyl | methoxy | $Y^1$ is CH, $Y^2$ is CH, $Y^3$ is CH |
| P.0393 | $X^1$ is chloro, $X^2$ is CH, $X^3$ is bromo | trifluoromethyl | methyl | $Y^1$ is CH, $Y^2$ is CH, $Y^3$ is CH |
| P.0394 | $X^1$ is chloro, $X^2$ is CH, $X^3$ is bromo | trifluoromethyl | nitro | $Y^1$ is CH, $Y^2$ is CH, $Y^3$ is CH |
| P.0395 | $X^1$ is chloro, $X^2$ is CH, $X^3$ is bromo | trifluoromethyl | trifluoromethoxy | $Y^1$ is CH, $Y^2$ is CH, $Y^3$ is CH |
| P.0396 | $X^1$ is chloro, $X^2$ is CH, $X^3$ is bromo | trifluoromethyl | trifluoromethyl | $Y^1$ is CH, $Y^2$ is CH, $Y^3$ is CH |
| P.0397 | $X^1$ is chloro, $X^2$ is CH, $X^3$ is bromo | chlorodifluoromethyl | bromo | $Y^1$ is CH, $Y^2$ is CH, $Y^3$ is CH |
| P.0398 | $X^1$ is chloro, $X^2$ is CH, $X^3$ is bromo | chlorodifluoromethyl | chloro | $Y^1$ is CH, $Y^2$ is CH, $Y^3$ is CH |
| P.0399 | $X^1$ is chloro, $X^2$ is CH, $X^3$ is bromo | chlorodifluoromethyl | cyano | $Y^1$ is CH, $Y^2$ is CH, $Y^3$ is CH |
| P.0400 | $X^1$ is chloro, $X^2$ is CH, $X^3$ is bromo | chlorodifluoromethyl | cyclopropyl | $Y^1$ is CH, $Y^2$ is CH, $Y^3$ is CH |
| P.0401 | $X^1$ is chloro, $X^2$ is CH, $X^3$ is bromo | chlorodifluoromethyl | ethyl | $Y^1$ is CH, $Y^2$ is CH, $Y^3$ is CH |
| P.0402 | $X^1$ is chloro, $X^2$ is CH, $X^3$ is bromo | chlorodifluoromethyl | fluoro | $Y^1$ is CH, $Y^2$ is CH, $Y^3$ is CH |
| P.0403 | $X^1$ is chloro, $X^2$ is CH, $X^3$ is bromo | chlorodifluoromethyl | hydrogen | $Y^1$ is CH, $Y^2$ is CH, $Y^3$ is CH |
| P.0404 | $X^1$ is chloro, $X^2$ is CH, $X^3$ is bromo | chlorodifluoromethyl | methoxy | $Y^1$ is CH, $Y^2$ is CH, $Y^3$ is CH |
| P.0405 | $X^1$ is chloro, $X^2$ is CH, $X^3$ is bromo | chlorodifluoromethyl | methyl | $Y^1$ is CH, $Y^2$ is CH, $Y^3$ is CH |
| P.0406 | $X^1$ is chloro, $X^2$ is CH, $X^3$ is bromo | chlorodifluoromethyl | nitro | $Y^1$ is CH, $Y^2$ is CH, $Y^3$ is CH |
| P.0407 | $X^1$ is chloro, $X^2$ is CH, $X^3$ is bromo | chlorodifluoromethyl | trifluoromethoxy | $Y^1$ is CH, $Y^2$ is CH, $Y^3$ is CH |
| P.0408 | $X^1$ is chloro, $X^2$ is CH, $X^3$ is bromo | chlorodifluoromethyl | trifluoromethyl | $Y^1$ is CH, $Y^2$ is CH, $Y^3$ is CH |
| P.0409 | $X^1$ is chloro, $X^2$ is CH, $X^3$ is bromo | difluoromethyl | bromo | $Y^1$ is CH, $Y^2$ is CH, $Y^3$ is CH |
| P.0410 | $X^1$ is chloro, $X^2$ is CH, $X^3$ is bromo | difluoromethyl | chloro | $Y^1$ is CH, $Y^2$ is CH, $Y^3$ is CH |
| P.0411 | $X^1$ is chloro, $X^2$ is CH, $X^3$ is bromo | difluoromethyl | cyano | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0412 | $X^1$ is chloro, $X^2$ is CH, $X^3$ is bromo | difluoromethyl | cyclopropyl | $Y^1$ is CH, $Y^2$ is CH, $Y^3$ is CH |
| P.0413 | $X^1$ is chloro, $X^2$ is CH, $X^3$ is bromo | difluoromethyl | ethyl | $Y^1$ is CH, $Y^2$ is CH, $Y^3$ is CH |
| P.0414 | $X^1$ is chloro, $X^2$ is CH, $X^3$ is bromo | difluoromethyl | fluoro | $Y^1$ is CH, $Y^2$ is CH, $Y^3$ is CH |
| P.0415 | $X^1$ is chloro, $X^2$ is CH, $X^3$ is bromo | difluoromethyl | hydrogen | $Y^1$ is CH, $Y^2$ is CH, $Y^3$ is CH |
| P.0416 | $X^1$ is chloro, $X^2$ is CH, $X^3$ is bromo | difluoromethyl | methoxy | $Y^1$ is CH, $Y^2$ is CH, $Y^3$ is CH |
| P.0417 | $X^1$ is chloro, $X^2$ is CH, $X^3$ is bromo | difluoromethyl | methyl | $Y^1$ is CH, $Y^2$ is CH, $Y^3$ is CH |
| P.0418 | $X^1$ is chloro, $X^2$ is CH, $X^3$ is bromo | difluoromethyl | nitro | $Y^1$ is CH, $Y^2$ is CH, $Y^3$ is CH |
| P.0419 | $X^1$ is chloro, $X^2$ is CH, $X^3$ is bromo | difluoromethyl | trifluoromethoxy | $Y^1$ is CH, $Y^2$ is CH, $Y^3$ is CH |
| P.0420 | $X^1$ is chloro, $X^2$ is CH, $X^3$ is bromo | difluoromethyl | trifluoromethyl | $Y^1$ is CH, $Y^2$ is CH, $Y^3$ is CH |
| P.0421 | $X^1$ is chloro, $X^2$ is CH, $X^3$ is bromo | trifluoromethyl | bromo | $Y^1$ is CH, $Y^2$ is CH, $Y^3$ is CH |
| P.0422 | $X^1$ is chloro, $X^2$ is CH, $X^3$ is bromo | trifluoromethyl | chloro | $Y^1$ is CH, $Y^2$ is CH, $Y^3$ is CH |
| P.0423 | $X^1$ is chloro, $X^2$ is CH, $X^3$ is bromo | trifluoromethyl | cyano | $Y^1$ is CH, $Y^2$ is CH, $Y^3$ is CH |
| P.0424 | $X^1$ is chloro, $X^2$ is CH, $X^3$ is bromo | trifluoromethyl | cyclopropyl | $Y^1$ is CH, $Y^2$ is CH, $Y^3$ is CH |
| P.0425 | $X^1$ is chloro, $X^2$ is CH, $X^3$ is bromo | trifluoromethyl | ethyl | $Y^1$ is CH, $Y^2$ is CH, $Y^3$ is CH |
| P.0426 | $X^1$ is chloro, $X^2$ is CH, $X^3$ is bromo | trifluoromethyl | fluoro | $Y^1$ is CH, $Y^2$ is CH, $Y^3$ is CH |
| P.0427 | $X^1$ is chloro, $X^2$ is CH, $X^3$ is bromo | trifluoromethyl | hydrogen | $Y^1$ is CH, $Y^2$ is CH, $Y^3$ is CH |
| P.0428 | $X^1$ is chloro, $X^2$ is CH, $X^3$ is bromo | trifluoromethyl | methoxy | $Y^1$ is CH, $Y^2$ is CH, $Y^3$ is CH |
| P.0429 | $X^1$ is chloro, $X^2$ is CH, $X^3$ is bromo | trifluoromethyl | methyl | $Y^1$ is CH, $Y^2$ is CH, $Y^3$ is CH |
| P.0430 | $X^1$ is chloro, $X^2$ is CH, $X^3$ is bromo | trifluoromethyl | nitro | $Y^1$ is CH, $Y^2$ is CH, $Y^3$ is CH |
| P.0431 | $X^1$ is chloro, $X^2$ is CH, $X^3$ is bromo | trifluoromethyl | trifluoromethoxy | $Y^1$ is CH, $Y^2$ is CH, $Y^3$ is CH |
| P.0432 | $X^1$ is chloro, $X^2$ is CH, $X^3$ is bromo | trifluoromethyl | trifluoromethyl | $Y^1$ is CH, $Y^2$ is CH, $Y^3$ is CH |
| P.0433 | $X^1$ is chloro, $X^2$ is C—Cl, $X^3$ is trifluoromethyl | chlorodifluoromethyl | bromo | $Y^1$ is CH, $Y^2$ is CH, $Y^3$ is CH |
| P.0434 | $X^1$ is chloro, $X^2$ is C—Cl, $X^3$ is trifluoromethyl | chlorodifluoromethyl | chloro | $Y^1$ is CH, $Y^2$ is CH, $Y^3$ is CH |
| P.0435 | $X^1$ is chloro, $X^2$ is C—Cl, $X^3$ is trifluoromethyl | chlorodifluoromethyl | cyano | $Y^1$ is CH, $Y^2$ is CH, $Y^3$ is CH |
| P.0436 | $X^1$ is chloro, $X^2$ is C—Cl, $X^3$ is trifluoromethyl | chlorodifluoromethyl | cyclopropyl | $Y^1$ is CH, $Y^2$ is CH, $Y^3$ is CH |
| P.0437 | $X^1$ is chloro, $X^2$ is C—Cl, $X^3$ is trifluoromethyl | chlorodifluoromethyl | ethyl | $Y^1$ is CH, $Y^2$ is CH, $Y^3$ is CH |
| P.0438 | $X^1$ is chloro, $X^2$ is C—Cl, $X^3$ is trifluoromethyl | chlorodifluoromethyl | fluoro | $Y^1$ is CH, $Y^2$ is CH, $Y^3$ is CH |
| P.0439 | $X^1$ is chloro, $X^2$ is C—Cl, $X^3$ is trifluoromethyl | chlorodifluoromethyl | hydrogen | $Y^1$ is CH, $Y^2$ is CH, $Y^3$ is CH |
| P.0440 | $X^1$ is chloro, $X^2$ is C—Cl, $X^3$ is trifluoromethyl | chlorodifluoromethyl | methoxy | $Y^1$ is CH, $Y^2$ is CH, $Y^3$ is CH |
| P.0441 | $X^1$ is chloro, $X^2$ is C—Cl, $X^3$ is trifluoromethyl | chlorodifluoromethyl | methyl | $Y^1$ is CH, $Y^2$ is CH, $Y^3$ is CH |
| P.0442 | $X^1$ is chloro, $X^2$ is C—Cl, $X^3$ is trifluoromethyl | chlorodifluoromethyl | nitro | $Y^1$ is CH, $Y^2$ is CH, $Y^3$ is CH |
| P.0443 | $X^1$ is chloro, $X^2$ is C—Cl, $X^3$ is trifluoromethyl | chlorodifluoromethyl | trifluoromethoxy | $Y^1$ is CH, $Y^2$ is CH, $Y^3$ is CH |
| P.0444 | $X^1$ is chloro, $X^2$ is C—Cl, $X^3$ is trifluoromethyl | chlorodifluoromethyl | trifluoromethyl | $Y^1$ is CH, $Y^2$ is CH, $Y^3$ is CH |
| P.0445 | $X^1$ is chloro, $X^2$ is C—Cl, $X^3$ is trifluoromethyl | difluoromethyl | bromo | $Y^1$ is CH, $Y^2$ is CH, $Y^3$ is CH |
| P.0446 | $X^1$ is chloro, $X^2$ is C—Cl, $X^3$ is trifluoromethyl | difluoromethyl | chloro | $Y^1$ is CH, $Y^2$ is CH, $Y^3$ is CH |
| P.0447 | $X^1$ is chloro, $X^2$ is C—Cl, $X^3$ is trifluoromethyl | difluoromethyl | cyano | $Y^1$ is CH, $Y^2$ is CH, $Y^3$ is CH |
| P.0448 | $X^1$ is chloro, $X^2$ is C—Cl, $X^3$ is trifluoromethyl | difluoromethyl | cyclopropyl | $Y^1$ is CH, $Y^2$ is CH, $Y^3$ is CH |
| P.0449 | $X^1$ is chloro, $X^2$ is C—Cl, $X^3$ is trifluoromethyl | difluoromethyl | ethyl | $Y^1$ is CH, $Y^2$ is CH, $Y^3$ is CH |
| P.0450 | $X^1$ is chloro, $X^2$ is C—Cl, $X^3$ is trifluoromethyl | difluoromethyl | fluoro | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0451 | $X^1$ is chloro, $X^2$ is C—Cl, $X^3$ is trifluoromethyl | difluoromethyl | hydrogen | $Y^1$ is CH, $Y^2$ is CH, $Y^3$ is CH |
| P.0452 | $X^1$ is chloro, $X^2$ is C—Cl, $X^3$ is trifluoromethyl | difluoromethyl | methoxy | $Y^1$ is CH, $Y^2$ is CH, $Y^3$ is CH |
| P.0453 | $X^1$ is chloro, $X^2$ is C—Cl, $X^3$ is trifluoromethyl | difluoromethyl | methyl | $Y^1$ is CH, $Y^2$ is CH, $Y^3$ is CH |
| P.0454 | $X^1$ is chloro, $X^2$ is C—Cl, $X^3$ is trifluoromethyl | difluoromethyl | nitro | $Y^1$ is CH, $Y^2$ is CH, $Y^3$ is CH |
| P.0455 | $X^1$ is chloro, $X^2$ is C—Cl, $X^3$ is trifluoromethyl | difluoromethyl | trifluoromethoxy | $Y^1$ is CH, $Y^2$ is CH, $Y^3$ is CH |
| P.0456 | $X^1$ is chloro, $X^2$ is C—Cl, $X^3$ is trifluoromethyl | difluoromethyl | trifluoromethyl | $Y^1$ is CH, $Y^2$ is CH, $Y^3$ is CH |
| P.0457 | $X^1$ is chloro, $X^2$ is C—Cl, $X^3$ is trifluoromethyl | trifluoromethyl | bromo | $Y^1$ is CH, $Y^2$ is CH, $Y^3$ is CH |
| P.0458 | $X^1$ is chloro, $X^2$ is C—Cl, $X^3$ is trifluoromethyl | trifluoromethyl | chloro | $Y^1$ is CH, $Y^2$ is CH, $Y^3$ is CH |
| P.0459 | $X^1$ is chloro, $X^2$ is C—Cl, $X^3$ is trifluoromethyl | trifluoromethyl | cyano | $Y^1$ is CH, $Y^2$ is CH, $Y^3$ is CH |
| P.0460 | $X^1$ is chloro, $X^2$ is C—Cl, $X^3$ is trifluoromethyl | trifluoromethyl | cyclopropyl | $Y^1$ is CH, $Y^2$ is CH, $Y^3$ is CH |
| P.0461 | $X^1$ is chloro, $X^2$ is C—Cl, $X^3$ is trifluoromethyl | trifluoromethyl | ethyl | $Y^1$ is CH, $Y^2$ is CH, $Y^3$ is CH |
| P.0462 | $X^1$ is chloro, $X^2$ is C—Cl, $X^3$ is trifluoromethyl | trifluoromethyl | fluoro | $Y^1$ is CH, $Y^2$ is CH, $Y^3$ is CH |
| P.0463 | $X^1$ is chloro, $X^2$ is C—Cl, $X^3$ is trifluoromethyl | trifluoromethyl | hydrogen | $Y^1$ is CH, $Y^2$ is CH, $Y^3$ is CH |
| P.0464 | $X^1$ is chloro, $X^2$ is C—Cl, $X^3$ is trifluoromethyl | trifluoromethyl | methoxy | $Y^1$ is CH, $Y^2$ is CH, $Y^3$ is CH |
| P.0465 | $X^1$ is chloro, $X^2$ is C—Cl, $X^3$ is trifluoromethyl | trifluoromethyl | methyl | $Y^1$ is CH, $Y^2$ is CH, $Y^3$ is CH |
| P.0466 | $X^1$ is chloro, $X^2$ is C—Cl, $X^3$ is trifluoromethyl | trifluoromethyl | nitro | $Y^1$ is CH, $Y^2$ is CH, $Y^3$ is CH |
| P.0467 | $X^1$ is chloro, $X^2$ is C—Cl, $X^3$ is trifluoromethyl | trifluoromethyl | trifluoromethoxy | $Y^1$ is CH, $Y^2$ is CH, $Y^3$ is CH |
| P.0468 | $X^1$ is chloro, $X^2$ is C—Cl, $X^3$ is trifluoromethyl | trifluoromethyl | trifluoromethyl | $Y^1$ is CH, $Y^2$ is CH, $Y^3$ is CH |
| P.0469 | $X^1$ is trifluoromethyl, $X^2$ is CH, $X^3$ is trifluoromethyl | chlorodifluoromethyl | bromo | $Y^1$ is CH, $Y^2$ is CH, $Y^3$ is CH |
| P.0470 | $X^1$ is trifluoromethyl, $X^2$ is CH, $X^3$ is trifluoromethyl | chlorodifluoromethyl | chloro | $Y^1$ is CH, $Y^2$ is CH, $Y^3$ is CH |
| P.0471 | $X^1$ is trifluoromethyl, $X^2$ is CH, $X^3$ is trifluoromethyl | chlorodifluoromethyl | cyano | $Y^1$ is CH, $Y^2$ is CH, $Y^3$ is CH |
| P.0472 | $X^1$ is trifluoromethyl, $X^2$ is CH, $X^3$ is trifluoromethyl | chlorodifluoromethyl | cyclopropyl | $Y^1$ is CH, $Y^2$ is CH, $Y^3$ is CH |
| P.0473 | $X^1$ is trifluoromethyl, $X^2$ is CH, $X^3$ is trifluoromethyl | chlorodifluoromethyl | ethyl | $Y^1$ is CH, $Y^2$ is CH, $Y^3$ is CH |
| P.0474 | $X^1$ is trifluoromethyl, $X^2$ is CH, $X^3$ is trifluoromethyl | chlorodifluoromethyl | fluoro | $Y^1$ is CH, $Y^2$ is CH, $Y^3$ is CH |
| P.0475 | $X^1$ is trifluoromethyl, $X^2$ is CH, $X^3$ is trifluoromethyl | chlorodifluoromethyl | hydrogen | $Y^1$ is CH, $Y^2$ is CH, $Y^3$ is CH |
| P.0476 | $X^1$ is trifluoromethyl, $X^2$ is CH, $X^3$ is trifluoromethyl | chlorodifluoromethyl | methoxy | $Y^1$ is CH, $Y^2$ is CH, $Y^3$ is CH |
| P.0477 | $X^1$ is trifluoromethyl, $X^2$ is CH, $X^3$ is trifluoromethyl | chlorodifluoromethyl | methyl | $Y^1$ is CH, $Y^2$ is CH, $Y^3$ is CH |
| P.0478 | $X^1$ is trifluoromethyl, $X^2$ is CH, $X^3$ is trifluoromethyl | chlorodifluoromethyl | nitro | $Y^1$ is CH, $Y^2$ is CH, $Y^3$ is CH |
| P.0479 | $X^1$ is trifluoromethyl, $X^2$ is CH, $X^3$ is trifluoromethyl | chlorodifluoromethyl | trifluoromethoxy | $Y^1$ is CH, $Y^2$ is CH, $Y^3$ is CH |
| P.0480 | $X^1$ is trifluoromethyl, $X^2$ is CH, $X^3$ is trifluoromethyl | chlorodifluoromethyl | trifluoromethyl | $Y^1$ is CH, $Y^2$ is CH, $Y^3$ is CH |
| P.0481 | $X^1$ is trifluoromethyl, $X^2$ is CH, $X^3$ is trifluoromethyl | difluoromethyl | bromo | $Y^1$ is CH, $Y^2$ is CH, $Y^3$ is CH |
| P.0482 | $X^1$ is trifluoromethyl, $X^2$ is CH, $X^3$ is trifluoromethyl | difluoromethyl | chloro | $Y^1$ is CH, $Y^2$ is CH, $Y^3$ is CH |
| P.0483 | $X^1$ is trifluoromethyl, $X^2$ is CH, $X^3$ is trifluoromethyl | difluoromethyl | cyano | $Y^1$ is CH, $Y^2$ is CH, $Y^3$ is CH |
| P.0484 | $X^1$ is trifluoromethyl, $X^2$ is CH, $X^3$ is trifluoromethyl | difluoromethyl | cyclopropyl | $Y^1$ is CH, $Y^2$ is CH, $Y^3$ is CH |
| P.0485 | $X^1$ is trifluoromethyl, $X^2$ is CH, $X^3$ is trifluoromethyl | difluoromethyl | ethyl | $Y^1$ is CH, $Y^2$ is CH, $Y^3$ is CH |
| P.0486 | $X^1$ is trifluoromethyl, $X^2$ is CH, $X^3$ is trifluoromethyl | difluoromethyl | fluoro | $Y^1$ is CH, $Y^2$ is CH, $Y^3$ is CH |
| P.0487 | $X^1$ is trifluoromethyl, $X^2$ is CH, $X^3$ is trifluoromethyl | difluoromethyl | hydrogen | $Y^1$ is CH, $Y^2$ is CH, $Y^3$ is CH |
| P.0488 | $X^1$ is trifluoromethyl, $X^2$ is CH, $X^3$ is trifluoromethyl | difluoromethyl | methoxy | $Y^1$ is CH, $Y^2$ is CH, $Y^3$ is CH |
| P.0489 | $X^1$ is trifluoromethyl, $X^2$ is CH, $X^3$ is trifluoromethyl | difluoromethyl | methyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0490 | $X^1$ is trifluoromethyl, $X^2$ is CH, $X^3$ is trifluoromethyl | difluoromethyl | nitro | $Y^1$ is CH, $Y^2$ is CH, $Y^3$ is CH |
| P.0491 | $X^1$ is trifluoromethyl, $X^2$ is CH, $X^3$ is trifluoromethyl | difluoromethyl | trifluoromethoxy | $Y^1$ is CH, $Y^2$ is CH, $Y^3$ is CH |
| P.0492 | $X^1$ is trifluoromethyl, $X^2$ is CH, $X^3$ is trifluoromethyl | difluoromethyl | trifluoromethyl | $Y^1$ is CH, $Y^2$ is CH, $Y^3$ is CH |
| P.0493 | $X^1$ is trifluoromethyl, $X^2$ is CH, $X^3$ is trifluoromethyl | trifluoromethyl | bromo | $Y^1$ is CH, $Y^2$ is CH, $Y^3$ is CH |
| P.0494 | $X^1$ is trifluoromethyl, $X^2$ is CH, $X^3$ is trifluoromethyl | trifluoromethyl | chloro | $Y^1$ is CH, $Y^2$ is CH, $Y^3$ is CH |
| P.0495 | $X^1$ is trifluoromethyl, $X^2$ is CH, $X^3$ is trifluoromethyl | trifluoromethyl | cyano | $Y^1$ is CH, $Y^2$ is CH, $Y^3$ is CH |
| P.0496 | $X^1$ is trifluoromethyl, $X^2$ is CH, $X^3$ is trifluoromethyl | trifluoromethyl | cyclopropyl | $Y^1$ is CH, $Y^2$ is CH, $Y^3$ is CH |
| P.0497 | $X^1$ is trifluoromethyl, $X^2$ is CH, $X^3$ is trifluoromethyl | trifluoromethyl | ethyl | $Y^1$ is CH, $Y^2$ is CH, $Y^3$ is CH |
| P.0498 | $X^1$ is trifluoromethyl, $X^2$ is CH, $X^3$ is trifluoromethyl | trifluoromethyl | fluoro | $Y^1$ is CH, $Y^2$ is CH, $Y^3$ is CH |
| P.0499 | $X^1$ is trifluoromethyl, $X^2$ is CH, $X^3$ is trifluoromethyl | trifluoromethyl | hydrogen | $Y^1$ is CH, $Y^2$ is CH, $Y^3$ is CH |
| P.0500 | $X^1$ is trifluoromethyl, $X^2$ is CH, $X^3$ is trifluoromethyl | trifluoromethyl | methoxy | $Y^1$ is CH, $Y^2$ is CH, $Y^3$ is CH |
| P.0501 | $X^1$ is trifluoromethyl, $X^2$ is CH, $X^3$ is trifluoromethyl | trifluoromethyl | methyl | $Y^1$ is CH, $Y^2$ is CH, $Y^3$ is CH |
| P.0502 | $X^1$ is trifluoromethyl, $X^2$ is CH, $X^3$ is trifluoromethyl | trifluoromethyl | nitro | $Y^1$ is CH, $Y^2$ is CH, $Y^3$ is CH |
| P.0503 | $X^1$ is trifluoromethyl, $X^2$ is CH, $X^3$ is trifluoromethyl | trifluoromethyl | trifluoromethoxy | $Y^1$ is CH, $Y^2$ is CH, $Y^3$ is CH |
| P.0504 | $X^1$ is trifluoromethyl, $X^2$ is CH, $X^3$ is trifluoromethyl | trifluoromethyl | trifluoromethyl | $Y^1$ is CH, $Y^2$ is CH, $Y^3$ is CH |
| P.0505 | $X^1$ is trifluoromethyl, $X^2$ is CH, $X^3$ is trifluoromethyl | chlorodifluoromethyl | bromo | $Y^1$ is CH, $Y^2$ is CH, $Y^3$ is CH |
| P.0506 | $X^1$ is trifluoromethyl, $X^2$ is CH, $X^3$ is trifluoromethyl | chlorodifluoromethyl | chloro | $Y^1$ is CH, $Y^2$ is CH, $Y^3$ is CH |
| P.0507 | $X^1$ is trifluoromethyl, $X^2$ is CH, $X^3$ is trifluoromethyl | chlorodifluoromethyl | cyano | $Y^1$ is CH, $Y^2$ is CH, $Y^3$ is CH |
| P.0508 | $X^1$ is trifluoromethyl, $X^2$ is CH, $X^3$ is trifluoromethyl | chlorodifluoromethyl | cyclopropyl | $Y^1$ is CH, $Y^2$ is CH, $Y^3$ is CH |
| P.0509 | $X^1$ is trifluoromethyl, $X^2$ is CH, $X^3$ is trifluoromethyl | chlorodifluoromethyl | ethyl | $Y^1$ is CH, $Y^2$ is CH, $Y^3$ is CH |
| P.0510 | $X^1$ is trifluoromethyl, $X^2$ is CH, $X^3$ is trifluoromethyl | chlorodifluoromethyl | fluoro | $Y^1$ is CH, $Y^2$ is CH, $Y^3$ is CH |
| P.0511 | $X^1$ is trifluoromethyl, $X^2$ is CH, $X^3$ is trifluoromethyl | chlorodifluoromethyl | hydrogen | $Y^1$ is CH, $Y^2$ is CH, $Y^3$ is CH |
| P.0512 | $X^1$ is trifluoromethyl, $X^2$ is CH, $X^3$ is trifluoromethyl | chlorodifluoromethyl | methoxy | $Y^1$ is CH, $Y^2$ is CH, $Y^3$ is CH |
| P.0513 | $X^1$ is trifluoromethyl, $X^2$ is CH, $X^3$ is trifluoromethyl | chlorodifluoromethyl | methyl | $Y^1$ is CH, $Y^2$ is CH, $Y^3$ is CH |
| P.0514 | $X^1$ is trifluoromethyl, $X^2$ is CH, $X^3$ is trifluoromethyl | chlorodifluoromethyl | nitro | $Y^1$ is CH, $Y^2$ is CH, $Y^3$ is CH |
| P.0515 | $X^1$ is trifluoromethyl, $X^2$ is CH, $X^3$ is trifluoromethyl | chlorodifluoromethyl | trifluoromethoxy | $Y^1$ is CH, $Y^2$ is CH, $Y^3$ is CH |
| P.0516 | $X^1$ is trifluoromethyl, $X^2$ is CH, $X^3$ is trifluoromethyl | chlorodifluoromethyl | trifluoromethyl | $Y^1$ is CH, $Y^2$ is CH, $Y^3$ is CH |
| P.0517 | $X^1$ is trifluoromethyl, $X^2$ is CH, $X^3$ is trifluoromethyl | difluoromethyl | bromo | $Y^1$ is CH, $Y^2$ is CH, $Y^3$ is CH |
| P.0518 | $X^1$ is trifluoromethyl, $X^2$ is CH, $X^3$ is trifluoromethyl | difluoromethyl | chloro | $Y^1$ is CH, $Y^2$ is CH, $Y^3$ is CH |
| P.0519 | $X^1$ is trifluoromethyl, $X^2$ is CH, $X^3$ is trifluoromethyl | difluoromethyl | cyano | $Y^1$ is CH, $Y^2$ is CH, $Y^3$ is CH |
| P.0520 | $X^1$ is trifluoromethyl, $X^2$ is CH, $X^3$ is trifluoromethyl | difluoromethyl | cyclopropyl | $Y^1$ is CH, $Y^2$ is CH, $Y^3$ is CH |
| P.0521 | $X^1$ is trifluoromethyl, $X^2$ is CH, $X^3$ is trifluoromethyl | difluoromethyl | ethyl | $Y^1$ is CH, $Y^2$ is CH, $Y^3$ is CH |
| P.0522 | $X^1$ is trifluoromethyl, $X^2$ is CH, $X^3$ is trifluoromethyl | difluoromethyl | fluoro | $Y^1$ is CH, $Y^2$ is CH, $Y^3$ is CH |
| P.0523 | $X^1$ is trifluoromethyl, $X^2$ is CH, $X^3$ is trifluoromethyl | difluoromethyl | hydrogen | $Y^1$ is CH, $Y^2$ is CH, $Y^3$ is CH |
| P.0524 | $X^1$ is trifluoromethyl, $X^2$ is CH, $X^3$ is trifluoromethyl | difluoromethyl | methoxy | $Y^1$ is CH, $Y^2$ is CH, $Y^3$ is CH |
| P.0525 | $X^1$ is trifluoromethyl, $X^2$ is CH, $X^3$ is trifluoromethyl | difluoromethyl | methyl | $Y^1$ is CH, $Y^2$ is CH, $Y^3$ is CH |
| P.0526 | $X^1$ is trifluoromethyl, $X^2$ is CH, $X^3$ is trifluoromethyl | difluoromethyl | nitro | $Y^1$ is CH, $Y^2$ is CH, $Y^3$ is CH |
| P.0527 | $X^1$ is trifluoromethyl, $X^2$ is CH, $X^3$ is trifluoromethyl | difluoromethyl | trifluoromethoxy | $Y^1$ is CH, $Y^2$ is CH, $Y^3$ is CH |
| P.0528 | $X^1$ is trifluoromethyl, $X^2$ is CH, $X^3$ is trifluoromethyl | difluoromethyl | trifluoromethyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0529 | $X^1$ is trifluoromethyl, $X^2$ is CH, $X^3$ is trifluoromethyl | trifluoromethyl | bromo | $Y^1$ is CH, $Y^2$ is CH, $Y^3$ is CH |
| P.0530 | $X^1$ is trifluoromethyl, $X^2$ is CH, $X^3$ is trifluoromethyl | trifluoromethyl | chloro | $Y^1$ is CH, $Y^2$ is CH, $Y^3$ is CH |
| P.0531 | $X^1$ is trifluoromethyl, $X^2$ is CH, $X^3$ is trifluoromethyl | trifluoromethyl | cyano | $Y^1$ is CH, $Y^2$ is CH, $Y^3$ is CH |
| P.0532 | $X^1$ is trifluoromethyl, $X^2$ is CH, $X^3$ is trifluoromethyl | trifluoromethyl | cyclopropyl | $Y^1$ is CH, $Y^2$ is CH, $Y^3$ is CH |
| P.0533 | $X^1$ is trifluoromethyl, $X^2$ is CH, $X^3$ is trifluoromethyl | trifluoromethyl | ethyl | $Y^1$ is CH, $Y^2$ is CH, $Y^3$ is CH |
| P.0534 | $X^1$ is trifluoromethyl, $X^2$ is CH, $X^3$ is trifluoromethyl | trifluoromethyl | fluoro | $Y^1$ is CH, $Y^2$ is CH, $Y^3$ is CH |
| P.0535 | $X^1$ is trifluoromethyl, $X^2$ is CH, $X^3$ is trifluoromethyl | trifluoromethyl | hydrogen | $Y^1$ is CH, $Y^2$ is CH, $Y^3$ is CH |
| P.0536 | $X^1$ is trifluoromethyl, $X^2$ is CH, $X^3$ is trifluoromethyl | trifluoromethyl | methoxy | $Y^1$ is CH, $Y^2$ is CH, $Y^3$ is CH |
| P.0537 | $X^1$ is trifluoromethyl, $X^2$ is CH, $X^3$ is trifluoromethyl | trifluoromethyl | methyl | $Y^1$ is CH, $Y^2$ is CH, $Y^3$ is CH |
| P.0538 | $X^1$ is trifluoromethyl, $X^2$ is CH, $X^3$ is trifluoromethyl | trifluoromethyl | nitro | $Y^1$ is CH, $Y^2$ is CH, $Y^3$ is CH |
| P.0539 | $X^1$ is trifluoromethyl, $X^2$ is CH, $X^3$ is trifluoromethyl | trifluoromethyl | trifluoromethoxy | $Y^1$ is CH, $Y^2$ is CH, $Y^3$ is CH |
| P.0540 | $X^1$ is trifluoromethyl, $X^2$ is CH, $X^3$ is trifluoromethyl | trifluoromethyl | trifluoromethyl | $Y^1$ is CH, $Y^2$ is CH, $Y^3$ is CH |
| P.0541 | $X^1$ is trifluoromethyl, $X^2$ is CH, $X^3$ is hydrogen | chlorodifluoromethyl | bromo | $Y^1$ is CH, $Y^2$ is CH, $Y^3$ is CH |
| P.0542 | $X^1$ is trifluoromethyl, $X^2$ is CH, $X^3$ is hydrogen | chlorodifluoromethyl | chloro | $Y^1$ is CH, $Y^2$ is CH, $Y^3$ is CH |
| P.0543 | $X^1$ is trifluoromethyl, $X^2$ is CH, $X^3$ is hydrogen | chlorodifluoromethyl | cyano | $Y^1$ is CH, $Y^2$ is CH, $Y^3$ is CH |
| P.0544 | $X^1$ is trifluoromethyl, $X^2$ is CH, $X^3$ is hydrogen | chlorodifluoromethyl | cyclopropyl | $Y^1$ is CH, $Y^2$ is CH, $Y^3$ is CH |
| P.0545 | $X^1$ is trifluoromethyl, $X^2$ is CH, $X^3$ is hydrogen | chlorodifluoromethyl | ethyl | $Y^1$ is CH, $Y^2$ is CH, $Y^3$ is CH |
| P.0546 | $X^1$ is trifluoromethyl, $X^2$ is CH, $X^3$ is hydrogen | chlorodifluoromethyl | fluoro | $Y^1$ is CH, $Y^2$ is CH, $Y^3$ is CH |
| P.0547 | $X^1$ is trifluoromethyl, $X^2$ is CH, $X^3$ is hydrogen | chlorodifluoromethyl | hydrogen | $Y^1$ is CH, $Y^2$ is CH, $Y^3$ is CH |
| P.0548 | $X^1$ is trifluoromethyl, $X^2$ is CH, $X^3$ is hydrogen | chlorodifluoromethyl | methoxy | $Y^1$ is CH, $Y^2$ is CH, $Y^3$ is CH |
| P.0549 | $X^1$ is trifluoromethyl, $X^2$ is CH, $X^3$ is hydrogen | chlorodifluoromethyl | methyl | $Y^1$ is CH, $Y^2$ is CH, $Y^3$ is CH |
| P.0550 | $X^1$ is trifluoromethyl, $X^2$ is CH, $X^3$ is hydrogen | chlorodifluoromethyl | nitro | $Y^1$ is CH, $Y^2$ is CH, $Y^3$ is CH |
| P.0551 | $X^1$ is trifluoromethyl, $X^2$ is CH, $X^3$ is hydrogen | chlorodifluoromethyl | trifluoromethoxy | $Y^1$ is CH, $Y^2$ is CH, $Y^3$ is CH |
| P.0552 | $X^1$ is trifluoromethyl, $X^2$ is CH, $X^3$ is hydrogen | chlorodifluoromethyl | trifluoromethyl | $Y^1$ is CH, $Y^2$ is CH, $Y^3$ is CH |
| P.0553 | $X^1$ is trifluoromethyl, $X^2$ is CH, $X^3$ is hydrogen | difluoromethyl | bromo | $Y^1$ is CH, $Y^2$ is CH, $Y^3$ is CH |
| P.0554 | $X^1$ is trifluoromethyl, $X^2$ is CH, $X^3$ is hydrogen | difluoromethyl | chloro | $Y^1$ is CH, $Y^2$ is CH, $Y^3$ is CH |
| P.0555 | $X^1$ is trifluoromethyl, $X^2$ is CH, $X^3$ is hydrogen | difluoromethyl | cyano | $Y^1$ is CH, $Y^2$ is CH, $Y^3$ is CH |
| P.0556 | $X^1$ is trifluoromethyl, $X^2$ is CH, $X^3$ is hydrogen | difluoromethyl | cyclopropyl | $Y^1$ is CH, $Y^2$ is CH, $Y^3$ is CH |
| P.0557 | $X^1$ is trifluoromethyl, $X^2$ is CH, $X^3$ is hydrogen | difluoromethyl | ethyl | $Y^1$ is CH, $Y^2$ is CH, $Y^3$ is CH |
| P.0558 | $X^1$ is trifluoromethyl, $X^2$ is CH, $X^3$ is hydrogen | difluoromethyl | fluoro | $Y^1$ is CH, $Y^2$ is CH, $Y^3$ is CH |
| P.0559 | $X^1$ is trifluoromethyl, $X^2$ is CH, $X^3$ is hydrogen | difluoromethyl | hydrogen | $Y^1$ is CH, $Y^2$ is CH, $Y^3$ is CH |
| P.0560 | $X^1$ is trifluoromethyl, $X^2$ is CH, $X^3$ is hydrogen | difluoromethyl | methoxy | $Y^1$ is CH, $Y^2$ is CH, $Y^3$ is CH |
| P.0561 | $X^1$ is trifluoromethyl, $X^2$ is CH, $X^3$ is hydrogen | difluoromethyl | methyl | $Y^1$ is CH, $Y^2$ is CH, $Y^3$ is CH |
| P.0562 | $X^1$ is trifluoromethyl, $X^2$ is CH, $X^3$ is hydrogen | difluoromethyl | nitro | $Y^1$ is CH, $Y^2$ is CH, $Y^3$ is CH |
| P.0563 | $X^1$ is trifluoromethyl, $X^2$ is CH, $X^3$ is hydrogen | difluoromethyl | trifluoromethoxy | $Y^1$ is CH, $Y^2$ is CH, $Y^3$ is CH |
| P.0564 | $X^1$ is trifluoromethyl, $X^2$ is CH, $X^3$ is hydrogen | difluoromethyl | trifluoromethyl | $Y^1$ is CH, $Y^2$ is CH, $Y^3$ is CH |
| P.0565 | $X^1$ is trifluoromethyl, $X^2$ is CH, $X^3$ is hydrogen | trifluoromethyl | bromo | $Y^1$ is CH, $Y^2$ is CH, $Y^3$ is CH |
| P.0566 | $X^1$ is trifluoromethyl, $X^2$ is CH, $X^3$ is hydrogen | trifluoromethyl | chloro | $Y^1$ is CH, $Y^2$ is CH, $Y^3$ is CH |
| P.0567 | $X^1$ is trifluoromethyl, $X^2$ is CH, $X^3$ is hydrogen | trifluoromethyl | cyano | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0568 | $X^1$ is trifluoromethyl, $X^2$ is CH, $X^3$ is hydrogen | trifluoromethyl | cyclopropyl | $Y^1$ is CH, $Y^2$ is CH, $Y^3$ is CH |
| P.0569 | $X^1$ is trifluoromethyl, $X^2$ is CH, $X^3$ is hydrogen | trifluoromethyl | ethyl | $Y^1$ is CH, $Y^2$ is CH, $Y^3$ is CH |
| P.0570 | $X^1$ is trifluoromethyl, $X^2$ is CH, $X^3$ is hydrogen | trifluoromethyl | fluoro | $Y^1$ is CH, $Y^2$ is CH, $Y^3$ is CH |
| P.0571 | $X^1$ is trifluoromethyl, $X^2$ is CH, $X^3$ is hydrogen | trifluoromethyl | hydrogen | $Y^1$ is CH, $Y^2$ is CH, $Y^3$ is CH |
| P.0572 | $X^1$ is trifluoromethyl, $X^2$ is CH, $X^3$ is hydrogen | trifluoromethyl | methoxy | $Y^1$ is CH, $Y^2$ is CH, $Y^3$ is CH |
| P.0573 | $X^1$ is trifluoromethyl, $X^2$ is CH, $X^3$ is hydrogen | trifluoromethyl | methyl | $Y^1$ is CH, $Y^2$ is CH, $Y^3$ is CH |
| P.0574 | $X^1$ is trifluoromethyl, $X^2$ is CH, $X^3$ is hydrogen | trifluoromethyl | nitro | $Y^1$ is CH, $Y^2$ is CH, $Y^3$ is CH |
| P.0575 | $X^1$ is trifluoromethyl, $X^2$ is CH, $X^3$ is hydrogen | trifluoromethyl | trifluoromethoxy | $Y^1$ is CH, $Y^2$ is CH, $Y^3$ is CH |
| P.0576 | $X^1$ is trifluoromethyl, $X^2$ is CH, $X^3$ is hydrogen | trifluoromethyl | trifluoromethyl | $Y^1$ is CH, $Y^2$ is CH, $Y^3$ is CH |
| P.0577 | $X^1$ is chloro, $X^2$ is N, $X^3$ is chloro | chlorodifluoromethyl | bromo | $Y^1$ is CH, $Y^2$ is CH, $Y^3$ is CH |
| P.0578 | $X^1$ is chloro, $X^2$ is N, $X^3$ is chloro | chlorodifluoromethyl | chloro | $Y^1$ is CH, $Y^2$ is CH, $Y^3$ is CH |
| P.0579 | $X^1$ is chloro, $X^2$ is N, $X^3$ is chloro | chlorodifluoromethyl | cyano | $Y^1$ is CH, $Y^2$ is CH, $Y^3$ is CH |
| P.0580 | $X^1$ is chloro, $X^2$ is N, $X^3$ is chloro | chlorodifluoromethyl | cyclopropyl | $Y^1$ is CH, $Y^2$ is CH, $Y^3$ is CH |
| P.0581 | $X^1$ is chloro, $X^2$ is N, $X^3$ is chloro | chlorodifluoromethyl | ethyl | $Y^1$ is CH, $Y^2$ is CH, $Y^3$ is CH |
| P.0582 | $X^1$ is chloro, $X^2$ is N, $X^3$ is chloro | chlorodifluoromethyl | fluoro | $Y^1$ is CH, $Y^2$ is CH, $Y^3$ is CH |
| P.0583 | $X^1$ is chloro, $X^2$ is N, $X^3$ is chloro | chlorodifluoromethyl | hydrogen | $Y^1$ is CH, $Y^2$ is CH, $Y^3$ is CH |
| P.0584 | $X^1$ is chloro, $X^2$ is N, $X^3$ is chloro | chlorodifluoromethyl | methoxy | $Y^1$ is CH, $Y^2$ is CH, $Y^3$ is CH |
| P.0585 | $X^1$ is chloro, $X^2$ is N, $X^3$ is chloro | chlorodifluoromethyl | methyl | $Y^1$ is CH, $Y^2$ is CH, $Y^3$ is CH |
| P.0586 | $X^1$ is chloro, $X^2$ is N, $X^3$ is chloro | chlorodifluoromethyl | nitro | $Y^1$ is CH, $Y^2$ is CH, $Y^3$ is CH |
| P.0587 | $X^1$ is chloro, $X^2$ is N, $X^3$ is chloro | chlorodifluoromethyl | trifluoromethoxy | $Y^1$ is CH, $Y^2$ is CH, $Y^3$ is CH |
| P.0588 | $X^1$ is chloro, $X^2$ is N, $X^3$ is chloro | chlorodifluoromethyl | trifluoromethyl | $Y^1$ is CH, $Y^2$ is CH, $Y^3$ is CH |
| P.0589 | $X^1$ is chloro, $X^2$ is N, $X^3$ is chloro | difluoromethyl | bromo | $Y^1$ is CH, $Y^2$ is CH, $Y^3$ is CH |
| P.0590 | $X^1$ is chloro, $X^2$ is N, $X^3$ is chloro | difluoromethyl | chloro | $Y^1$ is CH, $Y^2$ is CH, $Y^3$ is CH |
| P.0591 | $X^1$ is chloro, $X^2$ is N, $X^3$ is chloro | difluoromethyl | cyano | $Y^1$ is CH, $Y^2$ is CH, $Y^3$ is CH |
| P.0592 | $X^1$ is chloro, $X^2$ is N, $X^3$ is chloro | difluoromethyl | cyclopropyl | $Y^1$ is CH, $Y^2$ is CH, $Y^3$ is CH |
| P.0593 | $X^1$ is chloro, $X^2$ is N, $X^3$ is chloro | difluoromethyl | ethyl | $Y^1$ is CH, $Y^2$ is CH, $Y^3$ is CH |
| P.0594 | $X^1$ is chloro, $X^2$ is N, $X^3$ is chloro | difluoromethyl | fluoro | $Y^1$ is CH, $Y^2$ is CH, $Y^3$ is CH |
| P.0595 | $X^1$ is chloro, $X^2$ is N, $X^3$ is chloro | difluoromethyl | hydrogen | $Y^1$ is CH, $Y^2$ is CH, $Y^3$ is CH |
| P.0596 | $X^1$ is chloro, $X^2$ is N, $X^3$ is chloro | difluoromethyl | methoxy | $Y^1$ is CH, $Y^2$ is CH, $Y^3$ is CH |
| P.0597 | $X^1$ is chloro, $X^2$ is N, $X^3$ is chloro | difluoromethyl | methyl | $Y^1$ is CH, $Y^2$ is CH, $Y^3$ is CH |
| P.0598 | $X^1$ is chloro, $X^2$ is N, $X^3$ is chloro | difluoromethyl | nitro | $Y^1$ is CH, $Y^2$ is CH, $Y^3$ is CH |
| P.0599 | $X^1$ is chloro, $X^2$ is N, $X^3$ is chloro | difluoromethyl | trifluoromethyl | $Y^1$ is CH, $Y^2$ is CH, $Y^3$ is CH |
| P.0600 | $X^1$ is chloro, $X^2$ is N, $X^3$ is chloro | difluoromethyl | trifluoromethyl | $Y^1$ is CH, $Y^2$ is CH, $Y^3$ is CH |
| P.0601 | $X^1$ is chloro, $X^2$ is N, $X^3$ is chloro | trifluoromethyl | bromo | $Y^1$ is CH, $Y^2$ is CH, $Y^3$ is CH |
| P.0602 | $X^1$ is chloro, $X^2$ is N, $X^3$ is chloro | trifluoromethyl | chloro | $Y^1$ is CH, $Y^2$ is CH, $Y^3$ is CH |
| P.0603 | $X^1$ is chloro, $X^2$ is N, $X^3$ is chloro | trifluoromethyl | cyano | $Y^1$ is CH, $Y^2$ is CH, $Y^3$ is CH |
| P.0604 | $X^1$ is chloro, $X^2$ is N, $X^3$ is chloro | trifluoromethyl | cyclopropyl | $Y^1$ is CH, $Y^2$ is CH, $Y^3$ is CH |
| P.0605 | $X^1$ is chloro, $X^2$ is N, $X^3$ is chloro | trifluoromethyl | ethyl | $Y^1$ is CH, $Y^2$ is CH, $Y^3$ is CH |
| P.0606 | $X^1$ is chloro, $X^2$ is N, $X^3$ is chloro | trifluoromethyl | fluoro | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0607 | $X^1$ is chloro, $X^2$ is N, $X^3$ is chloro | trifluoromethyl | hydrogen | $Y^1$ is CH, $Y^2$ is CH, $Y^3$ is CH |
| P.0608 | $X^1$ is chloro, $X^2$ is N, $X^3$ is chloro | trifluoromethyl | methoxy | $Y^1$ is CH, $Y^2$ is CH, $Y^3$ is CH |
| P.0609 | $X^1$ is chloro, $X^2$ is N, $X^3$ is chloro | trifluoromethyl | methyl | $Y^1$ is CH, $Y^2$ is CH, $Y^3$ is CH |
| P.0610 | $X^1$ is chloro, $X^2$ is N, $X^3$ is chloro | trifluoromethyl | nitro | $Y^1$ is CH, $Y^2$ is CH, $Y^3$ is CH |
| P.0611 | $X^1$ is chloro, $X^2$ is N, $X^3$ is chloro | trifluoromethyl | trifluoromethoxy | $Y^1$ is CH, $Y^2$ is CH, $Y^3$ is CH |
| P.0612 | $X^1$ is chloro, $X^2$ is N, $X^3$ is chloro | trifluoromethyl | trifluoromethyl | $Y^1$ is CH, $Y^2$ is CH, $Y^3$ is CH |
| P.0613 | $X^1$ is trifluoromethyl, $X^2$ is N, $X^3$ is trifluoromethyl | chlorodifluoromethyl | bromo | $Y^1$ is CH, $Y^2$ is CH, $Y^3$ is CH |
| P.0614 | $X^1$ is trifluoromethyl, $X^2$ is N, $X^3$ is trifluoromethyl | chlorodifluoromethyl | chloro | $Y^1$ is CH, $Y^2$ is CH, $Y^3$ is CH |
| P.0615 | $X^1$ is trifluoromethyl, $X^2$ is N, $X^3$ is trifluoromethyl | chlorodifluoromethyl | cyano | $Y^1$ is CH, $Y^2$ is CH, $Y^3$ is CH |
| P.0616 | $X^1$ is trifluoromethyl, $X^2$ is N, $X^3$ is trifluoromethyl | chlorodifluoromethyl | cyclopropyl | $Y^1$ is CH, $Y^2$ is CH, $Y^3$ is CH |
| P.0617 | $X^1$ is trifluoromethyl, $X^2$ is N, $X^3$ is trifluoromethyl | chlorodifluoromethyl | ethyl | $Y^1$ is CH, $Y^2$ is CH, $Y^3$ is CH |
| P.0618 | $X^1$ is trifluoromethyl, $X^2$ is N, $X^3$ is trifluoromethyl | chlorodifluoromethyl | fluoro | $Y^1$ is CH, $Y^2$ is CH, $Y^3$ is CH |
| P.0619 | $X^1$ is trifluoromethyl, $X^2$ is N, $X^3$ is trifluoromethyl | chlorodifluoromethyl | hydrogen | $Y^1$ is CH, $Y^2$ is CH, $Y^3$ is CH |
| P.0620 | $X^1$ is trifluoromethyl, $X^2$ is N, $X^3$ is trifluoromethyl | chlorodifluoromethyl | methoxy | $Y^1$ is CH, $Y^2$ is CH, $Y^3$ is CH |
| P.0621 | $X^1$ is trifluoromethyl, $X^2$ is N, $X^3$ is trifluoromethyl | chlorodifluoromethyl | methyl | $Y^1$ is CH, $Y^2$ is CH, $Y^3$ is CH |
| P.0622 | $X^1$ is trifluoromethyl, $X^2$ is N, $X^3$ is trifluoromethyl | chlorodifluoromethyl | nitro | $Y^1$ is CH, $Y^2$ is CH, $Y^3$ is CH |
| P.0623 | $X^1$ is trifluoromethyl, $X^2$ is N, $X^3$ is trifluoromethyl | chlorodifluoromethyl | trifluoromethoxy | $Y^1$ is CH, $Y^2$ is CH, $Y^3$ is CH |
| P.0624 | $X^1$ is trifluoromethyl, $X^2$ is N, $X^3$ is trifluoromethyl | chlorodifluoromethyl | trifluoromethyl | $Y^1$ is CH, $Y^2$ is CH, $Y^3$ is CH |
| P.0625 | $X^1$ is trifluoromethyl, $X^2$ is N, $X^3$ is trifluoromethyl | difluoromethyl | bromo | $Y^1$ is CH, $Y^2$ is CH, $Y^3$ is CH |
| P.0626 | $X^1$ is trifluoromethyl, $X^2$ is N, $X^3$ is trifluoromethyl | difluoromethyl | chloro | $Y^1$ is CH, $Y^2$ is CH, $Y^3$ is CH |
| P.0627 | $X^1$ is trifluoromethyl, $X^2$ is N, $X^3$ is trifluoromethyl | difluoromethyl | cyano | $Y^1$ is CH, $Y^2$ is CH, $Y^3$ is CH |
| P.0628 | $X^1$ is trifluoromethyl, $X^2$ is N, $X^3$ is trifluoromethyl | difluoromethyl | cyclopropyl | $Y^1$ is CH, $Y^2$ is CH, $Y^3$ is CH |
| P.0629 | $X^1$ is trifluoromethyl, $X^2$ is N, $X^3$ is trifluoromethyl | difluoromethyl | ethyl | $Y^1$ is CH, $Y^2$ is CH, $Y^3$ is CH |
| P.0630 | $X^1$ is trifluoromethyl, $X^2$ is N, $X^3$ is trifluoromethyl | difluoromethyl | fluoro | $Y^1$ is CH, $Y^2$ is CH, $Y^3$ is CH |
| P.0631 | $X^1$ is trifluoromethyl, $X^2$ is N, $X^3$ is trifluoromethyl | difluoromethyl | hydrogen | $Y^1$ is CH, $Y^2$ is CH, $Y^3$ is CH |
| P.0632 | $X^1$ is trifluoromethyl, $X^2$ is N, $X^3$ is trifluoromethyl | difluoromethyl | methoxy | $Y^1$ is CH, $Y^2$ is CH, $Y^3$ is CH |
| P.0633 | $X^1$ is trifluoromethyl, $X^2$ is N, $X^3$ is trifluoromethyl | difluoromethyl | methyl | $Y^1$ is CH, $Y^2$ is CH, $Y^3$ is CH |
| P.0634 | $X^1$ is trifluoromethyl, $X^2$ is N, $X^3$ is trifluoromethyl | difluoromethyl | nitro | $Y^1$ is CH, $Y^2$ is CH, $Y^3$ is CH |
| P.0635 | $X^1$ is trifluoromethyl, $X^2$ is N, $X^3$ is trifluoromethyl | difluoromethyl | trifluoromethoxy | $Y^1$ is CH, $Y^2$ is CH, $Y^3$ is CH |
| P.0636 | $X^1$ is trifluoromethyl, $X^2$ is N, $X^3$ is trifluoromethyl | difluoromethyl | trifluoromethyl | $Y^1$ is CH, $Y^2$ is CH, $Y^3$ is CH |
| P.0637 | $X^1$ is trifluoromethyl, $X^2$ is N, $X^3$ is trifluoromethyl | trifluoromethyl | bromo | $Y^1$ is CH, $Y^2$ is CH, $Y^3$ is CH |
| P.0638 | $X^1$ is trifluoromethyl, $X^2$ is N, $X^3$ is trifluoromethyl | trifluoromethyl | chloro | $Y^1$ is CH, $Y^2$ is CH, $Y^3$ is CH |
| P.0639 | $X^1$ is trifluoromethyl, $X^2$ is N, $X^3$ is trifluoromethyl | trifluoromethyl | cyano | $Y^1$ is CH, $Y^2$ is CH, $Y^3$ is CH |
| P.0640 | $X^1$ is trifluoromethyl, $X^2$ is N, $X^3$ is trifluoromethyl | trifluoromethyl | cyclopropyl | $Y^1$ is CH, $Y^2$ is CH, $Y^3$ is CH |
| P.0641 | $X^1$ is trifluoromethyl, $X^2$ is N, $X^3$ is trifluoromethyl | trifluoromethyl | ethyl | $Y^1$ is CH, $Y^2$ is CH, $Y^3$ is CH |
| P.0642 | $X^1$ is trifluoromethyl, $X^2$ is N, $X^3$ is trifluoromethyl | trifluoromethyl | fluoro | $Y^1$ is CH, $Y^2$ is CH, $Y^3$ is CH |
| P.0643 | $X^1$ is trifluoromethyl, $X^2$ is N, $X^3$ is trifluoromethyl | trifluoromethyl | hydrogen | $Y^1$ is CH, $Y^2$ is CH, $Y^3$ is CH |
| P.0644 | $X^1$ is trifluoromethyl, $X^2$ is N, $X^3$ is trifluoromethyl | trifluoromethyl | methoxy | $Y^1$ is CH, $Y^2$ is CH, $Y^3$ is CH |
| P.0645 | $X^1$ is trifluoromethyl, $X^2$ is N, $X^3$ is trifluoromethyl | trifluoromethyl | methyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0646 | $X^1$ is trifluoromethyl, $X^2$ is N, $X^3$ is trifluoromethyl | trifluoromethyl | nitro | $Y^1$ is CH, $Y^2$ is CH, $Y^3$ is CH |
| P.0647 | $X^1$ is trifluoromethyl, $X^2$ is N, $X^3$ is trifluoromethyl | trifluoromethyl | trifluoromethoxy | $Y^1$ is CH, $Y^2$ is CH, $Y^3$ is CH |
| P.0648 | $X^1$ is trifluoromethyl, $X^2$ is N, $X^3$ is trifluoromethyl | trifluoromethyl | trifluoromethyl | $Y^1$ is CH, $Y^2$ is CH, $Y^3$ is CH |
| P.0649 | $X^1$ is chloro, $X^2$ is CH, $X^3$ is chloro | chlorodifluoromethyl | bromo | $Y^1$ is N, $Y^2$ is CH, $Y^3$ is CH |
| P.0650 | $X^1$ is chloro, $X^2$ is CH, $X^3$ is chloro | chlorodifluoromethyl | chloro | $Y^1$ is N, $Y^2$ is CH, $Y^3$ is CH |
| P.0651 | $X^1$ is chloro, $X^2$ is CH, $X^3$ is chloro | chlorodifluoromethyl | cyano | $Y^1$ is N, $Y^2$ is CH, $Y^3$ is CH |
| P.0652 | $X^1$ is chloro, $X^2$ is CH, $X^3$ is chloro | chlorodifluoromethyl | cyclopropyl | $Y^1$ is N, $Y^2$ is CH, $Y^3$ is CH |
| P.0653 | $X^1$ is chloro, $X^2$ is CH, $X^3$ is chloro | chlorodifluoromethyl | ethyl | $Y^1$ is N, $Y^2$ is CH, $Y^3$ is CH |
| P.0654 | $X^1$ is chloro, $X^2$ is CH, $X^3$ is chloro | chlorodifluoromethyl | fluoro | $Y^1$ is N, $Y^2$ is CH, $Y^3$ is CH |
| P.0655 | $X^1$ is chloro, $X^2$ is CH, $X^3$ is chloro | chlorodifluoromethyl | hydrogen | $Y^1$ is N, $Y^2$ is CH, $Y^3$ is CH |
| P.0656 | $X^1$ is chloro, $X^2$ is CH, $X^3$ is chloro | chlorodifluoromethyl | methoxy | $Y^1$ is N, $Y^2$ is CH, $Y^3$ is CH |
| P.0657 | $X^1$ is chloro, $X^2$ is CH, $X^3$ is chloro | chlorodifluoromethyl | methyl | $Y^1$ is N, $Y^2$ is CH, $Y^3$ is CH |
| P.0658 | $X^1$ is chloro, $X^2$ is CH, $X^3$ is chloro | chlorodifluoromethyl | nitro | $Y^1$ is N, $Y^2$ is CH, $Y^3$ is CH |
| P.0659 | $X^1$ is chloro, $X^2$ is CH, $X^3$ is chloro | chlorodifluoromethyl | trifluoromethoxy | $Y^1$ is N, $Y^2$ is CH, $Y^3$ is CH |
| P.0660 | $X^1$ is chloro, $X^2$ is CH, $X^3$ is chloro | chlorodifluoromethyl | trifluoromethyl | $Y^1$ is N, $Y^2$ is CH, $Y^3$ is CH |
| P.0661 | $X^1$ is chloro, $X^2$ is CH, $X^3$ is chloro | difluoromethyl | bromo | $Y^1$ is N, $Y^2$ is CH, $Y^3$ is CH |
| P.0662 | $X^1$ is chloro, $X^2$ is CH, $X^3$ is chloro | difluoromethyl | chloro | $Y^1$ is N, $Y^2$ is CH, $Y^3$ is CH |
| P.0663 | $X^1$ is chloro, $X^2$ is CH, $X^3$ is chloro | difluoromethyl | cyano | $Y^1$ is N, $Y^2$ is CH, $Y^3$ is CH |
| P.0664 | $X^1$ is chloro, $X^2$ is CH, $X^3$ is chloro | difluoromethyl | cyclopropyl | $Y^1$ is N, $Y^2$ is CH, $Y^3$ is CH |
| P.0665 | $X^1$ is chloro, $X^2$ is CH, $X^3$ is chloro | difluoromethyl | ethyl | $Y^1$ is N, $Y^2$ is CH, $Y^3$ is CH |
| P.0666 | $X^1$ is chloro, $X^2$ is CH, $X^3$ is chloro | difluoromethyl | fluoro | $Y^1$ is N, $Y^2$ is CH, $Y^3$ is CH |
| P.0667 | $X^1$ is chloro, $X^2$ is CH, $X^3$ is chloro | difluoromethyl | hydrogen | $Y^1$ is N, $Y^2$ is CH, $Y^3$ is CH |
| P.0668 | $X^1$ is chloro, $X^2$ is CH, $X^3$ is chloro | difluoromethyl | methoxy | $Y^1$ is N, $Y^2$ is CH, $Y^3$ is CH |
| P.0669 | $X^1$ is chloro, $X^2$ is CH, $X^3$ is chloro | difluoromethyl | methyl | $Y^1$ is N, $Y^2$ is CH, $Y^3$ is CH |
| P.0670 | $X^1$ is chloro, $X^2$ is CH, $X^3$ is chloro | difluoromethyl | nitro | $Y^1$ is N, $Y^2$ is CH, $Y^3$ is CH |
| P.0671 | $X^1$ is chloro, $X^2$ is CH, $X^3$ is chloro | difluoromethyl | trifluoromethoxy | $Y^1$ is N, $Y^2$ is CH, $Y^3$ is CH |
| P.0672 | $X^1$ is chloro, $X^2$ is CH, $X^3$ is chloro | difluoromethyl | trifluoromethyl | $Y^1$ is N, $Y^2$ is CH, $Y^3$ is CH |
| P.0673 | $X^1$ is chloro, $X^2$ is CH, $X^3$ is chloro | trifluoromethyl | bromo | $Y^1$ is N, $Y^2$ is CH, $Y^3$ is CH |
| P.0674 | $X^1$ is chloro, $X^2$ is CH, $X^3$ is chloro | trifluoromethyl | chloro | $Y^1$ is N, $Y^2$ is CH, $Y^3$ is CH |
| P.0675 | $X^1$ is chloro, $X^2$ is CH, $X^3$ is chloro | trifluoromethyl | cyano | $Y^1$ is N, $Y^2$ is CH, $Y^3$ is CH |
| P.0676 | $X^1$ is chloro, $X^2$ is CH, $X^3$ is chloro | trifluoromethyl | cyclopropyl | $Y^1$ is N, $Y^2$ is CH, $Y^3$ is CH |
| P.0677 | $X^1$ is chloro, $X^2$ is CH, $X^3$ is chloro | trifluoromethyl | ethyl | $Y^1$ is N, $Y^2$ is CH, $Y^3$ is CH |
| P.0678 | $X^1$ is chloro, $X^2$ is CH, $X^3$ is chloro | trifluoromethyl | fluoro | $Y^1$ is N, $Y^2$ is CH, $Y^3$ is CH |
| P.0679 | $X^1$ is chloro, $X^2$ is CH, $X^3$ is chloro | trifluoromethyl | hydrogen | $Y^1$ is N, $Y^2$ is CH, $Y^3$ is CH |
| P.0680 | $X^1$ is chloro, $X^2$ is CH, $X^3$ is chloro | trifluoromethyl | methoxy | $Y^1$ is N, $Y^2$ is CH, $Y^3$ is CH |
| P.0681 | $X^1$ is chloro, $X^2$ is CH, $X^3$ is chloro | trifluoromethyl | methyl | $Y^1$ is N, $Y^2$ is CH, $Y^3$ is CH |
| P.0682 | $X^1$ is chloro, $X^2$ is CH, $X^3$ is chloro | trifluoromethyl | nitro | $Y^1$ is N, $Y^2$ is CH, $Y^3$ is CH |
| P.0683 | $X^1$ is chloro, $X^2$ is CH, $X^3$ is chloro | trifluoromethyl | trifluoromethoxy | $Y^1$ is N, $Y^2$ is CH, $Y^3$ is CH |
| P.0684 | $X^1$ is chloro, $X^2$ is CH, $X^3$ is chloro | trifluoromethyl | trifluoromethyl | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.0685 | $X^1$ is chloro, $X^2$ is C—F, $X^3$ is hydrogen | chlorodifluoromethyl | bromo | $Y^1$ is N, $Y^2$ is CH, $Y^3$ is CH |
| P.0686 | $X^1$ is chloro, $X^2$ is C—F, $X^3$ is hydrogen | chlorodifluoromethyl | chloro | $Y^1$ is N, $Y^2$ is CH, $Y^3$ is CH |
| P.0687 | $X^1$ is chloro, $X^2$ is C—F, $X^3$ is hydrogen | chlorodifluoromethyl | cyano | $Y^1$ is N, $Y^2$ is CH, $Y^3$ is CH |
| P.0688 | $X^1$ is chloro, $X^2$ is C—F, $X^3$ is hydrogen | chlorodifluoromethyl | cyclopropyl | $Y^1$ is N, $Y^2$ is CH, $Y^3$ is CH |
| P.0689 | $X^1$ is chloro, $X^2$ is C—F, $X^3$ is hydrogen | chlorodifluoromethyl | ethyl | $Y^1$ is N, $Y^2$ is CH, $Y^3$ is CH |
| P.0690 | $X^1$ is chloro, $X^2$ is C—F, $X^3$ is hydrogen | chlorodifluoromethyl | fluoro | $Y^1$ is N, $Y^2$ is CH, $Y^3$ is CH |
| P.0691 | $X^1$ is chloro, $X^2$ is C—F, $X^3$ is hydrogen | chlorodifluoromethyl | hydrogen | $Y^1$ is N, $Y^2$ is CH, $Y^3$ is CH |
| P.0692 | $X^1$ is chloro, $X^2$ is C—F, $X^3$ is hydrogen | chlorodifluoromethyl | methoxy | $Y^1$ is N, $Y^2$ is CH, $Y^3$ is CH |
| P.0693 | $X^1$ is chloro, $X^2$ is C—F, $X^3$ is hydrogen | chlorodifluoromethyl | methyl | $Y^1$ is N, $Y^2$ is CH, $Y^3$ is CH |
| P.0694 | $X^1$ is chloro, $X^2$ is C—F, $X^3$ is hydrogen | chlorodifluoromethyl | nitro | $Y^1$ is N, $Y^2$ is CH, $Y^3$ is CH |
| P.0695 | $X^1$ is chloro, $X^2$ is C—F, $X^3$ is hydrogen | chlorodifluoromethyl | trifluoromethoxy | $Y^1$ is N, $Y^2$ is CH, $Y^3$ is CH |
| P.0696 | $X^1$ is chloro, $X^2$ is C—F, $X^3$ is hydrogen | chlorodifluoromethyl | trifluoromethyl | $Y^1$ is N, $Y^2$ is CH, $Y^3$ is CH |
| P.0697 | $X^1$ is chloro, $X^2$ is C—F, $X^3$ is hydrogen | difluoromethyl | bromo | $Y^1$ is N, $Y^2$ is CH, $Y^3$ is CH |
| P.0698 | $X^1$ is chloro, $X^2$ is C—F, $X^3$ is hydrogen | difluoromethyl | chloro | $Y^1$ is N, $Y^2$ is CH, $Y^3$ is CH |
| P.0699 | $X^1$ is chloro, $X^2$ is C—F, $X^3$ is hydrogen | difluoromethyl | cyano | $Y^1$ is N, $Y^2$ is CH, $Y^3$ is CH |
| P.0700 | $X^1$ is chloro, $X^2$ is C—F, $X^3$ is hydrogen | difluoromethyl | cyclopropyl | $Y^1$ is N, $Y^2$ is CH, $Y^3$ is CH |
| P.0701 | $X^1$ is chloro, $X^2$ is C—F, $X^3$ is hydrogen | difluoromethyl | ethyl | $Y^1$ is N, $Y^2$ is CH, $Y^3$ is CH |
| P.0702 | $X^1$ is chloro, $X^2$ is C—F, $X^3$ is hydrogen | difluoromethyl | fluoro | $Y^1$ is N, $Y^2$ is CH, $Y^3$ is CH |
| P.0703 | $X^1$ is chloro, $X^2$ is C—F, $X^3$ is hydrogen | difluoromethyl | hydrogen | $Y^1$ is N, $Y^2$ is CH, $Y^3$ is CH |
| P.0704 | $X^1$ is chloro, $X^2$ is C—F, $X^3$ is hydrogen | difluoromethyl | methoxy | $Y^1$ is N, $Y^2$ is CH, $Y^3$ is CH |
| P.0705 | $X^1$ is chloro, $X^2$ is C—F, $X^3$ is hydrogen | difluoromethyl | methyl | $Y^1$ is N, $Y^2$ is CH, $Y^3$ is CH |
| P.0706 | $X^1$ is chloro, $X^2$ is C—F, $X^3$ is hydrogen | difluoromethyl | nitro | $Y^1$ is N, $Y^2$ is CH, $Y^3$ is CH |
| P.0707 | $X^1$ is chloro, $X^2$ is C—F, $X^3$ is hydrogen | difluoromethyl | trifluoromethoxy | $Y^1$ is N, $Y^2$ is CH, $Y^3$ is CH |
| P.0708 | $X^1$ is chloro, $X^2$ is C—F, $X^3$ is hydrogen | difluoromethyl | trifluoromethyl | $Y^1$ is N, $Y^2$ is CH, $Y^3$ is CH |
| P.0709 | $X^1$ is chloro, $X^2$ is C—F, $X^3$ is hydrogen | trifluoromethyl | bromo | $Y^1$ is N, $Y^2$ is CH, $Y^3$ is CH |
| P.0710 | $X^1$ is chloro, $X^2$ is C—F, $X^3$ is hydrogen | trifluoromethyl | chloro | $Y^1$ is N, $Y^2$ is CH, $Y^3$ is CH |
| P.0711 | $X^1$ is chloro, $X^2$ is C—F, $X^3$ is hydrogen | trifluoromethyl | cyano | $Y^1$ is N, $Y^2$ is CH, $Y^3$ is CH |
| P.0712 | $X^1$ is chloro, $X^2$ is C—F, $X^3$ is hydrogen | trifluoromethyl | cyclopropyl | $Y^1$ is N, $Y^2$ is CH, $Y^3$ is CH |
| P.0713 | $X^1$ is chloro, $X^2$ is C—F, $X^3$ is hydrogen | trifluoromethyl | ethyl | $Y^1$ is N, $Y^2$ is CH, $Y^3$ is CH |
| P.0714 | $X^1$ is chloro, $X^2$ is C—F, $X^3$ is hydrogen | trifluoromethyl | fluoro | $Y^1$ is N, $Y^2$ is CH, $Y^3$ is CH |
| P.0715 | $X^1$ is chloro, $X^2$ is C—F, $X^3$ is hydrogen | trifluoromethyl | hydrogen | $Y^1$ is N, $Y^2$ is CH, $Y^3$ is CH |
| P.0716 | $X^1$ is chloro, $X^2$ is C—F, $X^3$ is hydrogen | trifluoromethyl | methoxy | $Y^1$ is N, $Y^2$ is CH, $Y^3$ is CH |
| P.0717 | $X^1$ is chloro, $X^2$ is C—F, $X^3$ is hydrogen | trifluoromethyl | methyl | $Y^1$ is N, $Y^2$ is CH, $Y^3$ is CH |
| P.0718 | $X^1$ is chloro, $X^2$ is C—F, $X^3$ is hydrogen | trifluoromethyl | nitro | $Y^1$ is N, $Y^2$ is CH, $Y^3$ is CH |
| P.0719 | $X^1$ is chloro, $X^2$ is C—F, $X^3$ is hydrogen | trifluoromethyl | trifluoromethoxy | $Y^1$ is N, $Y^2$ is CH, $Y^3$ is CH |
| P.0720 | $X^1$ is chloro, $X^2$ is C—F, $X^3$ is hydrogen | trifluoromethyl | trifluoromethyl | $Y^1$ is N, $Y^2$ is CH, $Y^3$ is CH |
| P.0721 | $X^1$ is fluoro, $X^2$ is C—Cl, $X^3$ is hydrogen | chlorodifluoromethyl | bromo | $Y^1$ is N, $Y^2$ is CH, $Y^3$ is CH |
| P.0722 | $X^1$ is fluoro, $X^2$ is C—Cl, $X^3$ is hydrogen | chlorodifluoromethyl | chloro | $Y^1$ is N, $Y^2$ is CH, $Y^3$ is CH |
| P.0723 | $X^1$ is fluoro, $X^2$ is C—Cl, $X^3$ is hydrogen | chlorodifluoromethyl | cyano | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.0724 | $X^1$ is fluoro, $X^2$ is C—Cl, $X^3$ is hydrogen | chlorodifluoromethyl | cyclopropyl | $Y^1$ is N, $Y^2$ is CH, $Y^3$ is CH |
| P.0725 | $X^1$ is fluoro, $X^2$ is C—Cl, $X^3$ is hydrogen | chlorodifluoromethyl | ethyl | $Y^1$ is N, $Y^2$ is CH, $Y^3$ is CH |
| P.0726 | $X^1$ is fluoro, $X^2$ is C—Cl, $X^3$ is hydrogen | chlorodifluoromethyl | fluoro | $Y^1$ is N, $Y^2$ is CH, $Y^3$ is CH |
| P.0727 | $X^1$ is fluoro, $X^2$ is C—Cl, $X^3$ is hydrogen | chlorodifluoromethyl | hydrogen | $Y^1$ is N, $Y^2$ is CH, $Y^3$ is CH |
| P.0728 | $X^1$ is fluoro, $X^2$ is C—Cl, $X^3$ is hydrogen | chlorodifluoromethyl | methoxy | $Y^1$ is N, $Y^2$ is CH, $Y^3$ is CH |
| P.0729 | $X^1$ is fluoro, $X^2$ is C—Cl, $X^3$ is hydrogen | chlorodifluoromethyl | methyl | $Y^1$ is N, $Y^2$ is CH, $Y^3$ is CH |
| P.0730 | $X^1$ is fluoro, $X^2$ is C—Cl, $X^3$ is hydrogen | chlorodifluoromethyl | nitro | $Y^1$ is N, $Y^2$ is CH, $Y^3$ is CH |
| P.0731 | $X^1$ is fluoro, $X^2$ is C—Cl, $X^3$ is hydrogen | chlorodifluoromethyl | trifluoromethoxy | $Y^1$ is N, $Y^2$ is CH, $Y^3$ is CH |
| P.0732 | $X^1$ is fluoro, $X^2$ is C—Cl, $X^3$ is hydrogen | chlorodifluoromethyl | trifluoromethyl | $Y^1$ is N, $Y^2$ is CH, $Y^3$ is CH |
| P.0733 | $X^1$ is fluoro, $X^2$ is C—Cl, $X^3$ is hydrogen | difluoromethyl | bromo | $Y^1$ is N, $Y^2$ is CH, $Y^3$ is CH |
| P.0734 | $X^1$ is fluoro, $X^2$ is C—Cl, $X^3$ is hydrogen | difluoromethyl | chloro | $Y^1$ is N, $Y^2$ is CH, $Y^3$ is CH |
| P.0735 | $X^1$ is fluoro, $X^2$ is C—Cl, $X^3$ is hydrogen | difluoromethyl | cyano | $Y^1$ is N, $Y^2$ is CH, $Y^3$ is CH |
| P.0736 | $X^1$ is fluoro, $X^2$ is C—Cl, $X^3$ is hydrogen | difluoromethyl | cyclopropyl | $Y^1$ is N, $Y^2$ is CH, $Y^3$ is CH |
| P.0737 | $X^1$ is fluoro, $X^2$ is C—Cl, $X^3$ is hydrogen | difluoromethyl | ethyl | $Y^1$ is N, $Y^2$ is CH, $Y^3$ is CH |
| P.0738 | $X^1$ is fluoro, $X^2$ is C—Cl, $X^3$ is hydrogen | difluoromethyl | fluoro | $Y^1$ is N, $Y^2$ is CH, $Y^3$ is CH |
| P.0739 | $X^1$ is fluoro, $X^2$ is C—Cl, $X^3$ is hydrogen | difluoromethyl | hydrogen | $Y^1$ is N, $Y^2$ is CH, $Y^3$ is CH |
| P.0740 | $X^1$ is fluoro, $X^2$ is C—Cl, $X^3$ is hydrogen | difluoromethyl | methoxy | $Y^1$ is N, $Y^2$ is CH, $Y^3$ is CH |
| P.0741 | $X^1$ is fluoro, $X^2$ is C—Cl, $X^3$ is hydrogen | difluoromethyl | methyl | $Y^1$ is N, $Y^2$ is CH, $Y^3$ is CH |
| P.0742 | $X^1$ is fluoro, $X^2$ is C—Cl, $X^3$ is hydrogen | difluoromethyl | nitro | $Y^1$ is N, $Y^2$ is CH, $Y^3$ is CH |
| P.0743 | $X^1$ is fluoro, $X^2$ is C—Cl, $X^3$ is hydrogen | difluoromethyl | trifluoromethoxy | $Y^1$ is N, $Y^2$ is CH, $Y^3$ is CH |
| P.0744 | $X^1$ is fluoro, $X^2$ is C—Cl, $X^3$ is hydrogen | difluoromethyl | trifluoromethyl | $Y^1$ is N, $Y^2$ is CH, $Y^3$ is CH |
| P.0745 | $X^1$ is fluoro, $X^2$ is C—Cl, $X^3$ is hydrogen | trifluoromethyl | bromo | $Y^1$ is N, $Y^2$ is CH, $Y^3$ is CH |
| P.0746 | $X^1$ is fluoro, $X^2$ is C—Cl, $X^3$ is hydrogen | trifluoromethyl | chloro | $Y^1$ is N, $Y^2$ is CH, $Y^3$ is CH |
| P.0747 | $X^1$ is fluoro, $X^2$ is C—Cl, $X^3$ is hydrogen | trifluoromethyl | cyano | $Y^1$ is N, $Y^2$ is CH, $Y^3$ is CH |
| P.0748 | $X^1$ is fluoro, $X^2$ is C—Cl, $X^3$ is hydrogen | trifluoromethyl | cyclopropyl | $Y^1$ is N, $Y^2$ is CH, $Y^3$ is CH |
| P.0749 | $X^1$ is fluoro, $X^2$ is C—Cl, $X^3$ is hydrogen | trifluoromethyl | ethyl | $Y^1$ is N, $Y^2$ is CH, $Y^3$ is CH |
| P.0750 | $X^1$ is fluoro, $X^2$ is C—Cl, $X^3$ is hydrogen | trifluoromethyl | fluoro | $Y^1$ is N, $Y^2$ is CH, $Y^3$ is CH |
| P.0751 | $X^1$ is fluoro, $X^2$ is C—Cl, $X^3$ is hydrogen | trifluoromethyl | hydrogen | $Y^1$ is N, $Y^2$ is CH, $Y^3$ is CH |
| P.0752 | $X^1$ is fluoro, $X^2$ is C—Cl, $X^3$ is hydrogen | trifluoromethyl | methoxy | $Y^1$ is N, $Y^2$ is CH, $Y^3$ is CH |
| P.0753 | $X^1$ is fluoro, $X^2$ is C—Cl, $X^3$ is hydrogen | trifluoromethyl | methyl | $Y^1$ is N, $Y^2$ is CH, $Y^3$ is CH |
| P.0754 | $X^1$ is fluoro, $X^2$ is C—Cl, $X^3$ is hydrogen | trifluoromethyl | nitro | $Y^1$ is N, $Y^2$ is CH, $Y^3$ is CH |
| P.0755 | $X^1$ is fluoro, $X^2$ is C—Cl, $X^3$ is hydrogen | trifluoromethyl | trifluoromethoxy | $Y^1$ is N, $Y^2$ is CH, $Y^3$ is CH |
| P.0756 | $X^1$ is fluoro, $X^2$ is C—Cl, $X^3$ is hydrogen | trifluoromethyl | trifluoromethyl | $Y^1$ is N, $Y^2$ is CH, $Y^3$ is CH |
| P.0757 | $X^1$ is chloro, $X^2$ is C—Cl, $X^3$ is hydrogen | chlorodifluoromethyl | bromo | $Y^1$ is N, $Y^2$ is CH, $Y^3$ is CH |
| P.0758 | $X^1$ is chloro, $X^2$ is C—Cl, $X^3$ is hydrogen | chlorodifluoromethyl | chloro | $Y^1$ is N, $Y^2$ is CH, $Y^3$ is CH |
| P.0759 | $X^1$ is chloro, $X^2$ is C—Cl, $X^3$ is hydrogen | chlorodifluoromethyl | cyano | $Y^1$ is N, $Y^2$ is CH, $Y^3$ is CH |
| P.0760 | $X^1$ is chloro, $X^2$ is C—Cl, $X^3$ is hydrogen | chlorodifluoromethyl | cyclopropyl | $Y^1$ is N, $Y^2$ is CH, $Y^3$ is CH |
| P.0761 | $X^1$ is chloro, $X^2$ is C—Cl, $X^3$ is hydrogen | chlorodifluoromethyl | ethyl | $Y^1$ is N, $Y^2$ is CH, $Y^3$ is CH |
| P.0762 | $X^1$ is chloro, $X^2$ is C—Cl, $X^3$ is hydrogen | chlorodifluoromethyl | fluoro | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.0763 | $X^1$ is chloro, $X^2$ is C—Cl, $X^3$ is hydrogen | chlorodifluoromethyl | hydrogen | $Y^1$ is N, $Y^2$ is CH, $Y^3$ is CH |
| P.0764 | $X^1$ is chloro, $X^2$ is C—Cl, $X^3$ is hydrogen | chlorodifluoromethyl | methoxy | $Y^1$ is N, $Y^2$ is CH, $Y^3$ is CH |
| P.0765 | $X^1$ is chloro, $X^2$ is C—Cl, $X^3$ is hydrogen | chlorodifluoromethyl | methyl | $Y^1$ is N, $Y^2$ is CH, $Y^3$ is CH |
| P.0766 | $X^1$ is chloro, $X^2$ is C—Cl, $X^3$ is hydrogen | chlorodifluoromethyl | nitro | $Y^1$ is N, $Y^2$ is CH, $Y^3$ is CH |
| P.0767 | $X^1$ is chloro, $X^2$ is C—Cl, $X^3$ is hydrogen | chlorodifluoromethyl | trifluoromethoxy | $Y^1$ is N, $Y^2$ is CH, $Y^3$ is CH |
| P.0768 | $X^1$ is chloro, $X^2$ is C—Cl, $X^3$ is hydrogen | chlorodifluoromethyl | trifluoromethyl | $Y^1$ is N, $Y^2$ is CH, $Y^3$ is CH |
| P.0769 | $X^1$ is chloro, $X^2$ is C—Cl, $X^3$ is hydrogen | difluoromethyl | bromo | $Y^1$ is N, $Y^2$ is CH, $Y^3$ is CH |
| P.0770 | $X^1$ is chloro, $X^2$ is C—Cl, $X^3$ is hydrogen | difluoromethyl | chloro | $Y^1$ is N, $Y^2$ is CH, $Y^3$ is CH |
| P.0771 | $X^1$ is chloro, $X^2$ is C—Cl, $X^3$ is hydrogen | difluoromethyl | cyano | $Y^1$ is N, $Y^2$ is CH, $Y^3$ is CH |
| P.0772 | $X^1$ is chloro, $X^2$ is C—Cl, $X^3$ is hydrogen | difluoromethyl | cyclopropyl | $Y^1$ is N, $Y^2$ is CH, $Y^3$ is CH |
| P.0773 | $X^1$ is chloro, $X^2$ is C—Cl, $X^3$ is hydrogen | difluoromethyl | ethyl | $Y^1$ is N, $Y^2$ is CH, $Y^3$ is CH |
| P.0774 | $X^1$ is chloro, $X^2$ is C—Cl, $X^3$ is hydrogen | difluoromethyl | fluoro | $Y^1$ is N, $Y^2$ is CH, $Y^3$ is CH |
| P.0775 | $X^1$ is chloro, $X^2$ is C—Cl, $X^3$ is hydrogen | difluoromethyl | hydrogen | $Y^1$ is N, $Y^2$ is CH, $Y^3$ is CH |
| P.0776 | $X^1$ is chloro, $X^2$ is C—Cl, $X^3$ is hydrogen | difluoromethyl | methoxy | $Y^1$ is N, $Y^2$ is CH, $Y^3$ is CH |
| P.0777 | $X^1$ is chloro, $X^2$ is C—Cl, $X^3$ is hydrogen | difluoromethyl | methyl | $Y^1$ is N, $Y^2$ is CH, $Y^3$ is CH |
| P.0778 | $X^1$ is chloro, $X^2$ is C—Cl, $X^3$ is hydrogen | difluoromethyl | nitro | $Y^1$ is N, $Y^2$ is CH, $Y^3$ is CH |
| P.0779 | $X^1$ is chloro, $X^2$ is C—Cl, $X^3$ is hydrogen | difluoromethyl | trifluoromethoxy | $Y^1$ is N, $Y^2$ is CH, $Y^3$ is CH |
| P.0780 | $X^1$ is chloro, $X^2$ is C—Cl, $X^3$ is hydrogen | difluoromethyl | trifluoromethyl | $Y^1$ is N, $Y^2$ is CH, $Y^3$ is CH |
| P.0781 | $X^1$ is chloro, $X^2$ is C—Cl, $X^3$ is hydrogen | trifluoromethyl | bromo | $Y^1$ is N, $Y^2$ is CH, $Y^3$ is CH |
| P.0782 | $X^1$ is chloro, $X^2$ is C—Cl, $X^3$ is hydrogen | trifluoromethyl | chloro | $Y^1$ is N, $Y^2$ is CH, $Y^3$ is CH |
| P.0783 | $X^1$ is chloro, $X^2$ is C—Cl, $X^3$ is hydrogen | trifluoromethyl | cyano | $Y^1$ is N, $Y^2$ is CH, $Y^3$ is CH |
| P.0784 | $X^1$ is chloro, $X^2$ is C—Cl, $X^3$ is hydrogen | trifluoromethyl | cyclopropyl | $Y^1$ is N, $Y^2$ is CH, $Y^3$ is CH |
| P.0785 | $X^1$ is chloro, $X^2$ is C—Cl, $X^3$ is hydrogen | trifluoromethyl | ethyl | $Y^1$ is N, $Y^2$ is CH, $Y^3$ is CH |
| P.0786 | $X^1$ is chloro, $X^2$ is C—Cl, $X^3$ is hydrogen | trifluoromethyl | fluoro | $Y^1$ is N, $Y^2$ is CH, $Y^3$ is CH |
| P.0787 | $X^1$ is chloro, $X^2$ is C—Cl, $X^3$ is hydrogen | trifluoromethyl | hydrogen | $Y^1$ is N, $Y^2$ is CH, $Y^3$ is CH |
| P.0788 | $X^1$ is chloro, $X^2$ is C—Cl, $X^3$ is hydrogen | trifluoromethyl | methoxy | $Y^1$ is N, $Y^2$ is CH, $Y^3$ is CH |
| P.0789 | $X^1$ is chloro, $X^2$ is C—Cl, $X^3$ is hydrogen | trifluoromethyl | methyl | $Y^1$ is N, $Y^2$ is CH, $Y^3$ is CH |
| P.0790 | $X^1$ is chloro, $X^2$ is C—Cl, $X^3$ is hydrogen | trifluoromethyl | nitro | $Y^1$ is N, $Y^2$ is CH, $Y^3$ is CH |
| P.0791 | $X^1$ is chloro, $X^2$ is C—Cl, $X^3$ is hydrogen | trifluoromethyl | trifluoromethoxy | $Y^1$ is N, $Y^2$ is CH, $Y^3$ is CH |
| P.0792 | $X^1$ is chloro, $X^2$ is C—Cl, $X^3$ is hydrogen | trifluoromethyl | trifluoromethyl | $Y^1$ is N, $Y^2$ is CH, $Y^3$ is CH |
| P.0793 | $X^1$ is chloro, $X^2$ is C—Br, $X^3$ is chloro | chlorodifluoromethyl | bromo | $Y^1$ is N, $Y^2$ is CH, $Y^3$ is CH |
| P.0794 | $X^1$ is chloro, $X^2$ is C—Br, $X^3$ is chloro | chlorodifluoromethyl | chloro | $Y^1$ is N, $Y^2$ is CH, $Y^3$ is CH |
| P.0795 | $X^1$ is chloro, $X^2$ is C—Br, $X^3$ is chloro | chlorodifluoromethyl | cyano | $Y^1$ is N, $Y^2$ is CH, $Y^3$ is CH |
| P.0796 | $X^1$ is chloro, $X^2$ is C—Br, $X^3$ is chloro | chlorodifluoromethyl | cyclopropyl | $Y^1$ is N, $Y^2$ is CH, $Y^3$ is CH |
| P.0797 | $X^1$ is chloro, $X^2$ is C—Br, $X^3$ is chloro | chlorodifluoromethyl | ethyl | $Y^1$ is N, $Y^2$ is CH, $Y^3$ is CH |
| P.0798 | $X^1$ is chloro, $X^2$ is C—Br, $X^3$ is chloro | chlorodifluoromethyl | fluoro | $Y^1$ is N, $Y^2$ is CH, $Y^3$ is CH |
| P.0799 | $X^1$ is chloro, $X^2$ is C—Br, $X^3$ is chloro | chlorodifluoromethyl | hydrogen | $Y^1$ is N, $Y^2$ is CH, $Y^3$ is CH |
| P.0800 | $X^1$ is chloro, $X^2$ is C—Br, $X^3$ is chloro | chlorodifluoromethyl | methoxy | $Y^1$ is N, $Y^2$ is CH, $Y^3$ is CH |
| P.0801 | $X^1$ is chloro, $X^2$ is C—Br, $X^3$ is chloro | chlorodifluoromethyl | methyl | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.0802 | $X^1$ is chloro, $X^2$ is C—Br, $X^3$ is chloro | chlorodifluoromethyl | nitro | $Y^1$ is N, $Y^2$ is CH, $Y^3$ is CH |
| P.0803 | $X^1$ is chloro, $X^2$ is C—Br, $X^3$ is chloro | chlorodifluoromethyl | trifluoromethoxy | $Y^1$ is N, $Y^2$ is CH, $Y^3$ is CH |
| P.0804 | $X^1$ is chloro, $X^2$ is C—Br, $X^3$ is chloro | chlorodifluoromethyl | trifluoromethyl | $Y^1$ is N, $Y^2$ is CH, $Y^3$ is CH |
| P.0805 | $X^1$ is chloro, $X^2$ is C—Br, $X^3$ is chloro | difluoromethyl | bromo | $Y^1$ is N, $Y^2$ is CH, $Y^3$ is CH |
| P.0806 | $X^1$ is chloro, $X^2$ is C—Br, $X^3$ is chloro | difluoromethyl | chloro | $Y^1$ is N, $Y^2$ is CH, $Y^3$ is CH |
| P.0807 | $X^1$ is chloro, $X^2$ is C—Br, $X^3$ is chloro | difluoromethyl | cyano | $Y^1$ is N, $Y^2$ is CH, $Y^3$ is CH |
| P.0808 | $X^1$ is chloro, $X^2$ is C—Br, $X^3$ is chloro | difluoromethyl | cyclopropyl | $Y^1$ is N, $Y^2$ is CH, $Y^3$ is CH |
| P.0809 | $X^1$ is chloro, $X^2$ is C—Br, $X^3$ is chloro | difluoromethyl | ethyl | $Y^1$ is N, $Y^2$ is CH, $Y^3$ is CH |
| P.0810 | $X^1$ is chloro, $X^2$ is C—Br, $X^3$ is chloro | difluoromethyl | fluoro | $Y^1$ is N, $Y^2$ is CH, $Y^3$ is CH |
| P.0811 | $X^1$ is chloro, $X^2$ is C—Br, $X^3$ is chloro | difluoromethyl | hydrogen | $Y^1$ is N, $Y^2$ is CH, $Y^3$ is CH |
| P.0812 | $X^1$ is chloro, $X^2$ is C—Br, $X^3$ is chloro | difluoromethyl | methoxy | $Y^1$ is N, $Y^2$ is CH, $Y^3$ is CH |
| P.0813 | $X^1$ is chloro, $X^2$ is C—Br, $X^3$ is chloro | difluoromethyl | methyl | $Y^1$ is N, $Y^2$ is CH, $Y^3$ is CH |
| P.0814 | $X^1$ is chloro, $X^2$ is C—Br, $X^3$ is chloro | difluoromethyl | nitro | $Y^1$ is N, $Y^2$ is CH, $Y^3$ is CH |
| P.0815 | $X^1$ is chloro, $X^2$ is C—Br, $X^3$ is chloro | difluoromethyl | trifluoromethoxy | $Y^1$ is N, $Y^2$ is CH, $Y^3$ is CH |
| P.0816 | $X^1$ is chloro, $X^2$ is C—Br, $X^3$ is chloro | difluoromethyl | trifluoromethyl | $Y^1$ is N, $Y^2$ is CH, $Y^3$ is CH |
| P.0817 | $X^1$ is chloro, $X^2$ is C—Br, $X^3$ is chloro | trifluoromethyl | bromo | $Y^1$ is N, $Y^2$ is CH, $Y^3$ is CH |
| P.0818 | $X^1$ is chloro, $X^2$ is C—Br, $X^3$ is chloro | trifluoromethyl | chloro | $Y^1$ is N, $Y^2$ is CH, $Y^3$ is CH |
| P.0819 | $X^1$ is chloro, $X^2$ is C—Br, $X^3$ is chloro | trifluoromethyl | cyano | $Y^1$ is N, $Y^2$ is CH, $Y^3$ is CH |
| P.0820 | $X^1$ is chloro, $X^2$ is C—Br, $X^3$ is chloro | trifluoromethyl | cyclopropyl | $Y^1$ is N, $Y^2$ is CH, $Y^3$ is CH |
| P.0821 | $X^1$ is chloro, $X^2$ is C—Br, $X^3$ is chloro | trifluoromethyl | ethyl | $Y^1$ is N, $Y^2$ is CH, $Y^3$ is CH |
| P.0822 | $X^1$ is chloro, $X^2$ is C—Br, $X^3$ is chloro | trifluoromethyl | fluoro | $Y^1$ is N, $Y^2$ is CH, $Y^3$ is CH |
| P.0823 | $X^1$ is chloro, $X^2$ is C—Br, $X^3$ is chloro | trifluoromethyl | hydrogen | $Y^1$ is N, $Y^2$ is CH, $Y^3$ is CH |
| P.0824 | $X^1$ is chloro, $X^2$ is C—Br, $X^3$ is chloro | trifluoromethyl | methoxy | $Y^1$ is N, $Y^2$ is CH, $Y^3$ is CH |
| P.0825 | $X^1$ is chloro, $X^2$ is C—Br, $X^3$ is chloro | trifluoromethyl | methyl | $Y^1$ is N, $Y^2$ is CH, $Y^3$ is CH |
| P.0826 | $X^1$ is chloro, $X^2$ is C—Br, $X^3$ is chloro | trifluoromethyl | nitro | $Y^1$ is N, $Y^2$ is CH, $Y^3$ is CH |
| P.0827 | $X^1$ is chloro, $X^2$ is C—Br, $X^3$ is chloro | trifluoromethyl | trifluoromethoxy | $Y^1$ is N, $Y^2$ is CH, $Y^3$ is CH |
| P.0828 | $X^1$ is chloro, $X^2$ is C—Br, $X^3$ is chloro | trifluoromethyl | trifluoromethyl | $Y^1$ is N, $Y^2$ is CH, $Y^3$ is CH |
| P.0829 | $X^1$ is chloro, $X^2$ is C—F, $X^3$ is chloro | chlorodifluoromethyl | bromo | $Y^1$ is N, $Y^2$ is CH, $Y^3$ is CH |
| P.0830 | $X^1$ is chloro, $X^2$ is C—F, $X^3$ is chloro | chlorodifluoromethyl | chloro | $Y^1$ is N, $Y^2$ is CH, $Y^3$ is CH |
| P.0831 | $X^1$ is chloro, $X^2$ is C—F, $X^3$ is chloro | chlorodifluoromethyl | cyano | $Y^1$ is N, $Y^2$ is CH, $Y^3$ is CH |
| P.0832 | $X^1$ is chloro, $X^2$ is C—F, $X^3$ is chloro | chlorodifluoromethyl | cyclopropyl | $Y^1$ is N, $Y^2$ is CH, $Y^3$ is CH |
| P.0833 | $X^1$ is chloro, $X^2$ is C—F, $X^3$ is chloro | chlorodifluoromethyl | ethyl | $Y^1$ is N, $Y^2$ is CH, $Y^3$ is CH |
| P.0834 | $X^1$ is chloro, $X^2$ is C—F, $X^3$ is chloro | chlorodifluoromethyl | fluoro | $Y^1$ is N, $Y^2$ is CH, $Y^3$ is CH |
| P.0835 | $X^1$ is chloro, $X^2$ is C—F, $X^3$ is chloro | chlorodifluoromethyl | hydrogen | $Y^1$ is N, $Y^2$ is CH, $Y^3$ is CH |
| P.0836 | $X^1$ is chloro, $X^2$ is C—F, $X^3$ is chloro | chlorodifluoromethyl | methoxy | $Y^1$ is N, $Y^2$ is CH, $Y^3$ is CH |
| P.0837 | $X^1$ is chloro, $X^2$ is C—F, $X^3$ is chloro | chlorodifluoromethyl | methyl | $Y^1$ is N, $Y^2$ is CH, $Y^3$ is CH |
| P.0838 | $X^1$ is chloro, $X^2$ is C—F, $X^3$ is chloro | chlorodifluoromethyl | nitro | $Y^1$ is N, $Y^2$ is CH, $Y^3$ is CH |
| P.0839 | $X^1$ is chloro, $X^2$ is C—F, $X^3$ is chloro | chlorodifluoromethyl | trifluoromethoxy | $Y^1$ is N, $Y^2$ is CH, $Y^3$ is CH |
| P.0840 | $X^1$ is chloro, $X^2$ is C—F, $X^3$ is chloro | chlorodifluoromethyl | trifluoromethyl | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.0841 | $X^1$ is chloro, $X^2$ is C—F, $X^3$ is chloro | difluoromethyl | bromo | $Y^1$ is N, $Y^2$ is CH, $Y^3$ is CH |
| P.0842 | $X^1$ is chloro, $X^2$ is C—F, $X^3$ is chloro | difluoromethyl | chloro | $Y^1$ is N, $Y^2$ is CH, $Y^3$ is CH |
| P.0843 | $X^1$ is chloro, $X^2$ is C—F, $X^3$ is chloro | difluoromethyl | cyano | $Y^1$ is N, $Y^2$ is CH, $Y^3$ is CH |
| P.0844 | $X^1$ is chloro, $X^2$ is C—F, $X^3$ is chloro | difluoromethyl | cyclopropyl | $Y^1$ is N, $Y^2$ is CH, $Y^3$ is CH |
| P.0845 | $X^1$ is chloro, $X^2$ is C—F, $X^3$ is chloro | difluoromethyl | ethyl | $Y^1$ is N, $Y^2$ is CH, $Y^3$ is CH |
| P.0846 | $X^1$ is chloro, $X^2$ is C—F, $X^3$ is chloro | difluoromethyl | fluoro | $Y^1$ is N, $Y^2$ is CH, $Y^3$ is CH |
| P.0847 | $X^1$ is chloro, $X^2$ is C—F, $X^3$ is chloro | difluoromethyl | hydrogen | $Y^1$ is N, $Y^2$ is CH, $Y^3$ is CH |
| P.0848 | $X^1$ is chloro, $X^2$ is C—F, $X^3$ is chloro | difluoromethyl | methoxy | $Y^1$ is N, $Y^2$ is CH, $Y^3$ is CH |
| P.0849 | $X^1$ is chloro, $X^2$ is C—F, $X^3$ is chloro | difluoromethyl | methyl | $Y^1$ is N, $Y^2$ is CH, $Y^3$ is CH |
| P.0850 | $X^1$ is chloro, $X^2$ is C—F, $X^3$ is chloro | difluoromethyl | nitro | $Y^1$ is N, $Y^2$ is CH, $Y^3$ is CH |
| P.0851 | $X^1$ is chloro, $X^2$ is C—F, $X^3$ is chloro | difluoromethyl | trifluoromethoxy | $Y^1$ is N, $Y^2$ is CH, $Y^3$ is CH |
| P.0852 | $X^1$ is chloro, $X^2$ is C—F, $X^3$ is chloro | difluoromethyl | trifluoromethyl | $Y^1$ is N, $Y^2$ is CH, $Y^3$ is CH |
| P.0853 | $X^1$ is chloro, $X^2$ is C—F, $X^3$ is chloro | trifluoromethyl | bromo | $Y^1$ is N, $Y^2$ is CH, $Y^3$ is CH |
| P.0854 | $X^1$ is chloro, $X^2$ is C—F, $X^3$ is chloro | trifluoromethyl | chloro | $Y^1$ is N, $Y^2$ is CH, $Y^3$ is CH |
| P.0855 | $X^1$ is chloro, $X^2$ is C—F, $X^3$ is chloro | trifluoromethyl | cyano | $Y^1$ is N, $Y^2$ is CH, $Y^3$ is CH |
| P.0856 | $X^1$ is chloro, $X^2$ is C—F, $X^3$ is chloro | trifluoromethyl | cyclopropyl | $Y^1$ is N, $Y^2$ is CH, $Y^3$ is CH |
| P.0857 | $X^1$ is chloro, $X^2$ is C—F, $X^3$ is chloro | trifluoromethyl | ethyl | $Y^1$ is N, $Y^2$ is CH, $Y^3$ is CH |
| P.0858 | $X^1$ is chloro, $X^2$ is C—F, $X^3$ is chloro | trifluoromethyl | fluoro | $Y^1$ is N, $Y^2$ is CH, $Y^3$ is CH |
| P.0859 | $X^1$ is chloro, $X^2$ is C—F, $X^3$ is chloro | trifluoromethyl | hydrogen | $Y^1$ is N, $Y^2$ is CH, $Y^3$ is CH |
| P.0860 | $X^1$ is chloro, $X^2$ is C—F, $X^3$ is chloro | trifluoromethyl | methoxy | $Y^1$ is N, $Y^2$ is CH, $Y^3$ is CH |
| P.0861 | $X^1$ is chloro, $X^2$ is C—F, $X^3$ is chloro | trifluoromethyl | methyl | $Y^1$ is N, $Y^2$ is CH, $Y^3$ is CH |
| P.0862 | $X^1$ is chloro, $X^2$ is C—F, $X^3$ is chloro | trifluoromethyl | nitro | $Y^1$ is N, $Y^2$ is CH, $Y^3$ is CH |
| P.0863 | $X^1$ is chloro, $X^2$ is C—F, $X^3$ is chloro | trifluoromethyl | trifluoromethoxy | $Y^1$ is N, $Y^2$ is CH, $Y^3$ is CH |
| P.0864 | $X^1$ is chloro, $X^2$ is C—F, $X^3$ is chloro | trifluoromethyl | trifluoromethyl | $Y^1$ is N, $Y^2$ is CH, $Y^3$ is CH |
| P.0865 | $X^1$ is chloro, $X^2$ is C—Cl, $X^3$ is chloro | chlorodifluoromethyl | bromo | $Y^1$ is N, $Y^2$ is CH, $Y^3$ is CH |
| P.0866 | $X^1$ is chloro, $X^2$ is C—Cl, $X^3$ is chloro | chlorodifluoromethyl | chloro | $Y^1$ is N, $Y^2$ is CH, $Y^3$ is CH |
| P.0867 | $X^1$ is chloro, $X^2$ is C—Cl, $X^3$ is chloro | chlorodifluoromethyl | cyano | $Y^1$ is N, $Y^2$ is CH, $Y^3$ is CH |
| P.0868 | $X^1$ is chloro, $X^2$ is C—Cl, $X^3$ is chloro | chlorodifluoromethyl | cyclopropyl | $Y^1$ is N, $Y^2$ is CH, $Y^3$ is CH |
| P.0869 | $X^1$ is chloro, $X^2$ is C—Cl, $X^3$ is chloro | chlorodifluoromethyl | ethyl | $Y^1$ is N, $Y^2$ is CH, $Y^3$ is CH |
| P.0870 | $X^1$ is chloro, $X^2$ is C—Cl, $X^3$ is chloro | chlorodifluoromethyl | fluoro | $Y^1$ is N, $Y^2$ is CH, $Y^3$ is CH |
| P.0871 | $X^1$ is chloro, $X^2$ is C—Cl, $X^3$ is chloro | chlorodifluoromethyl | hydrogen | $Y^1$ is N, $Y^2$ is CH, $Y^3$ is CH |
| P.0872 | $X^1$ is chloro, $X^2$ is C—Cl, $X^3$ is chloro | chlorodifluoromethyl | methoxy | $Y^1$ is N, $Y^2$ is CH, $Y^3$ is CH |
| P.0873 | $X^1$ is chloro, $X^2$ is C—Cl, $X^3$ is chloro | chlorodifluoromethyl | methyl | $Y^1$ is N, $Y^2$ is CH, $Y^3$ is CH |
| P.0874 | $X^1$ is chloro, $X^2$ is C—Cl, $X^3$ is chloro | chlorodifluoromethyl | nitro | $Y^1$ is N, $Y^2$ is CH, $Y^3$ is CH |
| P.0875 | $X^1$ is chloro, $X^2$ is C—Cl, $X^3$ is chloro | chlorodifluoromethyl | trifluoromethoxy | $Y^1$ is N, $Y^2$ is CH, $Y^3$ is CH |
| P.0876 | $X^1$ is chloro, $X^2$ is C—Cl, $X^3$ is chloro | chlorodifluoromethyl | trifluoromethyl | $Y^1$ is N, $Y^2$ is CH, $Y^3$ is CH |
| P.0877 | $X^1$ is chloro, $X^2$ is C—Cl, $X^3$ is chloro | difluoromethyl | bromo | $Y^1$ is N, $Y^2$ is CH, $Y^3$ is CH |
| P.0878 | $X^1$ is chloro, $X^2$ is C—Cl, $X^3$ is chloro | difluoromethyl | chloro | $Y^1$ is N, $Y^2$ is CH, $Y^3$ is CH |
| P.0879 | $X^1$ is chloro, $X^2$ is C—Cl, $X^3$ is chloro | difluoromethyl | cyano | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.0880 | $X^1$ is chloro, $X^2$ is C—Cl, $X^3$ is chloro | difluoromethyl | cyclopropyl | $Y^1$ is N, $Y^2$ is CH, $Y^3$ is CH |
| P.0881 | $X^1$ is chloro, $X^2$ is C—Cl, $X^3$ is chloro | difluoromethyl | ethyl | $Y^1$ is N, $Y^2$ is CH, $Y^3$ is CH |
| P.0882 | $X^1$ is chloro, $X^2$ is C—Cl, $X^3$ is chloro | difluoromethyl | fluoro | $Y^1$ is N, $Y^2$ is CH, $Y^3$ is CH |
| P.0883 | $X^1$ is chloro, $X^2$ is C—Cl, $X^3$ is chloro | difluoromethyl | hydrogen | $Y^1$ is N, $Y^2$ is CH, $Y^3$ is CH |
| P.0884 | $X^1$ is chloro, $X^2$ is C—Cl, $X^3$ is chloro | difluoromethyl | methoxy | $Y^1$ is N, $Y^2$ is CH, $Y^3$ is CH |
| P.0885 | $X^1$ is chloro, $X^2$ is C—Cl, $X^3$ is chloro | difluoromethyl | methyl | $Y^1$ is N, $Y^2$ is CH, $Y^3$ is CH |
| P.0886 | $X^1$ is chloro, $X^2$ is C—Cl, $X^3$ is chloro | difluoromethyl | nitro | $Y^1$ is N, $Y^2$ is CH, $Y^3$ is CH |
| P.0887 | $X^1$ is chloro, $X^2$ is C—Cl, $X^3$ is chloro | difluoromethyl | trifluoromethoxy | $Y^1$ is N, $Y^2$ is CH, $Y^3$ is CH |
| P.0888 | $X^1$ is chloro, $X^2$ is C—Cl, $X^3$ is chloro | difluoromethyl | trifluoromethyl | $Y^1$ is N, $Y^2$ is CH, $Y^3$ is CH |
| P.0889 | $X^1$ is chloro, $X^2$ is C—Cl, $X^3$ is chloro | trifluoromethyl | bromo | $Y^1$ is N, $Y^2$ is CH, $Y^3$ is CH |
| P.0890 | $X^1$ is chloro, $X^2$ is C—Cl, $X^3$ is chloro | trifluoromethyl | chloro | $Y^1$ is N, $Y^2$ is CH, $Y^3$ is CH |
| P.0891 | $X^1$ is chloro, $X^2$ is C—Cl, $X^3$ is chloro | trifluoromethyl | cyano | $Y^1$ is N, $Y^2$ is CH, $Y^3$ is CH |
| P.0892 | $X^1$ is chloro, $X^2$ is C—Cl, $X^3$ is chloro | trifluoromethyl | cyclopropyl | $Y^1$ is N, $Y^2$ is CH, $Y^3$ is CH |
| P.0893 | $X^1$ is chloro, $X^2$ is C—Cl, $X^3$ is chloro | trifluoromethyl | ethyl | $Y^1$ is N, $Y^2$ is CH, $Y^3$ is CH |
| P.0894 | $X^1$ is chloro, $X^2$ is C—Cl, $X^3$ is chloro | trifluoromethyl | fluoro | $Y^1$ is N, $Y^2$ is CH, $Y^3$ is CH |
| P.0895 | $X^1$ is chloro, $X^2$ is C—Cl, $X^3$ is chloro | trifluoromethyl | hydrogen | $Y^1$ is N, $Y^2$ is CH, $Y^3$ is CH |
| P.0896 | $X^1$ is chloro, $X^2$ is C—Cl, $X^3$ is chloro | trifluoromethyl | methoxy | $Y^1$ is N, $Y^2$ is CH, $Y^3$ is CH |
| P.0897 | $X^1$ is chloro, $X^2$ is C—Cl, $X^3$ is chloro | trifluoromethyl | methyl | $Y^1$ is N, $Y^2$ is CH, $Y^3$ is CH |
| P.0898 | $X^1$ is chloro, $X^2$ is C—Cl, $X^3$ is chloro | trifluoromethyl | nitro | $Y^1$ is N, $Y^2$ is CH, $Y^3$ is CH |
| P.0899 | $X^1$ is chloro, $X^2$ is C—Cl, $X^3$ is chloro | trifluoromethyl | trifluoromethoxy | $Y^1$ is N, $Y^2$ is CH, $Y^3$ is CH |
| P.0900 | $X^1$ is chloro, $X^2$ is C—Cl, $X^3$ is chloro | trifluoromethyl | trifluoromethyl | $Y^1$ is N, $Y^2$ is CH, $Y^3$ is CH |
| P.0901 | $X^1$ is chloro, $X^2$ is C—I, $X^3$ is chloro | chlorodifluoromethyl | bromo | $Y^1$ is N, $Y^2$ is CH, $Y^3$ is CH |
| P.0902 | $X^1$ is chloro, $X^2$ is C—I, $X^3$ is chloro | chlorodifluoromethyl | chloro | $Y^1$ is N, $Y^2$ is CH, $Y^3$ is CH |
| P.0903 | $X^1$ is chloro, $X^2$ is C—I, $X^3$ is chloro | chlorodifluoromethyl | cyano | $Y^1$ is N, $Y^2$ is CH, $Y^3$ is CH |
| P.0904 | $X^1$ is chloro, $X^2$ is C—I, $X^3$ is chloro | chlorodifluoromethyl | cyclopropyl | $Y^1$ is N, $Y^2$ is CH, $Y^3$ is CH |
| P.0905 | $X^1$ is chloro, $X^2$ is C—I, $X^3$ is chloro | chlorodifluoromethyl | ethyl | $Y^1$ is N, $Y^2$ is CH, $Y^3$ is CH |
| P.0906 | $X^1$ is chloro, $X^2$ is C—I, $X^3$ is chloro | chlorodifluoromethyl | fluoro | $Y^1$ is N, $Y^2$ is CH, $Y^3$ is CH |
| P.0907 | $X^1$ is chloro, $X^2$ is C—I, $X^3$ is chloro | chlorodifluoromethyl | hydrogen | $Y^1$ is N, $Y^2$ is CH, $Y^3$ is CH |
| P.0908 | $X^1$ is chloro, $X^2$ is C—I, $X^3$ is chloro | chlorodifluoromethyl | methoxy | $Y^1$ is N, $Y^2$ is CH, $Y^3$ is CH |
| P.0909 | $X^1$ is chloro, $X^2$ is C—I, $X^3$ is chloro | chlorodifluoromethyl | methyl | $Y^1$ is N, $Y^2$ is CH, $Y^3$ is CH |
| P.0910 | $X^1$ is chloro, $X^2$ is C—I, $X^3$ is chloro | chlorodifluoromethyl | nitro | $Y^1$ is N, $Y^2$ is CH, $Y^3$ is CH |
| P.0911 | $X^1$ is chloro, $X^2$ is C—I, $X^3$ is chloro | chlorodifluoromethyl | trifluoromethoxy | $Y^1$ is N, $Y^2$ is CH, $Y^3$ is CH |
| P.0912 | $X^1$ is chloro, $X^2$ is C—I, $X^3$ is chloro | chlorodifluoromethyl | trifluoromethyl | $Y^1$ is N, $Y^2$ is CH, $Y^3$ is CH |
| P.0913 | $X^1$ is chloro, $X^2$ is C—I, $X^3$ is chloro | difluoromethyl | bromo | $Y^1$ is N, $Y^2$ is CH, $Y^3$ is CH |
| P.0914 | $X^1$ is chloro, $X^2$ is C—I, $X^3$ is chloro | difluoromethyl | chloro | $Y^1$ is N, $Y^2$ is CH, $Y^3$ is CH |
| P.0915 | $X^1$ is chloro, $X^2$ is C—I, $X^3$ is chloro | difluoromethyl | cyano | $Y^1$ is N, $Y^2$ is CH, $Y^3$ is CH |
| P.0916 | $X^1$ is chloro, $X^2$ is C—I, $X^3$ is chloro | difluoromethyl | cyclopropyl | $Y^1$ is N, $Y^2$ is CH, $Y^3$ is CH |
| P.0917 | $X^1$ is chloro, $X^2$ is C—I, $X^3$ is chloro | difluoromethyl | ethyl | $Y^1$ is N, $Y^2$ is CH, $Y^3$ is CH |
| P.0918 | $X^1$ is chloro, $X^2$ is C—I, $X^3$ is chloro | difluoromethyl | fluoro | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.0919 | $X^1$ is chloro, $X^2$ is C—I, $X^3$ is chloro | difluoromethyl | hydrogen | $Y^1$ is N, $Y^2$ is CH, $Y^3$ is CH |
| P.0920 | $X^1$ is chloro, $X^2$ is C—I, $X^3$ is chloro | difluoromethyl | methoxy | $Y^1$ is N, $Y^2$ is CH, $Y^3$ is CH |
| P.0921 | $X^1$ is chloro, $X^2$ is C—I, $X^3$ is chloro | difluoromethyl | methyl | $Y^1$ is N, $Y^2$ is CH, $Y^3$ is CH |
| P.0922 | $X^1$ is chloro, $X^2$ is C—I, $X^3$ is chloro | difluoromethyl | nitro | $Y^1$ is N, $Y^2$ is CH, $Y^3$ is CH |
| P.0923 | $X^1$ is chloro, $X^2$ is C—I, $X^3$ is chloro | difluoromethyl | trifluoromethoxy | $Y^1$ is N, $Y^2$ is CH, $Y^3$ is CH |
| P.0924 | $X^1$ is chloro, $X^2$ is C—I, $X^3$ is chloro | difluoromethyl | trifluoromethyl | $Y^1$ is N, $Y^2$ is CH, $Y^3$ is CH |
| P.0925 | $X^1$ is chloro, $X^2$ is C—I, $X^3$ is chloro | trifluoromethyl | bromo | $Y^1$ is N, $Y^2$ is CH, $Y^3$ is CH |
| P.0926 | $X^1$ is chloro, $X^2$ is C—I, $X^3$ is chloro | trifluoromethyl | chloro | $Y^1$ is N, $Y^2$ is CH, $Y^3$ is CH |
| P.0927 | $X^1$ is chloro, $X^2$ is C—I, $X^3$ is chloro | trifluoromethyl | cyano | $Y^1$ is N, $Y^2$ is CH, $Y^3$ is CH |
| P.0928 | $X^1$ is chloro, $X^2$ is C—I, $X^3$ is chloro | trifluoromethyl | cyclopropyl | $Y^1$ is N, $Y^2$ is CH, $Y^3$ is CH |
| P.0929 | $X^1$ is chloro, $X^2$ is C—I, $X^3$ is chloro | trifluoromethyl | ethyl | $Y^1$ is N, $Y^2$ is CH, $Y^3$ is CH |
| P.0930 | $X^1$ is chloro, $X^2$ is C—I, $X^3$ is chloro | trifluoromethyl | fluoro | $Y^1$ is N, $Y^2$ is CH, $Y^3$ is CH |
| P.0931 | $X^1$ is chloro, $X^2$ is C—I, $X^3$ is chloro | trifluoromethyl | hydrogen | $Y^1$ is N, $Y^2$ is CH, $Y^3$ is CH |
| P.0932 | $X^1$ is chloro, $X^2$ is C—I, $X^3$ is chloro | trifluoromethyl | methoxy | $Y^1$ is N, $Y^2$ is CH, $Y^3$ is CH |
| P.0933 | $X^1$ is chloro, $X^2$ is C—I, $X^3$ is chloro | trifluoromethyl | methyl | $Y^1$ is N, $Y^2$ is CH, $Y^3$ is CH |
| P.0934 | $X^1$ is chloro, $X^2$ is C—I, $X^3$ is chloro | trifluoromethyl | nitro | $Y^1$ is N, $Y^2$ is CH, $Y^3$ is CH |
| P.0935 | $X^1$ is chloro, $X^2$ is C—I, $X^3$ is chloro | trifluoromethyl | trifluoromethoxy | $Y^1$ is N, $Y^2$ is CH, $Y^3$ is CH |
| P.0936 | $X^1$ is chloro, $X^2$ is C—I, $X^3$ is chloro | trifluoromethyl | trifluoromethyl | $Y^1$ is N, $Y^2$ is CH, $Y^3$ is CH |
| P.0937 | $X^1$ is fluoro, $X^2$ is C—F, $X^3$ is fluoro | chlorodifluoromethyl | bromo | $Y^1$ is N, $Y^2$ is CH, $Y^3$ is CH |
| P.0938 | $X^1$ is fluoro, $X^2$ is C—F, $X^3$ is fluoro | chlorodifluoromethyl | chloro | $Y^1$ is N, $Y^2$ is CH, $Y^3$ is CH |
| P.0939 | $X^1$ is fluoro, $X^2$ is C—F, $X^3$ is fluoro | chlorodifluoromethyl | cyano | $Y^1$ is N, $Y^2$ is CH, $Y^3$ is CH |
| P.0940 | $X^1$ is fluoro, $X^2$ is C—F, $X^3$ is fluoro | chlorodifluoromethyl | cyclopropyl | $Y^1$ is N, $Y^2$ is CH, $Y^3$ is CH |
| P.0941 | $X^1$ is fluoro, $X^2$ is C—F, $X^3$ is fluoro | chlorodifluoromethyl | ethyl | $Y^1$ is N, $Y^2$ is CH, $Y^3$ is CH |
| P.0942 | $X^1$ is fluoro, $X^2$ is C—F, $X^3$ is fluoro | chlorodifluoromethyl | fluoro | $Y^1$ is N, $Y^2$ is CH, $Y^3$ is CH |
| P.0943 | $X^1$ is fluoro, $X^2$ is C—F, $X^3$ is fluoro | chlorodifluoromethyl | hydrogen | $Y^1$ is N, $Y^2$ is CH, $Y^3$ is CH |
| P.0944 | $X^1$ is fluoro, $X^2$ is C—F, $X^3$ is fluoro | chlorodifluoromethyl | methoxy | $Y^1$ is N, $Y^2$ is CH, $Y^3$ is CH |
| P.0945 | $X^1$ is fluoro, $X^2$ is C—F, $X^3$ is fluoro | chlorodifluoromethyl | methyl | $Y^1$ is N, $Y^2$ is CH, $Y^3$ is CH |
| P.0946 | $X^1$ is fluoro, $X^2$ is C—F, $X^3$ is fluoro | chlorodifluoromethyl | nitro | $Y^1$ is N, $Y^2$ is CH, $Y^3$ is CH |
| P.0947 | $X^1$ is fluoro, $X^2$ is C—F, $X^3$ is fluoro | chlorodifluoromethyl | trifluoromethoxy | $Y^1$ is N, $Y^2$ is CH, $Y^3$ is CH |
| P.0948 | $X^1$ is fluoro, $X^2$ is C—F, $X^3$ is fluoro | chlorodifluoromethyl | trifluoromethyl | $Y^1$ is N, $Y^2$ is CH, $Y^3$ is CH |
| P.0949 | $X^1$ is fluoro, $X^2$ is C—F, $X^3$ is fluoro | difluoromethyl | bromo | $Y^1$ is N, $Y^2$ is CH, $Y^3$ is CH |
| P.0950 | $X^1$ is fluoro, $X^2$ is C—F, $X^3$ is fluoro | difluoromethyl | chloro | $Y^1$ is N, $Y^2$ is CH, $Y^3$ is CH |
| P.0951 | $X^1$ is fluoro, $X^2$ is C—F, $X^3$ is fluoro | difluoromethyl | cyano | $Y^1$ is N, $Y^2$ is CH, $Y^3$ is CH |
| P.0952 | $X^1$ is fluoro, $X^2$ is C—F, $X^3$ is fluoro | difluoromethyl | cyclopropyl | $Y^1$ is N, $Y^2$ is CH, $Y^3$ is CH |
| P.0953 | $X^1$ is fluoro, $X^2$ is C—F, $X^3$ is fluoro | difluoromethyl | ethyl | $Y^1$ is N, $Y^2$ is CH, $Y^3$ is CH |
| P.0954 | $X^1$ is fluoro, $X^2$ is C—F, $X^3$ is fluoro | difluoromethyl | fluoro | $Y^1$ is N, $Y^2$ is CH, $Y^3$ is CH |
| P.0955 | $X^1$ is fluoro, $X^2$ is C—F, $X^3$ is fluoro | difluoromethyl | hydrogen | $Y^1$ is N, $Y^2$ is CH, $Y^3$ is CH |
| P.0956 | $X^1$ is fluoro, $X^2$ is C—F, $X^3$ is fluoro | difluoromethyl | methoxy | $Y^1$ is N, $Y^2$ is CH, $Y^3$ is CH |
| P.0957 | $X^1$ is fluoro, $X^2$ is C—F, $X^3$ is fluoro | difluoromethyl | methyl | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.0958 | X$^1$ is fluoro, X$^2$ is C—F, X$^3$ is fluoro | difluoromethyl | nitro | Y$^1$ is N, Y$^2$ is CH, Y$^3$ is CH |
| P.0959 | X$^1$ is fluoro, X$^2$ is C—F, X$^3$ is fluoro | difluoromethyl | trifluoromethoxy | Y$^1$ is N, Y$^2$ is CH, Y$^3$ is CH |
| P.0960 | X$^1$ is fluoro, X$^2$ is C—F, X$^3$ is fluoro | difluoromethyl | trifluoromethyl | Y$^1$ is N, Y$^2$ is CH, Y$^3$ is CH |
| P.0961 | X$^1$ is fluoro, X$^2$ is C—F, X$^3$ is fluoro | trifluoromethyl | bromo | Y$^1$ is N, Y$^2$ is CH, Y$^3$ is CH |
| P.0962 | X$^1$ is fluoro, X$^2$ is C—F, X$^3$ is fluoro | trifluoromethyl | chloro | Y$^1$ is N, Y$^2$ is CH, Y$^3$ is CH |
| P.0963 | X$^1$ is fluoro, X$^2$ is C—F, X$^3$ is fluoro | trifluoromethyl | cyano | Y$^1$ is N, Y$^2$ is CH, Y$^3$ is CH |
| P.0964 | X$^1$ is fluoro, X$^2$ is C—F, X$^3$ is fluoro | trifluoromethyl | cyclopropyl | Y$^1$ is N, Y$^2$ is CH, Y$^3$ is CH |
| P.0965 | X$^1$ is fluoro, X$^2$ is C—F, X$^3$ is fluoro | trifluoromethyl | ethyl | Y$^1$ is N, Y$^2$ is CH, Y$^3$ is CH |
| P.0966 | X$^1$ is fluoro, X$^2$ is C—F, X$^3$ is fluoro | trifluoromethyl | fluoro | Y$^1$ is N, Y$^2$ is CH, Y$^3$ is CH |
| P.0967 | X$^1$ is fluoro, X$^2$ is C—F, X$^3$ is fluoro | trifluoromethyl | hydrogen | Y$^1$ is N, Y$^2$ is CH, Y$^3$ is CH |
| P.0968 | X$^1$ is fluoro, X$^2$ is C—F, X$^3$ is fluoro | trifluoromethyl | methoxy | Y$^1$ is N, Y$^2$ is CH, Y$^3$ is CH |
| P.0969 | X$^1$ is fluoro, X$^2$ is C—F, X$^3$ is fluoro | trifluoromethyl | methyl | Y$^1$ is N, Y$^2$ is CH, Y$^3$ is CH |
| P.0970 | X$^1$ is fluoro, X$^2$ is C—F, X$^3$ is fluoro | trifluoromethyl | nitro | Y$^1$ is N, Y$^2$ is CH, Y$^3$ is CH |
| P.0971 | X$^1$ is fluoro, X$^2$ is C—F, X$^3$ is fluoro | trifluoromethyl | trifluoromethoxy | Y$^1$ is N, Y$^2$ is CH, Y$^3$ is CH |
| P.0972 | X$^1$ is fluoro, X$^2$ is C—F, X$^3$ is fluoro | trifluoromethyl | trifluoromethyl | Y$^1$ is N, Y$^2$ is CH, Y$^3$ is CH |
| P.0973 | X$^1$ is chloro, X$^2$ is CH, X$^3$ is bromo | chlorodifluoromethyl | bromo | Y$^1$ is N, Y$^2$ is CH, Y$^3$ is CH |
| P.0974 | X$^1$ is chloro, X$^2$ is CH, X$^3$ is bromo | chlorodifluoromethyl | chloro | Y$^1$ is N, Y$^2$ is CH, Y$^3$ is CH |
| P.0975 | X$^1$ is chloro, X$^2$ is CH, X$^3$ is bromo | chlorodifluoromethyl | cyano | Y$^1$ is N, Y$^2$ is CH, Y$^3$ is CH |
| P.0976 | X$^1$ is chloro, X$^2$ is CH, X$^3$ is bromo | chlorodifluoromethyl | cyclopropyl | Y$^1$ is N, Y$^2$ is CH, Y$^3$ is CH |
| P.0977 | X$^1$ is chloro, X$^2$ is CH, X$^3$ is bromo | chlorodifluoromethyl | ethyl | Y$^1$ is N, Y$^2$ is CH, Y$^3$ is CH |
| P.0978 | X$^1$ is chloro, X$^2$ is CH, X$^3$ is bromo | chlorodifluoromethyl | fluoro | Y$^1$ is N, Y$^2$ is CH, Y$^3$ is CH |
| P.0979 | X$^1$ is chloro, X$^2$ is CH, X$^3$ is bromo | chlorodifluoromethyl | hydrogen | Y$^1$ is N, Y$^2$ is CH, Y$^3$ is CH |
| P.0980 | X$^1$ is chloro, X$^2$ is CH, X$^3$ is bromo | chlorodifluoromethyl | methoxy | Y$^1$ is N, Y$^2$ is CH, Y$^3$ is CH |
| P.0981 | X$^1$ is chloro, X$^2$ is CH, X$^3$ is bromo | chlorodifluoromethyl | methyl | Y$^1$ is N, Y$^2$ is CH, Y$^3$ is CH |
| P.0982 | X$^1$ is chloro, X$^2$ is CH, X$^3$ is bromo | chlorodifluoromethyl | nitro | Y$^1$ is N, Y$^2$ is CH, Y$^3$ is CH |
| P.0983 | X$^1$ is chloro, X$^2$ is CH, X$^3$ is bromo | chlorodifluoromethyl | trifluoromethoxy | Y$^1$ is N, Y$^2$ is CH, Y$^3$ is CH |
| P.0984 | X$^1$ is chloro, X$^2$ is CH, X$^3$ is bromo | chlorodifluoromethyl | trifluoromethyl | Y$^1$ is N, Y$^2$ is CH, Y$^3$ is CH |
| P.0985 | X$^1$ is chloro, X$^2$ is CH, X$^3$ is bromo | difluoromethyl | bromo | Y$^1$ is N, Y$^2$ is CH, Y$^3$ is CH |
| P.0986 | X$^1$ is chloro, X$^2$ is CH, X$^3$ is bromo | difluoromethyl | chloro | Y$^1$ is N, Y$^2$ is CH, Y$^3$ is CH |
| P.0987 | X$^1$ is chloro, X$^2$ is CH, X$^3$ is bromo | difluoromethyl | cyano | Y$^1$ is N, Y$^2$ is CH, Y$^3$ is CH |
| P.0988 | X$^1$ is chloro, X$^2$ is CH, X$^3$ is bromo | difluoromethyl | cyclopropyl | Y$^1$ is N, Y$^2$ is CH, Y$^3$ is CH |
| P.0989 | X$^1$ is chloro, X$^2$ is CH, X$^3$ is bromo | difluoromethyl | ethyl | Y$^1$ is N, Y$^2$ is CH, Y$^3$ is CH |
| P.0990 | X$^1$ is chloro, X$^2$ is CH, X$^3$ is bromo | difluoromethyl | fluoro | Y$^1$ is N, Y$^2$ is CH, Y$^3$ is CH |
| P.0991 | X$^1$ is chloro, X$^2$ is CH, X$^3$ is bromo | difluoromethyl | hydrogen | Y$^1$ is N, Y$^2$ is CH, Y$^3$ is CH |
| P.0992 | X$^1$ is chloro, X$^2$ is CH, X$^3$ is bromo | difluoromethyl | methoxy | Y$^1$ is N, Y$^2$ is CH, Y$^3$ is CH |
| P.0993 | X$^1$ is chloro, X$^2$ is CH, X$^3$ is bromo | difluoromethyl | methyl | Y$^1$ is N, Y$^2$ is CH, Y$^3$ is CH |
| P.0994 | X$^1$ is chloro, X$^2$ is CH, X$^3$ is bromo | difluoromethyl | nitro | Y$^1$ is N, Y$^2$ is CH, Y$^3$ is CH |
| P.0995 | X$^1$ is chloro, X$^2$ is CH, X$^3$ is bromo | difluoromethyl | trifluoromethoxy | Y$^1$ is N, Y$^2$ is CH, Y$^3$ is CH |
| P.0996 | X$^1$ is chloro, X$^2$ is CH, X$^3$ is bromo | difluoromethyl | trifluoromethyl | Y$^1$ is N, Y$^2$ is CH, Y$^3$ is CH |

TABLE P-continued

| | X1, X2, X3 | X4 | R5 | Y1, Y2, Y3 |
|---|---|---|---|---|
| P.0997 | $X^1$ is chloro, $X^2$ is CH, $X^3$ is bromo | trifluoromethyl | bromo | $Y^1$ is N, $Y^2$ is CH, $Y^3$ is CH |
| P.0998 | $X^1$ is chloro, $X^2$ is CH, $X^3$ is bromo | trifluoromethyl | chloro | $Y^1$ is N, $Y^2$ is CH, $Y^3$ is CH |
| P.0999 | $X^1$ is chloro, $X^2$ is CH, $X^3$ is bromo | trifluoromethyl | cyano | $Y^1$ is N, $Y^2$ is CH, $Y^3$ is CH |
| P.1000 | $X^1$ is chloro, $X^2$ is CH, $X^3$ is bromo | trifluoromethyl | cyclopropyl | $Y^1$ is N, $Y^2$ is CH, $Y^3$ is CH |
| P.1001 | $X^1$ is chloro, $X^2$ is CH, $X^3$ is bromo | trifluoromethyl | ethyl | $Y^1$ is N, $Y^2$ is CH, $Y^3$ is CH |
| P.1002 | $X^1$ is chloro, $X^2$ is CH, $X^3$ is bromo | trifluoromethyl | fluoro | $Y^1$ is N, $Y^2$ is CH, $Y^3$ is CH |
| P.1003 | $X^1$ is chloro, $X^2$ is CH, $X^3$ is bromo | trifluoromethyl | hydrogen | $Y^1$ is N, $Y^2$ is CH, $Y^3$ is CH |
| P.1004 | $X^1$ is chloro, $X^2$ is CH, $X^3$ is bromo | trifluoromethyl | methoxy | $Y^1$ is N, $Y^2$ is CH, $Y^3$ is CH |
| P.1005 | $X^1$ is chloro, $X^2$ is CH, $X^3$ is bromo | trifluoromethyl | methyl | $Y^1$ is N, $Y^2$ is CH, $Y^3$ is CH |
| P.1006 | $X^1$ is chloro, $X^2$ is CH, $X^3$ is bromo | trifluoromethyl | nitro | $Y^1$ is N, $Y^2$ is CH, $Y^3$ is CH |
| P.1007 | $X^1$ is chloro, $X^2$ is CH, $X^3$ is bromo | trifluoromethyl | trifluoromethoxy | $Y^1$ is N, $Y^2$ is CH, $Y^3$ is CH |
| P.1008 | $X^1$ is chloro, $X^2$ is CH, $X^3$ is bromo | trifluoromethyl | trifluoromethyl | $Y^1$ is N, $Y^2$ is CH, $Y^3$ is CH |
| P.1009 | $X^1$ is chloro, $X^2$ is CH, $X^3$ is bromo | chlorodifluoromethyl | bromo | $Y^1$ is N, $Y^2$ is CH, $Y^3$ is CH |
| P.1010 | $X^1$ is chloro, $X^2$ is CH, $X^3$ is bromo | chlorodifluoromethyl | chloro | $Y^1$ is N, $Y^2$ is CH, $Y^3$ is CH |
| P.1011 | $X^1$ is chloro, $X^2$ is CH, $X^3$ is bromo | chlorodifluoromethyl | cyano | $Y^1$ is N, $Y^2$ is CH, $Y^3$ is CH |
| P.1012 | $X^1$ is chloro, $X^2$ is CH, $X^3$ is bromo | chlorodifluoromethyl | cyclopropyl | $Y^1$ is N, $Y^2$ is CH, $Y^3$ is CH |
| P.1013 | $X^1$ is chloro, $X^2$ is CH, $X^3$ is bromo | chlorodifluoromethyl | ethyl | $Y^1$ is N, $Y^2$ is CH, $Y^3$ is CH |
| P.1014 | $X^1$ is chloro, $X^2$ is CH, $X^3$ is bromo | chlorodifluoromethyl | fluoro | $Y^1$ is N, $Y^2$ is CH, $Y^3$ is CH |
| P.1015 | $X^1$ is chloro, $X^2$ is CH, $X^3$ is bromo | chlorodifluoromethyl | hydrogen | $Y^1$ is N, $Y^2$ is CH, $Y^3$ is CH |
| P.1016 | $X^1$ is chloro, $X^2$ is CH, $X^3$ is bromo | chlorodifluoromethyl | methoxy | $Y^1$ is N, $Y^2$ is CH, $Y^3$ is CH |
| P.1017 | $X^1$ is chloro, $X^2$ is CH, $X^3$ is bromo | chlorodifluoromethyl | methyl | $Y^1$ is N, $Y^2$ is CH, $Y^3$ is CH |
| P.1018 | $X^1$ is chloro, $X^2$ is CH, $X^3$ is bromo | chlorodifluoromethyl | nitro | $Y^1$ is N, $Y^2$ is CH, $Y^3$ is CH |
| P.1019 | $X^1$ is chloro, $X^2$ is CH, $X^3$ is bromo | chlorodifluoromethyl | trifluoromethoxy | $Y^1$ is N, $Y^2$ is CH, $Y^3$ is CH |
| P.1020 | $X^1$ is chloro, $X^2$ is CH, $X^3$ is bromo | chlorodifluoromethyl | trifluoromethyl | $Y^1$ is N, $Y^2$ is CH, $Y^3$ is CH |
| P.1021 | $X^1$ is chloro, $X^2$ is CH, $X^3$ is bromo | difluoromethyl | bromo | $Y^1$ is N, $Y^2$ is CH, $Y^3$ is CH |
| P.1022 | $X^1$ is chloro, $X^2$ is CH, $X^3$ is bromo | difluoromethyl | chloro | $Y^1$ is N, $Y^2$ is CH, $Y^3$ is CH |
| P.1023 | $X^1$ is chloro, $X^2$ is CH, $X^3$ is bromo | difluoromethyl | cyano | $Y^1$ is N, $Y^2$ is CH, $Y^3$ is CH |
| P.1024 | $X^1$ is chloro, $X^2$ is CH, $X^3$ is bromo | difluoromethyl | cyclopropyl | $Y^1$ is N, $Y^2$ is CH, $Y^3$ is CH |
| P.1025 | $X^1$ is chloro, $X^2$ is CH, $X^3$ is bromo | difluoromethyl | ethyl | $Y^1$ is N, $Y^2$ is CH, $Y^3$ is CH |
| P.1026 | $X^1$ is chloro, $X^2$ is CH, $X^3$ is bromo | difluoromethyl | fluoro | $Y^1$ is N, $Y^2$ is CH, $Y^3$ is CH |
| P.1027 | $X^1$ is chloro, $X^2$ is CH, $X^3$ is bromo | difluoromethyl | hydrogen | $Y^1$ is N, $Y^2$ is CH, $Y^3$ is CH |
| P.1028 | $X^1$ is chloro, $X^2$ is CH, $X^3$ is bromo | difluoromethyl | methoxy | $Y^1$ is N, $Y^2$ is CH, $Y^3$ is CH |
| P.1029 | $X^1$ is chloro, $X^2$ is CH, $X^3$ is bromo | difluoromethyl | methyl | $Y^1$ is N, $Y^2$ is CH, $Y^3$ is CH |
| P.1030 | $X^1$ is chloro, $X^2$ is CH, $X^3$ is bromo | difluoromethyl | nitro | $Y^1$ is N, $Y^2$ is CH, $Y^3$ is CH |
| P.1031 | $X^1$ is chloro, $X^2$ is CH, $X^3$ is bromo | difluoromethyl | trifluoromethoxy | $Y^1$ is N, $Y^2$ is CH, $Y^3$ is CH |
| P.1032 | $X^1$ is chloro, $X^2$ is CH, $X^3$ is bromo | difluoromethyl | trifluoromethyl | $Y^1$ is N, $Y^2$ is CH, $Y^3$ is CH |
| P.1033 | $X^1$ is chloro, $X^2$ is CH, $X^3$ is bromo | trifluoromethyl | bromo | $Y^1$ is N, $Y^2$ is CH, $Y^3$ is CH |
| P.1034 | $X^1$ is chloro, $X^2$ is CH, $X^3$ is bromo | trifluoromethyl | chloro | $Y^1$ is N, $Y^2$ is CH, $Y^3$ is CH |
| P.1035 | $X^1$ is chloro, $X^2$ is CH, $X^3$ is bromo | trifluoromethyl | cyano | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.1036 | $X^1$ is chloro, $X^2$ is CH, $X^3$ is bromo | trifluoromethyl | cyclopropyl | $Y^1$ is N, $Y^2$ is CH, $Y^3$ is CH |
| P.1037 | $X^1$ is chloro, $X^2$ is CH, $X^3$ is bromo | trifluoromethyl | ethyl | $Y^1$ is N, $Y^2$ is CH, $Y^3$ is CH |
| P.1038 | $X^1$ is chloro, $X^2$ is CH, $X^3$ is bromo | trifluoromethyl | fluoro | $Y^1$ is N, $Y^2$ is CH, $Y^3$ is CH |
| P.1039 | $X^1$ is chloro, $X^2$ is CH, $X^3$ is bromo | trifluoromethyl | hydrogen | $Y^1$ is N, $Y^2$ is CH, $Y^3$ is CH |
| P.1040 | $X^1$ is chloro, $X^2$ is CH, $X^3$ is bromo | trifluoromethyl | methoxy | $Y^1$ is N, $Y^2$ is CH, $Y^3$ is CH |
| P.1041 | $X^1$ is chloro, $X^2$ is CH, $X^3$ is bromo | trifluoromethyl | methyl | $Y^1$ is N, $Y^2$ is CH, $Y^3$ is CH |
| P.1042 | $X^1$ is chloro, $X^2$ is CH, $X^3$ is bromo | trifluoromethyl | nitro | $Y^1$ is N, $Y^2$ is CH, $Y^3$ is CH |
| P.1043 | $X^1$ is chloro, $X^2$ is CH, $X^3$ is bromo | trifluoromethyl | trifluoromethoxy | $Y^1$ is N, $Y^2$ is CH, $Y^3$ is CH |
| P.1044 | $X^1$ is chloro, $X^2$ is CH, $X^3$ is bromo | trifluoromethyl | trifluoromethyl | $Y^1$ is N, $Y^2$ is CH, $Y^3$ is CH |
| P.1045 | $X^1$ is chloro, $X^2$ is CH, $X^3$ is bromo | chlorodifluoromethyl | bromo | $Y^1$ is N, $Y^2$ is CH, $Y^3$ is CH |
| P.1046 | $X^1$ is chloro, $X^2$ is CH, $X^3$ is bromo | chlorodifluoromethyl | chloro | $Y^1$ is N, $Y^2$ is CH, $Y^3$ is CH |
| P.1047 | $X^1$ is chloro, $X^2$ is CH, $X^3$ is bromo | chlorodifluoromethyl | cyano | $Y^1$ is N, $Y^2$ is CH, $Y^3$ is CH |
| P.1048 | $X^1$ is chloro, $X^2$ is CH, $X^3$ is bromo | chlorodifluoromethyl | cyclopropyl | $Y^1$ is N, $Y^2$ is CH, $Y^3$ is CH |
| P.1049 | $X^1$ is chloro, $X^2$ is CH, $X^3$ is bromo | chlorodifluoromethyl | ethyl | $Y^1$ is N, $Y^2$ is CH, $Y^3$ is CH |
| P.1050 | $X^1$ is chloro, $X^2$ is CH, $X^3$ is bromo | chlorodifluoromethyl | fluoro | $Y^1$ is N, $Y^2$ is CH, $Y^3$ is CH |
| P.1051 | $X^1$ is chloro, $X^2$ is CH, $X^3$ is bromo | chlorodifluoromethyl | hydrogen | $Y^1$ is N, $Y^2$ is CH, $Y^3$ is CH |
| P.1052 | $X^1$ is chloro, $X^2$ is CH, $X^3$ is bromo | chlorodifluoromethyl | methoxy | $Y^1$ is N, $Y^2$ is CH, $Y^3$ is CH |
| P.1053 | $X^1$ is chloro, $X^2$ is CH, $X^3$ is bromo | chlorodifluoromethyl | methyl | $Y^1$ is N, $Y^2$ is CH, $Y^3$ is CH |
| P.1054 | $X^1$ is chloro, $X^2$ is CH, $X^3$ is bromo | chlorodifluoromethyl | nitro | $Y^1$ is N, $Y^2$ is CH, $Y^3$ is CH |
| P.1055 | $X^1$ is chloro, $X^2$ is CH, $X^3$ is bromo | chlorodifluoromethyl | trifluoromethoxy | $Y^1$ is N, $Y^2$ is CH, $Y^3$ is CH |
| P.1056 | $X^1$ is chloro, $X^2$ is CH, $X^3$ is bromo | chlorodifluoromethyl | trifluoromethyl | $Y^1$ is N, $Y^2$ is CH, $Y^3$ is CH |
| P.1057 | $X^1$ is chloro, $X^2$ is CH, $X^3$ is bromo | difluoromethyl | bromo | $Y^1$ is N, $Y^2$ is CH, $Y^3$ is CH |
| P.1058 | $X^1$ is chloro, $X^2$ is CH, $X^3$ is bromo | difluoromethyl | chloro | $Y^1$ is N, $Y^2$ is CH, $Y^3$ is CH |
| P.1059 | $X^1$ is chloro, $X^2$ is CH, $X^3$ is bromo | difluoromethyl | cyano | $Y^1$ is N, $Y^2$ is CH, $Y^3$ is CH |
| P.1060 | $X^1$ is chloro, $X^2$ is CH, $X^3$ is bromo | difluoromethyl | cyclopropyl | $Y^1$ is N, $Y^2$ is CH, $Y^3$ is CH |
| P.1061 | $X^1$ is chloro, $X^2$ is CH, $X^3$ is bromo | difluoromethyl | ethyl | $Y^1$ is N, $Y^2$ is CH, $Y^3$ is CH |
| P.1062 | $X^1$ is chloro, $X^2$ is CH, $X^3$ is bromo | difluoromethyl | fluoro | $Y^1$ is N, $Y^2$ is CH, $Y^3$ is CH |
| P.1063 | $X^1$ is chloro, $X^2$ is CH, $X^3$ is bromo | difluoromethyl | hydrogen | $Y^1$ is N, $Y^2$ is CH, $Y^3$ is CH |
| P.1064 | $X^1$ is chloro, $X^2$ is CH, $X^3$ is bromo | difluoromethyl | methoxy | $Y^1$ is N, $Y^2$ is CH, $Y^3$ is CH |
| P.1065 | $X^1$ is chloro, $X^2$ is CH, $X^3$ is bromo | difluoromethyl | methyl | $Y^1$ is N, $Y^2$ is CH, $Y^3$ is CH |
| P.1066 | $X^1$ is chloro, $X^2$ is CH, $X^3$ is bromo | difluoromethyl | nitro | $Y^1$ is N, $Y^2$ is CH, $Y^3$ is CH |
| P.1067 | $X^1$ is chloro, $X^2$ is CH, $X^3$ is bromo | difluoromethyl | trifluoromethoxy | $Y^1$ is N, $Y^2$ is CH, $Y^3$ is CH |
| P.1068 | $X^1$ is chloro, $X^2$ is CH, $X^3$ is bromo | difluoromethyl | trifluoromethyl | $Y^1$ is N, $Y^2$ is CH, $Y^3$ is CH |
| P.1069 | $X^1$ is chloro, $X^2$ is CH, $X^3$ is bromo | trifluoromethyl | bromo | $Y^1$ is N, $Y^2$ is CH, $Y^3$ is CH |
| P.1070 | $X^1$ is chloro, $X^2$ is CH, $X^3$ is bromo | trifluoromethyl | chloro | $Y^1$ is N, $Y^2$ is CH, $Y^3$ is CH |
| P.1071 | $X^1$ is chloro, $X^2$ is CH, $X^3$ is bromo | trifluoromethyl | cyano | $Y^1$ is N, $Y^2$ is CH, $Y^3$ is CH |
| P.1072 | $X^1$ is chloro, $X^2$ is CH, $X^3$ is bromo | trifluoromethyl | cyclopropyl | $Y^1$ is N, $Y^2$ is CH, $Y^3$ is CH |
| P.1073 | $X^1$ is chloro, $X^2$ is CH, $X^3$ is bromo | trifluoromethyl | ethyl | $Y^1$ is N, $Y^2$ is CH, $Y^3$ is CH |
| P.1074 | $X^1$ is chloro, $X^2$ is CH, $X^3$ is bromo | trifluoromethyl | fluoro | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.1075 | $X^1$ is chloro, $X^2$ is CH, $X^3$ is bromo | trifluoromethyl | hydrogen | $Y^1$ is N, $Y^2$ is CH, $Y^3$ is CH |
| P.1076 | $X^1$ is chloro, $X^2$ is CH, $X^3$ is bromo | trifluoromethyl | methoxy | $Y^1$ is N, $Y^2$ is CH, $Y^3$ is CH |
| P.1077 | $X^1$ is chloro, $X^2$ is CH, $X^3$ is bromo | trifluoromethyl | methyl | $Y^1$ is N, $Y^2$ is CH, $Y^3$ is CH |
| P.1078 | $X^1$ is chloro, $X^2$ is CH, $X^3$ is bromo | trifluoromethyl | nitro | $Y^1$ is N, $Y^2$ is CH, $Y^3$ is CH |
| P.1079 | $X^1$ is chloro, $X^2$ is CH, $X^3$ is bromo | trifluoromethyl | trifluoromethoxy | $Y^1$ is N, $Y^2$ is CH, $Y^3$ is CH |
| P.1080 | $X^1$ is chloro, $X^2$ is CH, $X^3$ is bromo | trifluoromethyl | trifluoromethyl | $Y^1$ is N, $Y^2$ is CH, $Y^3$ is CH |
| P.1081 | $X^1$ is chloro, $X^2$ is C—Cl, $X^3$ is trifluoromethyl | chlorodifluoromethyl | bromo | $Y^1$ is N, $Y^2$ is CH, $Y^3$ is CH |
| P.1082 | $X^1$ is chloro, $X^2$ is C—Cl, $X^3$ is trifluoromethyl | chlorodifluoromethyl | chloro | $Y^1$ is N, $Y^2$ is CH, $Y^3$ is CH |
| P.1083 | $X^1$ is chloro, $X^2$ is C—Cl, $X^3$ is trifluoromethyl | chlorodifluoromethyl | cyano | $Y^1$ is N, $Y^2$ is CH, $Y^3$ is CH |
| P.1084 | $X^1$ is chloro, $X^2$ is C—Cl, $X^3$ is trifluoromethyl | chlorodifluoromethyl | cyclopropyl | $Y^1$ is N, $Y^2$ is CH, $Y^3$ is CH |
| P.1085 | $X^1$ is chloro, $X^2$ is C—Cl, $X^3$ is trifluoromethyl | chlorodifluoromethyl | ethyl | $Y^1$ is N, $Y^2$ is CH, $Y^3$ is CH |
| P.1086 | $X^1$ is chloro, $X^2$ is C—Cl, $X^3$ is trifluoromethyl | chlorodifluoromethyl | fluoro | $Y^1$ is N, $Y^2$ is CH, $Y^3$ is CH |
| P.1087 | $X^1$ is chloro, $X^2$ is C—Cl, $X^3$ is trifluoromethyl | chlorodifluoromethyl | hydrogen | $Y^1$ is N, $Y^2$ is CH, $Y^3$ is CH |
| P.1088 | $X^1$ is chloro, $X^2$ is C—Cl, $X^3$ is trifluoromethyl | chlorodifluoromethyl | methoxy | $Y^1$ is N, $Y^2$ is CH, $Y^3$ is CH |
| P.1089 | $X^1$ is chloro, $X^2$ is C—Cl, $X^3$ is trifluoromethyl | chlorodifluoromethyl | methyl | $Y^1$ is N, $Y^2$ is CH, $Y^3$ is CH |
| P.1090 | $X^1$ is chloro, $X^2$ is C—Cl, $X^3$ is trifluoromethyl | chlorodifluoromethyl | nitro | $Y^1$ is N, $Y^2$ is CH, $Y^3$ is CH |
| P.1091 | $X^1$ is chloro, $X^2$ is C—Cl, $X^3$ is trifluoromethyl | chlorodifluoromethyl | trifluoromethoxy | $Y^1$ is N, $Y^2$ is CH, $Y^3$ is CH |
| P.1092 | $X^1$ is chloro, $X^2$ is C—Cl, $X^3$ is trifluoromethyl | chlorodifluoromethyl | trifluoromethyl | $Y^1$ is N, $Y^2$ is CH, $Y^3$ is CH |
| P.1093 | $X^1$ is chloro, $X^2$ is C—Cl, $X^3$ is trifluoromethyl | difluoromethyl | bromo | $Y^1$ is N, $Y^2$ is CH, $Y^3$ is CH |
| P.1094 | $X^1$ is chloro, $X^2$ is C—Cl, $X^3$ is trifluoromethyl | difluoromethyl | chloro | $Y^1$ is N, $Y^2$ is CH, $Y^3$ is CH |
| P.1095 | $X^1$ is chloro, $X^2$ is C—Cl, $X^3$ is trifluoromethyl | difluoromethyl | cyano | $Y^1$ is N, $Y^2$ is CH, $Y^3$ is CH |
| P.1096 | $X^1$ is chloro, $X^2$ is C—Cl, $X^3$ is trifluoromethyl | difluoromethyl | cyclopropyl | $Y^1$ is N, $Y^2$ is CH, $Y^3$ is CH |
| P.1097 | $X^1$ is chloro, $X^2$ is C—Cl, $X^3$ is trifluoromethyl | difluoromethyl | ethyl | $Y^1$ is N, $Y^2$ is CH, $Y^3$ is CH |
| P.1098 | $X^1$ is chloro, $X^2$ is C—Cl, $X^3$ is trifluoromethyl | difluoromethyl | fluoro | $Y^1$ is N, $Y^2$ is CH, $Y^3$ is CH |
| P.1099 | $X^1$ is chloro, $X^2$ is C—Cl, $X^3$ is trifluoromethyl | difluoromethyl | hydrogen | $Y^1$ is N, $Y^2$ is CH, $Y^3$ is CH |
| P.1100 | $X^1$ is chloro, $X^2$ is C—Cl, $X^3$ is trifluoromethyl | difluoromethyl | methoxy | $Y^1$ is N, $Y^2$ is CH, $Y^3$ is CH |
| P.1101 | $X^1$ is chloro, $X^2$ is C—Cl, $X^3$ is trifluoromethyl | difluoromethyl | methyl | $Y^1$ is N, $Y^2$ is CH, $Y^3$ is CH |
| P.1102 | $X^1$ is chloro, $X^2$ is C—Cl, $X^3$ is trifluoromethyl | difluoromethyl | nitro | $Y^1$ is N, $Y^2$ is CH, $Y^3$ is CH |
| P.1103 | $X^1$ is chloro, $X^2$ is C—Cl, $X^3$ is trifluoromethyl | difluoromethyl | trifluoromethoxy | $Y^1$ is N, $Y^2$ is CH, $Y^3$ is CH |
| P.1104 | $X^1$ is chloro, $X^2$ is C—Cl, $X^3$ is trifluoromethyl | difluoromethyl | trifluoromethyl | $Y^1$ is N, $Y^2$ is CH, $Y^3$ is CH |
| P.1105 | $X^1$ is chloro, $X^2$ is C—Cl, $X^3$ is trifluoromethyl | trifluoromethyl | bromo | $Y^1$ is N, $Y^2$ is CH, $Y^3$ is CH |
| P.1106 | $X^1$ is chloro, $X^2$ is C—Cl, $X^3$ is trifluoromethyl | trifluoromethyl | chloro | $Y^1$ is N, $Y^2$ is CH, $Y^3$ is CH |
| P.1107 | $X^1$ is chloro, $X^2$ is C—Cl, $X^3$ is trifluoromethyl | trifluoromethyl | cyano | $Y^1$ is N, $Y^2$ is CH, $Y^3$ is CH |
| P.1108 | $X^1$ is chloro, $X^2$ is C—Cl, $X^3$ is trifluoromethyl | trifluoromethyl | cyclopropyl | $Y^1$ is N, $Y^2$ is CH, $Y^3$ is CH |
| P.1109 | $X^1$ is chloro, $X^2$ is C—Cl, $X^3$ is trifluoromethyl | trifluoromethyl | ethyl | $Y^1$ is N, $Y^2$ is CH, $Y^3$ is CH |
| P.1110 | $X^1$ is chloro, $X^2$ is C—Cl, $X^3$ is trifluoromethyl | trifluoromethyl | fluoro | $Y^1$ is N, $Y^2$ is CH, $Y^3$ is CH |
| P.1111 | $X^1$ is chloro, $X^2$ is C—Cl, $X^3$ is trifluoromethyl | trifluoromethyl | hydrogen | $Y^1$ is N, $Y^2$ is CH, $Y^3$ is CH |
| P.1112 | $X^1$ is chloro, $X^2$ is C—Cl, $X^3$ is trifluoromethyl | trifluoromethyl | methoxy | $Y^1$ is N, $Y^2$ is CH, $Y^3$ is CH |
| P.1113 | $X^1$ is chloro, $X^2$ is C—Cl, $X^3$ is trifluoromethyl | trifluoromethyl | methyl | $Y^1$ is N, $Y^2$ is CH, $Y^3$ is CH |

TABLE P-continued

|  | X1, X2, X3 | X4 | R5 | Y1, Y2, Y3 |
|---|---|---|---|---|
| P.1114 | $X^1$ is chloro, $X^2$ is C—Cl, $X^3$ is trifluoromethyl | trifluoromethyl | nitro | $Y^1$ is N, $Y^2$ is CH, $Y^3$ is CH |
| P.1115 | $X^1$ is chloro, $X^2$ is C—Cl, $X^3$ is trifluoromethyl | trifluoromethyl | trifluoromethoxy | $Y^1$ is N, $Y^2$ is CH, $Y^3$ is CH |
| P.1116 | $X^1$ is chloro, $X^2$ is C—Cl, $X^3$ is trifluoromethyl | trifluoromethyl | trifluoromethyl | $Y^1$ is N, $Y^2$ is CH, $Y^3$ is CH |
| P.1117 | $X^1$ is trifluoromethyl, $X^2$ is CH, $X^3$ is trifluoromethyl | chlorodifluoromethyl | bromo | $Y^1$ is N, $Y^2$ is CH, $Y^3$ is CH |
| P.1118 | $X^1$ is trifluoromethyl, $X^2$ is CH, $X^3$ is trifluoromethyl | chlorodifluoromethyl | chloro | $Y^1$ is N, $Y^2$ is CH, $Y^3$ is CH |
| P.1119 | $X^1$ is trifluoromethyl, $X^2$ is CH, $X^3$ is trifluoromethyl | chlorodifluoromethyl | cyano | $Y^1$ is N, $Y^2$ is CH, $Y^3$ is CH |
| P.1120 | $X^1$ is trifluoromethyl, $X^2$ is CH, $X^3$ is trifluoromethyl | chlorodifluoromethyl | cyclopropyl | $Y^1$ is N, $Y^2$ is CH, $Y^3$ is CH |
| P.1121 | $X^1$ is trifluoromethyl, $X^2$ is CH, $X^3$ is trifluoromethyl | chlorodifluoromethyl | ethyl | $Y^1$ is N, $Y^2$ is CH, $Y^3$ is CH |
| P.1122 | $X^1$ is trifluoromethyl, $X^2$ is CH, $X^3$ is trifluoromethyl | chlorodifluoromethyl | fluoro | $Y^1$ is N, $Y^2$ is CH, $Y^3$ is CH |
| P.1123 | $X^1$ is trifluoromethyl, $X^2$ is CH, $X^3$ is trifluoromethyl | chlorodifluoromethyl | hydrogen | $Y^1$ is N, $Y^2$ is CH, $Y^3$ is CH |
| P.1124 | $X^1$ is trifluoromethyl, $X^2$ is CH, $X^3$ is trifluoromethyl | chlorodifluoromethyl | methoxy | $Y^1$ is N, $Y^2$ is CH, $Y^3$ is CH |
| P.1125 | $X^1$ is trifluoromethyl, $X^2$ is CH, $X^3$ is trifluoromethyl | chlorodifluoromethyl | methyl | $Y^1$ is N, $Y^2$ is CH, $Y^3$ is CH |
| P.1126 | $X^1$ is trifluoromethyl, $X^2$ is CH, $X^3$ is trifluoromethyl | chlorodifluoromethyl | nitro | $Y^1$ is N, $Y^2$ is CH, $Y^3$ is CH |
| P.1127 | $X^1$ is trifluoromethyl, $X^2$ is CH, $X^3$ is trifluoromethyl | chlorodifluoromethyl | trifluoromethoxy | $Y^1$ is N, $Y^2$ is CH, $Y^3$ is CH |
| P.1128 | $X^1$ is trifluoromethyl, $X^2$ is CH, $X^3$ is trifluoromethyl | chlorodifluoromethyl | trifluoromethyl | $Y^1$ is N, $Y^2$ is CH, $Y^3$ is CH |
| P.1129 | $X^1$ is trifluoromethyl, $X^2$ is CH, $X^3$ is trifluoromethyl | difluoromethyl | bromo | $Y^1$ is N, $Y^2$ is CH, $Y^3$ is CH |
| P.1130 | $X^1$ is trifluoromethyl, $X^2$ is CH, $X^3$ is trifluoromethyl | difluoromethyl | chloro | $Y^1$ is N, $Y^2$ is CH, $Y^3$ is CH |
| P.1131 | $X^1$ is trifluoromethyl, $X^2$ is CH, $X^3$ is trifluoromethyl | difluoromethyl | cyano | $Y^1$ is N, $Y^2$ is CH, $Y^3$ is CH |
| P.1132 | $X^1$ is trifluoromethyl, $X^2$ is CH, $X^3$ is trifluoromethyl | difluoromethyl | cyclopropyl | $Y^1$ is N, $Y^2$ is CH, $Y^3$ is CH |
| P.1133 | $X^1$ is trifluoromethyl, $X^2$ is CH, $X^3$ is trifluoromethyl | difluoromethyl | ethyl | $Y^1$ is N, $Y^2$ is CH, $Y^3$ is CH |
| P.1134 | $X^1$ is trifluoromethyl, $X^2$ is CH, $X^3$ is trifluoromethyl | difluoromethyl | fluoro | $Y^1$ is N, $Y^2$ is CH, $Y^3$ is CH |
| P.1135 | $X^1$ is trifluoromethyl, $X^2$ is CH, $X^3$ is trifluoromethyl | difluoromethyl | hydrogen | $Y^1$ is N, $Y^2$ is CH, $Y^3$ is CH |
| P.1136 | $X^1$ is trifluoromethyl, $X^2$ is CH, $X^3$ is trifluoromethyl | difluoromethyl | methoxy | $Y^1$ is N, $Y^2$ is CH, $Y^3$ is CH |
| P.1137 | $X^1$ is trifluoromethyl, $X^2$ is CH, $X^3$ is trifluoromethyl | difluoromethyl | methyl | $Y^1$ is N, $Y^2$ is CH, $Y^3$ is CH |
| P.1138 | $X^1$ is trifluoromethyl, $X^2$ is CH, $X^3$ is trifluoromethyl | difluoromethyl | nitro | $Y^1$ is N, $Y^2$ is CH, $Y^3$ is CH |
| P.1139 | $X^1$ is trifluoromethyl, $X^2$ is CH, $X^3$ is trifluoromethyl | difluoromethyl | trifluoromethoxy | $Y^1$ is N, $Y^2$ is CH, $Y^3$ is CH |
| P.1140 | $X^1$ is trifluoromethyl, $X^2$ is CH, $X^3$ is trifluoromethyl | difluoromethyl | trifluoromethyl | $Y^1$ is N, $Y^2$ is CH, $Y^3$ is CH |
| P.1141 | $X^1$ is trifluoromethyl, $X^2$ is CH, $X^3$ is trifluoromethyl | trifluoromethyl | bromo | $Y^1$ is N, $Y^2$ is CH, $Y^3$ is CH |
| P.1142 | $X^1$ is trifluoromethyl, $X^2$ is CH, $X^3$ is trifluoromethyl | trifluoromethyl | chloro | $Y^1$ is N, $Y^2$ is CH, $Y^3$ is CH |
| P.1143 | $X^1$ is trifluoromethyl, $X^2$ is CH, $X^3$ is trifluoromethyl | trifluoromethyl | cyano | $Y^1$ is N, $Y^2$ is CH, $Y^3$ is CH |
| P.1144 | $X^1$ is trifluoromethyl, $X^2$ is CH, $X^3$ is trifluoromethyl | trifluoromethyl | cyclopropyl | $Y^1$ is N, $Y^2$ is CH, $Y^3$ is CH |
| P.1145 | $X^1$ is trifluoromethyl, $X^2$ is CH, $X^3$ is trifluoromethyl | trifluoromethyl | ethyl | $Y^1$ is N, $Y^2$ is CH, $Y^3$ is CH |
| P.1146 | $X^1$ is trifluoromethyl, $X^2$ is CH, $X^3$ is trifluoromethyl | trifluoromethyl | fluoro | $Y^1$ is N, $Y^2$ is CH, $Y^3$ is CH |
| P.1147 | $X^1$ is trifluoromethyl, $X^2$ is CH, $X^3$ is trifluoromethyl | trifluoromethyl | hydrogen | $Y^1$ is N, $Y^2$ is CH, $Y^3$ is CH |
| P.1148 | $X^1$ is trifluoromethyl, $X^2$ is CH, $X^3$ is trifluoromethyl | trifluoromethyl | methoxy | $Y^1$ is N, $Y^2$ is CH, $Y^3$ is CH |
| P.1149 | $X^1$ is trifluoromethyl, $X^2$ is CH, $X^3$ is trifluoromethyl | trifluoromethyl | methyl | $Y^1$ is N, $Y^2$ is CH, $Y^3$ is CH |
| P.1150 | $X^1$ is trifluoromethyl, $X^2$ is CH, $X^3$ is trifluoromethyl | trifluoromethyl | nitro | $Y^1$ is N, $Y^2$ is CH, $Y^3$ is CH |
| P.1151 | $X^1$ is trifluoromethyl, $X^2$ is CH, $X^3$ is trifluoromethyl | trifluoromethyl | trifluoromethoxy | $Y^1$ is N, $Y^2$ is CH, $Y^3$ is CH |
| P.1152 | $X^1$ is trifluoromethyl, $X^2$ is CH, $X^3$ is trifluoromethyl | trifluoromethyl | trifluoromethyl | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.1153 | $X^1$ is trifluoromethyl, $X^2$ is CH, $X^3$ is trifluoromethyl | chlorodifluoromethyl | bromo | $Y^1$ is N, $Y^2$ is CH, $Y^3$ is CH |
| P.1154 | $X^1$ is trifluoromethyl, $X^2$ is CH, $X^3$ is trifluoromethyl | chlorodifluoromethyl | chloro | $Y^1$ is N, $Y^2$ is CH, $Y^3$ is CH |
| P.1155 | $X^1$ is trifluoromethyl, $X^2$ is CH, $X^3$ is trifluoromethyl | chlorodifluoromethyl | cyano | $Y^1$ is N, $Y^2$ is CH, $Y^3$ is CH |
| P.1156 | $X^1$ is trifluoromethyl, $X^2$ is CH, $X^3$ is trifluoromethyl | chlorodifluoromethyl | cyclopropyl | $Y^1$ is N, $Y^2$ is CH, $Y^3$ is CH |
| P.1157 | $X^1$ is trifluoromethyl, $X^2$ is CH, $X^3$ is trifluoromethyl | chlorodifluoromethyl | ethyl | $Y^1$ is N, $Y^2$ is CH, $Y^3$ is CH |
| P.1158 | $X^1$ is trifluoromethyl, $X^2$ is CH, $X^3$ is trifluoromethyl | chlorodifluoromethyl | fluoro | $Y^1$ is N, $Y^2$ is CH, $Y^3$ is CH |
| P.1159 | $X^1$ is trifluoromethyl, $X^2$ is CH, $X^3$ is trifluoromethyl | chlorodifluoromethyl | hydrogen | $Y^1$ is N, $Y^2$ is CH, $Y^3$ is CH |
| P.1160 | $X^1$ is trifluoromethyl, $X^2$ is CH, $X^3$ is trifluoromethyl | chlorodifluoromethyl | methoxy | $Y^1$ is N, $Y^2$ is CH, $Y^3$ is CH |
| P.1161 | $X^1$ is trifluoromethyl, $X^2$ is CH, $X^3$ is trifluoromethyl | chlorodifluoromethyl | methyl | $Y^1$ is N, $Y^2$ is CH, $Y^3$ is CH |
| P.1162 | $X^1$ is trifluoromethyl, $X^2$ is CH, $X^3$ is trifluoromethyl | chlorodifluoromethyl | nitro | $Y^1$ is N, $Y^2$ is CH, $Y^3$ is CH |
| P.1163 | $X^1$ is trifluoromethyl, $X^2$ is CH, $X^3$ is trifluoromethyl | chlorodifluoromethyl | trifluoromethoxy | $Y^1$ is N, $Y^2$ is CH, $Y^3$ is CH |
| P.1164 | $X^1$ is trifluoromethyl, $X^2$ is CH, $X^3$ is trifluoromethyl | chlorodifluoromethyl | trifluoromethyl | $Y^1$ is N, $Y^2$ is CH, $Y^3$ is CH |
| P.1165 | $X^1$ is trifluoromethyl, $X^2$ is CH, $X^3$ is trifluoromethyl | difluoromethyl | bromo | $Y^1$ is N, $Y^2$ is CH, $Y^3$ is CH |
| P.1166 | $X^1$ is trifluoromethyl, $X^2$ is CH, $X^3$ is trifluoromethyl | difluoromethyl | chloro | $Y^1$ is N, $Y^2$ is CH, $Y^3$ is CH |
| P.1167 | $X^1$ is trifluoromethyl, $X^2$ is CH, $X^3$ is trifluoromethyl | difluoromethyl | cyano | $Y^1$ is N, $Y^2$ is CH, $Y^3$ is CH |
| P.1168 | $X^1$ is trifluoromethyl, $X^2$ is CH, $X^3$ is trifluoromethyl | difluoromethyl | cyclopropyl | $Y^1$ is N, $Y^2$ is CH, $Y^3$ is CH |
| P.1169 | $X^1$ is trifluoromethyl, $X^2$ is CH, $X^3$ is trifluoromethyl | difluoromethyl | ethyl | $Y^1$ is N, $Y^2$ is CH, $Y^3$ is CH |
| P.1170 | $X^1$ is trifluoromethyl, $X^2$ is CH, $X^3$ is trifluoromethyl | difluoromethyl | fluoro | $Y^1$ is N, $Y^2$ is CH, $Y^3$ is CH |
| P.1171 | $X^1$ is trifluoromethyl, $X^2$ is CH, $X^3$ is trifluoromethyl | difluoromethyl | hydrogen | $Y^1$ is N, $Y^2$ is CH, $Y^3$ is CH |
| P.1172 | $X^1$ is trifluoromethyl, $X^2$ is CH, $X^3$ is trifluoromethyl | difluoromethyl | methoxy | $Y^1$ is N, $Y^2$ is CH, $Y^3$ is CH |
| P.1173 | $X^1$ is trifluoromethyl, $X^2$ is CH, $X^3$ is trifluoromethyl | difluoromethyl | methyl | $Y^1$ is N, $Y^2$ is CH, $Y^3$ is CH |
| P.1174 | $X^1$ is trifluoromethyl, $X^2$ is CH, $X^3$ is trifluoromethyl | difluoromethyl | nitro | $Y^1$ is N, $Y^2$ is CH, $Y^3$ is CH |
| P.1175 | $X^1$ is trifluoromethyl, $X^2$ is CH, $X^3$ is trifluoromethyl | difluoromethyl | trifluoromethoxy | $Y^1$ is N, $Y^2$ is CH, $Y^3$ is CH |
| P.1176 | $X^1$ is trifluoromethyl, $X^2$ is CH, $X^3$ is trifluoromethyl | difluoromethyl | trifluoromethyl | $Y^1$ is N, $Y^2$ is CH, $Y^3$ is CH |
| P.1177 | $X^1$ is trifluoromethyl, $X^2$ is CH, $X^3$ is trifluoromethyl | trifluoromethyl | bromo | $Y^1$ is N, $Y^2$ is CH, $Y^3$ is CH |
| P.1178 | $X^1$ is trifluoromethyl, $X^2$ is CH, $X^3$ is trifluoromethyl | trifluoromethyl | chloro | $Y^1$ is N, $Y^2$ is CH, $Y^3$ is CH |
| P.1179 | $X^1$ is trifluoromethyl, $X^2$ is CH, $X^3$ is trifluoromethyl | trifluoromethyl | cyano | $Y^1$ is N, $Y^2$ is CH, $Y^3$ is CH |
| P.1180 | $X^1$ is trifluoromethyl, $X^2$ is CH, $X^3$ is trifluoromethyl | trifluoromethyl | cyclopropyl | $Y^1$ is N, $Y^2$ is CH, $Y^3$ is CH |
| P.1181 | $X^1$ is trifluoromethyl, $X^2$ is CH, $X^3$ is trifluoromethyl | trifluoromethyl | ethyl | $Y^1$ is N, $Y^2$ is CH, $Y^3$ is CH |
| P.1182 | $X^1$ is trifluoromethyl, $X^2$ is CH, $X^3$ is trifluoromethyl | trifluoromethyl | fluoro | $Y^1$ is N, $Y^2$ is CH, $Y^3$ is CH |
| P.1183 | $X^1$ is trifluoromethyl, $X^2$ is CH, $X^3$ is trifluoromethyl | trifluoromethyl | hydrogen | $Y^1$ is N, $Y^2$ is CH, $Y^3$ is CH |
| P.1184 | $X^1$ is trifluoromethyl, $X^2$ is CH, $X^3$ is trifluoromethyl | trifluoromethyl | methoxy | $Y^1$ is N, $Y^2$ is CH, $Y^3$ is CH |
| P.1185 | $X^1$ is trifluoromethyl, $X^2$ is CH, $X^3$ is trifluoromethyl | trifluoromethyl | methyl | $Y^1$ is N, $Y^2$ is CH, $Y^3$ is CH |
| P.1186 | $X^1$ is trifluoromethyl, $X^2$ is CH, $X^3$ is trifluoromethyl | trifluoromethyl | nitro | $Y^1$ is N, $Y^2$ is CH, $Y^3$ is CH |
| P.1187 | $X^1$ is trifluoromethyl, $X^2$ is CH, $X^3$ is trifluoromethyl | trifluoromethyl | trifluoromethoxy | $Y^1$ is N, $Y^2$ is CH, $Y^3$ is CH |
| P.1188 | $X^1$ is trifluoromethyl, $X^2$ is CH, $X^3$ is trifluoromethyl | trifluoromethyl | trifluoromethyl | $Y^1$ is N, $Y^2$ is CH, $Y^3$ is CH |
| P.1189 | $X^1$ is trifluoromethyl, $X^2$ is CH, $X^3$ is hydrogen | chlorodifluoromethyl | bromo | $Y^1$ is N, $Y^2$ is CH, $Y^3$ is CH |
| P.1190 | $X^1$ is trifluoromethyl, $X^2$ is CH, $X^3$ is hydrogen | chlorodifluoromethyl | chloro | $Y^1$ is N, $Y^2$ is CH, $Y^3$ is CH |
| P.1191 | $X^1$ is trifluoromethyl, $X^2$ is CH, $X^3$ is hydrogen | chlorodifluoromethyl | cyano | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.1192 | $X^1$ is trifluoromethyl, $X^2$ is CH, $X^3$ is hydrogen | chlorodifluoromethyl | cyclopropyl | $Y^1$ is N, $Y^2$ is CH, $Y^3$ is CH |
| P.1193 | $X^1$ is trifluoromethyl, $X^2$ is CH, $X^3$ is hydrogen | chlorodifluoromethyl | ethyl | $Y^1$ is N, $Y^2$ is CH, $Y^3$ is CH |
| P.1194 | $X^1$ is trifluoromethyl, $X^2$ is CH, $X^3$ is hydrogen | chlorodifluoromethyl | fluoro | $Y^1$ is N, $Y^2$ is CH, $Y^3$ is CH |
| P.1195 | $X^1$ is trifluoromethyl, $X^2$ is CH, $X^3$ is hydrogen | chlorodifluoromethyl | hydrogen | $Y^1$ is N, $Y^2$ is CH, $Y^3$ is CH |
| P.1196 | $X^1$ is trifluoromethyl, $X^2$ is CH, $X^3$ is hydrogen | chlorodifluoromethyl | methoxy | $Y^1$ is N, $Y^2$ is CH, $Y^3$ is CH |
| P.1197 | $X^1$ is trifluoromethyl, $X^2$ is CH, $X^3$ is hydrogen | chlorodifluoromethyl | methyl | $Y^1$ is N, $Y^2$ is CH, $Y^3$ is CH |
| P.1198 | $X^1$ is trifluoromethyl, $X^2$ is CH, $X^3$ is hydrogen | chlorodifluoromethyl | nitro | $Y^1$ is N, $Y^2$ is CH, $Y^3$ is CH |
| P.1199 | $X^1$ is trifluoromethyl, $X^2$ is CH, $X^3$ is hydrogen | chlorodifluoromethyl | trifluoromethoxy | $Y^1$ is N, $Y^2$ is CH, $Y^3$ is CH |
| P.1200 | $X^1$ is trifluoromethyl, $X^2$ is CH, $X^3$ is hydrogen | chlorodifluoromethyl | trifluoromethyl | $Y^1$ is N, $Y^2$ is CH, $Y^3$ is CH |
| P.1201 | $X^1$ is trifluoromethyl, $X^2$ is CH, $X^3$ is hydrogen | difluoromethyl | bromo | $Y^1$ is N, $Y^2$ is CH, $Y^3$ is CH |
| P.1202 | $X^1$ is trifluoromethyl, $X^2$ is CH, $X^3$ is hydrogen | difluoromethyl | chloro | $Y^1$ is N, $Y^2$ is CH, $Y^3$ is CH |
| P.1203 | $X^1$ is trifluoromethyl, $X^2$ is CH, $X^3$ is hydrogen | difluoromethyl | cyano | $Y^1$ is N, $Y^2$ is CH, $Y^3$ is CH |
| P.1204 | $X^1$ is trifluoromethyl, $X^2$ is CH, $X^3$ is hydrogen | difluoromethyl | cyclopropyl | $Y^1$ is N, $Y^2$ is CH, $Y^3$ is CH |
| P.1205 | $X^1$ is trifluoromethyl, $X^2$ is CH, $X^3$ is hydrogen | difluoromethyl | ethyl | $Y^1$ is N, $Y^2$ is CH, $Y^3$ is CH |
| P.1206 | $X^1$ is trifluoromethyl, $X^2$ is CH, $X^3$ is hydrogen | difluoromethyl | fluoro | $Y^1$ is N, $Y^2$ is CH, $Y^3$ is CH |
| P.1207 | $X^1$ is trifluoromethyl, $X^2$ is CH, $X^3$ is hydrogen | difluoromethyl | hydrogen | $Y^1$ is N, $Y^2$ is CH, $Y^3$ is CH |
| P.1208 | $X^1$ is trifluoromethyl, $X^2$ is CH, $X^3$ is hydrogen | difluoromethyl | methoxy | $Y^1$ is N, $Y^2$ is CH, $Y^3$ is CH |
| P.1209 | $X^1$ is trifluoromethyl, $X^2$ is CH, $X^3$ is hydrogen | difluoromethyl | methyl | $Y^1$ is N, $Y^2$ is CH, $Y^3$ is CH |
| P.1210 | $X^1$ is trifluoromethyl, $X^2$ is CH, $X^3$ is hydrogen | difluoromethyl | nitro | $Y^1$ is N, $Y^2$ is CH, $Y^3$ is CH |
| P.1211 | $X^1$ is trifluoromethyl, $X^2$ is CH, $X^3$ is hydrogen | difluoromethyl | trifluoromethoxy | $Y^1$ is N, $Y^2$ is CH, $Y^3$ is CH |
| P.1212 | $X^1$ is trifluoromethyl, $X^2$ is CH, $X^3$ is hydrogen | difluoromethyl | trifluoromethyl | $Y^1$ is N, $Y^2$ is CH, $Y^3$ is CH |
| P.1213 | $X^1$ is trifluoromethyl, $X^2$ is CH, $X^3$ is hydrogen | trifluoromethyl | bromo | $Y^1$ is N, $Y^2$ is CH, $Y^3$ is CH |
| P.1214 | $X^1$ is trifluoromethyl, $X^2$ is CH, $X^3$ is hydrogen | trifluoromethyl | chloro | $Y^1$ is N, $Y^2$ is CH, $Y^3$ is CH |
| P.1215 | $X^1$ is trifluoromethyl, $X^2$ is CH, $X^3$ is hydrogen | trifluoromethyl | cyano | $Y^1$ is N, $Y^2$ is CH, $Y^3$ is CH |
| P.1216 | $X^1$ is trifluoromethyl, $X^2$ is CH, $X^3$ is hydrogen | trifluoromethyl | cyclopropyl | $Y^1$ is N, $Y^2$ is CH, $Y^3$ is CH |
| P.1217 | $X^1$ is trifluoromethyl, $X^2$ is CH, $X^3$ is hydrogen | trifluoromethyl | ethyl | $Y^1$ is N, $Y^2$ is CH, $Y^3$ is CH |
| P.1218 | $X^1$ is trifluoromethyl, $X^2$ is CH, $X^3$ is hydrogen | trifluoromethyl | fluoro | $Y^1$ is N, $Y^2$ is CH, $Y^3$ is CH |
| P.1219 | $X^1$ is trifluoromethyl, $X^2$ is CH, $X^3$ is hydrogen | trifluoromethyl | hydrogen | $Y^1$ is N, $Y^2$ is CH, $Y^3$ is CH |
| P.1220 | $X^1$ is trifluoromethyl, $X^2$ is CH, $X^3$ is hydrogen | trifluoromethyl | methoxy | $Y^1$ is N, $Y^2$ is CH, $Y^3$ is CH |
| P.1221 | $X^1$ is trifluoromethyl, $X^2$ is CH, $X^3$ is hydrogen | trifluoromethyl | methyl | $Y^1$ is N, $Y^2$ is CH, $Y^3$ is CH |
| P.1222 | $X^1$ is trifluoromethyl, $X^2$ is CH, $X^3$ is hydrogen | trifluoromethyl | nitro | $Y^1$ is N, $Y^2$ is CH, $Y^3$ is CH |
| P.1223 | $X^1$ is trifluoromethyl, $X^2$ is CH, $X^3$ is hydrogen | trifluoromethyl | trifluoromethoxy | $Y^1$ is N, $Y^2$ is CH, $Y^3$ is CH |
| P.1224 | $X^1$ is trifluoromethyl, $X^2$ is CH, $X^3$ is hydrogen | trifluoromethyl | trifluoromethyl | $Y^1$ is N, $Y^2$ is CH, $Y^3$ is CH |
| P.1225 | $X^1$ is chloro, $X^2$ is N, $X^3$ is chloro | chlorodifluoromethyl | bromo | $Y^1$ is N, $Y^2$ is CH, $Y^3$ is CH |
| P.1226 | $X^1$ is chloro, $X^2$ is N, $X^3$ is chloro | chlorodifluoromethyl | chloro | $Y^1$ is N, $Y^2$ is CH, $Y^3$ is CH |
| P.1227 | $X^1$ is chloro, $X^2$ is N, $X^3$ is chloro | chlorodifluoromethyl | cyano | $Y^1$ is N, $Y^2$ is CH, $Y^3$ is CH |
| P.1228 | $X^1$ is chloro, $X^2$ is N, $X^3$ is chloro | chlorodifluoromethyl | cyclopropyl | $Y^1$ is N, $Y^2$ is CH, $Y^3$ is CH |
| P.1229 | $X^1$ is chloro, $X^2$ is N, $X^3$ is chloro | chlorodifluoromethyl | ethyl | $Y^1$ is N, $Y^2$ is CH, $Y^3$ is CH |
| P.1230 | $X^1$ is chloro, $X^2$ is N, $X^3$ is chloro | chlorodifluoromethyl | fluoro | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.1231 | $X^1$ is chloro, $X^2$ is N, $X^3$ is chloro | chlorodifluoromethyl | hydrogen | $Y^1$ is N, $Y^2$ is CH, $Y^3$ is CH |
| P.1232 | $X^1$ is chloro, $X^2$ is N, $X^3$ is chloro | chlorodifluoromethyl | methoxy | $Y^1$ is N, $Y^2$ is CH, $Y^3$ is CH |
| P.1233 | $X^1$ is chloro, $X^2$ is N, $X^3$ is chloro | chlorodifluoromethyl | methyl | $Y^1$ is N, $Y^2$ is CH, $Y^3$ is CH |
| P.1234 | $X^1$ is chloro, $X^2$ is N, $X^3$ is chloro | chlorodifluoromethyl | nitro | $Y^1$ is N, $Y^2$ is CH, $Y^3$ is CH |
| P.1235 | $X^1$ is chloro, $X^2$ is N, $X^3$ is chloro | chlorodifluoromethyl | trifluoromethoxy | $Y^1$ is N, $Y^2$ is CH, $Y^3$ is CH |
| P.1236 | $X^1$ is chloro, $X^2$ is N, $X^3$ is chloro | chlorodifluoromethyl | trifluoromethyl | $Y^1$ is N, $Y^2$ is CH, $Y^3$ is CH |
| P.1237 | $X^1$ is chloro, $X^2$ is N, $X^3$ is chloro | difluoromethyl | bromo | $Y^1$ is N, $Y^2$ is CH, $Y^3$ is CH |
| P.1238 | $X^1$ is chloro, $X^2$ is N, $X^3$ is chloro | difluoromethyl | chloro | $Y^1$ is N, $Y^2$ is CH, $Y^3$ is CH |
| P.1239 | $X^1$ is chloro, $X^2$ is N, $X^3$ is chloro | difluoromethyl | cyano | $Y^1$ is N, $Y^2$ is CH, $Y^3$ is CH |
| P.1240 | $X^1$ is chloro, $X^2$ is N, $X^3$ is chloro | difluoromethyl | cyclopropyl | $Y^1$ is N, $Y^2$ is CH, $Y^3$ is CH |
| P.1241 | $X^1$ is chloro, $X^2$ is N, $X^3$ is chloro | difluoromethyl | ethyl | $Y^1$ is N, $Y^2$ is CH, $Y^3$ is CH |
| P.1242 | $X^1$ is chloro, $X^2$ is N, $X^3$ is chloro | difluoromethyl | fluoro | $Y^1$ is N, $Y^2$ is CH, $Y^3$ is CH |
| P.1243 | $X^1$ is chloro, $X^2$ is N, $X^3$ is chloro | difluoromethyl | hydrogen | $Y^1$ is N, $Y^2$ is CH, $Y^3$ is CH |
| P.1244 | $X^1$ is chloro, $X^2$ is N, $X^3$ is chloro | difluoromethyl | methoxy | $Y^1$ is N, $Y^2$ is CH, $Y^3$ is CH |
| P.1245 | $X^1$ is chloro, $X^2$ is N, $X^3$ is chloro | difluoromethyl | methyl | $Y^1$ is N, $Y^2$ is CH, $Y^3$ is CH |
| P.1246 | $X^1$ is chloro, $X^2$ is N, $X^3$ is chloro | difluoromethyl | nitro | $Y^1$ is N, $Y^2$ is CH, $Y^3$ is CH |
| P.1247 | $X^1$ is chloro, $X^2$ is N, $X^3$ is chloro | difluoromethyl | trifluoromethoxy | $Y^1$ is N, $Y^2$ is CH, $Y^3$ is CH |
| P.1248 | $X^1$ is chloro, $X^2$ is N, $X^3$ is chloro | difluoromethyl | trifluoromethyl | $Y^1$ is N, $Y^2$ is CH, $Y^3$ is CH |
| P.1249 | $X^1$ is chloro, $X^2$ is N, $X^3$ is chloro | trifluoromethyl | bromo | $Y^1$ is N, $Y^2$ is CH, $Y^3$ is CH |
| P.1250 | $X^1$ is chloro, $X^2$ is N, $X^3$ is chloro | trifluoromethyl | chloro | $Y^1$ is N, $Y^2$ is CH, $Y^3$ is CH |
| P.1251 | $X^1$ is chloro, $X^2$ is N, $X^3$ is chloro | trifluoromethyl | cyano | $Y^1$ is N, $Y^2$ is CH, $Y^3$ is CH |
| P.1252 | $X^1$ is chloro, $X^2$ is N, $X^3$ is chloro | trifluoromethyl | cyclopropyl | $Y^1$ is N, $Y^2$ is CH, $Y^3$ is CH |
| P.1253 | $X^1$ is chloro, $X^2$ is N, $X^3$ is chloro | trifluoromethyl | ethyl | $Y^1$ is N, $Y^2$ is CH, $Y^3$ is CH |
| P.1254 | $X^1$ is chloro, $X^2$ is N, $X^3$ is chloro | trifluoromethyl | fluoro | $Y^1$ is N, $Y^2$ is CH, $Y^3$ is CH |
| P.1255 | $X^1$ is chloro, $X^2$ is N, $X^3$ is chloro | trifluoromethyl | hydrogen | $Y^1$ is N, $Y^2$ is CH, $Y^3$ is CH |
| P.1256 | $X^1$ is chloro, $X^2$ is N, $X^3$ is chloro | trifluoromethyl | methoxy | $Y^1$ is N, $Y^2$ is CH, $Y^3$ is CH |
| P.1257 | $X^1$ is chloro, $X^2$ is N, $X^3$ is chloro | trifluoromethyl | methyl | $Y^1$ is N, $Y^2$ is CH, $Y^3$ is CH |
| P.1258 | $X^1$ is chloro, $X^2$ is N, $X^3$ is chloro | trifluoromethyl | nitro | $Y^1$ is N, $Y^2$ is CH, $Y^3$ is CH |
| P.1259 | $X^1$ is chloro, $X^2$ is N, $X^3$ is chloro | trifluoromethyl | trifluoromethoxy | $Y^1$ is N, $Y^2$ is CH, $Y^3$ is CH |
| P.1260 | $X^1$ is chloro, $X^2$ is N, $X^3$ is chloro | trifluoromethyl | trifluoromethyl | $Y^1$ is N, $Y^2$ is CH, $Y^3$ is CH |
| P.1261 | $X^1$ is trifluoromethyl, $X^2$ is N, $X^3$ is trifluoromethyl | chlorodifluoromethyl | bromo | $Y^1$ is N, $Y^2$ is CH, $Y^3$ is CH |
| P.1262 | $X^1$ is trifluoromethyl, $X^2$ is N, $X^3$ is trifluoromethyl | chlorodifluoromethyl | chloro | $Y^1$ is N, $Y^2$ is CH, $Y^3$ is CH |
| P.1263 | $X^1$ is trifluoromethyl, $X^2$ is N, $X^3$ is trifluoromethyl | chlorodifluoromethyl | cyano | $Y^1$ is N, $Y^2$ is CH, $Y^3$ is CH |
| P.1264 | $X^1$ is trifluoromethyl, $X^2$ is N, $X^3$ is trifluoromethyl | chlorodifluoromethyl | cyclopropyl | $Y^1$ is N, $Y^2$ is CH, $Y^3$ is CH |
| P.1265 | $X^1$ is trifluoromethyl, $X^2$ is N, $X^3$ is trifluoromethyl | chlorodifluoromethyl | ethyl | $Y^1$ is N, $Y^2$ is CH, $Y^3$ is CH |
| P.1266 | $X^1$ is trifluoromethyl, $X^2$ is N, $X^3$ is trifluoromethyl | chlorodifluoromethyl | fluoro | $Y^1$ is N, $Y^2$ is CH, $Y^3$ is CH |
| P.1267 | $X^1$ is trifluoromethyl, $X^2$ is N, $X^3$ is trifluoromethyl | chlorodifluoromethyl | hydrogen | $Y^1$ is N, $Y^2$ is CH, $Y^3$ is CH |
| P.1268 | $X^1$ is trifluoromethyl, $X^2$ is N, $X^3$ is trifluoromethyl | chlorodifluoromethyl | methoxy | $Y^1$ is N, $Y^2$ is CH, $Y^3$ is CH |
| P.1269 | $X^1$ is trifluoromethyl, $X^2$ is N, $X^3$ is trifluoromethyl | chlorodifluoromethyl | methyl | $Y^1$ is N, $Y^2$ is CH, $Y^3$ is CH |

TABLE P-continued

| | X1, X2, X3 | X4 | R5 | Y1, Y2, Y3 |
|---|---|---|---|---|
| P.1270 | $X^1$ is trifluoromethyl, $X^2$ is N, $X^3$ is trifluoromethyl | chlorodifluoromethyl | nitro | $Y^1$ is N, $Y^2$ is CH, $Y^3$ is CH |
| P.1271 | $X^1$ is trifluoromethyl, $X^2$ is N, $X^3$ is trifluoromethyl | chlorodifluoromethyl | trifluoromethoxy | $Y^1$ is N, $Y^2$ is CH, $Y^3$ is CH |
| P.1272 | $X^1$ is trifluoromethyl, $X^2$ is N, $X^3$ is trifluoromethyl | chlorodifluoromethyl | trifluoromethyl | $Y^1$ is N, $Y^2$ is CH, $Y^3$ is CH |
| P.1273 | $X^1$ is trifluoromethyl, $X^2$ is N, $X^3$ is trifluoromethyl | difluoromethyl | bromo | $Y^1$ is N, $Y^2$ is CH, $Y^3$ is CH |
| P.1274 | $X^1$ is trifluoromethyl, $X^2$ is N, $X^3$ is trifluoromethyl | difluoromethyl | chloro | $Y^1$ is N, $Y^2$ is CH, $Y^3$ is CH |
| P.1275 | $X^1$ is trifluoromethyl, $X^2$ is N, $X^3$ is trifluoromethyl | difluoromethyl | cyano | $Y^1$ is N, $Y^2$ is CH, $Y^3$ is CH |
| P.1276 | $X^1$ is trifluoromethyl, $X^2$ is N, $X^3$ is trifluoromethyl | difluoromethyl | cyclopropyl | $Y^1$ is N, $Y^2$ is CH, $Y^3$ is CH |
| P.1277 | $X^1$ is trifluoromethyl, $X^2$ is N, $X^3$ is trifluoromethyl | difluoromethyl | ethyl | $Y^1$ is N, $Y^2$ is CH, $Y^3$ is CH |
| P.1278 | $X^1$ is trifluoromethyl, $X^2$ is N, $X^3$ is trifluoromethyl | difluoromethyl | fluoro | $Y^1$ is N, $Y^2$ is CH, $Y^3$ is CH |
| P.1279 | $X^1$ is trifluoromethyl, $X^2$ is N, $X^3$ is trifluoromethyl | difluoromethyl | hydrogen | $Y^1$ is N, $Y^2$ is CH, $Y^3$ is CH |
| P.1280 | $X^1$ is trifluoromethyl, $X^2$ is N, $X^3$ is trifluoromethyl | difluoromethyl | methoxy | $Y^1$ is N, $Y^2$ is CH, $Y^3$ is CH |
| P.1281 | $X^1$ is trifluoromethyl, $X^2$ is N, $X^3$ is trifluoromethyl | difluoromethyl | methyl | $Y^1$ is N, $Y^2$ is CH, $Y^3$ is CH |
| P.1282 | $X^1$ is trifluoromethyl, $X^2$ is N, $X^3$ is trifluoromethyl | difluoromethyl | nitro | $Y^1$ is N, $Y^2$ is CH, $Y^3$ is CH |
| P.1283 | $X^1$ is trifluoromethyl, $X^2$ is N, $X^3$ is trifluoromethyl | difluoromethyl | trifluoromethoxy | $Y^1$ is N, $Y^2$ is CH, $Y^3$ is CH |
| P.1284 | $X^1$ is trifluoromethyl, $X^2$ is N, $X^3$ is trifluoromethyl | difluoromethyl | trifluoromethyl | $Y^1$ is N, $Y^2$ is CH, $Y^3$ is CH |
| P.1285 | $X^1$ is trifluoromethyl, $X^2$ is N, $X^3$ is trifluoromethyl | trifluoromethyl | bromo | $Y^1$ is N, $Y^2$ is CH, $Y^3$ is CH |
| P.1286 | $X^1$ is trifluoromethyl, $X^2$ is N, $X^3$ is trifluoromethyl | trifluoromethyl | chloro | $Y^1$ is N, $Y^2$ is CH, $Y^3$ is CH |
| P.1287 | $X^1$ is trifluoromethyl, $X^2$ is N, $X^3$ is trifluoromethyl | trifluoromethyl | cyano | $Y^1$ is N, $Y^2$ is CH, $Y^3$ is CH |
| P.1288 | $X^1$ is trifluoromethyl, $X^2$ is N, $X^3$ is trifluoromethyl | trifluoromethyl | cyclopropyl | $Y^1$ is N, $Y^2$ is CH, $Y^3$ is CH |
| P.1289 | $X^1$ is trifluoromethyl, $X^2$ is N, $X^3$ is trifluoromethyl | trifluoromethyl | ethyl | $Y^1$ is N, $Y^2$ is CH, $Y^3$ is CH |
| P.1290 | $X^1$ is trifluoromethyl, $X^2$ is N, $X^3$ is trifluoromethyl | trifluoromethyl | fluoro | $Y^1$ is N, $Y^2$ is CH, $Y^3$ is CH |
| P.1291 | $X^1$ is trifluoromethyl, $X^2$ is N, $X^3$ is trifluoromethyl | trifluoromethyl | hydrogen | $Y^1$ is N, $Y^2$ is CH, $Y^3$ is CH |
| P.1292 | $X^1$ is trifluoromethyl, $X^2$ is N, $X^3$ is trifluoromethyl | trifluoromethyl | methoxy | $Y^1$ is N, $Y^2$ is CH, $Y^3$ is CH |
| P.1293 | $X^1$ is trifluoromethyl, $X^2$ is N, $X^3$ is trifluoromethyl | trifluoromethyl | methyl | $Y^1$ is N, $Y^2$ is CH, $Y^3$ is CH |
| P.1294 | $X^1$ is trifluoromethyl, $X^2$ is N, $X^3$ is trifluoromethyl | trifluoromethyl | nitro | $Y^1$ is N, $Y^2$ is CH, $Y^3$ is CH |
| P.1295 | $X^1$ is trifluoromethyl, $X^2$ is N, $X^3$ is trifluoromethyl | trifluoromethyl | trifluoromethoxy | $Y^1$ is N, $Y^2$ is CH, $Y^3$ is CH |
| P.1296 | $X^1$ is trifluoromethyl, $X^2$ is N, $X^3$ is trifluoromethyl | trifluoromethyl | trifluoromethyl | $Y^1$ is N, $Y^2$ is CH, $Y^3$ is CH |
| P.1297 | $X^1$ is chloro, $X^2$ is CH, $X^3$ is chloro | chlorodifluoromethyl | bromo | $Y^1$ is N, $Y^2$ is N, $Y^3$ is CH |
| P.1298 | $X^1$ is chloro, $X^2$ is CH, $X^3$ is chloro | chlorodifluoromethyl | chloro | $Y^1$ is N, $Y^2$ is N, $Y^3$ is CH |
| P.1299 | $X^1$ is chloro, $X^2$ is CH, $X^3$ is chloro | chlorodifluoromethyl | cyano | $Y^1$ is N, $Y^2$ is N, $Y^3$ is CH |
| P.1300 | $X^1$ is chloro, $X^2$ is CH, $X^3$ is chloro | chlorodifluoromethyl | cyclopropyl | $Y^1$ is N, $Y^2$ is N, $Y^3$ is CH |
| P.1301 | $X^1$ is chloro, $X^2$ is CH, $X^3$ is chloro | chlorodifluoromethyl | ethyl | $Y^1$ is N, $Y^2$ is N, $Y^3$ is CH |
| P.1302 | $X^1$ is chloro, $X^2$ is CH, $X^3$ is chloro | chlorodifluoromethyl | fluoro | $Y^1$ is N, $Y^2$ is N, $Y^3$ is CH |
| P.1303 | $X^1$ is chloro, $X^2$ is CH, $X^3$ is chloro | chlorodifluoromethyl | hydrogen | $Y^1$ is N, $Y^2$ is N, $Y^3$ is CH |
| P.1304 | $X^1$ is chloro, $X^2$ is CH, $X^3$ is chloro | chlorodifluoromethyl | methoxy | $Y^1$ is N, $Y^2$ is N, $Y^3$ is CH |
| P.1305 | $X^1$ is chloro, $X^2$ is CH, $X^3$ is chloro | chlorodifluoromethyl | methyl | $Y^1$ is N, $Y^2$ is N, $Y^3$ is CH |
| P.1306 | $X^1$ is chloro, $X^2$ is CH, $X^3$ is chloro | chlorodifluoromethyl | nitro | $Y^1$ is N, $Y^2$ is N, $Y^3$ is CH |
| P.1307 | $X^1$ is chloro, $X^2$ is CH, $X^3$ is chloro | chlorodifluoromethyl | trifluoromethoxy | $Y^1$ is N, $Y^2$ is N, $Y^3$ is CH |
| P.1308 | $X^1$ is chloro, $X^2$ is CH, $X^3$ is chloro | chlorodifluoromethyl | trifluoromethyl | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1309 | $X^1$ is chloro, $X^2$ is CH, $X^3$ is chloro | difluoromethyl | bromo | $Y^1$ is N, $Y^2$ is N, $Y^3$ is CH |
| P.1310 | $X^1$ is chloro, $X^2$ is CH, $X^3$ is chloro | difluoromethyl | chloro | $Y^1$ is N, $Y^2$ is N, $Y^3$ is CH |
| P.1311 | $X^1$ is chloro, $X^2$ is CH, $X^3$ is chloro | difluoromethyl | cyano | $Y^1$ is N, $Y^2$ is N, $Y^3$ is CH |
| P.1312 | $X^1$ is chloro, $X^2$ is CH, $X^3$ is chloro | difluoromethyl | cyclopropyl | $Y^1$ is N, $Y^2$ is N, $Y^3$ is CH |
| P.1313 | $X^1$ is chloro, $X^2$ is CH, $X^3$ is chloro | difluoromethyl | ethyl | $Y^1$ is N, $Y^2$ is N, $Y^3$ is CH |
| P.1314 | $X^1$ is chloro, $X^2$ is CH, $X^3$ is chloro | difluoromethyl | fluoro | $Y^1$ is N, $Y^2$ is N, $Y^3$ is CH |
| P.1315 | $X^1$ is chloro, $X^2$ is CH, $X^3$ is chloro | difluoromethyl | hydrogen | $Y^1$ is N, $Y^2$ is N, $Y^3$ is CH |
| P.1316 | $X^1$ is chloro, $X^2$ is CH, $X^3$ is chloro | difluoromethyl | methoxy | $Y^1$ is N, $Y^2$ is N, $Y^3$ is CH |
| P.1317 | $X^1$ is chloro, $X^2$ is CH, $X^3$ is chloro | difluoromethyl | methyl | $Y^1$ is N, $Y^2$ is N, $Y^3$ is CH |
| P.1318 | $X^1$ is chloro, $X^2$ is CH, $X^3$ is chloro | difluoromethyl | nitro | $Y^1$ is N, $Y^2$ is N, $Y^3$ is CH |
| P.1319 | $X^1$ is chloro, $X^2$ is CH, $X^3$ is chloro | difluoromethyl | trifluoromethoxy | $Y^1$ is N, $Y^2$ is N, $Y^3$ is CH |
| P.1320 | $X^1$ is chloro, $X^2$ is CH, $X^3$ is chloro | difluoromethyl | trifluoromethyl | $Y^1$ is N, $Y^2$ is N, $Y^3$ is CH |
| P.1321 | $X^1$ is chloro, $X^2$ is CH, $X^3$ is chloro | trifluoromethyl | bromo | $Y^1$ is N, $Y^2$ is N, $Y^3$ is CH |
| P.1322 | $X^1$ is chloro, $X^2$ is CH, $X^3$ is chloro | trifluoromethyl | chloro | $Y^1$ is N, $Y^2$ is N, $Y^3$ is CH |
| P.1323 | $X^1$ is chloro, $X^2$ is CH, $X^3$ is chloro | trifluoromethyl | cyano | $Y^1$ is N, $Y^2$ is N, $Y^3$ is CH |
| P.1324 | $X^1$ is chloro, $X^2$ is CH, $X^3$ is chloro | trifluoromethyl | cyclopropyl | $Y^1$ is N, $Y^2$ is N, $Y^3$ is CH |
| P.1325 | $X^1$ is chloro, $X^2$ is CH, $X^3$ is chloro | trifluoromethyl | ethyl | $Y^1$ is N, $Y^2$ is N, $Y^3$ is CH |
| P.1326 | $X^1$ is chloro, $X^2$ is CH, $X^3$ is chloro | trifluoromethyl | fluoro | $Y^1$ is N, $Y^2$ is N, $Y^3$ is CH |
| P.1327 | $X^1$ is chloro, $X^2$ is CH, $X^3$ is chloro | trifluoromethyl | hydrogen | $Y^1$ is N, $Y^2$ is N, $Y^3$ is CH |
| P.1328 | $X^1$ is chloro, $X^2$ is CH, $X^3$ is chloro | trifluoromethyl | methoxy | $Y^1$ is N, $Y^2$ is N, $Y^3$ is CH |
| P.1329 | $X^1$ is chloro, $X^2$ is CH, $X^3$ is chloro | trifluoromethyl | methyl | $Y^1$ is N, $Y^2$ is N, $Y^3$ is CH |
| P.1330 | $X^1$ is chloro, $X^2$ is CH, $X^3$ is chloro | trifluoromethyl | nitro | $Y^1$ is N, $Y^2$ is N, $Y^3$ is CH |
| P.1331 | $X^1$ is chloro, $X^2$ is CH, $X^3$ is chloro | trifluoromethyl | trifluoromethoxy | $Y^1$ is N, $Y^2$ is N, $Y^3$ is CH |
| P.1332 | $X^1$ is chloro, $X^2$ is CH, $X^3$ is chloro | trifluoromethyl | trifluoromethyl | $Y^1$ is N, $Y^2$ is N, $Y^3$ is CH |
| P.1333 | $X^1$ is chloro, $X^2$ is C—F, $X^3$ is hydrogen | chlorodifluoromethyl | bromo | $Y^1$ is N, $Y^2$ is N, $Y^3$ is CH |
| P.1334 | $X^1$ is chloro, $X^2$ is C—F, $X^3$ is hydrogen | chlorodifluoromethyl | chloro | $Y^1$ is N, $Y^2$ is N, $Y^3$ is CH |
| P.1335 | $X^1$ is chloro, $X^2$ is C—F, $X^3$ is hydrogen | chlorodifluoromethyl | cyano | $Y^1$ is N, $Y^2$ is N, $Y^3$ is CH |
| P.1336 | $X^1$ is chloro, $X^2$ is C—F, $X^3$ is hydrogen | chlorodifluoromethyl | cyclopropyl | $Y^1$ is N, $Y^2$ is N, $Y^3$ is CH |
| P.1337 | $X^1$ is chloro, $X^2$ is C—F, $X^3$ is hydrogen | chlorodifluoromethyl | ethyl | $Y^1$ is N, $Y^2$ is N, $Y^3$ is CH |
| P.1338 | $X^1$ is chloro, $X^2$ is C—F, $X^3$ is hydrogen | chlorodifluoromethyl | fluoro | $Y^1$ is N, $Y^2$ is N, $Y^3$ is CH |
| P.1339 | $X^1$ is chloro, $X^2$ is C—F, $X^3$ is hydrogen | chlorodifluoromethyl | hydrogen | $Y^1$ is N, $Y^2$ is N, $Y^3$ is CH |
| P.1340 | $X^1$ is chloro, $X^2$ is C—F, $X^3$ is hydrogen | chlorodifluoromethyl | methoxy | $Y^1$ is N, $Y^2$ is N, $Y^3$ is CH |
| P.1341 | $X^1$ is chloro, $X^2$ is C—F, $X^3$ is hydrogen | chlorodifluoromethyl | methyl | $Y^1$ is N, $Y^2$ is N, $Y^3$ is CH |
| P.1342 | $X^1$ is chloro, $X^2$ is C—F, $X^3$ is hydrogen | chlorodifluoromethyl | nitro | $Y^1$ is N, $Y^2$ is N, $Y^3$ is CH |
| P.1343 | $X^1$ is chloro, $X^2$ is C—F, $X^3$ is hydrogen | chlorodifluoromethyl | trifluoromethoxy | $Y^1$ is N, $Y^2$ is N, $Y^3$ is CH |
| P.1344 | $X^1$ is chloro, $X^2$ is C—F, $X^3$ is hydrogen | chlorodifluoromethyl | trifluoromethyl | $Y^1$ is N, $Y^2$ is N, $Y^3$ is CH |
| P.1345 | $X^1$ is chloro, $X^2$ is C—F, $X^3$ is hydrogen | difluoromethyl | bromo | $Y^1$ is N, $Y^2$ is N, $Y^3$ is CH |
| P.1346 | $X^1$ is chloro, $X^2$ is C—F, $X^3$ is hydrogen | difluoromethyl | chloro | $Y^1$ is N, $Y^2$ is N, $Y^3$ is CH |
| P.1347 | $X^1$ is chloro, $X^2$ is C—F, $X^3$ is hydrogen | difluoromethyl | cyano | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1348 | $X^1$ is chloro, $X^2$ is C—F, $X^3$ is hydrogen | difluoromethyl | cyclopropyl | $Y^1$ is N, $Y^2$ is N, $Y^3$ is CH |
| P.1349 | $X^1$ is chloro, $X^2$ is C—F, $X^3$ is hydrogen | difluoromethyl | ethyl | $Y^1$ is N, $Y^2$ is N, $Y^3$ is CH |
| P.1350 | $X^1$ is chloro, $X^2$ is C—F, $X^3$ is hydrogen | difluoromethyl | fluoro | $Y^1$ is N, $Y^2$ is N, $Y^3$ is CH |
| P.1351 | $X^1$ is chloro, $X^2$ is C—F, $X^3$ is hydrogen | difluoromethyl | hydrogen | $Y^1$ is N, $Y^2$ is N, $Y^3$ is CH |
| P.1352 | $X^1$ is chloro, $X^2$ is C—F, $X^3$ is hydrogen | difluoromethyl | methoxy | $Y^1$ is N, $Y^2$ is N, $Y^3$ is CH |
| P.1353 | $X^1$ is chloro, $X^2$ is C—F, $X^3$ is hydrogen | difluoromethyl | methyl | $Y^1$ is N, $Y^2$ is N, $Y^3$ is CH |
| P.1354 | $X^1$ is chloro, $X^2$ is C—F, $X^3$ is hydrogen | difluoromethyl | nitro | $Y^1$ is N, $Y^2$ is N, $Y^3$ is CH |
| P.1355 | $X^1$ is chloro, $X^2$ is C—F, $X^3$ is hydrogen | difluoromethyl | trifluoromethoxy | $Y^1$ is N, $Y^2$ is N, $Y^3$ is CH |
| P.1356 | $X^1$ is chloro, $X^2$ is C—F, $X^3$ is hydrogen | difluoromethyl | trifluoromethyl | $Y^1$ is N, $Y^2$ is N, $Y^3$ is CH |
| P.1357 | $X^1$ is chloro, $X^2$ is C—F, $X^3$ is hydrogen | trifluoromethyl | bromo | $Y^1$ is N, $Y^2$ is N, $Y^3$ is CH |
| P.1358 | $X^1$ is chloro, $X^2$ is C—F, $X^3$ is hydrogen | trifluoromethyl | chloro | $Y^1$ is N, $Y^2$ is N, $Y^3$ is CH |
| P.1359 | $X^1$ is chloro, $X^2$ is C—F, $X^3$ is hydrogen | trifluoromethyl | cyano | $Y^1$ is N, $Y^2$ is N, $Y^3$ is CH |
| P.1360 | $X^1$ is chloro, $X^2$ is C—F, $X^3$ is hydrogen | trifluoromethyl | cyclopropyl | $Y^1$ is N, $Y^2$ is N, $Y^3$ is CH |
| P.1361 | $X^1$ is chloro, $X^2$ is C—F, $X^3$ is hydrogen | trifluoromethyl | ethyl | $Y^1$ is N, $Y^2$ is N, $Y^3$ is CH |
| P.1362 | $X^1$ is chloro, $X^2$ is C—F, $X^3$ is hydrogen | trifluoromethyl | fluoro | $Y^1$ is N, $Y^2$ is N, $Y^3$ is CH |
| P.1363 | $X^1$ is chloro, $X^2$ is C—F, $X^3$ is hydrogen | trifluoromethyl | hydrogen | $Y^1$ is N, $Y^2$ is N, $Y^3$ is CH |
| P.1364 | $X^1$ is chloro, $X^2$ is C—F, $X^3$ is hydrogen | trifluoromethyl | methoxy | $Y^1$ is N, $Y^2$ is N, $Y^3$ is CH |
| P.1365 | $X^1$ is chloro, $X^2$ is C—F, $X^3$ is hydrogen | trifluoromethyl | methyl | $Y^1$ is N, $Y^2$ is N, $Y^3$ is CH |
| P.1366 | $X^1$ is chloro, $X^2$ is C—F, $X^3$ is hydrogen | trifluoromethyl | nitro | $Y^1$ is N, $Y^2$ is N, $Y^3$ is CH |
| P.1367 | $X^1$ is chloro, $X^2$ is C—F, $X^3$ is hydrogen | trifluoromethyl | trifluoromethoxy | $Y^1$ is N, $Y^2$ is N, $Y^3$ is CH |
| P.1368 | $X^1$ is chloro, $X^2$ is C—F, $X^3$ is hydrogen | trifluoromethyl | trifluoromethyl | $Y^1$ is N, $Y^2$ is N, $Y^3$ is CH |
| P.1369 | $X^1$ is fluoro, $X^2$ is C—Cl, $X^3$ is hydrogen | chlorodifluoromethyl | bromo | $Y^1$ is N, $Y^2$ is N, $Y^3$ is CH |
| P.1370 | $X^1$ is fluoro, $X^2$ is C—Cl, $X^3$ is hydrogen | chlorodifluoromethyl | chloro | $Y^1$ is N, $Y^2$ is N, $Y^3$ is CH |
| P.1371 | $X^1$ is fluoro, $X^2$ is C—Cl, $X^3$ is hydrogen | chlorodifluoromethyl | cyano | $Y^1$ is N, $Y^2$ is N, $Y^3$ is CH |
| P.1372 | $X^1$ is fluoro, $X^2$ is C—Cl, $X^3$ is hydrogen | chlorodifluoromethyl | cyclopropyl | $Y^1$ is N, $Y^2$ is N, $Y^3$ is CH |
| P.1373 | $X^1$ is fluoro, $X^2$ is C—Cl, $X^3$ is hydrogen | chlorodifluoromethyl | ethyl | $Y^1$ is N, $Y^2$ is N, $Y^3$ is CH |
| P.1374 | $X^1$ is fluoro, $X^2$ is C—Cl, $X^3$ is hydrogen | chlorodifluoromethyl | fluoro | $Y^1$ is N, $Y^2$ is N, $Y^3$ is CH |
| P.1375 | $X^1$ is fluoro, $X^2$ is C—Cl, $X^3$ is hydrogen | chlorodifluoromethyl | hydrogen | $Y^1$ is N, $Y^2$ is N, $Y^3$ is CH |
| P.1376 | $X^1$ is fluoro, $X^2$ is C—Cl, $X^3$ is hydrogen | chlorodifluoromethyl | methoxy | $Y^1$ is N, $Y^2$ is N, $Y^3$ is CH |
| P.1377 | $X^1$ is fluoro, $X^2$ is C—Cl, $X^3$ is hydrogen | chlorodifluoromethyl | methyl | $Y^1$ is N, $Y^2$ is N, $Y^3$ is CH |
| P.1378 | $X^1$ is fluoro, $X^2$ is C—Cl, $X^3$ is hydrogen | chlorodifluoromethyl | nitro | $Y^1$ is N, $Y^2$ is N, $Y^3$ is CH |
| P.1379 | $X^1$ is fluoro, $X^2$ is C—Cl, $X^3$ is hydrogen | chlorodifluoromethyl | trifluoromethoxy | $Y^1$ is N, $Y^2$ is N, $Y^3$ is CH |
| P.1380 | $X^1$ is fluoro, $X^2$ is C—Cl, $X^3$ is hydrogen | chlorodifluoromethyl | trifluoromethyl | $Y^1$ is N, $Y^2$ is N, $Y^3$ is CH |
| P.1381 | $X^1$ is fluoro, $X^2$ is C—Cl, $X^3$ is hydrogen | difluoromethyl | bromo | $Y^1$ is N, $Y^2$ is N, $Y^3$ is CH |
| P.1382 | $X^1$ is fluoro, $X^2$ is C—Cl, $X^3$ is hydrogen | difluoromethyl | chloro | $Y^1$ is N, $Y^2$ is N, $Y^3$ is CH |
| P.1383 | $X^1$ is fluoro, $X^2$ is C—Cl, $X^3$ is hydrogen | difluoromethyl | cyano | $Y^1$ is N, $Y^2$ is N, $Y^3$ is CH |
| P.1384 | $X^1$ is fluoro, $X^2$ is C—Cl, $X^3$ is hydrogen | difluoromethyl | cyclopropyl | $Y^1$ is N, $Y^2$ is N, $Y^3$ is CH |
| P.1385 | $X^1$ is fluoro, $X^2$ is C—Cl, $X^3$ is hydrogen | difluoromethyl | ethyl | $Y^1$ is N, $Y^2$ is N, $Y^3$ is CH |
| P.1386 | $X^1$ is fluoro, $X^2$ is C—Cl, $X^3$ is hydrogen | difluoromethyl | fluoro | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1387 | $X^1$ is fluoro, $X^2$ is C—Cl, $X^3$ is hydrogen | difluoromethyl | hydrogen | $Y^1$ is N, $Y^2$ is N, $Y^3$ is CH |
| P.1388 | $X^1$ is fluoro, $X^2$ is C—Cl, $X^3$ is hydrogen | difluoromethyl | methoxy | $Y^1$ is N, $Y^2$ is N, $Y^3$ is CH |
| P.1389 | $X^1$ is fluoro, $X^2$ is C—Cl, $X^3$ is hydrogen | difluoromethyl | methyl | $Y^1$ is N, $Y^2$ is N, $Y^3$ is CH |
| P.1390 | $X^1$ is fluoro, $X^2$ is C—Cl, $X^3$ is hydrogen | difluoromethyl | nitro | $Y^1$ is N, $Y^2$ is N, $Y^3$ is CH |
| P.1391 | $X^1$ is fluoro, $X^2$ is C—Cl, $X^3$ is hydrogen | difluoromethyl | trifluoromethoxy | $Y^1$ is N, $Y^2$ is N, $Y^3$ is CH |
| P.1392 | $X^1$ is fluoro, $X^2$ is C—Cl, $X^3$ is hydrogen | difluoromethyl | trifluoromethyl | $Y^1$ is N, $Y^2$ is N, $Y^3$ is CH |
| P.1393 | $X^1$ is fluoro, $X^2$ is C—Cl, $X^3$ is hydrogen | trifluoromethyl | bromo | $Y^1$ is N, $Y^2$ is N, $Y^3$ is CH |
| P.1394 | $X^1$ is fluoro, $X^2$ is C—Cl, $X^3$ is hydrogen | trifluoromethyl | chloro | $Y^1$ is N, $Y^2$ is N, $Y^3$ is CH |
| P.1395 | $X^1$ is fluoro, $X^2$ is C—Cl, $X^3$ is hydrogen | trifluoromethyl | cyano | $Y^1$ is N, $Y^2$ is N, $Y^3$ is CH |
| P.1396 | $X^1$ is fluoro, $X^2$ is C—Cl, $X^3$ is hydrogen | trifluoromethyl | cyclopropyl | $Y^1$ is N, $Y^2$ is N, $Y^3$ is CH |
| P.1397 | $X^1$ is fluoro, $X^2$ is C—Cl, $X^3$ is hydrogen | trifluoromethyl | ethyl | $Y^1$ is N, $Y^2$ is N, $Y^3$ is CH |
| P.1398 | $X^1$ is fluoro, $X^2$ is C—Cl, $X^3$ is hydrogen | trifluoromethyl | fluoro | $Y^1$ is N, $Y^2$ is N, $Y^3$ is CH |
| P.1399 | $X^1$ is fluoro, $X^2$ is C—Cl, $X^3$ is hydrogen | trifluoromethyl | hydrogen | $Y^1$ is N, $Y^2$ is N, $Y^3$ is CH |
| P.1400 | $X^1$ is fluoro, $X^2$ is C—Cl, $X^3$ is hydrogen | trifluoromethyl | methoxy | $Y^1$ is N, $Y^2$ is N, $Y^3$ is CH |
| P.1401 | $X^1$ is fluoro, $X^2$ is C—Cl, $X^3$ is hydrogen | trifluoromethyl | methyl | $Y^1$ is N, $Y^2$ is N, $Y^3$ is CH |
| P.1402 | $X^1$ is fluoro, $X^2$ is C—Cl, $X^3$ is hydrogen | trifluoromethyl | nitro | $Y^1$ is N, $Y^2$ is N, $Y^3$ is CH |
| P.1403 | $X^1$ is fluoro, $X^2$ is C—Cl, $X^3$ is hydrogen | trifluoromethyl | trifluoromethoxy | $Y^1$ is N, $Y^2$ is N, $Y^3$ is CH |
| P.1404 | $X^1$ is fluoro, $X^2$ is C—Cl, $X^3$ is hydrogen | trifluoromethyl | trifluoromethyl | $Y^1$ is N, $Y^2$ is N, $Y^3$ is CH |
| P.1405 | $X^1$ is chloro, $X^2$ is C—Cl, $X^3$ is hydrogen | chlorodifluoromethyl | bromo | $Y^1$ is N, $Y^2$ is N, $Y^3$ is CH |
| P.1406 | $X^1$ is chloro, $X^2$ is C—Cl, $X^3$ is hydrogen | chlorodifluoromethyl | chloro | $Y^1$ is N, $Y^2$ is N, $Y^3$ is CH |
| P.1407 | $X^1$ is chloro, $X^2$ is C—Cl, $X^3$ is hydrogen | chlorodifluoromethyl | cyano | $Y^1$ is N, $Y^2$ is N, $Y^3$ is CH |
| P.1408 | $X^1$ is chloro, $X^2$ is C—Cl, $X^3$ is hydrogen | chlorodifluoromethyl | cyclopropyl | $Y^1$ is N, $Y^2$ is N, $Y^3$ is CH |
| P.1409 | $X^1$ is chloro, $X^2$ is C—Cl, $X^3$ is hydrogen | chlorodifluoromethyl | ethyl | $Y^1$ is N, $Y^2$ is N, $Y^3$ is CH |
| P.1410 | $X^1$ is chloro, $X^2$ is C—Cl, $X^3$ is hydrogen | chlorodifluoromethyl | fluoro | $Y^1$ is N, $Y^2$ is N, $Y^3$ is CH |
| P.1411 | $X^1$ is chloro, $X^2$ is C—Cl, $X^3$ is hydrogen | chlorodifluoromethyl | hydrogen | $Y^1$ is N, $Y^2$ is N, $Y^3$ is CH |
| P.1412 | $X^1$ is chloro, $X^2$ is C—Cl, $X^3$ is hydrogen | chlorodifluoromethyl | methoxy | $Y^1$ is N, $Y^2$ is N, $Y^3$ is CH |
| P.1413 | $X^1$ is chloro, $X^2$ is C—Cl, $X^3$ is hydrogen | chlorodifluoromethyl | methyl | $Y^1$ is N, $Y^2$ is N, $Y^3$ is CH |
| P.1414 | $X^1$ is chloro, $X^2$ is C—Cl, $X^3$ is hydrogen | chlorodifluoromethyl | nitro | $Y^1$ is N, $Y^2$ is N, $Y^3$ is CH |
| P.1415 | $X^1$ is chloro, $X^2$ is C—Cl, $X^3$ is hydrogen | chlorodifluoromethyl | trifluoromethoxy | $Y^1$ is N, $Y^2$ is N, $Y^3$ is CH |
| P.1416 | $X^1$ is chloro, $X^2$ is C—Cl, $X^3$ is hydrogen | chlorodifluoromethyl | trifluoromethyl | $Y^1$ is N, $Y^2$ is N, $Y^3$ is CH |
| P.1417 | $X^1$ is chloro, $X^2$ is C—Cl, $X^3$ is hydrogen | difluoromethyl | bromo | $Y^1$ is N, $Y^2$ is N, $Y^3$ is CH |
| P.1418 | $X^1$ is chloro, $X^2$ is C—Cl, $X^3$ is hydrogen | difluoromethyl | chloro | $Y^1$ is N, $Y^2$ is N, $Y^3$ is CH |
| P.1419 | $X^1$ is chloro, $X^2$ is C—Cl, $X^3$ is hydrogen | difluoromethyl | cyano | $Y^1$ is N, $Y^2$ is N, $Y^3$ is CH |
| P.1420 | $X^1$ is chloro, $X^2$ is C—Cl, $X^3$ is hydrogen | difluoromethyl | cyclopropyl | $Y^1$ is N, $Y^2$ is N, $Y^3$ is CH |
| P.1421 | $X^1$ is chloro, $X^2$ is C—Cl, $X^3$ is hydrogen | difluoromethyl | ethyl | $Y^1$ is N, $Y^2$ is N, $Y^3$ is CH |
| P.1422 | $X^1$ is chloro, $X^2$ is C—Cl, $X^3$ is hydrogen | difluoromethyl | fluoro | $Y^1$ is N, $Y^2$ is N, $Y^3$ is CH |
| P.1423 | $X^1$ is chloro, $X^2$ is C—Cl, $X^3$ is hydrogen | difluoromethyl | hydrogen | $Y^1$ is N, $Y^2$ is N, $Y^3$ is CH |
| P.1424 | $X^1$ is chloro, $X^2$ is C—Cl, $X^3$ is hydrogen | difluoromethyl | methoxy | $Y^1$ is N, $Y^2$ is N, $Y^3$ is CH |
| P.1425 | $X^1$ is chloro, $X^2$ is C—Cl, $X^3$ is hydrogen | difluoromethyl | methyl | $Y^1$ is N, $Y^2$ is N, $Y^3$ is CH |

TABLE P-continued

|  | X1, X2, X3 | X4 | R5 | Y1, Y2, Y3 |
|---|---|---|---|---|
| P.1426 | $X^1$ is chloro, $X^2$ is C—Cl, $X^3$ is hydrogen | difluoromethyl | nitro | $Y^1$ is N, $Y^2$ is N, $Y^3$ is CH |
| P.1427 | $X^1$ is chloro, $X^2$ is C—Cl, $X^3$ is hydrogen | difluoromethyl | trifluoromethoxy | $Y^1$ is N, $Y^2$ is N, $Y^3$ is CH |
| P.1428 | $X^1$ is chloro, $X^2$ is C—Cl, $X^3$ is hydrogen | difluoromethyl | trifluoromethyl | $Y^1$ is N, $Y^2$ is N, $Y^3$ is CH |
| P.1429 | $X^1$ is chloro, $X^2$ is C—Cl, $X^3$ is hydrogen | trifluoromethyl | bromo | $Y^1$ is N, $Y^2$ is N, $Y^3$ is CH |
| P.1430 | $X^1$ is chloro, $X^2$ is C—Cl, $X^3$ is hydrogen | trifluoromethyl | chloro | $Y^1$ is N, $Y^2$ is N, $Y^3$ is CH |
| P.1431 | $X^1$ is chloro, $X^2$ is C—Cl, $X^3$ is hydrogen | trifluoromethyl | cyano | $Y^1$ is N, $Y^2$ is N, $Y^3$ is CH |
| P.1432 | $X^1$ is chloro, $X^2$ is C—Cl, $X^3$ is hydrogen | trifluoromethyl | cyclopropyl | $Y^1$ is N, $Y^2$ is N, $Y^3$ is CH |
| P.1433 | $X^1$ is chloro, $X^2$ is C—Cl, $X^3$ is hydrogen | trifluoromethyl | ethyl | $Y^1$ is N, $Y^2$ is N, $Y^3$ is CH |
| P.1434 | $X^1$ is chloro, $X^2$ is C—Cl, $X^3$ is hydrogen | trifluoromethyl | fluoro | $Y^1$ is N, $Y^2$ is N, $Y^3$ is CH |
| P.1435 | $X^1$ is chloro, $X^2$ is C—Cl, $X^3$ is hydrogen | trifluoromethyl | hydrogen | $Y^1$ is N, $Y^2$ is N, $Y^3$ is CH |
| P.1436 | $X^1$ is chloro, $X^2$ is C—Cl, $X^3$ is hydrogen | trifluoromethyl | methoxy | $Y^1$ is N, $Y^2$ is N, $Y^3$ is CH |
| P.1437 | $X^1$ is chloro, $X^2$ is C—Cl, $X^3$ is hydrogen | trifluoromethyl | methyl | $Y^1$ is N, $Y^2$ is N, $Y^3$ is CH |
| P.1438 | $X^1$ is chloro, $X^2$ is C—Cl, $X^3$ is hydrogen | trifluoromethyl | nitro | $Y^1$ is N, $Y^2$ is N, $Y^3$ is CH |
| P.1439 | $X^1$ is chloro, $X^2$ is C—Cl, $X^3$ is hydrogen | trifluoromethyl | trifluoromethoxy | $Y^1$ is N, $Y^2$ is N, $Y^3$ is CH |
| P.1440 | $X^1$ is chloro, $X^2$ is C—Cl, $X^3$ is hydrogen | trifluoromethyl | trifluoromethyl | $Y^1$ is N, $Y^2$ is N, $Y^3$ is CH |
| P.1441 | $X^1$ is chloro, $X^2$ is C—Br, $X^3$ is chloro | chlorodifluoromethyl | bromo | $Y^1$ is N, $Y^2$ is N, $Y^3$ is CH |
| P.1442 | $X^1$ is chloro, $X^2$ is C—Br, $X^3$ is chloro | chlorodifluoromethyl | chloro | $Y^1$ is N, $Y^2$ is N, $Y^3$ is CH |
| P.1443 | $X^1$ is chloro, $X^2$ is C—Br, $X^3$ is chloro | chlorodifluoromethyl | cyano | $Y^1$ is N, $Y^2$ is N, $Y^3$ is CH |
| P.1444 | $X^1$ is chloro, $X^2$ is C—Br, $X^3$ is chloro | chlorodifluoromethyl | cyclopropyl | $Y^1$ is N, $Y^2$ is N, $Y^3$ is CH |
| P.1445 | $X^1$ is chloro, $X^2$ is C—Br, $X^3$ is chloro | chlorodifluoromethyl | ethyl | $Y^1$ is N, $Y^2$ is N, $Y^3$ is CH |
| P.1446 | $X^1$ is chloro, $X^2$ is C—Br, $X^3$ is chloro | chlorodifluoromethyl | fluoro | $Y^1$ is N, $Y^2$ is N, $Y^3$ is CH |
| P.1447 | $X^1$ is chloro, $X^2$ is C—Br, $X^3$ is chloro | chlorodifluoromethyl | hydrogen | $Y^1$ is N, $Y^2$ is N, $Y^3$ is CH |
| P.1448 | $X^1$ is chloro, $X^2$ is C—Br, $X^3$ is chloro | chlorodifluoromethyl | methoxy | $Y^1$ is N, $Y^2$ is N, $Y^3$ is CH |
| P.1449 | $X^1$ is chloro, $X^2$ is C—Br, $X^3$ is chloro | chlorodifluoromethyl | methyl | $Y^1$ is N, $Y^2$ is N, $Y^3$ is CH |
| P.1450 | $X^1$ is chloro, $X^2$ is C—Br, $X^3$ is chloro | chlorodifluoromethyl | nitro | $Y^1$ is N, $Y^2$ is N, $Y^3$ is CH |
| P.1451 | $X^1$ is chloro, $X^2$ is C—Br, $X^3$ is chloro | chlorodifluoromethyl | trifluoromethoxy | $Y^1$ is N, $Y^2$ is N, $Y^3$ is CH |
| P.1452 | $X^1$ is chloro, $X^2$ is C—Br, $X^3$ is chloro | chlorodifluoromethyl | trifluoromethyl | $Y^1$ is N, $Y^2$ is N, $Y^3$ is CH |
| P.1453 | $X^1$ is chloro, $X^2$ is C—Br, $X^3$ is chloro | difluoromethyl | bromo | $Y^1$ is N, $Y^2$ is N, $Y^3$ is CH |
| P.1454 | $X^1$ is chloro, $X^2$ is C—Br, $X^3$ is chloro | difluoromethyl | chloro | $Y^1$ is N, $Y^2$ is N, $Y^3$ is CH |
| P.1455 | $X^1$ is chloro, $X^2$ is C—Br, $X^3$ is chloro | difluoromethyl | cyano | $Y^1$ is N, $Y^2$ is N, $Y^3$ is CH |
| P.1456 | $X^1$ is chloro, $X^2$ is C—Br, $X^3$ is chloro | difluoromethyl | cyclopropyl | $Y^1$ is N, $Y^2$ is N, $Y^3$ is CH |
| P.1457 | $X^1$ is chloro, $X^2$ is C—Br, $X^3$ is chloro | difluoromethyl | ethyl | $Y^1$ is N, $Y^2$ is N, $Y^3$ is CH |
| P.1458 | $X^1$ is chloro, $X^2$ is C—Br, $X^3$ is chloro | difluoromethyl | fluoro | $Y^1$ is N, $Y^2$ is N, $Y^3$ is CH |
| P.1459 | $X^1$ is chloro, $X^2$ is C—Br, $X^3$ is chloro | difluoromethyl | hydrogen | $Y^1$ is N, $Y^2$ is N, $Y^3$ is CH |
| P.1460 | $X^1$ is chloro, $X^2$ is C—Br, $X^3$ is chloro | difluoromethyl | methoxy | $Y^1$ is N, $Y^2$ is N, $Y^3$ is CH |
| P.1461 | $X^1$ is chloro, $X^2$ is C—Br, $X^3$ is chloro | difluoromethyl | methyl | $Y^1$ is N, $Y^2$ is N, $Y^3$ is CH |
| P.1462 | $X^1$ is chloro, $X^2$ is C—Br, $X^3$ is chloro | difluoromethyl | nitro | $Y^1$ is N, $Y^2$ is N, $Y^3$ is CH |
| P.1463 | $X^1$ is chloro, $X^2$ is C—Br, $X^3$ is chloro | difluoromethyl | trifluoromethoxy | $Y^1$ is N, $Y^2$ is N, $Y^3$ is CH |
| P.1464 | $X^1$ is chloro, $X^2$ is C—Br, $X^3$ is chloro | difluoromethyl | trifluoromethyl | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1465 | $X^1$ is chloro, $X^2$ is C—Br, $X^3$ is chloro | trifluoromethyl | bromo | $Y^1$ is N, $Y^2$ is N, $Y^3$ is CH |
| P.1466 | $X^1$ is chloro, $X^2$ is C—Br, $X^3$ is chloro | trifluoromethyl | chloro | $Y^1$ is N, $Y^2$ is N, $Y^3$ is CH |
| P.1467 | $X^1$ is chloro, $X^2$ is C—Br, $X^3$ is chloro | trifluoromethyl | cyano | $Y^1$ is N, $Y^2$ is N, $Y^3$ is CH |
| P.1468 | $X^1$ is chloro, $X^2$ is C—Br, $X^3$ is chloro | trifluoromethyl | cyclopropyl | $Y^1$ is N, $Y^2$ is N, $Y^3$ is CH |
| P.1469 | $X^1$ is chloro, $X^2$ is C—Br, $X^3$ is chloro | trifluoromethyl | ethyl | $Y^1$ is N, $Y^2$ is N, $Y^3$ is CH |
| P.1470 | $X^1$ is chloro, $X^2$ is C—Br, $X^3$ is chloro | trifluoromethyl | fluoro | $Y^1$ is N, $Y^2$ is N, $Y^3$ is CH |
| P.1471 | $X^1$ is chloro, $X^2$ is C—Br, $X^3$ is chloro | trifluoromethyl | hydrogen | $Y^1$ is N, $Y^2$ is N, $Y^3$ is CH |
| P.1472 | $X^1$ is chloro, $X^2$ is C—Br, $X^3$ is chloro | trifluoromethyl | methoxy | $Y^1$ is N, $Y^2$ is N, $Y^3$ is CH |
| P.1473 | $X^1$ is chloro, $X^2$ is C—Br, $X^3$ is chloro | trifluoromethyl | methyl | $Y^1$ is N, $Y^2$ is N, $Y^3$ is CH |
| P.1474 | $X^1$ is chloro, $X^2$ is C—Br, $X^3$ is chloro | trifluoromethyl | nitro | $Y^1$ is N, $Y^2$ is N, $Y^3$ is CH |
| P.1475 | $X^1$ is chloro, $X^2$ is C—Br, $X^3$ is chloro | trifluoromethyl | trifluoromethoxy | $Y^1$ is N, $Y^2$ is N, $Y^3$ is CH |
| P.1476 | $X^1$ is chloro, $X^2$ is C—Br, $X^3$ is chloro | trifluoromethyl | trifluoromethyl | $Y^1$ is N, $Y^2$ is N, $Y^3$ is CH |
| P.1477 | $X^1$ is chloro, $X^2$ is C—F, $X^3$ is chloro | chlorodifluoromethyl | bromo | $Y^1$ is N, $Y^2$ is N, $Y^3$ is CH |
| P.1478 | $X^1$ is chloro, $X^2$ is C—F, $X^3$ is chloro | chlorodifluoromethyl | chloro | $Y^1$ is N, $Y^2$ is N, $Y^3$ is CH |
| P.1479 | $X^1$ is chloro, $X^2$ is C—F, $X^3$ is chloro | chlorodifluoromethyl | cyano | $Y^1$ is N, $Y^2$ is N, $Y^3$ is CH |
| P.1480 | $X^1$ is chloro, $X^2$ is C—F, $X^3$ is chloro | chlorodifluoromethyl | cyclopropyl | $Y^1$ is N, $Y^2$ is N, $Y^3$ is CH |
| P.1481 | $X^1$ is chloro, $X^2$ is C—F, $X^3$ is chloro | chlorodifluoromethyl | ethyl | $Y^1$ is N, $Y^2$ is N, $Y^3$ is CH |
| P.1482 | $X^1$ is chloro, $X^2$ is C—F, $X^3$ is chloro | chlorodifluoromethyl | fluoro | $Y^1$ is N, $Y^2$ is N, $Y^3$ is CH |
| P.1483 | $X^1$ is chloro, $X^2$ is C—F, $X^3$ is chloro | chlorodifluoromethyl | hydrogen | $Y^1$ is N, $Y^2$ is N, $Y^3$ is CH |
| P.1484 | $X^1$ is chloro, $X^2$ is C—F, $X^3$ is chloro | chlorodifluoromethyl | methoxy | $Y^1$ is N, $Y^2$ is N, $Y^3$ is CH |
| P.1485 | $X^1$ is chloro, $X^2$ is C—F, $X^3$ is chloro | chlorodifluoromethyl | methyl | $Y^1$ is N, $Y^2$ is N, $Y^3$ is CH |
| P.1486 | $X^1$ is chloro, $X^2$ is C—F, $X^3$ is chloro | chlorodifluoromethyl | nitro | $Y^1$ is N, $Y^2$ is N, $Y^3$ is CH |
| P.1487 | $X^1$ is chloro, $X^2$ is C—F, $X^3$ is chloro | chlorodifluoromethyl | trifluoromethoxy | $Y^1$ is N, $Y^2$ is N, $Y^3$ is CH |
| P.1488 | $X^1$ is chloro, $X^2$ is C—F, $X^3$ is chloro | chlorodifluoromethyl | trifluoromethyl | $Y^1$ is N, $Y^2$ is N, $Y^3$ is CH |
| P.1489 | $X^1$ is chloro, $X^2$ is C—F, $X^3$ is chloro | difluoromethyl | bromo | $Y^1$ is N, $Y^2$ is N, $Y^3$ is CH |
| P.1490 | $X^1$ is chloro, $X^2$ is C—F, $X^3$ is chloro | difluoromethyl | chloro | $Y^1$ is N, $Y^2$ is N, $Y^3$ is CH |
| P.1491 | $X^1$ is chloro, $X^2$ is C—F, $X^3$ is chloro | difluoromethyl | cyano | $Y^1$ is N, $Y^2$ is N, $Y^3$ is CH |
| P.1492 | $X^1$ is chloro, $X^2$ is C—F, $X^3$ is chloro | difluoromethyl | cyclopropyl | $Y^1$ is N, $Y^2$ is N, $Y^3$ is CH |
| P.1493 | $X^1$ is chloro, $X^2$ is C—F, $X^3$ is chloro | difluoromethyl | ethyl | $Y^1$ is N, $Y^2$ is N, $Y^3$ is CH |
| P.1494 | $X^1$ is chloro, $X^2$ is C—F, $X^3$ is chloro | difluoromethyl | fluoro | $Y^1$ is N, $Y^2$ is N, $Y^3$ is CH |
| P.1495 | $X^1$ is chloro, $X^2$ is C—F, $X^3$ is chloro | difluoromethyl | hydrogen | $Y^1$ is N, $Y^2$ is N, $Y^3$ is CH |
| P.1496 | $X^1$ is chloro, $X^2$ is C—F, $X^3$ is chloro | difluoromethyl | methoxy | $Y^1$ is N, $Y^2$ is N, $Y^3$ is CH |
| P.1497 | $X^1$ is chloro, $X^2$ is C—F, $X^3$ is chloro | difluoromethyl | methyl | $Y^1$ is N, $Y^2$ is N, $Y^3$ is CH |
| P.1498 | $X^1$ is chloro, $X^2$ is C—F, $X^3$ is chloro | difluoromethyl | nitro | $Y^1$ is N, $Y^2$ is N, $Y^3$ is CH |
| P.1499 | $X^1$ is chloro, $X^2$ is C—F, $X^3$ is chloro | difluoromethyl | trifluoromethoxy | $Y^1$ is N, $Y^2$ is N, $Y^3$ is CH |
| P.1500 | $X^1$ is chloro, $X^2$ is C—F, $X^3$ is chloro | difluoromethyl | trifluoromethyl | $Y^1$ is N, $Y^2$ is N, $Y^3$ is CH |
| P.1501 | $X^1$ is chloro, $X^2$ is C—F, $X^3$ is chloro | trifluoromethyl | bromo | $Y^1$ is N, $Y^2$ is N, $Y^3$ is CH |
| P.1502 | $X^1$ is chloro, $X^2$ is C—F, $X^3$ is chloro | trifluoromethyl | chloro | $Y^1$ is N, $Y^2$ is N, $Y^3$ is CH |
| P.1503 | $X^1$ is chloro, $X^2$ is C—F, $X^3$ is chloro | trifluoromethyl | cyano | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1504 | $X^1$ is chloro, $X^2$ is C—F, $X^3$ is chloro | trifluoromethyl | cyclopropyl | $Y^1$ is N, $Y^2$ is N, $Y^3$ is CH |
| P.1505 | $X^1$ is chloro, $X^2$ is C—F, $X^3$ is chloro | trifluoromethyl | ethyl | $Y^1$ is N, $Y^2$ is N, $Y^3$ is CH |
| P.1506 | $X^1$ is chloro, $X^2$ is C—F, $X^3$ is chloro | trifluoromethyl | fluoro | $Y^1$ is N, $Y^2$ is N, $Y^3$ is CH |
| P.1507 | $X^1$ is chloro, $X^2$ is C—F, $X^3$ is chloro | trifluoromethyl | hydrogen | $Y^1$ is N, $Y^2$ is N, $Y^3$ is CH |
| P.1508 | $X^1$ is chloro, $X^2$ is C—F, $X^3$ is chloro | trifluoromethyl | methoxy | $Y^1$ is N, $Y^2$ is N, $Y^3$ is CH |
| P.1509 | $X^1$ is chloro, $X^2$ is C—F, $X^3$ is chloro | trifluoromethyl | methyl | $Y^1$ is N, $Y^2$ is N, $Y^3$ is CH |
| P.1510 | $X^1$ is chloro, $X^2$ is C—F, $X^3$ is chloro | trifluoromethyl | nitro | $Y^1$ is N, $Y^2$ is N, $Y^3$ is CH |
| P.1511 | $X^1$ is chloro, $X^2$ is C—F, $X^3$ is chloro | trifluoromethyl | trifluoromethoxy | $Y^1$ is N, $Y^2$ is N, $Y^3$ is CH |
| P.1512 | $X^1$ is chloro, $X^2$ is C—F, $X^3$ is chloro | trifluoromethyl | trifluoromethyl | $Y^1$ is N, $Y^2$ is N, $Y^3$ is CH |
| P.1513 | $X^1$ is chloro, $X^2$ is C—Cl, $X^3$ is chloro | chlorodifluoromethyl | bromo | $Y^1$ is N, $Y^2$ is N, $Y^3$ is CH |
| P.1514 | $X^1$ is chloro, $X^2$ is C—Cl, $X^3$ is chloro | chlorodifluoromethyl | chloro | $Y^1$ is N, $Y^2$ is N, $Y^3$ is CH |
| P.1515 | $X^1$ is chloro, $X^2$ is C—Cl, $X^3$ is chloro | chlorodifluoromethyl | cyano | $Y^1$ is N, $Y^2$ is N, $Y^3$ is CH |
| P.1516 | $X^1$ is chloro, $X^2$ is C—Cl, $X^3$ is chloro | chlorodifluoromethyl | cyclopropyl | $Y^1$ is N, $Y^2$ is N, $Y^3$ is CH |
| P.1517 | $X^1$ is chloro, $X^2$ is C—Cl, $X^3$ is chloro | chlorodifluoromethyl | ethyl | $Y^1$ is N, $Y^2$ is N, $Y^3$ is CH |
| P.1518 | $X^1$ is chloro, $X^2$ is C—Cl, $X^3$ is chloro | chlorodifluoromethyl | fluoro | $Y^1$ is N, $Y^2$ is N, $Y^3$ is CH |
| P.1519 | $X^1$ is chloro, $X^2$ is C—Cl, $X^3$ is chloro | chlorodifluoromethyl | hydrogen | $Y^1$ is N, $Y^2$ is N, $Y^3$ is CH |
| P.1520 | $X^1$ is chloro, $X^2$ is C—Cl, $X^3$ is chloro | chlorodifluoromethyl | methoxy | $Y^1$ is N, $Y^2$ is N, $Y^3$ is CH |
| P.1521 | $X^1$ is chloro, $X^2$ is C—Cl, $X^3$ is chloro | chlorodifluoromethyl | methyl | $Y^1$ is N, $Y^2$ is N, $Y^3$ is CH |
| P.1522 | $X^1$ is chloro, $X^2$ is C—Cl, $X^3$ is chloro | chlorodifluoromethyl | nitro | $Y^1$ is N, $Y^2$ is N, $Y^3$ is CH |
| P.1523 | $X^1$ is chloro, $X^2$ is C—Cl, $X^3$ is chloro | chlorodifluoromethyl | trifluoromethoxy | $Y^1$ is N, $Y^2$ is N, $Y^3$ is CH |
| P.1524 | $X^1$ is chloro, $X^2$ is C—Cl, $X^3$ is chloro | chlorodifluoromethyl | trifluoromethyl | $Y^1$ is N, $Y^2$ is N, $Y^3$ is CH |
| P.1525 | $X^1$ is chloro, $X^2$ is C—Cl, $X^3$ is chloro | difluoromethyl | bromo | $Y^1$ is N, $Y^2$ is N, $Y^3$ is CH |
| P.1526 | $X^1$ is chloro, $X^2$ is C—Cl, $X^3$ is chloro | difluoromethyl | chloro | $Y^1$ is N, $Y^2$ is N, $Y^3$ is CH |
| P.1527 | $X^1$ is chloro, $X^2$ is C—Cl, $X^3$ is chloro | difluoromethyl | cyano | $Y^1$ is N, $Y^2$ is N, $Y^3$ is CH |
| P.1528 | $X^1$ is chloro, $X^2$ is C—Cl, $X^3$ is chloro | difluoromethyl | cyclopropyl | $Y^1$ is N, $Y^2$ is N, $Y^3$ is CH |
| P.1529 | $X^1$ is chloro, $X^2$ is C—Cl, $X^3$ is chloro | difluoromethyl | ethyl | $Y^1$ is N, $Y^2$ is N, $Y^3$ is CH |
| P.1530 | $X^1$ is chloro, $X^2$ is C—Cl, $X^3$ is chloro | difluoromethyl | fluoro | $Y^1$ is N, $Y^2$ is N, $Y^3$ is CH |
| P.1531 | $X^1$ is chloro, $X^2$ is C—Cl, $X^3$ is chloro | difluoromethyl | hydrogen | $Y^1$ is N, $Y^2$ is N, $Y^3$ is CH |
| P.1532 | $X^1$ is chloro, $X^2$ is C—Cl, $X^3$ is chloro | difluoromethyl | methoxy | $Y^1$ is N, $Y^2$ is N, $Y^3$ is CH |
| P.1533 | $X^1$ is chloro, $X^2$ is C—Cl, $X^3$ is chloro | difluoromethyl | methyl | $Y^1$ is N, $Y^2$ is N, $Y^3$ is CH |
| P.1534 | $X^1$ is chloro, $X^2$ is C—Cl, $X^3$ is chloro | difluoromethyl | nitro | $Y^1$ is N, $Y^2$ is N, $Y^3$ is CH |
| P.1562 | $X^1$ is chloro, $X^2$ is C—I, $X^3$ is chloro | difluoromethyl | chloro | $Y^1$ is N, $Y^2$ is N, $Y^3$ is CH |
| P.1563 | $X^1$ is chloro, $X^2$ is C—I, $X^3$ is chloro | difluoromethyl | cyano | $Y^1$ is N, $Y^2$ is N, $Y^3$ is CH |
| P.1564 | $X^1$ is chloro, $X^2$ is C—I, $X^3$ is chloro | difluoromethyl | cyclopropyl | $Y^1$ is N, $Y^2$ is N, $Y^3$ is CH |
| P.1565 | $X^1$ is chloro, $X^2$ is C—I, $X^3$ is chloro | difluoromethyl | ethyl | $Y^1$ is N, $Y^2$ is N, $Y^3$ is CH |
| P.1566 | $X^1$ is chloro, $X^2$ is C—I, $X^3$ is chloro | difluoromethyl | fluoro | $Y^1$ is N, $Y^2$ is N, $Y^3$ is CH |
| P.1567 | $X^1$ is chloro, $X^2$ is C—I, $X^3$ is chloro | difluoromethyl | hydrogen | $Y^1$ is N, $Y^2$ is N, $Y^3$ is CH |
| P.1568 | $X^1$ is chloro, $X^2$ is C—I, $X^3$ is chloro | difluoromethyl | methoxy | $Y^1$ is N, $Y^2$ is N, $Y^3$ is CH |
| P.1569 | $X^1$ is chloro, $X^2$ is C—I, $X^3$ is chloro | difluoromethyl | methyl | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1570 | $X^1$ is chloro, $X^2$ is C—I, $X^3$ is chloro | difluoromethyl | nitro | $Y^1$ is N, $Y^2$ is N, $Y^3$ is CH |
| P.1571 | $X^1$ is chloro, $X^2$ is C—I, $X^3$ is chloro | difluoromethyl | trifluoromethoxy | $Y^1$ is N, $Y^2$ is N, $Y^3$ is CH |
| P.1572 | $X^1$ is chloro, $X^2$ is C—I, $X^3$ is chloro | difluoromethyl | trifluoromethyl | $Y^1$ is N, $Y^2$ is N, $Y^3$ is CH |
| P.1573 | $X^1$ is chloro, $X^2$ is C—I, $X^3$ is chloro | trifluoromethyl | bromo | $Y^1$ is N, $Y^2$ is N, $Y^3$ is CH |
| P.1574 | $X^1$ is chloro, $X^2$ is C—I, $X^3$ is chloro | trifluoromethyl | chloro | $Y^1$ is N, $Y^2$ is N, $Y^3$ is CH |
| P.1575 | $X^1$ is chloro, $X^2$ is C—I, $X^3$ is chloro | trifluoromethyl | cyano | $Y^1$ is N, $Y^2$ is N, $Y^3$ is CH |
| P.1576 | $X^1$ is chloro, $X^2$ is C—I, $X^3$ is chloro | trifluoromethyl | cyclopropyl | $Y^1$ is N, $Y^2$ is N, $Y^3$ is CH |
| P.1577 | $X^1$ is chloro, $X^2$ is C—I, $X^3$ is chloro | trifluoromethyl | ethyl | $Y^1$ is N, $Y^2$ is N, $Y^3$ is CH |
| P.1578 | $X^1$ is chloro, $X^2$ is C—I, $X^3$ is chloro | trifluoromethyl | fluoro | $Y^1$ is N, $Y^2$ is N, $Y^3$ is CH |
| P.1579 | $X^1$ is chloro, $X^2$ is C—I, $X^3$ is chloro | trifluoromethyl | hydrogen | $Y^1$ is N, $Y^2$ is N, $Y^3$ is CH |
| P.1580 | $X^1$ is chloro, $X^2$ is C—I, $X^3$ is chloro | trifluoromethyl | methoxy | $Y^1$ is N, $Y^2$ is N, $Y^3$ is CH |
| P.1581 | $X^1$ is chloro, $X^2$ is C—I, $X^3$ is chloro | trifluoromethyl | methyl | $Y^1$ is N, $Y^2$ is N, $Y^3$ is CH |
| P.1582 | $X^1$ is chloro, $X^2$ is C—I, $X^3$ is chloro | trifluoromethyl | nitro | $Y^1$ is N, $Y^2$ is N, $Y^3$ is CH |
| P.1583 | $X^1$ is chloro, $X^2$ is C—I, $X^3$ is chloro | trifluoromethyl | trifluoromethoxy | $Y^1$ is N, $Y^2$ is N, $Y^3$ is CH |
| P.1584 | $X^1$ is chloro, $X^2$ is C—I, $X^3$ is chloro | trifluoromethyl | trifluoromethyl | $Y^1$ is N, $Y^2$ is N, $Y^3$ is CH |
| P.1585 | $X^1$ is fluoro, $X^2$ is C—F, $X^3$ is fluoro | chlorodifluoromethyl | bromo | $Y^1$ is N, $Y^2$ is N, $Y^3$ is CH |
| P.1586 | $X^1$ is fluoro, $X^2$ is C—F, $X^3$ is fluoro | chlorodifluoromethyl | chloro | $Y^1$ is N, $Y^2$ is N, $Y^3$ is CH |
| P.1587 | $X^1$ is fluoro, $X^2$ is C—F, $X^3$ is fluoro | chlorodifluoromethyl | cyano | $Y^1$ is N, $Y^2$ is N, $Y^3$ is CH |
| P.1588 | $X^1$ is fluoro, $X^2$ is C—F, $X^3$ is fluoro | chlorodifluoromethyl | cyclopropyl | $Y^1$ is N, $Y^2$ is N, $Y^3$ is CH |
| P.1589 | $X^1$ is fluoro, $X^2$ is C—F, $X^3$ is fluoro | chlorodifluoromethyl | ethyl | $Y^1$ is N, $Y^2$ is N, $Y^3$ is CH |
| P.1590 | $X^1$ is fluoro, $X^2$ is C—F, $X^3$ is fluoro | chlorodifluoromethyl | fluoro | $Y^1$ is N, $Y^2$ is N, $Y^3$ is CH |
| P.1591 | $X^1$ is fluoro, $X^2$ is C—F, $X^3$ is fluoro | chlorodifluoromethyl | hydrogen | $Y^1$ is N, $Y^2$ is N, $Y^3$ is CH |
| P.1592 | $X^1$ is fluoro, $X^2$ is C—F, $X^3$ is fluoro | chlorodifluoromethyl | methoxy | $Y^1$ is N, $Y^2$ is N, $Y^3$ is CH |
| P.1593 | $X^1$ is fluoro, $X^2$ is C—F, $X^3$ is fluoro | chlorodifluoromethyl | methyl | $Y^1$ is N, $Y^2$ is N, $Y^3$ is CH |
| P.1594 | $X^1$ is fluoro, $X^2$ is C—F, $X^3$ is fluoro | chlorodifluoromethyl | nitro | $Y^1$ is N, $Y^2$ is N, $Y^3$ is CH |
| P.1595 | $X^1$ is fluoro, $X^2$ is C—F, $X^3$ is fluoro | chlorodifluoromethyl | trifluoromethoxy | $Y^1$ is N, $Y^2$ is N, $Y^3$ is CH |
| P.1596 | $X^1$ is fluoro, $X^2$ is C—F, $X^3$ is fluoro | chlorodifluoromethyl | trifluoromethyl | $Y^1$ is N, $Y^2$ is N, $Y^3$ is CH |
| P.1597 | $X^1$ is fluoro, $X^2$ is C—F, $X^3$ is fluoro | difluoromethyl | bromo | $Y^1$ is N, $Y^2$ is N, $Y^3$ is CH |
| P.1598 | $X^1$ is fluoro, $X^2$ is C—F, $X^3$ is fluoro | difluoromethyl | chloro | $Y^1$ is N, $Y^2$ is N, $Y^3$ is CH |
| P.1599 | $X^1$ is fluoro, $X^2$ is C—F, $X^3$ is fluoro | difluoromethyl | cyano | $Y^1$ is N, $Y^2$ is N, $Y^3$ is CH |
| P.1600 | $X^1$ is fluoro, $X^2$ is C—F, $X^3$ is fluoro | difluoromethyl | cyclopropyl | $Y^1$ is N, $Y^2$ is N, $Y^3$ is CH |
| P.1601 | $X^1$ is fluoro, $X^2$ is C—F, $X^3$ is fluoro | difluoromethyl | ethyl | $Y^1$ is N, $Y^2$ is N, $Y^3$ is CH |
| P.1602 | $X^1$ is fluoro, $X^2$ is C—F, $X^3$ is fluoro | difluoromethyl | fluoro | $Y^1$ is N, $Y^2$ is N, $Y^3$ is CH |
| P.1603 | $X^1$ is fluoro, $X^2$ is C—F, $X^3$ is fluoro | difluoromethyl | hydrogen | $Y^1$ is N, $Y^2$ is N, $Y^3$ is CH |
| P.1604 | $X^1$ is fluoro, $X^2$ is C—F, $X^3$ is fluoro | difluoromethyl | methoxy | $Y^1$ is N, $Y^2$ is N, $Y^3$ is CH |
| P.1605 | $X^1$ is fluoro, $X^2$ is C—F, $X^3$ is fluoro | difluoromethyl | methyl | $Y^1$ is N, $Y^2$ is N, $Y^3$ is CH |
| P.1606 | $X^1$ is fluoro, $X^2$ is C—F, $X^3$ is fluoro | difluoromethyl | nitro | $Y^1$ is N, $Y^2$ is N, $Y^3$ is CH |
| P.1607 | $X^1$ is fluoro, $X^2$ is C—F, $X^3$ is fluoro | difluoromethyl | trifluoromethoxy | $Y^1$ is N, $Y^2$ is N, $Y^3$ is CH |
| P.1608 | $X^1$ is fluoro, $X^2$ is C—F, $X^3$ is fluoro | difluoromethyl | trifluoromethyl | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1609 | $X^1$ is fluoro, $X^2$ is C—F, $X^3$ is fluoro | trifluoromethyl | bromo | $Y^1$ is N, $Y^2$ is N, $Y^3$ is CH |
| P.1610 | $X^1$ is fluoro, $X^2$ is C—F, $X^3$ is fluoro | trifluoromethyl | chloro | $Y^1$ is N, $Y^2$ is N, $Y^3$ is CH |
| P.1611 | $X^1$ is fluoro, $X^2$ is C—F, $X^3$ is fluoro | trifluoromethyl | cyano | $Y^1$ is N, $Y^2$ is N, $Y^3$ is CH |
| P.1612 | $X^1$ is fluoro, $X^2$ is C—F, $X^3$ is fluoro | trifluoromethyl | cyclopropyl | $Y^1$ is N, $Y^2$ is N, $Y^3$ is CH |
| P.1613 | $X^1$ is fluoro, $X^2$ is C—F, $X^3$ is fluoro | trifluoromethyl | ethyl | $Y^1$ is N, $Y^2$ is N, $Y^3$ is CH |
| P.1614 | $X^1$ is fluoro, $X^2$ is C—F, $X^3$ is fluoro | trifluoromethyl | fluoro | $Y^1$ is N, $Y^2$ is N, $Y^3$ is CH |
| P.1615 | $X^1$ is fluoro, $X^2$ is C—F, $X^3$ is fluoro | trifluoromethyl | hydrogen | $Y^1$ is N, $Y^2$ is N, $Y^3$ is CH |
| P.1616 | $X^1$ is fluoro, $X^2$ is C—F, $X^3$ is fluoro | trifluoromethyl | methoxy | $Y^1$ is N, $Y^2$ is N, $Y^3$ is CH |
| P.1617 | $X^1$ is fluoro, $X^2$ is C—F, $X^3$ is fluoro | trifluoromethyl | methyl | $Y^1$ is N, $Y^2$ is N, $Y^3$ is CH |
| P.1618 | $X^1$ is fluoro, $X^2$ is C—F, $X^3$ is fluoro | trifluoromethyl | nitro | $Y^1$ is N, $Y^2$ is N, $Y^3$ is CH |
| P.1619 | $X^1$ is fluoro, $X^2$ is C—F, $X^3$ is fluoro | trifluoromethyl | trifluoromethoxy | $Y^1$ is N, $Y^2$ is N, $Y^3$ is CH |
| P.1620 | $X^1$ is fluoro, $X^2$ is C—F, $X^3$ is fluoro | trifluoromethyl | trifluoromethyl | $Y^1$ is N, $Y^2$ is N, $Y^3$ is CH |
| P.1621 | $X^1$ is chloro, $X^2$ is CH, $X^3$ is bromo | chlorodifluoromethyl | bromo | $Y^1$ is N, $Y^2$ is N, $Y^3$ is CH |
| P.1622 | $X^1$ is chloro, $X^2$ is CH, $X^3$ is bromo | chlorodifluoromethyl | chloro | $Y^1$ is N, $Y^2$ is N, $Y^3$ is CH |
| P.1623 | $X^1$ is chloro, $X^2$ is CH, $X^3$ is bromo | chlorodifluoromethyl | cyano | $Y^1$ is N, $Y^2$ is N, $Y^3$ is CH |
| P.1624 | $X^1$ is chloro, $X^2$ is CH, $X^3$ is bromo | chlorodifluoromethyl | cyclopropyl | $Y^1$ is N, $Y^2$ is N, $Y^3$ is CH |
| P.1625 | $X^1$ is chloro, $X^2$ is CH, $X^3$ is bromo | chlorodifluoromethyl | ethyl | $Y^1$ is N, $Y^2$ is N, $Y^3$ is CH |
| P.1626 | $X^1$ is chloro, $X^2$ is CH, $X^3$ is bromo | chlorodifluoromethyl | fluoro | $Y^1$ is N, $Y^2$ is N, $Y^3$ is CH |
| P.1627 | $X^1$ is chloro, $X^2$ is CH, $X^3$ is bromo | chlorodifluoromethyl | hydrogen | $Y^1$ is N, $Y^2$ is N, $Y^3$ is CH |
| P.1628 | $X^1$ is chloro, $X^2$ is CH, $X^3$ is bromo | chlorodifluoromethyl | methoxy | $Y^1$ is N, $Y^2$ is N, $Y^3$ is CH |
| P.1629 | $X^1$ is chloro, $X^2$ is CH, $X^3$ is bromo | chlorodifluoromethyl | methyl | $Y^1$ is N, $Y^2$ is N, $Y^3$ is CH |
| P.1630 | $X^1$ is chloro, $X^2$ is CH, $X^3$ is bromo | chlorodifluoromethyl | nitro | $Y^1$ is N, $Y^2$ is N, $Y^3$ is CH |
| P.1631 | $X^1$ is chloro, $X^2$ is CH, $X^3$ is bromo | chlorodifluoromethyl | trifluoromethoxy | $Y^1$ is N, $Y^2$ is N, $Y^3$ is CH |
| P.1632 | $X^1$ is chloro, $X^2$ is CH, $X^3$ is bromo | chlorodifluoromethyl | trifluoromethyl | $Y^1$ is N, $Y^2$ is N, $Y^3$ is CH |
| P.1633 | $X^1$ is chloro, $X^2$ is CH, $X^3$ is bromo | difluoromethyl | bromo | $Y^1$ is N, $Y^2$ is N, $Y^3$ is CH |
| P.1634 | $X^1$ is chloro, $X^2$ is CH, $X^3$ is bromo | difluoromethyl | chloro | $Y^1$ is N, $Y^2$ is N, $Y^3$ is CH |
| P.1635 | $X^1$ is chloro, $X^2$ is CH, $X^3$ is bromo | difluoromethyl | cyano | $Y^1$ is N, $Y^2$ is N, $Y^3$ is CH |
| P.1636 | $X^1$ is chloro, $X^2$ is CH, $X^3$ is bromo | difluoromethyl | cyclopropyl | $Y^1$ is N, $Y^2$ is N, $Y^3$ is CH |
| P.1637 | $X^1$ is chloro, $X^2$ is CH, $X^3$ is bromo | difluoromethyl | ethyl | $Y^1$ is N, $Y^2$ is N, $Y^3$ is CH |
| P.1638 | $X^1$ is chloro, $X^2$ is CH, $X^3$ is bromo | difluoromethyl | fluoro | $Y^1$ is N, $Y^2$ is N, $Y^3$ is CH |
| P.1639 | $X^1$ is chloro, $X^2$ is CH, $X^3$ is bromo | difluoromethyl | hydrogen | $Y^1$ is N, $Y^2$ is N, $Y^3$ is CH |
| P.1640 | $X^1$ is chloro, $X^2$ is CH, $X^3$ is bromo | difluoromethyl | methoxy | $Y^1$ is N, $Y^2$ is N, $Y^3$ is CH |
| P.1641 | $X^1$ is chloro, $X^2$ is CH, $X^3$ is bromo | difluoromethyl | methyl | $Y^1$ is N, $Y^2$ is N, $Y^3$ is CH |
| P.1642 | $X^1$ is chloro, $X^2$ is CH, $X^3$ is bromo | difluoromethyl | nitro | $Y^1$ is N, $Y^2$ is N, $Y^3$ is CH |
| P.1643 | $X^1$ is chloro, $X^2$ is CH, $X^3$ is bromo | difluoromethyl | trifluoromethoxy | $Y^1$ is N, $Y^2$ is N, $Y^3$ is CH |
| P.1644 | $X^1$ is chloro, $X^2$ is CH, $X^3$ is bromo | difluoromethyl | trifluoromethyl | $Y^1$ is N, $Y^2$ is N, $Y^3$ is CH |
| P.1645 | $X^1$ is chloro, $X^2$ is CH, $X^3$ is bromo | trifluoromethyl | bromo | $Y^1$ is N, $Y^2$ is N, $Y^3$ is CH |
| P.1646 | $X^1$ is chloro, $X^2$ is CH, $X^3$ is bromo | trifluoromethyl | chloro | $Y^1$ is N, $Y^2$ is N, $Y^3$ is CH |
| P.1647 | $X^1$ is chloro, $X^2$ is CH, $X^3$ is bromo | trifluoromethyl | cyano | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1648 | X$^1$ is chloro, X$^2$ is CH, X$^3$ is bromo | trifluoromethyl | cyclopropyl | Y$^1$ is N, Y$^2$ is N, Y$^3$ is CH |
| P.1649 | X$^1$ is chloro, X$^2$ is CH, X$^3$ is bromo | trifluoromethyl | ethyl | Y$^1$ is N, Y$^2$ is N, Y$^3$ is CH |
| P.1650 | X$^1$ is chloro, X$^2$ is CH, X$^3$ is bromo | trifluoromethyl | fluoro | Y$^1$ is N, Y$^2$ is N, Y$^3$ is CH |
| P.1651 | X$^1$ is chloro, X$^2$ is CH, X$^3$ is bromo | trifluoromethyl | hydrogen | Y$^1$ is N, Y$^2$ is N, Y$^3$ is CH |
| P.1652 | X$^1$ is chloro, X$^2$ is CH, X$^3$ is bromo | trifluoromethyl | methoxy | Y$^1$ is N, Y$^2$ is N, Y$^3$ is CH |
| P.1653 | X$^1$ is chloro, X$^2$ is CH, X$^3$ is bromo | trifluoromethyl | methyl | Y$^1$ is N, Y$^2$ is N, Y$^3$ is CH |
| P.1654 | X$^1$ is chloro, X$^2$ is CH, X$^3$ is bromo | trifluoromethyl | nitro | Y$^1$ is N, Y$^2$ is N, Y$^3$ is CH |
| P.1655 | X$^1$ is chloro, X$^2$ is CH, X$^3$ is bromo | trifluoromethyl | trifluoromethoxy | Y$^1$ is N, Y$^2$ is N, Y$^3$ is CH |
| P.1656 | X$^1$ is chloro, X$^2$ is CH, X$^3$ is bromo | trifluoromethyl | trifluoromethyl | Y$^1$ is N, Y$^2$ is N, Y$^3$ is CH |
| P.1657 | X$^1$ is chloro, X$^2$ is CH, X$^3$ is bromo | chlorodifluoromethyl | bromo | Y$^1$ is N, Y$^2$ is N, Y$^3$ is CH |
| P.1658 | X$^1$ is chloro, X$^2$ is CH, X$^3$ is bromo | chlorodifluoromethyl | chloro | Y$^1$ is N, Y$^2$ is N, Y$^3$ is CH |
| P.1659 | X$^1$ is chloro, X$^2$ is CH, X$^3$ is bromo | chlorodifluoromethyl | cyano | Y$^1$ is N, Y$^2$ is N, Y$^3$ is CH |
| P.1660 | X$^1$ is chloro, X$^2$ is CH, X$^3$ is bromo | chlorodifluoromethyl | cyclopropyl | Y$^1$ is N, Y$^2$ is N, Y$^3$ is CH |
| P.1661 | X$^1$ is chloro, X$^2$ is CH, X$^3$ is bromo | chlorodifluoromethyl | ethyl | Y$^1$ is N, Y$^2$ is N, Y$^3$ is CH |
| P.1662 | X$^1$ is chloro, X$^2$ is CH, X$^3$ is bromo | chlorodifluoromethyl | fluoro | Y$^1$ is N, Y$^2$ is N, Y$^3$ is CH |
| P.1663 | X$^1$ is chloro, X$^2$ is CH, X$^3$ is bromo | chlorodifluoromethyl | hydrogen | Y$^1$ is N, Y$^2$ is N, Y$^3$ is CH |
| P.1664 | X$^1$ is chloro, X$^2$ is CH, X$^3$ is bromo | chlorodifluoromethyl | methoxy | Y$^1$ is N, Y$^2$ is N, Y$^3$ is CH |
| P.1665 | X$^1$ is chloro, X$^2$ is CH, X$^3$ is bromo | chlorodifluoromethyl | methyl | Y$^1$ is N, Y$^2$ is N, Y$^3$ is CH |
| P.1666 | X$^1$ is chloro, X$^2$ is CH, X$^3$ is bromo | chlorodifluoromethyl | nitro | Y$^1$ is N, Y$^2$ is N, Y$^3$ is CH |
| P.1667 | X$^1$ is chloro, X$^2$ is CH, X$^3$ is bromo | chlorodifluoromethyl | trifluoromethoxy | Y$^1$ is N, Y$^2$ is N, Y$^3$ is CH |
| P.1668 | X$^1$ is chloro, X$^2$ is CH, X$^3$ is bromo | chlorodifluoromethyl | trifluoromethyl | Y$^1$ is N, Y$^2$ is N, Y$^3$ is CH |
| P.1669 | X$^1$ is chloro, X$^2$ is CH, X$^3$ is bromo | difluoromethyl | bromo | Y$^1$ is N, Y$^2$ is N, Y$^3$ is CH |
| P.1670 | X$^1$ is chloro, X$^2$ is CH, X$^3$ is bromo | difluoromethyl | chloro | Y$^1$ is N, Y$^2$ is N, Y$^3$ is CH |
| P.1671 | X$^1$ is chloro, X$^2$ is CH, X$^3$ is bromo | difluoromethyl | cyano | Y$^1$ is N, Y$^2$ is N, Y$^3$ is CH |
| P.1672 | X$^1$ is chloro, X$^2$ is CH, X$^3$ is bromo | difluoromethyl | cyclopropyl | Y$^1$ is N, Y$^2$ is N, Y$^3$ is CH |
| P.1673 | X$^1$ is chloro, X$^2$ is CH, X$^3$ is bromo | difluoromethyl | ethyl | Y$^1$ is N, Y$^2$ is N, Y$^3$ is CH |
| P.1674 | X$^1$ is chloro, X$^2$ is CH, X$^3$ is bromo | difluoromethyl | fluoro | Y$^1$ is N, Y$^2$ is N, Y$^3$ is CH |
| P.1675 | X$^1$ is chloro, X$^2$ is CH, X$^3$ is bromo | difluoromethyl | hydrogen | Y$^1$ is N, Y$^2$ is N, Y$^3$ is CH |
| P.1676 | X$^1$ is chloro, X$^2$ is CH, X$^3$ is bromo | difluoromethyl | methoxy | Y$^1$ is N, Y$^2$ is N, Y$^3$ is CH |
| P.1677 | X$^1$ is chloro, X$^2$ is CH, X$^3$ is bromo | difluoromethyl | methyl | Y$^1$ is N, Y$^2$ is N, Y$^3$ is CH |
| P.1678 | X$^1$ is chloro, X$^2$ is CH, X$^3$ is bromo | difluoromethyl | nitro | Y$^1$ is N, Y$^2$ is N, Y$^3$ is CH |
| P.1679 | X$^1$ is chloro, X$^2$ is CH, X$^3$ is bromo | difluoromethyl | trifluoromethoxy | Y$^1$ is N, Y$^2$ is N, Y$^3$ is CH |
| P.1680 | X$^1$ is chloro, X$^2$ is CH, X$^3$ is bromo | difluoromethyl | trifluoromethyl | Y$^1$ is N, Y$^2$ is N, Y$^3$ is CH |
| P.1681 | X$^1$ is chloro, X$^2$ is CH, X$^3$ is bromo | trifluoromethyl | bromo | Y$^1$ is N, Y$^2$ is N, Y$^3$ is CH |
| P.1682 | X$^1$ is chloro, X$^2$ is CH, X$^3$ is bromo | trifluoromethyl | chloro | Y$^1$ is N, Y$^2$ is N, Y$^3$ is CH |
| P.1683 | X$^1$ is chloro, X$^2$ is CH, X$^3$ is bromo | trifluoromethyl | cyano | Y$^1$ is N, Y$^2$ is N, Y$^3$ is CH |
| P.1684 | X$^1$ is chloro, X$^2$ is CH, X$^3$ is bromo | trifluoromethyl | cyclopropyl | Y$^1$ is N, Y$^2$ is N, Y$^3$ is CH |
| P.1685 | X$^1$ is chloro, X$^2$ is CH, X$^3$ is bromo | trifluoromethyl | ethyl | Y$^1$ is N, Y$^2$ is N, Y$^3$ is CH |
| P.1686 | X$^1$ is chloro, X$^2$ is CH, X$^3$ is bromo | trifluoromethyl | fluoro | Y$^1$ is N, Y$^2$ is N, Y$^3$ is CH |

TABLE P-continued

| | X1, X2, X3 | X4 | R5 | Y1, Y2, Y3 |
|---|---|---|---|---|
| P.1687 | $X^1$ is chloro, $X^2$ is CH, $X^3$ is bromo | trifluoromethyl | hydrogen | $Y^1$ is N, $Y^2$ is N, $Y^3$ is CH |
| P.1688 | $X^1$ is chloro, $X^2$ is CH, $X^3$ is bromo | trifluoromethyl | methoxy | $Y^1$ is N, $Y^2$ is N, $Y^3$ is CH |
| P.1689 | $X^1$ is chloro, $X^2$ is CH, $X^3$ is bromo | trifluoromethyl | methyl | $Y^1$ is N, $Y^2$ is N, $Y^3$ is CH |
| P.1690 | $X^1$ is chloro, $X^2$ is CH, $X^3$ is bromo | trifluoromethyl | nitro | $Y^1$ is N, $Y^2$ is N, $Y^3$ is CH |
| P.1691 | $X^1$ is chloro, $X^2$ is CH, $X^3$ is bromo | trifluoromethyl | trifluoromethoxy | $Y^1$ is N, $Y^2$ is N, $Y^3$ is CH |
| P.1692 | $X^1$ is chloro, $X^2$ is CH, $X^3$ is bromo | trifluoromethyl | trifluoromethyl | $Y^1$ is N, $Y^2$ is N, $Y^3$ is CH |
| P.1693 | $X^1$ is chloro, $X^2$ is CH, $X^3$ is bromo | chlorodifluoromethyl | bromo | $Y^1$ is N, $Y^2$ is N, $Y^3$ is CH |
| P.1694 | $X^1$ is chloro, $X^2$ is CH, $X^3$ is bromo | chlorodifluoromethyl | chloro | $Y^1$ is N, $Y^2$ is N, $Y^3$ is CH |
| P.1695 | $X^1$ is chloro, $X^2$ is CH, $X^3$ is bromo | chlorodifluoromethyl | cyano | $Y^1$ is N, $Y^2$ is N, $Y^3$ is CH |
| P.1696 | $X^1$ is chloro, $X^2$ is CH, $X^3$ is bromo | chlorodifluoromethyl | cyclopropyl | $Y^1$ is N, $Y^2$ is N, $Y^3$ is CH |
| P.1697 | $X^1$ is chloro, $X^2$ is CH, $X^3$ is bromo | chlorodifluoromethyl | ethyl | $Y^1$ is N, $Y^2$ is N, $Y^3$ is CH |
| P.1698 | $X^1$ is chloro, $X^2$ is CH, $X^3$ is bromo | chlorodifluoromethyl | fluoro | $Y^1$ is N, $Y^2$ is N, $Y^3$ is CH |
| P.1699 | $X^1$ is chloro, $X^2$ is CH, $X^3$ is bromo | chlorodifluoromethyl | hydrogen | $Y^1$ is N, $Y^2$ is N, $Y^3$ is CH |
| P.1700 | $X^1$ is chloro, $X^2$ is CH, $X^3$ is bromo | chlorodifluoromethyl | methoxy | $Y^1$ is N, $Y^2$ is N, $Y^3$ is CH |
| P.1701 | $X^1$ is chloro, $X^2$ is CH, $X^3$ is bromo | chlorodifluoromethyl | methyl | $Y^1$ is N, $Y^2$ is N, $Y^3$ is CH |
| P.1702 | $X^1$ is chloro, $X^2$ is CH, $X^3$ is bromo | chlorodifluoromethyl | nitro | $Y^1$ is N, $Y^2$ is N, $Y^3$ is CH |
| P.1703 | $X^1$ is chloro, $X^2$ is CH, $X^3$ is bromo | chlorodifluoromethyl | trifluoromethoxy | $Y^1$ is N, $Y^2$ is N, $Y^3$ is CH |
| P.1704 | $X^1$ is chloro, $X^2$ is CH, $X^3$ is bromo | chlorodifluoromethyl | trifluoromethyl | $Y^1$ is N, $Y^2$ is N, $Y^3$ is CH |
| P.1705 | $X^1$ is chloro, $X^2$ is CH, $X^3$ is bromo | difluoromethyl | bromo | $Y^1$ is N, $Y^2$ is N, $Y^3$ is CH |
| P.1706 | $X^1$ is chloro, $X^2$ is CH, $X^3$ is bromo | difluoromethyl | chloro | $Y^1$ is N, $Y^2$ is N, $Y^3$ is CH |
| P.1707 | $X^1$ is chloro, $X^2$ is CH, $X^3$ is bromo | difluoromethyl | cyano | $Y^1$ is N, $Y^2$ is N, $Y^3$ is CH |
| P.1708 | $X^1$ is chloro, $X^2$ is CH, $X^3$ is bromo | difluoromethyl | cyclopropyl | $Y^1$ is N, $Y^2$ is N, $Y^3$ is CH |
| P.1709 | $X^1$ is chloro, $X^2$ is CH, $X^3$ is bromo | difluoromethyl | ethyl | $Y^1$ is N, $Y^2$ is N, $Y^3$ is CH |
| P.1710 | $X^1$ is chloro, $X^2$ is CH, $X^3$ is bromo | difluoromethyl | fluoro | $Y^1$ is N, $Y^2$ is N, $Y^3$ is CH |
| P.1711 | $X^1$ is chloro, $X^2$ is CH, $X^3$ is bromo | difluoromethyl | hydrogen | $Y^1$ is N, $Y^2$ is N, $Y^3$ is CH |
| P.1712 | $X^1$ is chloro, $X^2$ is CH, $X^3$ is bromo | difluoromethyl | methoxy | $Y^1$ is N, $Y^2$ is N, $Y^3$ is CH |
| P.1713 | $X^1$ is chloro, $X^2$ is CH, $X^3$ is bromo | difluoromethyl | methyl | $Y^1$ is N, $Y^2$ is N, $Y^3$ is CH |
| P.1714 | $X^1$ is chloro, $X^2$ is CH, $X^3$ is bromo | difluoromethyl | nitro | $Y^1$ is N, $Y^2$ is N, $Y^3$ is CH |
| P.1715 | $X^1$ is chloro, $X^2$ is CH, $X^3$ is bromo | difluoromethyl | trifluoromethoxy | $Y^1$ is N, $Y^2$ is N, $Y^3$ is CH |
| P.1716 | $X^1$ is chloro, $X^2$ is CH, $X^3$ is bromo | difluoromethyl | trifluoromethyl | $Y^1$ is N, $Y^2$ is N, $Y^3$ is CH |
| P.1717 | $X^1$ is chloro, $X^2$ is CH, $X^3$ is bromo | trifluoromethyl | bromo | $Y^1$ is N, $Y^2$ is N, $Y^3$ is CH |
| P.1718 | $X^1$ is chloro, $X^2$ is CH, $X^3$ is bromo | trifluoromethyl | chloro | $Y^1$ is N, $Y^2$ is N, $Y^3$ is CH |
| P.1719 | $X^1$ is chloro, $X^2$ is CH, $X^3$ is bromo | trifluoromethyl | cyano | $Y^1$ is N, $Y^2$ is N, $Y^3$ is CH |
| P.1720 | $X^1$ is chloro, $X^2$ is CH, $X^3$ is bromo | trifluoromethyl | cyclopropyl | $Y^1$ is N, $Y^2$ is N, $Y^3$ is CH |
| P.1721 | $X^1$ is chloro, $X^2$ is CH, $X^3$ is bromo | trifluoromethyl | ethyl | $Y^1$ is N, $Y^2$ is N, $Y^3$ is CH |
| P.1722 | $X^1$ is chloro, $X^2$ is CH, $X^3$ is bromo | trifluoromethyl | fluoro | $Y^1$ is N, $Y^2$ is N, $Y^3$ is CH |
| P.1723 | $X^1$ is chloro, $X^2$ is CH, $X^3$ is bromo | trifluoromethyl | hydrogen | $Y^1$ is N, $Y^2$ is N, $Y^3$ is CH |
| P.1724 | $X^1$ is chloro, $X^2$ is CH, $X^3$ is bromo | trifluoromethyl | methoxy | $Y^1$ is N, $Y^2$ is N, $Y^3$ is CH |
| P.1725 | $X^1$ is chloro, $X^2$ is CH, $X^3$ is bromo | trifluoromethyl | methyl | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1726 | $X^1$ is chloro, $X^2$ is CH, $X^3$ is bromo | trifluoromethyl | nitro | $Y^1$ is N, $Y^2$ is N, $Y^3$ is CH |
| P.1727 | $X^1$ is chloro, $X^2$ is CH, $X^3$ is bromo | trifluoromethyl | trifluoromethoxy | $Y^1$ is N, $Y^2$ is N, $Y^3$ is CH |
| P.1728 | $X^1$ is chloro, $X^2$ is CH, $X^3$ is bromo | trifluoromethyl | trifluoromethyl | $Y^1$ is N, $Y^2$ is N, $Y^3$ is CH |
| P.1729 | $X^1$ is chloro, $X^2$ is C—Cl, $X^3$ is trifluoromethyl | chlorodifluoromethyl | bromo | $Y^1$ is N, $Y^2$ is N, $Y^3$ is CH |
| P.1730 | $X^1$ is chloro, $X^2$ is C—Cl, $X^3$ is trifluoromethyl | chlorodifluoromethyl | chloro | $Y^1$ is N, $Y^2$ is N, $Y^3$ is CH |
| P.1731 | $X^1$ is chloro, $X^2$ is C—Cl, $X^3$ is trifluoromethyl | chlorodifluoromethyl | cyano | $Y^1$ is N, $Y^2$ is N, $Y^3$ is CH |
| P.1732 | $X^1$ is chloro, $X^2$ is C—Cl, $X^3$ is trifluoromethyl | chlorodifluoromethyl | cyclopropyl | $Y^1$ is N, $Y^2$ is N, $Y^3$ is CH |
| P.1733 | $X^1$ is chloro, $X^2$ is C—Cl, $X^3$ is trifluoromethyl | chlorodifluoromethyl | ethyl | $Y^1$ is N, $Y^2$ is N, $Y^3$ is CH |
| P.1734 | $X^1$ is chloro, $X^2$ is C—Cl, $X^3$ is trifluoromethyl | chlorodifluoromethyl | fluoro | $Y^1$ is N, $Y^2$ is N, $Y^3$ is CH |
| P.1735 | $X^1$ is chloro, $X^2$ is C—Cl, $X^3$ is trifluoromethyl | chlorodifluoromethyl | hydrogen | $Y^1$ is N, $Y^2$ is N, $Y^3$ is CH |
| P.1736 | $X^1$ is chloro, $X^2$ is C—Cl, $X^3$ is trifluoromethyl | chlorodifluoromethyl | methoxy | $Y^1$ is N, $Y^2$ is N, $Y^3$ is CH |
| P.1737 | $X^1$ is chloro, $X^2$ is C—Cl, $X^3$ is trifluoromethyl | chlorodifluoromethyl | methyl | $Y^1$ is N, $Y^2$ is N, $Y^3$ is CH |
| P.1738 | $X^1$ is chloro, $X^2$ is C—Cl, $X^3$ is trifluoromethyl | chlorodifluoromethyl | nitro | $Y^1$ is N, $Y^2$ is N, $Y^3$ is CH |
| P.1739 | $X^1$ is chloro, $X^2$ is C—Cl, $X^3$ is trifluoromethyl | chlorodifluoromethyl | trifluoromethoxy | $Y^1$ is N, $Y^2$ is N, $Y^3$ is CH |
| P.1740 | $X^1$ is chloro, $X^2$ is C—Cl, $X^3$ is trifluoromethyl | chlorodifluoromethyl | trifluoromethyl | $Y^1$ is N, $Y^2$ is N, $Y^3$ is CH |
| P.1741 | $X^1$ is chloro, $X^2$ is C—Cl, $X^3$ is trifluoromethyl | difluoromethyl | bromo | $Y^1$ is N, $Y^2$ is N, $Y^3$ is CH |
| P.1742 | $X^1$ is chloro, $X^2$ is C—Cl, $X^3$ is trifluoromethyl | difluoromethyl | chloro | $Y^1$ is N, $Y^2$ is N, $Y^3$ is CH |
| P.1743 | $X^1$ is chloro, $X^2$ is C—Cl, $X^3$ is trifluoromethyl | difluoromethyl | cyano | $Y^1$ is N, $Y^2$ is N, $Y^3$ is CH |
| P.1744 | $X^1$ is chloro, $X^2$ is C—Cl, $X^3$ is trifluoromethyl | difluoromethyl | cyclopropyl | $Y^1$ is N, $Y^2$ is N, $Y^3$ is CH |
| P.1745 | $X^1$ is chloro, $X^2$ is C—Cl, $X^3$ is trifluoromethyl | difluoromethyl | ethyl | $Y^1$ is N, $Y^2$ is N, $Y^3$ is CH |
| P.1746 | $X^1$ is chloro, $X^2$ is C—Cl, $X^3$ is trifluoromethyl | difluoromethyl | fluoro | $Y^1$ is N, $Y^2$ is N, $Y^3$ is CH |
| P.1747 | $X^1$ is chloro, $X^2$ is C—Cl, $X^3$ is trifluoromethyl | difluoromethyl | hydrogen | $Y^1$ is N, $Y^2$ is N, $Y^3$ is CH |
| P.1748 | $X^1$ is chloro, $X^2$ is C—Cl, $X^3$ is trifluoromethyl | difluoromethyl | methoxy | $Y^1$ is N, $Y^2$ is N, $Y^3$ is CH |
| P.1749 | $X^1$ is chloro, $X^2$ is C—Cl, $X^3$ is trifluoromethyl | difluoromethyl | methyl | $Y^1$ is N, $Y^2$ is N, $Y^3$ is CH |
| P.1750 | $X^1$ is chloro, $X^2$ is C—Cl, $X^3$ is trifluoromethyl | difluoromethyl | nitro | $Y^1$ is N, $Y^2$ is N, $Y^3$ is CH |
| P.1751 | $X^1$ is chloro, $X^2$ is C—Cl, $X^3$ is trifluoromethyl | difluoromethyl | trifluoromethoxy | $Y^1$ is N, $Y^2$ is N, $Y^3$ is CH |
| P.1752 | $X^1$ is chloro, $X^2$ is C—Cl, $X^3$ is trifluoromethyl | difluoromethyl | trifluoromethyl | $Y^1$ is N, $Y^2$ is N, $Y^3$ is CH |
| P.1753 | $X^1$ is chloro, $X^2$ is C—Cl, $X^3$ is trifluoromethyl | trifluoromethyl | bromo | $Y^1$ is N, $Y^2$ is N, $Y^3$ is CH |
| P.1754 | $X^1$ is chloro, $X^2$ is C—Cl, $X^3$ is trifluoromethyl | trifluoromethyl | chloro | $Y^1$ is N, $Y^2$ is N, $Y^3$ is CH |
| P.1755 | $X^1$ is chloro, $X^2$ is C—Cl, $X^3$ is trifluoromethyl | trifluoromethyl | cyano | $Y^1$ is N, $Y^2$ is N, $Y^3$ is CH |
| P.1756 | $X^1$ is chloro, $X^2$ is C—Cl, $X^3$ is trifluoromethyl | trifluoromethyl | cyclopropyl | $Y^1$ is N, $Y^2$ is N, $Y^3$ is CH |
| P.1757 | $X^1$ is chloro, $X^2$ is C—Cl, $X^3$ is trifluoromethyl | trifluoromethyl | ethyl | $Y^1$ is N, $Y^2$ is N, $Y^3$ is CH |
| P.1758 | $X^1$ is chloro, $X^2$ is C—Cl, $X^3$ is trifluoromethyl | trifluoromethyl | fluoro | $Y^1$ is N, $Y^2$ is N, $Y^3$ is CH |
| P.1759 | $X^1$ is chloro, $X^2$ is C—Cl, $X^3$ is trifluoromethyl | trifluoromethyl | hydrogen | $Y^1$ is N, $Y^2$ is N, $Y^3$ is CH |
| P.1760 | $X^1$ is chloro, $X^2$ is C—Cl, $X^3$ is trifluoromethyl | trifluoromethyl | methoxy | $Y^1$ is N, $Y^2$ is N, $Y^3$ is CH |
| P.1761 | $X^1$ is chloro, $X^2$ is C—Cl, $X^3$ is trifluoromethyl | trifluoromethyl | methyl | $Y^1$ is N, $Y^2$ is N, $Y^3$ is CH |
| P.1762 | $X^1$ is chloro, $X^2$ is C—Cl, $X^3$ is trifluoromethyl | trifluoromethyl | nitro | $Y^1$ is N, $Y^2$ is N, $Y^3$ is CH |
| P.1763 | $X^1$ is chloro, $X^2$ is C—Cl, $X^3$ is trifluoromethyl | trifluoromethyl | trifluoromethoxy | $Y^1$ is N, $Y^2$ is N, $Y^3$ is CH |
| P.1764 | $X^1$ is chloro, $X^2$ is C—Cl, $X^3$ is trifluoromethyl | trifluoromethyl | trifluoromethyl | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1765 | $X^1$ is trifluoromethyl, $X^2$ is CH, $X^3$ is trifluoromethyl | chlorodifluoromethyl | bromo | $Y^1$ is N, $Y^2$ is N, $Y^3$ is CH |
| P.1766 | $X^1$ is trifluoromethyl, $X^2$ is CH, $X^3$ is trifluoromethyl | chlorodifluoromethyl | chloro | $Y^1$ is N, $Y^2$ is N, $Y^3$ is CH |
| P.1767 | $X^1$ is trifluoromethyl, $X^2$ is CH, $X^3$ is trifluoromethyl | chlorodifluoromethyl | cyano | $Y^1$ is N, $Y^2$ is N, $Y^3$ is CH |
| P.1768 | $X^1$ is trifluoromethyl, $X^2$ is CH, $X^3$ is trifluoromethyl | chlorodifluoromethyl | cyclopropyl | $Y^1$ is N, $Y^2$ is N, $Y^3$ is CH |
| P.1769 | $X^1$ is trifluoromethyl, $X^2$ is CH, $X^3$ is trifluoromethyl | chlorodifluoromethyl | ethyl | $Y^1$ is N, $Y^2$ is N, $Y^3$ is CH |
| P.1770 | $X^1$ is trifluoromethyl, $X^2$ is CH, $X^3$ is trifluoromethyl | chlorodifluoromethyl | fluoro | $Y^1$ is N, $Y^2$ is N, $Y^3$ is CH |
| P.1771 | $X^1$ is trifluoromethyl, $X^2$ is CH, $X^3$ is trifluoromethyl | chlorodifluoromethyl | hydrogen | $Y^1$ is N, $Y^2$ is N, $Y^3$ is CH |
| P.1772 | $X^1$ is trifluoromethyl, $X^2$ is CH, $X^3$ is trifluoromethyl | chlorodifluoromethyl | methoxy | $Y^1$ is N, $Y^2$ is N, $Y^3$ is CH |
| P.1773 | $X^1$ is trifluoromethyl, $X^2$ is CH, $X^3$ is trifluoromethyl | chlorodifluoromethyl | methyl | $Y^1$ is N, $Y^2$ is N, $Y^3$ is CH |
| P.1774 | $X^1$ is trifluoromethyl, $X^2$ is CH, $X^3$ is trifluoromethyl | chlorodifluoromethyl | nitro | $Y^1$ is N, $Y^2$ is N, $Y^3$ is CH |
| P.1775 | $X^1$ is trifluoromethyl, $X^2$ is CH, $X^3$ is trifluoromethyl | chlorodifluoromethyl | trifluoromethoxy | $Y^1$ is N, $Y^2$ is N, $Y^3$ is CH |
| P.1776 | $X^1$ is trifluoromethyl, $X^2$ is CH, $X^3$ is trifluoromethyl | chlorodifluoromethyl | trifluoromethyl | $Y^1$ is N, $Y^2$ is N, $Y^3$ is CH |
| P.1777 | $X^1$ is trifluoromethyl, $X^2$ is CH, $X^3$ is trifluoromethyl | difluoromethyl | bromo | $Y^1$ is N, $Y^2$ is N, $Y^3$ is CH |
| P.1778 | $X^1$ is trifluoromethyl, $X^2$ is CH, $X^3$ is trifluoromethyl | difluoromethyl | chloro | $Y^1$ is N, $Y^2$ is N, $Y^3$ is CH |
| P.1779 | $X^1$ is trifluoromethyl, $X^2$ is CH, $X^3$ is trifluoromethyl | difluoromethyl | cyano | $Y^1$ is N, $Y^2$ is N, $Y^3$ is CH |
| P.1780 | $X^1$ is trifluoromethyl, $X^2$ is CH, $X^3$ is trifluoromethyl | difluoromethyl | cyclopropyl | $Y^1$ is N, $Y^2$ is N, $Y^3$ is CH |
| P.1781 | $X^1$ is trifluoromethyl, $X^2$ is CH, $X^3$ is trifluoromethyl | difluoromethyl | ethyl | $Y^1$ is N, $Y^2$ is N, $Y^3$ is CH |
| P.1782 | $X^1$ is trifluoromethyl, $X^2$ is CH, $X^3$ is trifluoromethyl | difluoromethyl | fluoro | $Y^1$ is N, $Y^2$ is N, $Y^3$ is CH |
| P.1783 | $X^1$ is trifluoromethyl, $X^2$ is CH, $X^3$ is trifluoromethyl | difluoromethyl | hydrogen | $Y^1$ is N, $Y^2$ is N, $Y^3$ is CH |
| P.1784 | $X^1$ is trifluoromethyl, $X^2$ is CH, $X^3$ is trifluoromethyl | difluoromethyl | methoxy | $Y^1$ is N, $Y^2$ is N, $Y^3$ is CH |
| P.1785 | $X^1$ is trifluoromethyl, $X^2$ is CH, $X^3$ is trifluoromethyl | difluoromethyl | methyl | $Y^1$ is N, $Y^2$ is N, $Y^3$ is CH |
| P.1786 | $X^1$ is trifluoromethyl, $X^2$ is CH, $X^3$ is trifluoromethyl | difluoromethyl | nitro | $Y^1$ is N, $Y^2$ is N, $Y^3$ is CH |
| P.1787 | $X^1$ is trifluoromethyl, $X^2$ is CH, $X^3$ is trifluoromethyl | difluoromethyl | trifluoromethoxy | $Y^1$ is N, $Y^2$ is N, $Y^3$ is CH |
| P.1788 | $X^1$ is trifluoromethyl, $X^2$ is CH, $X^3$ is trifluoromethyl | difluoromethyl | trifluoromethyl | $Y^1$ is N, $Y^2$ is N, $Y^3$ is CH |
| P.1789 | $X^1$ is trifluoromethyl, $X^2$ is CH, $X^3$ is trifluoromethyl | trifluoromethyl | bromo | $Y^1$ is N, $Y^2$ is N, $Y^3$ is CH |
| P.1790 | $X^1$ is trifluoromethyl, $X^2$ is CH, $X^3$ is trifluoromethyl | trifluoromethyl | chloro | $Y^1$ is N, $Y^2$ is N, $Y^3$ is CH |
| P.1791 | $X^1$ is trifluoromethyl, $X^2$ is CH, $X^3$ is trifluoromethyl | trifluoromethyl | cyano | $Y^1$ is N, $Y^2$ is N, $Y^3$ is CH |
| P.1792 | $X^1$ is trifluoromethyl, $X^2$ is CH, $X^3$ is trifluoromethyl | trifluoromethyl | cyclopropyl | $Y^1$ is N, $Y^2$ is N, $Y^3$ is CH |
| P.1793 | $X^1$ is trifluoromethyl, $X^2$ is CH, $X^3$ is trifluoromethyl | trifluoromethyl | ethyl | $Y^1$ is N, $Y^2$ is N, $Y^3$ is CH |
| P.1794 | $X^1$ is trifluoromethyl, $X^2$ is CH, $X^3$ is trifluoromethyl | trifluoromethyl | fluoro | $Y^1$ is N, $Y^2$ is N, $Y^3$ is CH |
| P.1795 | $X^1$ is trifluoromethyl, $X^2$ is CH, $X^3$ is trifluoromethyl | trifluoromethyl | hydrogen | $Y^1$ is N, $Y^2$ is N, $Y^3$ is CH |
| P.1796 | $X^1$ is trifluoromethyl, $X^2$ is CH, $X^3$ is trifluoromethyl | trifluoromethyl | methoxy | $Y^1$ is N, $Y^2$ is N, $Y^3$ is CH |
| P.1797 | $X^1$ is trifluoromethyl, $X^2$ is CH, $X^3$ is trifluoromethyl | trifluoromethyl | methyl | $Y^1$ is N, $Y^2$ is N, $Y^3$ is CH |
| P.1798 | $X^1$ is trifluoromethyl, $X^2$ is CH, $X^3$ is trifluoromethyl | trifluoromethyl | nitro | $Y^1$ is N, $Y^2$ is N, $Y^3$ is CH |
| P.1799 | $X^1$ is trifluoromethyl, $X^2$ is CH, $X^3$ is trifluoromethyl | trifluoromethyl | trifluoromethoxy | $Y^1$ is N, $Y^2$ is N, $Y^3$ is CH |
| P.1800 | $X^1$ is trifluoromethyl, $X^2$ is CH, $X^3$ is trifluoromethyl | trifluoromethyl | trifluoromethyl | $Y^1$ is N, $Y^2$ is N, $Y^3$ is CH |
| P.1801 | $X^1$ is trifluoromethyl, $X^2$ is CH, $X^3$ is trifluoromethyl | chlorodifluoromethyl | bromo | $Y^1$ is N, $Y^2$ is N, $Y^3$ is CH |
| P.1802 | $X^1$ is trifluoromethyl, $X^2$ is CH, $X^3$ is trifluoromethyl | chlorodifluoromethyl | chloro | $Y^1$ is N, $Y^2$ is N, $Y^3$ is CH |
| P.1803 | $X^1$ is trifluoromethyl, $X^2$ is CH, $X^3$ is trifluoromethyl | chlorodifluoromethyl | cyano | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1804 | $X^1$ is trifluoromethyl, $X^2$ is CH, $X^3$ is trifluoromethyl | chlorodifluoromethyl | cyclopropyl | $Y^1$ is N, $Y^2$ is N, $Y^3$ is CH |
| P.1805 | $X^1$ is trifluoromethyl, $X^2$ is CH, $X^3$ is trifluoromethyl | chlorodifluoromethyl | ethyl | $Y^1$ is N, $Y^2$ is N, $Y^3$ is CH |
| P.1806 | $X^1$ is trifluoromethyl, $X^2$ is CH, $X^3$ is trifluoromethyl | chlorodifluoromethyl | fluoro | $Y^1$ is N, $Y^2$ is N, $Y^3$ is CH |
| P.1807 | $X^1$ is trifluoromethyl, $X^2$ is CH, $X^3$ is trifluoromethyl | chlorodifluoromethyl | hydrogen | $Y^1$ is N, $Y^2$ is N, $Y^3$ is CH |
| P.1808 | $X^1$ is trifluoromethyl, $X^2$ is CH, $X^3$ is trifluoromethyl | chlorodifluoromethyl | methoxy | $Y^1$ is N, $Y^2$ is N, $Y^3$ is CH |
| P.1809 | $X^1$ is trifluoromethyl, $X^2$ is CH, $X^3$ is trifluoromethyl | chlorodifluoromethyl | methyl | $Y^1$ is N, $Y^2$ is N, $Y^3$ is CH |
| P.1810 | $X^1$ is trifluoromethyl, $X^2$ is CH, $X^3$ is trifluoromethyl | chlorodifluoromethyl | nitro | $Y^1$ is N, $Y^2$ is N, $Y^3$ is CH |
| P.1811 | $X^1$ is trifluoromethyl, $X^2$ is CH, $X^3$ is trifluoromethyl | chlorodifluoromethyl | trifluoromethoxy | $Y^1$ is N, $Y^2$ is N, $Y^3$ is CH |
| P.1812 | $X^1$ is trifluoromethyl, $X^2$ is CH, $X^3$ is trifluoromethyl | chlorodifluoromethyl | trifluoromethyl | $Y^1$ is N, $Y^2$ is N, $Y^3$ is CH |
| P.1813 | $X^1$ is trifluoromethyl, $X^2$ is CH, $X^3$ is trifluoromethyl | difluoromethyl | bromo | $Y^1$ is N, $Y^2$ is N, $Y^3$ is CH |
| P.1814 | $X^1$ is trifluoromethyl, $X^2$ is CH, $X^3$ is trifluoromethyl | difluoromethyl | chloro | $Y^1$ is N, $Y^2$ is N, $Y^3$ is CH |
| P.1815 | $X^1$ is trifluoromethyl, $X^2$ is CH, $X^3$ is trifluoromethyl | difluoromethyl | cyano | $Y^1$ is N, $Y^2$ is N, $Y^3$ is CH |
| P.1816 | $X^1$ is trifluoromethyl, $X^2$ is CH, $X^3$ is trifluoromethyl | difluoromethyl | cyclopropyl | $Y^1$ is N, $Y^2$ is N, $Y^3$ is CH |
| P.1817 | $X^1$ is trifluoromethyl, $X^2$ is CH, $X^3$ is trifluoromethyl | difluoromethyl | ethyl | $Y^1$ is N, $Y^2$ is N, $Y^3$ is CH |
| P.1818 | $X^1$ is trifluoromethyl, $X^2$ is CH, $X^3$ is trifluoromethyl | difluoromethyl | fluoro | $Y^1$ is N, $Y^2$ is N, $Y^3$ is CH |
| P.1819 | $X^1$ is trifluoromethyl, $X^2$ is CH, $X^3$ is trifluoromethyl | difluoromethyl | hydrogen | $Y^1$ is N, $Y^2$ is N, $Y^3$ is CH |
| P.1820 | $X^1$ is trifluoromethyl, $X^2$ is CH, $X^3$ is trifluoromethyl | difluoromethyl | methoxy | $Y^1$ is N, $Y^2$ is N, $Y^3$ is CH |
| P.1821 | $X^1$ is trifluoromethyl, $X^2$ is CH, $X^3$ is trifluoromethyl | difluoromethyl | methyl | $Y^1$ is N, $Y^2$ is N, $Y^3$ is CH |
| P.1822 | $X^1$ is trifluoromethyl, $X^2$ is CH, $X^3$ is trifluoromethyl | difluoromethyl | nitro | $Y^1$ is N, $Y^2$ is N, $Y^3$ is CH |
| P.1823 | $X^1$ is trifluoromethyl, $X^2$ is CH, $X^3$ is trifluoromethyl | difluoromethyl | trifluoromethoxy | $Y^1$ is N, $Y^2$ is N, $Y^3$ is CH |
| P.1824 | $X^1$ is trifluoromethyl, $X^2$ is CH, $X^3$ is trifluoromethyl | difluoromethyl | trifluoromethyl | $Y^1$ is N, $Y^2$ is N, $Y^3$ is CH |
| P.1825 | $X^1$ is trifluoromethyl, $X^2$ is CH, $X^3$ is trifluoromethyl | trifluoromethyl | bromo | $Y^1$ is N, $Y^2$ is N, $Y^3$ is CH |
| P.1826 | $X^1$ is trifluoromethyl, $X^2$ is CH, $X^3$ is trifluoromethyl | trifluoromethyl | chloro | $Y^1$ is N, $Y^2$ is N, $Y^3$ is CH |
| P.1827 | $X^1$ is trifluoromethyl, $X^2$ is CH, $X^3$ is trifluoromethyl | trifluoromethyl | cyano | $Y^1$ is N, $Y^2$ is N, $Y^3$ is CH |
| P.1828 | $X^1$ is trifluoromethyl, $X^2$ is CH, $X^3$ is trifluoromethyl | trifluoromethyl | cyclopropyl | $Y^1$ is N, $Y^2$ is N, $Y^3$ is CH |
| P.1829 | $X^1$ is trifluoromethyl, $X^2$ is CH, $X^3$ is trifluoromethyl | trifluoromethyl | ethyl | $Y^1$ is N, $Y^2$ is N, $Y^3$ is CH |
| P.1830 | $X^1$ is trifluoromethyl, $X^2$ is CH, $X^3$ is trifluoromethyl | trifluoromethyl | fluoro | $Y^1$ is N, $Y^2$ is N, $Y^3$ is CH |
| P.1831 | $X^1$ is trifluoromethyl, $X^2$ is CH, $X^3$ is trifluoromethyl | trifluoromethyl | hydrogen | $Y^1$ is N, $Y^2$ is N, $Y^3$ is CH |
| P.1832 | $X^1$ is trifluoromethyl, $X^2$ is CH, $X^3$ is trifluoromethyl | trifluoromethyl | methoxy | $Y^1$ is N, $Y^2$ is N, $Y^3$ is CH |
| P.1833 | $X^1$ is trifluoromethyl, $X^2$ is CH, $X^3$ is trifluoromethyl | trifluoromethyl | methyl | $Y^1$ is N, $Y^2$ is N, $Y^3$ is CH |
| P.1834 | $X^1$ is trifluoromethyl, $X^2$ is CH, $X^3$ is trifluoromethyl | trifluoromethyl | nitro | $Y^1$ is N, $Y^2$ is N, $Y^3$ is CH |
| P.1835 | $X^1$ is trifluoromethyl, $X^2$ is CH, $X^3$ is trifluoromethyl | trifluoromethyl | trifluoromethoxy | $Y^1$ is N, $Y^2$ is N, $Y^3$ is CH |
| P.1836 | $X^1$ is trifluoromethyl, $X^2$ is CH, $X^3$ is trifluoromethyl | trifluoromethyl | trifluoromethyl | $Y^1$ is N, $Y^2$ is N, $Y^3$ is CH |
| P.1837 | $X^1$ is trifluoromethyl, $X^2$ is CH, $X^3$ is hydrogen | chlorodifluoromethyl | bromo | $Y^1$ is N, $Y^2$ is N, $Y^3$ is CH |
| P.1838 | $X^1$ is trifluoromethyl, $X^2$ is CH, $X^3$ is hydrogen | chlorodifluoromethyl | chloro | $Y^1$ is N, $Y^2$ is N, $Y^3$ is CH |
| P.1839 | $X^1$ is trifluoromethyl, $X^2$ is CH, $X^3$ is hydrogen | chlorodifluoromethyl | cyano | $Y^1$ is N, $Y^2$ is N, $Y^3$ is CH |
| P.1840 | $X^1$ is trifluoromethyl, $X^2$ is CH, $X^3$ is hydrogen | chlorodifluoromethyl | cyclopropyl | $Y^1$ is N, $Y^2$ is N, $Y^3$ is CH |
| P.1841 | $X^1$ is trifluoromethyl, $X^2$ is CH, $X^3$ is hydrogen | chlorodifluoromethyl | ethyl | $Y^1$ is N, $Y^2$ is N, $Y^3$ is CH |
| P.1842 | $X^1$ is trifluoromethyl, $X^2$ is CH, $X^3$ is hydrogen | chlorodifluoromethyl | fluoro | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1843 | $X^1$ is trifluoromethyl, $X^2$ is CH, $X^3$ is hydrogen | chlorodifluoromethyl | hydrogen | $Y^1$ is N, $Y^2$ is N, $Y^3$ is CH |
| P.1844 | $X^1$ is trifluoromethyl, $X^2$ is CH, $X^3$ is hydrogen | chlorodifluoromethyl | methoxy | $Y^1$ is N, $Y^2$ is N, $Y^3$ is CH |
| P.1845 | $X^1$ is trifluoromethyl, $X^2$ is CH, $X^3$ is hydrogen | chlorodifluoromethyl | methyl | $Y^1$ is N, $Y^2$ is N, $Y^3$ is CH |
| P.1846 | $X^1$ is trifluoromethyl, $X^2$ is CH, $X^3$ is hydrogen | chlorodifluoromethyl | nitro | $Y^1$ is N, $Y^2$ is N, $Y^3$ is CH |
| P.1847 | $X^1$ is trifluoromethyl, $X^2$ is CH, $X^3$ is hydrogen | chlorodifluoromethyl | trifluoromethoxy | $Y^1$ is N, $Y^2$ is N, $Y^3$ is CH |
| P.1848 | $X^1$ is trifluoromethyl, $X^2$ is CH, $X^3$ is hydrogen | chlorodifluoromethyl | trifluoromethyl | $Y^1$ is N, $Y^2$ is N, $Y^3$ is CH |
| P.1849 | $X^1$ is trifluoromethyl, $X^2$ is CH, $X^3$ is hydrogen | difluoromethyl | bromo | $Y^1$ is N, $Y^2$ is N, $Y^3$ is CH |
| P.1850 | $X^1$ is trifluoromethyl, $X^2$ is CH, $X^3$ is hydrogen | difluoromethyl | chloro | $Y^1$ is N, $Y^2$ is N, $Y^3$ is CH |
| P.1851 | $X^1$ is trifluoromethyl, $X^2$ is CH, $X^3$ is hydrogen | difluoromethyl | cyano | $Y^1$ is N, $Y^2$ is N, $Y^3$ is CH |
| P.1852 | $X^1$ is trifluoromethyl, $X^2$ is CH, $X^3$ is hydrogen | difluoromethyl | cyclopropyl | $Y^1$ is N, $Y^2$ is N, $Y^3$ is CH |
| P.1853 | $X^1$ is trifluoromethyl, $X^2$ is CH, $X^3$ is hydrogen | difluoromethyl | ethyl | $Y^1$ is N, $Y^2$ is N, $Y^3$ is CH |
| P.1854 | $X^1$ is trifluoromethyl, $X^2$ is CH, $X^3$ is hydrogen | difluoromethyl | fluoro | $Y^1$ is N, $Y^2$ is N, $Y^3$ is CH |
| P.1855 | $X^1$ is trifluoromethyl, $X^2$ is CH, $X^3$ is hydrogen | difluoromethyl | hydrogen | $Y^1$ is N, $Y^2$ is N, $Y^3$ is CH |
| P.1856 | $X^1$ is trifluoromethyl, $X^2$ is CH, $X^3$ is hydrogen | difluoromethyl | methoxy | $Y^1$ is N, $Y^2$ is N, $Y^3$ is CH |
| P.1857 | $X^1$ is trifluoromethyl, $X^2$ is CH, $X^3$ is hydrogen | difluoromethyl | methyl | $Y^1$ is N, $Y^2$ is N, $Y^3$ is CH |
| P.1858 | $X^1$ is trifluoromethyl, $X^2$ is CH, $X^3$ is hydrogen | difluoromethyl | nitro | $Y^1$ is N, $Y^2$ is N, $Y^3$ is CH |
| P.1859 | $X^1$ is trifluoromethyl, $X^2$ is CH, $X^3$ is hydrogen | difluoromethyl | trifluoromethoxy | $Y^1$ is N, $Y^2$ is N, $Y^3$ is CH |
| P.1860 | $X^1$ is trifluoromethyl, $X^2$ is CH, $X^3$ is hydrogen | difluoromethyl | trifluoromethyl | $Y^1$ is N, $Y^2$ is N, $Y^3$ is CH |
| P.1861 | $X^1$ is trifluoromethyl, $X^2$ is CH, $X^3$ is hydrogen | trifluoromethyl | bromo | $Y^1$ is N, $Y^2$ is N, $Y^3$ is CH |
| P.1862 | $X^1$ is trifluoromethyl, $X^2$ is CH, $X^3$ is hydrogen | trifluoromethyl | chloro | $Y^1$ is N, $Y^2$ is N, $Y^3$ is CH |
| P.1863 | $X^1$ is trifluoromethyl, $X^2$ is CH, $X^3$ is hydrogen | trifluoromethyl | cyano | $Y^1$ is N, $Y^2$ is N, $Y^3$ is CH |
| P.1864 | $X^1$ is trifluoromethyl, $X^2$ is CH, $X^3$ is hydrogen | trifluoromethyl | cyclopropyl | $Y^1$ is N, $Y^2$ is N, $Y^3$ is CH |
| P.1865 | $X^1$ is trifluoromethyl, $X^2$ is CH, $X^3$ is hydrogen | trifluoromethyl | ethyl | $Y^1$ is N, $Y^2$ is N, $Y^3$ is CH |
| P.1866 | $X^1$ is trifluoromethyl, $X^2$ is CH, $X^3$ is hydrogen | trifluoromethyl | fluoro | $Y^1$ is N, $Y^2$ is N, $Y^3$ is CH |
| P.1867 | $X^1$ is trifluoromethyl, $X^2$ is CH, $X^3$ is hydrogen | trifluoromethyl | hydrogen | $Y^1$ is N, $Y^2$ is N, $Y^3$ is CH |
| P.1868 | $X^1$ is trifluoromethyl, $X^2$ is CH, $X^3$ is hydrogen | trifluoromethyl | methoxy | $Y^1$ is N, $Y^2$ is N, $Y^3$ is CH |
| P.1869 | $X^1$ is trifluoromethyl, $X^2$ is CH, $X^3$ is hydrogen | trifluoromethyl | methyl | $Y^1$ is N, $Y^2$ is N, $Y^3$ is CH |
| P.1870 | $X^1$ is trifluoromethyl, $X^2$ is CH, $X^3$ is hydrogen | trifluoromethyl | nitro | $Y^1$ is N, $Y^2$ is N, $Y^3$ is CH |
| P.1871 | $X^1$ is trifluoromethyl, $X^2$ is CH, $X^3$ is hydrogen | trifluoromethyl | trifluoromethoxy | $Y^1$ is N, $Y^2$ is N, $Y^3$ is CH |
| P.1872 | $X^1$ is trifluoromethyl, $X^2$ is CH, $X^3$ is hydrogen | trifluoromethyl | trifluoromethyl | $Y^1$ is N, $Y^2$ is N, $Y^3$ is CH |
| P.1873 | $X^1$ is chloro, $X^2$ is N, $X^3$ is chloro | chlorodifluoromethyl | bromo | $Y^1$ is N, $Y^2$ is N, $Y^3$ is CH |
| P.1874 | $X^1$ is chloro, $X^2$ is N, $X^3$ is chloro | chlorodifluoromethyl | chloro | $Y^1$ is N, $Y^2$ is N, $Y^3$ is CH |
| P.1875 | $X^1$ is chloro, $X^2$ is N, $X^3$ is chloro | chlorodifluoromethyl | cyano | $Y^1$ is N, $Y^2$ is N, $Y^3$ is CH |
| P.1876 | $X^1$ is chloro, $X^2$ is N, $X^3$ is chloro | chlorodifluoromethyl | cyclopropyl | $Y^1$ is N, $Y^2$ is N, $Y^3$ is CH |
| P.1877 | $X^1$ is chloro, $X^2$ is N, $X^3$ is chloro | chlorodifluoromethyl | ethyl | $Y^1$ is N, $Y^2$ is N, $Y^3$ is CH |
| P.1878 | $X^1$ is chloro, $X^2$ is N, $X^3$ is chloro | chlorodifluoromethyl | fluoro | $Y^1$ is N, $Y^2$ is N, $Y^3$ is CH |
| P.1879 | $X^1$ is chloro, $X^2$ is N, $X^3$ is chloro | chlorodifluoromethyl | hydrogen | $Y^1$ is N, $Y^2$ is N, $Y^3$ is CH |
| P.1880 | $X^1$ is chloro, $X^2$ is N, $X^3$ is chloro | chlorodifluoromethyl | methoxy | $Y^1$ is N, $Y^2$ is N, $Y^3$ is CH |
| P.1881 | $X^1$ is chloro, $X^2$ is N, $X^3$ is chloro | chlorodifluoromethyl | methyl | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1882 | $X^1$ is chloro, $X^2$ is N, $X^3$ is chloro | chlorodifluoromethyl | nitro | $Y^1$ is N, $Y^2$ is N, $Y^3$ is CH |
| P.1883 | $X^1$ is chloro, $X^2$ is N, $X^3$ is chloro | chlorodifluoromethyl | trifluoromethoxy | $Y^1$ is N, $Y^2$ is N, $Y^3$ is CH |
| P.1884 | $X^1$ is chloro, $X^2$ is N, $X^3$ is chloro | chlorodifluoromethyl | trifluoromethyl | $Y^1$ is N, $Y^2$ is N, $Y^3$ is CH |
| P.1885 | $X^1$ is chloro, $X^2$ is N, $X^3$ is chloro | difluoromethyl | bromo | $Y^1$ is N, $Y^2$ is N, $Y^3$ is CH |
| P.1886 | $X^1$ is chloro, $X^2$ is N, $X^3$ is chloro | difluoromethyl | chloro | $Y^1$ is N, $Y^2$ is N, $Y^3$ is CH |
| P.1887 | $X^1$ is chloro, $X^2$ is N, $X^3$ is chloro | difluoromethyl | cyano | $Y^1$ is N, $Y^2$ is N, $Y^3$ is CH |
| P.1888 | $X^1$ is chloro, $X^2$ is N, $X^3$ is chloro | difluoromethyl | cyclopropyl | $Y^1$ is N, $Y^2$ is N, $Y^3$ is CH |
| P.1889 | $X^1$ is chloro, $X^2$ is N, $X^3$ is chloro | difluoromethyl | ethyl | $Y^1$ is N, $Y^2$ is N, $Y^3$ is CH |
| P.1890 | $X^1$ is chloro, $X^2$ is N, $X^3$ is chloro | difluoromethyl | fluoro | $Y^1$ is N, $Y^2$ is N, $Y^3$ is CH |
| P.1891 | $X^1$ is chloro, $X^2$ is N, $X^3$ is chloro | difluoromethyl | hydrogen | $Y^1$ is N, $Y^2$ is N, $Y^3$ is CH |
| P.1892 | $X^1$ is chloro, $X^2$ is N, $X^3$ is chloro | difluoromethyl | methoxy | $Y^1$ is N, $Y^2$ is N, $Y^3$ is CH |
| P.1893 | $X^1$ is chloro, $X^2$ is N, $X^3$ is chloro | difluoromethyl | methyl | $Y^1$ is N, $Y^2$ is N, $Y^3$ is CH |
| P.1894 | $X^1$ is chloro, $X^2$ is N, $X^3$ is chloro | difluoromethyl | nitro | $Y^1$ is N, $Y^2$ is N, $Y^3$ is CH |
| P.1895 | $X^1$ is chloro, $X^2$ is N, $X^3$ is chloro | difluoromethyl | trifluoromethoxy | $Y^1$ is N, $Y^2$ is N, $Y^3$ is CH |
| P.1896 | $X^1$ is chloro, $X^2$ is N, $X^3$ is chloro | difluoromethyl | trifluoromethyl | $Y^1$ is N, $Y^2$ is N, $Y^3$ is CH |
| P.1897 | $X^1$ is chloro, $X^2$ is N, $X^3$ is chloro | trifluoromethyl | bromo | $Y^1$ is N, $Y^2$ is N, $Y^3$ is CH |
| P.1898 | $X^1$ is chloro, $X^2$ is N, $X^3$ is chloro | trifluoromethyl | chloro | $Y^1$ is N, $Y^2$ is N, $Y^3$ is CH |
| P.1899 | $X^1$ is chloro, $X^2$ is N, $X^3$ is chloro | trifluoromethyl | cyano | $Y^1$ is N, $Y^2$ is N, $Y^3$ is CH |
| P.1900 | $X^1$ is chloro, $X^2$ is N, $X^3$ is chloro | trifluoromethyl | cyclopropyl | $Y^1$ is N, $Y^2$ is N, $Y^3$ is CH |
| P.1901 | $X^1$ is chloro, $X^2$ is N, $X^3$ is chloro | trifluoromethyl | ethyl | $Y^1$ is N, $Y^2$ is N, $Y^3$ is CH |
| P.1902 | $X^1$ is chloro, $X^2$ is N, $X^3$ is chloro | trifluoromethyl | fluoro | $Y^1$ is N, $Y^2$ is N, $Y^3$ is CH |
| P.1903 | $X^1$ is chloro, $X^2$ is N, $X^3$ is chloro | trifluoromethyl | hydrogen | $Y^1$ is N, $Y^2$ is N, $Y^3$ is CH |
| P.1904 | $X^1$ is chloro, $X^2$ is N, $X^3$ is chloro | trifluoromethyl | methoxy | $Y^1$ is N, $Y^2$ is N, $Y^3$ is CH |
| P.1905 | $X^1$ is chloro, $X^2$ is N, $X^3$ is chloro | trifluoromethyl | methyl | $Y^1$ is N, $Y^2$ is N, $Y^3$ is CH |
| P.1906 | $X^1$ is chloro, $X^2$ is N, $X^3$ is chloro | trifluoromethyl | nitro | $Y^1$ is N, $Y^2$ is N, $Y^3$ is CH |
| P.1907 | $X^1$ is chloro, $X^2$ is N, $X^3$ is chloro | trifluoromethyl | trifluoromethoxy | $Y^1$ is N, $Y^2$ is N, $Y^3$ is CH |
| P.1908 | $X^1$ is chloro, $X^2$ is N, $X^3$ is chloro | trifluoromethyl | trifluoromethyl | $Y^1$ is N, $Y^2$ is N, $Y^3$ is CH |
| P.1909 | $X^1$ is trifluoromethyl, $X^2$ is N, $X^3$ is trifluoromethyl | chlorodifluoromethyl | bromo | $Y^1$ is N, $Y^2$ is N, $Y^3$ is CH |
| P.1910 | $X^1$ is trifluoromethyl, $X^2$ is N, $X^3$ is trifluoromethyl | chlorodifluoromethyl | chloro | $Y^1$ is N, $Y^2$ is N, $Y^3$ is CH |
| P.1911 | $X^1$ is trifluoromethyl, $X^2$ is N, $X^3$ is trifluoromethyl | chlorodifluoromethyl | cyano | $Y^1$ is N, $Y^2$ is N, $Y^3$ is CH |
| P.1912 | $X^1$ is trifluoromethyl, $X^2$ is N, $X^3$ is trifluoromethyl | chlorodifluoromethyl | cyclopropyl | $Y^1$ is N, $Y^2$ is N, $Y^3$ is CH |
| P.1913 | $X^1$ is trifluoromethyl, $X^2$ is N, $X^3$ is trifluoromethyl | chlorodifluoromethyl | ethyl | $Y^1$ is N, $Y^2$ is N, $Y^3$ is CH |
| P.1914 | $X^1$ is trifluoromethyl, $X^2$ is N, $X^3$ is trifluoromethyl | chlorodifluoromethyl | fluoro | $Y^1$ is N, $Y^2$ is N, $Y^3$ is CH |
| P.1915 | $X^1$ is trifluoromethyl, $X^2$ is N, $X^3$ is trifluoromethyl | chlorodifluoromethyl | hydrogen | $Y^1$ is N, $Y^2$ is N, $Y^3$ is CH |
| P.1916 | $X^1$ is trifluoromethyl, $X^2$ is N, $X^3$ is trifluoromethyl | chlorodifluoromethyl | methoxy | $Y^1$ is N, $Y^2$ is N, $Y^3$ is CH |
| P.1917 | $X^1$ is trifluoromethyl, $X^2$ is N, $X^3$ is trifluoromethyl | chlorodifluoromethyl | methyl | $Y^1$ is N, $Y^2$ is N, $Y^3$ is CH |
| P.1918 | $X^1$ is trifluoromethyl, $X^2$ is N, $X^3$ is trifluoromethyl | chlorodifluoromethyl | nitro | $Y^1$ is N, $Y^2$ is N, $Y^3$ is CH |
| P.1919 | $X^1$ is trifluoromethyl, $X^2$ is N, $X^3$ is trifluoromethyl | chlorodifluoromethyl | trifluoromethoxy | $Y^1$ is N, $Y^2$ is N, $Y^3$ is CH |
| P.1920 | $X^1$ is trifluoromethyl, $X^2$ is N, $X^3$ is trifluoromethyl | chlorodifluoromethyl | trifluoromethyl | $Y^1$ is N, $Y^2$ is N, $Y^3$ is CH |

TABLE P-continued

| | X1, X2, X3 | X4 | R5 | Y1, Y2, Y3 |
|---|---|---|---|---|
| P.1921 | $X^1$ is trifluoromethyl, $X^2$ is N, $X^3$ is trifluoromethyl | difluoromethyl | bromo | $Y^1$ is N, $Y^2$ is N, $Y^3$ is CH |
| P.1922 | $X^1$ is trifluoromethyl, $X^2$ is N, $X^3$ is trifluoromethyl | difluoromethyl | chloro | $Y^1$ is N, $Y^2$ is N, $Y^3$ is CH |
| P.1923 | $X^1$ is trifluoromethyl, $X^2$ is N, $X^3$ is trifluoromethyl | difluoromethyl | cyano | $Y^1$ is N, $Y^2$ is N, $Y^3$ is CH |
| P.1924 | $X^1$ is trifluoromethyl, $X^2$ is N, $X^3$ is trifluoromethyl | difluoromethyl | cyclopropyl | $Y^1$ is N, $Y^2$ is N, $Y^3$ is CH |
| P.1925 | $X^1$ is trifluoromethyl, $X^2$ is N, $X^3$ is trifluoromethyl | difluoromethyl | ethyl | $Y^1$ is N, $Y^2$ is N, $Y^3$ is CH |
| P.1926 | $X^1$ is trifluoromethyl, $X^2$ is N, $X^3$ is trifluoromethyl | difluoromethyl | fluoro | $Y^1$ is N, $Y^2$ is N, $Y^3$ is CH |
| P.1927 | $X^1$ is trifluoromethyl, $X^2$ is N, $X^3$ is trifluoromethyl | difluoromethyl | hydrogen | $Y^1$ is N, $Y^2$ is N, $Y^3$ is CH |
| P.1928 | $X^1$ is trifluoromethyl, $X^2$ is N, $X^3$ is trifluoromethyl | difluoromethyl | methoxy | $Y^1$ is N, $Y^2$ is N, $Y^3$ is CH |
| P.1929 | $X^1$ is trifluoromethyl, $X^2$ is N, $X^3$ is trifluoromethyl | difluoromethyl | methyl | $Y^1$ is N, $Y^2$ is N, $Y^3$ is CH |
| P.1930 | $X^1$ is trifluoromethyl, $X^2$ is N, $X^3$ is trifluoromethyl | difluoromethyl | nitro | $Y^1$ is N, $Y^2$ is N, $Y^3$ is CH |
| P.1931 | $X^1$ is trifluoromethyl, $X^2$ is N, $X^3$ is trifluoromethyl | difluoromethyl | trifluoromethoxy | $Y^1$ is N, $Y^2$ is N, $Y^3$ is CH |
| P.1932 | $X^1$ is trifluoromethyl, $X^2$ is N, $X^3$ is trifluoromethyl | difluoromethyl | trifluoromethyl | $Y^1$ is N, $Y^2$ is N, $Y^3$ is CH |
| P.1933 | $X^1$ is trifluoromethyl, $X^2$ is N, $X^3$ is trifluoromethyl | trifluoromethyl | bromo | $Y^1$ is N, $Y^2$ is N, $Y^3$ is CH |
| P.1934 | $X^1$ is trifluoromethyl, $X^2$ is N, $X^3$ is trifluoromethyl | trifluoromethyl | chloro | $Y^1$ is N, $Y^2$ is N, $Y^3$ is CH |
| P.1935 | $X^1$ is trifluoromethyl, $X^2$ is N, $X^3$ is trifluoromethyl | trifluoromethyl | cyano | $Y^1$ is N, $Y^2$ is N, $Y^3$ is CH |
| P.1936 | $X^1$ is trifluoromethyl, $X^2$ is N, $X^3$ is trifluoromethyl | trifluoromethyl | cyclopropyl | $Y^1$ is N, $Y^2$ is N, $Y^3$ is CH |
| P.1937 | $X^1$ is trifluoromethyl, $X^2$ is N, $X^3$ is trifluoromethyl | trifluoromethyl | ethyl | $Y^1$ is N, $Y^2$ is N, $Y^3$ is CH |
| P.1938 | $X^1$ is trifluoromethyl, $X^2$ is N, $X^3$ is trifluoromethyl | trifluoromethyl | fluoro | $Y^1$ is N, $Y^2$ is N, $Y^3$ is CH |
| P.1939 | $X^1$ is trifluoromethyl, $X^2$ is N, $X^3$ is trifluoromethyl | trifluoromethyl | hydrogen | $Y^1$ is N, $Y^2$ is N, $Y^3$ is CH |
| P.1940 | $X^1$ is trifluoromethyl, $X^2$ is N, $X^3$ is trifluoromethyl | trifluoromethyl | methoxy | $Y^1$ is N, $Y^2$ is N, $Y^3$ is CH |
| P.1941 | $X^1$ is trifluoromethyl, $X^2$ is N, $X^3$ is trifluoromethyl | trifluoromethyl | methyl | $Y^1$ is N, $Y^2$ is N, $Y^3$ is CH |
| P.1942 | $X^1$ is trifluoromethyl, $X^2$ is N, $X^3$ is trifluoromethyl | trifluoromethyl | nitro | $Y^1$ is N, $Y^2$ is N, $Y^3$ is CH |
| P.1943 | $X^1$ is trifluoromethyl, $X^2$ is N, $X^3$ is trifluoromethyl | trifluoromethyl | trifluoromethoxy | $Y^1$ is N, $Y^2$ is N, $Y^3$ is CH |
| P.1944 | $X^1$ is trifluoromethyl, $X^2$ is N, $X^3$ is trifluoromethyl | trifluoromethyl | trifluoromethyl | $Y^1$ is N, $Y^2$ is N, $Y^3$ is CH |
| P.1945 | $X^1$ is chloro, $X^2$ is CH, $X^3$ is chloro | chlorodifluoromethyl | bromo | $Y^1$ is CH, $Y^2$ is N, $Y^3$ is CH |
| P.1946 | $X^1$ is chloro, $X^2$ is CH, $X^3$ is chloro | chlorodifluoromethyl | chloro | $Y^1$ is CH, $Y^2$ is N, $Y^3$ is CH |
| P.1947 | $X^1$ is chloro, $X^2$ is CH, $X^3$ is chloro | chlorodifluoromethyl | cyano | $Y^1$ is CH, $Y^2$ is N, $Y^3$ is CH |
| P.1948 | $X^1$ is chloro, $X^2$ is CH, $X^3$ is chloro | chlorodifluoromethyl | cyclopropyl | $Y^1$ is CH, $Y^2$ is N, $Y^3$ is CH |
| P.1949 | $X^1$ is chloro, $X^2$ is CH, $X^3$ is chloro | chlorodifluoromethyl | ethyl | $Y^1$ is CH, $Y^2$ is N, $Y^3$ is CH |
| P.1950 | $X^1$ is chloro, $X^2$ is CH, $X^3$ is chloro | chlorodifluoromethyl | fluoro | $Y^1$ is CH, $Y^2$ is N, $Y^3$ is CH |
| P.1951 | $X^1$ is chloro, $X^2$ is CH, $X^3$ is chloro | chlorodifluoromethyl | hydrogen | $Y^1$ is CH, $Y^2$ is N, $Y^3$ is CH |
| P.1952 | $X^1$ is chloro, $X^2$ is CH, $X^3$ is chloro | chlorodifluoromethyl | methoxy | $Y^1$ is CH, $Y^2$ is N, $Y^3$ is CH |
| P.1953 | $X^1$ is chloro, $X^2$ is CH, $X^3$ is chloro | chlorodifluoromethyl | methyl | $Y^1$ is CH, $Y^2$ is N, $Y^3$ is CH |
| P.1954 | $X^1$ is chloro, $X^2$ is CH, $X^3$ is chloro | chlorodifluoromethyl | nitro | $Y^1$ is CH, $Y^2$ is N, $Y^3$ is CH |
| P.1955 | $X^1$ is chloro, $X^2$ is CH, $X^3$ is chloro | chlorodifluoromethyl | trifluoromethoxy | $Y^1$ is CH, $Y^2$ is N, $Y^3$ is CH |
| P.1956 | $X^1$ is chloro, $X^2$ is CH, $X^3$ is chloro | chlorodifluoromethyl | trifluoromethyl | $Y^1$ is CH, $Y^2$ is N, $Y^3$ is CH |
| P.1957 | $X^1$ is chloro, $X^2$ is CH, $X^3$ is chloro | difluoromethyl | bromo | $Y^1$ is CH, $Y^2$ is N, $Y^3$ is CH |
| P.1958 | $X^1$ is chloro, $X^2$ is CH, $X^3$ is chloro | difluoromethyl | chloro | $Y^1$ is CH, $Y^2$ is N, $Y^3$ is CH |
| P.1959 | $X^1$ is chloro, $X^2$ is CH, $X^3$ is chloro | difluoromethyl | cyano | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.1960 | $X^1$ is chloro, $X^2$ is CH, $X^3$ is chloro | difluoromethyl | cyclopropyl | $Y^1$ is CH, $Y^2$ is N, $Y^3$ is CH |
| P.1961 | $X^1$ is chloro, $X^2$ is CH, $X^3$ is chloro | difluoromethyl | ethyl | $Y^1$ is CH, $Y^2$ is N, $Y^3$ is CH |
| P.1962 | $X^1$ is chloro, $X^2$ is CH, $X^3$ is chloro | difluoromethyl | fluoro | $Y^1$ is CH, $Y^2$ is N, $Y^3$ is CH |
| P.1963 | $X^1$ is chloro, $X^2$ is CH, $X^3$ is chloro | difluoromethyl | hydrogen | $Y^1$ is CH, $Y^2$ is N, $Y^3$ is CH |
| P.1964 | $X^1$ is chloro, $X^2$ is CH, $X^3$ is chloro | difluoromethyl | methoxy | $Y^1$ is CH, $Y^2$ is N, $Y^3$ is CH |
| P.1965 | $X^1$ is chloro, $X^2$ is CH, $X^3$ is chloro | difluoromethyl | methyl | $Y^1$ is CH, $Y^2$ is N, $Y^3$ is CH |
| P.1966 | $X^1$ is chloro, $X^2$ is CH, $X^3$ is chloro | difluoromethyl | nitro | $Y^1$ is CH, $Y^2$ is N, $Y^3$ is CH |
| P.1967 | $X^1$ is chloro, $X^2$ is CH, $X^3$ is chloro | difluoromethyl | trifluoromethoxy | $Y^1$ is CH, $Y^2$ is N, $Y^3$ is CH |
| P.1968 | $X^1$ is chloro, $X^2$ is CH, $X^3$ is chloro | difluoromethyl | trifluoromethyl | $Y^1$ is CH, $Y^2$ is N, $Y^3$ is CH |
| P.1969 | $X^1$ is chloro, $X^2$ is CH, $X^3$ is chloro | trifluoromethyl | bromo | $Y^1$ is CH, $Y^2$ is N, $Y^3$ is CH |
| P.1970 | $X^1$ is chloro, $X^2$ is CH, $X^3$ is chloro | trifluoromethyl | chloro | $Y^1$ is CH, $Y^2$ is N, $Y^3$ is CH |
| P.1971 | $X^1$ is chloro, $X^2$ is CH, $X^3$ is chloro | trifluoromethyl | cyano | $Y^1$ is CH, $Y^2$ is N, $Y^3$ is CH |
| P.1972 | $X^1$ is chloro, $X^2$ is CH, $X^3$ is chloro | trifluoromethyl | cyclopropyl | $Y^1$ is CH, $Y^2$ is N, $Y^3$ is CH |
| P.1973 | $X^1$ is chloro, $X^2$ is CH, $X^3$ is chloro | trifluoromethyl | ethyl | $Y^1$ is CH, $Y^2$ is N, $Y^3$ is CH |
| P.1974 | $X^1$ is chloro, $X^2$ is CH, $X^3$ is chloro | trifluoromethyl | fluoro | $Y^1$ is CH, $Y^2$ is N, $Y^3$ is CH |
| P.1975 | $X^1$ is chloro, $X^2$ is CH, $X^3$ is chloro | trifluoromethyl | hydrogen | $Y^1$ is CH, $Y^2$ is N, $Y^3$ is CH |
| P.1976 | $X^1$ is chloro, $X^2$ is CH, $X^3$ is chloro | trifluoromethyl | methoxy | $Y^1$ is CH, $Y^2$ is N, $Y^3$ is CH |
| P.1977 | $X^1$ is chloro, $X^2$ is CH, $X^3$ is chloro | trifluoromethyl | methyl | $Y^1$ is CH, $Y^2$ is N, $Y^3$ is CH |
| P.1978 | $X^1$ is chloro, $X^2$ is CH, $X^3$ is chloro | trifluoromethyl | nitro | $Y^1$ is CH, $Y^2$ is N, $Y^3$ is CH |
| P.1979 | $X^1$ is chloro, $X^2$ is CH, $X^3$ is chloro | trifluoromethyl | trifluoromethoxy | $Y^1$ is CH, $Y^2$ is N, $Y^3$ is CH |
| P.1980 | $X^1$ is chloro, $X^2$ is CH, $X^3$ is chloro | trifluoromethyl | trifluoromethyl | $Y^1$ is CH, $Y^2$ is N, $Y^3$ is CH |
| P.1981 | $X^1$ is chloro, $X^2$ is C—F, $X^3$ is hydrogen | chlorodifluoromethyl | bromo | $Y^1$ is CH, $Y^2$ is N, $Y^3$ is CH |
| P.1982 | $X^1$ is chloro, $X^2$ is C—F, $X^3$ is hydrogen | chlorodifluoromethyl | chloro | $Y^1$ is CH, $Y^2$ is N, $Y^3$ is CH |
| P.1983 | $X^1$ is chloro, $X^2$ is C—F, $X^3$ is hydrogen | chlorodifluoromethyl | cyano | $Y^1$ is CH, $Y^2$ is N, $Y^3$ is CH |
| P.1984 | $X^1$ is chloro, $X^2$ is C—F, $X^3$ is hydrogen | chlorodifluoromethyl | cyclopropyl | $Y^1$ is CH, $Y^2$ is N, $Y^3$ is CH |
| P.1985 | $X^1$ is chloro, $X^2$ is C—F, $X^3$ is hydrogen | chlorodifluoromethyl | ethyl | $Y^1$ is CH, $Y^2$ is N, $Y^3$ is CH |
| P.1986 | $X^1$ is chloro, $X^2$ is C—F, $X^3$ is hydrogen | chlorodifluoromethyl | fluoro | $Y^1$ is CH, $Y^2$ is N, $Y^3$ is CH |
| P.1987 | $X^1$ is chloro, $X^2$ is C—F, $X^3$ is hydrogen | chlorodifluoromethyl | hydrogen | $Y^1$ is CH, $Y^2$ is N, $Y^3$ is CH |
| P.1988 | $X^1$ is chloro, $X^2$ is C—F, $X^3$ is hydrogen | chlorodifluoromethyl | methoxy | $Y^1$ is CH, $Y^2$ is N, $Y^3$ is CH |
| P.1989 | $X^1$ is chloro, $X^2$ is C—F, $X^3$ is hydrogen | chlorodifluoromethyl | methyl | $Y^1$ is CH, $Y^2$ is N, $Y^3$ is CH |
| P.1990 | $X^1$ is chloro, $X^2$ is C—F, $X^3$ is hydrogen | chlorodifluoromethyl | nitro | $Y^1$ is CH, $Y^2$ is N, $Y^3$ is CH |
| P.1991 | $X^1$ is chloro, $X^2$ is C—F, $X^3$ is hydrogen | chlorodifluoromethyl | trifluoromethoxy | $Y^1$ is CH, $Y^2$ is N, $Y^3$ is CH |
| P.1992 | $X^1$ is chloro, $X^2$ is C—F, $X^3$ is hydrogen | chlorodifluoromethyl | trifluoromethyl | $Y^1$ is CH, $Y^2$ is N, $Y^3$ is CH |
| P.1993 | $X^1$ is chloro, $X^2$ is C—F, $X^3$ is hydrogen | difluoromethyl | bromo | $Y^1$ is CH, $Y^2$ is N, $Y^3$ is CH |
| P.1994 | $X^1$ is chloro, $X^2$ is C—F, $X^3$ is hydrogen | difluoromethyl | chloro | $Y^1$ is CH, $Y^2$ is N, $Y^3$ is CH |
| P.1995 | $X^1$ is chloro, $X^2$ is C—F, $X^3$ is hydrogen | difluoromethyl | cyano | $Y^1$ is CH, $Y^2$ is N, $Y^3$ is CH |
| P.1996 | $X^1$ is chloro, $X^2$ is C—F, $X^3$ is hydrogen | difluoromethyl | cyclopropyl | $Y^1$ is CH, $Y^2$ is N, $Y^3$ is CH |
| P.1997 | $X^1$ is chloro, $X^2$ is C—F, $X^3$ is hydrogen | difluoromethyl | ethyl | $Y^1$ is CH, $Y^2$ is N, $Y^3$ is CH |
| P.1998 | $X^1$ is chloro, $X^2$ is C—F, $X^3$ is hydrogen | difluoromethyl | fluoro | $Y^1$ is CH, $Y^2$ is N, $Y^3$ is CH |

TABLE P-continued

|  | X1, X2, X3 | X4 | R5 | Y1, Y2, Y3 |
| --- | --- | --- | --- | --- |
| P.1999 | $X^1$ is chloro, $X^2$ is C—F, $X^3$ is hydrogen | difluoromethyl | hydrogen | $Y^1$ is CH, $Y^2$ is N, $Y^3$ is CH |
| P.2000 | $X^1$ is chloro, $X^2$ is C—F, $X^3$ is hydrogen | difluoromethyl | methoxy | $Y^1$ is CH, $Y^2$ is N, $Y^3$ is CH |
| P.2001 | $X^1$ is chloro, $X^2$ is C—F, $X^3$ is hydrogen | difluoromethyl | methyl | $Y^1$ is CH, $Y^2$ is N, $Y^3$ is CH |
| P.2002 | $X^1$ is chloro, $X^2$ is C—F, $X^3$ is hydrogen | difluoromethyl | nitro | $Y^1$ is CH, $Y^2$ is N, $Y^3$ is CH |
| P.2003 | $X^1$ is chloro, $X^2$ is C—F, $X^3$ is hydrogen | difluoromethyl | trifluoromethoxy | $Y^1$ is CH, $Y^2$ is N, $Y^3$ is CH |
| P.2004 | $X^1$ is chloro, $X^2$ is C—F, $X^3$ is hydrogen | difluoromethyl | trifluoromethyl | $Y^1$ is CH, $Y^2$ is N, $Y^3$ is CH |
| P.2005 | $X^1$ is chloro, $X^2$ is C—F, $X^3$ is hydrogen | trifluoromethyl | bromo | $Y^1$ is CH, $Y^2$ is N, $Y^3$ is CH |
| P.2006 | $X^1$ is chloro, $X^2$ is C—F, $X^3$ is hydrogen | trifluoromethyl | chloro | $Y^1$ is CH, $Y^2$ is N, $Y^3$ is CH |
| P.2007 | $X^1$ is chloro, $X^2$ is C—F, $X^3$ is hydrogen | trifluoromethyl | cyano | $Y^1$ is CH, $Y^2$ is N, $Y^3$ is CH |
| P.2008 | $X^1$ is chloro, $X^2$ is C—F, $X^3$ is hydrogen | trifluoromethyl | cyclopropyl | $Y^1$ is CH, $Y^2$ is N, $Y^3$ is CH |
| P.2009 | $X^1$ is chloro, $X^2$ is C—F, $X^3$ is hydrogen | trifluoromethyl | ethyl | $Y^1$ is CH, $Y^2$ is N, $Y^3$ is CH |
| P.2010 | $X^1$ is chloro, $X^2$ is C—F, $X^3$ is hydrogen | trifluoromethyl | fluoro | $Y^1$ is CH, $Y^2$ is N, $Y^3$ is CH |
| P.2011 | $X^1$ is chloro, $X^2$ is C—F, $X^3$ is hydrogen | trifluoromethyl | hydrogen | $Y^1$ is CH, $Y^2$ is N, $Y^3$ is CH |
| P.2012 | $X^1$ is chloro, $X^2$ is C—F, $X^3$ is hydrogen | trifluoromethyl | methoxy | $Y^1$ is CH, $Y^2$ is N, $Y^3$ is CH |
| P.2013 | $X^1$ is chloro, $X^2$ is C—F, $X^3$ is hydrogen | trifluoromethyl | methyl | $Y^1$ is CH, $Y^2$ is N, $Y^3$ is CH |
| P.2014 | $X^1$ is chloro, $X^2$ is C—F, $X^3$ is hydrogen | trifluoromethyl | nitro | $Y^1$ is CH, $Y^2$ is N, $Y^3$ is CH |
| P.2015 | $X^1$ is chloro, $X^2$ is C—F, $X^3$ is hydrogen | trifluoromethyl | trifluoromethoxy | $Y^1$ is CH, $Y^2$ is N, $Y^3$ is CH |
| P.2016 | $X^1$ is chloro, $X^2$ is C—F, $X^3$ is hydrogen | trifluoromethyl | trifluoromethyl | $Y^1$ is CH, $Y^2$ is N, $Y^3$ is CH |
| P.2017 | $X^1$ is fluoro, $X^2$ is C—Cl, $X^3$ is hydrogen | chlorodifluoromethyl | bromo | $Y^1$ is CH, $Y^2$ is N, $Y^3$ is CH |
| P.2018 | $X^1$ is fluoro, $X^2$ is C—Cl, $X^3$ is hydrogen | chlorodifluoromethyl | chloro | $Y^1$ is CH, $Y^2$ is N, $Y^3$ is CH |
| P.2019 | $X^1$ is fluoro, $X^2$ is C—Cl, $X^3$ is hydrogen | chlorodifluoromethyl | cyano | $Y^1$ is CH, $Y^2$ is N, $Y^3$ is CH |
| P.2020 | $X^1$ is fluoro, $X^2$ is C—Cl, $X^3$ is hydrogen | chlorodifluoromethyl | cyclopropyl | $Y^1$ is CH, $Y^2$ is N, $Y^3$ is CH |
| P.2021 | $X^1$ is fluoro, $X^2$ is C—Cl, $X^3$ is hydrogen | chlorodifluoromethyl | ethyl | $Y^1$ is CH, $Y^2$ is N, $Y^3$ is CH |
| P.2022 | $X^1$ is fluoro, $X^2$ is C—Cl, $X^3$ is hydrogen | chlorodifluoromethyl | fluoro | $Y^1$ is CH, $Y^2$ is N, $Y^3$ is CH |
| P.2023 | $X^1$ is fluoro, $X^2$ is C—Cl, $X^3$ is hydrogen | chlorodifluoromethyl | hydrogen | $Y^1$ is CH, $Y^2$ is N, $Y^3$ is CH |
| P.2024 | $X^1$ is fluoro, $X^2$ is C—Cl, $X^3$ is hydrogen | chlorodifluoromethyl | methoxy | $Y^1$ is CH, $Y^2$ is N, $Y^3$ is CH |
| P.2025 | $X^1$ is fluoro, $X^2$ is C—Cl, $X^3$ is hydrogen | chlorodifluoromethyl | methyl | $Y^1$ is CH, $Y^2$ is N, $Y^3$ is CH |
| P.2026 | $X^1$ is fluoro, $X^2$ is C—Cl, $X^3$ is hydrogen | chlorodifluoromethyl | nitro | $Y^1$ is CH, $Y^2$ is N, $Y^3$ is CH |
| P.2027 | $X^1$ is fluoro, $X^2$ is C—Cl, $X^3$ is hydrogen | chlorodifluoromethyl | trifluoromethoxy | $Y^1$ is CH, $Y^2$ is N, $Y^3$ is CH |
| P.2028 | $X^1$ is fluoro, $X^2$ is C—Cl, $X^3$ is hydrogen | chlorodifluoromethyl | trifluoromethyl | $Y^1$ is CH, $Y^2$ is N, $Y^3$ is CH |
| P.2029 | $X^1$ is fluoro, $X^2$ is C—Cl, $X^3$ is hydrogen | difluoromethyl | bromo | $Y^1$ is CH, $Y^2$ is N, $Y^3$ is CH |
| P.2030 | $X^1$ is fluoro, $X^2$ is C—Cl, $X^3$ is hydrogen | difluoromethyl | chloro | $Y^1$ is CH, $Y^2$ is N, $Y^3$ is CH |
| P.2031 | $X^1$ is fluoro, $X^2$ is C—Cl, $X^3$ is hydrogen | difluoromethyl | cyano | $Y^1$ is CH, $Y^2$ is N, $Y^3$ is CH |
| P.2032 | $X^1$ is fluoro, $X^2$ is C—Cl, $X^3$ is hydrogen | difluoromethyl | cyclopropyl | $Y^1$ is CH, $Y^2$ is N, $Y^3$ is CH |
| P.2033 | $X^1$ is fluoro, $X^2$ is C—Cl, $X^3$ is hydrogen | difluoromethyl | ethyl | $Y^1$ is CH, $Y^2$ is N, $Y^3$ is CH |
| P.2034 | $X^1$ is fluoro, $X^2$ is C—Cl, $X^3$ is hydrogen | difluoromethyl | fluoro | $Y^1$ is CH, $Y^2$ is N, $Y^3$ is CH |
| P.2035 | $X^1$ is fluoro, $X^2$ is C—Cl, $X^3$ is hydrogen | difluoromethyl | hydrogen | $Y^1$ is CH, $Y^2$ is N, $Y^3$ is CH |
| P.2036 | $X^1$ is fluoro, $X^2$ is C—Cl, $X^3$ is hydrogen | difluoromethyl | methoxy | $Y^1$ is CH, $Y^2$ is N, $Y^3$ is CH |
| P.2037 | $X^1$ is fluoro, $X^2$ is C—Cl, $X^3$ is hydrogen | difluoromethyl | methyl | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2038 | $X^1$ is fluoro, $X^2$ is C—Cl, $X^3$ is hydrogen | difluoromethyl | nitro | $Y^1$ is CH, $Y^2$ is N, $Y^3$ is CH |
| P.2039 | $X^1$ is fluoro, $X^2$ is C—Cl, $X^3$ is hydrogen | difluoromethyl | trifluoromethoxy | $Y^1$ is CH, $Y^2$ is N, $Y^3$ is CH |
| P.2040 | $X^1$ is fluoro, $X^2$ is C—Cl, $X^3$ is hydrogen | difluoromethyl | trifluoromethyl | $Y^1$ is CH, $Y^2$ is N, $Y^3$ is CH |
| P.2041 | $X^1$ is fluoro, $X^2$ is C—Cl, $X^3$ is hydrogen | trifluoromethyl | bromo | $Y^1$ is CH, $Y^2$ is N, $Y^3$ is CH |
| P.2042 | $X^1$ is fluoro, $X^2$ is C—Cl, $X^3$ is hydrogen | trifluoromethyl | chloro | $Y^1$ is CH, $Y^2$ is N, $Y^3$ is CH |
| P.2043 | $X^1$ is fluoro, $X^2$ is C—Cl, $X^3$ is hydrogen | trifluoromethyl | cyano | $Y^1$ is CH, $Y^2$ is N, $Y^3$ is CH |
| P.2044 | $X^1$ is fluoro, $X^2$ is C—Cl, $X^3$ is hydrogen | trifluoromethyl | cyclopropyl | $Y^1$ is CH, $Y^2$ is N, $Y^3$ is CH |
| P.2045 | $X^1$ is fluoro, $X^2$ is C—Cl, $X^3$ is hydrogen | trifluoromethyl | ethyl | $Y^1$ is CH, $Y^2$ is N, $Y^3$ is CH |
| P.2046 | $X^1$ is fluoro, $X^2$ is C—Cl, $X^3$ is hydrogen | trifluoromethyl | fluoro | $Y^1$ is CH, $Y^2$ is N, $Y^3$ is CH |
| P.2047 | $X^1$ is fluoro, $X^2$ is C—Cl, $X^3$ is hydrogen | trifluoromethyl | hydrogen | $Y^1$ is CH, $Y^2$ is N, $Y^3$ is CH |
| P.2048 | $X^1$ is fluoro, $X^2$ is C—Cl, $X^3$ is hydrogen | trifluoromethyl | methoxy | $Y^1$ is CH, $Y^2$ is N, $Y^3$ is CH |
| P.2049 | $X^1$ is fluoro, $X^2$ is C—Cl, $X^3$ is hydrogen | trifluoromethyl | methyl | $Y^1$ is CH, $Y^2$ is N, $Y^3$ is CH |
| P.2050 | $X^1$ is fluoro, $X^2$ is C—Cl, $X^3$ is hydrogen | trifluoromethyl | nitro | $Y^1$ is CH, $Y^2$ is N, $Y^3$ is CH |
| P.2051 | $X^1$ is fluoro, $X^2$ is C—Cl, $X^3$ is hydrogen | trifluoromethyl | trifluoromethoxy | $Y^1$ is CH, $Y^2$ is N, $Y^3$ is CH |
| P.2052 | $X^1$ is fluoro, $X^2$ is C—Cl, $X^3$ is hydrogen | trifluoromethyl | trifluoromethyl | $Y^1$ is CH, $Y^2$ is N, $Y^3$ is CH |
| P.2053 | $X^1$ is chloro, $X^2$ is C—Cl, $X^3$ is hydrogen | chlorodifluoromethyl | bromo | $Y^1$ is CH, $Y^2$ is N, $Y^3$ is CH |
| P.2054 | $X^1$ is chloro, $X^2$ is C—Cl, $X^3$ is hydrogen | chlorodifluoromethyl | chloro | $Y^1$ is CH, $Y^2$ is N, $Y^3$ is CH |
| P.2055 | $X^1$ is chloro, $X^2$ is C—Cl, $X^3$ is hydrogen | chlorodifluoromethyl | cyano | $Y^1$ is CH, $Y^2$ is N, $Y^3$ is CH |
| P.2056 | $X^1$ is chloro, $X^2$ is C—Cl, $X^3$ is hydrogen | chlorodifluoromethyl | cyclopropyl | $Y^1$ is CH, $Y^2$ is N, $Y^3$ is CH |
| P.2057 | $X^1$ is chloro, $X^2$ is C—Cl, $X^3$ is hydrogen | chlorodifluoromethyl | ethyl | $Y^1$ is CH, $Y^2$ is N, $Y^3$ is CH |
| P.2058 | $X^1$ is chloro, $X^2$ is C—Cl, $X^3$ is hydrogen | chlorodifluoromethyl | fluoro | $Y^1$ is CH, $Y^2$ is N, $Y^3$ is CH |
| P.2059 | $X^1$ is chloro, $X^2$ is C—Cl, $X^3$ is hydrogen | chlorodifluoromethyl | hydrogen | $Y^1$ is CH, $Y^2$ is N, $Y^3$ is CH |
| P.2060 | $X^1$ is chloro, $X^2$ is C—Cl, $X^3$ is hydrogen | chlorodifluoromethyl | methoxy | $Y^1$ is CH, $Y^2$ is N, $Y^3$ is CH |
| P.2061 | $X^1$ is chloro, $X^2$ is C—Cl, $X^3$ is hydrogen | chlorodifluoromethyl | methyl | $Y^1$ is CH, $Y^2$ is N, $Y^3$ is CH |
| P.2062 | $X^1$ is chloro, $X^2$ is C—Cl, $X^3$ is hydrogen | chlorodifluoromethyl | nitro | $Y^1$ is CH, $Y^2$ is N, $Y^3$ is CH |
| P.2063 | $X^1$ is chloro, $X^2$ is C—Cl, $X^3$ is hydrogen | chlorodifluoromethyl | trifluoromethoxy | $Y^1$ is CH, $Y^2$ is N, $Y^3$ is CH |
| P.2064 | $X^1$ is chloro, $X^2$ is C—Cl, $X^3$ is hydrogen | chlorodifluoromethyl | trifluoromethyl | $Y^1$ is CH, $Y^2$ is N, $Y^3$ is CH |
| P.2065 | $X^1$ is chloro, $X^2$ is C—Cl, $X^3$ is hydrogen | difluoromethyl | bromo | $Y^1$ is CH, $Y^2$ is N, $Y^3$ is CH |
| P.2066 | $X^1$ is chloro, $X^2$ is C—Cl, $X^3$ is hydrogen | difluoromethyl | chloro | $Y^1$ is CH, $Y^2$ is N, $Y^3$ is CH |
| P.2067 | $X^1$ is chloro, $X^2$ is C—Cl, $X^3$ is hydrogen | difluoromethyl | cyano | $Y^1$ is CH, $Y^2$ is N, $Y^3$ is CH |
| P.2068 | $X^1$ is chloro, $X^2$ is C—Cl, $X^3$ is hydrogen | difluoromethyl | cyclopropyl | $Y^1$ is CH, $Y^2$ is N, $Y^3$ is CH |
| P.2069 | $X^1$ is chloro, $X^2$ is C—Cl, $X^3$ is hydrogen | difluoromethyl | ethyl | $Y^1$ is CH, $Y^2$ is N, $Y^3$ is CH |
| P.2070 | $X^1$ is chloro, $X^2$ is C—Cl, $X^3$ is hydrogen | difluoromethyl | fluoro | $Y^1$ is CH, $Y^2$ is N, $Y^3$ is CH |
| P.2071 | $X^1$ is chloro, $X^2$ is C—Cl, $X^3$ is hydrogen | difluoromethyl | hydrogen | $Y^1$ is CH, $Y^2$ is N, $Y^3$ is CH |
| P.2072 | $X^1$ is chloro, $X^2$ is C—Cl, $X^3$ is hydrogen | difluoromethyl | methoxy | $Y^1$ is CH, $Y^2$ is N, $Y^3$ is CH |
| P.2073 | $X^1$ is chloro, $X^2$ is C—Cl, $X^3$ is hydrogen | difluoromethyl | methyl | $Y^1$ is CH, $Y^2$ is N, $Y^3$ is CH |
| P.2074 | $X^1$ is chloro, $X^2$ is C—Cl, $X^3$ is hydrogen | difluoromethyl | nitro | $Y^1$ is CH, $Y^2$ is N, $Y^3$ is CH |
| P.2075 | $X^1$ is chloro, $X^2$ is C—Cl, $X^3$ is hydrogen | difluoromethyl | trifluoromethoxy | $Y^1$ is CH, $Y^2$ is N, $Y^3$ is CH |
| P.2076 | $X^1$ is chloro, $X^2$ is C—Cl, $X^3$ is hydrogen | difluoromethyl | trifluoromethyl | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2077 | $X^1$ is chloro, $X^2$ is C—Cl, $X^3$ is hydrogen | trifluoromethyl | bromo | $Y^1$ is CH, $Y^2$ is N, $Y^3$ is CH |
| P.2078 | $X^1$ is chloro, $X^2$ is C—Cl, $X^3$ is hydrogen | trifluoromethyl | chloro | $Y^1$ is CH, $Y^2$ is N, $Y^3$ is CH |
| P.2079 | $X^1$ is chloro, $X^2$ is C—Cl, $X^3$ is hydrogen | trifluoromethyl | cyano | $Y^1$ is CH, $Y^2$ is N, $Y^3$ is CH |
| P.2080 | $X^1$ is chloro, $X^2$ is C—Cl, $X^3$ is hydrogen | trifluoromethyl | cyclopropyl | $Y^1$ is CH, $Y^2$ is N, $Y^3$ is CH |
| P.2081 | $X^1$ is chloro, $X^2$ is C—Cl, $X^3$ is hydrogen | trifluoromethyl | ethyl | $Y^1$ is CH, $Y^2$ is N, $Y^3$ is CH |
| P.2082 | $X^1$ is chloro, $X^2$ is C—Cl, $X^3$ is hydrogen | trifluoromethyl | fluoro | $Y^1$ is CH, $Y^2$ is N, $Y^3$ is CH |
| P.2083 | $X^1$ is chloro, $X^2$ is C—Cl, $X^3$ is hydrogen | trifluoromethyl | hydrogen | $Y^1$ is CH, $Y^2$ is N, $Y^3$ is CH |
| P.2084 | $X^1$ is chloro, $X^2$ is C—Cl, $X^3$ is hydrogen | trifluoromethyl | methoxy | $Y^1$ is CH, $Y^2$ is N, $Y^3$ is CH |
| P.2085 | $X^1$ is chloro, $X^2$ is C—Cl, $X^3$ is hydrogen | trifluoromethyl | methyl | $Y^1$ is CH, $Y^2$ is N, $Y^3$ is CH |
| P.2086 | $X^1$ is chloro, $X^2$ is C—Cl, $X^3$ is hydrogen | trifluoromethyl | nitro | $Y^1$ is CH, $Y^2$ is N, $Y^3$ is CH |
| P.2087 | $X^1$ is chloro, $X^2$ is C—Cl, $X^3$ is hydrogen | trifluoromethyl | trifluoromethoxy | $Y^1$ is CH, $Y^2$ is N, $Y^3$ is CH |
| P.2088 | $X^1$ is chloro, $X^2$ is C—Cl, $X^3$ is hydrogen | trifluoromethyl | trifluoromethyl | $Y^1$ is CH, $Y^2$ is N, $Y^3$ is CH |
| P.2089 | $X^1$ is chloro, $X^2$ is C—Br, $X^3$ is chloro | chlorodifluoromethyl | bromo | $Y^1$ is CH, $Y^2$ is N, $Y^3$ is CH |
| P.2090 | $X^1$ is chloro, $X^2$ is C—Br, $X^3$ is chloro | chlorodifluoromethyl | chloro | $Y^1$ is CH, $Y^2$ is N, $Y^3$ is CH |
| P.2091 | $X^1$ is chloro, $X^2$ is C—Br, $X^3$ is chloro | chlorodifluoromethyl | cyano | $Y^1$ is CH, $Y^2$ is N, $Y^3$ is CH |
| P.2092 | $X^1$ is chloro, $X^2$ is C—Br, $X^3$ is chloro | chlorodifluoromethyl | cyclopropyl | $Y^1$ is CH, $Y^2$ is N, $Y^3$ is CH |
| P.2093 | $X^1$ is chloro, $X^2$ is C—Br, $X^3$ is chloro | chlorodifluoromethyl | ethyl | $Y^1$ is CH, $Y^2$ is N, $Y^3$ is CH |
| P.2094 | $X^1$ is chloro, $X^2$ is C—Br, $X^3$ is chloro | chlorodifluoromethyl | fluoro | $Y^1$ is CH, $Y^2$ is N, $Y^3$ is CH |
| P.2095 | $X^1$ is chloro, $X^2$ is C—Br, $X^3$ is chloro | chlorodifluoromethyl | hydrogen | $Y^1$ is CH, $Y^2$ is N, $Y^3$ is CH |
| P.2096 | $X^1$ is chloro, $X^2$ is C—Br, $X^3$ is chloro | chlorodifluoromethyl | methoxy | $Y^1$ is CH, $Y^2$ is N, $Y^3$ is CH |
| P.2097 | $X^1$ is chloro, $X^2$ is C—Br, $X^3$ is chloro | chlorodifluoromethyl | methyl | $Y^1$ is CH, $Y^2$ is N, $Y^3$ is CH |
| P.2098 | $X^1$ is chloro, $X^2$ is C—Br, $X^3$ is chloro | chlorodifluoromethyl | nitro | $Y^1$ is CH, $Y^2$ is N, $Y^3$ is CH |
| P.2099 | $X^1$ is chloro, $X^2$ is C—Br, $X^3$ is chloro | chlorodifluoromethyl | trifluoromethoxy | $Y^1$ is CH, $Y^2$ is N, $Y^3$ is CH |
| P.2100 | $X^1$ is chloro, $X^2$ is C—Br, $X^3$ is chloro | chlorodifluoromethyl | trifluoromethyl | $Y^1$ is CH, $Y^2$ is N, $Y^3$ is CH |
| P.2101 | $X^1$ is chloro, $X^2$ is C—Br, $X^3$ is chloro | difluoromethyl | bromo | $Y^1$ is CH, $Y^2$ is N, $Y^3$ is CH |
| P.2102 | $X^1$ is chloro, $X^2$ is C—Br, $X^3$ is chloro | difluoromethyl | chloro | $Y^1$ is CH, $Y^2$ is N, $Y^3$ is CH |
| P.2103 | $X^1$ is chloro, $X^2$ is C—Br, $X^3$ is chloro | difluoromethyl | cyano | $Y^1$ is CH, $Y^2$ is N, $Y^3$ is CH |
| P.2104 | $X^1$ is chloro, $X^2$ is C—Br, $X^3$ is chloro | difluoromethyl | cyclopropyl | $Y^1$ is CH, $Y^2$ is N, $Y^3$ is CH |
| P.2105 | $X^1$ is chloro, $X^2$ is C—Br, $X^3$ is chloro | difluoromethyl | ethyl | $Y^1$ is CH, $Y^2$ is N, $Y^3$ is CH |
| P.2106 | $X^1$ is chloro, $X^2$ is C—Br, $X^3$ is chloro | difluoromethyl | fluoro | $Y^1$ is CH, $Y^2$ is N, $Y^3$ is CH |
| P.2107 | $X^1$ is chloro, $X^2$ is C—Br, $X^3$ is chloro | difluoromethyl | hydrogen | $Y^1$ is CH, $Y^2$ is N, $Y^3$ is CH |
| P.2108 | $X^1$ is chloro, $X^2$ is C—Br, $X^3$ is chloro | difluoromethyl | methoxy | $Y^1$ is CH, $Y^2$ is N, $Y^3$ is CH |
| P.2109 | $X^1$ is chloro, $X^2$ is C—Br, $X^3$ is chloro | difluoromethyl | methyl | $Y^1$ is CH, $Y^2$ is N, $Y^3$ is CH |
| P.2110 | $X^1$ is chloro, $X^2$ is C—Br, $X^3$ is chloro | difluoromethyl | nitro | $Y^1$ is CH, $Y^2$ is N, $Y^3$ is CH |
| P.2111 | $X^1$ is chloro, $X^2$ is C—Br, $X^3$ is chloro | difluoromethyl | trifluoromethoxy | $Y^1$ is CH, $Y^2$ is N, $Y^3$ is CH |
| P.2112 | $X^1$ is chloro, $X^2$ is C—Br, $X^3$ is chloro | difluoromethyl | trifluoromethyl | $Y^1$ is CH, $Y^2$ is N, $Y^3$ is CH |
| P.2113 | $X^1$ is chloro, $X^2$ is C—Br, $X^3$ is chloro | trifluoromethyl | bromo | $Y^1$ is CH, $Y^2$ is N, $Y^3$ is CH |
| P.2114 | $X^1$ is chloro, $X^2$ is C—Br, $X^3$ is chloro | trifluoromethyl | chloro | $Y^1$ is CH, $Y^2$ is N, $Y^3$ is CH |
| P.2115 | $X^1$ is chloro, $X^2$ is C—Br, $X^3$ is chloro | trifluoromethyl | cyano | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2116 | $X^1$ is chloro, $X^2$ is C—Br, $X^3$ is chloro | trifluoromethyl | cyclopropyl | $Y^1$ is CH, $Y^2$ is N, $Y^3$ is CH |
| P.2117 | $X^1$ is chloro, $X^2$ is C—Br, $X^3$ is chloro | trifluoromethyl | ethyl | $Y^1$ is CH, $Y^2$ is N, $Y^3$ is CH |
| P.2118 | $X^1$ is chloro, $X^2$ is C—Br, $X^3$ is chloro | trifluoromethyl | fluoro | $Y^1$ is CH, $Y^2$ is N, $Y^3$ is CH |
| P.2119 | $X^1$ is chloro, $X^2$ is C—Br, $X^3$ is chloro | trifluoromethyl | hydrogen | $Y^1$ is CH, $Y^2$ is N, $Y^3$ is CH |
| P.2120 | $X^1$ is chloro, $X^2$ is C—Br, $X^3$ is chloro | trifluoromethyl | methoxy | $Y^1$ is CH, $Y^2$ is N, $Y^3$ is CH |
| P.2121 | $X^1$ is chloro, $X^2$ is C—Br, $X^3$ is chloro | trifluoromethyl | methyl | $Y^1$ is CH, $Y^2$ is N, $Y^3$ is CH |
| P.2122 | $X^1$ is chloro, $X^2$ is C—Br, $X^3$ is chloro | trifluoromethyl | nitro | $Y^1$ is CH, $Y^2$ is N, $Y^3$ is CH |
| P.2123 | $X^1$ is chloro, $X^2$ is C—Br, $X^3$ is chloro | trifluoromethyl | trifluoromethoxy | $Y^1$ is CH, $Y^2$ is N, $Y^3$ is CH |
| P.2124 | $X^1$ is chloro, $X^2$ is C—Br, $X^3$ is chloro | trifluoromethyl | trifluoromethyl | $Y^1$ is CH, $Y^2$ is N, $Y^3$ is CH |
| P.2125 | $X^1$ is chloro, $X^2$ is C—F, $X^3$ is chloro | chlorodifluoromethyl | bromo | $Y^1$ is CH, $Y^2$ is N, $Y^3$ is CH |
| P.2126 | $X^1$ is chloro, $X^2$ is C—F, $X^3$ is chloro | chlorodifluoromethyl | chloro | $Y^1$ is CH, $Y^2$ is N, $Y^3$ is CH |
| P.2127 | $X^1$ is chloro, $X^2$ is C—F, $X^3$ is chloro | chlorodifluoromethyl | cyano | $Y^1$ is CH, $Y^2$ is N, $Y^3$ is CH |
| P.2128 | $X^1$ is chloro, $X^2$ is C—F, $X^3$ is chloro | chlorodifluoromethyl | cyclopropyl | $Y^1$ is CH, $Y^2$ is N, $Y^3$ is CH |
| P.2129 | $X^1$ is chloro, $X^2$ is C—F, $X^3$ is chloro | chlorodifluoromethyl | ethyl | $Y^1$ is CH, $Y^2$ is N, $Y^3$ is CH |
| P.2130 | $X^1$ is chloro, $X^2$ is C—F, $X^3$ is chloro | chlorodifluoromethyl | fluoro | $Y^1$ is CH, $Y^2$ is N, $Y^3$ is CH |
| P.2131 | $X^1$ is chloro, $X^2$ is C—F, $X^3$ is chloro | chlorodifluoromethyl | hydrogen | $Y^1$ is CH, $Y^2$ is N, $Y^3$ is CH |
| P.2132 | $X^1$ is chloro, $X^2$ is C—F, $X^3$ is chloro | chlorodifluoromethyl | methoxy | $Y^1$ is CH, $Y^2$ is N, $Y^3$ is CH |
| P.2133 | $X^1$ is chloro, $X^2$ is C—F, $X^3$ is chloro | chlorodifluoromethyl | methyl | $Y^1$ is CH, $Y^2$ is N, $Y^3$ is CH |
| P.2134 | $X^1$ is chloro, $X^2$ is C—F, $X^3$ is chloro | chlorodifluoromethyl | nitro | $Y^1$ is CH, $Y^2$ is N, $Y^3$ is CH |
| P.2135 | $X^1$ is chloro, $X^2$ is C—F, $X^3$ is chloro | chlorodifluoromethyl | trifluoromethoxy | $Y^1$ is CH, $Y^2$ is N, $Y^3$ is CH |
| P.2136 | $X^1$ is chloro, $X^2$ is C—F, $X^3$ is chloro | chlorodifluoromethyl | trifluoromethyl | $Y^1$ is CH, $Y^2$ is N, $Y^3$ is CH |
| P.2137 | $X^1$ is chloro, $X^2$ is C—F, $X^3$ is chloro | difluoromethyl | bromo | $Y^1$ is CH, $Y^2$ is N, $Y^3$ is CH |
| P.2138 | $X^1$ is chloro, $X^2$ is C—F, $X^3$ is chloro | difluoromethyl | chloro | $Y^1$ is CH, $Y^2$ is N, $Y^3$ is CH |
| P.2139 | $X^1$ is chloro, $X^2$ is C—F, $X^3$ is chloro | difluoromethyl | cyano | $Y^1$ is CH, $Y^2$ is N, $Y^3$ is CH |
| P.2140 | $X^1$ is chloro, $X^2$ is C—F, $X^3$ is chloro | difluoromethyl | cyclopropyl | $Y^1$ is CH, $Y^2$ is N, $Y^3$ is CH |
| P.2141 | $X^1$ is chloro, $X^2$ is C—F, $X^3$ is chloro | difluoromethyl | ethyl | $Y^1$ is CH, $Y^2$ is N, $Y^3$ is CH |
| P.2142 | $X^1$ is chloro, $X^2$ is C—F, $X^3$ is chloro | difluoromethyl | fluoro | $Y^1$ is CH, $Y^2$ is N, $Y^3$ is CH |
| P.2143 | $X^1$ is chloro, $X^2$ is C—F, $X^3$ is chloro | difluoromethyl | hydrogen | $Y^1$ is CH, $Y^2$ is N, $Y^3$ is CH |
| P.2144 | $X^1$ is chloro, $X^2$ is C—F, $X^3$ is chloro | difluoromethyl | methoxy | $Y^1$ is CH, $Y^2$ is N, $Y^3$ is CH |
| P.2145 | $X^1$ is chloro, $X^2$ is C—F, $X^3$ is chloro | difluoromethyl | methyl | $Y^1$ is CH, $Y^2$ is N, $Y^3$ is CH |
| P.2146 | $X^1$ is chloro, $X^2$ is C—F, $X^3$ is chloro | difluoromethyl | nitro | $Y^1$ is CH, $Y^2$ is N, $Y^3$ is CH |
| P.2147 | $X^1$ is chloro, $X^2$ is C—F, $X^3$ is chloro | difluoromethyl | trifluoromethoxy | $Y^1$ is CH, $Y^2$ is N, $Y^3$ is CH |
| P.2148 | $X^1$ is chloro, $X^2$ is C—F, $X^3$ is chloro | difluoromethyl | trifluoromethyl | $Y^1$ is CH, $Y^2$ is N, $Y^3$ is CH |
| P.2149 | $X^1$ is chloro, $X^2$ is C—F, $X^3$ is chloro | trifluoromethyl | bromo | $Y^1$ is CH, $Y^2$ is N, $Y^3$ is CH |
| P.2150 | $X^1$ is chloro, $X^2$ is C—F, $X^3$ is chloro | trifluoromethyl | chloro | $Y^1$ is CH, $Y^2$ is N, $Y^3$ is CH |
| P.2151 | $X^1$ is chloro, $X^2$ is C—F, $X^3$ is chloro | trifluoromethyl | cyano | $Y^1$ is CH, $Y^2$ is N, $Y^3$ is CH |
| P.2152 | $X^1$ is chloro, $X^2$ is C—F, $X^3$ is chloro | trifluoromethyl | cyclopropyl | $Y^1$ is CH, $Y^2$ is N, $Y^3$ is CH |
| P.2153 | $X^1$ is chloro, $X^2$ is C—F, $X^3$ is chloro | trifluoromethyl | ethyl | $Y^1$ is CH, $Y^2$ is N, $Y^3$ is CH |
| P.2154 | $X^1$ is chloro, $X^2$ is C—F, $X^3$ is chloro | trifluoromethyl | fluoro | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2155 | $X^1$ is chloro, $X^2$ is C—F, $X^3$ is chloro | trifluoromethyl | hydrogen | $Y^1$ is CH, $Y^2$ is N, $Y^3$ is CH |
| P.2156 | $X^1$ is chloro, $X^2$ is C—F, $X^3$ is chloro | trifluoromethyl | methoxy | $Y^1$ is CH, $Y^2$ is N, $Y^3$ is CH |
| P.2157 | $X^1$ is chloro, $X^2$ is C—F, $X^3$ is chloro | trifluoromethyl | methyl | $Y^1$ is CH, $Y^2$ is N, $Y^3$ is CH |
| P.2158 | $X^1$ is chloro, $X^2$ is C—F, $X^3$ is chloro | trifluoromethyl | nitro | $Y^1$ is CH, $Y^2$ is N, $Y^3$ is CH |
| P.2159 | $X^1$ is chloro, $X^2$ is C—F, $X^3$ is chloro | trifluoromethyl | trifluoromethoxy | $Y^1$ is CH, $Y^2$ is N, $Y^3$ is CH |
| P.2160 | $X^1$ is chloro, $X^2$ is C—F, $X^3$ is chloro | trifluoromethyl | trifluoromethyl | $Y^1$ is CH, $Y^2$ is N, $Y^3$ is CH |
| P.2161 | $X^1$ is chloro, $X^2$ is C—Cl, $X^3$ is chloro | chlorodifluoromethyl | bromo | $Y^1$ is CH, $Y^2$ is N, $Y^3$ is CH |
| P.2162 | $X^1$ is chloro, $X^2$ is C—Cl, $X^3$ is chloro | chlorodifluoromethyl | chloro | $Y^1$ is CH, $Y^2$ is N, $Y^3$ is CH |
| P.2163 | $X^1$ is chloro, $X^2$ is C—Cl, $X^3$ is chloro | chlorodifluoromethyl | cyano | $Y^1$ is CH, $Y^2$ is N, $Y^3$ is CH |
| P.2164 | $X^1$ is chloro, $X^2$ is C—Cl, $X^3$ is chloro | chlorodifluoromethyl | cyclopropyl | $Y^1$ is CH, $Y^2$ is N, $Y^3$ is CH |
| P.2165 | $X^1$ is chloro, $X^2$ is C—Cl, $X^3$ is chloro | chlorodifluoromethyl | ethyl | $Y^1$ is CH, $Y^2$ is N, $Y^3$ is CH |
| P.2166 | $X^1$ is chloro, $X^2$ is C—Cl, $X^3$ is chloro | chlorodifluoromethyl | fluoro | $Y^1$ is CH, $Y^2$ is N, $Y^3$ is CH |
| P.2167 | $X^1$ is chloro, $X^2$ is C—Cl, $X^3$ is chloro | chlorodifluoromethyl | hydrogen | $Y^1$ is CH, $Y^2$ is N, $Y^3$ is CH |
| P.2168 | $X^1$ is chloro, $X^2$ is C—Cl, $X^3$ is chloro | chlorodifluoromethyl | methoxy | $Y^1$ is CH, $Y^2$ is N, $Y^3$ is CH |
| P.2169 | $X^1$ is chloro, $X^2$ is C—Cl, $X^3$ is chloro | chlorodifluoromethyl | methyl | $Y^1$ is CH, $Y^2$ is N, $Y^3$ is CH |
| P.2170 | $X^1$ is chloro, $X^2$ is C—Cl, $X^3$ is chloro | chlorodifluoromethyl | nitro | $Y^1$ is CH, $Y^2$ is N, $Y^3$ is CH |
| P.2171 | $X^1$ is chloro, $X^2$ is C—Cl, $X^3$ is chloro | chlorodifluoromethyl | trifluoromethoxy | $Y^1$ is CH, $Y^2$ is N, $Y^3$ is CH |
| P.2172 | $X^1$ is chloro, $X^2$ is C—Cl, $X^3$ is chloro | chlorodifluoromethyl | trifluoromethyl | $Y^1$ is CH, $Y^2$ is N, $Y^3$ is CH |
| P.2173 | $X^1$ is chloro, $X^2$ is C—Cl, $X^3$ is chloro | difluoromethyl | bromo | $Y^1$ is CH, $Y^2$ is N, $Y^3$ is CH |
| P.2174 | $X^1$ is chloro, $X^2$ is C—Cl, $X^3$ is chloro | difluoromethyl | chloro | $Y^1$ is CH, $Y^2$ is N, $Y^3$ is CH |
| P.2175 | $X^1$ is chloro, $X^2$ is C—Cl, $X^3$ is chloro | difluoromethyl | cyano | $Y^1$ is CH, $Y^2$ is N, $Y^3$ is CH |
| P.2176 | $X^1$ is chloro, $X^2$ is C—Cl, $X^3$ is chloro | difluoromethyl | cyclopropyl | $Y^1$ is CH, $Y^2$ is N, $Y^3$ is CH |
| P.2177 | $X^1$ is chloro, $X^2$ is C—Cl, $X^3$ is chloro | difluoromethyl | ethyl | $Y^1$ is CH, $Y^2$ is N, $Y^3$ is CH |
| P.2178 | $X^1$ is chloro, $X^2$ is C—Cl, $X^3$ is chloro | difluoromethyl | fluoro | $Y^1$ is CH, $Y^2$ is N, $Y^3$ is CH |
| P.2179 | $X^1$ is chloro, $X^2$ is C—Cl, $X^3$ is chloro | difluoromethyl | hydrogen | $Y^1$ is CH, $Y^2$ is N, $Y^3$ is CH |
| P.2180 | $X^1$ is chloro, $X^2$ is C—Cl, $X^3$ is chloro | difluoromethyl | methoxy | $Y^1$ is CH, $Y^2$ is N, $Y^3$ is CH |
| P.2181 | $X^1$ is chloro, $X^2$ is C—Cl, $X^3$ is chloro | difluoromethyl | methyl | $Y^1$ is CH, $Y^2$ is N, $Y^3$ is CH |
| P.2182 | $X^1$ is chloro, $X^2$ is C—Cl, $X^3$ is chloro | difluoromethyl | nitro | $Y^1$ is CH, $Y^2$ is N, $Y^3$ is CH |
| P.2183 | $X^1$ is chloro, $X^2$ is C—Cl, $X^3$ is chloro | difluoromethyl | trifluoromethoxy | $Y^1$ is CH, $Y^2$ is N, $Y^3$ is CH |
| P.2184 | $X^1$ is chloro, $X^2$ is C—Cl, $X^3$ is chloro | difluoromethyl | trifluoromethyl | $Y^1$ is CH, $Y^2$ is N, $Y^3$ is CH |
| P.2185 | $X^1$ is chloro, $X^2$ is C—Cl, $X^3$ is chloro | trifluoromethyl | bromo | $Y^1$ is CH, $Y^2$ is N, $Y^3$ is CH |
| P.2186 | $X^1$ is chloro, $X^2$ is C—Cl, $X^3$ is chloro | trifluoromethyl | chloro | $Y^1$ is CH, $Y^2$ is N, $Y^3$ is CH |
| P.2187 | $X^1$ is chloro, $X^2$ is C—Cl, $X^3$ is chloro | trifluoromethyl | cyano | $Y^1$ is CH, $Y^2$ is N, $Y^3$ is CH |
| P.2188 | $X^1$ is chloro, $X^2$ is C—Cl, $X^3$ is chloro | trifluoromethyl | cyclopropyl | $Y^1$ is CH, $Y^2$ is N, $Y^3$ is CH |
| P.2189 | $X^1$ is chloro, $X^2$ is C—Cl, $X^3$ is chloro | trifluoromethyl | ethyl | $Y^1$ is CH, $Y^2$ is N, $Y^3$ is CH |
| P.2190 | $X^1$ is chloro, $X^2$ is C—Cl, $X^3$ is chloro | trifluoromethyl | fluoro | $Y^1$ is CH, $Y^2$ is N, $Y^3$ is CH |
| P.2191 | $X^1$ is chloro, $X^2$ is C—Cl, $X^3$ is chloro | trifluoromethyl | hydrogen | $Y^1$ is CH, $Y^2$ is N, $Y^3$ is CH |
| P.2192 | $X^1$ is chloro, $X^2$ is C—Cl, $X^3$ is chloro | trifluoromethyl | methoxy | $Y^1$ is CH, $Y^2$ is N, $Y^3$ is CH |
| P.2193 | $X^1$ is chloro, $X^2$ is C—Cl, $X^3$ is chloro | trifluoromethyl | methyl | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2194 | $X^1$ is chloro, $X^2$ is C—Cl, $X^3$ is chloro | trifluoromethyl | nitro | $Y^1$ is CH, $Y^2$ is N, $Y^3$ is CH |
| P.2195 | $X^1$ is chloro, $X^2$ is C—Cl, $X^3$ is chloro | trifluoromethyl | trifluoromethoxy | $Y^1$ is CH, $Y^2$ is N, $Y^3$ is CH |
| P.2196 | $X^1$ is chloro, $X^2$ is C—Cl, $X^3$ is chloro | trifluoromethyl | trifluoromethyl | $Y^1$ is CH, $Y^2$ is N, $Y^3$ is CH |
| P.2197 | $X^1$ is chloro, $X^2$ is C—I, $X^3$ is chloro | chlorodifluoromethyl | bromo | $Y^1$ is CH, $Y^2$ is N, $Y^3$ is CH |
| P.2198 | $X^1$ is chloro, $X^2$ is C—I, $X^3$ is chloro | chlorodifluoromethyl | chloro | $Y^1$ is CH, $Y^2$ is N, $Y^3$ is CH |
| P.2199 | $X^1$ is chloro, $X^2$ is C—I, $X^3$ is chloro | chlorodifluoromethyl | cyano | $Y^1$ is CH, $Y^2$ is N, $Y^3$ is CH |
| P.2200 | $X^1$ is chloro, $X^2$ is C—I, $X^3$ is chloro | chlorodifluoromethyl | cyclopropyl | $Y^1$ is CH, $Y^2$ is N, $Y^3$ is CH |
| P.2201 | $X^1$ is chloro, $X^2$ is C—I, $X^3$ is chloro | chlorodifluoromethyl | ethyl | $Y^1$ is CH, $Y^2$ is N, $Y^3$ is CH |
| P.2202 | $X^1$ is chloro, $X^2$ is C—I, $X^3$ is chloro | chlorodifluoromethyl | fluoro | $Y^1$ is CH, $Y^2$ is N, $Y^3$ is CH |
| P.2203 | $X^1$ is chloro, $X^2$ is C—I, $X^3$ is chloro | chlorodifluoromethyl | hydrogen | $Y^1$ is CH, $Y^2$ is N, $Y^3$ is CH |
| P.2204 | $X^1$ is chloro, $X^2$ is C—I, $X^3$ is chloro | chlorodifluoromethyl | methoxy | $Y^1$ is CH, $Y^2$ is N, $Y^3$ is CH |
| P.2205 | $X^1$ is chloro, $X^2$ is C—I, $X^3$ is chloro | chlorodifluoromethyl | methyl | $Y^1$ is CH, $Y^2$ is N, $Y^3$ is CH |
| P.2206 | $X^1$ is chloro, $X^2$ is C—I, $X^3$ is chloro | chlorodifluoromethyl | nitro | $Y^1$ is CH, $Y^2$ is N, $Y^3$ is CH |
| P.2207 | $X^1$ is chloro, $X^2$ is C—I, $X^3$ is chloro | chlorodifluoromethyl | trifluoromethoxy | $Y^1$ is CH, $Y^2$ is N, $Y^3$ is CH |
| P.2208 | $X^1$ is chloro, $X^2$ is C—I, $X^3$ is chloro | chlorodifluoromethyl | trifluoromethyl | $Y^1$ is CH, $Y^2$ is N, $Y^3$ is CH |
| P.2209 | $X^1$ is chloro, $X^2$ is C—I, $X^3$ is chloro | difluoromethyl | bromo | $Y^1$ is CH, $Y^2$ is N, $Y^3$ is CH |
| P.2210 | $X^1$ is chloro, $X^2$ is C—I, $X^3$ is chloro | difluoromethyl | chloro | $Y^1$ is CH, $Y^2$ is N, $Y^3$ is CH |
| P.2211 | $X^1$ is chloro, $X^2$ is C—I, $X^3$ is chloro | difluoromethyl | cyano | $Y^1$ is CH, $Y^2$ is N, $Y^3$ is CH |
| P.2212 | $X^1$ is chloro, $X^2$ is C—I, $X^3$ is chloro | difluoromethyl | cyclopropyl | $Y^1$ is CH, $Y^2$ is N, $Y^3$ is CH |
| P.2213 | $X^1$ is chloro, $X^2$ is C—I, $X^3$ is chloro | difluoromethyl | ethyl | $Y^1$ is CH, $Y^2$ is N, $Y^3$ is CH |
| P.2214 | $X^1$ is chloro, $X^2$ is C—I, $X^3$ is chloro | difluoromethyl | fluoro | $Y^1$ is CH, $Y^2$ is N, $Y^3$ is CH |
| P.2215 | $X^1$ is chloro, $X^2$ is C—I, $X^3$ is chloro | difluoromethyl | hydrogen | $Y^1$ is CH, $Y^2$ is N, $Y^3$ is CH |
| P.2216 | $X^1$ is chloro, $X^2$ is C—I, $X^3$ is chloro | difluoromethyl | methoxy | $Y^1$ is CH, $Y^2$ is N, $Y^3$ is CH |
| P.2217 | $X^1$ is chloro, $X^2$ is C—I, $X^3$ is chloro | difluoromethyl | methyl | $Y^1$ is CH, $Y^2$ is N, $Y^3$ is CH |
| P.2218 | $X^1$ is chloro, $X^2$ is C—I, $X^3$ is chloro | difluoromethyl | nitro | $Y^1$ is CH, $Y^2$ is N, $Y^3$ is CH |
| P.2219 | $X^1$ is chloro, $X^2$ is C—I, $X^3$ is chloro | difluoromethyl | trifluoromethoxy | $Y^1$ is CH, $Y^2$ is N, $Y^3$ is CH |
| P.2220 | $X^1$ is chloro, $X^2$ is C—I, $X^3$ is chloro | difluoromethyl | trifluoromethyl | $Y^1$ is CH, $Y^2$ is N, $Y^3$ is CH |
| P.2221 | $X^1$ is chloro, $X^2$ is C—I, $X^3$ is chloro | trifluoromethyl | bromo | $Y^1$ is CH, $Y^2$ is N, $Y^3$ is CH |
| P.2222 | $X^1$ is chloro, $X^2$ is C—I, $X^3$ is chloro | trifluoromethyl | chloro | $Y^1$ is CH, $Y^2$ is N, $Y^3$ is CH |
| P.2223 | $X^1$ is chloro, $X^2$ is C—I, $X^3$ is chloro | trifluoromethyl | cyano | $Y^1$ is CH, $Y^2$ is N, $Y^3$ is CH |
| P.2224 | $X^1$ is chloro, $X^2$ is C—I, $X^3$ is chloro | trifluoromethyl | cyclopropyl | $Y^1$ is CH, $Y^2$ is N, $Y^3$ is CH |
| P.2225 | $X^1$ is chloro, $X^2$ is C—I, $X^3$ is chloro | trifluoromethyl | ethyl | $Y^1$ is CH, $Y^2$ is N, $Y^3$ is CH |
| P.2226 | $X^1$ is chloro, $X^2$ is C—I, $X^3$ is chloro | trifluoromethyl | fluoro | $Y^1$ is CH, $Y^2$ is N, $Y^3$ is CH |
| P.2227 | $X^1$ is chloro, $X^2$ is C—I, $X^3$ is chloro | trifluoromethyl | hydrogen | $Y^1$ is CH, $Y^2$ is N, $Y^3$ is CH |
| P.2228 | $X^1$ is chloro, $X^2$ is C—I, $X^3$ is chloro | trifluoromethyl | methoxy | $Y^1$ is CH, $Y^2$ is N, $Y^3$ is CH |
| P.2229 | $X^1$ is chloro, $X^2$ is C—I, $X^3$ is chloro | trifluoromethyl | methyl | $Y^1$ is CH, $Y^2$ is N, $Y^3$ is CH |
| P.2230 | $X^1$ is chloro, $X^2$ is C—I, $X^3$ is chloro | trifluoromethyl | nitro | $Y^1$ is CH, $Y^2$ is N, $Y^3$ is CH |
| P.2231 | $X^1$ is chloro, $X^2$ is C—I, $X^3$ is chloro | trifluoromethyl | trifluoromethoxy | $Y^1$ is CH, $Y^2$ is N, $Y^3$ is CH |
| P.2232 | $X^1$ is chloro, $X^2$ is C—I, $X^3$ is chloro | trifluoromethyl | trifluoromethyl | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2233 | $X^1$ is fluoro, $X^2$ is C—F, $X^3$ is fluoro | chlorodifluoromethyl | bromo | $Y^1$ is CH, $Y^2$ is N, $Y^3$ is CH |
| P.2234 | $X^1$ is fluoro, $X^2$ is C—F, $X^3$ is fluoro | chlorodifluoromethyl | chloro | $Y^1$ is CH, $Y^2$ is N, $Y^3$ is CH |
| P.2235 | $X^1$ is fluoro, $X^2$ is C—F, $X^3$ is fluoro | chlorodifluoromethyl | cyano | $Y^1$ is CH, $Y^2$ is N, $Y^3$ is CH |
| P.2236 | $X^1$ is fluoro, $X^2$ is C—F, $X^3$ is fluoro | chlorodifluoromethyl | cyclopropyl | $Y^1$ is CH, $Y^2$ is N, $Y^3$ is CH |
| P.2237 | $X^1$ is fluoro, $X^2$ is C—F, $X^3$ is fluoro | chlorodifluoromethyl | ethyl | $Y^1$ is CH, $Y^2$ is N, $Y^3$ is CH |
| P.2238 | $X^1$ is fluoro, $X^2$ is C—F, $X^3$ is fluoro | chlorodifluoromethyl | fluoro | $Y^1$ is CH, $Y^2$ is N, $Y^3$ is CH |
| P.2239 | $X^1$ is fluoro, $X^2$ is C—F, $X^3$ is fluoro | chlorodifluoromethyl | hydrogen | $Y^1$ is CH, $Y^2$ is N, $Y^3$ is CH |
| P.2240 | $X^1$ is fluoro, $X^2$ is C—F, $X^3$ is fluoro | chlorodifluoromethyl | methoxy | $Y^1$ is CH, $Y^2$ is N, $Y^3$ is CH |
| P.2241 | $X^1$ is fluoro, $X^2$ is C—F, $X^3$ is fluoro | chlorodifluoromethyl | methyl | $Y^1$ is CH, $Y^2$ is N, $Y^3$ is CH |
| P.2242 | $X^1$ is fluoro, $X^2$ is C—F, $X^3$ is fluoro | chlorodifluoromethyl | nitro | $Y^1$ is CH, $Y^2$ is N, $Y^3$ is CH |
| P.2243 | $X^1$ is fluoro, $X^2$ is C—F, $X^3$ is fluoro | chlorodifluoromethyl | trifluoromethoxy | $Y^1$ is CH, $Y^2$ is N, $Y^3$ is CH |
| P.2244 | $X^1$ is fluoro, $X^2$ is C—F, $X^3$ is fluoro | chlorodifluoromethyl | trifluoromethyl | $Y^1$ is CH, $Y^2$ is N, $Y^3$ is CH |
| P.2245 | $X^1$ is fluoro, $X^2$ is C—F, $X^3$ is fluoro | difluoromethyl | bromo | $Y^1$ is CH, $Y^2$ is N, $Y^3$ is CH |
| P.2246 | $X^1$ is fluoro, $X^2$ is C—F, $X^3$ is fluoro | difluoromethyl | chloro | $Y^1$ is CH, $Y^2$ is N, $Y^3$ is CH |
| P.2247 | $X^1$ is fluoro, $X^2$ is C—F, $X^3$ is fluoro | difluoromethyl | cyano | $Y^1$ is CH, $Y^2$ is N, $Y^3$ is CH |
| P.2248 | $X^1$ is fluoro, $X^2$ is C—F, $X^3$ is fluoro | difluoromethyl | cyclopropyl | $Y^1$ is CH, $Y^2$ is N, $Y^3$ is CH |
| P.2249 | $X^1$ is fluoro, $X^2$ is C—F, $X^3$ is fluoro | difluoromethyl | ethyl | $Y^1$ is CH, $Y^2$ is N, $Y^3$ is CH |
| P.2250 | $X^1$ is fluoro, $X^2$ is C—F, $X^3$ is fluoro | difluoromethyl | fluoro | $Y^1$ is CH, $Y^2$ is N, $Y^3$ is CH |
| P.2251 | $X^1$ is fluoro, $X^2$ is C—F, $X^3$ is fluoro | difluoromethyl | hydrogen | $Y^1$ is CH, $Y^2$ is N, $Y^3$ is CH |
| P.2252 | $X^1$ is fluoro, $X^2$ is C—F, $X^3$ is fluoro | difluoromethyl | methoxy | $Y^1$ is CH, $Y^2$ is N, $Y^3$ is CH |
| P.2253 | $X^1$ is fluoro, $X^2$ is C—F, $X^3$ is fluoro | difluoromethyl | methyl | $Y^1$ is CH, $Y^2$ is N, $Y^3$ is CH |
| P.2254 | $X^1$ is fluoro, $X^2$ is C—F, $X^3$ is fluoro | difluoromethyl | nitro | $Y^1$ is CH, $Y^2$ is N, $Y^3$ is CH |
| P.2255 | $X^1$ is fluoro, $X^2$ is C—F, $X^3$ is fluoro | difluoromethyl | trifluoromethoxy | $Y^1$ is CH, $Y^2$ is N, $Y^3$ is CH |
| P.2256 | $X^1$ is fluoro, $X^2$ is C—F, $X^3$ is fluoro | difluoromethyl | trifluoromethyl | $Y^1$ is CH, $Y^2$ is N, $Y^3$ is CH |
| P.2257 | $X^1$ is fluoro, $X^2$ is C—F, $X^3$ is fluoro | trifluoromethyl | bromo | $Y^1$ is CH, $Y^2$ is N, $Y^3$ is CH |
| P.2258 | $X^1$ is fluoro, $X^2$ is C—F, $X^3$ is fluoro | trifluoromethyl | chloro | $Y^1$ is CH, $Y^2$ is N, $Y^3$ is CH |
| P.2259 | $X^1$ is fluoro, $X^2$ is C—F, $X^3$ is fluoro | trifluoromethyl | cyano | $Y^1$ is CH, $Y^2$ is N, $Y^3$ is CH |
| P.2260 | $X^1$ is fluoro, $X^2$ is C—F, $X^3$ is fluoro | trifluoromethyl | cyclopropyl | $Y^1$ is CH, $Y^2$ is N, $Y^3$ is CH |
| P.2261 | $X^1$ is fluoro, $X^2$ is C—F, $X^3$ is fluoro | trifluoromethyl | ethyl | $Y^1$ is CH, $Y^2$ is N, $Y^3$ is CH |
| P.2262 | $X^1$ is fluoro, $X^2$ is C—F, $X^3$ is fluoro | trifluoromethyl | fluoro | $Y^1$ is CH, $Y^2$ is N, $Y^3$ is CH |
| P.2263 | $X^1$ is fluoro, $X^2$ is C—F, $X^3$ is fluoro | trifluoromethyl | hydrogen | $Y^1$ is CH, $Y^2$ is N, $Y^3$ is CH |
| P.2264 | $X^1$ is fluoro, $X^2$ is C—F, $X^3$ is fluoro | trifluoromethyl | methoxy | $Y^1$ is CH, $Y^2$ is N, $Y^3$ is CH |
| P.2265 | $X^1$ is fluoro, $X^2$ is C—F, $X^3$ is fluoro | trifluoromethyl | methyl | $Y^1$ is CH, $Y^2$ is N, $Y^3$ is CH |
| P.2266 | $X^1$ is fluoro, $X^2$ is C—F, $X^3$ is fluoro | trifluoromethyl | nitro | $Y^1$ is CH, $Y^2$ is N, $Y^3$ is CH |
| P.2267 | $X^1$ is fluoro, $X^2$ is C—F, $X^3$ is fluoro | trifluoromethyl | trifluoromethoxy | $Y^1$ is CH, $Y^2$ is N, $Y^3$ is CH |
| P.2268 | $X^1$ is fluoro, $X^2$ is C—F, $X^3$ is fluoro | trifluoromethyl | trifluoromethyl | $Y^1$ is CH, $Y^2$ is N, $Y^3$ is CH |
| P.2269 | $X^1$ is chloro, $X^2$ is CH, $X^3$ is bromo | chlorodifluoromethyl | bromo | $Y^1$ is CH, $Y^2$ is N, $Y^3$ is CH |
| P.2270 | $X^1$ is chloro, $X^2$ is CH, $X^3$ is bromo | chlorodifluoromethyl | chloro | $Y^1$ is CH, $Y^2$ is N, $Y^3$ is CH |
| P.2271 | $X^1$ is chloro, $X^2$ is CH, $X^3$ is bromo | chlorodifluoromethyl | cyano | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2272 | $X^1$ is chloro, $X^2$ is CH, $X^3$ is bromo | chlorodifluoromethyl | cyclopropyl | $Y^1$ is CH, $Y^2$ is N, $Y^3$ is CH |
| P.2273 | $X^1$ is chloro, $X^2$ is CH, $X^3$ is bromo | chlorodifluoromethyl | ethyl | $Y^1$ is CH, $Y^2$ is N, $Y^3$ is CH |
| P.2274 | $X^1$ is chloro, $X^2$ is CH, $X^3$ is bromo | chlorodifluoromethyl | fluoro | $Y^1$ is CH, $Y^2$ is N, $Y^3$ is CH |
| P.2275 | $X^1$ is chloro, $X^2$ is CH, $X^3$ is bromo | chlorodifluoromethyl | hydrogen | $Y^1$ is CH, $Y^2$ is N, $Y^3$ is CH |
| P.2276 | $X^1$ is chloro, $X^2$ is CH, $X^3$ is bromo | chlorodifluoromethyl | methoxy | $Y^1$ is CH, $Y^2$ is N, $Y^3$ is CH |
| P.2277 | $X^1$ is chloro, $X^2$ is CH, $X^3$ is bromo | chlorodifluoromethyl | methyl | $Y^1$ is CH, $Y^2$ is N, $Y^3$ is CH |
| P.2278 | $X^1$ is chloro, $X^2$ is CH, $X^3$ is bromo | chlorodifluoromethyl | nitro | $Y^1$ is CH, $Y^2$ is N, $Y^3$ is CH |
| P.2279 | $X^1$ is chloro, $X^2$ is CH, $X^3$ is bromo | chlorodifluoromethyl | trifluoromethoxy | $Y^1$ is CH, $Y^2$ is N, $Y^3$ is CH |
| P.2280 | $X^1$ is chloro, $X^2$ is CH, $X^3$ is bromo | chlorodifluoromethyl | trifluoromethyl | $Y^1$ is CH, $Y^2$ is N, $Y^3$ is CH |
| P.2281 | $X^1$ is chloro, $X^2$ is CH, $X^3$ is bromo | difluoromethyl | bromo | $Y^1$ is CH, $Y^2$ is N, $Y^3$ is CH |
| P.2282 | $X^1$ is chloro, $X^2$ is CH, $X^3$ is bromo | difluoromethyl | chloro | $Y^1$ is CH, $Y^2$ is N, $Y^3$ is CH |
| P.2283 | $X^1$ is chloro, $X^2$ is CH, $X^3$ is bromo | difluoromethyl | cyano | $Y^1$ is CH, $Y^2$ is N, $Y^3$ is CH |
| P.2284 | $X^1$ is chloro, $X^2$ is CH, $X^3$ is bromo | difluoromethyl | cyclopropyl | $Y^1$ is CH, $Y^2$ is N, $Y^3$ is CH |
| P.2285 | $X^1$ is chloro, $X^2$ is CH, $X^3$ is bromo | difluoromethyl | ethyl | $Y^1$ is CH, $Y^2$ is N, $Y^3$ is CH |
| P.2286 | $X^1$ is chloro, $X^2$ is CH, $X^3$ is bromo | difluoromethyl | fluoro | $Y^1$ is CH, $Y^2$ is N, $Y^3$ is CH |
| P.2287 | $X^1$ is chloro, $X^2$ is CH, $X^3$ is bromo | difluoromethyl | hydrogen | $Y^1$ is CH, $Y^2$ is N, $Y^3$ is CH |
| P.2288 | $X^1$ is chloro, $X^2$ is CH, $X^3$ is bromo | difluoromethyl | methoxy | $Y^1$ is CH, $Y^2$ is N, $Y^3$ is CH |
| P.2289 | $X^1$ is chloro, $X^2$ is CH, $X^3$ is bromo | difluoromethyl | methyl | $Y^1$ is CH, $Y^2$ is N, $Y^3$ is CH |
| P.2290 | $X^1$ is chloro, $X^2$ is CH, $X^3$ is bromo | difluoromethyl | nitro | $Y^1$ is CH, $Y^2$ is N, $Y^3$ is CH |
| P.2291 | $X^1$ is chloro, $X^2$ is CH, $X^3$ is bromo | difluoromethyl | trifluoromethoxy | $Y^1$ is CH, $Y^2$ is N, $Y^3$ is CH |
| P.2292 | $X^1$ is chloro, $X^2$ is CH, $X^3$ is bromo | difluoromethyl | trifluoromethyl | $Y^1$ is CH, $Y^2$ is N, $Y^3$ is CH |
| P.2293 | $X^1$ is chloro, $X^2$ is CH, $X^3$ is bromo | trifluoromethyl | bromo | $Y^1$ is CH, $Y^2$ is N, $Y^3$ is CH |
| P.2294 | $X^1$ is chloro, $X^2$ is CH, $X^3$ is bromo | trifluoromethyl | chloro | $Y^1$ is CH, $Y^2$ is N, $Y^3$ is CH |
| P.2295 | $X^1$ is chloro, $X^2$ is CH, $X^3$ is bromo | trifluoromethyl | cyano | $Y^1$ is CH, $Y^2$ is N, $Y^3$ is CH |
| P.2296 | $X^1$ is chloro, $X^2$ is CH, $X^3$ is bromo | trifluoromethyl | cyclopropyl | $Y^1$ is CH, $Y^2$ is N, $Y^3$ is CH |
| P.2297 | $X^1$ is chloro, $X^2$ is CH, $X^3$ is bromo | trifluoromethyl | ethyl | $Y^1$ is CH, $Y^2$ is N, $Y^3$ is CH |
| P.2298 | $X^1$ is chloro, $X^2$ is CH, $X^3$ is bromo | trifluoromethyl | fluoro | $Y^1$ is CH, $Y^2$ is N, $Y^3$ is CH |
| P.2299 | $X^1$ is chloro, $X^2$ is CH, $X^3$ is bromo | trifluoromethyl | hydrogen | $Y^1$ is CH, $Y^2$ is N, $Y^3$ is CH |
| P.2300 | $X^1$ is chloro, $X^2$ is CH, $X^3$ is bromo | trifluoromethyl | methoxy | $Y^1$ is CH, $Y^2$ is N, $Y^3$ is CH |
| P.2301 | $X^1$ is chloro, $X^2$ is CH, $X^3$ is bromo | trifluoromethyl | methyl | $Y^1$ is CH, $Y^2$ is N, $Y^3$ is CH |
| P.2302 | $X^1$ is chloro, $X^2$ is CH, $X^3$ is bromo | trifluoromethyl | nitro | $Y^1$ is CH, $Y^2$ is N, $Y^3$ is CH |
| P.2303 | $X^1$ is chloro, $X^2$ is CH, $X^3$ is bromo | trifluoromethyl | trifluoromethoxy | $Y^1$ is CH, $Y^2$ is N, $Y^3$ is CH |
| P.2304 | $X^1$ is chloro, $X^2$ is CH, $X^3$ is bromo | trifluoromethyl | trifluoromethyl | $Y^1$ is CH, $Y^2$ is N, $Y^3$ is CH |
| P.2305 | $X^1$ is chloro, $X^2$ is CH, $X^3$ is bromo | chlorodifluoromethyl | bromo | $Y^1$ is CH, $Y^2$ is N, $Y^3$ is CH |
| P.2306 | $X^1$ is chloro, $X^2$ is CH, $X^3$ is bromo | chlorodifluoromethyl | chloro | $Y^1$ is CH, $Y^2$ is N, $Y^3$ is CH |
| P.2307 | $X^1$ is chloro, $X^2$ is CH, $X^3$ is bromo | chlorodifluoromethyl | cyano | $Y^1$ is CH, $Y^2$ is N, $Y^3$ is CH |
| P.2308 | $X^1$ is chloro, $X^2$ is CH, $X^3$ is bromo | chlorodifluoromethyl | cyclopropyl | $Y^1$ is CH, $Y^2$ is N, $Y^3$ is CH |
| P.2309 | $X^1$ is chloro, $X^2$ is CH, $X^3$ is bromo | chlorodifluoromethyl | ethyl | $Y^1$ is CH, $Y^2$ is N, $Y^3$ is CH |
| P.2310 | $X^1$ is chloro, $X^2$ is CH, $X^3$ is bromo | chlorodifluoromethyl | fluoro | $Y^1$ is CH, $Y^2$ is N, $Y^3$ is CH |

TABLE P-continued

|  | X1, X2, X3 | X4 | R5 | Y1, Y2, Y3 |
|---|---|---|---|---|
| P.2311 | $X^1$ is chloro, $X^2$ is CH, $X^3$ is bromo | chlorodifluoromethyl | hydrogen | $Y^1$ is CH, $Y^2$ is N, $Y^3$ is CH |
| P.2312 | $X^1$ is chloro, $X^2$ is CH, $X^3$ is bromo | chlorodifluoromethyl | methoxy | $Y^1$ is CH, $Y^2$ is N, $Y^3$ is CH |
| P.2313 | $X^1$ is chloro, $X^2$ is CH, $X^3$ is bromo | chlorodifluoromethyl | methyl | $Y^1$ is CH, $Y^2$ is N, $Y^3$ is CH |
| P.2314 | $X^1$ is chloro, $X^2$ is CH, $X^3$ is bromo | chlorodifluoromethyl | nitro | $Y^1$ is CH, $Y^2$ is N, $Y^3$ is CH |
| P.2315 | $X^1$ is chloro, $X^2$ is CH, $X^3$ is bromo | chlorodifluoromethyl | trifluoromethoxy | $Y^1$ is CH, $Y^2$ is N, $Y^3$ is CH |
| P.2316 | $X^1$ is chloro, $X^2$ is CH, $X^3$ is bromo | chlorodifluoromethyl | trifluoromethyl | $Y^1$ is CH, $Y^2$ is N, $Y^3$ is CH |
| P.2317 | $X^1$ is chloro, $X^2$ is CH, $X^3$ is bromo | difluoromethyl | bromo | $Y^1$ is CH, $Y^2$ is N, $Y^3$ is CH |
| P.2318 | $X^1$ is chloro, $X^2$ is CH, $X^3$ is bromo | difluoromethyl | chloro | $Y^1$ is CH, $Y^2$ is N, $Y^3$ is CH |
| P.2319 | $X^1$ is chloro, $X^2$ is CH, $X^3$ is bromo | difluoromethyl | cyano | $Y^1$ is CH, $Y^2$ is N, $Y^3$ is CH |
| P.2320 | $X^1$ is chloro, $X^2$ is CH, $X^3$ is bromo | difluoromethyl | cyclopropyl | $Y^1$ is CH, $Y^2$ is N, $Y^3$ is CH |
| P.2321 | $X^1$ is chloro, $X^2$ is CH, $X^3$ is bromo | difluoromethyl | ethyl | $Y^1$ is CH, $Y^2$ is N, $Y^3$ is CH |
| P.2322 | $X^1$ is chloro, $X^2$ is CH, $X^3$ is bromo | difluoromethyl | fluoro | $Y^1$ is CH, $Y^2$ is N, $Y^3$ is CH |
| P.2323 | $X^1$ is chloro, $X^2$ is CH, $X^3$ is bromo | difluoromethyl | hydrogen | $Y^1$ is CH, $Y^2$ is N, $Y^3$ is CH |
| P.2324 | $X^1$ is chloro, $X^2$ is CH, $X^3$ is bromo | difluoromethyl | methoxy | $Y^1$ is CH, $Y^2$ is N, $Y^3$ is CH |
| P.2325 | $X^1$ is chloro, $X^2$ is CH, $X^3$ is bromo | difluoromethyl | methyl | $Y^1$ is CH, $Y^2$ is N, $Y^3$ is CH |
| P.2326 | $X^1$ is chloro, $X^2$ is CH, $X^3$ is bromo | difluoromethyl | nitro | $Y^1$ is CH, $Y^2$ is N, $Y^3$ is CH |
| P.2327 | $X^1$ is chloro, $X^2$ is CH, $X^3$ is bromo | difluoromethyl | trifluoromethoxy | $Y^1$ is CH, $Y^2$ is N, $Y^3$ is CH |
| P.2328 | $X^1$ is chloro, $X^2$ is CH, $X^3$ is bromo | difluoromethyl | trifluoromethyl | $Y^1$ is CH, $Y^2$ is N, $Y^3$ is CH |
| P.2329 | $X^1$ is chloro, $X^2$ is CH, $X^3$ is bromo | trifluoromethyl | bromo | $Y^1$ is CH, $Y^2$ is N, $Y^3$ is CH |
| P.2330 | $X^1$ is chloro, $X^2$ is CH, $X^3$ is bromo | trifluoromethyl | chloro | $Y^1$ is CH, $Y^2$ is N, $Y^3$ is CH |
| P.2331 | $X^1$ is chloro, $X^2$ is CH, $X^3$ is bromo | trifluoromethyl | cyano | $Y^1$ is CH, $Y^2$ is N, $Y^3$ is CH |
| P.2332 | $X^1$ is chloro, $X^2$ is CH, $X^3$ is bromo | trifluoromethyl | cyclopropyl | $Y^1$ is CH, $Y^2$ is N, $Y^3$ is CH |
| P.2333 | $X^1$ is chloro, $X^2$ is CH, $X^3$ is bromo | trifluoromethyl | ethyl | $Y^1$ is CH, $Y^2$ is N, $Y^3$ is CH |
| P.2334 | $X^1$ is chloro, $X^2$ is CH, $X^3$ is bromo | trifluoromethyl | fluoro | $Y^1$ is CH, $Y^2$ is N, $Y^3$ is CH |
| P.2335 | $X^1$ is chloro, $X^2$ is CH, $X^3$ is bromo | trifluoromethyl | hydrogen | $Y^1$ is CH, $Y^2$ is N, $Y^3$ is CH |
| P.2336 | $X^1$ is chloro, $X^2$ is CH, $X^3$ is bromo | trifluoromethyl | methoxy | $Y^1$ is CH, $Y^2$ is N, $Y^3$ is CH |
| P.2337 | $X^1$ is chloro, $X^2$ is CH, $X^3$ is bromo | trifluoromethyl | methyl | $Y^1$ is CH, $Y^2$ is N, $Y^3$ is CH |
| P.2338 | $X^1$ is chloro, $X^2$ is CH, $X^3$ is bromo | trifluoromethyl | nitro | $Y^1$ is CH, $Y^2$ is N, $Y^3$ is CH |
| P.2339 | $X^1$ is chloro, $X^2$ is CH, $X^3$ is bromo | trifluoromethyl | trifluoromethoxy | $Y^1$ is CH, $Y^2$ is N, $Y^3$ is CH |
| P.2340 | $X^1$ is chloro, $X^2$ is CH, $X^3$ is bromo | trifluoromethyl | trifluoromethyl | $Y^1$ is CH, $Y^2$ is N, $Y^3$ is CH |
| P.2341 | $X^1$ is chloro, $X^2$ is CH, $X^3$ is bromo | chlorodifluoromethyl | bromo | $Y^1$ is CH, $Y^2$ is N, $Y^3$ is CH |
| P.2342 | $X^1$ is chloro, $X^2$ is CH, $X^3$ is bromo | chlorodifluoromethyl | chloro | $Y^1$ is CH, $Y^2$ is N, $Y^3$ is CH |
| P.2343 | $X^1$ is chloro, $X^2$ is CH, $X^3$ is bromo | chlorodifluoromethyl | cyano | $Y^1$ is CH, $Y^2$ is N, $Y^3$ is CH |
| P.2344 | $X^1$ is chloro, $X^2$ is CH, $X^3$ is bromo | chlorodifluoromethyl | cyclopropyl | $Y^1$ is CH, $Y^2$ is N, $Y^3$ is CH |
| P.2345 | $X^1$ is chloro, $X^2$ is CH, $X^3$ is bromo | chlorodifluoromethyl | ethyl | $Y^1$ is CH, $Y^2$ is N, $Y^3$ is CH |
| P.2346 | $X^1$ is chloro, $X^2$ is CH, $X^3$ is bromo | chlorodifluoromethyl | fluoro | $Y^1$ is CH, $Y^2$ is N, $Y^3$ is CH |
| P.2347 | $X^1$ is chloro, $X^2$ is CH, $X^3$ is bromo | chlorodifluoromethyl | hydrogen | $Y^1$ is CH, $Y^2$ is N, $Y^3$ is CH |
| P.2348 | $X^1$ is chloro, $X^2$ is CH, $X^3$ is bromo | chlorodifluoromethyl | methoxy | $Y^1$ is CH, $Y^2$ is N, $Y^3$ is CH |
| P.2349 | $X^1$ is chloro, $X^2$ is CH, $X^3$ is bromo | chlorodifluoromethyl | methyl | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2350 | $X^1$ is chloro, $X^2$ is CH, $X^3$ is bromo | chlorodifluoromethyl | nitro | $Y^1$ is CH, $Y^2$ is N, $Y^3$ is CH |
| P.2351 | $X^1$ is chloro, $X^2$ is CH, $X^3$ is bromo | chlorodifluoromethyl | trifluoromethoxy | $Y^1$ is CH, $Y^2$ is N, $Y^3$ is CH |
| P.2352 | $X^1$ is chloro, $X^2$ is CH, $X^3$ is bromo | chlorodifluoromethyl | trifluoromethyl | $Y^1$ is CH, $Y^2$ is N, $Y^3$ is CH |
| P.2353 | $X^1$ is chloro, $X^2$ is CH, $X^3$ is bromo | difluoromethyl | bromo | $Y^1$ is CH, $Y^2$ is N, $Y^3$ is CH |
| P.2354 | $X^1$ is chloro, $X^2$ is CH, $X^3$ is bromo | difluoromethyl | chloro | $Y^1$ is CH, $Y^2$ is N, $Y^3$ is CH |
| P.2355 | $X^1$ is chloro, $X^2$ is CH, $X^3$ is bromo | difluoromethyl | cyano | $Y^1$ is CH, $Y^2$ is N, $Y^3$ is CH |
| P.2356 | $X^1$ is chloro, $X^2$ is CH, $X^3$ is bromo | difluoromethyl | cyclopropyl | $Y^1$ is CH, $Y^2$ is N, $Y^3$ is CH |
| P.2357 | $X^1$ is chloro, $X^2$ is CH, $X^3$ is bromo | difluoromethyl | ethyl | $Y^1$ is CH, $Y^2$ is N, $Y^3$ is CH |
| P.2358 | $X^1$ is chloro, $X^2$ is CH, $X^3$ is bromo | difluoromethyl | fluoro | $Y^1$ is CH, $Y^2$ is N, $Y^3$ is CH |
| P.2359 | $X^1$ is chloro, $X^2$ is CH, $X^3$ is bromo | difluoromethyl | hydrogen | $Y^1$ is CH, $Y^2$ is N, $Y^3$ is CH |
| P.2360 | $X^1$ is chloro, $X^2$ is CH, $X^3$ is bromo | difluoromethyl | methoxy | $Y^1$ is CH, $Y^2$ is N, $Y^3$ is CH |
| P.2361 | $X^1$ is chloro, $X^2$ is CH, $X^3$ is bromo | difluoromethyl | methyl | $Y^1$ is CH, $Y^2$ is N, $Y^3$ is CH |
| P.2362 | $X^1$ is chloro, $X^2$ is CH, $X^3$ is bromo | difluoromethyl | nitro | $Y^1$ is CH, $Y^2$ is N, $Y^3$ is CH |
| P.2363 | $X^1$ is chloro, $X^2$ is CH, $X^3$ is bromo | difluoromethyl | trifluoromethoxy | $Y^1$ is CH, $Y^2$ is N, $Y^3$ is CH |
| P.2364 | $X^1$ is chloro, $X^2$ is CH, $X^3$ is bromo | difluoromethyl | trifluoromethyl | $Y^1$ is CH, $Y^2$ is N, $Y^3$ is CH |
| P.2365 | $X^1$ is chloro, $X^2$ is CH, $X^3$ is bromo | trifluoromethyl | bromo | $Y^1$ is CH, $Y^2$ is N, $Y^3$ is CH |
| P.2366 | $X^1$ is chloro, $X^2$ is CH, $X^3$ is bromo | trifluoromethyl | chloro | $Y^1$ is CH, $Y^2$ is N, $Y^3$ is CH |
| P.2367 | $X^1$ is chloro, $X^2$ is CH, $X^3$ is bromo | trifluoromethyl | cyano | $Y^1$ is CH, $Y^2$ is N, $Y^3$ is CH |
| P.2368 | $X^1$ is chloro, $X^2$ is CH, $X^3$ is bromo | trifluoromethyl | cyclopropyl | $Y^1$ is CH, $Y^2$ is N, $Y^3$ is CH |
| P.2369 | $X^1$ is chloro, $X^2$ is CH, $X^3$ is bromo | trifluoromethyl | ethyl | $Y^1$ is CH, $Y^2$ is N, $Y^3$ is CH |
| P.2370 | $X^1$ is chloro, $X^2$ is CH, $X^3$ is bromo | trifluoromethyl | fluoro | $Y^1$ is CH, $Y^2$ is N, $Y^3$ is CH |
| P.2371 | $X^1$ is chloro, $X^2$ is CH, $X^3$ is bromo | trifluoromethyl | hydrogen | $Y^1$ is CH, $Y^2$ is N, $Y^3$ is CH |
| P.2372 | $X^1$ is chloro, $X^2$ is CH, $X^3$ is bromo | trifluoromethyl | methoxy | $Y^1$ is CH, $Y^2$ is N, $Y^3$ is CH |
| P.2373 | $X^1$ is chloro, $X^2$ is CH, $X^3$ is bromo | trifluoromethyl | methyl | $Y^1$ is CH, $Y^2$ is N, $Y^3$ is CH |
| P.2374 | $X^1$ is chloro, $X^2$ is CH, $X^3$ is bromo | trifluoromethyl | nitro | $Y^1$ is CH, $Y^2$ is N, $Y^3$ is CH |
| P.2375 | $X^1$ is chloro, $X^2$ is CH, $X^3$ is bromo | trifluoromethyl | trifluoromethoxy | $Y^1$ is CH, $Y^2$ is N, $Y^3$ is CH |
| P.2376 | $X^1$ is chloro, $X^2$ is CH, $X^3$ is bromo | trifluoromethyl | trifluoromethyl | $Y^1$ is CH, $Y^2$ is N, $Y^3$ is CH |
| P.2377 | $X^1$ is chloro, $X^2$ is C—Cl, $X^3$ is trifluoromethyl | chlorodifluoromethyl | bromo | $Y^1$ is CH, $Y^2$ is N, $Y^3$ is CH |
| P.2378 | $X^1$ is chloro, $X^2$ is C—Cl, $X^3$ is trifluoromethyl | chlorodifluoromethyl | chloro | $Y^1$ is CH, $Y^2$ is N, $Y^3$ is CH |
| P.2379 | $X^1$ is chloro, $X^2$ is C—Cl, $X^3$ is trifluoromethyl | chlorodifluoromethyl | cyano | $Y^1$ is CH, $Y^2$ is N, $Y^3$ is CH |
| P.2380 | $X^1$ is chloro, $X^2$ is C—Cl, $X^3$ is trifluoromethyl | chlorodifluoromethyl | cyclopropyl | $Y^1$ is CH, $Y^2$ is N, $Y^3$ is CH |
| P.2381 | $X^1$ is chloro, $X^2$ is C—Cl, $X^3$ is trifluoromethyl | chlorodifluoromethyl | ethyl | $Y^1$ is CH, $Y^2$ is N, $Y^3$ is CH |
| P.2382 | $X^1$ is chloro, $X^2$ is C—Cl, $X^3$ is trifluoromethyl | chlorodifluoromethyl | fluoro | $Y^1$ is CH, $Y^2$ is N, $Y^3$ is CH |
| P.2383 | $X^1$ is chloro, $X^2$ is C—Cl, $X^3$ is trifluoromethyl | chlorodifluoromethyl | hydrogen | $Y^1$ is CH, $Y^2$ is N, $Y^3$ is CH |
| P.2384 | $X^1$ is chloro, $X^2$ is C—Cl, $X^3$ is trifluoromethyl | chlorodifluoromethyl | methoxy | $Y^1$ is CH, $Y^2$ is N, $Y^3$ is CH |
| P.2385 | $X^1$ is chloro, $X^2$ is C—Cl, $X^3$ is trifluoromethyl | chlorodifluoromethyl | methyl | $Y^1$ is CH, $Y^2$ is N, $Y^3$ is CH |
| P.2386 | $X^1$ is chloro, $X^2$ is C—Cl, $X^3$ is trifluoromethyl | chlorodifluoromethyl | nitro | $Y^1$ is CH, $Y^2$ is N, $Y^3$ is CH |
| P.2387 | $X^1$ is chloro, $X^2$ is C—Cl, $X^3$ is trifluoromethyl | chlorodifluoromethyl | trifluoromethoxy | $Y^1$ is CH, $Y^2$ is N, $Y^3$ is CH |
| P.2388 | $X^1$ is chloro, $X^2$ is C—Cl, $X^3$ is trifluoromethyl | chlorodifluoromethyl | trifluoromethyl | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2389 | $X^1$ is chloro, $X^2$ is C—Cl, $X^3$ is trifluoromethyl | difluoromethyl | bromo | $Y^1$ is CH, $Y^2$ is N, $Y^3$ is CH |
| P.2390 | $X^1$ is chloro, $X^2$ is C—Cl, $X^3$ is trifluoromethyl | difluoromethyl | chloro | $Y^1$ is CH, $Y^2$ is N, $Y^3$ is CH |
| P.2391 | $X^1$ is chloro, $X^2$ is C—Cl, $X^3$ is trifluoromethyl | difluoromethyl | cyano | $Y^1$ is CH, $Y^2$ is N, $Y^3$ is CH |
| P.2392 | $X^1$ is chloro, $X^2$ is C—Cl, $X^3$ is trifluoromethyl | difluoromethyl | cyclopropyl | $Y^1$ is CH, $Y^2$ is N, $Y^3$ is CH |
| P.2393 | $X^1$ is chloro, $X^2$ is C—Cl, $X^3$ is trifluoromethyl | difluoromethyl | ethyl | $Y^1$ is CH, $Y^2$ is N, $Y^3$ is CH |
| P.2394 | $X^1$ is chloro, $X^2$ is C—Cl, $X^3$ is trifluoromethyl | difluoromethyl | fluoro | $Y^1$ is CH, $Y^2$ is N, $Y^3$ is CH |
| P.2395 | $X^1$ is chloro, $X^2$ is C—Cl, $X^3$ is trifluoromethyl | difluoromethyl | hydrogen | $Y^1$ is CH, $Y^2$ is N, $Y^3$ is CH |
| P.2396 | $X^1$ is chloro, $X^2$ is C—Cl, $X^3$ is trifluoromethyl | difluoromethyl | methoxy | $Y^1$ is CH, $Y^2$ is N, $Y^3$ is CH |
| P.2397 | $X^1$ is chloro, $X^2$ is C—Cl, $X^3$ is trifluoromethyl | difluoromethyl | methyl | $Y^1$ is CH, $Y^2$ is N, $Y^3$ is CH |
| P.2398 | $X^1$ is chloro, $X^2$ is C—Cl, $X^3$ is trifluoromethyl | difluoromethyl | nitro | $Y^1$ is CH, $Y^2$ is N, $Y^3$ is CH |
| P.2399 | $X^1$ is chloro, $X^2$ is C—Cl, $X^3$ is trifluoromethyl | difluoromethyl | trifluoromethoxy | $Y^1$ is CH, $Y^2$ is N, $Y^3$ is CH |
| P.2400 | $X^1$ is chloro, $X^2$ is C—Cl, $X^3$ is trifluoromethyl | difluoromethyl | trifluoromethyl | $Y^1$ is CH, $Y^2$ is N, $Y^3$ is CH |
| P.2401 | $X^1$ is chloro, $X^2$ is C—Cl, $X^3$ is trifluoromethyl | trifluoromethyl | bromo | $Y^1$ is CH, $Y^2$ is N, $Y^3$ is CH |
| P.2402 | $X^1$ is chloro, $X^2$ is C—Cl, $X^3$ is trifluoromethyl | trifluoromethyl | chloro | $Y^1$ is CH, $Y^2$ is N, $Y^3$ is CH |
| P.2403 | $X^1$ is chloro, $X^2$ is C—Cl, $X^3$ is trifluoromethyl | trifluoromethyl | cyano | $Y^1$ is CH, $Y^2$ is N, $Y^3$ is CH |
| P.2404 | $X^1$ is chloro, $X^2$ is C—Cl, $X^3$ is trifluoromethyl | trifluoromethyl | cyclopropyl | $Y^1$ is CH, $Y^2$ is N, $Y^3$ is CH |
| P.2405 | $X^1$ is chloro, $X^2$ is C—Cl, $X^3$ is trifluoromethyl | trifluoromethyl | ethyl | $Y^1$ is CH, $Y^2$ is N, $Y^3$ is CH |
| P.2406 | $X^1$ is chloro, $X^2$ is C—Cl, $X^3$ is trifluoromethyl | trifluoromethyl | fluoro | $Y^1$ is CH, $Y^2$ is N, $Y^3$ is CH |
| P.2407 | $X^1$ is chloro, $X^2$ is C—Cl, $X^3$ is trifluoromethyl | trifluoromethyl | hydrogen | $Y^1$ is CH, $Y^2$ is N, $Y^3$ is CH |
| P.2408 | $X^1$ is chloro, $X^2$ is C—Cl, $X^3$ is trifluoromethyl | trifluoromethyl | methoxy | $Y^1$ is CH, $Y^2$ is N, $Y^3$ is CH |
| P.2409 | $X^1$ is chloro, $X^2$ is C—Cl, $X^3$ is trifluoromethyl | trifluoromethyl | methyl | $Y^1$ is CH, $Y^2$ is N, $Y^3$ is CH |
| P.2410 | $X^1$ is chloro, $X^2$ is C—Cl, $X^3$ is trifluoromethyl | trifluoromethyl | nitro | $Y^1$ is CH, $Y^2$ is N, $Y^3$ is CH |
| P.2411 | $X^1$ is chloro, $X^2$ is C—Cl, $X^3$ is trifluoromethyl | trifluoromethyl | trifluoromethoxy | $Y^1$ is CH, $Y^2$ is N, $Y^3$ is CH |
| P.2412 | $X^1$ is chloro, $X^2$ is C—Cl, $X^3$ is trifluoromethyl | trifluoromethyl | trifluoromethyl | $Y^1$ is CH, $Y^2$ is N, $Y^3$ is CH |
| P.2413 | $X^1$ is trifluoromethyl, $X^2$ is CH, $X^3$ is trifluoromethyl | chlorodifluoromethyl | bromo | $Y^1$ is CH, $Y^2$ is N, $Y^3$ is CH |
| P.2414 | $X^1$ is trifluoromethyl, $X^2$ is CH, $X^3$ is trifluoromethyl | chlorodifluoromethyl | chloro | $Y^1$ is CH, $Y^2$ is N, $Y^3$ is CH |
| P.2415 | $X^1$ is trifluoromethyl, $X^2$ is CH, $X^3$ is trifluoromethyl | chlorodifluoromethyl | cyano | $Y^1$ is CH, $Y^2$ is N, $Y^3$ is CH |
| P.2416 | $X^1$ is trifluoromethyl, $X^2$ is CH, $X^3$ is trifluoromethyl | chlorodifluoromethyl | cyclopropyl | $Y^1$ is CH, $Y^2$ is N, $Y^3$ is CH |
| P.2417 | $X^1$ is trifluoromethyl, $X^2$ is CH, $X^3$ is trifluoromethyl | chlorodifluoromethyl | ethyl | $Y^1$ is CH, $Y^2$ is N, $Y^3$ is CH |
| P.2418 | $X^1$ is trifluoromethyl, $X^2$ is CH, $X^3$ is trifluoromethyl | chlorodifluoromethyl | fluoro | $Y^1$ is CH, $Y^2$ is N, $Y^3$ is CH |
| P.2419 | $X^1$ is trifluoromethyl, $X^2$ is CH, $X^3$ is trifluoromethyl | chlorodifluoromethyl | hydrogen | $Y^1$ is CH, $Y^2$ is N, $Y^3$ is CH |
| P.2420 | $X^1$ is trifluoromethyl, $X^2$ is CH, $X^3$ is trifluoromethyl | chlorodifluoromethyl | methoxy | $Y^1$ is CH, $Y^2$ is N, $Y^3$ is CH |
| P.2421 | $X^1$ is trifluoromethyl, $X^2$ is CH, $X^3$ is trifluoromethyl | chlorodifluoromethyl | methyl | $Y^1$ is CH, $Y^2$ is N, $Y^3$ is CH |
| P.2422 | $X^1$ is trifluoromethyl, $X^2$ is CH, $X^3$ is trifluoromethyl | chlorodifluoromethyl | nitro | $Y^1$ is CH, $Y^2$ is N, $Y^3$ is CH |
| P.2423 | $X^1$ is trifluoromethyl, $X^2$ is CH, $X^3$ is trifluoromethyl | chlorodifluoromethyl | trifluoromethoxy | $Y^1$ is CH, $Y^2$ is N, $Y^3$ is CH |
| P.2424 | $X^1$ is trifluoromethyl, $X^2$ is CH, $X^3$ is trifluoromethyl | chlorodifluoromethyl | trifluoromethyl | $Y^1$ is CH, $Y^2$ is N, $Y^3$ is CH |
| P.2425 | $X^1$ is trifluoromethyl, $X^2$ is CH, $X^3$ is trifluoromethyl | difluoromethyl | bromo | $Y^1$ is CH, $Y^2$ is N, $Y^3$ is CH |
| P.2426 | $X^1$ is trifluoromethyl, $X^2$ is CH, $X^3$ is trifluoromethyl | difluoromethyl | chloro | $Y^1$ is CH, $Y^2$ is N, $Y^3$ is CH |
| P.2427 | $X^1$ is trifluoromethyl, $X^2$ is CH, $X^3$ is trifluoromethyl | difluoromethyl | cyano | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2428 | $X^1$ is trifluoromethyl, $X^2$ is CH, $X^3$ is trifluoromethyl | difluoromethyl | cyclopropyl | $Y^1$ is CH, $Y^2$ is N, $Y^3$ is CH |
| P.2429 | $X^1$ is trifluoromethyl, $X^2$ is CH, $X^3$ is trifluoromethyl | difluoromethyl | ethyl | $Y^1$ is CH, $Y^2$ is N, $Y^3$ is CH |
| P.2430 | $X^1$ is trifluoromethyl, $X^2$ is CH, $X^3$ is trifluoromethyl | difluoromethyl | fluoro | $Y^1$ is CH, $Y^2$ is N, $Y^3$ is CH |
| P.2431 | $X^1$ is trifluoromethyl, $X^2$ is CH, $X^3$ is trifluoromethyl | difluoromethyl | hydrogen | $Y^1$ is CH, $Y^2$ is N, $Y^3$ is CH |
| P.2432 | $X^1$ is trifluoromethyl, $X^2$ is CH, $X^3$ is trifluoromethyl | difluoromethyl | methoxy | $Y^1$ is CH, $Y^2$ is N, $Y^3$ is CH |
| P.2433 | $X^1$ is trifluoromethyl, $X^2$ is CH, $X^3$ is trifluoromethyl | difluoromethyl | methyl | $Y^1$ is CH, $Y^2$ is N, $Y^3$ is CH |
| P.2434 | $X^1$ is trifluoromethyl, $X^2$ is CH, $X^3$ is trifluoromethyl | difluoromethyl | nitro | $Y^1$ is CH, $Y^2$ is N, $Y^3$ is CH |
| P.2435 | $X^1$ is trifluoromethyl, $X^2$ is CH, $X^3$ is trifluoromethyl | difluoromethyl | trifluoromethoxy | $Y^1$ is CH, $Y^2$ is N, $Y^3$ is CH |
| P.2436 | $X^1$ is trifluoromethyl, $X^2$ is CH, $X^3$ is trifluoromethyl | difluoromethyl | trifluoromethyl | $Y^1$ is CH, $Y^2$ is N, $Y^3$ is CH |
| P.2437 | $X^1$ is trifluoromethyl, $X^2$ is CH, $X^3$ is trifluoromethyl | trifluoromethyl | bromo | $Y^1$ is CH, $Y^2$ is N, $Y^3$ is CH |
| P.2438 | $X^1$ is trifluoromethyl, $X^2$ is CH, $X^3$ is trifluoromethyl | trifluoromethyl | chloro | $Y^1$ is CH, $Y^2$ is N, $Y^3$ is CH |
| P.2439 | $X^1$ is trifluoromethyl, $X^2$ is CH, $X^3$ is trifluoromethyl | trifluoromethyl | cyano | $Y^1$ is CH, $Y^2$ is N, $Y^3$ is CH |
| P.2440 | $X^1$ is trifluoromethyl, $X^2$ is CH, $X^3$ is trifluoromethyl | trifluoromethyl | cyclopropyl | $Y^1$ is CH, $Y^2$ is N, $Y^3$ is CH |
| P.2441 | $X^1$ is trifluoromethyl, $X^2$ is CH, $X^3$ is trifluoromethyl | trifluoromethyl | ethyl | $Y^1$ is CH, $Y^2$ is N, $Y^3$ is CH |
| P.2442 | $X^1$ is trifluoromethyl, $X^2$ is CH, $X^3$ is trifluoromethyl | trifluoromethyl | fluoro | $Y^1$ is CH, $Y^2$ is N, $Y^3$ is CH |
| P.2443 | $X^1$ is trifluoromethyl, $X^2$ is CH, $X^3$ is trifluoromethyl | trifluoromethyl | hydrogen | $Y^1$ is CH, $Y^2$ is N, $Y^3$ is CH |
| P.2444 | $X^1$ is trifluoromethyl, $X^2$ is CH, $X^3$ is trifluoromethyl | trifluoromethyl | methoxy | $Y^1$ is CH, $Y^2$ is N, $Y^3$ is CH |
| P.2445 | $X^1$ is trifluoromethyl, $X^2$ is CH, $X^3$ is trifluoromethyl | trifluoromethyl | methyl | $Y^1$ is CH, $Y^2$ is N, $Y^3$ is CH |
| P.2446 | $X^1$ is trifluoromethyl, $X^2$ is CH, $X^3$ is trifluoromethyl | trifluoromethyl | nitro | $Y^1$ is CH, $Y^2$ is N, $Y^3$ is CH |
| P.2447 | $X^1$ is trifluoromethyl, $X^2$ is CH, $X^3$ is trifluoromethyl | trifluoromethyl | trifluoromethoxy | $Y^1$ is CH, $Y^2$ is N, $Y^3$ is CH |
| P.2448 | $X^1$ is trifluoromethyl, $X^2$ is CH, $X^3$ is trifluoromethyl | trifluoromethyl | trifluoromethyl | $Y^1$ is CH, $Y^2$ is N, $Y^3$ is CH |
| P.2449 | $X^1$ is trifluoromethyl, $X^2$ is CH, $X^3$ is trifluoromethyl | chlorodifluoromethyl | bromo | $Y^1$ is CH, $Y^2$ is N, $Y^3$ is CH |
| P.2450 | $X^1$ is trifluoromethyl, $X^2$ is CH, $X^3$ is trifluoromethyl | chlorodifluoromethyl | chloro | $Y^1$ is CH, $Y^2$ is N, $Y^3$ is CH |
| P.2451 | $X^1$ is trifluoromethyl, $X^2$ is CH, $X^3$ is trifluoromethyl | chlorodifluoromethyl | cyano | $Y^1$ is CH, $Y^2$ is N, $Y^3$ is CH |
| P.2452 | $X^1$ is trifluoromethyl, $X^2$ is CH, $X^3$ is trifluoromethyl | chlorodifluoromethyl | cyclopropyl | $Y^1$ is CH, $Y^2$ is N, $Y^3$ is CH |
| P.2453 | $X^1$ is trifluoromethyl, $X^2$ is CH, $X^3$ is trifluoromethyl | chlorodifluoromethyl | ethyl | $Y^1$ is CH, $Y^2$ is N, $Y^3$ is CH |
| P.2454 | $X^1$ is trifluoromethyl, $X^2$ is CH, $X^3$ is trifluoromethyl | chlorodifluoromethyl | fluoro | $Y^1$ is CH, $Y^2$ is N, $Y^3$ is CH |
| P.2455 | $X^1$ is trifluoromethyl, $X^2$ is CH, $X^3$ is trifluoromethyl | chlorodifluoromethyl | hydrogen | $Y^1$ is CH, $Y^2$ is N, $Y^3$ is CH |
| P.2456 | $X^1$ is trifluoromethyl, $X^2$ is CH, $X^3$ is trifluoromethyl | chlorodifluoromethyl | methoxy | $Y^1$ is CH, $Y^2$ is N, $Y^3$ is CH |
| P.2457 | $X^1$ is trifluoromethyl, $X^2$ is CH, $X^3$ is trifluoromethyl | chlorodifluoromethyl | methyl | $Y^1$ is CH, $Y^2$ is N, $Y^3$ is CH |
| P.2458 | $X^1$ is trifluoromethyl, $X^2$ is CH, $X^3$ is trifluoromethyl | chlorodifluoromethyl | nitro | $Y^1$ is CH, $Y^2$ is N, $Y^3$ is CH |
| P.2459 | $X^1$ is trifluoromethyl, $X^2$ is CH, $X^3$ is trifluoromethyl | chlorodifluoromethyl | trifluoromethoxy | $Y^1$ is CH, $Y^2$ is N, $Y^3$ is CH |
| P.2460 | $X^1$ is trifluoromethyl, $X^2$ is CH, $X^3$ is trifluoromethyl | chlorodifluoromethyl | trifluoromethyl | $Y^1$ is CH, $Y^2$ is N, $Y^3$ is CH |
| P.2461 | $X^1$ is trifluoromethyl, $X^2$ is CH, $X^3$ is trifluoromethyl | difluoromethyl | bromo | $Y^1$ is CH, $Y^2$ is N, $Y^3$ is CH |
| P.2462 | $X^1$ is trifluoromethyl, $X^2$ is CH, $X^3$ is trifluoromethyl | difluoromethyl | chloro | $Y^1$ is CH, $Y^2$ is N, $Y^3$ is CH |
| P.2463 | $X^1$ is trifluoromethyl, $X^2$ is CH, $X^3$ is trifluoromethyl | difluoromethyl | cyano | $Y^1$ is CH, $Y^2$ is N, $Y^3$ is CH |
| P.2464 | $X^1$ is trifluoromethyl, $X^2$ is CH, $X^3$ is trifluoromethyl | difluoromethyl | cyclopropyl | $Y^1$ is CH, $Y^2$ is N, $Y^3$ is CH |
| P.2465 | $X^1$ is trifluoromethyl, $X^2$ is CH, $X^3$ is trifluoromethyl | difluoromethyl | ethyl | $Y^1$ is CH, $Y^2$ is N, $Y^3$ is CH |
| P.2466 | $X^1$ is trifluoromethyl, $X^2$ is CH, $X^3$ is trifluoromethyl | difluoromethyl | fluoro | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2467 | $X^1$ is trifluoromethyl, $X^2$ is CH, $X^3$ is trifluoromethyl | difluoromethyl | hydrogen | $Y^1$ is CH, $Y^2$ is N, $Y^3$ is CH |
| P.2468 | $X^1$ is trifluoromethyl, $X^2$ is CH, $X^3$ is trifluoromethyl | difluoromethyl | methoxy | $Y^1$ is CH, $Y^2$ is N, $Y^3$ is CH |
| P.2469 | $X^1$ is trifluoromethyl, $X^2$ is CH, $X^3$ is trifluoromethyl | difluoromethyl | methyl | $Y^1$ is CH, $Y^2$ is N, $Y^3$ is CH |
| P.2470 | $X^1$ is trifluoromethyl, $X^2$ is CH, $X^3$ is trifluoromethyl | difluoromethyl | nitro | $Y^1$ is CH, $Y^2$ is N, $Y^3$ is CH |
| P.2471 | $X^1$ is trifluoromethyl, $X^2$ is CH, $X^3$ is trifluoromethyl | difluoromethyl | trifluoromethoxy | $Y^1$ is CH, $Y^2$ is N, $Y^3$ is CH |
| P.2472 | $X^1$ is trifluoromethyl, $X^2$ is CH, $X^3$ is trifluoromethyl | difluoromethyl | trifluoromethyl | $Y^1$ is CH, $Y^2$ is N, $Y^3$ is CH |
| P.2473 | $X^1$ is trifluoromethyl, $X^2$ is CH, $X^3$ is trifluoromethyl | trifluoromethyl | bromo | $Y^1$ is CH, $Y^2$ is N, $Y^3$ is CH |
| P.2474 | $X^1$ is trifluoromethyl, $X^2$ is CH, $X^3$ is trifluoromethyl | trifluoromethyl | chloro | $Y^1$ is CH, $Y^2$ is N, $Y^3$ is CH |
| P.2475 | $X^1$ is trifluoromethyl, $X^2$ is CH, $X^3$ is trifluoromethyl | trifluoromethyl | cyano | $Y^1$ is CH, $Y^2$ is N, $Y^3$ is CH |
| P.2476 | $X^1$ is trifluoromethyl, $X^2$ is CH, $X^3$ is trifluoromethyl | trifluoromethyl | cyclopropyl | $Y^1$ is CH, $Y^2$ is N, $Y^3$ is CH |
| P.2477 | $X^1$ is trifluoromethyl, $X^2$ is CH, $X^3$ is trifluoromethyl | trifluoromethyl | ethyl | $Y^1$ is CH, $Y^2$ is N, $Y^3$ is CH |
| P.2478 | $X^1$ is trifluoromethyl, $X^2$ is CH, $X^3$ is trifluoromethyl | trifluoromethyl | fluoro | $Y^1$ is CH, $Y^2$ is N, $Y^3$ is CH |
| P.2479 | $X^1$ is trifluoromethyl, $X^2$ is CH, $X^3$ is trifluoromethyl | trifluoromethyl | hydrogen | $Y^1$ is CH, $Y^2$ is N, $Y^3$ is CH |
| P.2480 | $X^1$ is trifluoromethyl, $X^2$ is CH, $X^3$ is trifluoromethyl | trifluoromethyl | methoxy | $Y^1$ is CH, $Y^2$ is N, $Y^3$ is CH |
| P.2481 | $X^1$ is trifluoromethyl, $X^2$ is CH, $X^3$ is trifluoromethyl | trifluoromethyl | methyl | $Y^1$ is CH, $Y^2$ is N, $Y^3$ is CH |
| P.2482 | $X^1$ is trifluoromethyl, $X^2$ is CH, $X^3$ is trifluoromethyl | trifluoromethyl | nitro | $Y^1$ is CH, $Y^2$ is N, $Y^3$ is CH |
| P.2483 | $X^1$ is trifluoromethyl, $X^2$ is CH, $X^3$ is trifluoromethyl | trifluoromethyl | trifluoromethoxy | $Y^1$ is CH, $Y^2$ is N, $Y^3$ is CH |
| P.2484 | $X^1$ is trifluoromethyl, $X^2$ is CH, $X^3$ is trifluoromethyl | trifluoromethyl | trifluoromethyl | $Y^1$ is CH, $Y^2$ is N, $Y^3$ is CH |
| P.2485 | $X^1$ is trifluoromethyl, $X^2$ is CH, $X^3$ is hydrogen | chlorodifluoromethyl | bromo | $Y^1$ is CH, $Y^2$ is N, $Y^3$ is CH |
| P.2486 | $X^1$ is trifluoromethyl, $X^2$ is CH, $X^3$ is hydrogen | chlorodifluoromethyl | chloro | $Y^1$ is CH, $Y^2$ is N, $Y^3$ is CH |
| P.2487 | $X^1$ is trifluoromethyl, $X^2$ is CH, $X^3$ is hydrogen | chlorodifluoromethyl | cyano | $Y^1$ is CH, $Y^2$ is N, $Y^3$ is CH |
| P.2488 | $X^1$ is trifluoromethyl, $X^2$ is CH, $X^3$ is hydrogen | chlorodifluoromethyl | cyclopropyl | $Y^1$ is CH, $Y^2$ is N, $Y^3$ is CH |
| P.2489 | $X^1$ is trifluoromethyl, $X^2$ is CH, $X^3$ is hydrogen | chlorodifluoromethyl | ethyl | $Y^1$ is CH, $Y^2$ is N, $Y^3$ is CH |
| P.2490 | $X^1$ is trifluoromethyl, $X^2$ is CH, $X^3$ is hydrogen | chlorodifluoromethyl | fluoro | $Y^1$ is CH, $Y^2$ is N, $Y^3$ is CH |
| P.2491 | $X^1$ is trifluoromethyl, $X^2$ is CH, $X^3$ is hydrogen | chlorodifluoromethyl | hydrogen | $Y^1$ is CH, $Y^2$ is N, $Y^3$ is CH |
| P.2492 | $X^1$ is trifluoromethyl, $X^2$ is CH, $X^3$ is hydrogen | chlorodifluoromethyl | methoxy | $Y^1$ is CH, $Y^2$ is N, $Y^3$ is CH |
| P.2493 | $X^1$ is trifluoromethyl, $X^2$ is CH, $X^3$ is hydrogen | chlorodifluoromethyl | methyl | $Y^1$ is CH, $Y^2$ is N, $Y^3$ is CH |
| P.2494 | $X^1$ is trifluoromethyl, $X^2$ is CH, $X^3$ is hydrogen | chlorodifluoromethyl | nitro | $Y^1$ is CH, $Y^2$ is N, $Y^3$ is CH |
| P.2495 | $X^1$ is trifluoromethyl, $X^2$ is CH, $X^3$ is hydrogen | chlorodifluoromethyl | trifluoromethoxy | $Y^1$ is CH, $Y^2$ is N, $Y^3$ is CH |
| P.2496 | $X^1$ is trifluoromethyl, $X^2$ is CH, $X^3$ is hydrogen | chlorodifluoromethyl | trifluoromethyl | $Y^1$ is CH, $Y^2$ is N, $Y^3$ is CH |
| P.2497 | $X^1$ is trifluoromethyl, $X^2$ is CH, $X^3$ is hydrogen | difluoromethyl | bromo | $Y^1$ is CH, $Y^2$ is N, $Y^3$ is CH |
| P.2498 | $X^1$ is trifluoromethyl, $X^2$ is CH, $X^3$ is hydrogen | difluoromethyl | chloro | $Y^1$ is CH, $Y^2$ is N, $Y^3$ is CH |
| P.2499 | $X^1$ is trifluoromethyl, $X^2$ is CH, $X^3$ is hydrogen | difluoromethyl | cyano | $Y^1$ is CH, $Y^2$ is N, $Y^3$ is CH |
| P.2500 | $X^1$ is trifluoromethyl, $X^2$ is CH, $X^3$ is hydrogen | difluoromethyl | cyclopropyl | $Y^1$ is CH, $Y^2$ is N, $Y^3$ is CH |
| P.2501 | $X^1$ is trifluoromethyl, $X^2$ is CH, $X^3$ is hydrogen | difluoromethyl | ethyl | $Y^1$ is CH, $Y^2$ is N, $Y^3$ is CH |
| P.2502 | $X^1$ is trifluoromethyl, $X^2$ is CH, $X^3$ is hydrogen | difluoromethyl | fluoro | $Y^1$ is CH, $Y^2$ is N, $Y^3$ is CH |
| P.2503 | $X^1$ is trifluoromethyl, $X^2$ is CH, $X^3$ is hydrogen | difluoromethyl | hydrogen | $Y^1$ is CH, $Y^2$ is N, $Y^3$ is CH |
| P.2504 | $X^1$ is trifluoromethyl, $X^2$ is CH, $X^3$ is hydrogen | difluoromethyl | methoxy | $Y^1$ is CH, $Y^2$ is N, $Y^3$ is CH |
| P.2505 | $X^1$ is trifluoromethyl, $X^2$ is CH, $X^3$ is hydrogen | difluoromethyl | methyl | $Y^1$ is CH, $Y^2$ is N, $Y^3$ is CH |

TABLE P-continued

|  | X1, X2, X3 | X4 | R5 | Y1, Y2, Y3 |
|---|---|---|---|---|
| P.2506 | $X^1$ is trifluoromethyl, $X^2$ is CH, $X^3$ is hydrogen | difluoromethyl | nitro | $Y^1$ is CH, $Y^2$ is N, $Y^3$ is CH |
| P.2507 | $X^1$ is trifluoromethyl, $X^2$ is CH, $X^3$ is hydrogen | difluoromethyl | trifluoromethoxy | $Y^1$ is CH, $Y^2$ is N, $Y^3$ is CH |
| P.2508 | $X^1$ is trifluoromethyl, $X^2$ is CH, $X^3$ is hydrogen | difluoromethyl | trifluoromethyl | $Y^1$ is CH, $Y^2$ is N, $Y^3$ is CH |
| P.2509 | $X^1$ is trifluoromethyl, $X^2$ is CH, $X^3$ is hydrogen | trifluoromethyl | bromo | $Y^1$ is CH, $Y^2$ is N, $Y^3$ is CH |
| P.2510 | $X^1$ is trifluoromethyl, $X^2$ is CH, $X^3$ is hydrogen | trifluoromethyl | chloro | $Y^1$ is CH, $Y^2$ is N, $Y^3$ is CH |
| P.2511 | $X^1$ is trifluoromethyl, $X^2$ is CH, $X^3$ is hydrogen | trifluoromethyl | cyano | $Y^1$ is CH, $Y^2$ is N, $Y^3$ is CH |
| P.2512 | $X^1$ is trifluoromethyl, $X^2$ is CH, $X^3$ is hydrogen | trifluoromethyl | cyclopropyl | $Y^1$ is CH, $Y^2$ is N, $Y^3$ is CH |
| P.2513 | $X^1$ is trifluoromethyl, $X^2$ is CH, $X^3$ is hydrogen | trifluoromethyl | ethyl | $Y^1$ is CH, $Y^2$ is N, $Y^3$ is CH |
| P.2514 | $X^1$ is trifluoromethyl, $X^2$ is CH, $X^3$ is hydrogen | trifluoromethyl | fluoro | $Y^1$ is CH, $Y^2$ is N, $Y^3$ is CH |
| P.2515 | $X^1$ is trifluoromethyl, $X^2$ is CH, $X^3$ is hydrogen | trifluoromethyl | hydrogen | $Y^1$ is CH, $Y^2$ is N, $Y^3$ is CH |
| P.2516 | $X^1$ is trifluoromethyl, $X^2$ is CH, $X^3$ is hydrogen | trifluoromethyl | methoxy | $Y^1$ is CH, $Y^2$ is N, $Y^3$ is CH |
| P.2517 | $X^1$ is trifluoromethyl, $X^2$ is CH, $X^3$ is hydrogen | trifluoromethyl | methyl | $Y^1$ is CH, $Y^2$ is N, $Y^3$ is CH |
| P.2518 | $X^1$ is trifluoromethyl, $X^2$ is CH, $X^3$ is hydrogen | trifluoromethyl | nitro | $Y^1$ is CH, $Y^2$ is N, $Y^3$ is CH |
| P.2519 | $X^1$ is trifluoromethyl, $X^2$ is CH, $X^3$ is hydrogen | trifluoromethyl | trifluoromethoxy | $Y^1$ is CH, $Y^2$ is N, $Y^3$ is CH |
| P.2520 | $X^1$ is trifluoromethyl, $X^2$ is CH, $X^3$ is hydrogen | trifluoromethyl | trifluoromethyl | $Y^1$ is CH, $Y^2$ is N, $Y^3$ is CH |
| P.2521 | $X^1$ is chloro, $X^2$ is N, $X^3$ is chloro | chlorodifluoromethyl | bromo | $Y^1$ is CH, $Y^2$ is N, $Y^3$ is CH |
| P.2522 | $X^1$ is chloro, $X^2$ is N, $X^3$ is chloro | chlorodifluoromethyl | chloro | $Y^1$ is CH, $Y^2$ is N, $Y^3$ is CH |
| P.2523 | $X^1$ is chloro, $X^2$ is N, $X^3$ is chloro | chlorodifluoromethyl | cyano | $Y^1$ is CH, $Y^2$ is N, $Y^3$ is CH |
| P.2524 | $X^1$ is chloro, $X^2$ is N, $X^3$ is chloro | chlorodifluoromethyl | cyclopropyl | $Y^1$ is CH, $Y^2$ is N, $Y^3$ is CH |
| P.2525 | $X^1$ is chloro, $X^2$ is N, $X^3$ is chloro | chlorodifluoromethyl | ethyl | $Y^1$ is CH, $Y^2$ is N, $Y^3$ is CH |
| P.2526 | $X^1$ is chloro, $X^2$ is N, $X^3$ is chloro | chlorodifluoromethyl | fluoro | $Y^1$ is CH, $Y^2$ is N, $Y^3$ is CH |
| P.2527 | $X^1$ is chloro, $X^2$ is N, $X^3$ is chloro | chlorodifluoromethyl | hydrogen | $Y^1$ is CH, $Y^2$ is N, $Y^3$ is CH |
| P.2528 | $X^1$ is chloro, $X^2$ is N, $X^3$ is chloro | chlorodifluoromethyl | methoxy | $Y^1$ is CH, $Y^2$ is N, $Y^3$ is CH |
| P.2529 | $X^1$ is chloro, $X^2$ is N, $X^3$ is chloro | chlorodifluoromethyl | methyl | $Y^1$ is CH, $Y^2$ is N, $Y^3$ is CH |
| P.2530 | $X^1$ is chloro, $X^2$ is N, $X^3$ is chloro | chlorodifluoromethyl | nitro | $Y^1$ is CH, $Y^2$ is N, $Y^3$ is CH |
| P.2531 | $X^1$ is chloro, $X^2$ is N, $X^3$ is chloro | chlorodifluoromethyl | trifluoromethoxy | $Y^1$ is CH, $Y^2$ is N, $Y^3$ is CH |
| P.2532 | $X^1$ is chloro, $X^2$ is N, $X^3$ is chloro | chlorodifluoromethyl | trifluoromethyl | $Y^1$ is CH, $Y^2$ is N, $Y^3$ is CH |
| P.2533 | $X^1$ is chloro, $X^2$ is N, $X^3$ is chloro | difluoromethyl | bromo | $Y^1$ is CH, $Y^2$ is N, $Y^3$ is CH |
| P.2534 | $X^1$ is chloro, $X^2$ is N, $X^3$ is chloro | difluoromethyl | chloro | $Y^1$ is CH, $Y^2$ is N, $Y^3$ is CH |
| P.2535 | $X^1$ is chloro, $X^2$ is N, $X^3$ is chloro | difluoromethyl | cyano | $Y^1$ is CH, $Y^2$ is N, $Y^3$ is CH |
| P.2536 | $X^1$ is chloro, $X^2$ is N, $X^3$ is chloro | difluoromethyl | cyclopropyl | $Y^1$ is CH, $Y^2$ is N, $Y^3$ is CH |
| P.2537 | $X^1$ is chloro, $X^2$ is N, $X^3$ is chloro | difluoromethyl | ethyl | $Y^1$ is CH, $Y^2$ is N, $Y^3$ is CH |
| P.2538 | $X^1$ is chloro, $X^2$ is N, $X^3$ is chloro | difluoromethyl | fluoro | $Y^1$ is CH, $Y^2$ is N, $Y^3$ is CH |
| P.2539 | $X^1$ is chloro, $X^2$ is N, $X^3$ is chloro | difluoromethyl | hydrogen | $Y^1$ is CH, $Y^2$ is N, $Y^3$ is CH |
| P.2540 | $X^1$ is chloro, $X^2$ is N, $X^3$ is chloro | difluoromethyl | methoxy | $Y^1$ is CH, $Y^2$ is N, $Y^3$ is CH |
| P.2541 | $X^1$ is chloro, $X^2$ is N, $X^3$ is chloro | difluoromethyl | methyl | $Y^1$ is CH, $Y^2$ is N, $Y^3$ is CH |
| P.2542 | $X^1$ is chloro, $X^2$ is N, $X^3$ is chloro | difluoromethyl | nitro | $Y^1$ is CH, $Y^2$ is N, $Y^3$ is CH |
| P.2543 | $X^1$ is chloro, $X^2$ is N, $X^3$ is chloro | difluoromethyl | trifluoromethoxy | $Y^1$ is CH, $Y^2$ is N, $Y^3$ is CH |
| P.2544 | $X^1$ is chloro, $X^2$ is N, $X^3$ is chloro | difluoromethyl | trifluoromethyl | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2545 | $X^1$ is chloro, $X^2$ is N, $X^3$ is chloro | trifluoromethyl | bromo | $Y^1$ is CH, $Y^2$ is N, $Y^3$ is CH |
| P.2546 | $X^1$ is chloro, $X^2$ is N, $X^3$ is chloro | trifluoromethyl | chloro | $Y^1$ is CH, $Y^2$ is N, $Y^3$ is CH |
| P.2547 | $X^1$ is chloro, $X^2$ is N, $X^3$ is chloro | trifluoromethyl | cyano | $Y^1$ is CH, $Y^2$ is N, $Y^3$ is CH |
| P.2548 | $X^1$ is chloro, $X^2$ is N, $X^3$ is chloro | trifluoromethyl | cyclopropyl | $Y^1$ is CH, $Y^2$ is N, $Y^3$ is CH |
| P.2549 | $X^1$ is chloro, $X^2$ is N, $X^3$ is chloro | trifluoromethyl | ethyl | $Y^1$ is CH, $Y^2$ is N, $Y^3$ is CH |
| P.2550 | $X^1$ is chloro, $X^2$ is N, $X^3$ is chloro | trifluoromethyl | fluoro | $Y^1$ is CH, $Y^2$ is N, $Y^3$ is CH |
| P.2551 | $X^1$ is chloro, $X^2$ is N, $X^3$ is chloro | trifluoromethyl | hydrogen | $Y^1$ is CH, $Y^2$ is N, $Y^3$ is CH |
| P.2552 | $X^1$ is chloro, $X^2$ is N, $X^3$ is chloro | trifluoromethyl | methoxy | $Y^1$ is CH, $Y^2$ is N, $Y^3$ is CH |
| P.2553 | $X^1$ is chloro, $X^2$ is N, $X^3$ is chloro | trifluoromethyl | methyl | $Y^1$ is CH, $Y^2$ is N, $Y^3$ is CH |
| P.2554 | $X^1$ is chloro, $X^2$ is N, $X^3$ is chloro | trifluoromethyl | nitro | $Y^1$ is CH, $Y^2$ is N, $Y^3$ is CH |
| P.2555 | $X^1$ is chloro, $X^2$ is N, $X^3$ is chloro | trifluoromethyl | trifluoromethoxy | $Y^1$ is CH, $Y^2$ is N, $Y^3$ is CH |
| P.2556 | $X^1$ is chloro, $X^2$ is N, $X^3$ is chloro | trifluoromethyl | trifluoromethyl | $Y^1$ is CH, $Y^2$ is N, $Y^3$ is CH |
| P.2557 | $X^1$ is trifluoromethyl, $X^2$ is N, $X^3$ is trifluoromethyl | chlorodifluoromethyl | bromo | $Y^1$ is CH, $Y^2$ is N, $Y^3$ is CH |
| P.2558 | $X^1$ is trifluoromethyl, $X^2$ is N, $X^3$ is trifluoromethyl | chlorodifluoromethyl | chloro | $Y^1$ is CH, $Y^2$ is N, $Y^3$ is CH |
| P.2559 | $X^1$ is trifluoromethyl, $X^2$ is N, $X^3$ is trifluoromethyl | chlorodifluoromethyl | cyano | $Y^1$ is CH, $Y^2$ is N, $Y^3$ is CH |
| P.2560 | $X^1$ is trifluoromethyl, $X^2$ is N, $X^3$ is trifluoromethyl | chlorodifluoromethyl | cyclopropyl | $Y^1$ is CH, $Y^2$ is N, $Y^3$ is CH |
| P.2561 | $X^1$ is trifluoromethyl, $X^2$ is N, $X^3$ is trifluoromethyl | chlorodifluoromethyl | ethyl | $Y^1$ is CH, $Y^2$ is N, $Y^3$ is CH |
| P.2562 | $X^1$ is trifluoromethyl, $X^2$ is N, $X^3$ is trifluoromethyl | chlorodifluoromethyl | fluoro | $Y^1$ is CH, $Y^2$ is N, $Y^3$ is CH |
| P.2563 | $X^1$ is trifluoromethyl, $X^2$ is N, $X^3$ is trifluoromethyl | chlorodifluoromethyl | hydrogen | $Y^1$ is CH, $Y^2$ is N, $Y^3$ is CH |
| P.2564 | $X^1$ is trifluoromethyl, $X^2$ is N, $X^3$ is trifluoromethyl | chlorodifluoromethyl | methoxy | $Y^1$ is CH, $Y^2$ is N, $Y^3$ is CH |
| P.2565 | $X^1$ is trifluoromethyl, $X^2$ is N, $X^3$ is trifluoromethyl | chlorodifluoromethyl | methyl | $Y^1$ is CH, $Y^2$ is N, $Y^3$ is CH |
| P.2566 | $X^1$ is trifluoromethyl, $X^2$ is N, $X^3$ is trifluoromethyl | chlorodifluoromethyl | nitro | $Y^1$ is CH, $Y^2$ is N, $Y^3$ is CH |
| P.2567 | $X^1$ is trifluoromethyl, $X^2$ is N, $X^3$ is trifluoromethyl | chlorodifluoromethyl | trifluoromethoxy | $Y^1$ is CH, $Y^2$ is N, $Y^3$ is CH |
| P.2568 | $X^1$ is trifluoromethyl, $X^2$ is N, $X^3$ is trifluoromethyl | chlorodifluoromethyl | trifluoromethyl | $Y^1$ is CH, $Y^2$ is N, $Y^3$ is CH |
| P.2569 | $X^1$ is trifluoromethyl, $X^2$ is N, $X^3$ is trifluoromethyl | difluoromethyl | bromo | $Y^1$ is CH, $Y^2$ is N, $Y^3$ is CH |
| P.2570 | $X^1$ is trifluoromethyl, $X^2$ is N, $X^3$ is trifluoromethyl | difluoromethyl | chloro | $Y^1$ is CH, $Y^2$ is N, $Y^3$ is CH |
| P.2571 | $X^1$ is trifluoromethyl, $X^2$ is N, $X^3$ is trifluoromethyl | difluoromethyl | cyano | $Y^1$ is CH, $Y^2$ is N, $Y^3$ is CH |
| P.2572 | $X^1$ is trifluoromethyl, $X^2$ is N, $X^3$ is trifluoromethyl | difluoromethyl | cyclopropyl | $Y^1$ is CH, $Y^2$ is N, $Y^3$ is CH |
| P.2573 | $X^1$ is trifluoromethyl, $X^2$ is N, $X^3$ is trifluoromethyl | difluoromethyl | ethyl | $Y^1$ is CH, $Y^2$ is N, $Y^3$ is CH |
| P.2574 | $X^1$ is trifluoromethyl, $X^2$ is N, $X^3$ is trifluoromethyl | difluoromethyl | fluoro | $Y^1$ is CH, $Y^2$ is N, $Y^3$ is CH |
| P.2575 | $X^1$ is trifluoromethyl, $X^2$ is N, $X^3$ is trifluoromethyl | difluoromethyl | hydrogen | $Y^1$ is CH, $Y^2$ is N, $Y^3$ is CH |
| P.2576 | $X^1$ is trifluoromethyl, $X^2$ is N, $X^3$ is trifluoromethyl | difluoromethyl | methoxy | $Y^1$ is CH, $Y^2$ is N, $Y^3$ is CH |
| P.2577 | $X^1$ is trifluoromethyl, $X^2$ is N, $X^3$ is trifluoromethyl | difluoromethyl | methyl | $Y^1$ is CH, $Y^2$ is N, $Y^3$ is CH |
| P.2578 | $X^1$ is trifluoromethyl, $X^2$ is N, $X^3$ is trifluoromethyl | difluoromethyl | nitro | $Y^1$ is CH, $Y^2$ is N, $Y^3$ is CH |
| P.2579 | $X^1$ is trifluoromethyl, $X^2$ is N, $X^3$ is trifluoromethyl | difluoromethyl | trifluoromethoxy | $Y^1$ is CH, $Y^2$ is N, $Y^3$ is CH |
| P.2580 | $X^1$ is trifluoromethyl, $X^2$ is N, $X^3$ is trifluoromethyl | difluoromethyl | trifluoromethyl | $Y^1$ is CH, $Y^2$ is N, $Y^3$ is CH |
| P.2581 | $X^1$ is trifluoromethyl, $X^2$ is N, $X^3$ is trifluoromethyl | trifluoromethyl | bromo | $Y^1$ is CH, $Y^2$ is N, $Y^3$ is CH |
| P.2582 | $X^1$ is trifluoromethyl, $X^2$ is N, $X^3$ is trifluoromethyl | trifluoromethyl | chloro | $Y^1$ is CH, $Y^2$ is N, $Y^3$ is CH |
| P.2583 | $X^1$ is trifluoromethyl, $X^2$ is N, $X^3$ is trifluoromethyl | trifluoromethyl | cyano | $Y^1$ is CH, $Y^2$ is N, $Y^3$ is CH |

TABLE P-continued

| | X1, X2, X3 | X4 | R5 | Y1, Y2, Y3 |
|---|---|---|---|---|
| P.2584 | $X^1$ is trifluoromethyl, $X^2$ is N, $X^3$ is trifluoromethyl | trifluoromethyl | cyclopropyl | $Y^1$ is CH, $Y^2$ is N, $Y^3$ is CH |
| P.2585 | $X^1$ is trifluoromethyl, $X^2$ is N, $X^3$ is trifluoromethyl | trifluoromethyl | ethyl | $Y^1$ is CH, $Y^2$ is N, $Y^3$ is CH |
| P.2586 | $X^1$ is trifluoromethyl, $X^2$ is N, $X^3$ is trifluoromethyl | trifluoromethyl | fluoro | $Y^1$ is CH, $Y^2$ is N, $Y^3$ is CH |
| P.2587 | $X^1$ is trifluoromethyl, $X^2$ is N, $X^3$ is trifluoromethyl | trifluoromethyl | hydrogen | $Y^1$ is CH, $Y^2$ is N, $Y^3$ is CH |
| P.2588 | $X^1$ is trifluoromethyl, $X^2$ is N, $X^3$ is trifluoromethyl | trifluoromethyl | methoxy | $Y^1$ is CH, $Y^2$ is N, $Y^3$ is CH |
| P.2589 | $X^1$ is trifluoromethyl, $X^2$ is N, $X^3$ is trifluoromethyl | trifluoromethyl | methyl | $Y^1$ is CH, $Y^2$ is N, $Y^3$ is CH |
| P.2590 | $X^1$ is trifluoromethyl, $X^2$ is N, $X^3$ is trifluoromethyl | trifluoromethyl | nitro | $Y^1$ is CH, $Y^2$ is N, $Y^3$ is CH |
| P.2591 | $X^1$ is trifluoromethyl, $X^2$ is N, $X^3$ is trifluoromethyl | trifluoromethyl | trifluoromethoxy | $Y^1$ is CH, $Y^2$ is N, $Y^3$ is CH |
| P.2592 | $X^1$ is trifluoromethyl, $X^2$ is N, $X^3$ is trifluoromethyl | trifluoromethyl | trifluoromethyl | $Y^1$ is CH, $Y^2$ is N, $Y^3$ is CH |
| P.2593 | $X^1$ is chloro, $X^2$ is CH, $X^3$ is chloro | chlorodifluoromethyl | bromo | $Y^1$ is CH, $Y^2$ is CH, $Y^3$ is N |
| P.2594 | $X^1$ is chloro, $X^2$ is CH, $X^3$ is chloro | chlorodifluoromethyl | chloro | $Y^1$ is CH, $Y^2$ is CH, $Y^3$ is N |
| P.2595 | $X^1$ is chloro, $X^2$ is CH, $X^3$ is chloro | chlorodifluoromethyl | cyano | $Y^1$ is CH, $Y^2$ is CH, $Y^3$ is N |
| P.2596 | $X^1$ is chloro, $X^2$ is CH, $X^3$ is chloro | chlorodifluoromethyl | cyclopropyl | $Y^1$ is CH, $Y^2$ is CH, $Y^3$ is N |
| P.2597 | $X^1$ is chloro, $X^2$ is CH, $X^3$ is chloro | chlorodifluoromethyl | ethyl | $Y^1$ is CH, $Y^2$ is CH, $Y^3$ is N |
| P.2598 | $X^1$ is chloro, $X^2$ is CH, $X^3$ is chloro | chlorodifluoromethyl | fluoro | $Y^1$ is CH, $Y^2$ is CH, $Y^3$ is N |
| P.2599 | $X^1$ is chloro, $X^2$ is CH, $X^3$ is chloro | chlorodifluoromethyl | hydrogen | $Y^1$ is CH, $Y^2$ is CH, $Y^3$ is N |
| P.2600 | $X^1$ is chloro, $X^2$ is CH, $X^3$ is chloro | chlorodifluoromethyl | methoxy | $Y^1$ is CH, $Y^2$ is CH, $Y^3$ is N |
| P.2601 | $X^1$ is chloro, $X^2$ is CH, $X^3$ is chloro | chlorodifluoromethyl | methyl | $Y^1$ is CH, $Y^2$ is CH, $Y^3$ is N |
| P.2602 | $X^1$ is chloro, $X^2$ is CH, $X^3$ is chloro | chlorodifluoromethyl | nitro | $Y^1$ is CH, $Y^2$ is CH, $Y^3$ is N |
| P.2603 | $X^1$ is chloro, $X^2$ is CH, $X^3$ is chloro | chlorodifluoromethyl | trifluoromethoxy | $Y^1$ is CH, $Y^2$ is CH, $Y^3$ is N |
| P.2604 | $X^1$ is chloro, $X^2$ is CH, $X^3$ is chloro | chlorodifluoromethyl | trifluoromethyl | $Y^1$ is CH, $Y^2$ is CH, $Y^3$ is N |
| P.2605 | $X^1$ is chloro, $X^2$ is CH, $X^3$ is chloro | difluoromethyl | bromo | $Y^1$ is CH, $Y^2$ is CH, $Y^3$ is N |
| P.2606 | $X^1$ is chloro, $X^2$ is CH, $X^3$ is chloro | difluoromethyl | chloro | $Y^1$ is CH, $Y^2$ is CH, $Y^3$ is N |
| P.2607 | $X^1$ is chloro, $X^2$ is CH, $X^3$ is chloro | difluoromethyl | cyano | $Y^1$ is CH, $Y^2$ is CH, $Y^3$ is N |
| P.2608 | $X^1$ is chloro, $X^2$ is CH, $X^3$ is chloro | difluoromethyl | cyclopropyl | $Y^1$ is CH, $Y^2$ is CH, $Y^3$ is N |
| P.2609 | $X^1$ is chloro, $X^2$ is CH, $X^3$ is chloro | difluoromethyl | ethyl | $Y^1$ is CH, $Y^2$ is CH, $Y^3$ is N |
| P.2610 | $X^1$ is chloro, $X^2$ is CH, $X^3$ is chloro | difluoromethyl | fluoro | $Y^1$ is CH, $Y^2$ is CH, $Y^3$ is N |
| P.2611 | $X^1$ is chloro, $X^2$ is CH, $X^3$ is chloro | difluoromethyl | hydrogen | $Y^1$ is CH, $Y^2$ is CH, $Y^3$ is N |
| P.2612 | $X^1$ is chloro, $X^2$ is CH, $X^3$ is chloro | difluoromethyl | methoxy | $Y^1$ is CH, $Y^2$ is CH, $Y^3$ is N |
| P.2613 | $X^1$ is chloro, $X^2$ is CH, $X^3$ is chloro | difluoromethyl | methyl | $Y^1$ is CH, $Y^2$ is CH, $Y^3$ is N |
| P.2614 | $X^1$ is chloro, $X^2$ is CH, $X^3$ is chloro | difluoromethyl | nitro | $Y^1$ is CH, $Y^2$ is CH, $Y^3$ is N |
| P.2615 | $X^1$ is chloro, $X^2$ is CH, $X^3$ is chloro | difluoromethyl | trifluoromethoxy | $Y^1$ is CH, $Y^2$ is CH, $Y^3$ is N |
| P.2616 | $X^1$ is chloro, $X^2$ is CH, $X^3$ is chloro | difluoromethyl | trifluoromethyl | $Y^1$ is CH, $Y^2$ is CH, $Y^3$ is N |
| P.2617 | $X^1$ is chloro, $X^2$ is CH, $X^3$ is chloro | trifluoromethyl | bromo | $Y^1$ is CH, $Y^2$ is CH, $Y^3$ is N |
| P.2618 | $X^1$ is chloro, $X^2$ is CH, $X^3$ is chloro | trifluoromethyl | chloro | $Y^1$ is CH, $Y^2$ is CH, $Y^3$ is N |
| P.2619 | $X^1$ is chloro, $X^2$ is CH, $X^3$ is chloro | trifluoromethyl | cyano | $Y^1$ is CH, $Y^2$ is CH, $Y^3$ is N |
| P.2620 | $X^1$ is chloro, $X^2$ is CH, $X^3$ is chloro | trifluoromethyl | cyclopropyl | $Y^1$ is CH, $Y^2$ is CH, $Y^3$ is N |
| P.2621 | $X^1$ is chloro, $X^2$ is CH, $X^3$ is chloro | trifluoromethyl | ethyl | $Y^1$ is CH, $Y^2$ is CH, $Y^3$ is N |
| P.2622 | $X^1$ is chloro, $X^2$ is CH, $X^3$ is chloro | trifluoromethyl | fluoro | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.2623 | $X^1$ is chloro, $X^2$ is CH, $X^3$ is chloro | trifluoromethyl | hydrogen | $Y^1$ is CH, $Y^2$ is CH, $Y^3$ is N |
| P.2624 | $X^1$ is chloro, $X^2$ is CH, $X^3$ is chloro | trifluoromethyl | methoxy | $Y^1$ is CH, $Y^2$ is CH, $Y^3$ is N |
| P.2625 | $X^1$ is chloro, $X^2$ is CH, $X^3$ is chloro | trifluoromethyl | methyl | $Y^1$ is CH, $Y^2$ is CH, $Y^3$ is N |
| P.2626 | $X^1$ is chloro, $X^2$ is CH, $X^3$ is chloro | trifluoromethyl | nitro | $Y^1$ is CH, $Y^2$ is CH, $Y^3$ is N |
| P.2627 | $X^1$ is chloro, $X^2$ is CH, $X^3$ is chloro | trifluoromethyl | trifluoromethoxy | $Y^1$ is CH, $Y^2$ is CH, $Y^3$ is N |
| P.2628 | $X^1$ is chloro, $X^2$ is CH, $X^3$ is chloro | trifluoromethyl | trifluoromethyl | $Y^1$ is CH, $Y^2$ is CH, $Y^3$ is N |
| P.2629 | $X^1$ is chloro, $X^2$ is C—F, $X^3$ is hydrogen | chlorodifluoromethyl | bromo | $Y^1$ is CH, $Y^2$ is CH, $Y^3$ is N |
| P.2630 | $X^1$ is chloro, $X^2$ is C—F, $X^3$ is hydrogen | chlorodifluoromethyl | chloro | $Y^1$ is CH, $Y^2$ is CH, $Y^3$ is N |
| P.2631 | $X^1$ is chloro, $X^2$ is C—F, $X^3$ is hydrogen | chlorodifluoromethyl | cyano | $Y^1$ is CH, $Y^2$ is CH, $Y^3$ is N |
| P.2632 | $X^1$ is chloro, $X^2$ is C—F, $X^3$ is hydrogen | chlorodifluoromethyl | cyclopropyl | $Y^1$ is CH, $Y^2$ is CH, $Y^3$ is N |
| P.2633 | $X^1$ is chloro, $X^2$ is C—F, $X^3$ is hydrogen | chlorodifluoromethyl | ethyl | $Y^1$ is CH, $Y^2$ is CH, $Y^3$ is N |
| P.2634 | $X^1$ is chloro, $X^2$ is C—F, $X^3$ is hydrogen | chlorodifluoromethyl | fluoro | $Y^1$ is CH, $Y^2$ is CH, $Y^3$ is N |
| P.2635 | $X^1$ is chloro, $X^2$ is C—F, $X^3$ is hydrogen | chlorodifluoromethyl | hydrogen | $Y^1$ is CH, $Y^2$ is CH, $Y^3$ is N |
| P.2636 | $X^1$ is chloro, $X^2$ is C—F, $X^3$ is hydrogen | chlorodifluoromethyl | methoxy | $Y^1$ is CH, $Y^2$ is CH, $Y^3$ is N |
| P.2637 | $X^1$ is chloro, $X^2$ is C—F, $X^3$ is hydrogen | chlorodifluoromethyl | methyl | $Y^1$ is CH, $Y^2$ is CH, $Y^3$ is N |
| P.2638 | $X^1$ is chloro, $X^2$ is C—F, $X^3$ is hydrogen | chlorodifluoromethyl | nitro | $Y^1$ is CH, $Y^2$ is CH, $Y^3$ is N |
| P.2639 | $X^1$ is chloro, $X^2$ is C—F, $X^3$ is hydrogen | chlorodifluoromethyl | trifluoromethoxy | $Y^1$ is CH, $Y^2$ is CH, $Y^3$ is N |
| P.2640 | $X^1$ is chloro, $X^2$ is C—F, $X^3$ is hydrogen | chlorodifluoromethyl | trifluoromethyl | $Y^1$ is CH, $Y^2$ is CH, $Y^3$ is N |
| P.2641 | $X^1$ is chloro, $X^2$ is C—F, $X^3$ is hydrogen | difluoromethyl | bromo | $Y^1$ is CH, $Y^2$ is CH, $Y^3$ is N |
| P.2642 | $X^1$ is chloro, $X^2$ is C—F, $X^3$ is hydrogen | difluoromethyl | chloro | $Y^1$ is CH, $Y^2$ is CH, $Y^3$ is N |
| P.2643 | $X^1$ is chloro, $X^2$ is C—F, $X^3$ is hydrogen | difluoromethyl | cyano | $Y^1$ is CH, $Y^2$ is CH, $Y^3$ is N |
| P.2644 | $X^1$ is chloro, $X^2$ is C—F, $X^3$ is hydrogen | difluoromethyl | cyclopropyl | $Y^1$ is CH, $Y^2$ is CH, $Y^3$ is N |
| P.2645 | $X^1$ is chloro, $X^2$ is C—F, $X^3$ is hydrogen | difluoromethyl | ethyl | $Y^1$ is CH, $Y^2$ is CH, $Y^3$ is N |
| P.2646 | $X^1$ is chloro, $X^2$ is C—F, $X^3$ is hydrogen | difluoromethyl | fluoro | $Y^1$ is CH, $Y^2$ is CH, $Y^3$ is N |
| P.2647 | $X^1$ is chloro, $X^2$ is C—F, $X^3$ is hydrogen | difluoromethyl | hydrogen | $Y^1$ is CH, $Y^2$ is CH, $Y^3$ is N |
| P.2648 | $X^1$ is chloro, $X^2$ is C—F, $X^3$ is hydrogen | difluoromethyl | methoxy | $Y^1$ is CH, $Y^2$ is CH, $Y^3$ is N |
| P.2649 | $X^1$ is chloro, $X^2$ is C—F, $X^3$ is hydrogen | difluoromethyl | methyl | $Y^1$ is CH, $Y^2$ is CH, $Y^3$ is N |
| P.2650 | $X^1$ is chloro, $X^2$ is C—F, $X^3$ is hydrogen | difluoromethyl | nitro | $Y^1$ is CH, $Y^2$ is CH, $Y^3$ is N |
| P.2651 | $X^1$ is chloro, $X^2$ is C—F, $X^3$ is hydrogen | difluoromethyl | trifluoromethoxy | $Y^1$ is CH, $Y^2$ is CH, $Y^3$ is N |
| P.2652 | $X^1$ is chloro, $X^2$ is C—F, $X^3$ is hydrogen | difluoromethyl | trifluoromethyl | $Y^1$ is CH, $Y^2$ is CH, $Y^3$ is N |
| P.2653 | $X^1$ is chloro, $X^2$ is C—F, $X^3$ is hydrogen | trifluoromethyl | bromo | $Y^1$ is CH, $Y^2$ is CH, $Y^3$ is N |
| P.2654 | $X^1$ is chloro, $X^2$ is C—F, $X^3$ is hydrogen | trifluoromethyl | chloro | $Y^1$ is CH, $Y^2$ is CH, $Y^3$ is N |
| P.2655 | $X^1$ is chloro, $X^2$ is C—F, $X^3$ is hydrogen | trifluoromethyl | cyano | $Y^1$ is CH, $Y^2$ is CH, $Y^3$ is N |
| P.2656 | $X^1$ is chloro, $X^2$ is C—F, $X^3$ is hydrogen | trifluoromethyl | cyclopropyl | $Y^1$ is CH, $Y^2$ is CH, $Y^3$ is N |
| P.2657 | $X^1$ is chloro, $X^2$ is C—F, $X^3$ is hydrogen | trifluoromethyl | ethyl | $Y^1$ is CH, $Y^2$ is CH, $Y^3$ is N |
| P.2658 | $X^1$ is chloro, $X^2$ is C—F, $X^3$ is hydrogen | trifluoromethyl | fluoro | $Y^1$ is CH, $Y^2$ is CH, $Y^3$ is N |
| P.2659 | $X^1$ is chloro, $X^2$ is C—F, $X^3$ is hydrogen | trifluoromethyl | hydrogen | $Y^1$ is CH, $Y^2$ is CH, $Y^3$ is N |
| P.2660 | $X^1$ is chloro, $X^2$ is C—F, $X^3$ is hydrogen | trifluoromethyl | methoxy | $Y^1$ is CH, $Y^2$ is CH, $Y^3$ is N |
| P.2661 | $X^1$ is chloro, $X^2$ is C—F, $X^3$ is hydrogen | trifluoromethyl | methyl | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.2662 | $X^1$ is chloro, $X^2$ is C—F, $X^3$ is hydrogen | trifluoromethyl | nitro | $Y^1$ is CH, $Y^2$ is CH, $Y^3$ is N |
| P.2663 | $X^1$ is chloro, $X^2$ is C—F, $X^3$ is hydrogen | trifluoromethyl | trifluoromethoxy | $Y^1$ is CH, $Y^2$ is CH, $Y^3$ is N |
| P.2664 | $X^1$ is chloro, $X^2$ is C—F, $X^3$ is hydrogen | trifluoromethyl | trifluoromethyl | $Y^1$ is CH, $Y^2$ is CH, $Y^3$ is N |
| P.2665 | $X^1$ is fluoro, $X^2$ is C—Cl, $X^3$ is hydrogen | chlorodifluoromethyl | bromo | $Y^1$ is CH, $Y^2$ is CH, $Y^3$ is N |
| P.2666 | $X^1$ is fluoro, $X^2$ is C—Cl, $X^3$ is hydrogen | chlorodifluoromethyl | chloro | $Y^1$ is CH, $Y^2$ is CH, $Y^3$ is N |
| P.2667 | $X^1$ is fluoro, $X^2$ is C—Cl, $X^3$ is hydrogen | chlorodifluoromethyl | cyano | $Y^1$ is CH, $Y^2$ is CH, $Y^3$ is N |
| P.2668 | $X^1$ is fluoro, $X^2$ is C—Cl, $X^3$ is hydrogen | chlorodifluoromethyl | cyclopropyl | $Y^1$ is CH, $Y^2$ is CH, $Y^3$ is N |
| P.2669 | $X^1$ is fluoro, $X^2$ is C—Cl, $X^3$ is hydrogen | chlorodifluoromethyl | ethyl | $Y^1$ is CH, $Y^2$ is CH, $Y^3$ is N |
| P.2670 | $X^1$ is fluoro, $X^2$ is C—Cl, $X^3$ is hydrogen | chlorodifluoromethyl | fluoro | $Y^1$ is CH, $Y^2$ is CH, $Y^3$ is N |
| P.2671 | $X^1$ is fluoro, $X^2$ is C—Cl, $X^3$ is hydrogen | chlorodifluoromethyl | hydrogen | $Y^1$ is CH, $Y^2$ is CH, $Y^3$ is N |
| P.2672 | $X^1$ is fluoro, $X^2$ is C—Cl, $X^3$ is hydrogen | chlorodifluoromethyl | methoxy | $Y^1$ is CH, $Y^2$ is CH, $Y^3$ is N |
| P.2673 | $X^1$ is fluoro, $X^2$ is C—Cl, $X^3$ is hydrogen | chlorodifluoromethyl | methyl | $Y^1$ is CH, $Y^2$ is CH, $Y^3$ is N |
| P.2674 | $X^1$ is fluoro, $X^2$ is C—Cl, $X^3$ is hydrogen | chlorodifluoromethyl | nitro | $Y^1$ is CH, $Y^2$ is CH, $Y^3$ is N |
| P.2675 | $X^1$ is fluoro, $X^2$ is C—Cl, $X^3$ is hydrogen | chlorodifluoromethyl | trifluoromethoxy | $Y^1$ is CH, $Y^2$ is CH, $Y^3$ is N |
| P.2676 | $X^1$ is fluoro, $X^2$ is C—Cl, $X^3$ is hydrogen | chlorodifluoromethyl | trifluoromethyl | $Y^1$ is CH, $Y^2$ is CH, $Y^3$ is N |
| P.2677 | $X^1$ is fluoro, $X^2$ is C—Cl, $X^3$ is hydrogen | difluoromethyl | bromo | $Y^1$ is CH, $Y^2$ is CH, $Y^3$ is N |
| P.2678 | $X^1$ is fluoro, $X^2$ is C—Cl, $X^3$ is hydrogen | difluoromethyl | chloro | $Y^1$ is CH, $Y^2$ is CH, $Y^3$ is N |
| P.2679 | $X^1$ is fluoro, $X^2$ is C—Cl, $X^3$ is hydrogen | difluoromethyl | cyano | $Y^1$ is CH, $Y^2$ is CH, $Y^3$ is N |
| P.2680 | $X^1$ is fluoro, $X^2$ is C—Cl, $X^3$ is hydrogen | difluoromethyl | cyclopropyl | $Y^1$ is CH, $Y^2$ is CH, $Y^3$ is N |
| P.2681 | $X^1$ is fluoro, $X^2$ is C—Cl, $X^3$ is hydrogen | difluoromethyl | ethyl | $Y^1$ is CH, $Y^2$ is CH, $Y^3$ is N |
| P.2682 | $X^1$ is fluoro, $X^2$ is C—Cl, $X^3$ is hydrogen | difluoromethyl | fluoro | $Y^1$ is CH, $Y^2$ is CH, $Y^3$ is N |
| P.2683 | $X^1$ is fluoro, $X^2$ is C—Cl, $X^3$ is hydrogen | difluoromethyl | hydrogen | $Y^1$ is CH, $Y^2$ is CH, $Y^3$ is N |
| P.2684 | $X^1$ is fluoro, $X^2$ is C—Cl, $X^3$ is hydrogen | difluoromethyl | methoxy | $Y^1$ is CH, $Y^2$ is CH, $Y^3$ is N |
| P.2685 | $X^1$ is fluoro, $X^2$ is C—Cl, $X^3$ is hydrogen | difluoromethyl | methyl | $Y^1$ is CH, $Y^2$ is CH, $Y^3$ is N |
| P.2686 | $X^1$ is fluoro, $X^2$ is C—Cl, $X^3$ is hydrogen | difluoromethyl | nitro | $Y^1$ is CH, $Y^2$ is CH, $Y^3$ is N |
| P.2687 | $X^1$ is fluoro, $X^2$ is C—Cl, $X^3$ is hydrogen | difluoromethyl | trifluoromethoxy | $Y^1$ is CH, $Y^2$ is CH, $Y^3$ is N |
| P.2688 | $X^1$ is fluoro, $X^2$ is C—Cl, $X^3$ is hydrogen | difluoromethyl | trifluoromethyl | $Y^1$ is CH, $Y^2$ is CH, $Y^3$ is N |
| P.2689 | $X^1$ is fluoro, $X^2$ is C—Cl, $X^3$ is hydrogen | trifluoromethyl | bromo | $Y^1$ is CH, $Y^2$ is CH, $Y^3$ is N |
| P.2690 | $X^1$ is fluoro, $X^2$ is C—Cl, $X^3$ is hydrogen | trifluoromethyl | chloro | $Y^1$ is CH, $Y^2$ is CH, $Y^3$ is N |
| P.2691 | $X^1$ is fluoro, $X^2$ is C—Cl, $X^3$ is hydrogen | trifluoromethyl | cyano | $Y^1$ is CH, $Y^2$ is CH, $Y^3$ is N |
| P.2692 | $X^1$ is fluoro, $X^2$ is C—Cl, $X^3$ is hydrogen | trifluoromethyl | cyclopropyl | $Y^1$ is CH, $Y^2$ is CH, $Y^3$ is N |
| P.2693 | $X^1$ is fluoro, $X^2$ is C—Cl, $X^3$ is hydrogen | trifluoromethyl | ethyl | $Y^1$ is CH, $Y^2$ is CH, $Y^3$ is N |
| P.2694 | $X^1$ is fluoro, $X^2$ is C—Cl, $X^3$ is hydrogen | trifluoromethyl | fluoro | $Y^1$ is CH, $Y^2$ is CH, $Y^3$ is N |
| P.2695 | $X^1$ is fluoro, $X^2$ is C—Cl, $X^3$ is hydrogen | trifluoromethyl | hydrogen | $Y^1$ is CH, $Y^2$ is CH, $Y^3$ is N |
| P.2696 | $X^1$ is fluoro, $X^2$ is C—Cl, $X^3$ is hydrogen | trifluoromethyl | methoxy | $Y^1$ is CH, $Y^2$ is CH, $Y^3$ is N |
| P.2697 | $X^1$ is fluoro, $X^2$ is C—Cl, $X^3$ is hydrogen | trifluoromethyl | methyl | $Y^1$ is CH, $Y^2$ is CH, $Y^3$ is N |
| P.2698 | $X^1$ is fluoro, $X^2$ is C—Cl, $X^3$ is hydrogen | trifluoromethyl | nitro | $Y^1$ is CH, $Y^2$ is CH, $Y^3$ is N |
| P.2699 | $X^1$ is fluoro, $X^2$ is C—Cl, $X^3$ is hydrogen | trifluoromethyl | trifluoromethoxy | $Y^1$ is CH, $Y^2$ is CH, $Y^3$ is N |
| P.2700 | $X^1$ is fluoro, $X^2$ is C—Cl, $X^3$ is hydrogen | trifluoromethyl | trifluoromethyl | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.2701 | $X^1$ is chloro, $X^2$ is C—Cl, $X^3$ is hydrogen | chlorodifluoromethyl | bromo | $Y^1$ is CH, $Y^2$ is CH, $Y^3$ is N |
| P.2702 | $X^1$ is chloro, $X^2$ is C—Cl, $X^3$ is hydrogen | chlorodifluoromethyl | chloro | $Y^1$ is CH, $Y^2$ is CH, $Y^3$ is N |
| P.2703 | $X^1$ is chloro, $X^2$ is C—Cl, $X^3$ is hydrogen | chlorodifluoromethyl | cyano | $Y^1$ is CH, $Y^2$ is CH, $Y^3$ is N |
| P.2704 | $X^1$ is chloro, $X^2$ is C—Cl, $X^3$ is hydrogen | chlorodifluoromethyl | cyclopropyl | $Y^1$ is CH, $Y^2$ is CH, $Y^3$ is N |
| P.2705 | $X^1$ is chloro, $X^2$ is C—Cl, $X^3$ is hydrogen | chlorodifluoromethyl | ethyl | $Y^1$ is CH, $Y^2$ is CH, $Y^3$ is N |
| P.2706 | $X^1$ is chloro, $X^2$ is C—Cl, $X^3$ is hydrogen | chlorodifluoromethyl | fluoro | $Y^1$ is CH, $Y^2$ is CH, $Y^3$ is N |
| P.2707 | $X^1$ is chloro, $X^2$ is C—Cl, $X^3$ is hydrogen | chlorodifluoromethyl | hydrogen | $Y^1$ is CH, $Y^2$ is CH, $Y^3$ is N |
| P.2708 | $X^1$ is chloro, $X^2$ is C—Cl, $X^3$ is hydrogen | chlorodifluoromethyl | methoxy | $Y^1$ is CH, $Y^2$ is CH, $Y^3$ is N |
| P.2709 | $X^1$ is chloro, $X^2$ is C—Cl, $X^3$ is hydrogen | chlorodifluoromethyl | methyl | $Y^1$ is CH, $Y^2$ is CH, $Y^3$ is N |
| P.2710 | $X^1$ is chloro, $X^2$ is C—Cl, $X^3$ is hydrogen | chlorodifluoromethyl | nitro | $Y^1$ is CH, $Y^2$ is CH, $Y^3$ is N |
| P.2711 | $X^1$ is chloro, $X^2$ is C—Cl, $X^3$ is hydrogen | chlorodifluoromethyl | trifluoromethoxy | $Y^1$ is CH, $Y^2$ is CH, $Y^3$ is N |
| P.2712 | $X^1$ is chloro, $X^2$ is C—Cl, $X^3$ is hydrogen | chlorodifluoromethyl | trifluoromethyl | $Y^1$ is CH, $Y^2$ is CH, $Y^3$ is N |
| P.2713 | $X^1$ is chloro, $X^2$ is C—Cl, $X^3$ is hydrogen | difluoromethyl | bromo | $Y^1$ is CH, $Y^2$ is CH, $Y^3$ is N |
| P.2714 | $X^1$ is chloro, $X^2$ is C—Cl, $X^3$ is hydrogen | difluoromethyl | chloro | $Y^1$ is CH, $Y^2$ is CH, $Y^3$ is N |
| P.2715 | $X^1$ is chloro, $X^2$ is C—Cl, $X^3$ is hydrogen | difluoromethyl | cyano | $Y^1$ is CH, $Y^2$ is CH, $Y^3$ is N |
| P.2716 | $X^1$ is chloro, $X^2$ is C—Cl, $X^3$ is hydrogen | difluoromethyl | cyclopropyl | $Y^1$ is CH, $Y^2$ is CH, $Y^3$ is N |
| P.2717 | $X^1$ is chloro, $X^2$ is C—Cl, $X^3$ is hydrogen | difluoromethyl | ethyl | $Y^1$ is CH, $Y^2$ is CH, $Y^3$ is N |
| P.2718 | $X^1$ is chloro, $X^2$ is C—Cl, $X^3$ is hydrogen | difluoromethyl | fluoro | $Y^1$ is CH, $Y^2$ is CH, $Y^3$ is N |
| P.2719 | $X^1$ is chloro, $X^2$ is C—Cl, $X^3$ is hydrogen | difluoromethyl | hydrogen | $Y^1$ is CH, $Y^2$ is CH, $Y^3$ is N |
| P.2720 | $X^1$ is chloro, $X^2$ is C—Cl, $X^3$ is hydrogen | difluoromethyl | methoxy | $Y^1$ is CH, $Y^2$ is CH, $Y^3$ is N |
| P.2721 | $X^1$ is chloro, $X^2$ is C—Cl, $X^3$ is hydrogen | difluoromethyl | methyl | $Y^1$ is CH, $Y^2$ is CH, $Y^3$ is N |
| P.2722 | $X^1$ is chloro, $X^2$ is C—Cl, $X^3$ is hydrogen | difluoromethyl | nitro | $Y^1$ is CH, $Y^2$ is CH, $Y^3$ is N |
| P.2723 | $X^1$ is chloro, $X^2$ is C—Cl, $X^3$ is hydrogen | difluoromethyl | trifluoromethoxy | $Y^1$ is CH, $Y^2$ is CH, $Y^3$ is N |
| P.2724 | $X^1$ is chloro, $X^2$ is C—Cl, $X^3$ is hydrogen | difluoromethyl | trifluoromethyl | $Y^1$ is CH, $Y^2$ is CH, $Y^3$ is N |
| P.2725 | $X^1$ is chloro, $X^2$ is C—Cl, $X^3$ is hydrogen | trifluoromethyl | bromo | $Y^1$ is CH, $Y^2$ is CH, $Y^3$ is N |
| P.2726 | $X^1$ is chloro, $X^2$ is C—Cl, $X^3$ is hydrogen | trifluoromethyl | chloro | $Y^1$ is CH, $Y^2$ is CH, $Y^3$ is N |
| P.2727 | $X^1$ is chloro, $X^2$ is C—Cl, $X^3$ is hydrogen | trifluoromethyl | cyano | $Y^1$ is CH, $Y^2$ is CH, $Y^3$ is N |
| P.2728 | $X^1$ is chloro, $X^2$ is C—Cl, $X^3$ is hydrogen | trifluoromethyl | cyclopropyl | $Y^1$ is CH, $Y^2$ is CH, $Y^3$ is N |
| P.2729 | $X^1$ is chloro, $X^2$ is C—Cl, $X^3$ is hydrogen | trifluoromethyl | ethyl | $Y^1$ is CH, $Y^2$ is CH, $Y^3$ is N |
| P.2730 | $X^1$ is chloro, $X^2$ is C—Cl, $X^3$ is hydrogen | trifluoromethyl | fluoro | $Y^1$ is CH, $Y^2$ is CH, $Y^3$ is N |
| P.2731 | $X^1$ is chloro, $X^2$ is C—Cl, $X^3$ is hydrogen | trifluoromethyl | hydrogen | $Y^1$ is CH, $Y^2$ is CH, $Y^3$ is N |
| P.2732 | $X^1$ is chloro, $X^2$ is C—Cl, $X^3$ is hydrogen | trifluoromethyl | methoxy | $Y^1$ is CH, $Y^2$ is CH, $Y^3$ is N |
| P.2733 | $X^1$ is chloro, $X^2$ is C—Cl, $X^3$ is hydrogen | trifluoromethyl | methyl | $Y^1$ is CH, $Y^2$ is CH, $Y^3$ is N |
| P.2734 | $X^1$ is chloro, $X^2$ is C—Cl, $X^3$ is hydrogen | trifluoromethyl | nitro | $Y^1$ is CH, $Y^2$ is CH, $Y^3$ is N |
| P.2735 | $X^1$ is chloro, $X^2$ is C—Cl, $X^3$ is hydrogen | trifluoromethyl | trifluoromethoxy | $Y^1$ is CH, $Y^2$ is CH, $Y^3$ is N |
| P.2736 | $X^1$ is chloro, $X^2$ is C—Cl, $X^3$ is hydrogen | trifluoromethyl | trifluoromethyl | $Y^1$ is CH, $Y^2$ is CH, $Y^3$ is N |
| P.2737 | $X^1$ is chloro, $X^2$ is C—Br, $X^3$ is chloro | chlorodifluoromethyl | bromo | $Y^1$ is CH, $Y^2$ is CH, $Y^3$ is N |
| P.2738 | $X^1$ is chloro, $X^2$ is C—Br, $X^3$ is chloro | chlorodifluoromethyl | chloro | $Y^1$ is CH, $Y^2$ is CH, $Y^3$ is N |
| P.2739 | $X^1$ is chloro, $X^2$ is C—Br, $X^3$ is chloro | chlorodifluoromethyl | cyano | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.2740 | $X^1$ is chloro, $X^2$ is C—Br, $X^3$ is chloro | chlorodifluoromethyl | cyclopropyl | $Y^1$ is CH, $Y^2$ is CH, $Y^3$ is N |
| P.2741 | $X^1$ is chloro, $X^2$ is C—Br, $X^3$ is chloro | chlorodifluoromethyl | ethyl | $Y^1$ is CH, $Y^2$ is CH, $Y^3$ is N |
| P.2742 | $X^1$ is chloro, $X^2$ is C—Br, $X^3$ is chloro | chlorodifluoromethyl | fluoro | $Y^1$ is CH, $Y^2$ is CH, $Y^3$ is N |
| P.2743 | $X^1$ is chloro, $X^2$ is C—Br, $X^3$ is chloro | chlorodifluoromethyl | hydrogen | $Y^1$ is CH, $Y^2$ is CH, $Y^3$ is N |
| P.2744 | $X^1$ is chloro, $X^2$ is C—Br, $X^3$ is chloro | chlorodifluoromethyl | methoxy | $Y^1$ is CH, $Y^2$ is CH, $Y^3$ is N |
| P.2745 | $X^1$ is chloro, $X^2$ is C—Br, $X^3$ is chloro | chlorodifluoromethyl | methyl | $Y^1$ is CH, $Y^2$ is CH, $Y^3$ is N |
| P.2746 | $X^1$ is chloro, $X^2$ is C—Br, $X^3$ is chloro | chlorodifluoromethyl | nitro | $Y^1$ is CH, $Y^2$ is CH, $Y^3$ is N |
| P.2747 | $X^1$ is chloro, $X^2$ is C—Br, $X^3$ is chloro | chlorodifluoromethyl | trifluoromethoxy | $Y^1$ is CH, $Y^2$ is CH, $Y^3$ is N |
| P.2748 | $X^1$ is chloro, $X^2$ is C—Br, $X^3$ is chloro | chlorodifluoromethyl | trifluoromethyl | $Y^1$ is CH, $Y^2$ is CH, $Y^3$ is N |
| P.2749 | $X^1$ is chloro, $X^2$ is C—Br, $X^3$ is chloro | difluoromethyl | bromo | $Y^1$ is CH, $Y^2$ is CH, $Y^3$ is N |
| P.2750 | $X^1$ is chloro, $X^2$ is C—Br, $X^3$ is chloro | difluoromethyl | chloro | $Y^1$ is CH, $Y^2$ is CH, $Y^3$ is N |
| P.2751 | $X^1$ is chloro, $X^2$ is C—Br, $X^3$ is chloro | difluoromethyl | cyano | $Y^1$ is CH, $Y^2$ is CH, $Y^3$ is N |
| P.2752 | $X^1$ is chloro, $X^2$ is C—Br, $X^3$ is chloro | difluoromethyl | cyclopropyl | $Y^1$ is CH, $Y^2$ is CH, $Y^3$ is N |
| P.2753 | $X^1$ is chloro, $X^2$ is C—Br, $X^3$ is chloro | difluoromethyl | ethyl | $Y^1$ is CH, $Y^2$ is CH, $Y^3$ is N |
| P.2754 | $X^1$ is chloro, $X^2$ is C—Br, $X^3$ is chloro | difluoromethyl | fluoro | $Y^1$ is CH, $Y^2$ is CH, $Y^3$ is N |
| P.2755 | $X^1$ is chloro, $X^2$ is C—Br, $X^3$ is chloro | difluoromethyl | hydrogen | $Y^1$ is CH, $Y^2$ is CH, $Y^3$ is N |
| P.2756 | $X^1$ is chloro, $X^2$ is C—Br, $X^3$ is chloro | difluoromethyl | methoxy | $Y^1$ is CH, $Y^2$ is CH, $Y^3$ is N |
| P.2757 | $X^1$ is chloro, $X^2$ is C—Br, $X^3$ is chloro | difluoromethyl | methyl | $Y^1$ is CH, $Y^2$ is CH, $Y^3$ is N |
| P.2758 | $X^1$ is chloro, $X^2$ is C—Br, $X^3$ is chloro | difluoromethyl | nitro | $Y^1$ is CH, $Y^2$ is CH, $Y^3$ is N |
| P.2759 | $X^1$ is chloro, $X^2$ is C—Br, $X^3$ is chloro | difluoromethyl | trifluoromethoxy | $Y^1$ is CH, $Y^2$ is CH, $Y^3$ is N |
| P.2760 | $X^1$ is chloro, $X^2$ is C—Br, $X^3$ is chloro | difluoromethyl | trifluoromethyl | $Y^1$ is CH, $Y^2$ is CH, $Y^3$ is N |
| P.2761 | $X^1$ is chloro, $X^2$ is C—Br, $X^3$ is chloro | trifluoromethyl | bromo | $Y^1$ is CH, $Y^2$ is CH, $Y^3$ is N |
| P.2762 | $X^1$ is chloro, $X^2$ is C—Br, $X^3$ is chloro | trifluoromethyl | chloro | $Y^1$ is CH, $Y^2$ is CH, $Y^3$ is N |
| P.2763 | $X^1$ is chloro, $X^2$ is C—Br, $X^3$ is chloro | trifluoromethyl | cyano | $Y^1$ is CH, $Y^2$ is CH, $Y^3$ is N |
| P.2764 | $X^1$ is chloro, $X^2$ is C—Br, $X^3$ is chloro | trifluoromethyl | cyclopropyl | $Y^1$ is CH, $Y^2$ is CH, $Y^3$ is N |
| P.2765 | $X^1$ is chloro, $X^2$ is C—Br, $X^3$ is chloro | trifluoromethyl | ethyl | $Y^1$ is CH, $Y^2$ is CH, $Y^3$ is N |
| P.2766 | $X^1$ is chloro, $X^2$ is C—Br, $X^3$ is chloro | trifluoromethyl | fluoro | $Y^1$ is CH, $Y^2$ is CH, $Y^3$ is N |
| P.2767 | $X^1$ is chloro, $X^2$ is C—Br, $X^3$ is chloro | trifluoromethyl | hydrogen | $Y^1$ is CH, $Y^2$ is CH, $Y^3$ is N |
| P.2768 | $X^1$ is chloro, $X^2$ is C—Br, $X^3$ is chloro | trifluoromethyl | methoxy | $Y^1$ is CH, $Y^2$ is CH, $Y^3$ is N |
| P.2769 | $X^1$ is chloro, $X^2$ is C—Br, $X^3$ is chloro | trifluoromethyl | methyl | $Y^1$ is CH, $Y^2$ is CH, $Y^3$ is N |
| P.2770 | $X^1$ is chloro, $X^2$ is C—Br, $X^3$ is chloro | trifluoromethyl | nitro | $Y^1$ is CH, $Y^2$ is CH, $Y^3$ is N |
| P.2771 | $X^1$ is chloro, $X^2$ is C—Br, $X^3$ is chloro | trifluoromethyl | trifluoromethoxy | $Y^1$ is CH, $Y^2$ is CH, $Y^3$ is N |
| P.2772 | $X^1$ is chloro, $X^2$ is C—Br, $X^3$ is chloro | trifluoromethyl | trifluoromethyl | $Y^1$ is CH, $Y^2$ is CH, $Y^3$ is N |
| P.2773 | $X^1$ is chloro, $X^2$ is C—F, $X^3$ is chloro | chlorodifluoromethyl | bromo | $Y^1$ is CH, $Y^2$ is CH, $Y^3$ is N |
| P.2774 | $X^1$ is chloro, $X^2$ is C—F, $X^3$ is chloro | chlorodifluoromethyl | chloro | $Y^1$ is CH, $Y^2$ is CH, $Y^3$ is N |
| P.2775 | $X^1$ is chloro, $X^2$ is C—F, $X^3$ is chloro | chlorodifluoromethyl | cyano | $Y^1$ is CH, $Y^2$ is CH, $Y^3$ is N |
| P.2776 | $X^1$ is chloro, $X^2$ is C—F, $X^3$ is chloro | chlorodifluoromethyl | cyclopropyl | $Y^1$ is CH, $Y^2$ is CH, $Y^3$ is N |
| P.2777 | $X^1$ is chloro, $X^2$ is C—F, $X^3$ is chloro | chlorodifluoromethyl | ethyl | $Y^1$ is CH, $Y^2$ is CH, $Y^3$ is N |
| P.2778 | $X^1$ is chloro, $X^2$ is C—F, $X^3$ is chloro | chlorodifluoromethyl | fluoro | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.2779 | $X^1$ is chloro, $X^2$ is C—F, $X^3$ is chloro | chlorodifluoromethyl | hydrogen | $Y^1$ is CH, $Y^2$ is CH, $Y^3$ is N |
| P.2780 | $X^1$ is chloro, $X^2$ is C—F, $X^3$ is chloro | chlorodifluoromethyl | methoxy | $Y^1$ is CH, $Y^2$ is CH, $Y^3$ is N |
| P.2781 | $X^1$ is chloro, $X^2$ is C—F, $X^3$ is chloro | chlorodifluoromethyl | methyl | $Y^1$ is CH, $Y^2$ is CH, $Y^3$ is N |
| P.2782 | $X^1$ is chloro, $X^2$ is C—F, $X^3$ is chloro | chlorodifluoromethyl | nitro | $Y^1$ is CH, $Y^2$ is CH, $Y^3$ is N |
| P.2783 | $X^1$ is chloro, $X^2$ is C—F, $X^3$ is chloro | chlorodifluoromethyl | trifluoromethoxy | $Y^1$ is CH, $Y^2$ is CH, $Y^3$ is N |
| P.2784 | $X^1$ is chloro, $X^2$ is C—F, $X^3$ is chloro | chlorodifluoromethyl | trifluoromethyl | $Y^1$ is CH, $Y^2$ is CH, $Y^3$ is N |
| P.2785 | $X^1$ is chloro, $X^2$ is C—F, $X^3$ is chloro | difluoromethyl | bromo | $Y^1$ is CH, $Y^2$ is CH, $Y^3$ is N |
| P.2786 | $X^1$ is chloro, $X^2$ is C—F, $X^3$ is chloro | difluoromethyl | chloro | $Y^1$ is CH, $Y^2$ is CH, $Y^3$ is N |
| P.2787 | $X^1$ is chloro, $X^2$ is C—F, $X^3$ is chloro | difluoromethyl | cyano | $Y^1$ is CH, $Y^2$ is CH, $Y^3$ is N |
| P.2788 | $X^1$ is chloro, $X^2$ is C—F, $X^3$ is chloro | difluoromethyl | cyclopropyl | $Y^1$ is CH, $Y^2$ is CH, $Y^3$ is N |
| P.2789 | $X^1$ is chloro, $X^2$ is C—F, $X^3$ is chloro | difluoromethyl | ethyl | $Y^1$ is CH, $Y^2$ is CH, $Y^3$ is N |
| P.2790 | $X^1$ is chloro, $X^2$ is C—F, $X^3$ is chloro | difluoromethyl | fluoro | $Y^1$ is CH, $Y^2$ is CH, $Y^3$ is N |
| P.2791 | $X^1$ is chloro, $X^2$ is C—F, $X^3$ is chloro | difluoromethyl | hydrogen | $Y^1$ is CH, $Y^2$ is CH, $Y^3$ is N |
| P.2792 | $X^1$ is chloro, $X^2$ is C—F, $X^3$ is chloro | difluoromethyl | methoxy | $Y^1$ is CH, $Y^2$ is CH, $Y^3$ is N |
| P.2793 | $X^1$ is chloro, $X^2$ is C—F, $X^3$ is chloro | difluoromethyl | methyl | $Y^1$ is CH, $Y^2$ is CH, $Y^3$ is N |
| P.2794 | $X^1$ is chloro, $X^2$ is C—F, $X^3$ is chloro | difluoromethyl | nitro | $Y^1$ is CH, $Y^2$ is CH, $Y^3$ is N |
| P.2795 | $X^1$ is chloro, $X^2$ is C—F, $X^3$ is chloro | difluoromethyl | trifluoromethoxy | $Y^1$ is CH, $Y^2$ is CH, $Y^3$ is N |
| P.2796 | $X^1$ is chloro, $X^2$ is C—F, $X^3$ is chloro | difluoromethyl | trifluoromethyl | $Y^1$ is CH, $Y^2$ is CH, $Y^3$ is N |
| P.2797 | $X^1$ is chloro, $X^2$ is C—F, $X^3$ is chloro | trifluoromethyl | bromo | $Y^1$ is CH, $Y^2$ is CH, $Y^3$ is N |
| P.2798 | $X^1$ is chloro, $X^2$ is C—F, $X^3$ is chloro | trifluoromethyl | chloro | $Y^1$ is CH, $Y^2$ is CH, $Y^3$ is N |
| P.2799 | $X^1$ is chloro, $X^2$ is C—F, $X^3$ is chloro | trifluoromethyl | cyano | $Y^1$ is CH, $Y^2$ is CH, $Y^3$ is N |
| P.2800 | $X^1$ is chloro, $X^2$ is C—F, $X^3$ is chloro | trifluoromethyl | cyclopropyl | $Y^1$ is CH, $Y^2$ is CH, $Y^3$ is N |
| P.2801 | $X^1$ is chloro, $X^2$ is C—F, $X^3$ is chloro | trifluoromethyl | ethyl | $Y^1$ is CH, $Y^2$ is CH, $Y^3$ is N |
| P.2802 | $X^1$ is chloro, $X^2$ is C—F, $X^3$ is chloro | trifluoromethyl | fluoro | $Y^1$ is CH, $Y^2$ is CH, $Y^3$ is N |
| P.2803 | $X^1$ is chloro, $X^2$ is C—F, $X^3$ is chloro | trifluoromethyl | hydrogen | $Y^1$ is CH, $Y^2$ is CH, $Y^3$ is N |
| P.2804 | $X^1$ is chloro, $X^2$ is C—F, $X^3$ is chloro | trifluoromethyl | methoxy | $Y^1$ is CH, $Y^2$ is CH, $Y^3$ is N |
| P.2805 | $X^1$ is chloro, $X^2$ is C—F, $X^3$ is chloro | trifluoromethyl | methyl | $Y^1$ is CH, $Y^2$ is CH, $Y^3$ is N |
| P.2806 | $X^1$ is chloro, $X^2$ is C—F, $X^3$ is chloro | trifluoromethyl | nitro | $Y^1$ is CH, $Y^2$ is CH, $Y^3$ is N |
| P.2807 | $X^1$ is chloro, $X^2$ is C—F, $X^3$ is chloro | trifluoromethyl | trifluoromethoxy | $Y^1$ is CH, $Y^2$ is CH, $Y^3$ is N |
| P.2808 | $X^1$ is chloro, $X^2$ is C—F, $X^3$ is chloro | trifluoromethyl | trifluoromethyl | $Y^1$ is CH, $Y^2$ is CH, $Y^3$ is N |
| P.2809 | $X^1$ is chloro, $X^2$ is C—Cl, $X^3$ is chloro | chlorodifluoromethyl | bromo | $Y^1$ is CH, $Y^2$ is CH, $Y^3$ is N |
| P.2810 | $X^1$ is chloro, $X^2$ is C—Cl, $X^3$ is chloro | chlorodifluoromethyl | chloro | $Y^1$ is CH, $Y^2$ is CH, $Y^3$ is N |
| P.2811 | $X^1$ is chloro, $X^2$ is C—Cl, $X^3$ is chloro | chlorodifluoromethyl | cyano | $Y^1$ is CH, $Y^2$ is CH, $Y^3$ is N |
| P.2812 | $X^1$ is chloro, $X^2$ is C—Cl, $X^3$ is chloro | chlorodifluoromethyl | cyclopropyl | $Y^1$ is CH, $Y^2$ is CH, $Y^3$ is N |
| P.2813 | $X^1$ is chloro, $X^2$ is C—Cl, $X^3$ is chloro | chlorodifluoromethyl | ethyl | $Y^1$ is CH, $Y^2$ is CH, $Y^3$ is N |
| P.2814 | $X^1$ is chloro, $X^2$ is C—Cl, $X^3$ is chloro | chlorodifluoromethyl | fluoro | $Y^1$ is CH, $Y^2$ is CH, $Y^3$ is N |
| P.2815 | $X^1$ is chloro, $X^2$ is C—Cl, $X^3$ is chloro | chlorodifluoromethyl | hydrogen | $Y^1$ is CH, $Y^2$ is CH, $Y^3$ is N |
| P.2816 | $X^1$ is chloro, $X^2$ is C—Cl, $X^3$ is chloro | chlorodifluoromethyl | methoxy | $Y^1$ is CH, $Y^2$ is CH, $Y^3$ is N |
| P.2817 | $X^1$ is chloro, $X^2$ is C—Cl, $X^3$ is chloro | chlorodifluoromethyl | methyl | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.2818 | $X^1$ is chloro, $X^2$ is C—Cl, $X^3$ is chloro | chlorodifluoromethyl | nitro | $Y^1$ is CH, $Y^2$ is CH, $Y^3$ is N |
| P.2819 | $X^1$ is chloro, $X^2$ is C—Cl, $X^3$ is chloro | chlorodifluoromethyl | trifluoromethoxy | $Y^1$ is CH, $Y^2$ is CH, $Y^3$ is N |
| P.2820 | $X^1$ is chloro, $X^2$ is C—Cl, $X^3$ is chloro | chlorodifluoromethyl | trifluoromethyl | $Y^1$ is CH, $Y^2$ is CH, $Y^3$ is N |
| P.2821 | $X^1$ is chloro, $X^2$ is C—Cl, $X^3$ is chloro | difluoromethyl | bromo | $Y^1$ is CH, $Y^2$ is CH, $Y^3$ is N |
| P.2822 | $X^1$ is chloro, $X^2$ is C—Cl, $X^3$ is chloro | difluoromethyl | chloro | $Y^1$ is CH, $Y^2$ is CH, $Y^3$ is N |
| P.2823 | $X^1$ is chloro, $X^2$ is C—Cl, $X^3$ is chloro | difluoromethyl | cyano | $Y^1$ is CH, $Y^2$ is CH, $Y^3$ is N |
| P.2824 | $X^1$ is chloro, $X^2$ is C—Cl, $X^3$ is chloro | difluoromethyl | cyclopropyl | $Y^1$ is CH, $Y^2$ is CH, $Y^3$ is N |
| P.2825 | $X^1$ is chloro, $X^2$ is C—Cl, $X^3$ is chloro | difluoromethyl | ethyl | $Y^1$ is CH, $Y^2$ is CH, $Y^3$ is N |
| P.2826 | $X^1$ is chloro, $X^2$ is C—Cl, $X^3$ is chloro | difluoromethyl | fluoro | $Y^1$ is CH, $Y^2$ is CH, $Y^3$ is N |
| P.2827 | $X^1$ is chloro, $X^2$ is C—Cl, $X^3$ is chloro | difluoromethyl | hydrogen | $Y^1$ is CH, $Y^2$ is CH, $Y^3$ is N |
| P.2828 | $X^1$ is chloro, $X^2$ is C—Cl, $X^3$ is chloro | difluoromethyl | methoxy | $Y^1$ is CH, $Y^2$ is CH, $Y^3$ is N |
| P.2829 | $X^1$ is chloro, $X^2$ is C—Cl, $X^3$ is chloro | difluoromethyl | methyl | $Y^1$ is CH, $Y^2$ is CH, $Y^3$ is N |
| P.2830 | $X^1$ is chloro, $X^2$ is C—Cl, $X^3$ is chloro | difluoromethyl | nitro | $Y^1$ is CH, $Y^2$ is CH, $Y^3$ is N |
| P.2831 | $X^1$ is chloro, $X^2$ is C—Cl, $X^3$ is chloro | difluoromethyl | trifluoromethoxy | $Y^1$ is CH, $Y^2$ is CH, $Y^3$ is N |
| P.2832 | $X^1$ is chloro, $X^2$ is C—Cl, $X^3$ is chloro | difluoromethyl | trifluoromethyl | $Y^1$ is CH, $Y^2$ is CH, $Y^3$ is N |
| P.2833 | $X^1$ is chloro, $X^2$ is C—Cl, $X^3$ is chloro | trifluoromethyl | bromo | $Y^1$ is CH, $Y^2$ is CH, $Y^3$ is N |
| P.2834 | $X^1$ is chloro, $X^2$ is C—Cl, $X^3$ is chloro | trifluoromethyl | chloro | $Y^1$ is CH, $Y^2$ is CH, $Y^3$ is N |
| P.2835 | $X^1$ is chloro, $X^2$ is C—Cl, $X^3$ is chloro | trifluoromethyl | cyano | $Y^1$ is CH, $Y^2$ is CH, $Y^3$ is N |
| P.2836 | $X^1$ is chloro, $X^2$ is C—Cl, $X^3$ is chloro | trifluoromethyl | cyclopropyl | $Y^1$ is CH, $Y^2$ is CH, $Y^3$ is N |
| P.2837 | $X^1$ is chloro, $X^2$ is C—Cl, $X^3$ is chloro | trifluoromethyl | ethyl | $Y^1$ is CH, $Y^2$ is CH, $Y^3$ is N |
| P.2838 | $X^1$ is chloro, $X^2$ is C—Cl, $X^3$ is chloro | trifluoromethyl | fluoro | $Y^1$ is CH, $Y^2$ is CH, $Y^3$ is N |
| P.2839 | $X^1$ is chloro, $X^2$ is C—Cl, $X^3$ is chloro | trifluoromethyl | hydrogen | $Y^1$ is CH, $Y^2$ is CH, $Y^3$ is N |
| P.2840 | $X^1$ is chloro, $X^2$ is C—Cl, $X^3$ is chloro | trifluoromethyl | methoxy | $Y^1$ is CH, $Y^2$ is CH, $Y^3$ is N |
| P.2841 | $X^1$ is chloro, $X^2$ is C—Cl, $X^3$ is chloro | trifluoromethyl | methyl | $Y^1$ is CH, $Y^2$ is CH, $Y^3$ is N |
| P.2842 | $X^1$ is chloro, $X^2$ is C—Cl, $X^3$ is chloro | trifluoromethyl | nitro | $Y^1$ is CH, $Y^2$ is CH, $Y^3$ is N |
| P.2843 | $X^1$ is chloro, $X^2$ is C—Cl, $X^3$ is chloro | trifluoromethyl | trifluoromethoxy | $Y^1$ is CH, $Y^2$ is CH, $Y^3$ is N |
| P.2844 | $X^1$ is chloro, $X^2$ is C—Cl, $X^3$ is chloro | trifluoromethyl | trifluoromethyl | $Y^1$ is CH, $Y^2$ is CH, $Y^3$ is N |
| P.2845 | $X^1$ is chloro, $X^2$ is C—I, $X^3$ is chloro | chlorodifluoromethyl | bromo | $Y^1$ is CH, $Y^2$ is CH, $Y^3$ is N |
| P.2846 | $X^1$ is chloro, $X^2$ is C—I, $X^3$ is chloro | chlorodifluoromethyl | chloro | $Y^1$ is CH, $Y^2$ is CH, $Y^3$ is N |
| P.2847 | $X^1$ is chloro, $X^2$ is C—I, $X^3$ is chloro | chlorodifluoromethyl | cyano | $Y^1$ is CH, $Y^2$ is CH, $Y^3$ is N |
| P.2848 | $X^1$ is chloro, $X^2$ is C—I, $X^3$ is chloro | chlorodifluoromethyl | cyclopropyl | $Y^1$ is CH, $Y^2$ is CH, $Y^3$ is N |
| P.2849 | $X^1$ is chloro, $X^2$ is C—I, $X^3$ is chloro | chlorodifluoromethyl | ethyl | $Y^1$ is CH, $Y^2$ is CH, $Y^3$ is N |
| P.2850 | $X^1$ is chloro, $X^2$ is C—I, $X^3$ is chloro | chlorodifluoromethyl | fluoro | $Y^1$ is CH, $Y^2$ is CH, $Y^3$ is N |
| P.2851 | $X^1$ is chloro, $X^2$ is C—I, $X^3$ is chloro | chlorodifluoromethyl | hydrogen | $Y^1$ is CH, $Y^2$ is CH, $Y^3$ is N |
| P.2852 | $X^1$ is chloro, $X^2$ is C—I, $X^3$ is chloro | chlorodifluoromethyl | methoxy | $Y^1$ is CH, $Y^2$ is CH, $Y^3$ is N |
| P.2853 | $X^1$ is chloro, $X^2$ is C—I, $X^3$ is chloro | chlorodifluoromethyl | methyl | $Y^1$ is CH, $Y^2$ is CH, $Y^3$ is N |
| P.2854 | $X^1$ is chloro, $X^2$ is C—I, $X^3$ is chloro | chlorodifluoromethyl | nitro | $Y^1$ is CH, $Y^2$ is CH, $Y^3$ is N |
| P.2855 | $X^1$ is chloro, $X^2$ is C—I, $X^3$ is chloro | chlorodifluoromethyl | trifluoromethoxy | $Y^1$ is CH, $Y^2$ is CH, $Y^3$ is N |
| P.2856 | $X^1$ is chloro, $X^2$ is C—I, $X^3$ is chloro | chlorodifluoromethyl | trifluoromethyl | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.2857 | $X^1$ is chloro, $X^2$ is C—I, $X^3$ is chloro | difluoromethyl | bromo | $Y^1$ is CH, $Y^2$ is CH, $Y^3$ is N |
| P.2858 | $X^1$ is chloro, $X^2$ is C—I, $X^3$ is chloro | difluoromethyl | chloro | $Y^1$ is CH, $Y^2$ is CH, $Y^3$ is N |
| P.2859 | $X^1$ is chloro, $X^2$ is C—I, $X^3$ is chloro | difluoromethyl | cyano | $Y^1$ is CH, $Y^2$ is CH, $Y^3$ is N |
| P.2860 | $X^1$ is chloro, $X^2$ is C—I, $X^3$ is chloro | difluoromethyl | cyclopropyl | $Y^1$ is CH, $Y^2$ is CH, $Y^3$ is N |
| P.2861 | $X^1$ is chloro, $X^2$ is C—I, $X^3$ is chloro | difluoromethyl | ethyl | $Y^1$ is CH, $Y^2$ is CH, $Y^3$ is N |
| P.2862 | $X^1$ is chloro, $X^2$ is C—I, $X^3$ is chloro | difluoromethyl | fluoro | $Y^1$ is CH, $Y^2$ is CH, $Y^3$ is N |
| P.2863 | $X^1$ is chloro, $X^2$ is C—I, $X^3$ is chloro | difluoromethyl | hydrogen | $Y^1$ is CH, $Y^2$ is CH, $Y^3$ is N |
| P.2864 | $X^1$ is chloro, $X^2$ is C—I, $X^3$ is chloro | difluoromethyl | methoxy | $Y^1$ is CH, $Y^2$ is CH, $Y^3$ is N |
| P.2865 | $X^1$ is chloro, $X^2$ is C—I, $X^3$ is chloro | difluoromethyl | methyl | $Y^1$ is CH, $Y^2$ is CH, $Y^3$ is N |
| P.2866 | $X^1$ is chloro, $X^2$ is C—I, $X^3$ is chloro | difluoromethyl | nitro | $Y^1$ is CH, $Y^2$ is CH, $Y^3$ is N |
| P.2867 | $X^1$ is chloro, $X^2$ is C—I, $X^3$ is chloro | difluoromethyl | trifluoromethoxy | $Y^1$ is CH, $Y^2$ is CH, $Y^3$ is N |
| P.2868 | $X^1$ is chloro, $X^2$ is C—I, $X^3$ is chloro | difluoromethyl | trifluoromethyl | $Y^1$ is CH, $Y^2$ is CH, $Y^3$ is N |
| P.2869 | $X^1$ is chloro, $X^2$ is C—I, $X^3$ is chloro | trifluoromethyl | bromo | $Y^1$ is CH, $Y^2$ is CH, $Y^3$ is N |
| P.2870 | $X^1$ is chloro, $X^2$ is C—I, $X^3$ is chloro | trifluoromethyl | chloro | $Y^1$ is CH, $Y^2$ is CH, $Y^3$ is N |
| P.2871 | $X^1$ is chloro, $X^2$ is C—I, $X^3$ is chloro | trifluoromethyl | cyano | $Y^1$ is CH, $Y^2$ is CH, $Y^3$ is N |
| P.2872 | $X^1$ is chloro, $X^2$ is C—I, $X^3$ is chloro | trifluoromethyl | cyclopropyl | $Y^1$ is CH, $Y^2$ is CH, $Y^3$ is N |
| P.2873 | $X^1$ is chloro, $X^2$ is C—I, $X^3$ is chloro | trifluoromethyl | ethyl | $Y^1$ is CH, $Y^2$ is CH, $Y^3$ is N |
| P.2874 | $X^1$ is chloro, $X^2$ is C—I, $X^3$ is chloro | trifluoromethyl | fluoro | $Y^1$ is CH, $Y^2$ is CH, $Y^3$ is N |
| P.2875 | $X^1$ is chloro, $X^2$ is C—I, $X^3$ is chloro | trifluoromethyl | hydrogen | $Y^1$ is CH, $Y^2$ is CH, $Y^3$ is N |
| P.2876 | $X^1$ is chloro, $X^2$ is C—I, $X^3$ is chloro | trifluoromethyl | methoxy | $Y^1$ is CH, $Y^2$ is CH, $Y^3$ is N |
| P.2877 | $X^1$ is chloro, $X^2$ is C—I, $X^3$ is chloro | trifluoromethyl | methyl | $Y^1$ is CH, $Y^2$ is CH, $Y^3$ is N |
| P.2878 | $X^1$ is chloro, $X^2$ is C—I, $X^3$ is chloro | trifluoromethyl | nitro | $Y^1$ is CH, $Y^2$ is CH, $Y^3$ is N |
| P.2879 | $X^1$ is chloro, $X^2$ is C—I, $X^3$ is chloro | trifluoromethyl | trifluoromethoxy | $Y^1$ is CH, $Y^2$ is CH, $Y^3$ is N |
| P.2880 | $X^1$ is chloro, $X^2$ is C—I, $X^3$ is chloro | trifluoromethyl | trifluoromethyl | $Y^1$ is CH, $Y^2$ is CH, $Y^3$ is N |
| P.2881 | $X^1$ is fluoro, $X^2$ is C—F, $X^3$ is fluoro | chlorodifluoromethyl | bromo | $Y^1$ is CH, $Y^2$ is CH, $Y^3$ is N |
| P.2882 | $X^1$ is fluoro, $X^2$ is C—F, $X^3$ is fluoro | chlorodifluoromethyl | chloro | $Y^1$ is CH, $Y^2$ is CH, $Y^3$ is N |
| P.2883 | $X^1$ is fluoro, $X^2$ is C—F, $X^3$ is fluoro | chlorodifluoromethyl | cyano | $Y^1$ is CH, $Y^2$ is CH, $Y^3$ is N |
| P.2884 | $X^1$ is fluoro, $X^2$ is C—F, $X^3$ is fluoro | chlorodifluoromethyl | cyclopropyl | $Y^1$ is CH, $Y^2$ is CH, $Y^3$ is N |
| P.2885 | $X^1$ is fluoro, $X^2$ is C—F, $X^3$ is fluoro | chlorodifluoromethyl | ethyl | $Y^1$ is CH, $Y^2$ is CH, $Y^3$ is N |
| P.2886 | $X^1$ is fluoro, $X^2$ is C—F, $X^3$ is fluoro | chlorodifluoromethyl | fluoro | $Y^1$ is CH, $Y^2$ is CH, $Y^3$ is N |
| P.2887 | $X^1$ is fluoro, $X^2$ is C—F, $X^3$ is fluoro | chlorodifluoromethyl | hydrogen | $Y^1$ is CH, $Y^2$ is CH, $Y^3$ is N |
| P.2888 | $X^1$ is fluoro, $X^2$ is C—F, $X^3$ is fluoro | chlorodifluoromethyl | methoxy | $Y^1$ is CH, $Y^2$ is CH, $Y^3$ is N |
| P.2889 | $X^1$ is fluoro, $X^2$ is C—F, $X^3$ is fluoro | chlorodifluoromethyl | methyl | $Y^1$ is CH, $Y^2$ is CH, $Y^3$ is N |
| P.2890 | $X^1$ is fluoro, $X^2$ is C—F, $X^3$ is fluoro | chlorodifluoromethyl | nitro | $Y^1$ is CH, $Y^2$ is CH, $Y^3$ is N |
| P.2891 | $X^1$ is fluoro, $X^2$ is C—F, $X^3$ is fluoro | chlorodifluoromethyl | trifluoromethoxy | $Y^1$ is CH, $Y^2$ is CH, $Y^3$ is N |
| P.2892 | $X^1$ is fluoro, $X^2$ is C—F, $X^3$ is fluoro | chlorodifluoromethyl | trifluoromethyl | $Y^1$ is CH, $Y^2$ is CH, $Y^3$ is N |
| P.2893 | $X^1$ is fluoro, $X^2$ is C—F, $X^3$ is fluoro | difluoromethyl | bromo | $Y^1$ is CH, $Y^2$ is CH, $Y^3$ is N |
| P.2894 | $X^1$ is fluoro, $X^2$ is C—F, $X^3$ is fluoro | difluoromethyl | chloro | $Y^1$ is CH, $Y^2$ is CH, $Y^3$ is N |
| P.2895 | $X^1$ is fluoro, $X^2$ is C—F, $X^3$ is fluoro | difluoromethyl | cyano | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.2896 | $X^1$ is fluoro, $X^2$ is C—F, $X^3$ is fluoro | difluoromethyl | cyclopropyl | $Y^1$ is CH, $Y^2$ is CH, $Y^3$ is N |
| P.2897 | $X^1$ is fluoro, $X^2$ is C—F, $X^3$ is fluoro | difluoromethyl | ethyl | $Y^1$ is CH, $Y^2$ is CH, $Y^3$ is N |
| P.2898 | $X^1$ is fluoro, $X^2$ is C—F, $X^3$ is fluoro | difluoromethyl | fluoro | $Y^1$ is CH, $Y^2$ is CH, $Y^3$ is N |
| P.2899 | $X^1$ is fluoro, $X^2$ is C—F, $X^3$ is fluoro | difluoromethyl | hydrogen | $Y^1$ is CH, $Y^2$ is CH, $Y^3$ is N |
| P.2900 | $X^1$ is fluoro, $X^2$ is C—F, $X^3$ is fluoro | difluoromethyl | methoxy | $Y^1$ is CH, $Y^2$ is CH, $Y^3$ is N |
| P.2901 | $X^1$ is fluoro, $X^2$ is C—F, $X^3$ is fluoro | difluoromethyl | methyl | $Y^1$ is CH, $Y^2$ is CH, $Y^3$ is N |
| P.2902 | $X^1$ is fluoro, $X^2$ is C—F, $X^3$ is fluoro | difluoromethyl | nitro | $Y^1$ is CH, $Y^2$ is CH, $Y^3$ is N |
| P.2903 | $X^1$ is fluoro, $X^2$ is C—F, $X^3$ is fluoro | difluoromethyl | trifluoromethoxy | $Y^1$ is CH, $Y^2$ is CH, $Y^3$ is N |
| P.2904 | $X^1$ is fluoro, $X^2$ is C—F, $X^3$ is fluoro | difluoromethyl | trifluoromethyl | $Y^1$ is CH, $Y^2$ is CH, $Y^3$ is N |
| P.2905 | $X^1$ is fluoro, $X^2$ is C—F, $X^3$ is fluoro | trifluoromethyl | bromo | $Y^1$ is CH, $Y^2$ is CH, $Y^3$ is N |
| P.2906 | $X^1$ is fluoro, $X^2$ is C—F, $X^3$ is fluoro | trifluoromethyl | chloro | $Y^1$ is CH, $Y^2$ is CH, $Y^3$ is N |
| P.2907 | $X^1$ is fluoro, $X^2$ is C—F, $X^3$ is fluoro | trifluoromethyl | cyano | $Y^1$ is CH, $Y^2$ is CH, $Y^3$ is N |
| P.2908 | $X^1$ is fluoro, $X^2$ is C—F, $X^3$ is fluoro | trifluoromethyl | cyclopropyl | $Y^1$ is CH, $Y^2$ is CH, $Y^3$ is N |
| P.2909 | $X^1$ is fluoro, $X^2$ is C—F, $X^3$ is fluoro | trifluoromethyl | ethyl | $Y^1$ is CH, $Y^2$ is CH, $Y^3$ is N |
| P.2910 | $X^1$ is fluoro, $X^2$ is C—F, $X^3$ is fluoro | trifluoromethyl | fluoro | $Y^1$ is CH, $Y^2$ is CH, $Y^3$ is N |
| P.2911 | $X^1$ is fluoro, $X^2$ is C—F, $X^3$ is fluoro | trifluoromethyl | hydrogen | $Y^1$ is CH, $Y^2$ is CH, $Y^3$ is N |
| P.2912 | $X^1$ is fluoro, $X^2$ is C—F, $X^3$ is fluoro | trifluoromethyl | methoxy | $Y^1$ is CH, $Y^2$ is CH, $Y^3$ is N |
| P.2913 | $X^1$ is fluoro, $X^2$ is C—F, $X^3$ is fluoro | trifluoromethyl | methyl | $Y^1$ is CH, $Y^2$ is CH, $Y^3$ is N |
| P.2914 | $X^1$ is fluoro, $X^2$ is C—F, $X^3$ is fluoro | trifluoromethyl | nitro | $Y^1$ is CH, $Y^2$ is CH, $Y^3$ is N |
| P.2915 | $X^1$ is fluoro, $X^2$ is C—F, $X^3$ is fluoro | trifluoromethyl | trifluoromethoxy | $Y^1$ is CH, $Y^2$ is CH, $Y^3$ is N |
| P.2916 | $X^1$ is fluoro, $X^2$ is C—F, $X^3$ is fluoro | trifluoromethyl | trifluoromethyl | $Y^1$ is CH, $Y^2$ is CH, $Y^3$ is N |
| P.2917 | $X^1$ is chloro, $X^2$ is CH, $X^3$ is bromo | chlorodifluoromethyl | bromo | $Y^1$ is CH, $Y^2$ is CH, $Y^3$ is N |
| P.2918 | $X^1$ is chloro, $X^2$ is CH, $X^3$ is bromo | chlorodifluoromethyl | chloro | $Y^1$ is CH, $Y^2$ is CH, $Y^3$ is N |
| P.2919 | $X^1$ is chloro, $X^2$ is CH, $X^3$ is bromo | chlorodifluoromethyl | cyano | $Y^1$ is CH, $Y^2$ is CH, $Y^3$ is N |
| P.2920 | $X^1$ is chloro, $X^2$ is CH, $X^3$ is bromo | chlorodifluoromethyl | cyclopropyl | $Y^1$ is CH, $Y^2$ is CH, $Y^3$ is N |
| P.2921 | $X^1$ is chloro, $X^2$ is CH, $X^3$ is bromo | chlorodifluoromethyl | ethyl | $Y^1$ is CH, $Y^2$ is CH, $Y^3$ is N |
| P.2922 | $X^1$ is chloro, $X^2$ is CH, $X^3$ is bromo | chlorodifluoromethyl | fluoro | $Y^1$ is CH, $Y^2$ is CH, $Y^3$ is N |
| P.2923 | $X^1$ is chloro, $X^2$ is CH, $X^3$ is bromo | chlorodifluoromethyl | hydrogen | $Y^1$ is CH, $Y^2$ is CH, $Y^3$ is N |
| P.2924 | $X^1$ is chloro, $X^2$ is CH, $X^3$ is bromo | chlorodifluoromethyl | methoxy | $Y^1$ is CH, $Y^2$ is CH, $Y^3$ is N |
| P.2925 | $X^1$ is chloro, $X^2$ is CH, $X^3$ is bromo | chlorodifluoromethyl | methyl | $Y^1$ is CH, $Y^2$ is CH, $Y^3$ is N |
| P.2926 | $X^1$ is chloro, $X^2$ is CH, $X^3$ is bromo | chlorodifluoromethyl | nitro | $Y^1$ is CH, $Y^2$ is CH, $Y^3$ is N |
| P.2927 | $X^1$ is chloro, $X^2$ is CH, $X^3$ is bromo | chlorodifluoromethyl | trifluoromethoxy | $Y^1$ is CH, $Y^2$ is CH, $Y^3$ is N |
| P.2928 | $X^1$ is chloro, $X^2$ is CH, $X^3$ is bromo | chlorodifluoromethyl | trifluoromethyl | $Y^1$ is CH, $Y^2$ is CH, $Y^3$ is N |
| P.2929 | $X^1$ is chloro, $X^2$ is CH, $X^3$ is bromo | difluoromethyl | bromo | $Y^1$ is CH, $Y^2$ is CH, $Y^3$ is N |
| P.2930 | $X^1$ is chloro, $X^2$ is CH, $X^3$ is bromo | difluoromethyl | chloro | $Y^1$ is CH, $Y^2$ is CH, $Y^3$ is N |
| P.2931 | $X^1$ is chloro, $X^2$ is CH, $X^3$ is bromo | difluoromethyl | cyano | $Y^1$ is CH, $Y^2$ is CH, $Y^3$ is N |
| P.2932 | $X^1$ is chloro, $X^2$ is CH, $X^3$ is bromo | difluoromethyl | cyclopropyl | $Y^1$ is CH, $Y^2$ is CH, $Y^3$ is N |
| P.2933 | $X^1$ is chloro, $X^2$ is CH, $X^3$ is bromo | difluoromethyl | ethyl | $Y^1$ is CH, $Y^2$ is CH, $Y^3$ is N |
| P.2934 | $X^1$ is chloro, $X^2$ is CH, $X^3$ is bromo | difluoromethyl | fluoro | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.2935 | $X^1$ is chloro, $X^2$ is CH, $X^3$ is bromo | difluoromethyl | hydrogen | $Y^1$ is CH, $Y^2$ is CH, $Y^3$ is N |
| P.2936 | $X^1$ is chloro, $X^2$ is CH, $X^3$ is bromo | difluoromethyl | methoxy | $Y^1$ is CH, $Y^2$ is CH, $Y^3$ is N |
| P.2937 | $X^1$ is chloro, $X^2$ is CH, $X^3$ is bromo | difluoromethyl | methyl | $Y^1$ is CH, $Y^2$ is CH, $Y^3$ is N |
| P.2938 | $X^1$ is chloro, $X^2$ is CH, $X^3$ is bromo | difluoromethyl | nitro | $Y^1$ is CH, $Y^2$ is CH, $Y^3$ is N |
| P.2939 | $X^1$ is chloro, $X^2$ is CH, $X^3$ is bromo | difluoromethyl | trifluoromethoxy | $Y^1$ is CH, $Y^2$ is CH, $Y^3$ is N |
| P.2940 | $X^1$ is chloro, $X^2$ is CH, $X^3$ is bromo | difluoromethyl | trifluoromethyl | $Y^1$ is CH, $Y^2$ is CH, $Y^3$ is N |
| P.2941 | $X^1$ is chloro, $X^2$ is CH, $X^3$ is bromo | trifluoromethyl | bromo | $Y^1$ is CH, $Y^2$ is CH, $Y^3$ is N |
| P.2942 | $X^1$ is chloro, $X^2$ is CH, $X^3$ is bromo | trifluoromethyl | chloro | $Y^1$ is CH, $Y^2$ is CH, $Y^3$ is N |
| P.2943 | $X^1$ is chloro, $X^2$ is CH, $X^3$ is bromo | trifluoromethyl | cyano | $Y^1$ is CH, $Y^2$ is CH, $Y^3$ is N |
| P.2944 | $X^1$ is chloro, $X^2$ is CH, $X^3$ is bromo | trifluoromethyl | cyclopropyl | $Y^1$ is CH, $Y^2$ is CH, $Y^3$ is N |
| P.2945 | $X^1$ is chloro, $X^2$ is CH, $X^3$ is bromo | trifluoromethyl | ethyl | $Y^1$ is CH, $Y^2$ is CH, $Y^3$ is N |
| P.2946 | $X^1$ is chloro, $X^2$ is CH, $X^3$ is bromo | trifluoromethyl | fluoro | $Y^1$ is CH, $Y^2$ is CH, $Y^3$ is N |
| P.2947 | $X^1$ is chloro, $X^2$ is CH, $X^3$ is bromo | trifluoromethyl | hydrogen | $Y^1$ is CH, $Y^2$ is CH, $Y^3$ is N |
| P.2948 | $X^1$ is chloro, $X^2$ is CH, $X^3$ is bromo | trifluoromethyl | methoxy | $Y^1$ is CH, $Y^2$ is CH, $Y^3$ is N |
| P.2949 | $X^1$ is chloro, $X^2$ is CH, $X^3$ is bromo | trifluoromethyl | methyl | $Y^1$ is CH, $Y^2$ is CH, $Y^3$ is N |
| P.2950 | $X^1$ is chloro, $X^2$ is CH, $X^3$ is bromo | trifluoromethyl | nitro | $Y^1$ is CH, $Y^2$ is CH, $Y^3$ is N |
| P.2951 | $X^1$ is chloro, $X^2$ is CH, $X^3$ is bromo | trifluoromethyl | trifluoromethoxy | $Y^1$ is CH, $Y^2$ is CH, $Y^3$ is N |
| P.2952 | $X^1$ is chloro, $X^2$ is CH, $X^3$ is bromo | trifluoromethyl | trifluoromethyl | $Y^1$ is CH, $Y^2$ is CH, $Y^3$ is N |
| P.2953 | $X^1$ is chloro, $X^2$ is CH, $X^3$ is bromo | chlorodifluoromethyl | bromo | $Y^1$ is CH, $Y^2$ is CH, $Y^3$ is N |
| P.2954 | $X^1$ is chloro, $X^2$ is CH, $X^3$ is bromo | chlorodifluoromethyl | chloro | $Y^1$ is CH, $Y^2$ is CH, $Y^3$ is N |
| P.2955 | $X^1$ is chloro, $X^2$ is CH, $X^3$ is bromo | chlorodifluoromethyl | cyano | $Y^1$ is CH, $Y^2$ is CH, $Y^3$ is N |
| P.2956 | $X^1$ is chloro, $X^2$ is CH, $X^3$ is bromo | chlorodifluoromethyl | cyclopropyl | $Y^1$ is CH, $Y^2$ is CH, $Y^3$ is N |
| P.2957 | $X^1$ is chloro, $X^2$ is CH, $X^3$ is bromo | chlorodifluoromethyl | ethyl | $Y^1$ is CH, $Y^2$ is CH, $Y^3$ is N |
| P.2958 | $X^1$ is chloro, $X^2$ is CH, $X^3$ is bromo | chlorodifluoromethyl | fluoro | $Y^1$ is CH, $Y^2$ is CH, $Y^3$ is N |
| P.2959 | $X^1$ is chloro, $X^2$ is CH, $X^3$ is bromo | chlorodifluoromethyl | hydrogen | $Y^1$ is CH, $Y^2$ is CH, $Y^3$ is N |
| P.2960 | $X^1$ is chloro, $X^2$ is CH, $X^3$ is bromo | chlorodifluoromethyl | methoxy | $Y^1$ is CH, $Y^2$ is CH, $Y^3$ is N |
| P.2961 | $X^1$ is chloro, $X^2$ is CH, $X^3$ is bromo | chlorodifluoromethyl | methyl | $Y^1$ is CH, $Y^2$ is CH, $Y^3$ is N |
| P.2962 | $X^1$ is chloro, $X^2$ is CH, $X^3$ is bromo | chlorodifluoromethyl | nitro | $Y^1$ is CH, $Y^2$ is CH, $Y^3$ is N |
| P.2963 | $X^1$ is chloro, $X^2$ is CH, $X^3$ is bromo | chlorodifluoromethyl | trifluoromethoxy | $Y^1$ is CH, $Y^2$ is CH, $Y^3$ is N |
| P.2964 | $X^1$ is chloro, $X^2$ is CH, $X^3$ is bromo | chlorodifluoromethyl | trifluoromethyl | $Y^1$ is CH, $Y^2$ is CH, $Y^3$ is N |
| P.2965 | $X^1$ is chloro, $X^2$ is CH, $X^3$ is bromo | difluoromethyl | bromo | $Y^1$ is CH, $Y^2$ is CH, $Y^3$ is N |
| P.2966 | $X^1$ is chloro, $X^2$ is CH, $X^3$ is bromo | difluoromethyl | chloro | $Y^1$ is CH, $Y^2$ is CH, $Y^3$ is N |
| P.2967 | $X^1$ is chloro, $X^2$ is CH, $X^3$ is bromo | difluoromethyl | cyano | $Y^1$ is CH, $Y^2$ is CH, $Y^3$ is N |
| P.2968 | $X^1$ is chloro, $X^2$ is CH, $X^3$ is bromo | difluoromethyl | cyclopropyl | $Y^1$ is CH, $Y^2$ is CH, $Y^3$ is N |
| P.2969 | $X^1$ is chloro, $X^2$ is CH, $X^3$ is bromo | difluoromethyl | ethyl | $Y^1$ is CH, $Y^2$ is CH, $Y^3$ is N |
| P.2970 | $X^1$ is chloro, $X^2$ is CH, $X^3$ is bromo | difluoromethyl | fluoro | $Y^1$ is CH, $Y^2$ is CH, $Y^3$ is N |
| P.2971 | $X^1$ is chloro, $X^2$ is CH, $X^3$ is bromo | difluoromethyl | hydrogen | $Y^1$ is CH, $Y^2$ is CH, $Y^3$ is N |
| P.2972 | $X^1$ is chloro, $X^2$ is CH, $X^3$ is bromo | difluoromethyl | methoxy | $Y^1$ is CH, $Y^2$ is CH, $Y^3$ is N |
| P.2973 | $X^1$ is chloro, $X^2$ is CH, $X^3$ is bromo | difluoromethyl | methyl | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.2974 | $X^1$ is chloro, $X^2$ is CH, $X^3$ is bromo | difluoromethyl | nitro | $Y^1$ is CH, $Y^2$ is CH, $Y^3$ is N |
| P.2975 | $X^1$ is chloro, $X^2$ is CH, $X^3$ is bromo | difluoromethyl | trifluoromethoxy | $Y^1$ is CH, $Y^2$ is CH, $Y^3$ is N |
| P.2976 | $X^1$ is chloro, $X^2$ is CH, $X^3$ is bromo | difluoromethyl | trifluoromethyl | $Y^1$ is CH, $Y^2$ is CH, $Y^3$ is N |
| P.2977 | $X^1$ is chloro, $X^2$ is CH, $X^3$ is bromo | trifluoromethyl | bromo | $Y^1$ is CH, $Y^2$ is CH, $Y^3$ is N |
| P.2978 | $X^1$ is chloro, $X^2$ is CH, $X^3$ is bromo | trifluoromethyl | chloro | $Y^1$ is CH, $Y^2$ is CH, $Y^3$ is N |
| P.2979 | $X^1$ is chloro, $X^2$ is CH, $X^3$ is bromo | trifluoromethyl | cyano | $Y^1$ is CH, $Y^2$ is CH, $Y^3$ is N |
| P.2980 | $X^1$ is chloro, $X^2$ is CH, $X^3$ is bromo | trifluoromethyl | cyclopropyl | $Y^1$ is CH, $Y^2$ is CH, $Y^3$ is N |
| P.2981 | $X^1$ is chloro, $X^2$ is CH, $X^3$ is bromo | trifluoromethyl | ethyl | $Y^1$ is CH, $Y^2$ is CH, $Y^3$ is N |
| P.2982 | $X^1$ is chloro, $X^2$ is CH, $X^3$ is bromo | trifluoromethyl | fluoro | $Y^1$ is CH, $Y^2$ is CH, $Y^3$ is N |
| P.2983 | $X^1$ is chloro, $X^2$ is CH, $X^3$ is bromo | trifluoromethyl | hydrogen | $Y^1$ is CH, $Y^2$ is CH, $Y^3$ is N |
| P.2984 | $X^1$ is chloro, $X^2$ is CH, $X^3$ is bromo | trifluoromethyl | methoxy | $Y^1$ is CH, $Y^2$ is CH, $Y^3$ is N |
| P.2985 | $X^1$ is chloro, $X^2$ is CH, $X^3$ is bromo | trifluoromethyl | methyl | $Y^1$ is CH, $Y^2$ is CH, $Y^3$ is N |
| P.2986 | $X^1$ is chloro, $X^2$ is CH, $X^3$ is bromo | trifluoromethyl | nitro | $Y^1$ is CH, $Y^2$ is CH, $Y^3$ is N |
| P.2987 | $X^1$ is chloro, $X^2$ is CH, $X^3$ is bromo | trifluoromethyl | trifluoromethoxy | $Y^1$ is CH, $Y^2$ is CH, $Y^3$ is N |
| P.2988 | $X^1$ is chloro, $X^2$ is CH, $X^3$ is bromo | trifluoromethyl | trifluoromethyl | $Y^1$ is CH, $Y^2$ is CH, $Y^3$ is N |
| P.2989 | $X^1$ is chloro, $X^2$ is CH, $X^3$ is bromo | chlorodifluoromethyl | bromo | $Y^1$ is CH, $Y^2$ is CH, $Y^3$ is N |
| P.2990 | $X^1$ is chloro, $X^2$ is CH, $X^3$ is bromo | chlorodifluoromethyl | chloro | $Y^1$ is CH, $Y^2$ is CH, $Y^3$ is N |
| P.2991 | $X^1$ is chloro, $X^2$ is CH, $X^3$ is bromo | chlorodifluoromethyl | cyano | $Y^1$ is CH, $Y^2$ is CH, $Y^3$ is N |
| P.2992 | $X^1$ is chloro, $X^2$ is CH, $X^3$ is bromo | chlorodifluoromethyl | cyclopropyl | $Y^1$ is CH, $Y^2$ is CH, $Y^3$ is N |
| P.2993 | $X^1$ is chloro, $X^2$ is CH, $X^3$ is bromo | chlorodifluoromethyl | ethyl | $Y^1$ is CH, $Y^2$ is CH, $Y^3$ is N |
| P.2994 | $X^1$ is chloro, $X^2$ is CH, $X^3$ is bromo | chlorodifluoromethyl | fluoro | $Y^1$ is CH, $Y^2$ is CH, $Y^3$ is N |
| P.2995 | $X^1$ is chloro, $X^2$ is CH, $X^3$ is bromo | chlorodifluoromethyl | hydrogen | $Y^1$ is CH, $Y^2$ is CH, $Y^3$ is N |
| P.2996 | $X^1$ is chloro, $X^2$ is CH, $X^3$ is bromo | chlorodifluoromethyl | methoxy | $Y^1$ is CH, $Y^2$ is CH, $Y^3$ is N |
| P.2997 | $X^1$ is chloro, $X^2$ is CH, $X^3$ is bromo | chlorodifluoromethyl | methyl | $Y^1$ is CH, $Y^2$ is CH, $Y^3$ is N |
| P.2998 | $X^1$ is chloro, $X^2$ is CH, $X^3$ is bromo | chlorodifluoromethyl | nitro | $Y^1$ is CH, $Y^2$ is CH, $Y^3$ is N |
| P.2999 | $X^1$ is chloro, $X^2$ is CH, $X^3$ is bromo | chlorodifluoromethyl | trifluoromethoxy | $Y^1$ is CH, $Y^2$ is CH, $Y^3$ is N |
| P.3000 | $X^1$ is chloro, $X^2$ is CH, $X^3$ is bromo | chlorodifluoromethyl | trifluoromethyl | $Y^1$ is CH, $Y^2$ is CH, $Y^3$ is N |
| P.3001 | $X^1$ is chloro, $X^2$ is CH, $X^3$ is bromo | difluoromethyl | bromo | $Y^1$ is CH, $Y^2$ is CH, $Y^3$ is N |
| P.3002 | $X^1$ is chloro, $X^2$ is CH, $X^3$ is bromo | difluoromethyl | chloro | $Y^1$ is CH, $Y^2$ is CH, $Y^3$ is N |
| P.3003 | $X^1$ is chloro, $X^2$ is CH, $X^3$ is bromo | difluoromethyl | cyano | $Y^1$ is CH, $Y^2$ is CH, $Y^3$ is N |
| P.3004 | $X^1$ is chloro, $X^2$ is CH, $X^3$ is bromo | difluoromethyl | cyclopropyl | $Y^1$ is CH, $Y^2$ is CH, $Y^3$ is N |
| P.3005 | $X^1$ is chloro, $X^2$ is CH, $X^3$ is bromo | difluoromethyl | ethyl | $Y^1$ is CH, $Y^2$ is CH, $Y^3$ is N |
| P.3006 | $X^1$ is chloro, $X^2$ is CH, $X^3$ is bromo | difluoromethyl | fluoro | $Y^1$ is CH, $Y^2$ is CH, $Y^3$ is N |
| P.3007 | $X^1$ is chloro, $X^2$ is CH, $X^3$ is bromo | difluoromethyl | hydrogen | $Y^1$ is CH, $Y^2$ is CH, $Y^3$ is N |
| P.3008 | $X^1$ is chloro, $X^2$ is CH, $X^3$ is bromo | difluoromethyl | methoxy | $Y^1$ is CH, $Y^2$ is CH, $Y^3$ is N |
| P.3009 | $X^1$ is chloro, $X^2$ is CH, $X^3$ is bromo | difluoromethyl | methyl | $Y^1$ is CH, $Y^2$ is CH, $Y^3$ is N |
| P.3010 | $X^1$ is chloro, $X^2$ is CH, $X^3$ is bromo | difluoromethyl | nitro | $Y^1$ is CH, $Y^2$ is CH, $Y^3$ is N |
| P.3011 | $X^1$ is chloro, $X^2$ is CH, $X^3$ is bromo | difluoromethyl | trifluoromethoxy | $Y^1$ is CH, $Y^2$ is CH, $Y^3$ is N |
| P.3012 | $X^1$ is chloro, $X^2$ is CH, $X^3$ is bromo | difluoromethyl | trifluoromethyl | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.3013 | $X^1$ is chloro, $X^2$ is CH, $X^3$ is bromo | trifluoromethyl | bromo | $Y^1$ is CH, $Y^2$ is CH, $Y^3$ is N |
| P.3014 | $X^1$ is chloro, $X^2$ is CH, $X^3$ is bromo | trifluoromethyl | chloro | $Y^1$ is CH, $Y^2$ is CH, $Y^3$ is N |
| P.3015 | $X^1$ is chloro, $X^2$ is CH, $X^3$ is bromo | trifluoromethyl | cyano | $Y^1$ is CH, $Y^2$ is CH, $Y^3$ is N |
| P.3016 | $X^1$ is chloro, $X^2$ is CH, $X^3$ is bromo | trifluoromethyl | cyclopropyl | $Y^1$ is CH, $Y^2$ is CH, $Y^3$ is N |
| P.3017 | $X^1$ is chloro, $X^2$ is CH, $X^3$ is bromo | trifluoromethyl | ethyl | $Y^1$ is CH, $Y^2$ is CH, $Y^3$ is N |
| P.3018 | $X^1$ is chloro, $X^2$ is CH, $X^3$ is bromo | trifluoromethyl | fluoro | $Y^1$ is CH, $Y^2$ is CH, $Y^3$ is N |
| P.3019 | $X^1$ is chloro, $X^2$ is CH, $X^3$ is bromo | trifluoromethyl | hydrogen | $Y^1$ is CH, $Y^2$ is CH, $Y^3$ is N |
| P.3020 | $X^1$ is chloro, $X^2$ is CH, $X^3$ is bromo | trifluoromethyl | methoxy | $Y^1$ is CH, $Y^2$ is CH, $Y^3$ is N |
| P.3021 | $X^1$ is chloro, $X^2$ is CH, $X^3$ is bromo | trifluoromethyl | methyl | $Y^1$ is CH, $Y^2$ is CH, $Y^3$ is N |
| P.3022 | $X^1$ is chloro, $X^2$ is CH, $X^3$ is bromo | trifluoromethyl | nitro | $Y^1$ is CH, $Y^2$ is CH, $Y^3$ is N |
| P.3023 | $X^1$ is chloro, $X^2$ is CH, $X^3$ is bromo | trifluoromethyl | trifluoromethoxy | $Y^1$ is CH, $Y^2$ is CH, $Y^3$ is N |
| P.3024 | $X^1$ is chloro, $X^2$ is CH, $X^3$ is bromo | trifluoromethyl | trifluoromethyl | $Y^1$ is CH, $Y^2$ is CH, $Y^3$ is N |
| P.3025 | $X^1$ is chloro, $X^2$ is C—Cl, $X^3$ is trifluoromethyl | chlorodifluoromethyl | bromo | $Y^1$ is CH, $Y^2$ is CH, $Y^3$ is N |
| P.3026 | $X^1$ is chloro, $X^2$ is C—Cl, $X^3$ is trifluoromethyl | chlorodifluoromethyl | chloro | $Y^1$ is CH, $Y^2$ is CH, $Y^3$ is N |
| P.3027 | $X^1$ is chloro, $X^2$ is C—Cl, $X^3$ is trifluoromethyl | chlorodifluoromethyl | cyano | $Y^1$ is CH, $Y^2$ is CH, $Y^3$ is N |
| P.3028 | $X^1$ is chloro, $X^2$ is C—Cl, $X^3$ is trifluoromethyl | chlorodifluoromethyl | cyclopropyl | $Y^1$ is CH, $Y^2$ is CH, $Y^3$ is N |
| P.3029 | $X^1$ is chloro, $X^2$ is C—Cl, $X^3$ is trifluoromethyl | chlorodifluoromethyl | ethyl | $Y^1$ is CH, $Y^2$ is CH, $Y^3$ is N |
| P.3030 | $X^1$ is chloro, $X^2$ is C—Cl, $X^3$ is trifluoromethyl | chlorodifluoromethyl | fluoro | $Y^1$ is CH, $Y^2$ is CH, $Y^3$ is N |
| P.3031 | $X^1$ is chloro, $X^2$ is C—Cl, $X^3$ is trifluoromethyl | chlorodifluoromethyl | hydrogen | $Y^1$ is CH, $Y^2$ is CH, $Y^3$ is N |
| P.3032 | $X^1$ is chloro, $X^2$ is C—Cl, $X^3$ is trifluoromethyl | chlorodifluoromethyl | methoxy | $Y^1$ is CH, $Y^2$ is CH, $Y^3$ is N |
| P.3033 | $X^1$ is chloro, $X^2$ is C—Cl, $X^3$ is trifluoromethyl | chlorodifluoromethyl | methyl | $Y^1$ is CH, $Y^2$ is CH, $Y^3$ is N |
| P.3034 | $X^1$ is chloro, $X^2$ is C—Cl, $X^3$ is trifluoromethyl | chlorodifluoromethyl | nitro | $Y^1$ is CH, $Y^2$ is CH, $Y^3$ is N |
| P.3035 | $X^1$ is chloro, $X^2$ is C—Cl, $X^3$ is trifluoromethyl | chlorodifluoromethyl | trifluoromethoxy | $Y^1$ is CH, $Y^2$ is CH, $Y^3$ is N |
| P.3036 | $X^1$ is chloro, $X^2$ is C—Cl, $X^3$ is trifluoromethyl | chlorodifluoromethyl | trifluoromethyl | $Y^1$ is CH, $Y^2$ is CH, $Y^3$ is N |
| P.3037 | $X^1$ is chloro, $X^2$ is C—Cl, $X^3$ is trifluoromethyl | difluoromethyl | bromo | $Y^1$ is CH, $Y^2$ is CH, $Y^3$ is N |
| P.3038 | $X^1$ is chloro, $X^2$ is C—Cl, $X^3$ is trifluoromethyl | difluoromethyl | chloro | $Y^1$ is CH, $Y^2$ is CH, $Y^3$ is N |
| P.3039 | $X^1$ is chloro, $X^2$ is C—Cl, $X^3$ is trifluoromethyl | difluoromethyl | cyano | $Y^1$ is CH, $Y^2$ is CH, $Y^3$ is N |
| P.3040 | $X^1$ is chloro, $X^2$ is C—Cl, $X^3$ is trifluoromethyl | difluoromethyl | cyclopropyl | $Y^1$ is CH, $Y^2$ is CH, $Y^3$ is N |
| P.3041 | $X^1$ is chloro, $X^2$ is C—Cl, $X^3$ is trifluoromethyl | difluoromethyl | ethyl | $Y^1$ is CH, $Y^2$ is CH, $Y^3$ is N |
| P.3042 | $X^1$ is chloro, $X^2$ is C—Cl, $X^3$ is trifluoromethyl | difluoromethyl | fluoro | $Y^1$ is CH, $Y^2$ is CH, $Y^3$ is N |
| P.3043 | $X^1$ is chloro, $X^2$ is C—Cl, $X^3$ is trifluoromethyl | difluoromethyl | hydrogen | $Y^1$ is CH, $Y^2$ is CH, $Y^3$ is N |
| P.3044 | $X^1$ is chloro, $X^2$ is C—Cl, $X^3$ is trifluoromethyl | difluoromethyl | methoxy | $Y^1$ is CH, $Y^2$ is CH, $Y^3$ is N |
| P.3045 | $X^1$ is chloro, $X^2$ is C—Cl, $X^3$ is trifluoromethyl | difluoromethyl | methyl | $Y^1$ is CH, $Y^2$ is CH, $Y^3$ is N |
| P.3046 | $X^1$ is chloro, $X^2$ is C—Cl, $X^3$ is trifluoromethyl | difluoromethyl | nitro | $Y^1$ is CH, $Y^2$ is CH, $Y^3$ is N |
| P.3047 | $X^1$ is chloro, $X^2$ is C—Cl, $X^3$ is trifluoromethyl | difluoromethyl | trifluoromethoxy | $Y^1$ is CH, $Y^2$ is CH, $Y^3$ is N |
| P.3048 | $X^1$ is chloro, $X^2$ is C—Cl, $X^3$ is trifluoromethyl | difluoromethyl | trifluoromethyl | $Y^1$ is CH, $Y^2$ is CH, $Y^3$ is N |
| P.3049 | $X^1$ is chloro, $X^2$ is C—Cl, $X^3$ is trifluoromethyl | trifluoromethyl | bromo | $Y^1$ is CH, $Y^2$ is CH, $Y^3$ is N |
| P.3050 | $X^1$ is chloro, $X^2$ is C—Cl, $X^3$ is trifluoromethyl | trifluoromethyl | chloro | $Y^1$ is CH, $Y^2$ is CH, $Y^3$ is N |
| P.3051 | $X^1$ is chloro, $X^2$ is C—Cl, $X^3$ is trifluoromethyl | trifluoromethyl | cyano | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.3052 | $X^1$ is chloro, $X^2$ is C—Cl, $X^3$ is trifluoromethyl | trifluoromethyl | cyclopropyl | $Y^1$ is CH, $Y^2$ is CH, $Y^3$ is N |
| P.3053 | $X^1$ is chloro, $X^2$ is C—Cl, $X^3$ is trifluoromethyl | trifluoromethyl | ethyl | $Y^1$ is CH, $Y^2$ is CH, $Y^3$ is N |
| P.3054 | $X^1$ is chloro, $X^2$ is C—Cl, $X^3$ is trifluoromethyl | trifluoromethyl | fluoro | $Y^1$ is CH, $Y^2$ is CH, $Y^3$ is N |
| P.3055 | $X^1$ is chloro, $X^2$ is C—Cl, $X^3$ is trifluoromethyl | trifluoromethyl | hydrogen | $Y^1$ is CH, $Y^2$ is CH, $Y^3$ is N |
| P.3056 | $X^1$ is chloro, $X^2$ is C—Cl, $X^3$ is trifluoromethyl | trifluoromethyl | methoxy | $Y^1$ is CH, $Y^2$ is CH, $Y^3$ is N |
| P.3057 | $X^1$ is chloro, $X^2$ is C—Cl, $X^3$ is trifluoromethyl | trifluoromethyl | methyl | $Y^1$ is CH, $Y^2$ is CH, $Y^3$ is N |
| P.3058 | $X^1$ is chloro, $X^2$ is C—Cl, $X^3$ is trifluoromethyl | trifluoromethyl | nitro | $Y^1$ is CH, $Y^2$ is CH, $Y^3$ is N |
| P.3059 | $X^1$ is chloro, $X^2$ is C—Cl, $X^3$ is trifluoromethyl | trifluoromethyl | trifluoromethoxy | $Y^1$ is CH, $Y^2$ is CH, $Y^3$ is N |
| P.3060 | $X^1$ is chloro, $X^2$ is C—Cl, $X^3$ is trifluoromethyl | trifluoromethyl | trifluoromethyl | $Y^1$ is CH, $Y^2$ is CH, $Y^3$ is N |
| P.3061 | $X^1$ is trifluoromethyl, $X^2$ is CH, $X^3$ is trifluoromethyl | chlorodifluoromethyl | bromo | $Y^1$ is CH, $Y^2$ is CH, $Y^3$ is N |
| P.3062 | $X^1$ is trifluoromethyl, $X^2$ is CH, $X^3$ is trifluoromethyl | chlorodifluoromethyl | chloro | $Y^1$ is CH, $Y^2$ is CH, $Y^3$ is N |
| P.3063 | $X^1$ is trifluoromethyl, $X^2$ is CH, $X^3$ is trifluoromethyl | chlorodifluoromethyl | cyano | $Y^1$ is CH, $Y^2$ is CH, $Y^3$ is N |
| P.3064 | $X^1$ is trifluoromethyl, $X^2$ is CH, $X^3$ is trifluoromethyl | chlorodifluoromethyl | cyclopropyl | $Y^1$ is CH, $Y^2$ is CH, $Y^3$ is N |
| P.3065 | $X^1$ is trifluoromethyl, $X^2$ is CH, $X^3$ is trifluoromethyl | chlorodifluoromethyl | ethyl | $Y^1$ is CH, $Y^2$ is CH, $Y^3$ is N |
| P.3066 | $X^1$ is trifluoromethyl, $X^2$ is CH, $X^3$ is trifluoromethyl | chlorodifluoromethyl | fluoro | $Y^1$ is CH, $Y^2$ is CH, $Y^3$ is N |
| P.3067 | $X^1$ is trifluoromethyl, $X^2$ is CH, $X^3$ is trifluoromethyl | chlorodifluoromethyl | hydrogen | $Y^1$ is CH, $Y^2$ is CH, $Y^3$ is N |
| P.3068 | $X^1$ is trifluoromethyl, $X^2$ is CH, $X^3$ is trifluoromethyl | chlorodifluoromethyl | methoxy | $Y^1$ is CH, $Y^2$ is CH, $Y^3$ is N |
| P.3069 | $X^1$ is trifluoromethyl, $X^2$ is CH, $X^3$ is trifluoromethyl | chlorodifluoromethyl | methyl | $Y^1$ is CH, $Y^2$ is CH, $Y^3$ is N |
| P.3070 | $X^1$ is trifluoromethyl, $X^2$ is CH, $X^3$ is trifluoromethyl | chlorodifluoromethyl | nitro | $Y^1$ is CH, $Y^2$ is CH, $Y^3$ is N |
| P.3071 | $X^1$ is trifluoromethyl, $X^2$ is CH, $X^3$ is trifluoromethyl | chlorodifluoromethyl | trifluoromethoxy | $Y^1$ is CH, $Y^2$ is CH, $Y^3$ is N |
| P.3072 | $X^1$ is trifluoromethyl, $X^2$ is CH, $X^3$ is trifluoromethyl | chlorodifluoromethyl | trifluoromethyl | $Y^1$ is CH, $Y^2$ is CH, $Y^3$ is N |
| P.3073 | $X^1$ is trifluoromethyl, $X^2$ is CH, $X^3$ is trifluoromethyl | difluoromethyl | bromo | $Y^1$ is CH, $Y^2$ is CH, $Y^3$ is N |
| P.3074 | $X^1$ is trifluoromethyl, $X^2$ is CH, $X^3$ is trifluoromethyl | difluoromethyl | chloro | $Y^1$ is CH, $Y^2$ is CH, $Y^3$ is N |
| P.3075 | $X^1$ is trifluoromethyl, $X^2$ is CH, $X^3$ is trifluoromethyl | difluoromethyl | cyano | $Y^1$ is CH, $Y^2$ is CH, $Y^3$ is N |
| P.3076 | $X^1$ is trifluoromethyl, $X^2$ is CH, $X^3$ is trifluoromethyl | difluoromethyl | cyclopropyl | $Y^1$ is CH, $Y^2$ is CH, $Y^3$ is N |
| P.3077 | $X^1$ is trifluoromethyl, $X^2$ is CH, $X^3$ is trifluoromethyl | difluoromethyl | ethyl | $Y^1$ is CH, $Y^2$ is CH, $Y^3$ is N |
| P.3078 | $X^1$ is trifluoromethyl, $X^2$ is CH, $X^3$ is trifluoromethyl | difluoromethyl | fluoro | $Y^1$ is CH, $Y^2$ is CH, $Y^3$ is N |
| P.3079 | $X^1$ is trifluoromethyl, $X^2$ is CH, $X^3$ is trifluoromethyl | difluoromethyl | hydrogen | $Y^1$ is CH, $Y^2$ is CH, $Y^3$ is N |
| P.3080 | $X^1$ is trifluoromethyl, $X^2$ is CH, $X^3$ is trifluoromethyl | difluoromethyl | methoxy | $Y^1$ is CH, $Y^2$ is CH, $Y^3$ is N |
| P.3081 | $X^1$ is trifluoromethyl, $X^2$ is CH, $X^3$ is trifluoromethyl | difluoromethyl | methyl | $Y^1$ is CH, $Y^2$ is CH, $Y^3$ is N |
| P.3082 | $X^1$ is trifluoromethyl, $X^2$ is CH, $X^3$ is trifluoromethyl | difluoromethyl | nitro | $Y^1$ is CH, $Y^2$ is CH, $Y^3$ is N |
| P.3083 | $X^1$ is trifluoromethyl, $X^2$ is CH, $X^3$ is trifluoromethyl | difluoromethyl | trifluoromethoxy | $Y^1$ is CH, $Y^2$ is CH, $Y^3$ is N |
| P.3084 | $X^1$ is trifluoromethyl, $X^2$ is CH, $X^3$ is trifluoromethyl | difluoromethyl | trifluoromethyl | $Y^1$ is CH, $Y^2$ is CH, $Y^3$ is N |
| P.3085 | $X^1$ is trifluoromethyl, $X^2$ is CH, $X^3$ is trifluoromethyl | trifluoromethyl | bromo | $Y^1$ is CH, $Y^2$ is CH, $Y^3$ is N |
| P.3086 | $X^1$ is trifluoromethyl, $X^2$ is CH, $X^3$ is trifluoromethyl | trifluoromethyl | chloro | $Y^1$ is CH, $Y^2$ is CH, $Y^3$ is N |
| P.3087 | $X^1$ is trifluoromethyl, $X^2$ is CH, $X^3$ is trifluoromethyl | trifluoromethyl | cyano | $Y^1$ is CH, $Y^2$ is CH, $Y^3$ is N |
| P.3088 | $X^1$ is trifluoromethyl, $X^2$ is CH, $X^3$ is trifluoromethyl | trifluoromethyl | cyclopropyl | $Y^1$ is CH, $Y^2$ is CH, $Y^3$ is N |
| P.3089 | $X^1$ is trifluoromethyl, $X^2$ is CH, $X^3$ is trifluoromethyl | trifluoromethyl | ethyl | $Y^1$ is CH, $Y^2$ is CH, $Y^3$ is N |
| P.3090 | $X^1$ is trifluoromethyl, $X^2$ is CH, $X^3$ is trifluoromethyl | trifluoromethyl | fluoro | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.3091 | $X^1$ is trifluoromethyl, $X^2$ is CH, $X^3$ is trifluoromethyl | trifluoromethyl | hydrogen | $Y^1$ is CH, $Y^2$ is CH, $Y^3$ is N |
| P.3092 | $X^1$ is trifluoromethyl, $X^2$ is CH, $X^3$ is trifluoromethyl | trifluoromethyl | methoxy | $Y^1$ is CH, $Y^2$ is CH, $Y^3$ is N |
| P.3093 | $X^1$ is trifluoromethyl, $X^2$ is CH, $X^3$ is trifluoromethyl | trifluoromethyl | methyl | $Y^1$ is CH, $Y^2$ is CH, $Y^3$ is N |
| P.3094 | $X^1$ is trifluoromethyl, $X^2$ is CH, $X^3$ is trifluoromethyl | trifluoromethyl | nitro | $Y^1$ is CH, $Y^2$ is CH, $Y^3$ is N |
| P.3095 | $X^1$ is trifluoromethyl, $X^2$ is CH, $X^3$ is trifluoromethyl | trifluoromethyl | trifluoromethoxy | $Y^1$ is CH, $Y^2$ is CH, $Y^3$ is N |
| P.3096 | $X^1$ is trifluoromethyl, $X^2$ is CH, $X^3$ is trifluoromethyl | trifluoromethyl | trifluoromethyl | $Y^1$ is CH, $Y^2$ is CH, $Y^3$ is N |
| P.3097 | $X^1$ is trifluoromethyl, $X^2$ is CH, $X^3$ is trifluoromethyl | chlorodifluoromethyl | bromo | $Y^1$ is CH, $Y^2$ is CH, $Y^3$ is N |
| P.3098 | $X^1$ is trifluoromethyl, $X^2$ is CH, $X^3$ is trifluoromethyl | chlorodifluoromethyl | chloro | $Y^1$ is CH, $Y^2$ is CH, $Y^3$ is N |
| P.3099 | $X^1$ is trifluoromethyl, $X^2$ is CH, $X^3$ is trifluoromethyl | chlorodifluoromethyl | cyano | $Y^1$ is CH, $Y^2$ is CH, $Y^3$ is N |
| P.3100 | $X^1$ is trifluoromethyl, $X^2$ is CH, $X^3$ is trifluoromethyl | chlorodifluoromethyl | cyclopropyl | $Y^1$ is CH, $Y^2$ is CH, $Y^3$ is N |
| P.3101 | $X^1$ is trifluoromethyl, $X^2$ is CH, $X^3$ is trifluoromethyl | chlorodifluoromethyl | ethyl | $Y^1$ is CH, $Y^2$ is CH, $Y^3$ is N |
| P.3102 | $X^1$ is trifluoromethyl, $X^2$ is CH, $X^3$ is trifluoromethyl | chlorodifluoromethyl | fluoro | $Y^1$ is CH, $Y^2$ is CH, $Y^3$ is N |
| P.3103 | $X^1$ is trifluoromethyl, $X^2$ is CH, $X^3$ is trifluoromethyl | chlorodifluoromethyl | hydrogen | $Y^1$ is CH, $Y^2$ is CH, $Y^3$ is N |
| P.3104 | $X^1$ is trifluoromethyl, $X^2$ is CH, $X^3$ is trifluoromethyl | chlorodifluoromethyl | methoxy | $Y^1$ is CH, $Y^2$ is CH, $Y^3$ is N |
| P.3105 | $X^1$ is trifluoromethyl, $X^2$ is CH, $X^3$ is trifluoromethyl | chlorodifluoromethyl | methyl | $Y^1$ is CH, $Y^2$ is CH, $Y^3$ is N |
| P.3106 | $X^1$ is trifluoromethyl, $X^2$ is CH, $X^3$ is trifluoromethyl | chlorodifluoromethyl | nitro | $Y^1$ is CH, $Y^2$ is CH, $Y^3$ is N |
| P.3107 | $X^1$ is trifluoromethyl, $X^2$ is CH, $X^3$ is trifluoromethyl | chlorodifluoromethyl | trifluoromethoxy | $Y^1$ is CH, $Y^2$ is CH, $Y^3$ is N |
| P.3108 | $X^1$ is trifluoromethyl, $X^2$ is CH, $X^3$ is trifluoromethyl | chlorodifluoromethyl | trifluoromethyl | $Y^1$ is CH, $Y^2$ is CH, $Y^3$ is N |
| P.3109 | $X^1$ is trifluoromethyl, $X^2$ is CH, $X^3$ is trifluoromethyl | difluoromethyl | bromo | $Y^1$ is CH, $Y^2$ is CH, $Y^3$ is N |
| P.3110 | $X^1$ is trifluoromethyl, $X^2$ is CH, $X^3$ is trifluoromethyl | difluoromethyl | chloro | $Y^1$ is CH, $Y^2$ is CH, $Y^3$ is N |
| P.3111 | $X^1$ is trifluoromethyl, $X^2$ is CH, $X^3$ is trifluoromethyl | difluoromethyl | cyano | $Y^1$ is CH, $Y^2$ is CH, $Y^3$ is N |
| P.3112 | $X^1$ is trifluoromethyl, $X^2$ is CH, $X^3$ is trifluoromethyl | difluoromethyl | cyclopropyl | $Y^1$ is CH, $Y^2$ is CH, $Y^3$ is N |
| P.3113 | $X^1$ is trifluoromethyl, $X^2$ is CH, $X^3$ is trifluoromethyl | difluoromethyl | ethyl | $Y^1$ is CH, $Y^2$ is CH, $Y^3$ is N |
| P.3114 | $X^1$ is trifluoromethyl, $X^2$ is CH, $X^3$ is trifluoromethyl | difluoromethyl | fluoro | $Y^1$ is CH, $Y^2$ is CH, $Y^3$ is N |
| P.3115 | $X^1$ is trifluoromethyl, $X^2$ is CH, $X^3$ is trifluoromethyl | difluoromethyl | hydrogen | $Y^1$ is CH, $Y^2$ is CH, $Y^3$ is N |
| P.3116 | $X^1$ is trifluoromethyl, $X^2$ is CH, $X^3$ is trifluoromethyl | difluoromethyl | methoxy | $Y^1$ is CH, $Y^2$ is CH, $Y^3$ is N |
| P.3117 | $X^1$ is trifluoromethyl, $X^2$ is CH, $X^3$ is trifluoromethyl | difluoromethyl | methyl | $Y^1$ is CH, $Y^2$ is CH, $Y^3$ is N |
| P.3118 | $X^1$ is trifluoromethyl, $X^2$ is CH, $X^3$ is trifluoromethyl | difluoromethyl | nitro | $Y^1$ is CH, $Y^2$ is CH, $Y^3$ is N |
| P.3119 | $X^1$ is trifluoromethyl, $X^2$ is CH, $X^3$ is trifluoromethyl | difluoromethyl | trifluoromethoxy | $Y^1$ is CH, $Y^2$ is CH, $Y^3$ is N |
| P.3120 | $X^1$ is trifluoromethyl, $X^2$ is CH, $X^3$ is trifluoromethyl | difluoromethyl | trifluoromethyl | $Y^1$ is CH, $Y^2$ is CH, $Y^3$ is N |
| P.3121 | $X^1$ is trifluoromethyl, $X^2$ is CH, $X^3$ is trifluoromethyl | trifluoromethyl | bromo | $Y^1$ is CH, $Y^2$ is CH, $Y^3$ is N |
| P.3122 | $X^1$ is trifluoromethyl, $X^2$ is CH, $X^3$ is trifluoromethyl | trifluoromethyl | chloro | $Y^1$ is CH, $Y^2$ is CH, $Y^3$ is N |
| P.3123 | $X^1$ is trifluoromethyl, $X^2$ is CH, $X^3$ is trifluoromethyl | trifluoromethyl | cyano | $Y^1$ is CH, $Y^2$ is CH, $Y^3$ is N |
| P.3124 | $X^1$ is trifluoromethyl, $X^2$ is CH, $X^3$ is trifluoromethyl | trifluoromethyl | cyclopropyl | $Y^1$ is CH, $Y^2$ is CH, $Y^3$ is N |
| P.3125 | $X^1$ is trifluoromethyl, $X^2$ is CH, $X^3$ is trifluoromethyl | trifluoromethyl | ethyl | $Y^1$ is CH, $Y^2$ is CH, $Y^3$ is N |
| P.3126 | $X^1$ is trifluoromethyl, $X^2$ is CH, $X^3$ is trifluoromethyl | trifluoromethyl | fluoro | $Y^1$ is CH, $Y^2$ is CH, $Y^3$ is N |
| P.3127 | $X^1$ is trifluoromethyl, $X^2$ is CH, $X^3$ is trifluoromethyl | trifluoromethyl | hydrogen | $Y^1$ is CH, $Y^2$ is CH, $Y^3$ is N |
| P.3128 | $X^1$ is trifluoromethyl, $X^2$ is CH, $X^3$ is trifluoromethyl | trifluoromethyl | methoxy | $Y^1$ is CH, $Y^2$ is CH, $Y^3$ is N |
| P.3129 | $X^1$ is trifluoromethyl, $X^2$ is CH, $X^3$ is trifluoromethyl | trifluoromethyl | methyl | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.3130 | $X^1$ is trifluoromethyl, $X^2$ is CH, $X^3$ is trifluoromethyl | trifluoromethyl | nitro | $Y^1$ is CH, $Y^2$ is CH, $Y^3$ is N |
| P.3131 | $X^1$ is trifluoromethyl, $X^2$ is CH, $X^3$ is trifluoromethyl | trifluoromethyl | trifluoromethoxy | $Y^1$ is CH, $Y^2$ is CH, $Y^3$ is N |
| P.3132 | $X^1$ is trifluoromethyl, $X^2$ is CH, $X^3$ is trifluoromethyl | trifluoromethyl | trifluoromethyl | $Y^1$ is CH, $Y^2$ is CH, $Y^3$ is N |
| P.3133 | $X^1$ is trifluoromethyl, $X^2$ is CH, $X^3$ is hydrogen | chlorodifluoromethyl | bromo | $Y^1$ is CH, $Y^2$ is CH, $Y^3$ is N |
| P.3134 | $X^1$ is trifluoromethyl, $X^2$ is CH, $X^3$ is hydrogen | chlorodifluoromethyl | chloro | $Y^1$ is CH, $Y^2$ is CH, $Y^3$ is N |
| P.3135 | $X^1$ is trifluoromethyl, $X^2$ is CH, $X^3$ is hydrogen | chlorodifluoromethyl | cyano | $Y^1$ is CH, $Y^2$ is CH, $Y^3$ is N |
| P.3136 | $X^1$ is trifluoromethyl, $X^2$ is CH, $X^3$ is hydrogen | chlorodifluoromethyl | cyclopropyl | $Y^1$ is CH, $Y^2$ is CH, $Y^3$ is N |
| P.3137 | $X^1$ is trifluoromethyl, $X^2$ is CH, $X^3$ is hydrogen | chlorodifluoromethyl | ethyl | $Y^1$ is CH, $Y^2$ is CH, $Y^3$ is N |
| P.3138 | $X^1$ is trifluoromethyl, $X^2$ is CH, $X^3$ is hydrogen | chlorodifluoromethyl | fluoro | $Y^1$ is CH, $Y^2$ is CH, $Y^3$ is N |
| P.3139 | $X^1$ is trifluoromethyl, $X^2$ is CH, $X^3$ is hydrogen | chlorodifluoromethyl | hydrogen | $Y^1$ is CH, $Y^2$ is CH, $Y^3$ is N |
| P.3140 | $X^1$ is trifluoromethyl, $X^2$ is CH, $X^3$ is hydrogen | chlorodifluoromethyl | methoxy | $Y^1$ is CH, $Y^2$ is CH, $Y^3$ is N |
| P.3141 | $X^1$ is trifluoromethyl, $X^2$ is CH, $X^3$ is hydrogen | chlorodifluoromethyl | methyl | $Y^1$ is CH, $Y^2$ is CH, $Y^3$ is N |
| P.3142 | $X^1$ is trifluoromethyl, $X^2$ is CH, $X^3$ is hydrogen | chlorodifluoromethyl | nitro | $Y^1$ is CH, $Y^2$ is CH, $Y^3$ is N |
| P.3143 | $X^1$ is trifluoromethyl, $X^2$ is CH, $X^3$ is hydrogen | chlorodifluoromethyl | trifluoromethoxy | $Y^1$ is CH, $Y^2$ is CH, $Y^3$ is N |
| P.3144 | $X^1$ is trifluoromethyl, $X^2$ is CH, $X^3$ is hydrogen | chlorodifluoromethyl | trifluoromethyl | $Y^1$ is CH, $Y^2$ is CH, $Y^3$ is N |
| P.3145 | $X^1$ is trifluoromethyl, $X^2$ is CH, $X^3$ is hydrogen | difluoromethyl | bromo | $Y^1$ is CH, $Y^2$ is CH, $Y^3$ is N |
| P.3146 | $X^1$ is trifluoromethyl, $X^2$ is CH, $X^3$ is hydrogen | difluoromethyl | chloro | $Y^1$ is CH, $Y^2$ is CH, $Y^3$ is N |
| P.3147 | $X^1$ is trifluoromethyl, $X^2$ is CH, $X^3$ is hydrogen | difluoromethyl | cyano | $Y^1$ is CH, $Y^2$ is CH, $Y^3$ is N |
| P.3148 | $X^1$ is trifluoromethyl, $X^2$ is CH, $X^3$ is hydrogen | difluoromethyl | cyclopropyl | $Y^1$ is CH, $Y^2$ is CH, $Y^3$ is N |
| P.3149 | $X^1$ is trifluoromethyl, $X^2$ is CH, $X^3$ is hydrogen | difluoromethyl | ethyl | $Y^1$ is CH, $Y^2$ is CH, $Y^3$ is N |
| P.3150 | $X^1$ is trifluoromethyl, $X^2$ is CH, $X^3$ is hydrogen | difluoromethyl | fluoro | $Y^1$ is CH, $Y^2$ is CH, $Y^3$ is N |
| P.3151 | $X^1$ is trifluoromethyl, $X^2$ is CH, $X^3$ is hydrogen | difluoromethyl | hydrogen | $Y^1$ is CH, $Y^2$ is CH, $Y^3$ is N |
| P.3152 | $X^1$ is trifluoromethyl, $X^2$ is CH, $X^3$ is hydrogen | difluoromethyl | methoxy | $Y^1$ is CH, $Y^2$ is CH, $Y^3$ is N |
| P.3153 | $X^1$ is trifluoromethyl, $X^2$ is CH, $X^3$ is hydrogen | difluoromethyl | methyl | $Y^1$ is CH, $Y^2$ is CH, $Y^3$ is N |
| P.3154 | $X^1$ is trifluoromethyl, $X^2$ is CH, $X^3$ is hydrogen | difluoromethyl | nitro | $Y^1$ is CH, $Y^2$ is CH, $Y^3$ is N |
| P.3155 | $X^1$ is trifluoromethyl, $X^2$ is CH, $X^3$ is hydrogen | difluoromethyl | trifluoromethoxy | $Y^1$ is CH, $Y^2$ is CH, $Y^3$ is N |
| P.3156 | $X^1$ is trifluoromethyl, $X^2$ is CH, $X^3$ is hydrogen | difluoromethyl | trifluoromethyl | $Y^1$ is CH, $Y^2$ is CH, $Y^3$ is N |
| P.3157 | $X^1$ is trifluoromethyl, $X^2$ is CH, $X^3$ is hydrogen | trifluoromethyl | bromo | $Y^1$ is CH, $Y^2$ is CH, $Y^3$ is N |
| P.3158 | $X^1$ is trifluoromethyl, $X^2$ is CH, $X^3$ is hydrogen | trifluoromethyl | chloro | $Y^1$ is CH, $Y^2$ is CH, $Y^3$ is N |
| P.3159 | $X^1$ is trifluoromethyl, $X^2$ is CH, $X^3$ is hydrogen | trifluoromethyl | cyano | $Y^1$ is CH, $Y^2$ is CH, $Y^3$ is N |
| P.3160 | $X^1$ is trifluoromethyl, $X^2$ is CH, $X^3$ is hydrogen | trifluoromethyl | cyclopropyl | $Y^1$ is CH, $Y^2$ is CH, $Y^3$ is N |
| P.3161 | $X^1$ is trifluoromethyl, $X^2$ is CH, $X^3$ is hydrogen | trifluoromethyl | ethyl | $Y^1$ is CH, $Y^2$ is CH, $Y^3$ is N |
| P.3162 | $X^1$ is trifluoromethyl, $X^2$ is CH, $X^3$ is hydrogen | trifluoromethyl | fluoro | $Y^1$ is CH, $Y^2$ is CH, $Y^3$ is N |
| P.3163 | $X^1$ is trifluoromethyl, $X^2$ is CH, $X^3$ is hydrogen | trifluoromethyl | hydrogen | $Y^1$ is CH, $Y^2$ is CH, $Y^3$ is N |
| P.3164 | $X^1$ is trifluoromethyl, $X^2$ is CH, $X^3$ is hydrogen | trifluoromethyl | methoxy | $Y^1$ is CH, $Y^2$ is CH, $Y^3$ is N |
| P.3165 | $X^1$ is trifluoromethyl, $X^2$ is CH, $X^3$ is hydrogen | trifluoromethyl | methyl | $Y^1$ is CH, $Y^2$ is CH, $Y^3$ is N |
| P.3166 | $X^1$ is trifluoromethyl, $X^2$ is CH, $X^3$ is hydrogen | trifluoromethyl | nitro | $Y^1$ is CH, $Y^2$ is CH, $Y^3$ is N |
| P.3167 | $X^1$ is trifluoromethyl, $X^2$ is CH, $X^3$ is hydrogen | trifluoromethyl | trifluoromethoxy | $Y^1$ is CH, $Y^2$ is CH, $Y^3$ is N |
| P.3168 | $X^1$ is trifluoromethyl, $X^2$ is CH, $X^3$ is hydrogen | trifluoromethyl | trifluoromethyl | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.3169 | $X^1$ is chloro, $X^2$ is N, $X^3$ is chloro | chlorodifluoromethyl | bromo | $Y^1$ is CH, $Y^2$ is CH, $Y^3$ is N |
| P.3170 | $X^1$ is chloro, $X^2$ is N, $X^3$ is chloro | chlorodifluoromethyl | chloro | $Y^1$ is CH, $Y^2$ is CH, $Y^3$ is N |
| P.3171 | $X^1$ is chloro, $X^2$ is N, $X^3$ is chloro | chlorodifluoromethyl | cyano | $Y^1$ is CH, $Y^2$ is CH, $Y^3$ is N |
| P.3172 | $X^1$ is chloro, $X^2$ is N, $X^3$ is chloro | chlorodifluoromethyl | cyclopropyl | $Y^1$ is CH, $Y^2$ is CH, $Y^3$ is N |
| P.3173 | $X^1$ is chloro, $X^2$ is N, $X^3$ is chloro | chlorodifluoromethyl | ethyl | $Y^1$ is CH, $Y^2$ is CH, $Y^3$ is N |
| P.3174 | $X^1$ is chloro, $X^2$ is N, $X^3$ is chloro | chlorodifluoromethyl | fluoro | $Y^1$ is CH, $Y^2$ is CH, $Y^3$ is N |
| P.3175 | $X^1$ is chloro, $X^2$ is N, $X^3$ is chloro | chlorodifluoromethyl | hydrogen | $Y^1$ is CH, $Y^2$ is CH, $Y^3$ is N |
| P.3176 | $X^1$ is chloro, $X^2$ is N, $X^3$ is chloro | chlorodifluoromethyl | methoxy | $Y^1$ is CH, $Y^2$ is CH, $Y^3$ is N |
| P.3177 | $X^1$ is chloro, $X^2$ is N, $X^3$ is chloro | chlorodifluoromethyl | methyl | $Y^1$ is CH, $Y^2$ is CH, $Y^3$ is N |
| P.3178 | $X^1$ is chloro, $X^2$ is N, $X^3$ is chloro | chlorodifluoromethyl | nitro | $Y^1$ is CH, $Y^2$ is CH, $Y^3$ is N |
| P.3179 | $X^1$ is chloro, $X^2$ is N, $X^3$ is chloro | chlorodifluoromethyl | trifluoromethoxy | $Y^1$ is CH, $Y^2$ is CH, $Y^3$ is N |
| P.3180 | $X^1$ is chloro, $X^2$ is N, $X^3$ is chloro | chlorodifluoromethyl | trifluoromethyl | $Y^1$ is CH, $Y^2$ is CH, $Y^3$ is N |
| P.3181 | $X^1$ is chloro, $X^2$ is N, $X^3$ is chloro | difluoromethyl | bromo | $Y^1$ is CH, $Y^2$ is CH, $Y^3$ is N |
| P.3182 | $X^1$ is chloro, $X^2$ is N, $X^3$ is chloro | difluoromethyl | chloro | $Y^1$ is CH, $Y^2$ is CH, $Y^3$ is N |
| P.3183 | $X^1$ is chloro, $X^2$ is N, $X^3$ is chloro | difluoromethyl | cyano | $Y^1$ is CH, $Y^2$ is CH, $Y^3$ is N |
| P.3184 | $X^1$ is chloro, $X^2$ is N, $X^3$ is chloro | difluoromethyl | cyclopropyl | $Y^1$ is CH, $Y^2$ is CH, $Y^3$ is N |
| P.3185 | $X^1$ is chloro, $X^2$ is N, $X^3$ is chloro | difluoromethyl | ethyl | $Y^1$ is CH, $Y^2$ is CH, $Y^3$ is N |
| P.3186 | $X^1$ is chloro, $X^2$ is N, $X^3$ is chloro | difluoromethyl | fluoro | $Y^1$ is CH, $Y^2$ is CH, $Y^3$ is N |
| P.3187 | $X^1$ is chloro, $X^2$ is N, $X^3$ is chloro | difluoromethyl | hydrogen | $Y^1$ is CH, $Y^2$ is CH, $Y^3$ is N |
| P.3188 | $X^1$ is chloro, $X^2$ is N, $X^3$ is chloro | difluoromethyl | methoxy | $Y^1$ is CH, $Y^2$ is CH, $Y^3$ is N |
| P.3189 | $X^1$ is chloro, $X^2$ is N, $X^3$ is chloro | difluoromethyl | methyl | $Y^1$ is CH, $Y^2$ is CH, $Y^3$ is N |
| P.3190 | $X^1$ is chloro, $X^2$ is N, $X^3$ is chloro | difluoromethyl | nitro | $Y^1$ is CH, $Y^2$ is CH, $Y^3$ is N |
| P.3191 | $X^1$ is chloro, $X^2$ is N, $X^3$ is chloro | difluoromethyl | trifluoromethoxy | $Y^1$ is CH, $Y^2$ is CH, $Y^3$ is N |
| P.3192 | $X^1$ is chloro, $X^2$ is N, $X^3$ is chloro | difluoromethyl | trifluoromethyl | $Y^1$ is CH, $Y^2$ is CH, $Y^3$ is N |
| P.3193 | $X^1$ is chloro, $X^2$ is N, $X^3$ is chloro | trifluoromethyl | bromo | $Y^1$ is CH, $Y^2$ is CH, $Y^3$ is N |
| P.3194 | $X^1$ is chloro, $X^2$ is N, $X^3$ is chloro | trifluoromethyl | chloro | $Y^1$ is CH, $Y^2$ is CH, $Y^3$ is N |
| P.3195 | $X^1$ is chloro, $X^2$ is N, $X^3$ is chloro | trifluoromethyl | cyano | $Y^1$ is CH, $Y^2$ is CH, $Y^3$ is N |
| P.3196 | $X^1$ is chloro, $X^2$ is N, $X^3$ is chloro | trifluoromethyl | cyclopropyl | $Y^1$ is CH, $Y^2$ is CH, $Y^3$ is N |
| P.3197 | $X^1$ is chloro, $X^2$ is N, $X^3$ is chloro | trifluoromethyl | ethyl | $Y^1$ is CH, $Y^2$ is CH, $Y^3$ is N |
| P.3198 | $X^1$ is chloro, $X^2$ is N, $X^3$ is chloro | trifluoromethyl | fluoro | $Y^1$ is CH, $Y^2$ is CH, $Y^3$ is N |
| P.3199 | $X^1$ is chloro, $X^2$ is N, $X^3$ is chloro | trifluoromethyl | hydrogen | $Y^1$ is CH, $Y^2$ is CH, $Y^3$ is N |
| P.3200 | $X^1$ is chloro, $X^2$ is N, $X^3$ is chloro | trifluoromethyl | methoxy | $Y^1$ is CH, $Y^2$ is CH, $Y^3$ is N |
| P.3201 | $X^1$ is chloro, $X^2$ is N, $X^3$ is chloro | trifluoromethyl | methyl | $Y^1$ is CH, $Y^2$ is CH, $Y^3$ is N |
| P.3202 | $X^1$ is chloro, $X^2$ is N, $X^3$ is chloro | trifluoromethyl | nitro | $Y^1$ is CH, $Y^2$ is CH, $Y^3$ is N |
| P.3203 | $X^1$ is chloro, $X^2$ is N, $X^3$ is chloro | trifluoromethyl | trifluoromethoxy | $Y^1$ is CH, $Y^2$ is CH, $Y^3$ is N |
| P.3204 | $X^1$ is chloro, $X^2$ is N, $X^3$ is chloro | trifluoromethyl | trifluoromethyl | $Y^1$ is CH, $Y^2$ is CH, $Y^3$ is N |
| P.3205 | $X^1$ is trifluoromethyl, $X^2$ is N, $X^3$ is trifluoromethyl | chlorodifluoromethyl | bromo | $Y^1$ is CH, $Y^2$ is CH, $Y^3$ is N |
| P.3206 | $X^1$ is trifluoromethyl, $X^2$ is N, $X^3$ is trifluoromethyl | chlorodifluoromethyl | chloro | $Y^1$ is CH, $Y^2$ is CH, $Y^3$ is N |
| P.3207 | $X^1$ is trifluoromethyl, $X^2$ is N, $X^3$ is trifluoromethyl | chlorodifluoromethyl | cyano | $Y^1$ is CH, $Y^2$ is CH, $Y^3$ is N |

TABLE P-continued

| | X1, X2, X3 | X4 | R5 | Y1, Y2, Y3 |
|---|---|---|---|---|
| P.3208 | $X^1$ is trifluoromethyl, $X^2$ is N, $X^3$ is trifluoromethyl | chlorodifluoromethyl | cyclopropyl | $Y^1$ is CH, $Y^2$ is CH, $Y^3$ is N |
| P.3209 | $X^1$ is trifluoromethyl, $X^2$ is N, $X^3$ is trifluoromethyl | chlorodifluoromethyl | ethyl | $Y^1$ is CH, $Y^2$ is CH, $Y^3$ is N |
| P.3210 | $X^1$ is trifluoromethyl, $X^2$ is N, $X^3$ is trifluoromethyl | chlorodifluoromethyl | fluoro | $Y^1$ is CH, $Y^2$ is CH, $Y^3$ is N |
| P.3211 | $X^1$ is trifluoromethyl, $X^2$ is N, $X^3$ is trifluoromethyl | chlorodifluoromethyl | hydrogen | $Y^1$ is CH, $Y^2$ is CH, $Y^3$ is N |
| P.3212 | $X^1$ is trifluoromethyl, $X^2$ is N, $X^3$ is trifluoromethyl | chlorodifluoromethyl | methoxy | $Y^1$ is CH, $Y^2$ is CH, $Y^3$ is N |
| P.3213 | $X^1$ is trifluoromethyl, $X^2$ is N, $X^3$ is trifluoromethyl | chlorodifluoromethyl | methyl | $Y^1$ is CH, $Y^2$ is CH, $Y^3$ is N |
| P.3214 | $X^1$ is trifluoromethyl, $X^2$ is N, $X^3$ is trifluoromethyl | chlorodifluoromethyl | nitro | $Y^1$ is CH, $Y^2$ is CH, $Y^3$ is N |
| P.3215 | $X^1$ is trifluoromethyl, $X^2$ is N, $X^3$ is trifluoromethyl | chlorodifluoromethyl | trifluoromethoxy | $Y^1$ is CH, $Y^2$ is CH, $Y^3$ is N |
| P.3216 | $X^1$ is trifluoromethyl, $X^2$ is N, $X^3$ is trifluoromethyl | chlorodifluoromethyl | trifluoromethyl | $Y^1$ is CH, $Y^2$ is CH, $Y^3$ is N |
| P.3217 | $X^1$ is trifluoromethyl, $X^2$ is N, $X^3$ is trifluoromethyl | difluoromethyl | bromo | $Y^1$ is CH, $Y^2$ is CH, $Y^3$ is N |
| P.3218 | $X^1$ is trifluoromethyl, $X^2$ is N, $X^3$ is trifluoromethyl | difluoromethyl | chloro | $Y^1$ is CH, $Y^2$ is CH, $Y^3$ is N |
| P.3219 | $X^1$ is trifluoromethyl, $X^2$ is N, $X^3$ is trifluoromethyl | difluoromethyl | cyano | $Y^1$ is CH, $Y^2$ is CH, $Y^3$ is N |
| P.3220 | $X^1$ is trifluoromethyl, $X^2$ is N, $X^3$ is trifluoromethyl | difluoromethyl | cyclopropyl | $Y^1$ is CH, $Y^2$ is CH, $Y^3$ is N |
| P.3221 | $X^1$ is trifluoromethyl, $X^2$ is N, $X^3$ is trifluoromethyl | difluoromethyl | ethyl | $Y^1$ is CH, $Y^2$ is CH, $Y^3$ is N |
| P.3222 | $X^1$ is trifluoromethyl, $X^2$ is N, $X^3$ is trifluoromethyl | difluoromethyl | fluoro | $Y^1$ is CH, $Y^2$ is CH, $Y^3$ is N |
| P.3223 | $X^1$ is trifluoromethyl, $X^2$ is N, $X^3$ is trifluoromethyl | difluoromethyl | hydrogen | $Y^1$ is CH, $Y^2$ is CH, $Y^3$ is N |
| P.3224 | $X^1$ is trifluoromethyl, $X^2$ is N, $X^3$ is trifluoromethyl | difluoromethyl | methoxy | $Y^1$ is CH, $Y^2$ is CH, $Y^3$ is N |
| P.3225 | $X^1$ is trifluoromethyl, $X^2$ is N, $X^3$ is trifluoromethyl | difluoromethyl | methyl | $Y^1$ is CH, $Y^2$ is CH, $Y^3$ is N |
| P.3226 | $X^1$ is trifluoromethyl, $X^2$ is N, $X^3$ is trifluoromethyl | difluoromethyl | nitro | $Y^1$ is CH, $Y^2$ is CH, $Y^3$ is N |
| P.3227 | $X^1$ is trifluoromethyl, $X^2$ is N, $X^3$ is trifluoromethyl | difluoromethyl | trifluoromethoxy | $Y^1$ is CH, $Y^2$ is CH, $Y^3$ is N |
| P.3228 | $X^1$ is trifluoromethyl, $X^2$ is N, $X^3$ is trifluoromethyl | difluoromethyl | trifluoromethyl | $Y^1$ is CH, $Y^2$ is CH, $Y^3$ is N |
| P.3229 | $X^1$ is trifluoromethyl, $X^2$ is N, $X^3$ is trifluoromethyl | trifluoromethyl | bromo | $Y^1$ is CH, $Y^2$ is CH, $Y^3$ is N |
| P.3230 | $X^1$ is trifluoromethyl, $X^2$ is N, $X^3$ is trifluoromethyl | trifluoromethyl | chloro | $Y^1$ is CH, $Y^2$ is CH, $Y^3$ is N |
| P.3231 | $X^1$ is trifluoromethyl, $X^2$ is N, $X^3$ is trifluoromethyl | trifluoromethyl | cyano | $Y^1$ is CH, $Y^2$ is CH, $Y^3$ is N |
| P.3232 | $X^1$ is trifluoromethyl, $X^2$ is N, $X^3$ is trifluoromethyl | trifluoromethyl | cyclopropyl | $Y^1$ is CH, $Y^2$ is CH, $Y^3$ is N |
| P.3233 | $X^1$ is trifluoromethyl, $X^2$ is N, $X^3$ is trifluoromethyl | trifluoromethyl | ethyl | $Y^1$ is CH, $Y^2$ is CH, $Y^3$ is N |
| P.3234 | $X^1$ is trifluoromethyl, $X^2$ is N, $X^3$ is trifluoromethyl | trifluoromethyl | fluoro | $Y^1$ is CH, $Y^2$ is CH, $Y^3$ is N |
| P.3235 | $X^1$ is trifluoromethyl, $X^2$ is N, $X^3$ is trifluoromethyl | trifluoromethyl | hydrogen | $Y^1$ is CH, $Y^2$ is CH, $Y^3$ is N |
| P.3236 | $X^1$ is trifluoromethyl, $X^2$ is N, $X^3$ is trifluoromethyl | trifluoromethyl | methoxy | $Y^1$ is CH, $Y^2$ is CH, $Y^3$ is N |
| P.3237 | $X^1$ is trifluoromethyl, $X^2$ is N, $X^3$ is trifluoromethyl | trifluoromethyl | methyl | $Y^1$ is CH, $Y^2$ is CH, $Y^3$ is N |
| P.3238 | $X^1$ is trifluoromethyl, $X^2$ is N, $X^3$ is trifluoromethyl | trifluoromethyl | nitro | $Y^1$ is CH, $Y^2$ is CH, $Y^3$ is N |
| P.3239 | $X^1$ is trifluoromethyl, $X^2$ is N, $X^3$ is trifluoromethyl | trifluoromethyl | trifluoromethoxy | $Y^1$ is CH, $Y^2$ is CH, $Y^3$ is N |
| P.3240 | $X^1$ is trifluoromethyl, $X^2$ is N, $X^3$ is trifluoromethyl | trifluoromethyl | trifluoromethyl | $Y^1$ is CH, $Y^2$ is CH, $Y^3$ is N |

(I-A)

[Chemical structure of formula (I-A) showing a phenyl ring with X¹, X², X³ substituents connected to X⁴ of an isothiazoline ring, linked to a pyridine-type ring with Y¹, Y², Y³, R⁵ substituents and a carboxamide group with G¹, N, R¹, R²]

Table 1P:
  Table 1P provides 3240 compounds of formula (I-A) wherein $G^1$ is oxygen, $R^1$ is hydrogen, $R^2$ is G.001, $X^1$, $X^2$, $X^3$, $Y^1$, $Y^2$, $Y^3$, $X^4$ and $R^5$ have the values listed in the table P.

Table 2P:
  Table 2P provides 3240 compounds of formula (I-A) wherein $G^1$ is oxygen, $R^1$ is hydrogen, $R^2$ is G.002, $X^1$, $X^2$, $X^3$, $Y^1$, $Y^2$, $Y^3$, $X^4$ and $R^5$ have the values listed in the table P.

Table 3P:
  Table 3P provides 3240 compounds of formula (I-A) wherein $G^1$ is oxygen, $R^1$ is hydrogen, $R^2$ is G.003, $X^1$, $X^2$, $X^3$, $Y^1$, $Y^2$, $Y^3$, $X^4$ and $R^5$ have the values listed in the table P.

Table 4P:
  Table 4P provides 3240 compounds of formula (I-A) wherein $G^1$ is oxygen, $R^1$ is hydrogen, $R^2$ is G.004, $X^1$, $X^2$, $X^3$, $Y^1$, $Y^2$, $Y^3$, $X^4$ and $R^5$ have the values listed in the table P.

Table 5P:
  Table 5P provides 3240 compounds of formula (I-A) wherein $G^1$ is oxygen, $R^1$ is hydrogen, $R^2$ is G.005, $X^1$, $X^2$, $X^3$, $Y^1$, $Y^2$, $Y^3$, $X^4$ and $R^5$ have the values listed in the table P.

Table 6P:
  Table 6P provides 3240 compounds of formula (I-A) wherein $G^1$ is oxygen, $R^1$ is hydrogen, $R^2$ is G.006, $X^1$, $X^2$, $X^3$, $Y^1$, $Y^2$, $Y^3$, $X^4$ and $R^5$ have the values listed in the table P.

Table 7P:
  Table 7P provides 3240 compounds of formula (I-A) wherein $G^1$ is oxygen, $R^1$ is hydrogen, $R^2$ is G.007, $X^1$, $X^2$, $X^3$, $Y^1$, $Y^2$, $Y^3$, $X^4$ and $R^5$ have the values listed in the table P.

Table 8P:
  Table 8P provides 3240 compounds of formula (I-A) wherein $G^1$ is oxygen, $R^1$ is hydrogen, $R^2$ is G.008, $X^1$, $X^2$, $X^3$, $Y^1$, $Y^2$, $Y^3$, $X^4$ and $R^5$ have the values listed in the table P.

Table 9P:
  Table 9P provides 3240 compounds of formula (I-A) wherein $G^1$ is oxygen, $R^1$ is hydrogen, $R^2$ is G.009, $X^1$, $X^2$, $X^3$, $Y^1$, $Y^2$, $Y^3$, $X^4$ and $R^5$ have the values listed in the table P.

Table 10P:
  Table 10P provides 3240 compounds of formula (I-A) wherein $G^1$ is oxygen, $R^1$ is hydrogen, $R^2$ is G.010, $X^1$, $X^2$, $X^3$, $Y^1$, $Y^2$, $Y^3$, $X^4$ and $R^5$ have the values listed in the table P.

Table 11P:
  Table 11P provides 3240 compounds of formula (I-A) wherein $G^1$ is oxygen, $R^1$ is hydrogen, $R^2$ is G.011, $X^1$, $X^2$, $X^3$, $Y^1$, $Y^2$, $Y^3$, $X^4$ and $R^5$ have the values listed in the table P.

Table 12P:
  Table 12P provides 3240 compounds of formula (I-A) wherein $G^1$ is oxygen, $R^1$ is hydrogen, $R^2$ is G.012, $X^1$, $X^2$, $X^3$, $Y^1$, $Y^2$, $Y^3$, $X^4$ and $R^5$ have the values listed in the table P.

Table 13P:
  Table 13P provides 3240 compounds of formula (I-A) wherein $G^1$ is oxygen, $R^1$ is hydrogen, $R^2$ is G.013, $X^1$, $X^2$, $X^3$, $Y^1$, $Y^2$, $Y^3$, $X^4$ and $R^5$ have the values listed in the table P.

Table 14P:
  Table 14P provides 3240 compounds of formula (I-A) wherein $G^1$ is oxygen, $R^1$ is hydrogen, $R^2$ is G.014, $X^1$, $X^2$, $X^3$, $Y^1$, $Y^2$, $Y^3$, $X^4$ and $R^5$ have the values listed in the table P.

Table 15P:
  Table 15P provides 3240 compounds of formula (I-A) wherein $G^1$ is oxygen, $R^1$ is hydrogen, $R^2$ is G.015, $X^1$, $X^2$, $X^3$, $Y^1$, $Y^2$, $Y^3$, $X^4$ and $R^5$ have the values listed in the table P.

Table 16P:
  Table 16P provides 3240 compounds of formula (I-A) wherein $G^1$ is oxygen, $R^1$ is hydrogen, $R^2$ is G.016, $X^1$, $X^2$, $X^3$, $Y^1$, $Y^2$, $Y^3$, $X^4$ and $R^5$ have the values listed in the table P.

Table 17P:
  Table 17P provides 3240 compounds of formula (I-A) wherein $G^1$ is oxygen, $R^1$ is hydrogen, $R^2$ is G.017, $X^1$, $X^2$, $X^3$, $Y^1$, $Y^2$, $Y^3$, $X^4$ and $R^5$ have the values listed in the table P.

Table 18P:
  Table 18P provides 3240 compounds of formula (I-A) wherein $G^1$ is oxygen, $R^1$ is hydrogen, $R^2$ is G.018, $X^1$, $X^2$, $X^3$, $Y^1$, $Y^2$, $Y^3$, $X^4$ and $R^5$ have the values listed in the table P.

Table 19P:
  Table 19P provides 3240 compounds of formula (I-A) wherein $G^1$ is oxygen, $R^1$ is hydrogen, $R^2$ is G.019, $X^1$, $X^2$, $X^3$, $Y^1$, $Y^2$, $Y^3$, $X^4$ and $R^5$ have the values listed in the table P.

Table 20P:
  Table 20P provides 3240 compounds of formula (I-A) wherein $G^1$ is oxygen, $R^1$ is hydrogen, $R^2$ is G.020, $X^1$, $X^2$, $X^3$, $Y^1$, $Y^2$, $Y^3$, $X^4$ and $R^5$ have the values listed in the table P.

Table 21P:
  Table 21P provides 3240 compounds of formula (I-A) wherein $G^1$ is oxygen, $R^1$ is hydrogen, $R^2$ is G.021, $X^1$, $X^2$, $X^3$, $Y^1$, $Y^2$, $Y^3$, $X^4$ and $R^5$ have the values listed in the table P.

Table 22P:
  Table 22P provides 3240 compounds of formula (I-A) wherein $G^1$ is oxygen, $R^1$ is hydrogen, $R^2$ is G.022, $X^1$, $X^2$, $X^3$, $Y^1$, $Y^2$, $Y^3$, $X^4$ and $R^5$ have the values listed in the table P.

Table 23P:
  Table 23P provides 3240 compounds of formula (I-A) wherein $G^1$ is oxygen, $R^1$ is hydrogen, $R^2$ is G.023, $X^1$, $X^2$, $X^3$, $Y^1$, $Y^2$, $Y^3$, $X^4$ and $R^5$ have the values listed in the table P.

Table 24P:
  Table 24P provides 3240 compounds of formula (I-A) wherein $G^1$ is oxygen, $R^1$ is hydrogen, $R^2$ is G.024, $X^1$, $X^2$, $X^3$, $Y^1$, $Y^2$, $Y^3$, $X^4$ and $R^5$ have the values listed in the table P.

Table 25P:
  Table 25P provides 3240 compounds of formula (I-A) wherein $G^1$ is oxygen, $R^1$ is hydrogen, $R^2$ is G.025, $X^1$, $X^2$, $X^3$, $Y^1$, $Y^2$, $Y^3$, $X^4$ and $R^5$ have the values listed in the table P.

Table 26P:
  Table 26P provides 3240 compounds of formula (I-A) wherein $G^1$ is oxygen, $R^1$ is hydrogen, $R^2$ is G.026, $X^1$, $X^2$, $X^3$, $Y^1$, $Y^2$, $Y^3$, $X^4$ and $R^5$ have the values listed in the table P.

Table 27P:
  Table 27P provides 3240 compounds of formula (I-A) wherein $G^1$ is oxygen, $R^1$ is hydrogen, $R^2$ is G.027, $X^1$, $X^2$, $X^3$, $Y^1$, $Y^2$, $Y^3$, $X^4$ and $R^5$ have the values listed in the table P.

Table 28P:
  Table 28P provides 3240 compounds of formula (I-A) wherein $G^1$ is oxygen, $R^1$ is hydrogen, $R^2$ is G.028, $X^1$, $X^2$, $X^3$, $Y^1$, $Y^2$, $Y^3$, $X^4$ and $R^5$ have the values listed in the table P.

Table 29P:
  Table 29P provides 3240 compounds of formula (I-A) wherein $G^1$ is oxygen, $R^1$ is hydrogen, $R^2$ is G.029, $X^1$, $X^2$, $X^3$, $Y^1$, $Y^2$, $Y^3$, $X^4$ and $R^5$ have the values listed in the table P.

Table 30P:
  Table 30P provides 3240 compounds of formula (I-A) wherein $G^1$ is oxygen, $R^1$ is hydrogen, $R^2$ is G.030, $X^1$, $X^2$, $X^3$, $Y^1$, $Y^2$, $Y^3$, $X^4$ and $R^5$ have the values listed in the table P.

Table 31P:
Table 31P provides 3240 compounds of formula (I-A) wherein $G^1$ is oxygen, $R^1$ is hydrogen, $R^2$ is G.031, $X^1$, $X^2$, $X^3$, $Y^1$, $Y^2$, $Y^3$, $X^4$ and $R^5$ have the values listed in the table P.

Table 32P:
Table 32P provides 3240 compounds of formula (I-A) wherein $G^1$ is oxygen, $R^1$ is hydrogen, $R^2$ is G.032, $X^1$, $X^2$, $X^3$, $Y^1$, $Y^2$, $Y^3$, $X^4$ and $R^5$ have the values listed in the table P.

Table 33P:
Table 33P provides 3240 compounds of formula (I-A) wherein $G^1$ is oxygen, $R^1$ is hydrogen, $R^2$ is G.033, $X^1$, $X^2$, $X^3$, $Y^1$, $Y^2$, $Y^3$, $X^4$ and $R^5$ have the values listed in the table P.

Table 34P:
Table 34P provides 3240 compounds of formula (I-A) wherein $G^1$ is oxygen, $R^1$ is hydrogen, $R^2$ is G.034, $X^1$, $X^2$, $X^3$, $Y^1$, $Y^2$, $Y^3$, $X^4$ and $R^5$ have the values listed in the table P.

Table 35P:
Table 35P provides 3240 compounds of formula (I-A) wherein $G^1$ is oxygen, $R^1$ is hydrogen, $R^2$ is G.035, $X^1$, $X^2$, $X^3$, $Y^1$, $Y^2$, $Y^3$, $X^4$ and $R^5$ have the values listed in the table P.

Table 36P:
Table 36P provides 3240 compounds of formula (I-A) wherein $G^1$ is oxygen, $R^1$ is hydrogen, $R^2$ is G.036, $X^1$, $X^2$, $X^3$, $Y^1$, $Y^2$, $Y^3$, $X^4$ and $R^5$ have the values listed in the table P.

Table 37P:
Table 37P provides 3240 compounds of formula (I-A) wherein $G^1$ is oxygen, $R^1$ is hydrogen, $R^2$ is G.037, $X^1$, $X^2$, $X^3$, $Y^1$, $Y^2$, $Y^3$, $X^4$ and $R^5$ have the values listed in the table P.

Table 38P:
Table 38P provides 3240 compounds of formula (I-A) wherein $G^1$ is oxygen, $R^1$ is hydrogen, $R^2$ is G.038, $X^1$, $X^2$, $X^3$, $Y^1$, $Y^2$, $Y^3$, $X^4$ and $R^5$ have the values listed in the table P.

Table 39P:
Table 39P provides 3240 compounds of formula (I-A) wherein $G^1$ is oxygen, $R^1$ is hydrogen, $R^2$ is G.039, $X^1$, $X^2$, $X^3$, $Y^1$, $Y^2$, $Y^3$, $X^4$ and $R^5$ have the values listed in the table P.

Table 40P:
Table 40P provides 3240 compounds of formula (I-A) wherein $G^1$ is oxygen, $R^1$ is hydrogen, $R^2$ is G.040, $X^1$, $X^2$, $X^3$, $Y^1$, $Y^2$, $Y^3$, $X^4$ and $R^5$ have the values listed in the table P.

Table 41P:
Table 41P provides 3240 compounds of formula (I-A) wherein $G^1$ is oxygen, $R^1$ is hydrogen, $R^2$ is G.041, $X^1$, $X^2$, $X^3$, $Y^1$, $Y^2$, $Y^3$, $X^4$ and $R^5$ have the values listed in the table P.

Table 42P:
Table 42P provides 3240 compounds of formula (I-A) wherein $G^1$ is oxygen, $R^1$ is hydrogen, $R^2$ is G.042, $X^1$, $X^2$, $X^3$, $Y^1$, $Y^2$, $Y^3$, $X^4$ and $R^5$ have the values listed in the table P.

Table 43P:
Table 43P provides 3240 compounds of formula (I-A) wherein $G^1$ is oxygen, $R^1$ is hydrogen, $R^2$ is G.043, $X^1$, $X^2$, $X^3$, $Y^1$, $Y^2$, $Y^3$, $X^4$ and $R^5$ have the values listed in the table P.

Table 44P:
Table 44P provides 3240 compounds of formula (I-A) wherein $G^1$ is oxygen, $R^1$ is hydrogen, $R^2$ is G.044, $X^1$, $X^2$, $X^3$, $Y^1$, $Y^2$, $Y^3$, $X^4$ and $R^5$ have the values listed in the table P.

Table 45P:
Table 45P provides 3240 compounds of formula (I-A) wherein $G^1$ is oxygen, $R^1$ is hydrogen, $R^2$ is G.045, $X^1$, $X^2$, $X^3$, $Y^1$, $Y^2$, $Y^3$, $X^4$ and $R^5$ have the values listed in the table P.

Table 46P:
Table 46P provides 3240 compounds of formula (I-A) wherein $G^1$ is oxygen, $R^1$ is hydrogen, $R^2$ is G.046, $X^1$, $X^2$, $X^3$, $Y^1$, $Y^2$, $Y^3$, $X^4$ and $R^5$ have the values listed in the table P.

Table 47P:
Table 47P provides 3240 compounds of formula (I-A) wherein $G^1$ is oxygen, $R^1$ is hydrogen, $R^2$ is G.047, $X^1$, $X^2$, $X^3$, $Y^1$, $Y^2$, $Y^3$, $X^4$ and $R^5$ have the values listed in the table P.

Table 48P:
Table 48P provides 3240 compounds of formula (I-A) wherein $G^1$ is oxygen, $R^1$ is hydrogen, $R^2$ is G.048, $X^1$, $X^2$, $X^3$, $Y^1$, $Y^2$, $Y^3$, $X^4$ and $R^5$ have the values listed in the table P.

Table 49P:
Table 49P provides 3240 compounds of formula (I-A) wherein $G^1$ is oxygen, $R^1$ is hydrogen, $R^2$ is G.049, $X^1$, $X^2$, $X^3$, $Y^1$, $Y^2$, $Y^3$, $X^4$ and $R^5$ have the values listed in the table P.

Table 50P:
Table 50P provides 3240 compounds of formula (I-A) wherein $G^1$ is oxygen, $R^1$ is hydrogen, $R^2$ is G.050, $X^1$, $X^2$, $X^3$, $Y^1$, $Y^2$, $Y^3$, $X^4$ and $R^5$ have the values listed in the table P.

Table 51P:
Table 51P provides 3240 compounds of formula (I-A) wherein $G^1$ is oxygen, $R^1$ is hydrogen, $R^2$ is G.051, $X^1$, $X^2$, $X^3$, $Y^1$, $Y^2$, $Y^3$, $X^4$ and $R^5$ have the values listed in the table P.

Table 52P:
Table 52P provides 3240 compounds of formula (I-A) wherein $G^1$ is oxygen, $R^1$ is hydrogen, $R^2$ is G.052, $X^1$, $X^2$, $X^3$, $Y^1$, $Y^2$, $Y^3$, $X^4$ and $R^5$ have the values listed in the table P.

Table 53P:
Table 53P provides 3240 compounds of formula (I-A) wherein $G^1$ is oxygen, $R^1$ is hydrogen, $R^2$ is G.053, $X^1$, $X^2$, $X^3$, $Y^1$, $Y^2$, $Y^3$, $X^4$ and $R^5$ have the values listed in the table P.

Table 54P:
Table 54P provides 3240 compounds of formula (I-A) wherein $G^1$ is oxygen, $R^1$ is hydrogen, $R^2$ is G.054, $X^1$, $X^2$, $X^3$, $Y^1$, $Y^2$, $Y^3$, $X^4$ and $R^5$ have the values listed in the table P.

Table 55P:
Table 55P provides 3240 compounds of formula (I-A) wherein $G^1$ is oxygen, $R^1$ is hydrogen, $R^2$ is G.055, $X^1$, $X^2$, $X^3$, $Y^1$, $Y^2$, $Y^3$, $X^4$ and $R^5$ have the values listed in the table P.

Table 56P:
Table 56P provides 3240 compounds of formula (I-A) wherein $G^1$ is oxygen, $R^1$ is hydrogen, $R^2$ is G.056, $X^1$, $X^2$, $X^3$, $Y^1$, $Y^2$, $Y^3$, $X^4$ and $R^5$ have the values listed in the table P.

Table 57P:
Table 57P provides 3240 compounds of formula (I-A) wherein $G^1$ is oxygen, $R^1$ is hydrogen, $R^2$ is G.057, $X^1$, $X^2$, $X^3$, $Y^1$, $Y^2$, $Y^3$, $X^4$ and $R^5$ have the values listed in the table P.

Table 58P:
Table 58P provides 3240 compounds of formula (I-A) wherein $G^1$ is oxygen, $R^1$ is hydrogen, $R^2$ is G.058, $X^1$, $X^2$, $X^3$, $Y^1$, $Y^2$, $Y^3$, $X^4$ and $R^5$ have the values listed in the table P.

Table 59P:
Table 59P provides 3240 compounds of formula (I-A) wherein $G^1$ is oxygen, $R^1$ is hydrogen, $R^2$ is G.059, $X^1$, $X^2$, $X^3$, $Y^1$, $Y^2$, $Y^3$, $X^4$ and $R^5$ have the values listed in the table P.

Table 60P:
Table 60P provides 3240 compounds of formula (I-A) wherein $G^1$ is oxygen, $R^1$ is hydrogen, $R^2$ is G.060, $X^1$, $X^2$, $X^3$, $Y^1$, $Y^2$, $Y^3$, $X^4$ and $R^5$ have the values listed in the table P.

Table 61P:
Table 61P provides 3240 compounds of formula (I-A) wherein $G^1$ is oxygen, $R^1$ is hydrogen, $R^2$ is G.061, $X^1$, $X^2$, $X^3$, $Y^1$, $Y^2$, $Y^3$, $X^4$ and $R^5$ have the values listed in the table P.

Table 62P:
Table 62P provides 3240 compounds of formula (I-A) wherein $G^1$ is oxygen, $R^1$ is hydrogen, $R^2$ is G.062, $X^1$, $X^2$, $X^3$, $Y^1$, $Y^2$, $Y^3$, $X^4$ and $R^5$ have the values listed in the table P.

Table 63P:
Table 63P provides 3240 compounds of formula (I-A) wherein $G^1$ is oxygen, $R^1$ is hydrogen, $R^2$ is G.063, $X^1$, $X^2$, $X^3$, $Y^1$, $Y^2$, $Y^3$, $X^4$ and $R^5$ have the values listed in the table P.

Table 64P:
Table 64P provides 3240 compounds of formula (I-A) wherein $G^1$ is oxygen, $R^1$ is hydrogen, $R^2$ is G.064, $X^1$, $X^2$, $X^3$, $Y^1$, $Y^2$, $Y^3$, $X^4$ and $R^5$ have the values listed in the table P.

Table 65P:
Table 65P provides 3240 compounds of formula (I-A) wherein $G^1$ is oxygen, $R^1$ is hydrogen, $R^2$ is G.065, $X^1$, $X^2$, $X^3$, $Y^1$, $Y^2$, $Y^3$, $X^4$ and $R^5$ have the values listed in the table P.

Table 66P:
Table 66P provides 3240 compounds of formula (I-A) wherein $G^1$ is oxygen, $R^1$ is hydrogen, $R^2$ is G.066, $X^1$, $X^2$, $X^3$, $Y^1$, $Y^2$, $Y^3$, $X^4$ and $R^5$ have the values listed in the table P.

Table 67P:
Table 67P provides 3240 compounds of formula (I-A) wherein $G^1$ is oxygen, $R^1$ is hydrogen, $R^2$ is G.067, $X^1$, $X^2$, $X^3$, $Y^1$, $Y^2$, $Y^3$, $X^4$ and $R^5$ have the values listed in the table P.

Table 68P:
Table 68P provides 3240 compounds of formula (I-A) wherein $G^1$ is oxygen, $R^1$ is hydrogen, $R^2$ is G.068, $X^1$, $X^2$, $X^3$, $Y^1$, $Y^2$, $Y^3$, $X^4$ and $R^5$ have the values listed in the table P.

Table 69P:
Table 69P provides 3240 compounds of formula (I-A) wherein $G^1$ is oxygen, $R^1$ is hydrogen, $R^2$ is G.069, $X^1$, $X^2$, $X^3$, $Y^1$, $Y^2$, $Y^3$, $X^4$ and $R^5$ have the values listed in the table P.

Table 70P:
Table 70P provides 3240 compounds of formula (I-A) wherein $G^1$ is oxygen, $R^1$ is hydrogen, $R^2$ is G.070, $X^1$, $X^2$, $X^3$, $Y^1$, $Y^2$, $Y^3$, $X^4$ and $R^5$ have the values listed in the table P.

Table 71P:
Table 71P provides 3240 compounds of formula (I-A) wherein $G^1$ is oxygen, $R^1$ is hydrogen, $R^2$ is G.071, $X^1$, $X^2$, $X^3$, $Y^1$, $Y^2$, $Y^3$, $X^4$ and $R^5$ have the values listed in the table P.

Table 72P:
Table 72P provides 3240 compounds of formula (I-A) wherein $G^1$ is oxygen, $R^1$ is hydrogen, $R^2$ is G.072, $X^1$, $X^2$, $X^3$, $Y^1$, $Y^2$, $Y^3$, $X^4$ and $R^5$ have the values listed in the table P.

Table 73P:
Table 73P provides 3240 compounds of formula (I-A) wherein $G^1$ is oxygen, $R^1$ is hydrogen, $R^2$ is G.073, $X^1$, $X^2$, $X^3$, $Y^1$, $Y^2$, $Y^3$, $X^4$ and $R^5$ have the values listed in the table P.

Table 74P:
Table 74P provides 3240 compounds of formula (I-A) wherein $G^1$ is oxygen, $R^1$ is hydrogen, $R^2$ is G.074, $X^1$, $X^2$, $X^3$, $Y^1$, $Y^2$, $Y^3$, $X^4$ and $R^5$ have the values listed in the table P.

Table 75P:
Table 75P provides 3240 compounds of formula (I-A) wherein $G^1$ is oxygen, $R^1$ is hydrogen, $R^2$ is G.075, $X^1$, $X^2$, $X^3$, $Y^1$, $Y^2$, $Y^3$, $X^4$ and $R^5$ have the values listed in the table P.

Table 76P:
Table 76P provides 3240 compounds of formula (I-A) wherein $G^1$ is oxygen, $R^1$ is hydrogen, $R^2$ is G.076, $X^1$, $X^2$, $X^3$, $Y^1$, $Y^2$, $Y^3$, $X^4$ and $R^5$ have the values listed in the table P.

Table 77P:
Table 77P provides 3240 compounds of formula (I-A) wherein $G^1$ is oxygen, $R^1$ is hydrogen, $R^2$ is G.077, $X^1$, $X^2$, $X^3$, $Y^1$, $Y^2$, $Y^3$, $X^4$ and $R^5$ have the values listed in the table P.

Table 78P:
Table 78P provides 3240 compounds of formula (I-A) wherein $G^1$ is oxygen, $R^1$ is hydrogen, $R^2$ is G.078, $X^1$, $X^2$, $X^3$, $Y^1$, $Y^2$, $Y^3$, $X^4$ and $R^5$ have the values listed in the table P.

Table 79P:
Table 79P provides 3240 compounds of formula (I-A) wherein $G^1$ is oxygen, $R^1$ is hydrogen, $R^2$ is G.079, $X^1$, $X^2$, $X^3$, $Y^1$, $Y^2$, $Y^3$, $X^4$ and $R^5$ have the values listed in the table P.

Table 80P:
Table 80P provides 3240 compounds of formula (I-A) wherein $G^1$ is oxygen, $R^1$ is hydrogen, $R^2$ is G.080, $X^1$, $X^2$, $X^3$, $Y^1$, $Y^2$, $Y^3$, $X^4$ and $R^5$ have the values listed in the table P.

Table 81P:
Table 81P provides 3240 compounds of formula (I-A) wherein $G^1$ is oxygen, $R^1$ is hydrogen, $R^2$ is G.081, $X^1$, $X^2$, $X^3$, $Y^1$, $Y^2$, $Y^3$, $X^4$ and $R^5$ have the values listed in the table P.

Table 82P:
Table 82P provides 3240 compounds of formula (I-A) wherein $G^1$ is oxygen, $R^1$ is hydrogen, $R^2$ is G.082, $X^1$, $X^2$, $X^3$, $Y^1$, $Y^2$, $Y^3$, $X^4$ and $R^5$ have the values listed in the table P.

Table 83P:
Table 83P provides 3240 compounds of formula (I-A) wherein $G^1$ is oxygen, $R^1$ is hydrogen, $R^2$ is G.083, $X^1$, $X^2$, $X^3$, $Y^1$, $Y^2$, $Y^3$, $X^4$ and $R^5$ have the values listed in the table P.

Table 84P:
Table 84P provides 3240 compounds of formula (I-A) wherein $G^1$ is oxygen, $R^1$ is hydrogen, $R^2$ is G.084, $X^1$, $X^2$, $X^3$, $Y^1$, $Y^2$, $Y^3$, $X^4$ and $R^5$ have the values listed in the table P.

Table 85P:
Table 85P provides 3240 compounds of formula (I-A) wherein $G^1$ is oxygen, $R^1$ is hydrogen, $R^2$ is G.085, $X^1$, $X^2$, $X^3$, $Y^1$, $Y^2$, $Y^3$, $X^4$ and $R^5$ have the values listed in the table P.

Table 86P:
Table 86P provides 3240 compounds of formula (I-A) wherein $G^1$ is oxygen, $R^1$ is hydrogen, $R^2$ is G.086, $X^1$, $X^2$, $X^3$, $Y^1$, $Y^2$, $Y^3$, $X^4$ and $R^5$ have the values listed in the table P.

Table 87P:
Table 87P provides 3240 compounds of formula (I-A) wherein $G^1$ is oxygen, $R^1$ is hydrogen, $R^2$ is G.087, $X^1$, $X^2$, $X^3$, $Y^1$, $Y^2$, $Y^3$, $X^4$ and $R^5$ have the values listed in the table P.

Table 88P:
Table 88P provides 3240 compounds of formula (I-A) wherein $G^1$ is oxygen, $R^1$ is hydrogen, $R^2$ is G.088, $X^1$, $X^2$, $X^3$, $Y^1$, $Y^2$, $Y^3$, $X^4$ and $R^5$ have the values listed in the table P.

Table 89P:
Table 89P provides 3240 compounds of formula (I-A) wherein $G^1$ is oxygen, $R^1$ is hydrogen, $R^2$ is G.089, $X^1$, $X^2$, $X^3$, $Y^1$, $Y^2$, $Y^3$, $X^4$ and $R^5$ have the values listed in the table P.

Table 90P:
Table 90P provides 3240 compounds of formula (I-A) wherein $G^1$ is oxygen, $R^1$ is hydrogen, $R^2$ is G.090, $X^1$, $X^2$, $X^3$, $Y^1$, $Y^2$, $Y^3$, $X^4$ and $R^5$ have the values listed in the table P.

Table 91P
Table 91P provides 3240 compounds of formula (I-A) wherein $G^1$ is oxygen, $R^1$ is hydrogen, $R^2$ is G.091, $X^1$, $X^2$, $X^3$, $Y^1$, $Y^2$, $Y^3$, $X^4$ and $R^5$ have the values listed in the table P.

Table 92P
Table 92P provides 3240 compounds of formula (I-A) wherein $G^1$ is oxygen, $R^1$ is hydrogen, $R^2$ is G.092, $X^1$, $X^2$, $X^3$, $Y^1$, $Y^2$, $Y^3$, $X^4$ and $R^5$ have the values listed in the table P.

Table 93P
Table 93P provides 3240 compounds of formula (I-A) wherein $G^1$ is oxygen, $R^1$ is hydrogen, $R^2$ is G.093, $X^1$, $X^2$, $X^3$, $Y^1$, $Y^2$, $Y^3$, $X^4$ and $R^5$ have the values listed in the table P.

Table 94P
Table 94P provides 3240 compounds of formula (I-A) wherein $G^1$ is oxygen, $R^1$ is hydrogen, $R^2$ is G.094, $X^1$, $X^2$, $X^3$, $Y^1$, $Y^2$, $Y^3$, $X^4$ and $R^5$ have the values listed in the table P.

Table 95P
Table 95P provides 3240 compounds of formula (I-A) wherein $G^1$ is oxygen, $R^1$ is hydrogen, $R^2$ is G.095, $X^1$, $X^2$, $X^3$, $Y^1$, $Y^2$, $Y^3$, $X^4$ and $R^5$ have the values listed in the table P.

Table 96P
Table 96P provides 3240 compounds of formula (I-A) wherein $G^1$ is oxygen, $R^1$ is hydrogen, $R^2$ is G.096, $X^1$, $X^2$, $X^3$, $Y^1$, $Y^2$, $Y^3$, $X^4$ and $R^5$ have the values listed in the table P.

Table 97P

Table 97P provides 3240 compounds of formula (I-A) wherein $G^1$ is oxygen, $R^1$ is hydrogen, $R^2$ is G.097, $X^1, X^2, X^3, Y^1, Y^2, Y^3, X^4$ and $R^5$ have the values listed in the table P.

Table 98P

Table 98P provides 3240 compounds of formula (I-A) wherein $G^1$ is oxygen, $R^1$ is hydrogen, $R^2$ is G.098, $X^1, X^2, X^3, Y^1, Y^2, Y^3, X^4$ and $R^5$ have the values listed in the table P.

Table 99P

Table 99P provides 3240 compounds of formula (I-A) wherein $G^1$ is oxygen, $R^1$ is hydrogen, $R^2$ is G.099, $X^1, X^2, X^3, Y^1, Y^2, Y^3, X^4$ and $R^5$ have the values listed in the table P.

Table 100P

Table 100P provides 3240 compounds of formula (I-A) wherein $G^1$ is oxygen, $R^1$ is hydrogen, $R^2$ is G.100, $X^1, X^2, X^3, Y^1, Y^2, Y^3, X^4$ and $R^5$ have the values listed in the table P.

Table 101P

Table 101P provides 3240 compounds of formula (I-A) wherein $G^1$ is oxygen, $R^1$ is hydrogen, $R^2$ is G.101, $X^1, X^2, X^3, Y^1, Y^2, Y^3, X^4$ and $R^5$ have the values listed in the table P.

Table 102P

Table 102P provides 3240 compounds of formula (I-A) wherein $G^1$ is oxygen, $R^1$ is hydrogen, $R^2$ is G.102, $X^1, X^2, X^3, Y^1, Y^2, Y^3, X^4$ and $R^5$ have the values listed in the table P.

Table 103P

Table 103P provides 3240 compounds of formula (I-A) wherein $G^1$ is oxygen, $R^1$ is hydrogen, $R^2$ is G.103, $X^1, X^2, X^3, Y^1, Y^2, Y^3, X^4$ and $R^5$ have the values listed in the table P.

Table 104P

Table 104P provides 3240 compounds of formula (I-A) wherein $G^1$ is oxygen, $R^1$ is hydrogen, $R^2$ is G.104, $X^1, X^2, X^3, Y^1, Y^2, Y^3, X^4$ and $R^5$ have the values listed in the table P.

Table 105P

Table 105P provides 3240 compounds of formula (I-A) wherein $G^1$ is oxygen, $R^1$ is hydrogen, $R^2$ is G.105, $X^1, X^2, X^3, Y^1, Y^2, Y^3, X^4$ and $R^5$ have the values listed in the table P.

Table 106P

Table 106P provides 3240 compounds of formula (I-A) wherein $G^1$ is oxygen, $R^1$ is hydrogen, $R^2$ is G.106, $X^1, X^2, X^3, Y^1, Y^2, Y^3, X^4$ and $R^5$ have the values listed in the table P.

Table 107P

Table 107P provides 3240 compounds of formula (I-A) wherein $G^1$ is oxygen, $R^1$ is hydrogen, $R^2$ is G.107, $X^1, X^2, X^3, Y^1, Y^2, Y^3, X^4$ and $R^5$ have the values listed in the table P.

Table 108P

Table 108P provides 3240 compounds of formula (I-A) wherein $G^1$ is oxygen, $R^1$ is hydrogen, $R^2$ is G.108, $X^1, X^2, X^3, Y^1, Y^2, Y^3, X^4$ and $R^5$ have the values listed in the table P.

Table 109P

Table 109P provides 3240 compounds of formula (I-A) wherein $G^1$ is oxygen, $R^1$ is hydrogen, $R^2$ is G.109, $X^1, X^2, X^3, Y^1, Y^2, Y^3, X^4$ and $R^5$ have the values listed in the table P.

Table 110P

Table 110P provides 3240 compounds of formula (I-A) wherein $G^1$ is oxygen, $R^1$ is hydrogen, $R^2$ is G.110, $X^1, X^2, X^3, Y^1, Y^2, Y^3, X^4$ and $R^5$ have the values listed in the table P.

Table 111P:

Table 111P provides 3240 compounds of formula (I-A) wherein $G^1$ is oxygen, $R^1$ is hydrogen, $R^2$ is G.111, $X^1, X^2, X^3, Y^1, Y^2, Y^3, X^4$ and $R^5$ have the values listed in the table P.

Table 112 P

Table 112P provides 3240 compounds of formula (I-A) wherein $G^1$ is oxygen, $R^1$ is hydrogen, $R^2$ is G.112, $X^1, X^2, X^3, Y^1, Y^2, Y^3, X^4$ and $R^5$ have the values listed in the table P.

Table 113 P

Table 113P provides 3240 compounds of formula (I-A) wherein $G^1$ is oxygen, $R^1$ is hydrogen, $R^2$ is G.113, $X^1, X^2, X^3, Y^1, Y^2, Y^3, X^4$ and $R^5$ have the values listed in the table P.

Table 114 P

Table 114P provides 3240 compounds of formula (I-A) wherein $G^1$ is oxygen, $R^1$ is hydrogen, $R^2$ is G.114, $X^1, X^2, X^3, Y^1, Y^2, Y^3, X^4$ and $R^5$ have the values listed in the table P.

Table 115 P

Table 115P provides 3240 compounds of formula (I-A) wherein $G^1$ is oxygen, $R^1$ is hydrogen, $R^2$ is G.115, $X^1, X^2, X^3, Y^1, Y^2, Y^3, X^4$ and $R^5$ have the values listed in the table P.

Table 116 P

Table 116P provides 3240 compounds of formula (I-A) wherein $G^1$ is oxygen, $R^1$ is hydrogen, $R^2$ is G.116, $X^1, X^2, X^3, Y^1, Y^2, Y^3, X^4$ and $R^5$ have the values listed in the table P.

TABLE Q

|  | X1, X2, X3 | X4 |
|---|---|---|
| Q.001 | $X^1$ is chloro, $X^2$ is CH, $X^3$ is chloro | chlorodifluoromethyl |
| Q.002 | $X^1$ is chloro, $X^2$ is CH, $X^3$ is chloro | difluoromethyl |
| Q.003 | $X^1$ is chloro, $X^2$ is CH, $X^3$ is chloro | trifluoromethyl |
| Q.004 | $X^1$ is chloro, $X^2$ is C—F, $X^3$ is hydrogen | chlorodifluoromethyl |
| Q.005 | $X^1$ is chloro, $X^2$ is C—F, $X^3$ is hydrogen | difluoromethyl |
| Q.006 | $X^1$ is chloro, $X^2$ is C—F, $X^3$ is hydrogen | trifluoromethyl |
| Q.007 | $X^1$ is fluoro, $X^2$ is C—Cl, $X^3$ is hydrogen | chlorodifluoromethyl |
| Q.008 | $X^1$ is fluoro, $X^2$ is C—Cl, $X^3$ is hydrogen | difluoromethyl |
| Q.009 | $X^1$ is fluoro, $X^2$ is C—Cl, $X^3$ is hydrogen | trifluoromethyl |
| Q.010 | $X^1$ is chloro, $X^2$ is C—Cl, $X^3$ is hydrogen | chlorodifluoromethyl |
| Q.011 | $X^1$ is chloro, $X^2$ is C—Cl, $X^3$ is hydrogen | difluoromethyl |
| Q.012 | $X^1$ is chloro, $X^2$ is C—Cl, $X^3$ is hydrogen | trifluoromethyl |
| Q.013 | $X^1$ is chloro, $X^2$ is C—Br, $X^3$ is chloro | chlorodifluoromethyl |
| Q.014 | $X^1$ is chloro, $X^2$ is C—Br, $X^3$ is chloro | difluoromethyl |
| Q.015 | $X^1$ is chloro, $X^2$ is C—Br, $X^3$ is chloro | trifluoromethyl |
| Q.016 | $X^1$ is chloro, $X^2$ is C—F, $X^3$ is chloro | chlorodifluoromethyl |
| Q.017 | $X^1$ is chloro, $X^2$ is C—F, $X^3$ is chloro | difluoromethyl |
| Q.018 | $X^1$ is chloro, $X^2$ is C—F, $X^3$ is chloro | trifluoromethyl |
| Q.019 | $X^1$ is chloro, $X^2$ is C—Cl, $X^3$ is chloro | chlorodifluoromethyl |
| Q.020 | $X^1$ is chloro, $X^2$ is C—Cl, $X^3$ is chloro | difluoromethyl |
| Q.021 | $X^1$ is chloro, $X^2$ is C—Cl, $X^3$ is chloro | trifluoromethyl |
| Q.022 | $X^1$ is chloro, $X^2$ is C—I, $X^3$ is chloro | chlorodifluoromethyl |
| Q.023 | $X^1$ is chloro, $X^2$ is C—I, $X^3$ is chloro | difluoromethyl |
| Q.024 | $X^1$ is chloro, $X^2$ is C—I, $X^3$ is chloro | trifluoromethyl |
| Q.025 | $X^1$ is fluoro, $X^2$ is C—F, $X^3$ is fluoro | chlorodifluoromethyl |
| Q.026 | $X^1$ is fluoro, $X^2$ is C—F, $X^3$ is fluoro | difluoromethyl |
| Q.027 | $X^1$ is fluoro, $X^2$ is C—F, $X^3$ is fluoro | trifluoromethyl |

TABLE Q-continued

| | X1, X2, X3 | X4 |
|---|---|---|
| Q.028 | $X^1$ is chloro, $X^2$ is CH, $X^3$ is bromo | chlorodifluoromethyl |
| Q.029 | $X^1$ is chloro, $X^2$ is CH, $X^3$ is bromo | difluoromethyl |
| Q.030 | $X^1$ is chloro, $X^2$ is CH, $X^3$ is bromo | trifluoromethyl |
| Q.031 | $X^1$ is chloro, $X^2$ is CH, $X^3$ is bromo | chlorodifluoromethyl |
| Q.032 | $X^1$ is chloro, $X^2$ is CH, $X^3$ is bromo | difluoromethyl |
| Q.033 | $X^1$ is chloro, $X^2$ is CH, $X^3$ is bromo | trifluoromethyl |
| Q.034 | $X^1$ is chloro, $X^2$ is CH, $X^3$ is bromo | chlorodifluoromethyl |
| Q.035 | $X^1$ is chloro, $X^2$ is CH, $X^3$ is bromo | difluoromethyl |
| Q.036 | $X^1$ is chloro, $X^2$ is CH, $X^3$ is bromo | trifluoromethyl |
| Q.037 | $X^1$ is chloro, $X^2$ is C—Cl, $X^3$ is trifluoromethyl | chlorodifluoromethyl |
| Q.038 | $X^1$ is chloro, $X^2$ is C—Cl, $X^3$ is trifluoromethyl | difluoromethyl |
| Q.039 | $X^1$ is chloro, $X^2$ is C—Cl, $X^3$ is trifluoromethyl | trifluoromethyl |
| Q.040 | $X^1$ is trifluoromethyl, $X^2$ is CH, $X^3$ is trifluoromethyl | chlorodifluoromethyl |
| Q.041 | $X^1$ is trifluoromethyl, $X^2$ is CH, $X^3$ is trifluoromethyl | difluoromethyl |
| Q.042 | $X^1$ is trifluoromethyl, $X^2$ is CH, $X^3$ is trifluoromethyl | trifluoromethyl |
| Q.043 | $X^1$ is trifluoromethyl, $X^2$ is CH, $X^3$ is trifluoromethyl | chlorodifluoromethyl |
| Q.044 | $X^1$ is trifluoromethyl, $X^2$ is CH, $X^3$ is trifluoromethyl | difluoromethyl |
| Q.045 | $X^1$ is trifluoromethyl, $X^2$ is CH, $X^3$ is trifluoromethyl | trifluoromethyl |
| Q.046 | $X^1$ is trifluoromethyl, $X^2$ is CH, $X^3$ is hydrogen | chlorodifluoromethyl |
| Q.047 | $X^1$ is trifluoromethyl, $X^2$ is CH, $X^3$ is hydrogen | difluoromethyl |
| Q.048 | $X^1$ is trifluoromethyl, $X^2$ is CH, $X^3$ is hydrogen | trifluoromethyl |
| Q.049 | $X^1$ is chloro, $X^2$ is N, $X^3$ is chloro | chlorodifluoromethyl |
| Q.050 | $X^1$ is chloro, $X^2$ is N, $X^3$ is chloro | difluoromethyl |
| Q.051 | $X^1$ is chloro, $X^2$ is N, $X^3$ is chloro | trifluoromethyl |
| Q.052 | $X^1$ is trifluoromethyl, $X^2$ is N, $X^3$ is trifluoromethyl | chlorodifluoromethyl |
| Q.053 | $X^1$ is trifluoromethyl, $X^2$ is N, $X^3$ is trifluoromethyl | difluoromethyl |
| Q.054 | $X^1$ is trifluoromethyl, $X^2$ is N, $X^3$ is trifluoromethyl | trifluoromethyl |

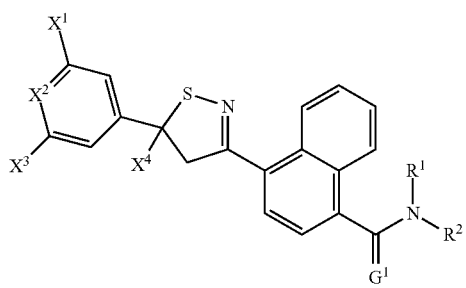

(I-B)

Table 1Q:

Table 1 Q provides 54 compounds of formula (I-B) wherein $G^1$ is oxygen, $R^1$ is hydrogen, $R^2$ is G.001, $X^1$, $X^2$, $X^3$ and X4 have the values listed in the table Q.

Table 2Q:

Table 2 Q provides 54 compounds of formula (I-B) wherein $G^1$ is oxygen, $R^1$ is hydrogen, $R^2$ is G.002, $X^1$, $X^2$, $X^3$ and X4 have the values listed in the table Q.

Table 3Q:

Table 3 Q provides 54 compounds of formula (I-B) wherein $G^1$ is oxygen, $R^1$ is hydrogen, $R^2$ is G.003, $X^1$, $X^2$, $X^3$ and X4 have the values listed in the table Q.

Table 4Q:

Table 4 Q provides 54 compounds of formula (I-B) wherein $G^1$ is oxygen, $R^1$ is hydrogen, $R^2$ is G.004, $X^1$, $X^2$, $X^3$ and X4 have the values listed in the table Q.

Table 5Q:

Table 5 Q provides 54 compounds of formula (I-B) wherein $G^1$ is oxygen, $R^1$ is hydrogen, $R^2$ is G.005, $X^1$, $X^2$, $X^3$ and X4 have the values listed in the table Q.

Table 6Q:

Table 6 Q provides 54 compounds of formula (I-B) wherein $G^1$ is oxygen, $R^1$ is hydrogen, $R^2$ is G.006, $X^1$, $X^2$, $X^3$ and X4 have the values listed in the table Q.

Table 7Q:

Table 7 Q provides 54 compounds of formula (I-B) wherein $G^1$ is oxygen, $R^1$ is hydrogen, $R^2$ is G.007, $X^1$, $X^2$, $X^3$ and X4 have the values listed in the table Q.

Table 8Q:

Table 8 Q provides 54 compounds of formula (I-B) wherein $G^1$ is oxygen, $R^1$ is hydrogen, $R^2$ is G.008, $X^1$, $X^2$, $X^3$ and X4 have the values listed in the table Q.

Table 9Q:

Table 9 Q provides 54 compounds of formula (I-B) wherein $G^1$ is oxygen, $R^1$ is hydrogen, $R^2$ is G.009, $X^1$, $X^2$, $X^3$ and X4 have the values listed in the table Q.

Table 10Q:

Table 10 Q provides 54 compounds of formula (I-B) wherein $G^1$ is oxygen, $R^1$ is hydrogen, $R^2$ is G.010, $X^1$, $X^2$, $X^3$ and X4 have the values listed in the table Q.

Table 11Q:

Table 11 Q provides 54 compounds of formula (I-B) wherein $G^1$ is oxygen, $R^1$ is hydrogen, $R^2$ is G.011, $X^1$, $X^2$, $X^3$ and X4 have the values listed in the table Q.

Table 12Q:

Table 12 Q provides 54 compounds of formula (I-B) wherein $G^1$ is oxygen, $R^1$ is hydrogen, $R^2$ is G.012, $X^1$, $X^2$, $X^3$ and X4 have the values listed in the table Q.

Table 13Q

Table 13 Q provides 54 compounds of formula (I-B) wherein $G^1$ is oxygen, $R^1$ is hydrogen, $R^2$ is G.013, $X^1$, $X^2$, $X^3$ and X4 have the values listed in the table Q.

Table 14Q:

Table 14 Q provides 54 compounds of formula (I-B) wherein $G^1$ is oxygen, $R^1$ is hydrogen, $R^2$ is G.014, $X^1$, $X^2$, $X^3$ and X4 have the values listed in the table Q.

Table 15Q:

Table 15 Q provides 54 compounds of formula (I-B) wherein $G^1$ is oxygen, $R^1$ is hydrogen, $R^2$ is G.015, $X^1$, $X^2$, $X^3$ and X4 have the values listed in the table Q.

Table 16Q:

Table 16 Q provides 54 compounds of formula (I-B) wherein $G^1$ is oxygen, $R^1$ is hydrogen, $R^2$ is G.016, $X^1$, $X^2$, $X^3$ and X4 have the values listed in the table Q.

Table 17Q:
Table 17 Q provides 54 compounds of formula (I-B) wherein $G^1$ is oxygen, $R^1$ is hydrogen, $R^2$ is G.017, $X^1$, $X^2$, $X^3$ and X4 have the values listed in the table Q.

Table 18Q:
Table 18 Q provides 54 compounds of formula (I-B) wherein $G^1$ is oxygen, $R^1$ is hydrogen, $R^2$ is G.018, $X^1$, $X^2$, $X^3$ and X4 have the values listed in the table Q.

Table 19Q:
Table 19 Q provides 54 compounds of formula (I-B) wherein $G^1$ is oxygen, $R^1$ is hydrogen, $R^2$ is G.019, $X^1$, $X^2$, $X^3$ and X4 have the values listed in the table Q.

Table 20Q:
Table 20 Q provides 54 compounds of formula (I-B) wherein $G^1$ is oxygen, $R^1$ is hydrogen, $R^2$ is G.020, $X^1$, $X^2$, $X^3$ and X4 have the values listed in the table Q.

Table 21Q:
Table 21Q provides 54 compounds of formula (I-B) wherein $G^1$ is oxygen, $R^1$ is hydrogen, $R^2$ is G.021, $X^1$, $X^2$, $X^3$ and X4 have the values listed in the table Q.

Table 22Q:
Table 22 Q provides 54 compounds of formula (I-B) wherein $G^1$ is oxygen, $R^1$ is hydrogen, $R^2$ is G.022, $X^1$, $X^2$, $X^3$ and X4 have the values listed in the table Q.

Table 23Q:
Table 23 Q provides 54 compounds of formula (I-B) wherein $G^1$ is oxygen, $R^1$ is hydrogen, $R^2$ is G.023, $X^1$, $X^2$, $X^3$ and X4 have the values listed in the table Q.

Table 24Q:
Table 24 Q provides 54 compounds of formula (I-B) wherein $G^1$ is oxygen, $R^1$ is hydrogen, $R^2$ is G.024, $X^1$, $X^2$, $X^3$ and X4 have the values listed in the table Q.

Table 25Q:
Table 25 Q provides 54 compounds of formula (I-B) wherein $G^1$ is oxygen, $R^1$ is hydrogen, $R^2$ is G.025, $X^1$, $X^2$, $X^3$ and X4 have the values listed in the table Q.

Table 26Q:
Table 26 Q provides 54 compounds of formula (I-B) wherein $G^1$ is oxygen, $R^1$ is hydrogen, $R^2$ is G.026, $X^1$, $X^2$, $X^3$ and X4 have the values listed in the table Q.

Table 27Q:
Table 27 Q provides 54 compounds of formula (I-B) wherein $G^1$ is oxygen, $R^1$ is hydrogen, $R^2$ is G.027, $X^1$, $X^2$, $X^3$ and X4 have the values listed in the table Q.

Table 28Q:
Table 28 Q provides 54 compounds of formula (I-B) wherein $G^1$ is oxygen, $R^1$ is hydrogen, $R^2$ is G.028, $X^1$, $X^2$, $X^3$ and X4 have the values listed in the table Q.

Table 29Q:
Table 29 Q provides 54 compounds of formula (I-B) wherein $G^1$ is oxygen, $R^1$ is hydrogen, $R^2$ is G.029, $X^1$, $X^2$, $X^3$ and X4 have the values listed in the table Q.

Table 30Q:
Table 30 Q provides 54 compounds of formula (I-B) wherein $G^1$ is oxygen, $R^1$ is hydrogen, $R^2$ is G.030, $X^1$, $X^2$, $X^3$ and X4 have the values listed in the table Q.

Table 31Q:
Table 31Q provides 54 compounds of formula (I-B) wherein $G^1$ is oxygen, $R^1$ is hydrogen, $R^2$ is G.031, $X^1$, $X^2$, $X^3$ and X4 have the values listed in the table Q.

Table 32Q:
Table 32 Q provides 54 compounds of formula (I-B) wherein $G^1$ is oxygen, $R^1$ is hydrogen, $R^2$ is G.032, $X^1$, $X^2$, $X^3$ and X4 have the values listed in the table Q.

Table 33Q:
Table 33 Q provides 54 compounds of formula (I-B) wherein $G^1$ is oxygen, $R^1$ is hydrogen, $R^2$ is G.033, $X^1$, $X^2$, $X^3$ and X4 have the values listed in the table Q.

Table 34Q:
Table 34 Q provides 54 compounds of formula (I-B) wherein $G^1$ is oxygen, $R^1$ is hydrogen, $R^2$ is G.034, $X^1$, $X^2$, $X^3$ and X4 have the values listed in the table Q.

Table 35Q:
Table 35 Q provides 54 compounds of formula (I-B) wherein $G^1$ is oxygen, $R^1$ is hydrogen, $R^2$ is G.035, $X^1$, $X^2$, $X^3$ and X4 have the values listed in the table Q.

Table 36Q:
Table 36 Q provides 54 compounds of formula (I-B) wherein $G^1$ is oxygen, $R^1$ is hydrogen, $R^2$ is G.036, $X^1$, $X^2$, $X^3$ and X4 have the values listed in the table Q.

Table 37Q:
Table 37 Q provides 54 compounds of formula (I-B) wherein $G^1$ is oxygen, $R^1$ is hydrogen, $R^2$ is G.037, $X^1$, $X^2$, $X^3$ and X4 have the values listed in the table Q.

Table 38Q:
Table 38 Q provides 54 compounds of formula (I-B) wherein $G^1$ is oxygen, $R^1$ is hydrogen, $R^2$ is G.038, $X^1$, $X^2$, $X^3$ and X4 have the values listed in the table Q.

Table 39Q:
Table 39 Q provides 54 compounds of formula (I-B) wherein $G^1$ is oxygen, $R^1$ is hydrogen, $R^2$ is G.039, $X^1$, $X^2$, $X^3$ and X4 have the values listed in the table Q.

Table 40Q:
Table 40 Q provides 54 compounds of formula (I-B) wherein $G^1$ is oxygen, $R^1$ is hydrogen, $R^2$ is G.040, $X^1$, $X^2$, $X^3$ and X4 have the values listed in the table Q.

Table 41Q:
Table 41Q provides 54 compounds of formula (I-B) wherein $G^1$ is oxygen, $R^1$ is hydrogen, $R^2$ is G.041, $X^1$, $X^2$, $X^3$ and X4 have the values listed in the table Q.

Table 42Q:
Table 42 Q provides 54 compounds of formula (I-B) wherein $G^1$ is oxygen, $R^1$ is hydrogen, $R^2$ is G.042, $X^1$, $X^2$, $X^3$ and X4 have the values listed in the table Q.

Table 43Q:
Table 43 Q provides 54 compounds of formula (I-B) wherein $G^1$ is oxygen, $R^1$ is hydrogen, $R^2$ is G.043, $X^1$, $X^2$, $X^3$ and X4 have the values listed in the table Q.

Table 44Q:
Table 44 Q provides 54 compounds of formula (I-B) wherein $G^1$ is oxygen, $R^1$ is hydrogen, $R^2$ is G.044, $X^1$, $X^2$, $X^3$ and X4 have the values listed in the table Q.

Table 45Q:
Table 45 Q provides 54 compounds of formula (I-B) wherein $G^1$ is oxygen, $R^1$ is hydrogen, $R^2$ is G.045, $X^1$, $X^2$, $X^3$ and X4 have the values listed in the table Q.

Table 46Q:
Table 46 Q provides 54 compounds of formula (I-B) wherein $G^1$ is oxygen, $R^1$ is hydrogen, $R^2$ is G.046, $X^1$, $X^2$, $X^3$ and X4 have the values listed in the table Q.

Table 47Q:
Table 47 Q provides 54 compounds of formula (I-B) wherein $G^1$ is oxygen, $R^1$ is hydrogen, $R^2$ is G.047, $X^1$, $X^2$, $X^3$ and X4 have the values listed in the table Q.

Table 48Q:
Table 48 Q provides 54 compounds of formula (I-B) wherein $G^1$ is oxygen, $R^1$ is hydrogen, $R^2$ is G.048, $X^1$, $X^2$, $X^3$ and X4 have the values listed in the table Q.

Table 49Q:
Table 49 Q provides 54 compounds of formula (I-B) wherein $G^1$ is oxygen, $R^1$ is hydrogen, $R^2$ is G.049, $X^1$, $X^2$, $X^3$ and X4 have the values listed in the table Q.

Table 50Q:
Table 50 Q provides 54 compounds of formula (I-B) wherein $G^1$ is oxygen, $R^1$ is hydrogen, $R^2$ is G.050, $X^1$, $X^2$, $X^3$ and X4 have the values listed in the table Q.

Table 51Q:
Table 51Q provides 54 compounds of formula (I-B) wherein $G^1$ is oxygen, $R^1$ is hydrogen, $R^2$ is G.051, $X^1$, $X^2$, $X^3$ and X4 have the values listed in the table Q.

Table 52Q:
Table 52 Q provides 54 compounds of formula (I-B) wherein $G^1$ is oxygen, $R^1$ is hydrogen, $R^2$ is G.052, $X^1$, $X^2$, $X^3$ and X4 have the values listed in the table Q.

Table 53Q:
Table 53 Q provides 54 compounds of formula (I-B) wherein $G^1$ is oxygen, $R^1$ is hydrogen, $R^2$ is G.053, $X^1$, $X^2$, $X^3$ and X4 have the values listed in the table Q.

Table 54Q:
Table 54 Q provides 54 compounds of formula (I-B) wherein $G^1$ is oxygen, $R^1$ is hydrogen, $R^2$ is G.054, $X^1$, $X^2$, $X^3$ and X4 have the values listed in the table Q.

Table 55Q:
Table 55 Q provides 54 compounds of formula (I-B) wherein $G^1$ is oxygen, $R^1$ is hydrogen, $R^2$ is G.055, $X^1$, $X^2$, $X^3$ and X4 have the values listed in the table Q.

Table 56Q:
Table 56 Q provides 54 compounds of formula (I-B) wherein $G^1$ is oxygen, $R^1$ is hydrogen, $R^2$ is G.056, $X^1$, $X^2$, $X^3$ and X4 have the values listed in the table Q.

Table 57Q:
Table 57 Q provides 54 compounds of formula (I-B) wherein $G^1$ is oxygen, $R^1$ is hydrogen, $R^2$ is G.057, $X^1$, $X^2$, $X^3$ and X4 have the values listed in the table Q.

Table 58Q:
Table 58 Q provides 54 compounds of formula (I-B) wherein $G^1$ is oxygen, $R^1$ is hydrogen, $R^2$ is G.058, $X^1$, $X^2$, $X^3$ and X4 have the values listed in the table Q.

Table 59Q:
Table 59 Q provides 54 compounds of formula (I-B) wherein $G^1$ is oxygen, $R^1$ is hydrogen, $R^2$ is G.059, $X^1$, $X^2$, $X^3$ and X4 have the values listed in the table Q.

Table 60Q:
Table 60 Q provides 54 compounds of formula (I-B) wherein $G^1$ is oxygen, $R^1$ is hydrogen, $R^2$ is G.060, $X^1$, $X^2$, $X^3$ and X4 have the values listed in the table Q.

Table 61Q:
Table 61Q provides 54 compounds of formula (I-B) wherein $G^1$ is oxygen, $R^1$ is hydrogen, $R^2$ is G.061, $X^1$, $X^2$, $X^3$ and X4 have the values listed in the table Q.

Table 62Q:
Table 62 Q provides 54 compounds of formula (I-B) wherein $G^1$ is oxygen, $R^1$ is hydrogen, $R^2$ is G.062, $X^1$, $X^2$, $X^3$ and X4 have the values listed in the table Q.

Table 63Q:
Table 63 Q provides 54 compounds of formula (I-B) wherein $G^1$ is oxygen, $R^1$ is hydrogen, $R^2$ is G.063, $X^1$, $X^2$, $X^3$ and X4 have the values listed in the table Q.

Table 64Q:
Table 64 Q provides 54 compounds of formula (I-B) wherein $G^1$ is oxygen, $R^1$ is hydrogen, $R^2$ is G.064, $X^1$, $X^2$, $X^3$ and X4 have the values listed in the table Q.

Table 65Q:
Table 65 Q provides 54 compounds of formula (I-B) wherein $G^1$ is oxygen, $R^1$ is hydrogen, $R^2$ is G.065, $X^1$, $X^2$, $X^3$ and X4 have the values listed in the table Q.

Table 66Q:
Table 66 Q provides 54 compounds of formula (I-B) wherein $G^1$ is oxygen, $R^1$ is hydrogen, $R^2$ is G.066, $X^1$, $X^2$, $X^3$ and X4 have the values listed in the table Q.

Table 67Q
Table 67 Q provides 54 compounds of formula (I-B) wherein $G^1$ is oxygen, $R^1$ is hydrogen, $R^2$ is G.067, $X^1$, $X^2$, $X^3$ and X4 have the values listed in the table Q.

Table 68Q:
Table 68 Q provides 54 compounds of formula (I-B) wherein $G^1$ is oxygen, $R^1$ is hydrogen, $R^2$ is G.068, $X^1$, $X^2$, $X^3$ and $X^4$ have the values listed in the table Q.

Table 69Q:
Table 69 Q provides 54 compounds of formula (I-B) wherein $G^1$ is oxygen, $R^1$ is hydrogen, $R^2$ is G.069, $X^1$, $X^2$, $X^3$ and $X^4$ have the values listed in the table Q.

Table 70Q:
Table 70 Q provides 54 compounds of formula (I-B) wherein $G^1$ is oxygen, $R^1$ is hydrogen, $R^2$ is G.070, $X^1$, $X^2$, $X^3$ and $X^4$ have the values listed in the table Q.

Table 71Q:
Table 71 Q provides 54 compounds of formula (I-B) wherein $G^1$ is oxygen, $R^1$ is hydrogen, $R^2$ is G.071, $X^1$, $X^2$, $X^3$ and X4 have the values listed in the table Q.

Table 72Q:
Table 72 Q provides 54 compounds of formula (I-B) wherein $G^1$ is oxygen, $R^1$ is hydrogen, $R^2$ is G.072, $X^1$, $X^2$, $X^3$ and X4 have the values listed in the table Q.

Table 73Q:
Table 73 Q provides 54 compounds of formula (I-B) wherein $G^1$ is oxygen, $R^1$ is hydrogen, $R^2$ is G.073, $X^1$, $X^2$, $X^3$ and X4 have the values listed in the table Q.

Table 74Q:
Table 74 Q provides 54 compounds of formula (I-B) wherein $G^1$ is oxygen, $R^1$ is hydrogen, $R^2$ is G.074, $x^1$, $X^2$, $X^3$ and X4 have the values listed in the table Q.

Table 75Q:
Table 75 Q provides 54 compounds of formula (I-B) wherein $G^1$ is oxygen, $R^1$ is hydrogen, $R^2$ is G.075, $X^1$, $X^2$, $X^3$ and X4 have the values listed in the table Q.

Table 76Q:
Table 76 Q provides 54 compounds of formula (I-B) wherein $G^1$ is oxygen, $R^1$ is hydrogen, $R^2$ is G.076, $X^1$, $X^2$, $X^3$ and X4 have the values listed in the table Q.

Table 77Q:
Table 77 Q provides 54 compounds of formula (I-B) wherein $G^1$ is oxygen, $R^1$ is hydrogen, $R^2$ is G.077, $X^1$, $X^2$, $X^3$ and X4 have the values listed in the table Q.

Table 78Q:
Table 78 Q provides 54 compounds of formula (I-B) wherein $G^1$ is oxygen, $R^1$ is hydrogen, $R^2$ is G.078, $X^1$, $X^2$, $X^3$ and X4 have the values listed in the table Q.

Table 79Q:
Table 79 Q provides 54 compounds of formula (I-B) wherein $G^1$ is oxygen, $R^1$ is hydrogen, $R^2$ is G.079, $X^1$, $X^2$, $X^3$ and X4 have the values listed in the table Q.

Table 80Q:
Table 80 Q provides 54 compounds of formula (I-B) wherein $G^1$ is oxygen, $R^1$ is hydrogen, $R^2$ is G.080, $X^1$, $X^2$, $X^3$ and X4 have the values listed in the table Q.

Table 81Q:
Table 81 Q provides 54 compounds of formula (I-B) wherein $G^1$ is oxygen, $R^1$ is hydrogen, $R^2$ is G.081, $X^1$, $X^2$, $X^3$ and X4 have the values listed in the table Q.

Table 82Q:
Table 82 Q provides 54 compounds of formula (I-B) wherein $G^1$ is oxygen, $R^1$ is hydrogen, $R^2$ is G.082, $X^1$, $X^2$, $X^3$ and X4 have the values listed in the table Q.

Table 83Q:
Table 83 Q provides 54 compounds of formula (I-B) wherein $G^1$ is oxygen, $R^1$ is hydrogen, $R^2$ is G.083, $X^1$, $X^2$, $X^3$ and X4 have the values listed in the table Q.

Table 84Q:
Table 84 Q provides 54 compounds of formula (I-B) wherein $G^1$ is oxygen, $R^1$ is hydrogen, $R^2$ is G.084, $X^1$, $X^2$, $X^3$ and X4 have the values listed in the table Q.

Table 85Q:
Table 85 Q provides 54 compounds of formula (I-B) wherein $G^1$ is oxygen, $R^1$ is hydrogen, $R^2$ is G.085, $X^1$, $X^2$, $X^3$ and X4 have the values listed in the table Q.

Table 86Q:
Table 86 Q provides 54 compounds of formula (I-B) wherein $G^1$ is oxygen, $R^1$ is hydrogen, $R^2$ is G.086, $X^1$, $X^2$, $X^3$ and X4 have the values listed in the table Q.

Table 87Q:
Table 87 Q provides 54 compounds of formula (I-B) wherein $G^1$ is oxygen, $R^1$ is hydrogen, $R^2$ is G.087, $X^1$, $X^2$, $X^3$ and X4 have the values listed in the table Q.

Table 88Q:
Table 88 Q provides 54 compounds of formula (I-B) wherein $G^1$ is oxygen, $R^1$ is hydrogen, $R^2$ is G.088, $X^1$, $X^2$, $X^3$ and X4 have the values listed in the table Q.

Table 89Q:
Table 89 Q provides 54 compounds of formula (I-B) wherein $G^1$ is oxygen, $R^1$ is hydrogen, $R^2$ is G.089, $X^1$, $X^2$, $X^3$ and X4 have the values listed in the table Q.

Table 90Q:
Table 90 Q provides 54 compounds of formula (I-B) wherein $G^1$ is oxygen, $R^1$ is hydrogen, $R^2$ is G.090, $X^1$, $X^2$, $X^3$ and X4 have the values listed in the table Q.

Table 91Q:
Table 91 Q provides 54 compounds of formula (I-B) wherein $G^1$ is oxygen, $R^1$ is hydrogen, $R^2$ is G.091, $X^1$, $X^2$, $X^3$ and X4 have the values listed in the table Q.

Table 92 Q:
Table 92 Q provides 54 compounds of formula (I-B) wherein $G^1$ is oxygen, $R^1$ is hydrogen, $R^2$ is G.092, $X^1$, $X^2$, $X^3$ and X4 have the values listed in the table Q.

Table 93 Q:
Table 93 Q provides 54 compounds of formula (I-B) wherein $G^1$ is oxygen, $R^1$ is hydrogen, $R^2$ is G.093, $X^1$, $X^2$, $X^3$ and X4 have the values listed in the table Q.

Table 94 Q:
Table 94 Q provides 54 compounds of formula (I-B) wherein $G^1$ is oxygen, $R^1$ is hydrogen, $R^2$ is G.094, $X^1$, $X^2$, $X^3$ and X4 have the values listed in the table Q.

Table 95 Q:
Table 95 Q provides 54 compounds of formula (I-B) wherein $G^1$ is oxygen, $R^1$ is hydrogen, $R^2$ is G.095, $X^1$, $X^2$, $X^3$ and X4 have the values listed in the table Q.

Table 96 Q:
Table 96 Q provides 54 compounds of formula (I-B) wherein $G^1$ is oxygen, $R^1$ is hydrogen, $R^2$ is G.096, $X^1$, $X^2$, $X^3$ and X4 have the values listed in the table Q.

Table 97 Q:
Table 97 Q provides 54 compounds of formula (I-B) wherein $G^1$ is oxygen, $R^1$ is hydrogen, $R^2$ is G.097, $X^1$, $X^2$, $X^3$ and X4 have the values listed in the table Q.

Table 98 Q:
Table 98 Q provides 54 compounds of formula (I-B) wherein $G^1$ is oxygen, $R^1$ is hydrogen, $R^2$ is G.098, $X^1$, $X^2$, $X^3$ and X4 have the values listed in the table Q.

Table 99 Q:
Table 99 Q provides 54 compounds of formula (I-B) wherein $G^1$ is oxygen, $R^1$ is hydrogen, $R^2$ is G.099, $X^1$, $X^2$, $X^3$ and X4 have the values listed in the table Q.

Table 100 Q:
Table 100 Q provides 54 compounds of formula (I-B) wherein $G^1$ is oxygen, $R^1$ is hydrogen, $R^2$ is G.100, $X^1$, $X^2$, $X^3$ and X4 have the values listed in the table Q.

Table 101Q:
Table 101Q provides 54 compounds of formula (I-B) wherein $G^1$ is oxygen, $R^1$ is hydrogen, $R^2$ is G.101, $X^1$, $X^2$, $X^3$ and X4 have the values listed in the table Q.

Table 102 Q:
Table 102 Q provides 54 compounds of formula (I-B) wherein $G^1$ is oxygen, $R^1$ is hydrogen, $R^2$ is G.102, $X^1$, $X^2$, $X^3$ and X4 have the values listed in the table Q.

Table 103 Q:
Table 103 Q provides 54 compounds of formula (I-B) wherein $G^1$ is oxygen, $R^1$ is hydrogen, $R^2$ is G.103, $X^1$, $X^2$, $X^3$ and X4 have the values listed in the table Q.

Table 104 Q:
Table 104 Q provides 54 compounds of formula (I-B) wherein $G^1$ is oxygen, $R^1$ is hydrogen, $R^2$ is G.104, $X^1$, $X^2$, $X^3$ and X4 have the values listed in the table Q.

Table 105 Q:
Table 105 Q provides 54 compounds of formula (I-B) wherein $G^1$ is oxygen, $R^1$ is hydrogen, $R^2$ is G.105, $X^1$, $X^2$, $X^3$ and X4 have the values listed in the table Q.

Table 106 Q:
Table 106 Q provides 54 compounds of formula (I-B) wherein $G^1$ is oxygen, $R^1$ is hydrogen, $R^2$ is G.106, $X^1$, $X^2$, $X^3$ and X4 have the values listed in the table Q.

Table 107 Q:
Table 107 Q provides 54 compounds of formula (I-B) wherein $G^1$ is oxygen, $R^1$ is hydrogen, $R^2$ is G.107, $X^1$, $X^2$, $X^3$ and X4 have the values listed in the table Q.

Table 108 Q:
Table 108 Q provides 54 compounds of formula (I-B) wherein $G^1$ is oxygen, $R^1$ is hydrogen, $R^2$ is G.108, $X^1$, $X^2$, $X^3$ and X4 have the values listed in the table Q.

Table 109 Q:
Table 109 Q provides 54 compounds of formula (I-B) wherein $G^1$ is oxygen, $R^1$ is hydrogen, $R^2$ is G.109, $X^1$, $X^2$, $X^3$ and X4 have the values listed in the table Q.

Table 110 Q:
Table 110 Q provides 54 compounds of formula (I-B) wherein $G^1$ is oxygen, $R^1$ is hydrogen, $R^2$ is G.110, $X^1$, $X^2$, $X^3$ and X4 have the values listed in the table Q.

Table 111Q:
Table 111Q provides 54 compounds of formula (I-B) wherein $G^1$ is oxygen, $R^1$ is hydrogen, $R^2$ is G.111, $X^1$, $X^2$, $X^3$ and X4 have the values listed in the table Q.

Table 112 Q:
Table 112 Q provides 54 compounds of formula (I-B) wherein $G^1$ is oxygen, $R^1$ is hydrogen, $R^2$ is G.112, $X^1$, $X^2$, $X^3$ and X4 have the values listed in the table Q.

Table 113 Q:
Table 113 Q provides 54 compounds of formula (I-B) wherein $G^1$ is oxygen, $R^1$ is hydrogen, $R^2$ is G.113, $X^1$, $X^2$, $X^3$ and X4 have the values listed in the table Q.
Table 114 Q:
Table 114 Q provides 54 compounds of formula (I-B) wherein $G^1$ is oxygen, $R^1$ is hydrogen, $R^2$ is G.114, $X^1$, $X^2$, $X^3$ and X4 have the values listed in the table Q.
Table 115 Q:
Table 115 Q provides 54 compounds of formula (I-B) wherein $G^1$ is oxygen, $R^1$ is hydrogen, $R^2$ is G.115, $X^1$, $X^2$, $X^3$ and X4 have the values listed in the table Q.
Table 116 Q:
Table 116 Q provides 54 compounds of formula (I-B) wherein $G^1$ is oxygen, $R^1$ is hydrogen, $R^2$ is G.116, $X^1$, $X^2$, $X^3$ and X4 have the values listed in the table Q.

(I-C)

Table 117Q:
Table 117Q provides 54 compounds of formula (I-C) wherein $G^1$ is oxygen, $R^1$ is hydrogen, $R^2$ is G.001, $X^1$, $X^2$, $X^3$ and X4 have the values listed in the table Q.
Table 118Q:
Table 118Q provides 54 compounds of formula (I-C) wherein $G^1$ is oxygen, $R^1$ is hydrogen, $R^2$ is G.002, $X^1$, $X^2$, $X^3$ and X4 have the values listed in the table Q.
Table 119 Q:
Table 119Q provides 54 compounds of formula (I-C) wherein $G^1$ is oxygen, $R^1$ is hydrogen, $R^2$ is G.003, $X^1$, $X^2$, $X^3$ and X4 have the values listed in the table Q.
Table 120Q:
Table 120Q provides 54 compounds of formula (I-C) wherein $G^1$ is oxygen, $R^1$ is hydrogen, $R^2$ is G.004, $X^1$, $X^2$, $X^3$ and X4 have the values listed in the table Q.
Table 121 Q:
Table 121Q provides 54 compounds of formula (I-C) wherein $G^1$ is oxygen, $R^1$ is hydrogen, $R^2$ is G.005, $X^1$, $X^2$, $X^3$ and X4 have the values listed in the table Q.
Table 122Q:
Table 122Q provides 54 compounds of formula (I-C) wherein $G^1$ is oxygen, $R^1$ is hydrogen, $R^2$ is G.006, $X^1$, $X^2$, $X^3$ and X4 have the values listed in the table Q.
Table 123Q:
Table 123Q provides 54 compounds of formula (I-C) wherein $G^1$ is oxygen, $R^1$ is hydrogen, $R^2$ is G.007, $X^1$, $X^2$, $X^3$ and X4 have the values listed in the table Q.
Table 124Q:
Table 124Q provides 54 compounds of formula (I-C) wherein $G^1$ is oxygen, $R^1$ is hydrogen, $R^2$ is G.008, $X^1$, $X^2$, $X^3$ and X4 have the values listed in the table Q.
Table 125Q:
Table 125Q provides 54 compounds of formula (I-C) wherein $G^1$ is oxygen, $R^1$ is hydrogen, $R^2$ is G.009, $X^1$, $X^2$, $X^3$ and X4 have the values listed in the table Q.
Table 126Q:
Table 126Q provides 54 compounds of formula (I-C) wherein $G^1$ is oxygen, $R^1$ is hydrogen, $R^2$ is G.010, $X^1$, $X^2$, $X^3$ and X4 have the values listed in the table Q.
Table 127Q:
Table 127Q provides 54 compounds of formula (I-C) wherein $G^1$ is oxygen, $R^1$ is hydrogen, $R^2$ is G.011, $X^1$, $X^2$, $X^3$ and X4 have the values listed in the table Q.
Table 128Q:
Table 128Q provides 54 compounds of formula (I-C) wherein $G^1$ is oxygen, $R^1$ is hydrogen, $R^2$ is G.012, $X^1$, $X^2$, $X^3$ and X4 have the values listed in the table Q.
Table 129 Q:
Table 129Q provides 54 compounds of formula (I-C) wherein $G^1$ is oxygen, $R^1$ is hydrogen, $R^2$ is G.013, $X^1$, $X^2$, $X^3$ and X4 have the values listed in the table Q.
Table 130Q:
Table 130Q provides 54 compounds of formula (I-C) wherein $G^1$ is oxygen, $R^1$ is hydrogen, $R^2$ is G.014, $X^1$, $X^2$, $X^3$ and X4 have the values listed in the table Q.
Table 131Q:
Table 131Q provides 54 compounds of formula (I-C) wherein $G^1$ is oxygen, $R^1$ is hydrogen, $R^2$ is G.015, $X^1$, $X^2$, $X^3$ and X4 have the values listed in the table Q.
Table 132Q:
Table 132Q provides 54 compounds of formula (I-C) wherein $G^1$ is oxygen, $R^1$ is hydrogen, $R^2$ is G.016, $X^1$, $X^2$, $X^3$ and X4 have the values listed in the table Q.
Table 133Q:
Table 133Q provides 54 compounds of formula (I-C) wherein $G^1$ is oxygen, $R^1$ is hydrogen, $R^2$ is G.017, $X^1$, $X^2$, $X^3$ and X4 have the values listed in the table Q.
Table 134Q:
Table 134Q provides 54 compounds of formula (I-C) wherein $G^1$ is oxygen, $R^1$ is hydrogen, $R^2$ is G.018, $X^1$, $X^2$, $X^3$ and X4 have the values listed in the table Q.
Table 135Q:
Table 135Q provides 54 compounds of formula (I-C) wherein $G^1$ is oxygen, $R^1$ is hydrogen, $R^2$ is G.019, $X^1$, $X^2$, $X^3$ and X4 have the values listed in the table Q.
Table 136Q:
Table 136Q provides 54 compounds of formula (I-C) wherein $G^1$ is oxygen, $R^1$ is hydrogen, $R^2$ is G.020, $X^1$, $X^2$, $X^3$ and X4 have the values listed in the table Q.
Table 137Q:
Table 137Q provides 54 compounds of formula (I-C) wherein $G^1$ is oxygen, $R^1$ is hydrogen, $R^2$ is G.021, $X^1$, $X^2$, $X^3$ and X4 have the values listed in the table Q.
Table 138Q:
Table 138Q provides 54 compounds of formula (I-C) wherein $G^1$ is oxygen, $R^1$ is hydrogen, $R^2$ is G.022, $X^1$, $X^2$, $X^3$ and X4 have the values listed in the table Q.
Table 139Q:
Table 139Q provides 54 compounds of formula (I-C) wherein $G^1$ is oxygen, $R^1$ is hydrogen, $R^2$ is G.023, $X^1$, $X^2$, $X^3$ and X4 have the values listed in the table Q.
Table 140Q:
Table 140Q provides 54 compounds of formula (I-C) wherein $G^1$ is oxygen, $R^1$ is hydrogen, $R^2$ is G.024, $X^1$, $X^2$, $X^3$ and X4 have the values listed in the table Q.
Table 141Q:
Table 141Q provides 54 compounds of formula (I-C) wherein $G^1$ is oxygen, $R^1$ is hydrogen, $R^2$ is G.025, $X^1$, $X^2$, $X^3$ and X4 have the values listed in the table Q.

Table 142Q:
Table 142Q provides 54 compounds of formula (I-C) wherein $G^1$ is oxygen, $R^1$ is hydrogen, $R^2$ is G.026, $X^1$, $X^2$, $X^3$ and X4 have the values listed in the table Q.

Table 143Q:
Table 143Q provides 54 compounds of formula (I-C) wherein $G^1$ is oxygen, $R^1$ is hydrogen, $R^2$ is G.027, $X^1$, $X^2$, $X^3$ and X4 have the values listed in the table Q.

Table 144Q:
Table 144Q provides 54 compounds of formula (I-C) wherein $G^1$ is oxygen, $R^1$ is hydrogen, $R^2$ is G.028, $X^1$, $X^2$, $X^3$ and X4 have the values listed in the table Q.

Table 145 Q:
Table 145Q provides 54 compounds of formula (I-C) wherein $G^1$ is oxygen, $R^1$ is hydrogen, $R^2$ is G.029, $X^1$, $X^2$, $X^3$ and X4 have the values listed in the table Q.

Table 146 Q:
Table 146Q provides 54 compounds of formula (I-C) wherein $G^1$ is oxygen, $R^1$ is hydrogen, $R^2$ is G.030, $X^1$, $X^2$, $X^3$ and X4 have the values listed in the table Q.

Table 147 Q:
Table 147Q provides 54 compounds of formula (I-C) wherein $G^1$ is oxygen, $R^1$ is hydrogen, $R^2$ is G.031, $X^1$, $X^2$, $X^3$ and X4 have the values listed in the table Q.

Table 148Q:
Table 148Q provides 54 compounds of formula (I-C) wherein $G^1$ is oxygen, $R^1$ is hydrogen, $R^2$ is G.032, $X^1$, $X^2$, $X^3$ and X4 have the values listed in the table Q.

Table 149Q:
Table 149Q provides 54 compounds of formula (I-C) wherein $G^1$ is oxygen, $R^1$ is hydrogen, $R^2$ is G.033, $X^1$, $X^2$, $X^3$ and X4 have the values listed in the table Q.

Table 150 Q:
Table 150Q provides 54 compounds of formula (I-C) wherein $G^1$ is oxygen, $R^1$ is hydrogen, $R^2$ is G.034, $X^1$, $X^2$, $X^3$ and X4 have the values listed in the table Q.

Table 151 Q:
Table 151Q provides 54 compounds of formula (I-C) wherein $G^1$ is oxygen, $R^1$ is hydrogen, $R^2$ is G.035, $X^1$, $X^2$, $X^3$ and X4 have the values listed in the table Q.

Table 152Q:
Table 152Q provides 54 compounds of formula (I-C) wherein $G^1$ is oxygen, $R^1$ is hydrogen, $R^2$ is G.036, $X^1$, $X^2$, $X^3$ and X4 have the values listed in the table Q.

Table 153Q:
Table 153Q provides 54 compounds of formula (I-C) wherein $G^1$ is oxygen, $R^1$ is hydrogen, $R^2$ is G.037, $X^1$, $X^2$, $X^3$ and X4 have the values listed in the table Q.

Table 154Q:
Table 154Q provides 54 compounds of formula (I-C) wherein $G^1$ is oxygen, $R^1$ is hydrogen, $R^2$ is G.038, $X^1$, $X^2$, $X^3$ and X4 have the values listed in the table Q.

Table 155 Q:
Table 155Q provides 54 compounds of formula (I-C) wherein $G^1$ is oxygen, $R^1$ is hydrogen, $R^2$ is G.039, $X^1$, $X^2$, $X^3$ and X4 have the values listed in the table Q.

Table 156 Q:
Table 156Q provides 54 compounds of formula (I-C) wherein $G^1$ is oxygen, $R^1$ is hydrogen, $R^2$ is G.040, $X^1$, $X^2$, $X^3$ and X4 have the values listed in the table Q.

Table 157Q:
Table 157Q provides 54 compounds of formula (I-C) wherein $G^1$ is oxygen, $R^1$ is hydrogen, $R^2$ is G.041, $X^1$, $X^2$, $X^3$ and X4 have the values listed in the table Q.

Table 158Q:
Table 158Q provides 54 compounds of formula (I-C) wherein $G^1$ is oxygen, $R^1$ is hydrogen, $R^2$ is G.042, $X^1$, $X^2$, $X^3$ and X4 have the values listed in the table Q.

Table 159 Q:
Table 159Q provides 54 compounds of formula (I-C) wherein $G^1$ is oxygen, $R^1$ is hydrogen, $R^2$ is G.043, $X^1$, $X^2$, $X^3$ and X4 have the values listed in the table Q.

Table 160Q:
Table 160Q provides 54 compounds of formula (I-C) wherein $G^1$ is oxygen, $R^1$ is hydrogen, $R^2$ is G.044, $X^1$, $X^2$, $X^3$ and X4 have the values listed in the table Q.

Table 161Q:
Table 161Q provides 54 compounds of formula (I-C) wherein $G^1$ is oxygen, $R^1$ is hydrogen, $R^2$ is G.045, $X^1$, $X^2$, $X^3$ and X4 have the values listed in the table Q.

Table 162 Q:
Table 162Q provides 54 compounds of formula (I-C) wherein $G^1$ is oxygen, $R^1$ is hydrogen, $R^2$ is G.046, $X^1$, $X^2$, $X^3$ and X4 have the values listed in the table Q.

Table 163Q:
Table 163Q provides 54 compounds of formula (I-C) wherein $G^1$ is oxygen, $R^1$ is hydrogen, $R^2$ is G.047, $X^1$, $X^2$, $X^3$ and X4 have the values listed in the table Q.

Table 164 Q:
Table 164Q provides 54 compounds of formula (I-C) wherein $G^1$ is oxygen, $R^1$ is hydrogen, $R^2$ is G.048, $X^1$, $X^2$, $X^3$ and X4 have the values listed in the table Q.

Table 165 Q:
Table 165Q provides 54 compounds of formula (I-C) wherein $G^1$ is oxygen, $R^1$ is hydrogen, $R^2$ is G.049, $X^1$, $X^2$, $X^3$ and X4 have the values listed in the table Q.

Table 166Q:
Table 166Q provides 54 compounds of formula (I-C) wherein $G^1$ is oxygen, $R^1$ is hydrogen, $R^2$ is G.050, $X^1$, $X^2$, $X^3$ and X4 have the values listed in the table Q.

Table 167 Q:
Table 167Q provides 54 compounds of formula (I-C) wherein $G^1$ is oxygen, $R^1$ is hydrogen, $R^2$ is G.051, $X^1$, $X^2$, $X^3$ and X4 have the values listed in the table Q.

Table 168Q:
Table 168Q provides 54 compounds of formula (I-C) wherein $G^1$ is oxygen, $R^1$ is hydrogen, $R^2$ is G.052, $X^1$, $X^2$, $X^3$ and X4 have the values listed in the table Q.

Table 169Q:
Table 169Q provides 54 compounds of formula (I-C) wherein $G^1$ is oxygen, $R^1$ is hydrogen, $R^2$ is G.053, $X^1$, $X^2$, $X^3$ and X4 have the values listed in the table Q.

Table 170 Q:
Table 170Q provides 54 compounds of formula (I-C) wherein $G^1$ is oxygen, $R^1$ is hydrogen, $R^2$ is G.054, $X^1$, $X^2$, $X^3$ and X4 have the values listed in the table Q.

Table 171Q:
Table 171Q provides 54 compounds of formula (I-C) wherein $G^1$ is oxygen, $R^1$ is hydrogen, $R^2$ is G.055, $X^1$, $X^2$, $X^3$ and X4 have the values listed in the table Q.

Table 172Q:
Table 172Q provides 54 compounds of formula (I-C) wherein $G^1$ is oxygen, $R^1$ is hydrogen, $R^2$ is G.056, $X^1$, $X^2$, $X^3$ and X4 have the values listed in the table Q.

Table 173Q:
Table 173Q provides 54 compounds of formula (I-C) wherein $G^1$ is oxygen, $R^1$ is hydrogen, $R^2$ is G.057, $X^1$, $X^2$, $X^3$ and X4 have the values listed in the table Q.

Table 174Q:
Table 174Q provides 54 compounds of formula (I-C) wherein $G^1$ is oxygen, $R^1$ is hydrogen, $R^2$ is G.058, $X^1, X^2, X^3$ and X4 have the values listed in the table Q.

Table 175Q:
Table 175Q provides 54 compounds of formula (I-C) wherein $G^1$ is oxygen, $R^1$ is hydrogen, $R^2$ is G.059, $X^1, X^2, X^3$ and X4 have the values listed in the table Q.

Table 176Q:
Table 176Q provides 54 compounds of formula (I-C) wherein $G^1$ is oxygen, $R^1$ is hydrogen, $R^2$ is G.060, $X^1, X^2, X^3$ and X4 have the values listed in the table Q.

Table 177Q:
Table 177Q provides 54 compounds of formula (I-C) wherein $G^1$ is oxygen, $R^1$ is hydrogen, $R^2$ is G.061, $X^1, X^2, X^3$ and X4 have the values listed in the table Q.

Table 178Q:
Table 178Q provides 54 compounds of formula (I-C) wherein $G^1$ is oxygen, $R^1$ is hydrogen, $R^2$ is G.062, $X^1, X^2, X^3$ and X4 have the values listed in the table Q.

Table 179Q:
Table 179Q provides 54 compounds of formula (I-C) wherein $G^1$ is oxygen, $R^1$ is hydrogen, $R^2$ is G.063, $X^1, X^2, X^3$ and X4 have the values listed in the table Q.

Table 180 Q:
Table 180Q provides 54 compounds of formula (I-C) wherein $G^1$ is oxygen, $R^1$ is hydrogen, $R^2$ is G.064, $X^1, X^2, X^3$ and X4 have the values listed in the table Q.

Table 181 Q:
Table 181Q provides 54 compounds of formula (I-C) wherein $G^1$ is oxygen, $R^1$ is hydrogen, $R^2$ is G.065, $X^1, X^2, X^3$ and X4 have the values listed in the table Q.

Table 182 Q:
Table 182Q provides 54 compounds of formula (I-C) wherein $G^1$ is oxygen, $R^1$ is hydrogen, $R^2$ is G.066, $X^1, X^2, X^3$ and X4 have the values listed in the table Q.

Table 183Q:
Table 183Q provides 54 compounds of formula (I-C) wherein $G^1$ is oxygen, $R^1$ is hydrogen, $R^2$ is G.067, $X^1, X^2, X^3$ and X4 have the values listed in the table Q.

Table 184Q:
Table 184Q provides 54 compounds of formula (I-C) wherein $G^1$ is oxygen, $R^1$ is hydrogen, $R^2$ is G.068, $X^1, X^2, X^3$ and X4 have the values listed in the table Q.

Table 185Q:
Table 185Q provides 54 compounds of formula (I-C) wherein $G^1$ is oxygen, $R^1$ is hydrogen, $R^2$ is G.069, $X^1, X^2, X^3$ and X4 have the values listed in the table Q.

Table 186 Q:
Table 186Q provides 54 compounds of formula (I-C) wherein $G^1$ is oxygen, $R^1$ is hydrogen, $R^2$ is G.070, $X^1, X^2, X^3$ and X4 have the values listed in the table Q.

Table 187Q:
Table 187Q provides 54 compounds of formula (I-C) wherein $G^1$ is oxygen, $R^1$ is hydrogen, $R^2$ is G.071, $X^1, X^2, X^3$ and X4 have the values listed in the table Q.

Table 188Q:
Table 188Q provides 54 compounds of formula (I-C) wherein $G^1$ is oxygen, $R^1$ is hydrogen, $R^2$ is G.072, $X^1, X^2, X^3$ and X4 have the values listed in the table Q.

Table 189Q:
Table 189Q provides 54 compounds of formula (I-C) wherein $G^1$ is oxygen, $R^1$ is hydrogen, $R^2$ is G.073, $X^1, X^2, X^3$ and X4 have the values listed in the table Q.

Table 190 Q:
Table 190Q provides 54 compounds of formula (I-C) wherein $G^1$ is oxygen, $R^1$ is hydrogen, $R^2$ is G.074, $X^1, X^2, X^3$ and X4 have the values listed in the table Q.

Table 191Q:
Table 191Q provides 54 compounds of formula (I-C) wherein $G^1$ is oxygen, $R^1$ is hydrogen, $R^2$ is G.075, $X^1, X^2, X^3$ and X4 have the values listed in the table Q.

Table 192 Q:
Table 192Q provides 54 compounds of formula (I-C) wherein $G^1$ is oxygen, $R^1$ is hydrogen, $R^2$ is G.076, $X^1, X^2, X^3$ and X4 have the values listed in the table Q.

Table 193 Q:
Table 193Q provides 54 compounds of formula (I-C) wherein $G^1$ is oxygen, $R^1$ is hydrogen, $R^2$ is G.077, $X^1, X^2, X^3$ and X4 have the values listed in the table Q.

Table 194Q:
Table 194Q provides 54 compounds of formula (I-C) wherein $G^1$ is oxygen, $R^1$ is hydrogen, $R^2$ is G.078, $X^1, X^2, X^3$ and X4 have the values listed in the table Q.

Table 195Q:
Table 195Q provides 54 compounds of formula (I-C) wherein $G^1$ is oxygen, $R^1$ is hydrogen, $R^2$ is G.079, $X^1, X^2, X^3$ and X4 have the values listed in the table Q.

Table 196Q:
Table 196Q provides 54 compounds of formula (I-C) wherein $G^1$ is oxygen, $R^1$ is hydrogen, $R^2$ is G.080, $X^1, X^2, X^3$ and X4 have the values listed in the table Q.

Table 197Q:
Table 197Q provides 54 compounds of formula (I-C) wherein $G^1$ is oxygen, $R^1$ is hydrogen, $R^2$ is G.081, $X^1, X^2, X^3$ and X4 have the values listed in the table Q.

Table 198Q:
Table 198Q provides 54 compounds of formula (I-C) wherein $G^1$ is oxygen, $R^1$ is hydrogen, $R^2$ is G.082, $X^1, X^2, X^3$ and X4 have the values listed in the table Q.

Table 199Q:
Table 199Q provides 54 compounds of formula (I-C) wherein $G^1$ is oxygen, $R^1$ is hydrogen, $R^2$ is G.083, $X^1, X^2, X^3$ and X4 have the values listed in the table Q.

Table 200Q:
Table 200Q provides 54 compounds of formula (I-C) wherein $G^1$ is oxygen, $R^1$ is hydrogen, $R^2$ is G.084, $X^1, X^2, X^3$ and X4 have the values listed in the table Q.

Table 201Q:
Table 201Q provides 54 compounds of formula (I-C) wherein $G^1$ is oxygen, $R^1$ is hydrogen, $R^2$ is G.085, $X^1, X^2, X^3$ and X4 have the values listed in the table Q.

Table 202Q:
Table 202Q provides 54 compounds of formula (I-C) wherein $G^1$ is oxygen, $R^1$ is hydrogen, $R^2$ is G.086, $X^1, X^2, X^3$ and X4 have the values listed in the table Q.

Table 203Q:
Table 203Q provides 54 compounds of formula (I-C) wherein $G^1$ is oxygen, $R^1$ is hydrogen, $R^2$ is G.087, $X^1, X^2, X^3$ and X4 have the values listed in the table Q.

Table 204 Q:
Table 204Q provides 54 compounds of formula (I-C) wherein $G^1$ is oxygen, $R^1$ is hydrogen, $R^2$ is G.088, $X^1, X^2, X^3$ and X4 have the values listed in the table Q.

Table 205 Q:
Table 205Q provides 54 compounds of formula (I-C) wherein $G^1$ is oxygen, $R^1$ is hydrogen, $R^2$ is G.089, $X^1, X^2, X^3$ and X4 have the values listed in the table Q.

Table 206 Q:
Table 206Q provides 54 compounds of formula (I-C) wherein $G^1$ is oxygen, $R^1$ is hydrogen, $R^2$ is G.090, $X^1, X^2, X^3$ and X4 have the values listed in the table Q.

Table 207Q:
Table 207Q provides 54 compounds of formula (I-C) wherein $G^1$ is oxygen, $R^1$ is hydrogen, $R^2$ is G.091, $X^1, X^2, X^3$ and X4 have the values listed in the table Q.

Table 208Q:
Table 208Q provides 54 compounds of formula (I-C) wherein $G^1$ is oxygen, $R^1$ is hydrogen, $R^2$ is G.092, $X^1, X^2, X^3$ and X4 have the values listed in the table Q.

Table 209Q:
Table 209Q provides 54 compounds of formula (I-C) wherein $G^1$ is oxygen, $R^1$ is hydrogen, $R^2$ is G.093, $X^1, X^2, X^3$ and X4 have the values listed in the table Q.

Table 210Q:
Table 210Q provides 54 compounds of formula (I-C) wherein $G^1$ is oxygen, $R^1$ is hydrogen, $R^2$ is G.094, $X^1, X^2, X^3$ and X4 have the values listed in the table Q.

Table 211Q:
Table 211Q provides 54 compounds of formula (I-C) wherein $G^1$ is oxygen, $R^1$ is hydrogen, $R^2$ is G.095, $X^1, X^2, X^3$ and X4 have the values listed in the table Q.

Table 212Q:
Table 212Q provides 54 compounds of formula (I-C) wherein $G^1$ is oxygen, $R^1$ is hydrogen, $R^2$ is G.096, $X^1, X^2, X^3$ and X4 have the values listed in the table Q.

Table 213Q:
Table 213Q provides 54 compounds of formula (I-C) wherein $G^1$ is oxygen, $R^1$ is hydrogen, $R^2$ is G.097, $X^1, X^2, X^3$ and X4 have the values listed in the table Q.

Table 214 Q:
Table 214Q provides 54 compounds of formula (I-C) wherein $G^1$ is oxygen, $R^1$ is hydrogen, $R^2$ is G.098, $X^1, X^2, X^3$ and X4 have the values listed in the table Q.

Table 215 Q:
Table 215Q provides 54 compounds of formula (I-C) wherein $G^1$ is oxygen, $R^1$ is hydrogen, $R^2$ is G.099, $X^1, X^2, X^3$ and X4 have the values listed in the table Q.

Table 216Q:
Table 216Q provides 54 compounds of formula (I-C) wherein $G^1$ is oxygen, $R^1$ is hydrogen, $R^2$ is G.100, $X^1, X^2, X^3$ and X4 have the values listed in the table Q.

Table 217 Q:
Table 217Q provides 54 compounds of formula (I-C) wherein $G^1$ is oxygen, $R^1$ is hydrogen, $R^2$ is G.101, $X^1, X^2, X^3$ and X4 have the values listed in the table Q.

Table 218 Q:
Table 218Q provides 54 compounds of formula (I-C) wherein $G^1$ is oxygen, $R^1$ is hydrogen, $R^2$ is G.102, $X^1, X^2, X^3$ and X4 have the values listed in the table Q.

Table 219Q:
Table 219Q provides 54 compounds of formula (I-C) wherein $G^1$ is oxygen, $R^1$ is hydrogen, $R^2$ is G.103, $X^1, X^2, X^3$ and X4 have the values listed in the table Q.

Table 220 Q:
Table 220Q provides 54 compounds of formula (I-C) wherein $G^1$ is oxygen, $R^1$ is hydrogen, $R^2$ is G.104, $X^1, X^2, X^3$ and X4 have the values listed in the table Q.

Table 221Q:
Table 221Q provides 54 compounds of formula (I-C) wherein $G^1$ is oxygen, $R^1$ is hydrogen, $R^2$ is G.105, $X^1, X^2, X^3$ and X4 have the values listed in the table Q.

Table 222 Q:
Table 222Q provides 54 compounds of formula (I-C) wherein $G^1$ is oxygen, $R^1$ is hydrogen, $R^2$ is G.106, $X^1, X^2, X^3$ and X4 have the values listed in the table Q.

Table 223 Q:
Table 223Q provides 54 compounds of formula (I-C) wherein $G^1$ is oxygen, $R^1$ is hydrogen, $R^2$ is G.107, $X^1, X^2, X^3$ and X4 have the values listed in the table Q.

Table 224 Q:
Table 224Q provides 54 compounds of formula (I-C) wherein $G^1$ is oxygen, $R^1$ is hydrogen, $R^2$ is G.108, $X^1, X^2, X^3$ and X4 have the values listed in the table Q.

Table 225 Q:
Table 225Q provides 54 compounds of formula (I-C) wherein $G^1$ is oxygen, $R^1$ is hydrogen, $R^2$ is G.109, $X^1, X^2, X^3$ and X4 have the values listed in the table Q.

Table 226 Q:
Table 226Q provides 54 compounds of formula (I-C) wherein $G^1$ is oxygen, $R^1$ is hydrogen, $R^2$ is G.110, $X^1, X^2, X^3$ and X4 have the values listed in the table Q.

Table 227 Q:
Table 227Q provides 54 compounds of formula (I-C) wherein $G^1$ is oxygen, $R^1$ is hydrogen, $R^2$ is G.111, $X^1, X^2, X^3$ and X4 have the values listed in the table Q.

Table 228Q:
Table 228Q provides 54 compounds of formula (I-C) wherein $G^1$ is oxygen, $R^1$ is hydrogen, $R^2$ is G.112, $X^1, X^2, X^3$ and X4 have the values listed in the table Q.

Table 229 Q:
Table 229Q provides 54 compounds of formula (I-C) wherein $G^1$ is oxygen, $R^1$ is hydrogen, $R^2$ is G.113, $X^1, X^2, X^3$ and X4 have the values listed in the table Q.

Table 230Q:
Table 230Q provides 54 compounds of formula (I-C) wherein $G^1$ is oxygen, $R^1$ is hydrogen, $R^2$ is G.114, $X^1, X^2, X^3$ and X4 have the values listed in the table Q.

Table 231Q:
Table 231Q provides 54 compounds of formula (I-C) wherein $G^1$ is oxygen, $R^1$ is hydrogen, $R^2$ is G.115, $X^1, X^2, X^3$ and X4 have the values listed in the table Q.

Table 232 Q:
Table 232Q provides 54 compounds of formula (I-C) wherein $G^1$ is oxygen, $R^1$ is hydrogen, $R^2$ is G.116, $X^1, X^2, X^3$ and X4 have the values listed in the table Q.

TABLE HET

| Het | Chemical structure |
| --- | --- |
| Het.01 | (1,2,4-triazol-1-yl) |
| Het.02 | (4-cyanopyrazol-1-yl) |
| Het.03 | (4-fluoropyrazol-1-yl) |
| Het.04 | (4-chloropyrazol-1-yl) |

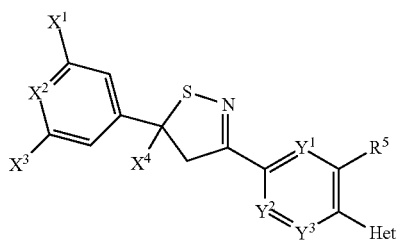

(I-D)

Table 117P

Table 117P provides 3240 compounds of formula (I-D) wherein Het is Het.01 and $X^1, X^2, X^3, Y^1, Y^2, Y^3, X^4$ and $R^5$ have the values listed in the table P.

Table 118P

Table 118P provides 3240 compounds of formula (I-D) wherein Het is Het.02 and $X^1, X^2, X^3, Y^1, Y^2, Y^3, X^4$ and $R^5$ have the values listed in the table P.

Table 119 P

Table 119P provides 3240 compounds of formula (I-D) wherein Het is Het.03 and $X^1, X^2, X^3, Y^1, Y^2, Y^3, X^4$ and $R^5$ have the values listed in the table P.

Table 120 P

Table 120P provides 3240 compounds of formula (I-D) wherein Het is Het.04 and $X^1, X^2, X^3, Y^1, Y^2, Y^3, X^4$ and $R^5$ have the values listed in the table P.

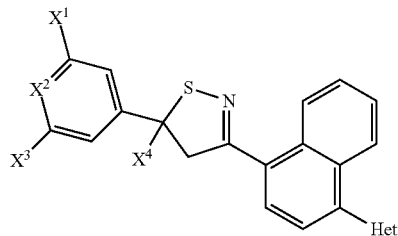

(I-E)

Table 233Q

Table 233Q provides 54 compounds of formula (I-E) wherein $G^1$ is oxygen, $R^1$ is hydrogen, Het is Het.01 and $X^1, X^2, X^3$ and X4 have the values listed in the table Q.

Table 234Q

Table 234Q provides 54 compounds of formula (I-E) wherein $G^1$ is oxygen, $R^1$ is hydrogen, Het is Het.02 and $X^1, X^2, X^3$ and X4 have the values listed in the table Q.

Table 235Q

Table 235Q provides 54 compounds of formula (I-E) wherein $G^1$ is oxygen, $R^1$ is hydrogen, Het is Het.03, $X^1, X^2, X^3$ and X4 have the values listed in the table Q.

Table 236Q

Table 236Q provides 54 compounds of formula (I-E) wherein $G^1$ is oxygen, $R^1$ is hydrogen, Het is Het.04, $X^1, X^2, X^3$ and X4 have the values listed in the table Q.

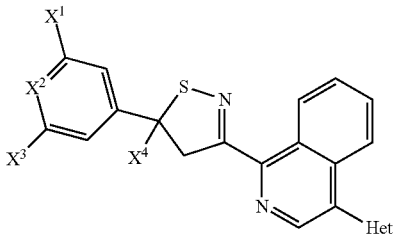

(I-F)

Table 237Q

Table 237Q provides 54 compounds of formula (I-F) wherein $G^1$ is oxygen, $R^1$ is hydrogen, Het is Het.01, $X^1, X^2, X^3$ and X4 have the values listed in the table Q.

Table 238Q

Table 238Q provides 54 compounds of formula (I-F) wherein $G^1$ is oxygen, $R^1$ is hydrogen, Het is Het.02, $X^1, X^2, X^3$ and X4 have the values listed in the table Q.

Table 239Q

Table 239Q provides 54 compounds of formula (I-F) wherein $G^1$ is oxygen, $R^1$ is hydrogen, Het is Het.03, $X^1, X^2, X^3$ and X4 have the values listed in the table Q.

Table 240Q

Table 240Q provides 54 compounds of formula (I-F) wherein $G^1$ is oxygen, $R^1$ is hydrogen, Het is Het.04, $X^1, X^2, X^3$ and X4 have the values listed in the table Q.

TABLE GI

| Gi | Chemical structure |
|---|---|
| G01 | ![triazole] |
| G02 | ![pyrazole-CN] |
| G03 | ![pyrazole-F] |
| G04 | ![pyrazole-Cl] |
| G05 | CN |
| G06 | F |
| G07 | Br |
| G08 | I |
| G09 | Cl |
| G10 | $NO_2$ |
| G11 | OH |
| G12 | $NH_2$ |
| G13 | COOH |
| G14 | COOMe |
| G15 | COOEt |
| G16 | COOPr |
| G17 | COOBu |
| G18 | COOtBu |
| G19 | COOPh |
| G20 | $CH_3$ |

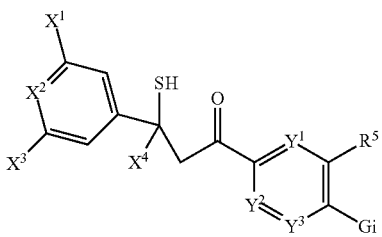

(II-A)

Table 121P
Table 121P provides 3240 compounds of formula (II-A) wherein Gi is G01 and $X^1, X^2, X^3, Y^1, Y^2, Y^3, X^4$ and $R^5$ have the values listed in the table P.
Table 122P
Table 122P provides 3240 compounds of formula (II-A) wherein Gi is G02 and $X^1, X^2, X^3, Y^1, Y^2, Y^3, X^4$ and $R^5$ have the values listed in the table P.
Table 123P
Table 123P provides 3240 compounds of formula (II-A) wherein Gi is G03 and $X^1, X^2, X^3, Y^1, Y^2, Y^3, X^4$ and $R^5$ have the values listed in the table P.
Table 124 P
Table 124P provides 3240 compounds of formula (II-A) wherein Gi is G04 and $X^1, X^2, X^3, Y^1, Y^2, Y^3, X^4$ and $R^5$ have the values listed in the table P.
Table 125P
Table 125P provides 3240 compounds of formula (II-A) wherein Gi is G051 and $X^1, X^2, X^3, Y^1, Y^2, Y^3, X^4$ and $R^5$ have the values listed in the table P.
Table 126P
Table 126P provides 3240 compounds of formula (II-A) wherein Gi is G06 and $X^1, X^2, X^3, Y^1, Y^2, Y^3, X^4$ and $R^5$ have the values listed in the table P.
Table 127P
Table 127P provides 3240 compounds of formula (II-A) wherein Gi is G07 and $X^1, X^2, X^3, Y^1, Y^2, Y^3, X^4$ and $R^5$ have the values listed in the table P.
Table 128 P
Table 128P provides 3240 compounds of formula (II-A) wherein Gi is G08 and $X^1, X^2, X^3, Y^1, Y^2, Y^3, X^4$ and $R^5$ have the values listed in the table P.
Table 129P
Table 129P provides 3240 compounds of formula (II-A) wherein Gi is G09 and $X^1, X^2, X^3, Y^1, Y^2, Y^3, X^4$ and $R^5$ have the values listed in the table P.
Table 130P
Table 130P provides 3240 compounds of formula (II-A) wherein Gi is G10 and $X^1, X^2, X^3, Y^1, Y^2, Y^3, X^4$ and $R^5$ have the values listed in the table P.
Table 131P
Table 131P provides 3240 compounds of formula (II-A) wherein Gi is G11 and $X^1, X^2, X^3, Y^1, Y^2, Y^3, X^4$ and $R^5$ have the values listed in the table P.
Table 132 P
Table 132P provides 3240 compounds of formula (II-A) wherein Gi is G12 and $X^1, X^2, X^3, Y^1, Y^2, Y^3, X^4$ and $R^5$ have the values listed in the table P.
Table 133P
Table 133P provides 3240 compounds of formula (II-A) wherein Gi is G13 and $X^1, X^2, X^3, Y^1, Y^2, Y^3, X^4$ and $R^5$ have the values listed in the table P.
Table 134P
Table 134P provides 3240 compounds of formula (II-A) wherein Gi is G14 and $X^1, X^2, X^3, Y^1, Y^2, Y^3, X^4$ and $R^5$ have the values listed in the table P.
Table 135P
Table 135P provides 3240 compounds of formula (II-A) wherein Gi is G15 and $X^1, X^2, X^3, Y^1, Y^2, Y^3, X^4$ and $R^5$ have the values listed in the table P.
Table 136 P
Table 136P provides 3240 compounds of formula (II-A) wherein Gi is G16 and $X^1, X^2, X^3, Y^1, Y^2, Y^3, X^4$ and $R^5$ have the values listed in the table P.
Table 137 P
Table 137P provides 3240 compounds of formula (II-A) wherein Gi is G17 and $X^1, X^2, X^3, Y^1, Y^2, Y^3, X^4$ and $R^5$ have the values listed in the table P.
Table 138P
Table 138P provides 3240 compounds of formula (II-A) wherein Gi is G18 and $X^1, X^2, X^3, Y^1, Y^2, Y^3, X^4$ and $R^5$ have the values listed in the table P.
Table 139P
Table 139P provides 3240 compounds of formula (II-A) wherein Gi is G19 and $X^1, X^2, X^3, Y^1, Y^2, Y^3, X^4$ and $R^5$ have the values listed in the table P.
Table 140P
Table 140P provides 3240 compounds of formula (II-A) wherein Gi is G20 and $X^1, X^2, X^3, Y^1, Y^2, Y^3, X^4$ and $R^5$ have the values listed in the table P.

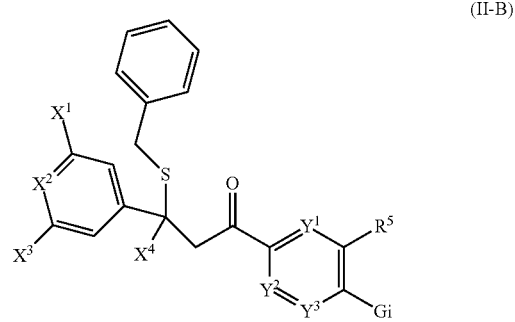

(II-B)

Table 141P
Table 141P provides 3240 compounds of formula (II-B) wherein Gi is G01 and $X^1, X^2, X^3, Y^1, Y^2, Y^3, X^4$ and $R^5$ have the values listed in the table P.
Table 142P
Table 142P provides 3240 compounds of formula (II-B) wherein Gi is G02 and $X^1, X^2, X^3, Y^1, Y^2, Y^3, X^4$ and $R^5$ have the values listed in the table P.
Table 143P
Table 143P provides 3240 compounds of formula (II-B) wherein Gi is G03 and $X^1, X^2, X^3, Y^1, Y^2, Y^3, X^4$ and $R^5$ have the values listed in the table P.
Table 144 P
Table 144P provides 3240 compounds of formula (II-B) wherein Gi is G04 and $X^1, X^2, X^3, Y^1, Y^2, Y^3, X^4$ and $R^5$ have the values listed in the table P.
Table 145P
Table 145P provides 3240 compounds of formula (II-B) wherein Gi is G051 and $X^1, X^2, X^3, Y^1, Y^2, Y^3, X^4$ and $R^5$ have the values listed in the table P.

Table 146P

Table 146P provides 3240 compounds of formula (II-B) wherein Gi is G06 and $X^1, X^2, X^3, Y^1, Y^2, Y^3, X^4$ and $R^5$ have the values listed in the table P.

Table 147P

Table 147P provides 3240 compounds of formula (II-B) wherein Gi is G07 and $X^1, X^2, X^3, Y^1, Y^2, Y^3, X^4$ and $R^5$ have the values listed in the table P.

Table 148 P

Table 148P provides 3240 compounds of formula (II-B) wherein Gi is G08 and $X^1, X^2, X^3, Y^1, Y^2, Y^3, X^4$ and $R^5$ have the values listed in the table P.

Table 149P

Table 149P provides 3240 compounds of formula (II-B) wherein Gi is G09 and $X^1, X^2, X^3, Y^1, Y^2, Y^3, X^4$ and $R^5$ have the values listed in the table P.

Table 150P

Table 150P provides 3240 compounds of formula (II-B) wherein Gi is G10 and $X^1, X^2, X^3, Y^1, Y^2, Y^3, X^4$ and $R^5$ have the values listed in the table P.

Table 151P

Table 151P provides 3240 compounds of formula (II-B) wherein Gi is G11 and $X^1, X^2, X^3, Y^1, Y^2, Y^3, X^4$ and $R^5$ have the values listed in the table P.

Table 152 P

Table 152P provides 3240 compounds of formula (II-B) wherein Gi is G12 and $X^1, X^2, X^3, Y^1, Y^2, Y^3, X^4$ and $R^5$ have the values listed in the table P.

Table 153P

Table 153P provides 3240 compounds of formula (II-B) wherein Gi is G13 and $X^1, X^2, X^3, Y^1, Y^2, Y^3, X^4$ and $R^5$ have the values listed in the table P.

Table 154P

Table 154P provides 3240 compounds of formula (II-B) wherein Gi is G14 and $X^1, X^2, X^3, Y^1, Y^2, Y^3, X^4$ and $R^5$ have the values listed in the table P.

Table 155P

Table 155P provides 3240 compounds of formula (II-B) wherein Gi is G15 and $X^1, X^2, X^3, Y^1, Y^2, Y^3, X^4$ and $R^5$ have the values listed in the table P.

Table 156 P

Table 156P provides 3240 compounds of formula (II-B) wherein Gi is G16 and $X^1, X^2, X^3, Y^1, Y^2, Y^3, X^4$ and $R^5$ have the values listed in the table P.

Table 157 P

Table 157P provides 3240 compounds of formula (II-B) wherein Gi is G17 and $X^1, X^2, X^3, Y^1, Y^2, Y^3, X^4$ and $R^5$ have the values listed in the table P.

Table 158P

Table 158P provides 3240 compounds of formula (II-B) wherein Gi is G18 and $X^1, X^2, X^3, Y^1, Y^2, Y^3, X^4$ and $R^5$ have the values listed in the table P.

Table 159P

Table 159P provides 3240 compounds of formula (II-B) wherein Gi is G19 and $X^1, X^2, X^3, Y^1, Y^2, Y^3, X^4$ and $R^5$ have the values listed in the table P.

Table 160P

Table 160P provides 3240 compounds of formula (II-B) wherein Gi is G20 and $X^1, X^2, X^3, Y^1, Y^2, Y^3, X^4$ and $R^5$ have the values listed in the table P.

(II-C)

Table 161P

Table 161P provides 3240 compounds of formula (II-C) wherein Gi is G01 and $X^1, X^2, X^3, Y^1, Y^2, Y^3, X^4$ and $R^5$ have the values listed in the table P.

Table 162P

Table 162P provides 3240 compounds of formula (II-C) wherein Gi is G02 and $X^1, X^2, X^3, Y^1, Y^2, Y^3, X^4$ and $R^5$ have the values listed in the table P.

Table 163P

Table 163P provides 3240 compounds of formula (II-C) wherein Gi is G03 and $X^1, X^2, X^3, Y^1, Y^2, Y^3, X^4$ and $R^5$ have the values listed in the table P.

Table 164 P

Table 164P provides 3240 compounds of formula (II-C) wherein Gi is G04 and $X^1, X^2, X^3, Y^1, Y^2, Y^3, X^4$ and $R^5$ have the values listed in the table P.

Table 165P

Table 165P provides 3240 compounds of formula (II-C) wherein Gi is G051 and $X^1, X^2, X^3, Y^1, Y^2, Y^3, X^4$ and $R^5$ have the values listed in the table P.

Table 166P

Table 166P provides 3240 compounds of formula (II-C) wherein Gi is G06 and $X^1, X^2, X^3, Y^1, Y^2, Y^3, X^4$ and $R^5$ have the values listed in the table P.

Table 167P

Table 167P provides 3240 compounds of formula (II-C) wherein Gi is G07 and $X^1, X^2, X^3, Y^1, Y^2, Y^3, X^4$ and $R^5$ have the values listed in the table P.

Table 168 P

Table 168P provides 3240 compounds of formula (II-C) wherein Gi is G08 and $X^1, X^2, X^3, Y^1, Y^2, Y^3, X^4$ and $R^5$ have the values listed in the table P.

Table 169P

Table 169P provides 3240 compounds of formula (II-C) wherein Gi is G09 and $X^1, X^2, X^3, Y^1, Y^2, Y^3, X^4$ and $R^5$ have the values listed in the table P.

Table 170P

Table 170P provides 3240 compounds of formula (II-C) wherein Gi is G10 and $X^1, X^2, X^3, Y^1, Y^2, Y^3, X^4$ and $R^5$ have the values listed in the table P.

Table 171P

Table 171P provides 3240 compounds of formula (II-C) wherein Gi is G11 and $X^1, X^2, X^3, Y^1, Y^2, Y^3, X^4$ and $R^5$ have the values listed in the table P.

Table 172 P

Table 172P provides 3240 compounds of formula (II-C) wherein Gi is G12 and $X^1, X^2, X^3, Y^1, Y^2, Y^3, X^4$ and $R^5$ have the values listed in the table P.

Table 173P

Table 173P provides 3240 compounds of formula (II-C) wherein Gi is G13 and $X^1, X^2, X^3, Y^1, Y^2, Y^3, X^4$ and $R^5$ have the values listed in the table P.

Table 174P

Table 174P provides 3240 compounds of formula (II-C) wherein Gi is G14 and $X^1, X^2, X^3, Y^1, Y^2, Y^3, X^4$ and $R^5$ have the values listed in the table P.

Table 175P

Table 175P provides 3240 compounds of formula (II-C) wherein Gi is G15 and $X^1, X^2, X^3, Y^1, Y^2, Y^3, X^4$ and $R^5$ have the values listed in the table P.

Table 176 P

Table 176P provides 3240 compounds of formula (II-C) wherein Gi is G16 and $X^1, X^2, X^3, Y^1, Y^2, Y^3, X^4$ and $R^5$ have the values listed in the table P.

Table 177 P

Table 177P provides 3240 compounds of formula (II-C) wherein Gi is G17 and $X^1, X^2, X^3, Y^1, Y^2, Y^3, X^4$ and $R^5$ have the values listed in the table P.

Table 178P

Table 178P provides 3240 compounds of formula (II-C) wherein Gi is G18 and $X^1, X^2, X^3, Y^1, Y^2, Y^3, X^4$ and $R^5$ have the values listed in the table P.

Table 179P

Table 179P provides 3240 compounds of formula (II-C) wherein Gi is G19 and $X^1, X^2, X^3, Y^1, Y^2, Y^3, X^4$ and $R^5$ have the values listed in the table P.

Table 180P

Table 180P provides 3240 compounds of formula (II-C) wherein Gi is G20 and $X^1, X^2, X^3, Y^1, Y^2, Y^3, X^4$ and $R^5$ have the values listed in the table P.

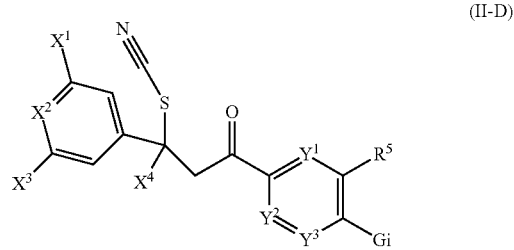

(II-D)

Table 181P

Table 181P provides 3240 compounds of formula (II-D) wherein Gi is G01 and $X^1, X^2, X^3, Y^1, Y^2, Y^3, X^4$ and $R^5$ have the values listed in the table P.

Table 182P

Table 182P provides 3240 compounds of formula (II-D) wherein Gi is G02 and $X^1, X^2, X^3, Y^1, Y^2, Y^3, X^4$ and $R^5$ have the values listed in the table P.

Table 183P

Table 183P provides 3240 compounds of formula (II-D) wherein Gi is G03 and $X^1, X^2, X^3, Y^1, Y^2, Y^3, X^4$ and $R^5$ have the values listed in the table P.

Table 184 P

Table 184P provides 3240 compounds of formula (II-D) wherein Gi is G04 and $X^1, X^2, X^3, Y^1, Y^2, Y^3, X^4$ and $R^5$ have the values listed in the table P.

Table 185P

Table 185P provides 3240 compounds of formula (II-D) wherein Gi is G051 and $X^1, X^2, X^3, Y^1, Y^2, Y^3, X^4$ and $R^5$ have the values listed in the table P.

Table 186P

Table 186P provides 3240 compounds of formula (II-D) wherein Gi is G06 and $X^1, X^2, X^3, Y^1, Y^2, Y^3, X^4$ and $R^5$ have the values listed in the table P.

Table 187P

Table 187P provides 3240 compounds of formula (II-D) wherein Gi is G07 and $X^1, X^2, X^3, Y^1, Y^2, Y^3, X^4$ and $R^5$ have the values listed in the table P.

Table 188 P

Table 188P provides 3240 compounds of formula (II-D) wherein Gi is G08 and $X^1, X^2, X^3, Y^1, Y^2, Y^3, X^4$ and $R^5$ have the values listed in the table P.

Table 189P

Table 189P provides 3240 compounds of formula (II-D) wherein Gi is G09 and $X^1, X^2, X^3, Y^1, Y^2, Y^3, X^4$ and $R^5$ have the values listed in the table P.

Table 190P

Table 190P provides 3240 compounds of formula (II-D) wherein Gi is G10 and $X^1, X^2, X^3, Y^1, Y^2, Y^3, X^4$ and $R^5$ have the values listed in the table P.

Table 191P

Table 191P provides 3240 compounds of formula (II-D) wherein Gi is G11 and $X^1, X^2, X^3, Y^1, Y^2, Y^3, X^4$ and $R^5$ have the values listed in the table P.

Table 192 P

Table 192P provides 3240 compounds of formula (II-D) wherein Gi is G12 and $X^1, X^2, X^3, Y^1, Y^2, Y^3, X^4$ and $R^5$ have the values listed in the table P.

Table 193P

Table 193P provides 3240 compounds of formula (II-D) wherein Gi is G13 and $X^1, X^2, X^3, Y^1, Y^2, Y^3, X^4$ and $R^5$ have the values listed in the table P.

Table 194P

Table 194P provides 3240 compounds of formula (II-D) wherein Gi is G14 and $X^1, X^2, X^3, Y^1, Y^2, Y^3, X^4$ and $R^5$ have the values listed in the table P.

Table 195P

Table 195P provides 3240 compounds of formula (II-D) wherein Gi is G15 and $X^1, X^2, X^3, Y^1, Y^2, Y^3, X^4$ and $R^5$ have the values listed in the table P.

Table 196 P

Table 196P provides 3240 compounds of formula (II-D) wherein Gi is G16 and $X^1, X^2, X^3, Y^1, Y^2, Y^3, X^4$ and $R^5$ have the values listed in the table P.

Table 197 P

Table 197P provides 3240 compounds of formula (II-D) wherein Gi is G17 and $X^1, X^2, X^3, Y^1, Y^2, Y^3, X^4$ and $R^5$ have the values listed in the table P.

Table 198P

Table 198P provides 3240 compounds of formula (II-D) wherein Gi is G18 and $X^1, X^2, X^3, Y^1, Y^2, Y^3, X^4$ and $R^5$ have the values listed in the table P.

Table 199P

Table 199P provides 3240 compounds of formula (II-D) wherein Gi is G19 and $X^1, X^2, X^3, Y^1, Y^2, Y^3, X^4$ and $R^5$ have the values listed in the table P.

Table 200P

Table 200P provides 3240 compounds of formula (II-D) wherein Gi is G20 and $X^1, X^2, X^3, Y^1, Y^2, Y^3, X^4$ and $R^5$ have the values listed in the table P.

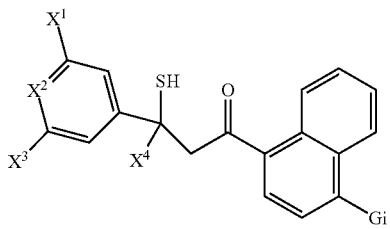

(II-E)

Table 241Q
Table 241Q provides 54 compounds of formula (II-E) wherein Gi is G01 and $X^1$, $X^2$, $X^3$ and X4 have the values listed in the table Q.

Table 242Q
Table 242Q provides 54 compounds of formula (II-E) wherein Gi is G02 and $X^1$, $X^2$, $X^3$ and X4 have the values listed in the table Q.

Table 243Q
Table 243Q provides 54 compounds of formula (II-E) wherein Gi is G03 and $X^1$, $X^2$, $X^3$ and X4 have the values listed in the table Q.

Table 244Q
Table 244Q provides 54 compounds of formula (II-E) wherein Gi is G04 and $X^1$, $X^2$, $X^3$ and X4 have the values listed in the table Q.

Table 245Q
Table 245Q provides 54 compounds of formula (II-E) wherein Gi is G05 and $X^1$, $X^2$, $X^3$ and X4 have the values listed in the table Q.

Table 246Q
Table 246Q provides 54 compounds of formula (II-E) wherein Gi is G06 and $X^1$, $X^2$, $X^3$ and X4 have the values listed in the table Q.

Table 247Q
Table 247Q provides 54 compounds of formula (II-E) wherein Gi is G07 and $X^1$, $X^2$, $X^3$ and X4 have the values listed in the table Q.

Table 248Q
Table 248Q provides 54 compounds of formula (II-E) wherein Gi is G08 and $X^1$, $X^2$, $X^3$ and X4 have the values listed in the table Q.

Table 249Q
Table 249Q provides 54 compounds of formula (II-E) wherein Gi is G09 and $X^1$, $X^2$, $X^3$ and X4 have the values listed in the table Q.

Table 250Q
Table 250Q provides 54 compounds of formula (II-E) wherein Gi is G10 and $X^1$, $X^2$, $X^3$ and X4 have the values listed in the table Q.

Table 251Q
Table 251Q provides 54 compounds of formula (II-E) wherein Gi is G11 and $X^1$, $X^2$, $X^3$ and X4 have the values listed in the table Q.

Table 252Q
Table 252Q provides 54 compounds of formula (II-E) wherein Gi is G12 and $X^1$, $X^2$, $X^3$ and X4 have the values listed in the table Q.

Table 253Q
Table 253Q provides 54 compounds of formula (II-E) wherein Gi is G13 and $X^1$, $X^2$, $X^3$ and X4 have the values listed in the table Q.

Table 254Q
Table 254Q provides 54 compounds of formula (II-E) wherein Gi is G14 and $X^1$, $X^2$, $X^3$ and X4 have the values listed in the table Q.

Table 255Q
Table 255Q provides 54 compounds of formula (II-E) wherein Gi is G15 and $X^1$, $X^2$, $X^3$ and X4 have the values listed in the table Q.

Table 256Q
Table 256Q provides 54 compounds of formula (II-E) wherein Gi is G16 and $X^1$, $X^2$, $X^3$ and X4 have the values listed in the table Q.

Table 257Q
Table 257Q provides 54 compounds of formula (II-E) wherein Gi is G17 and $X^1$, $X^2$, $X^3$ and X4 have the values listed in the table Q.

Table 258Q
Table 258Q provides 54 compounds of formula (II-E) wherein Gi is G18 and $X^1$, $X^2$, $X^3$ and X4 have the values listed in the table Q.

Table 259Q
Table 259Q provides 54 compounds of formula (II-E) wherein Gi is G19 and $X^1$, $X^2$, $X^3$ and X4 have the values listed in the table Q.

Table 260Q
Table 260Q provides 54 compounds of formula (II-E) wherein Gi is G20 and $X^1$, $X^2$, $X^3$ and X4 have the values listed in the table Q.

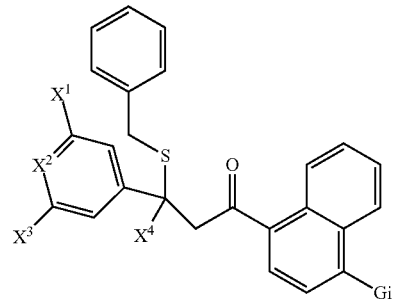

(II-F)

Table 261Q
Table 261Q provides 54 compounds of formula (II-F) wherein Gi is G01 and $X^1$, $X^2$, $X^3$ and X4 have the values listed in the table Q.

Table 262Q
Table 262Q provides 54 compounds of formula (II-F) wherein Gi is G02 and $X^1$, $X^2$, $X^3$ and X4 have the values listed in the table Q.

Table 263Q
Table 263Q provides 54 compounds of formula (II-F) wherein Gi is G03 and $X^1$, $X^2$, $X^3$ and X4 have the values listed in the table Q.

Table 264Q
Table 264Q provides 54 compounds of formula (II-F) wherein Gi is G04 and $X^1$, $X^2$, $X^3$ and X4 have the values listed in the table Q.

Table 265Q
Table 265Q provides 54 compounds of formula (II-F) wherein Gi is G05 and $X^1$, $X^2$, $X^3$ and X4 have the values listed in the table Q.

Table 266Q
Table 266Q provides 54 compounds of formula (II-F) wherein Gi is G06 and $X^1$, $X^2$, $X^3$ and X4 have the values listed in the table Q.

Table 267Q

Table 267Q provides 54 compounds of formula (II-F) wherein Gi is G07 and $X^1$, $X^2$, $X^3$ and X4 have the values listed in the table Q.

Table 268Q

Table 268Q provides 54 compounds of formula (II-F) wherein Gi is G08 and $X^1$, $X^2$, $X^3$ and X4 have the values listed in the table Q.

Table 269Q

Table 269Q provides 54 compounds of formula (II-F) wherein Gi is G09 and $X^1$, $X^2$, $X^3$ and X4 have the values listed in the table Q.

Table 270Q

Table 270Q provides 54 compounds of formula (II-F) wherein Gi is G10 and $X^1$, $X^2$, $X^3$ and X4 have the values listed in the table Q.

Table 271Q

Table 271Q provides 54 compounds of formula (II-F) wherein Gi is G11 and $X^1$, $X^2$, $X^3$ and X4 have the values listed in the table Q.

Table 272Q

Table 272Q provides 54 compounds of formula (II-F) wherein Gi is G12 and $X^1$, $X^2$, $X^3$ and X4 have the values listed in the table Q.

Table 273Q

Table 273Q provides 54 compounds of formula (II-F) wherein Gi is G13 and $X^1$, $X^2$, $X^3$ and X4 have the values listed in the table Q.

Table 274Q

Table 274Q provides 54 compounds of formula (II-F) wherein Gi is G14 and $X^1$, $X^2$, $X^3$ and X4 have the values listed in the table Q.

Table 275Q

Table 275Q provides 54 compounds of formula (II-F) wherein Gi is G15 and $X^1$, $X^2$, $X^3$ and X4 have the values listed in the table Q.

Table 276Q

Table 276Q provides 54 compounds of formula (II-F) wherein Gi is G16 and $X^1$, $X^2$, $X^3$ and X4 have the values listed in the table Q.

Table 277Q

Table 277Q provides 54 compounds of formula (II-F) wherein Gi is G17 and $X^1$, $X^2$, $X^3$ and X4 have the values listed in the table Q.

Table 278Q

Table 278Q provides 54 compounds of formula (II-F) wherein Gi is G18 and $X^1$, $X^2$, $X^3$ and X4 have the values listed in the table Q.

Table 279Q

Table 279Q provides 54 compounds of formula (II-F) wherein Gi is G19 and $X^1$, $X^2$, $X^3$ and X4 have the values listed in the table Q.

Table 280Q

Table 280Q provides 54 compounds of formula (II-F) wherein Gi is G20 and $X^1$, $X^2$, $X^3$ and X4 have the values listed in the table Q.

(II-G)

Table 281Q

Table 281Q provides 54 compounds of formula (II-G) wherein Gi is G01 and $X^1$, $X^2$, $X^3$ and X4 have the values listed in the table Q.

Table 282Q

Table 282Q provides 54 compounds of formula (II-G) wherein Gi is G02 and $X^1$, $X^2$, $X^3$ and X4 have the values listed in the table Q.

Table 283Q

Table 283Q provides 54 compounds of formula (II-G) wherein Gi is G03 and $X^1$, $X^2$, $X^3$ and X4 have the values listed in the table Q.

Table 284Q

Table 284Q provides 54 compounds of formula (II-G) wherein Gi is G04 and $X^1$, $X^2$, $X^3$ and X4 have the values listed in the table Q.

Table 285Q

Table 285Q provides 54 compounds of formula (II-G) wherein Gi is G05 and $X^1$, $X^2$, $X^3$ and X4 have the values listed in the table Q.

Table 286Q

Table 286Q provides 54 compounds of formula (II-G) wherein Gi is G06 and $X^1$, $X^2$, $X^3$ and X4 have the values listed in the table Q.

Table 287Q

Table 287Q provides 54 compounds of formula (II-G) wherein Gi is G07 and $X^1$, $X^2$, $X^3$ and X4 have the values listed in the table Q.

Table 288Q

Table 288Q provides 54 compounds of formula (II-G) wherein Gi is G08 and $X^1$, $X^2$, $X^3$ and X4 have the values listed in the table Q.

Table 289Q

Table 289Q provides 54 compounds of formula (II-G) wherein Gi is G09 and $X^1$, $X^2$, $X^3$ and X4 have the values listed in the table Q.

Table 290Q

Table 290Q provides 54 compounds of formula (II-G) wherein Gi is G10 and $X^1$, $X^2$, $X^3$ and X4 have the values listed in the table Q.

Table 291Q

Table 291Q provides 54 compounds of formula (II-G) wherein Gi is G11 and $X^1$, $X^2$, $X^3$ and X4 have the values listed in the table Q.

Table 292Q

Table 292Q provides 54 compounds of formula (II-G) wherein Gi is G12 and $X^1$, $X^2$, $X^3$ and X4 have the values listed in the table Q.

Table 293Q

Table 293Q provides 54 compounds of formula (II-G) wherein Gi is G13 and $X^1$, $X^2$, $X^3$ and X4 have the values listed in the table Q.

Table 294Q

Table 294Q provides 54 compounds of formula (II-G) wherein Gi is G14 and $X^1$, $X^2$, $X^3$ and X4 have the values listed in the table Q.

Table 295Q

Table 295Q provides 54 compounds of formula (II-G) wherein Gi is G15 and $X^1$, $X^2$, $X^3$ and X4 have the values listed in the table Q.

Table 296Q

Table 296Q provides 54 compounds of formula (II-G) wherein Gi is G16 and $X^1$, $X^2$, $X^3$ and X4 have the values listed in the table Q.

Table 297Q

Table 297Q provides 54 compounds of formula (II-G) wherein Gi is G17 and $X^1$, $X^2$, $X^3$ and X4 have the values listed in the table Q.

Table 298Q

Table 298Q provides 54 compounds of formula (II-G) wherein Gi is G18 and $X^1$, $X^2$, $X^3$ and X4 have the values listed in the table Q.

Table 299Q

Table 299Q provides 54 compounds of formula (II-G) wherein Gi is G19 and $X^1$, $X^2$, $X^3$ and X4 have the values listed in the table Q.

Table 300Q

Table 300Q provides 54 compounds of formula (II-G) wherein Gi is G20 and $X^1$, $X^2$, $X^3$ and X4 have the values listed in the table Q.

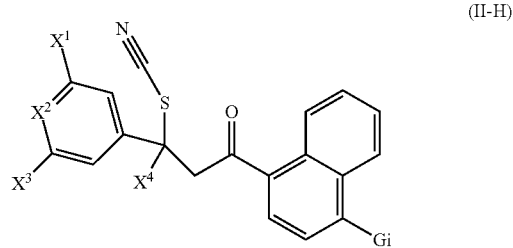

(II-H)

Table 301Q

Table 301Q provides 54 compounds of formula (II-H) wherein Gi is G01 and $X^1$, $X^2$, $X^3$ and X4 have the values listed in the table Q.

Table 302Q

Table 302Q provides 54 compounds of formula (II-H) wherein Gi is G02 and $X^1$, $X^2$, $X^3$ and X4 have the values listed in the table Q.

Table 303Q

Table 303Q provides 54 compounds of formula (II-H) wherein Gi is G03 and $X^1$, $X^2$, $X^3$ and X4 have the values listed in the table Q.

Table 304Q

Table 304Q provides 54 compounds of formula (II-H) wherein Gi is G04 and $X^1$, $X^2$, $X^3$ and X4 have the values listed in the table Q.

Table 305Q

Table 305Q provides 54 compounds of formula (II-H) wherein Gi is G05 and $X^1$, $X^2$, $X^3$ and X4 have the values listed in the table Q.

Table 306Q

Table 306Q provides 54 compounds of formula (II-H) wherein Gi is G06 and $X^1$, $X^2$, $X^3$ and X4 have the values listed in the table Q.

Table 307Q

Table 307Q provides 54 compounds of formula (II-H) wherein Gi is G07 and $X^1$, $X^2$, $X^3$ and X4 have the values listed in the table Q.

Table 308Q

Table 308Q provides 54 compounds of formula (II-H) wherein Gi is G08 and $X^1$, $X^2$, $X^3$ and X4 have the values listed in the table Q.

Table 309Q

Table 309Q provides 54 compounds of formula (II-H) wherein Gi is G09 and $X^1$, $X^2$, $X^3$ and X4 have the values listed in the table Q.

Table 310Q

Table 310Q provides 54 compounds of formula (II-H) wherein Gi is G10 and $X^1$, $X^2$, $X^3$ and X4 have the values listed in the table Q.

Table 311Q

Table 311Q provides 54 compounds of formula (II-H) wherein Gi is G11 and $X^1$, $X^2$, $X^3$ and X4 have the values listed in the table Q.

Table 312Q

Table 312Q provides 54 compounds of formula (II-H) wherein Gi is G12 and $X^1$, $X^2$, $X^3$ and X4 have the values listed in the table Q.

Table 313Q

Table 313Q provides 54 compounds of formula (II-H) wherein Gi is G13 and $X^1$, $X^2$, $X^3$ and X4 have the values listed in the table Q.

Table 314Q

Table 314Q provides 54 compounds of formula (II-H) wherein Gi is G14 and $X^1$, $X^2$, $X^3$ and X4 have the values listed in the table Q.

Table 315Q

Table 315Q provides 54 compounds of formula (II-H) wherein Gi is G15 and $X^1$, $X^2$, $X^3$ and X4 have the values listed in the table Q.

Table 316Q

Table 316Q provides 54 compounds of formula (II-H) wherein Gi is G16 and $X^1$, $X^2$, $X^3$ and X4 have the values listed in the table Q.

Table 317Q

Table 317Q provides 54 compounds of formula (II-H) wherein Gi is G17 and $X^1$, $X^2$, $X^3$ and X4 have the values listed in the table Q.

Table 318Q

Table 318Q provides 54 compounds of formula (II-H) wherein Gi is G18 and $X^1$, $X^2$, $X^3$ and X4 have the values listed in the table Q.

Table 319Q

Table 319Q provides 54 compounds of formula (II-H) wherein Gi is G19 and $X^1$, $X^2$, $X^3$ and X4 have the values listed in the table Q.

Table 320Q

Table 320Q provides 54 compounds of formula (II-H) wherein Gi is G20 and $X^1$, $X^2$, $X^3$ and X4 have the values listed in the table Q.

TABLE S

| | $R^5$ | $Y^1, Y^2, Y^3$ |
|---|---|---|
| S.001 | hydrogen | $Y^1$ is CH, $Y^2$ is CH, $Y^3$ is CH |
| S.002 | chloro | $Y^1$ is CH, $Y^2$ is CH, $Y^3$ is CH |
| S.003 | bromo | $Y^1$ is CH, $Y^2$ is CH, $Y^3$ is CH |
| S.004 | fluoro | $Y^1$ is CH, $Y^2$ is CH, $Y^3$ is CH |
| S.005 | trifluoromethyl | $Y^1$ is CH, $Y^2$ is CH, $Y^3$ is CH |
| S.006 | methyl | $Y^1$ is CH, $Y^2$ is CH, $Y^3$ is CH |
| S.007 | ethyl | $Y^1$ is CH, $Y^2$ is CH, $Y^3$ is CH |

TABLE S-continued

| | R⁵ | Y¹, Y², Y³ |
|---|---|---|
| S.008 | methoxy | Y¹ is CH, Y² is CH, Y³ is CH |
| S.009 | nitro | Y¹ is CH, Y² is CH, Y³ is CH |
| S.010 | trifluoromethoxy | Y¹ is CH, Y² is CH, Y³ is CH |
| S.011 | cyano | Y¹ is CH, Y² is CH, Y³ is CH |
| S.012 | cyclopropyl | Y¹ is CH, Y² is CH, Y³ is CH |
| S.013 | hydrogen | Y¹ is N, Y² is CH, Y³ is CH |
| S.014 | chloro | Y¹ is N, Y² is CH, Y³ is CH |
| S.015 | bromo | Y¹ is N, Y² is CH, Y³ is CH |
| S.016 | fluoro | Y¹ is N, Y² is CH, Y³ is CH |
| S.017 | trifluoromethyl | Y¹ is N, Y² is CH, Y³ is CH |
| S.018 | methyl | Y¹ is N, Y² is CH, Y³ is CH |
| S.019 | ethyl | Y¹ is N, Y² is CH, Y³ is CH |
| S.020 | methoxy | Y¹ is N, Y² is CH, Y³ is CH |
| S.021 | nitro | Y¹ is N, Y² is CH, Y³ is CH |
| S.022 | trifluoromethoxy | Y¹ is N, Y² is CH, Y³ is CH |
| S.023 | cyano | Y¹ is N, Y² is CH, Y³ is CH |
| S.024 | cyclopropyl | Y¹ is N, Y² is CH, Y³ is CH |
| S.025 | hydrogen | Y¹ is N, Y² is N, Y³ is CH |
| S.026 | chloro | Y¹ is N, Y² is N, Y³ is CH |
| S.027 | bromo | Y¹ is N, Y² is N, Y³ is CH |
| S.028 | fluoro | Y¹ is N, Y² is N, Y³ is CH |
| S.029 | trifluoromethyl | Y¹ is N, Y² is N, Y³ is CH |
| S.030 | methyl | Y¹ is N, Y² is N, Y³ is CH |
| S.031 | ethyl | Y¹ is N, Y² is N, Y³ is CH |
| S.032 | methoxy | Y¹ is N, Y² is N, Y³ is CH |
| S.033 | nitro | Y¹ is N, Y² is N, Y³ is CH |
| S.034 | trifluoromethoxy | Y¹ is N, Y² is N, Y³ is CH |
| S.035 | cyano | Y¹ is N, Y² is N, Y³ is CH |
| S.036 | cyclopropyl | Y¹ is N, Y² is N, Y³ is CH |
| S.037 | hydrogen | Y¹ is CH, Y² is N, Y³ is CH |
| S.038 | chloro | Y¹ is CH, Y² is N, Y³ is CH |
| S.039 | bromo | Y¹ is CH, Y² is N, Y³ is CH |
| S.040 | fluoro | Y¹ is CH, Y² is N, Y³ is CH |
| S.041 | trifluoromethyl | Y¹ is CH, Y² is N, Y³ is CH |
| S.042 | methyl | Y¹ is CH, Y² is N, Y³ is CH |
| S.043 | ethyl | Y¹ is CH, Y² is N, Y³ is CH |
| S.044 | methoxy | Y¹ is CH, Y² is N, Y³ is CH |
| S.045 | nitro | Y¹ is CH, Y² is N, Y³ is CH |
| S.046 | trifluoromethoxy | Y¹ is CH, Y² is N, Y³ is CH |
| S.047 | cyano | Y¹ is CH, Y² is N, Y³ is CH |
| S.048 | cyclopropyl | Y¹ is CH, Y² is N, Y³ is CH |
| S.049 | hydrogen | Y¹ is CH, Y² is CH, Y³ is N |
| S.050 | chloro | Y¹ is CH, Y² is CH, Y³ is N |
| S.051 | bromo | Y¹ is CH, Y² is CH, Y³ is N |
| S.052 | fluoro | Y¹ is CH, Y² is CH, Y³ is N |
| S.053 | trifluoromethyl | Y¹ is CH, Y² is CH, Y³ is N |
| S.054 | methyl | Y¹ is CH, Y² is CH, Y³ is N |
| S.055 | ethyl | Y¹ is CH, Y² is CH, Y³ is N |
| S.056 | methoxy | Y¹ is CH, Y² is CH, Y³ is N |
| S.0057 | nitro | Y¹ is CH, Y² is CH, Y³ is N |
| S.058 | trifluoromethoxy | Y¹ is CH, Y² is CH, Y³ is N |
| S.059 | cyano | Y¹ is CH, Y² is CH, Y³ is N |
| S.060 | cyclopropyl | Y¹ is CH, Y² is CH, Y³ is N |

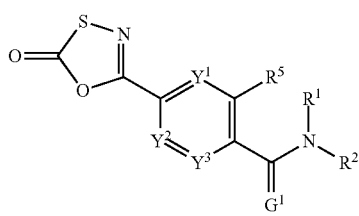

(III-A)

Table 1S

Table 1S provides 60 compounds of formula (III-A) wherein G¹ is oxygen, R¹ is hydrogen, R² is G.001, Y¹, Y², Y³ and R⁵ have the values listed in the table S.

Table 2S

Table 2S provides 60 compounds of formula (III-A) wherein G¹ is oxygen, R¹ is hydrogen, R² is G.002, Y¹, Y², Y³ and R⁵ have the values listed in the table S.

Table 3S

Table 3S provides 60 compounds of formula (III-A) wherein G¹ is oxygen, R¹ is hydrogen, R² is G.003, Y¹, Y², Y³ and R⁵ have the values listed in the table S.

Table 4S

Table 4S provides 60 compounds of formula (III-A) wherein G¹ is oxygen, R¹ is hydrogen, R² is G.004, Y¹, Y², Y³ and R⁵ have the values listed in the table S.

Table 5S

Table 5S provides 60 compounds of formula (III-A) wherein G¹ is oxygen, R¹ is hydrogen, R² is G.005, Y¹, Y², Y³ and R⁵ have the values listed in the table S.

Table 6S

Table 6S provides 60 compounds of formula (III-A) wherein G¹ is oxygen, R¹ is hydrogen, R² is G.006, Y¹, Y², Y³ and R⁵ have the values listed in the table S.

Table 7S

Table 7S provides 60 compounds of formula (III-A) wherein G¹ is oxygen, R¹ is hydrogen, R² is G.007, Y¹, Y², Y³ and R⁵ have the values listed in the table S.

Table 8S

Table 8S provides 60 compounds of formula (III-A) wherein G¹ is oxygen, R¹ is hydrogen, R² is G.008, Y¹, Y², Y³ and R⁵ have the values listed in the table S.

Table 9S

Table 9S provides 60 compounds of formula (III-A) wherein G¹ is oxygen, R¹ is hydrogen, R² is G.009, Y¹, Y², Y³ and R⁵ have the values listed in the table S.

Table 10S

Table 10S provides 60 compounds of formula (III-A) wherein G¹ is oxygen, R¹ is hydrogen, R² is G.010, Y¹, Y², Y³ and R⁵ have the values listed in the table S.

Table 11S

Table 11S provides 60 compounds of formula (III-A) wherein G¹ is oxygen, R¹ is hydrogen, R² is G.011, Y¹, Y², Y³ and R⁵ have the values listed in the table S.

Table 12S

Table 12S provides 60 compounds of formula (III-A) wherein G¹ is oxygen, R¹ is hydrogen, R² is G.012, Y¹, Y², Y³ and R⁵ have the values listed in the table S.

Table 13S

Table 13S provides 60 compounds of formula (III-A) wherein G¹ is oxygen, R¹ is hydrogen, R² is G.013, Y¹, Y², Y³ and R⁵ have the values listed in the table S.

Table 14S

Table 14S provides 60 compounds of formula (III-A) wherein G¹ is oxygen, R¹ is hydrogen, R² is G.014, Y¹, Y², Y³ and R⁵ have the values listed in the table S.

Table 15S

Table 15S provides 60 compounds of formula (III-A) wherein G¹ is oxygen, R¹ is hydrogen, R² is G.015, Y¹, Y², Y³ and R⁵ have the values listed in the table S.

Table 16S

Table 16S provides 60 compounds of formula (III-A) wherein G¹ is oxygen, R¹ is hydrogen, R² is G.016, Y¹, Y², Y³ and R⁵ have the values listed in the table S.

Table 17S

Table 17S provides 60 compounds of formula (III-A) wherein G¹ is oxygen, R¹ is hydrogen, R² is G.017, Y¹, Y², Y³ and R⁵ have the values listed in the table S.

Table 18S

Table 18S provides 60 compounds of formula (III-A) wherein G¹ is oxygen, R¹ is hydrogen, R² is G.018, Y¹, Y², Y³ and R⁵ have the values listed in the table S.

Table 19S
Table 19S provides 60 compounds of formula (III-A) wherein $G^1$ is oxygen, $R^1$ is hydrogen, $R^2$ is G.019, $Y^1$, $Y^2$, $Y^3$ and $R^5$ have the values listed in the table S.

Table 20S
Table 20S provides 60 compounds of formula (III-A) wherein $G^1$ is oxygen, $R^1$ is hydrogen, $R^2$ is G.020, $Y^1$, $Y^2$, $Y^3$ and $R^5$ have the values listed in the table S.

Table 21S
Table 21S provides 60 compounds of formula (III-A) wherein $G^1$ is oxygen, $R^1$ is hydrogen, $R^2$ is G.021, $Y^1$, $Y^2$, $Y^3$ and $R^5$ have the values listed in the table S.

Table 22S
Table 22S provides 60 compounds of formula (III-A) wherein $G^1$ is oxygen, $R^1$ is hydrogen, $R^2$ is G.022, $Y^1$, $Y^2$, $Y^3$ and $R^5$ have the values listed in the table S.

Table 23S
Table 23S provides 60 compounds of formula (III-A) wherein $G^1$ is oxygen, $R^1$ is hydrogen, $R^2$ is G.023, $Y^1$, $Y^2$, $Y^3$ and $R^5$ have the values listed in the table S.

Table 24S
Table 24S provides 60 compounds of formula (III-A) wherein $G^1$ is oxygen, $R^1$ is hydrogen, $R^2$ is G.024, $Y^1$, $Y^2$, $Y^3$ and $R^5$ have the values listed in the table S.

Table 25S
Table 25S provides 60 compounds of formula (III-A) wherein $G^1$ is oxygen, $R^1$ is hydrogen, $R^2$ is G.025, $Y^1$, $Y^2$, $Y^3$ and $R^5$ have the values listed in the table S.

Table 26S
Table 26S provides 60 compounds of formula (III-A) wherein $G^1$ is oxygen, $R^1$ is hydrogen, $R^2$ is G.026, $Y^1$, $Y^2$, $Y^3$ and $R^5$ have the values listed in the table S.

Table 27S
Table 27S provides 60 compounds of formula (III-A) wherein $G^1$ is oxygen, $R^1$ is hydrogen, $R^2$ is G.027, $Y^1$, $Y^2$, $Y^3$ and $R^5$ have the values listed in the table S.

Table 28S
Table 28S provides 60 compounds of formula (III-A) wherein $G^1$ is oxygen, $R^1$ is hydrogen, $R^2$ is G.028, $Y^1$, $Y^2$, $Y^3$ and $R^5$ have the values listed in the table S.

Table 29S
Table 29S provides 60 compounds of formula (III-A) wherein $G^1$ is oxygen, $R^1$ is hydrogen, $R^2$ is G.029, $Y^1$, $Y^2$, $Y^3$ and $R^5$ have the values listed in the table S.

Table 30S
Table 30S provides 60 compounds of formula (III-A) wherein $G^1$ is oxygen, $R^1$ is hydrogen, $R^2$ is G.030, $Y^1$, $Y^2$, $Y^3$ and $R^5$ have the values listed in the table S.

Table 31S
Table 31S provides 60 compounds of formula (III-A) wherein $G^1$ is oxygen, $R^1$ is hydrogen, $R^2$ is G.031, $Y^1$, $Y^2$, $Y^3$ and $R^5$ have the values listed in the table S.

Table 32S
Table 32S provides 60 compounds of formula (III-A) wherein $G^1$ is oxygen, $R^1$ is hydrogen, $R^2$ is G.032, $Y^1$, $Y^2$, $Y^3$ and $R^5$ have the values listed in the table S.

Table 33S
Table 33S provides 60 compounds of formula (III-A) wherein $G^1$ is oxygen, $R^1$ is hydrogen, $R^2$ is G.033, $Y^1$, $Y^2$, $Y^3$ and $R^5$ have the values listed in the table S.

Table 34S
Table 34S provides 60 compounds of formula (III-A) wherein $G^1$ is oxygen, $R^1$ is hydrogen, $R^2$ is G.034, $Y^1$, $Y^2$, $Y^3$ and $R^5$ have the values listed in the table S.

Table 35S
Table 35S provides 60 compounds of formula (III-A) wherein $G^1$ is oxygen, $R^1$ is hydrogen, $R^2$ is G.035, $Y^1$, $Y^2$, $Y^3$ and $R^5$ have the values listed in the table S.

Table 36S
Table 36S provides 60 compounds of formula (III-A) wherein $G^1$ is oxygen, $R^1$ is hydrogen, $R^2$ is G.036, $Y^1$, $Y^2$, $Y^3$ and $R^5$ have the values listed in the table S.

Table 37S
Table 37S provides 60 compounds of formula (III-A) wherein $G^1$ is oxygen, $R^1$ is hydrogen, $R^2$ is G.037, $Y^1$, $Y^2$, $Y^3$ and $R^5$ have the values listed in the table S.

Table 38S
Table 38S provides 60 compounds of formula (III-A) wherein $G^1$ is oxygen, $R^1$ is hydrogen, $R^2$ is G.038, $Y^1$, $Y^2$, $Y^3$ and $R^5$ have the values listed in the table S.

Table 39S
Table 39S provides 60 compounds of formula (III-A) wherein $G^1$ is oxygen, $R^1$ is hydrogen, $R^2$ is G.039, $Y^1$, $Y^2$, $Y^3$ and $R^5$ have the values listed in the table S.

Table 40S
Table 40S provides 60 compounds of formula (III-A) wherein $G^1$ is oxygen, $R^1$ is hydrogen, $R^2$ is G.040, $Y^1$, $Y^2$, $Y^3$ and $R^5$ have the values listed in the table S.

Table 41S
Table 41S provides 60 compounds of formula (III-A) wherein $G^1$ is oxygen, $R^1$ is hydrogen, $R^2$ is G.041, $Y^1$, $Y^2$, $Y^3$ and $R^5$ have the values listed in the table S.

Table 42S
Table 42S provides 60 compounds of formula (III-A) wherein $G^1$ is oxygen, $R^1$ is hydrogen, $R^2$ is G.042, $Y^1$, $Y^2$, $Y^3$ and $R^5$ have the values listed in the table S.

Table 43S
Table 43S provides 60 compounds of formula (III-A) wherein $G^1$ is oxygen, $R^1$ is hydrogen, $R^2$ is G.043, $Y^1$, $Y^2$, $Y^3$ and $R^5$ have the values listed in the table S.

Table 44S
Table 44S provides 60 compounds of formula (III-A) wherein $G^1$ is oxygen, $R^1$ is hydrogen, $R^2$ is G.044, $Y^1$, $Y^2$, $Y^3$ and $R^5$ have the values listed in the table S.

Table 45S
Table 45S provides 60 compounds of formula (III-A) wherein $G^1$ is oxygen, $R^1$ is hydrogen, $R^2$ is G.045, $Y^1$, $Y^2$, $Y^3$ and $R^5$ have the values listed in the table S.

Table 46S
Table 46S provides 60 compounds of formula (III-A) wherein $G^1$ is oxygen, $R^1$ is hydrogen, $R^2$ is G.046, $Y^1$, $Y^2$, $Y^3$ and $R^5$ have the values listed in the table S.

Table 47S
Table 47S provides 60 compounds of formula (III-A) wherein $G^1$ is oxygen, $R^1$ is hydrogen, $R^2$ is G.047, $Y^1$, $Y^2$, $Y^3$ and $R^5$ have the values listed in the table S.

Table 48S
Table 48S provides 60 compounds of formula (III-A) wherein $G^1$ is oxygen, $R^1$ is hydrogen, $R^2$ is G.048, $Y^1$, $Y^2$, $Y^3$ and $R^5$ have the values listed in the table S.

Table 49S
Table 49S provides 60 compounds of formula (III-A) wherein $G^1$ is oxygen, $R^1$ is hydrogen, $R^2$ is G.049, $Y^1$, $Y^2$, $Y^3$ and $R^5$ have the values listed in the table S.

Table 50S
Table 50S provides 60 compounds of formula (III-A) wherein $G^1$ is oxygen, $R^1$ is hydrogen, $R^2$ is G.050, $Y^1$, $Y^2$, $Y^3$ and $R^5$ have the values listed in the table S.

Table 51S
Table 51S provides 60 compounds of formula (III-A) wherein $G^1$ is oxygen, $R^1$ is hydrogen, $R^2$ is G.051, $Y^1$, $Y^2$, $Y^3$ and $R^5$ have the values listed in the table S.

Table 52S
Table 52S provides 60 compounds of formula (III-A) wherein $G^1$ is oxygen, $R^1$ is hydrogen, $R^2$ is G.052, $Y^1$, $Y^2$, $Y^3$ and $R^5$ have the values listed in the table S.

Table 53S
Table 53S provides 60 compounds of formula (III-A) wherein $G^1$ is oxygen, $R^1$ is hydrogen, $R^2$ is G.053, $Y^1$, $Y^2$, $Y^3$ and $R^5$ have the values listed in the table S.

Table 54S
Table 54S provides 60 compounds of formula (III-A) wherein $G^1$ is oxygen, $R^1$ is hydrogen, $R^2$ is G.054, $Y^1$, $Y^2$, $Y^3$ and $R^5$ have the values listed in the table S.

Table 55S
Table 55S provides 60 compounds of formula (III-A) wherein $G^1$ is oxygen, $R^1$ is hydrogen, $R^2$ is G.055, $Y^1$, $Y^2$, $Y^3$ and $R^5$ have the values listed in the table S.

Table 56S
Table 56S provides 60 compounds of formula (III-A) wherein $G^1$ is oxygen, $R^1$ is hydrogen, $R^2$ is G.056, $Y^1$, $Y^2$, $Y^3$ and $R^5$ have the values listed in the table S.

Table 57S
Table 57S provides 60 compounds of formula (III-A) wherein $G^1$ is oxygen, $R^1$ is hydrogen, $R^2$ is G.057, $Y^1$, $Y^2$, $Y^3$ and $R^5$ have the values listed in the table S.

Table 58S
Table 58S provides 60 compounds of formula (III-A) wherein $G^1$ is oxygen, $R^1$ is hydrogen, $R^2$ is G.058, $Y^1$, $Y^2$, $Y^3$ and $R^5$ have the values listed in the table S.

Table 59S
Table 59S provides 60 compounds of formula (III-A) wherein $G^1$ is oxygen, $R^1$ is hydrogen, $R^2$ is G.059, $Y^1$, $Y^2$, $Y^3$ and $R^5$ have the values listed in the table S.

Table 60S
Table 60S provides 60 compounds of formula (III-A) wherein $G^1$ is oxygen, $R^1$ is hydrogen, $R^2$ is G.060, $Y^1$, $Y^2$, $Y^3$ and $R^5$ have the values listed in the table S.

Table 61S
Table 61S provides 60 compounds of formula (III-A) wherein $G^1$ is oxygen, $R^1$ is hydrogen, $R^2$ is G.061, $Y^1$, $Y^2$, $Y^3$ and $R^5$ have the values listed in the table S.

Table 62S
Table 62S provides 60 compounds of formula (III-A) wherein $G^1$ is oxygen, $R^1$ is hydrogen, $R^2$ is G.062, $Y^1$, $Y^2$, $Y^3$ and $R^5$ have the values listed in the table S.

Table 63S
Table 63S provides 60 compounds of formula (III-A) wherein $G^1$ is oxygen, $R^1$ is hydrogen, $R^2$ is G.063, $Y^1$, $Y^2$, $Y^3$ and $R^5$ have the values listed in the table S.

Table 64S
Table 64S provides 60 compounds of formula (III-A) wherein $G^1$ is oxygen, $R^1$ is hydrogen, $R^2$ is G.064, $Y^1$, $Y^2$, $Y^3$ and $R^5$ have the values listed in the table S.

Table 65S
Table 65S provides 60 compounds of formula (III-A) wherein $G^1$ is oxygen, $R^1$ is hydrogen, $R^2$ is G.065, $Y^1$, $Y^2$, $Y^3$ and $R^5$ have the values listed in the table S.

Table 66S
Table 66S provides 3240 compounds of formula (III-A) wherein $G^1$ is oxygen, $R^1$ is hydrogen, $R^2$ is G.066, $X^1$, $X^2$, $X^3$, $Y^1$, $Y^2$, $Y^3$, $X^4$ and $R^5$ have the values listed in the table P.

Table 67S
Table 67S provides 60 compounds of formula (III-A) wherein $G^1$ is oxygen, $R^1$ is hydrogen, $R^2$ is G.067, $Y^1$, $Y^2$, $Y^3$ and $R^5$ have the values listed in the table S.

Table 68S
Table 68S provides 60 compounds of formula (III-A) wherein $G^1$ is oxygen, $R^1$ is hydrogen, $R^2$ is G.068, $Y^1$, $Y^2$, $Y^3$ and $R^5$ have the values listed in the table S.

Table 69S
Table 69S provides 60 compounds of formula (III-A) wherein $G^1$ is oxygen, $R^1$ is hydrogen, $R^2$ is G.069, $Y^1$, $Y^2$, $Y^3$ and $R^5$ have the values listed in the table S.

Table 70S
Table 70S provides 60 compounds of formula (III-A) wherein $G^1$ is oxygen, $R^1$ is hydrogen, $R^2$ is G.070, $Y^1$, $Y^2$, $Y^3$ and $R^5$ have the values listed in the table S.

Table 71S
Table 71S provides 60 compounds of formula (III-A) wherein $G^1$ is oxygen, $R^1$ is hydrogen, $R^2$ is G.071, $Y^1$, $Y^2$, $Y^3$ and $R^5$ have the values listed in the table S.

Table 72S
Table 72S provides 60 compounds of formula (III-A) wherein $G^1$ is oxygen, $R^1$ is hydrogen, $R^2$ is G.072, $Y^1$, $Y^2$, $Y^3$ and $R^5$ have the values listed in the table S.

Table 73S
Table 73S provides 60 compounds of formula (III-A) wherein $G^1$ is oxygen, $R^1$ is hydrogen, $R^2$ is G.073, $Y^1$, $Y^2$, $Y^3$ and $R^5$ have the values listed in the table S.

Table 74S
Table 74S provides 60 compounds of formula (III-A) wherein $G^1$ is oxygen, $R^1$ is hydrogen, $R^2$ is G.074, $Y^1$, $Y^2$, $Y^3$ and $R^5$ have the values listed in the table S.

Table 75S
Table 75S provides 60 compounds of formula (III-A) wherein $G^1$ is oxygen, $R^1$ is hydrogen, $R^2$ is G.075, $Y^1$, $Y^2$, $Y^3$ and $R^5$ have the values listed in the table S.

Table 76S
Table 76S provides 60 compounds of formula (III-A) wherein $G^1$ is oxygen, $R^1$ is hydrogen, $R^2$ is G.076, $Y^1$, $Y^2$, $Y^3$ and $R^5$ have the values listed in the table S.

Table 77S
Table 77S provides 60 compounds of formula (III-A) wherein $G^1$ is oxygen, $R^1$ is hydrogen, $R^2$ is G.077, $Y^1$, $Y^2$, $Y^3$ and $R^5$ have the values listed in the table S.

Table 78S
Table 78S provides 60 compounds of formula (III-A) wherein $G^1$ is oxygen, $R^1$ is hydrogen, $R^2$ is G.078, $Y^1$, $Y^2$, $Y^3$ and $R^5$ have the values listed in the table S.

Table 79S
Table 79S provides 60 compounds of formula (III-A) wherein $G^1$ is oxygen, $R^1$ is hydrogen, $R^2$ is G.079, $Y^1$, $Y^2$, $Y^3$ and $R^5$ have the values listed in the table S.

Table 80S
Table 80S provides 60 compounds of formula (III-A) wherein $G^1$ is oxygen, $R^1$ is hydrogen, $R^2$ is G.080, $Y^1$, $Y^2$, $Y^3$ and $R^5$ have the values listed in the table S.

Table 81S
Table 81S provides 60 compounds of formula (III-A) wherein $G^1$ is oxygen, $R^1$ is hydrogen, $R^2$ is G.081, $Y^1$, $Y^2$, $Y^3$ and $R^5$ have the values listed in the table S.

Table 82S
Table 82S provides 60 compounds of formula (III-A) wherein $G^1$ is oxygen, $R^1$ is hydrogen, $R^2$ is G.082, $Y^1$, $Y^2$, $Y^3$ and $R^5$ have the values listed in the table S.

Table 83S
Table 83S provides 60 compounds of formula (III-A) wherein $G^1$ is oxygen, $R^1$ is hydrogen, $R^2$ is G.083, $Y^1$, $Y^2$, $Y^3$ and $R^5$ have the values listed in the table S.

Table 84S
Table 84S provides 60 compounds of formula (III-A) wherein $G^1$ is oxygen, $R^1$ is hydrogen, $R^2$ is G.084, $Y^1$, $Y^2$, $Y^3$ and $R^5$ have the values listed in the table S.

Table 85S
Table 85S provides 60 compounds of formula (III-A) wherein $G^1$ is oxygen, $R^1$ is hydrogen, $R^2$ is G.085, $Y^1$, $Y^2$, $Y^3$ and $R^5$ have the values listed in the table S.

Table 86S
Table 86S provides 60 compounds of formula (III-A) wherein $G^1$ is oxygen, $R^1$ is hydrogen, $R^2$ is G.086, $Y^1$, $Y^2$, $Y^3$ and $R^5$ have the values listed in the table S.

Table 87S
Table 87S provides 60 compounds of formula (III-A) wherein $G^1$ is oxygen, $R^1$ is hydrogen, $R^2$ is G.087, $Y^1$, $Y^2$, $Y^3$ and $R^5$ have the values listed in the table S.

Table 88S
Table 88S provides 60 compounds of formula (III-A) wherein $G^1$ is oxygen, $R^1$ is hydrogen, $R^2$ is G.088, $Y^1$, $Y^2$, $Y^3$ and $R^5$ have the values listed in the table S.

Table 89S
Table 89S provides 60 compounds of formula (III-A) wherein $G^1$ is oxygen, $R^1$ is hydrogen, $R^2$ is G.089, $Y^1$, $Y^2$, $Y^3$ and $R^5$ have the values listed in the table S.

Table 90S
Table 90S provides 60 compounds of formula (III-A) wherein $G^1$ is oxygen, $R^1$ is hydrogen, $R^2$ is G.090, $Y^1$, $Y^2$, $Y^3$ and $R^5$ have the values listed in the table S.

Table 91S
Table 91S provides 60 compounds of formula (III-A) wherein $G^1$ is oxygen, $R^1$ is hydrogen, $R^2$ is G.091, $Y^1$, $Y^2$, $Y^3$ and $R^5$ have the values listed in the table S.

Table 92S
Table 92S provides 60 compounds of formula (III-A) wherein $G^1$ is oxygen, $R^1$ is hydrogen, $R^2$ is G.092, $Y^1$, $Y^2$, $Y^3$ and $R^5$ have the values listed in the table S.

Table 93S
Table 93S provides 60 compounds of formula (III-A) wherein $G^1$ is oxygen, $R^1$ is hydrogen, $R^2$ is G.093, $Y^1$, $Y^2$, $Y^3$ and $R^5$ have the values listed in the table S.

Table 94S
Table 94S provides 60 compounds of formula (III-A) wherein $G^1$ is oxygen, $R^1$ is hydrogen, $R^2$ is G.094, $Y^1$, $Y^2$, $Y^3$ and $R^5$ have the values listed in the table S.

Table 95S
Table 95S provides 60 compounds of formula (III-A) wherein $G^1$ is oxygen, $R^1$ is hydrogen, $R^2$ is G.095, $Y^1$, $Y^2$, $Y^3$ and $R^5$ have the values listed in the table S.

Table 96S
Table 96S provides 60 compounds of formula (III-A) wherein $G^1$ is oxygen, $R^1$ is hydrogen, $R^2$ is G.096, $Y^1$, $Y^2$, $Y^3$ and $R^5$ have the values listed in the table S.

Table 97S
Table 97S provides 60 compounds of formula (III-A) wherein $G^1$ is oxygen, $R^1$ is hydrogen, $R^2$ is G.097, $Y^1$, $Y^2$, $Y^3$ and $R^5$ have the values listed in the table S.

Table 98S
Table 98S provides 60 compounds of formula (III-A) wherein $G^1$ is oxygen, $R^1$ is hydrogen, $R^2$ is G.098, $Y^1$, $Y^2$, $Y^3$ and $R^5$ have the values listed in the table S.

Table 99S
Table 99S provides 60 compounds of formula (III-A) wherein $G^1$ is oxygen, $R^1$ is hydrogen, $R^2$ is G.099, $Y^1$, $Y^2$, $Y^3$ and $R^5$ have the values listed in the table S.

Table 100S
Table 100S provides 60 compounds of formula (III-A) wherein $G^1$ is oxygen, $R^1$ is hydrogen, $R^2$ is G.100, $Y^1$, $Y^2$, $Y^3$ and $R^5$ have the values listed in the table S.

Table 101S
Table 101S provides 60 compounds of formula (III-A) wherein $G^1$ is oxygen, $R^1$ is hydrogen, $R^2$ is G.101, $Y^1$, $Y^2$, $Y^3$ and $R^5$ have the values listed in the table S.

Table 102S
Table 102S provides 60 compounds of formula (III-A) wherein $G^1$ is oxygen, $R^1$ is hydrogen, $R^2$ is G.102, $Y^1$, $Y^2$, $Y^3$ and $R^5$ have the values listed in the table S.

Table 132S
Table 103S provides 60 compounds of formula (III-A) wherein $G^1$ is oxygen, $R^1$ is hydrogen, $R^2$ is G.103, $Y^1$, $Y^2$, $Y^3$ and $R^5$ have the values listed in the table S.

Table 104S
Table 104S provides 60 compounds of formula (III-A) wherein $G^1$ is oxygen, $R^1$ is hydrogen, $R^2$ is G.104, $Y^1$, $Y^2$, $Y^3$ and $R^5$ have the values listed in the table S.

Table 105S
Table 105S provides 60 compounds of formula (III-A) wherein $G^1$ is oxygen, $R^1$ is hydrogen, $R^2$ is G.105, $Y^1$, $Y^2$, $Y^3$ and $R^5$ have the values listed in the table S.

Table 106S
Table 106S provides 60 compounds of formula (III-A) wherein $G^1$ is oxygen, $R^1$ is hydrogen, $R^2$ is G.106, $Y^1$, $Y^2$, $Y^3$ and $R^5$ have the values listed in the table S.

Table 107S
Table 107S provides 60 compounds of formula (III-A) wherein $G^1$ is oxygen, $R^1$ is hydrogen, $R^2$ is G.107, $Y^1$, $Y^2$, $Y^3$ and $R^5$ have the values listed in the table S.

Table 108S
Table 108S provides 60 compounds of formula (III-A) wherein $G^1$ is oxygen, $R^1$ is hydrogen, $R^2$ is G.108, $Y^1$, $Y^2$, $Y^3$ and $R^5$ have the values listed in the table S.

Table 109S
Table 109S provides 60 compounds of formula (III-A) wherein $G^1$ is oxygen, $R^1$ is hydrogen, $R^2$ is G.109, $Y^1$, $Y^2$, $Y^3$ and $R^5$ have the values listed in the table S.

Table 110S
Table 110S provides 60 compounds of formula (III-A) wherein $G^1$ is oxygen, $R^1$ is hydrogen, $R^2$ is G.110, $Y^1$, $Y^2$, $Y^3$ and $R^5$ have the values listed in the table S.

Table 111S
Table 111S provides 60 compounds of formula (III-A) wherein $G^1$ is oxygen, $R^1$ is hydrogen, $R^2$ is G.111, $Y^1$, $Y^2$, $Y^3$ and $R^5$ have the values listed in the table S.

Table 112S
Table 112S provides 60 compounds of formula (III-A) wherein $G^1$ is oxygen, $R^1$ is hydrogen, $R^2$ is G.112, $Y^1$, $Y^2$, $Y^3$ and $R^5$ have the values listed in the table S.

Table 113S
Table 113S provides 60 compounds of formula (III-A) wherein $G^1$ is oxygen, $R^1$ is hydrogen, $R^2$ is G.113, $Y^1$, $Y^2$, $Y^3$ and $R^5$ have the values listed in the table S.

Table 114S
Table 114S provides 60 compounds of formula (III-A) wherein $G^1$ is oxygen, $R^1$ is hydrogen, $R^2$ is G.114, $Y^1$, $Y^2$, $Y^3$ and $R^5$ have the values listed in the table S.

Table 115S

Table 115S provides 60 compounds of formula (III-A) wherein $G^1$ is oxygen, $R^1$ is hydrogen, $R^2$ is G.115, $Y^1, Y^2, Y^3$ and $R^5$ have the values listed in the table S.

Table 116S

Table 116S provides 60 compounds of formula (III-A) wherein $G^1$ is oxygen, $R^1$ is hydrogen, $R^2$ is G.116, $Y^1, Y^2, Y^3$ and $R^5$ have the values listed in the table S.

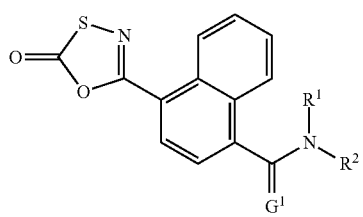

(III-B)

Table 1T:

Table 1T provides 116 compounds of formula (III-B) wherein $G^1$ is oxygen, $R^1$ is hydrogen, $R^2$ has the values listed in Table G.

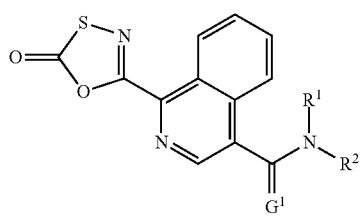

(III-C)

Table 1U:

Table 1U provides 116 compounds of formula (III-C) wherein $G^1$ is oxygen, $R^1$ is hydrogen, $R^2$ has the values listed in Table G.

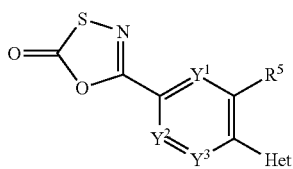

(III-D)

Table 117S

Table 117S provides 60 compounds of formula (III-D) wherein Het is Het.01, and $Y^1, Y^2, Y^3$ and $R^5$ have the values listed in the table S.

Table 118S

Table 118S provides 60 compounds of formula (III-D) wherein Het is Het.02 and $Y^1, Y^2, Y^3$ and $R^5$ have the values listed in the table S.

Table 119S

Table 119S provides 60 compounds of formula (III-D) wherein Het is Het.03 and $Y^1, Y^2, Y^3$ and $R^5$ have the values listed in the table S.

Table 120S

Table 120S provides 60 compounds of formula (III-D) wherein Het is Het.04 and $Y^1, Y^2, Y^3$ and $R^5$ have the values listed in the table S.

(III-E)

Table 1V

Table 1V provides 4 compounds of formula (III-E) wherein Het has the values as listed in Table Het.

(III-F)

Table 1W

Table 1W provides 4 compounds of formula (III-F) wherein Het has the values listed in Table Het.

In one embodiment the invention provides a compound selected from Tables 1P to 120P and 1Q to 240Q for use in controlling and/or preventing insects of the family Curculionidae, preferably in for use in controlling and/or preventing *Anthonomus grandis*.

Additional examples of insects from the family of Curculionidae. are *Anthonomus corvulus, Anthonomus elutus, Anthonomus elongatus, Anthonomus eugenii, Anthonomus consors, Anthonomus haematopus, Anthonomus lecontei, Anthonomus molochinus, Anthonomus morticinus, Anthonomus musculus, Anthonomus nigrinus, Anthonomus phyllocola, Anthonomus pictus, Anthonomus pomorum, Anthonomus quadrigibbus, Anthonomus rectirostris, Anthonomus rubi, Anthonomus santacruzi, Anthonomus signatus, Anthonomus subfasciatus*, and *Anthonomus tenebrosus*.

In one embodiment the invention provides a compound selected from Tables 1P to 120P and 1Q to 240Q for use against *Anthonomus grandis* in cotton.

In one embodiment the invention provides a compound selected from Tables 1P to 120P and 1Q to 240Q for use in controlling and/or preventing soil pests.

In one embodiment the invention provides a compound selected from Tables 1P to 120P and 1Q to 240Q for use in controlling and/or preventing corn rootworm, in particular for use against corn root worm from the genus *Diabrotica*.

In one embodiment the invention provides a compound selected from Tables 1P to 120P and 1Q to 240Q for use in controlling and/or preventing corn *Diabrotica virgifera*.

In one embodiment the invention provides a compound selected from Tables 1P to 120P and 1Q to 240Q for use in controlling and/or preventing corn *Diabrotica barberi*.

In one embodiment the invention provides a compound selected from Tables 1P to 120P and 1Q to 240Q for use in controlling and/or preventing corn *Diabrotica undecimpunctata howardi*.

In one embodiment the invention provides a compound selected from Tables 1P to 120P and 1Q to 240Q for use in controlling and/or preventing wireworms, in particular *Agriotes* spp.

In one embodiment the invention provides a compound selected from Tables 1P to 120P and 1Q to 240Q for use in controlling and/or preventing *Agriotes* spp. in cereals, potato or corn.

Additional examples of *Agriotes* spp. include *Agriotes lineatus, Agriotes obscurus, Agriotes brevis, Agriotes gurgistanus, Agriotes sputator, Agriotes ustulatus, Ctenicera destructor*, and *Limonius californicus*.

In one embodiment the invention provides a compound selected from Tables 1P to 120P and 1Q to 240Q for use in controlling and/or preventing grubs, in particular white grubs.

In one embodiment the invention provides a compound selected from Tables 1P to 120P and 1Q to 240Q for use in controlling and/or preventing *Phyllophaga* spp., particularly on corn, soybean or cotton.

In one embodiment the invention provides a compound selected from Tables 1P to 120P and 1Q to 240Q for use in controlling and/or preventing *Diloboderus* spp. particularly on corn, soybean or cotton.

In one embodiment the invention provides a compound selected from Tables 1P to 120P and 1Q to 240Q for use in controlling and/or preventing *Popillia japonica*, particularly on corn, soybean or cotton.

Additional examples of white grubs include *Phyllophaga anxia, Phyllophaga crinite, Phyllophaga subnitida, Diloboderus abderus*.

In one embodiment the invention provides a compound selected from Tables 1P to 120P and 1Q to 240Q for use in controlling and/or preventing termites, e.g. on sugarcane.

Examples of termites include *Reticulitermes, Coptotermes, Macrotermes, Microtermes, Globitermes*. Specific of subterranean termites include *Reticulitermes flavipes, Reticulitermes hesperus, Reticulitermes verginicus, Reticulitermes hageni, Reticulitermes speratus, Reticulitermes lucifugus, Heterotermes aureus, Coptotermes formosanus, Coptotermes acinaciformis, Coptotermes curvignathus, Nasutitermes exitiosus, Nasutitermes walkeri, Mastotermes darwiniensis, Schedorhinotermes* spp, *Macrotermes bellicosus, Macrotermes* spp., *Globitermes sulphureus, Odontotermes* spp. Specific examples of dry wood termites include *Incisitermes minor, Marginitermes hubbardi, Cryptotermes brevis, Kalotermes flavicollis*. Additional examples of termites include *procornitermes* spp. and *procornitermes araujoi*

In one embodiment the invention provides a compound selected from Tables 1P to 120P and 1Q to 240Q for use in controlling and/or preventing subterraneous stinkbugs, e.g. *Scaptocoris* spp.

In one embodiment the invention provides a compound selected from Tables 1P to 120P and 1Q to 240Q for use in controlling and/or preventing *Scaptocoris castaneus*, in particular on cereals, soybean or corn.

In one embodiment the invention provides a compound selected from Tables 1P to 120P and 1Q to 240Q for use in controlling and/or preventing cutworms, e.g. *agrotis* spp.

In one embodiment the invention provides a compound selected from Tables 1P to 120P and 1Q to 240Q for use in controlling and/or preventing *Agrotis ipsilon*, particularly on cereals, canola, soybean or corn.

In one embodiment the invention provides a compound selected from Tables 1P to 120P and 1Q to 240Q for use in controlling and/or preventing millipedes, e.g. *Julus* spp.

In one embodiment the invention provides a compound selected from Tables 1P to 120P and 1Q to 240Q for use in controlling and/or preventing *Julus* spp., particularly on cereals, canola, soybean & corn.

In one embodiment the invention provides a compound selected from Tables 1P to 120P and 1Q to 240Q for use in controlling and/or preventing broca gigante, e.g. *Telchin licus*, particularly on sugarcane.

In one embodiment the invention provides a compound selected from Tables 1P to 120P and 1Q to 240Q for use in controlling and/or preventing whitefly.

In one embodiment the invention provides a compound selected from Tables 1P to 120P and 1Q to 240Q for use in controlling and/or preventing *Bemisia tabaci*, particularly on vegetables, cotton, soybean, or potatoes.

In one embodiment the invention provides a compound selected from Tables 1P to 120P and 1Q to 240Q for use in controlling and/or preventing *Trialeurodes vaporariorum*, particularly on vegetables, cotton, soybean, or potatoes.

In one embodiment the invention provides a compound selected from Tables 1P to 120P and 1Q to 240Q for use in controlling and/or preventing stinkbugs, in particular *Euschistus* spp.

In one embodiment the invention provides a compound selected from Tables 1P to 120P and 1Q to 240Q for use in controlling and/or preventing *Euschistus* spp., particularly in soybean.

Examples of stinkbugs include *Nezara* spp. (e.g. *Nezara viridula, Nezara antennata, Nezara hilare*), *Piezodorus* spp. (e.g. *Piezodorus guildinii*), *Acrosternum* spp. *Euchistus* spp. (e.g. *Euchistus heros, Euschistus servus*), *Halyomorpha halys, Plautia crossota, Riptortus clavatus, Rhopalus msculatus, Antestiopsis orbitalus, Dichelops* spp. (e.g. *Dichelops furcatus, Dichelops melacanthus*), *Eurygaster* spp. (e.g. *Eurygaster intergriceps, Eurygaster maura*), *Oebalus* spp. (e.g. *Oebalus mexicana, Oebalus poecilus, Oebalus pugnase, Scotinophara* spp. (e.g. *Scotinophara lurida, Scotinophara coarctata*). Preferred targets include *Antestiopsis orbitalus, Dichelops furcatus, Dichelops melacanthus, Euchistus heros, Euschistus servus, Nezara viridula, Nezara hilare, Piezodorus guildinii, Halyomorpha halys*. In one embodiment the stinkbug target is *Nezara viridula, Piezodorus* spp., *Acrosternum* spp, *Euchistus heros*.

In one embodiment the invention provides a compound selected from Tables 1P to 120P and 1Q to 240Q for use against rice pests.

In one embodiment the invention provides a compound selected from Tables 1P to 120P and 1Q to 240Q for use against stemborer, particularly in rice.

Examples of stemborers include *Chilo* sp, *Chilo suppressalis, Chilo polychrysus, Chilo auricilius, Scirpophaga* spp., *Scirpophaga incertulas, Scirpophaga innotata, Scirpophaga nivella Sesamia* sp, *Sesamia inferens*.

In one embodiment the invention provides a compound selected from Tables 1P to 120P and 1Q to 240Q for use against leaffolder, particularly in rice.

Examples of leaffolders include *Cnaphalocrocis* spp., *Cnaphalocrocis medinalis, Marasmia* spp., *Marasmia patnalis, Marasmia exigua*.

In one embodiment the invention provides a compound selected from Tables 1P to 120P and 1Q to 240Q for use against hoppers, particularly in rice.

Examples of Hoppers include *Nephotettix* spp., *Nephotettix virescens, Nephotettix nigropictus, Nephotettix malayanus, Nephotettix cincticeps, Nilaparvata lugens, Sogatella furcifera*.

In one embodiment the invention provides a compound selected from Tables 1P to 120P and 1Q to 240Q for use against gallmidge, particularly in rice.

Examples of Gall midge include *Orseolia* sp, *Orseolia oryzae*.

In one embodiment the invention provides a compound selected from Tables 1P to 120P and 1Q to 240Q for use against whorl maggot, particularly in rice.

Examples of whorl maggots include *Hydrellia* sp., *Hydrellia philippina*.

In one embodiment the invention provides a compound selected from Tables 1P to 120P and 1Q to 240Q for use against Rice bugs, particularly in rice.

Examples of rice bugs include *Leptocorisa* sp, *Leptocorisa oratorius*, *Leptocorisa chinensis*, *Leptocorisa acuta*.

In one embodiment the invention provides a compound selected from Tables 1P to 120P and 1Q to 240Q for use against Black bugs, particularly in rice.

Examples of Black bugs include *Scotinophara* sp, *Scotinophara coarctata*, *Scotinophara lurida*, *Scotinophara latiuscula*.

In one embodiment the invention provides a compound selected from Tables 1P to 120P and 1Q to 240Q for use against *plutella* spp.

In one embodiment the invention provides a compound selected from Tables 1P to 120P and 1Q to 240Q for use against *Plutella xylostella*, particularly in *brassica* crops.

The compounds of the invention may be made by a variety of methods as shown in the following Schemes.

Scheme 1

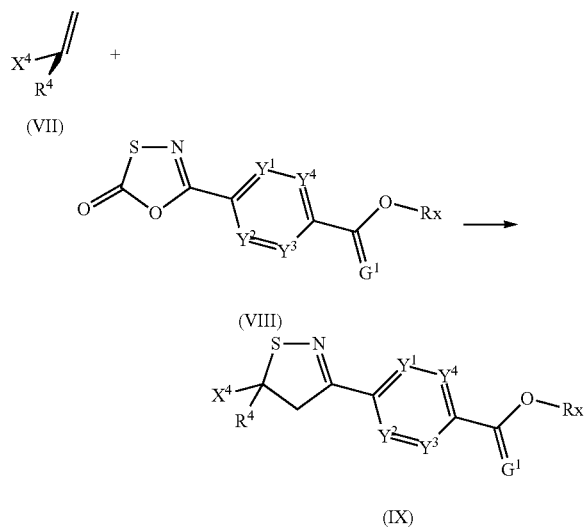

(IX)

1) Compounds of formula (IX) wherein Rx is $C_1$-$C_{15}$alkoxy can be prepared by reacting a compound of formula (VIII) with the vinyl compound of formula (VII) in the presence or not of a suitable solvent, for example N,N-dimethylformamide, xylene, toluene, chlorobenzene or dichlorobenzene. The reaction can be performed under microwave heating preferably at temperatures up to 200° C. and preferably under neat conditions using a large excess of the compound of formula VII (e.g. 40 equivalents). Vinyl compounds of formula (VII) are commercially available or can be made by methods known to a person skilled in the art. Compounds of formula (VIII) can be made by methods known to a person skilled in the art, as described in journal of Organic Chemistry (1981), 46(4), 771-775.

Scheme 2

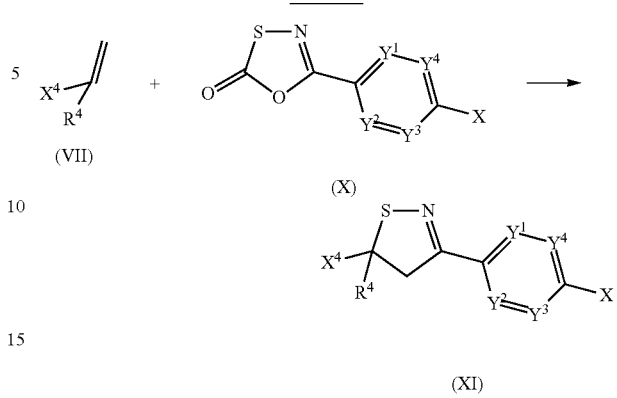

(XI)

2) Compounds of formula (XI) can be prepared by reacting a compound of formula (X) wherein X is a leaving group, for example a halogen, such as bromo, with a compound of formula (VII), using the same methods as described in 1).

Scheme 3

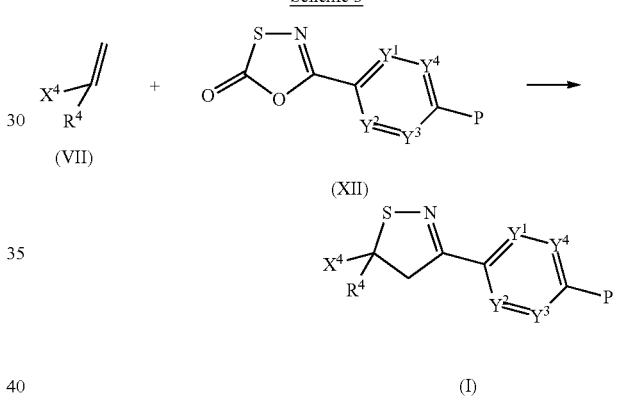

(I)

3) Compounds of formula (I) can be prepared by reacting a compound of formula (XII) wherein P is as described for the compound I, with a compound of formula (VII), using the same methods as described in 1).

Scheme 4

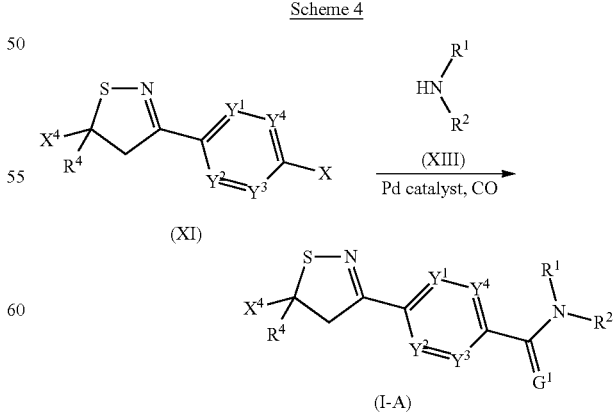

(I-A)

4) Compounds of formula (I-A) can be prepared by reacting a compound of formula (XI) wherein X is a leaving group, for example a halogen, such as bromo, with carbon monoxide and an amine of formula (XIII), in the presence of a catalyst, such as palladium(II) diacetate, a ligand, such as a phosphine ligand, such as tributylphosphine, and a base such as cesium carbonate, or diisopropylethylamine (Hunig's base). The reaction is carried out in a suitable solvent, such as toluene, at a temperature of from 50° C. to 200° C., preferably from 100° C. to 150° C., in particular at 115° C. The reaction is carried out at a pressure of from 50 to 200 bar, preferably from 100 to 150 bar, in particular at 120 bar.

7) Compounds of formula (XIV) can be made by treatment of a compound of formula (XI), wherein X is a halogen, for instance bromine, with a metallating agent, such as a metal, for instance magnesium, or an organometallic compound, for instance butyllithium, followed by the treatment with carbon dioxide. The reaction is carried out at a temperature of from −120° C. to +130° C., preferably from −100° C. to 100° C.

8) Compounds of formula (XIV) can be made by hydrolysis of a compound of formula (IX), and Rx is $C_1$-$C_{15}$alkyl, such as methyl or tert-butyl. For instance, in the case where Scheme 5

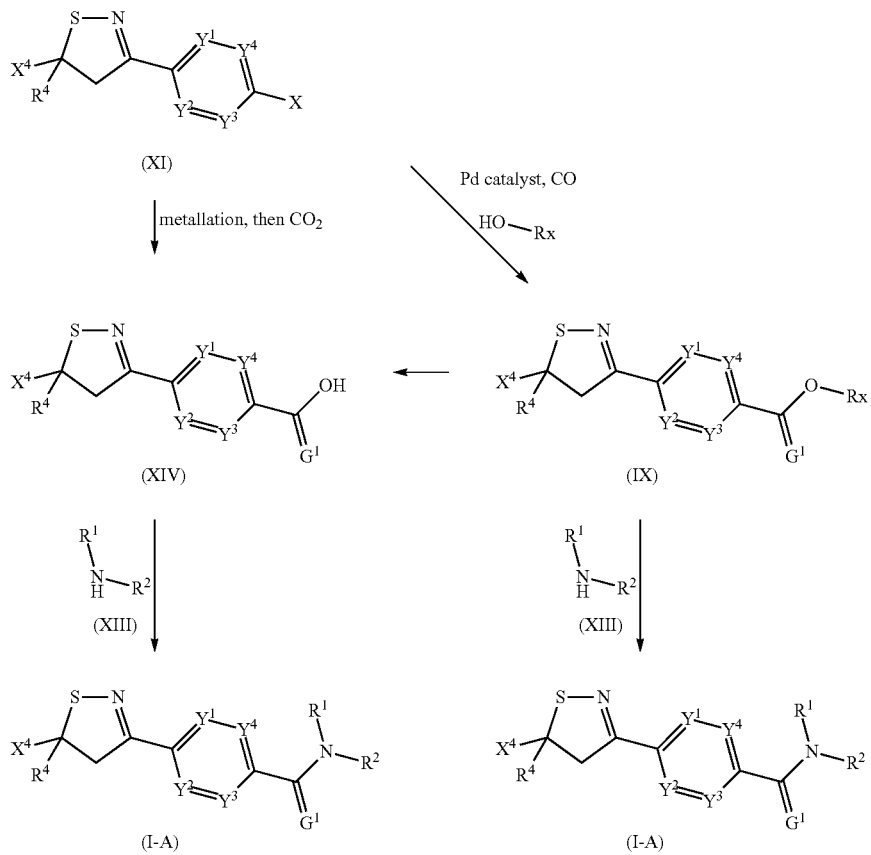

5) Compounds of formula (I-A) can be made by treatment of a compound of formula (XIV) with a compound of formula (XIII) and a dehydrating reagent. Alternatively, carboxylic acid (XIV) is transformed to an activated derivative, such as an acid chloride, for instance by treatment with thionyl chloride, or a mixed anhydride, for instance by treatment with ethyl chloroformate, and the activated derivative is reacted with a compound of formula (XIII), optionally in the presence of a base, and in a suitable solvent, such as, for instance, tetrahydrofuran. The reaction is carried out at a temperature of from −120° C. to +130° C., preferably from −100° C. to 100° C.

6) Alternatively, compounds of formula (I-A) can be made from a compound of formula (IX) wherein Rx is $C_1$-$C_{15}$alkoxy by heating the ester and an amine of formula (XIII) together in a thermal process Amines of formula (XIII) are known in the literature or can be prepared using methods known to a person skilled in the art.

Rx is methyl or ethyl, the hydrolysis can be done with water and a base, such as potassium hydroxide, in the absence or in the presence of a solvent, such as, for instance, tetrahydrofuran or methanol. In the case where Rx is, for example, tert-butyl, the hydrolysis is done in the presence of acid, such as trifluoroacetic acid or hydrochloric acid. The reaction is carried out at a temperature of from −120° C. to +130° C., preferably from −100° C. to 100° C.

9) Compounds of formula (IX) wherein Rx is $C_1$-$C_{15}$alkoxy, can be prepared by reacting a compound of formula (XI) wherein X is a leaving group, for example a halogen, such as bromo, with carbon monoxide and an alcohol of formula Rx-OH, such as ethanol, in the presence of a catalyst, such as bis(triphenylphosphine)palladium(II) dichloride, and a base, such as pyridine, triethylamine, 4-(dimethylamino)-pyridine ("DMAP") or diisopropylethylamine (Hunig's base). The reaction is carried out at a temperature of from 50° C. to 200° C., preferably from 100° C. to 150° C., in particular at 115° C. The reaction is carried out at a pressure of from 50 to 200 bar, preferably from 100 to 150 bar, in particular at 120 bar.

Scheme 6

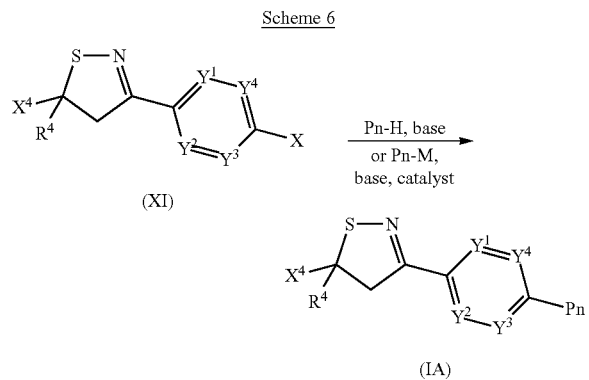

10) Compounds of formula (IA), wherein Pn is an optionally substituted heterocycle, can be made, for example in the case where the heterocycle is attached via a nitrogen atom, by treatment of a compound (XI) wherein X is a halogen, such as fluorine, with a heterocyclic compound Pn-H and a suitable base, such as potassium carbonate. Alternatively, compounds of formula (IA), wherein Pn is an optionally substituted heterocycle, can be made, for example in the case where the heterocycle is attached via a carbon atom, by treatment of a compound (XI) wherein X is a halogen, such as bromine, with a heterocyclic compound Pn-M, wherein M is hydrogen or a metal, such as boron, magnesium or zinc, in which case M can be optionally substituted, with a base and a suitable catalyst, such as a palladium or a copper catalyst, in the presence of a suitable ligand for the catalyst, such as, for example, a diamine ligand, or a phosphine ligand. Such reactions are carried out at a temperature of from −120° C. to +130° C., preferably from −100° C. to 100° C.

unsaturated ketone of formula (XV) wherein $G^1$ is oxygen, with a sulfur nucleophile, such as thioacetic acid, hydrogen sulfide, sodium sulfide, ammonium sulfide, thiourea, benzylmercaptan, Sodium benzenethiosulfonate, sodium thiomethoxide or tert-butyl mercaptan as shown on Scheme 7. Such reactions can be performed optionally in the presence of a base, such as sodium hydroxide, sodium ethoxide, sodium methoxide, sodium tert-butoxide or potassium hydroxide. Sometimes, such reactions can also be performed in the presence of an acid, for example p-toluenesulfonic acid, hydrochloric acid, acetic acid, in a solvent, such as methanol, ethanol, N,N-dimethylformamide, toluene, dichloromethane, ethyl acetate, acetonitrile or chlorobenzene or water, or mixtures thereof, at a temperature of from 0° C. to 100° C., preferably from ambient temperature to 80° C. Such conditions are described, for example, in Journal of the American Chemical Society (1949), 71, 3554-5 or in Tetrahedron: Asymmetry (2003), 14(1), 113-117 and Journal of Organic Chemistry (1996), 61, 1986.

12) Compounds of formula (XVI) wherein P is as defined for compounds (I) and $Z^3$ is thiol or aryl substituted $C_1$-$C_8$alkylsulfinyl-, can be made by reaction of the ketone of formula (XV) with an amine, such as triphenylmethanesulfenamide. Such reactions are usually carried out in the presence of an acid or not, for example p-toluenesulfonic acid, hydrochloric acid, acetic acid, optionally in the presence of a solvent, for example an alcohol, such as methanol or ethanol, or toluene, dichloromethane, water, or mixtures thereof. The reaction can be carried our in the presence or the absence of a dehydrating agent, such as anhydrous magnesium sulfate or molecular sieves. It can also be performed using a Dean Stark or Soxhlet apparatus that enables a constant removal of the water formed during the reaction. The reaction is carried out at a temperature of from 0° C. to 100° C., preferably from 15° C. to 30° C., in particular at ambient temperature.

13) Compounds of formula (XVIII) wherein P is as defined for compounds (I) and $Z^2$ is hydrogen or hydroxyl or $C_1$-$C_8$alkoxy- or $C_1$-$C_8$alkylsulfonyloxy- or Scheme 7

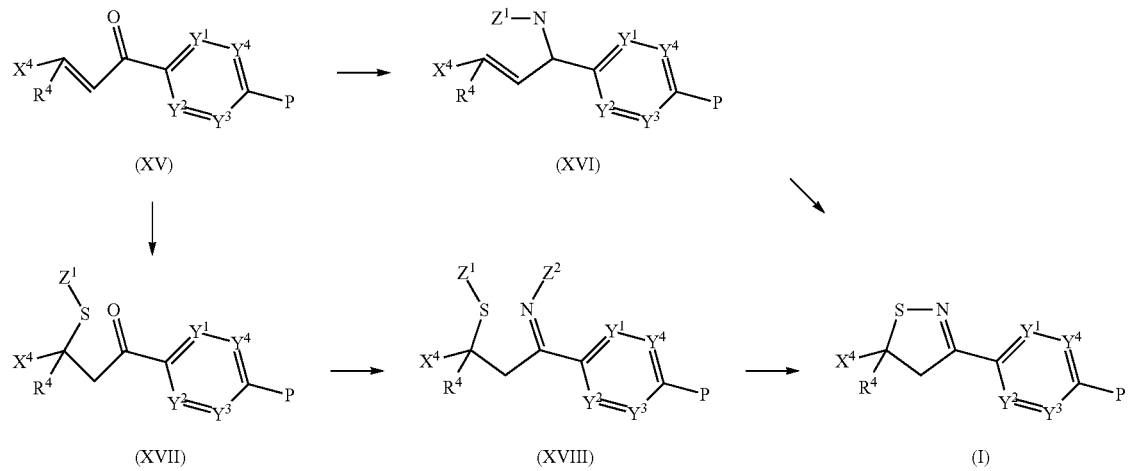

11) Compounds of formula (XVII) wherein P is as defined for compounds (I) and $Z^1$ is hydrogen, halogen, cyano, $C_1$-$C_8$alkyl, aryl-$C_1$-$C_4$alkylene-, $C_1$-$C_8$alkylcarbonyl-, arylsulfonyl- or arylthio-, can be obtained by reacting an $C_1$-$C_8$arylsulfonyloxy- or aryl-$C_1$-$C_4$alkylene- or aryl, can be made by reaction of the ketone of formula (XVII) with an amine, such as hydroxylamine hydrochloride, methoxylamine or ammonia. Such reactions are carried out in the presence of a base, for example an organic base, such as triethylamine or sodium acetate, or an inorganic base, such as sodium hydrogen carbonate, optionally in the presence of a solvent, for example an alcohol, such as methanol or ethanol, or water, or mixtures thereof. Such reactions can also be carried out in the presence of an acid or not, for example p-toluenesulfonic acid, hydrochloric acid, acetic acid, optionally in the presence of a solvent, for example an alcohol, such as methanol or ethanol, or toluene, dichloromethane, water, or mixtures thereof. The reaction can be carried our in the presence or the absence of a dehydrating agent, such as anhydrous magnesium sulfate or molecular sieves. It can also be performed using a Dean Stark or Soxhlet apparatus that enables a constant removal of the water formed during the reaction. The reaction is carried out at a temperature of from 0° C. to 100° C., preferably from 15° C. to 30° C., in particular at ambient temperature.

14) Compounds of formula (I) can be obtained by cyclising a compound of formula (XVI) wherein $Z^3$ is thiol. Such reactions are usually carried out in the presence of an acid or not, for example p-toluenesulfonic acid, optionally in the presence of a solvent, for example dichloroethane, methanol, ethanol, toluene, dichloromethane or chlorobenzene. The reaction is carried out at a temperature of from 0° C. to 200° C., preferably from 25° C. to 100° C. Alternatively, compounds of formula (I) wherein P is as defined for compounds (I) can be obtained by cyclising a compound of formula (XVI) wherein $Z^3$ is aryl substituted $C_1$-$C_8$alkylsulfinyl-. Such reactions are usually carried out in the presence of an acid or not, for example p-toluenesulfonic acid, trifluoroacetic acid or hydrochloric acid, optionally in the presence of a solvent, for example dichloroethane, methanol, ethanol, toluene, dichloromethane or chlorobenzene. The reaction is carried out at a temperature of from 0° C. to 200° C., preferably from 25° C. to 100° C. Such reactions usually involve first the deprotection of the thiol to give a compound of formula (XVI) wherein $Z^3$ is thiol, followed by the cyclization.

15) Compounds of formula (I) can be obtained from compound of formula (XVIII) wherein $Z^1$ is hydrogen or $C_1$-$C_8$alkyl or aryl-$C_1$-$C_4$alkylene- or $C_1$-$C_8$alkylcarbonyl- or arylsulfonyl- or arylthio-, and $Z^2$ is hydrogen or hydroxyl or $C_1$-$C_8$alkoxy- or $C_1$-$C_8$alkylsulfonyloxy- or $C_1$-$C_8$arylsulfonyloxy- or aryl-$C_1$-$C_4$alkylene- or aryl. Such reactions usually involve the deprotection of $Z^1$ and of $Z^2$ or of both groups. The reaction can then involve the following intermediates:

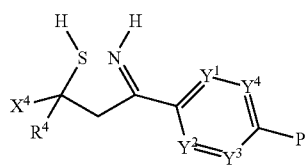
(XVIIIa)

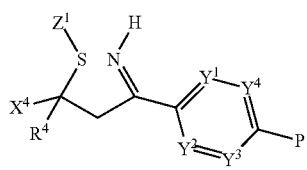
(XVIIIb)

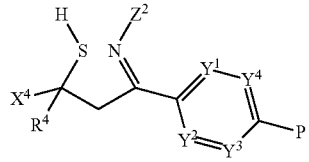
(XVIIIc)

Depending on the nature of $Z^1$ and $Z^2$, the deprotection conditions are different and can be made by methods known to a person skilled in the art or as described in T. W. Green, P. G. M. Wuts, *Protective Groups in Organic Synthesis*, Wiley-Interscience, New York, 1999, 564-566, 740-743.

16) Compounds of formula (I) can be obtained from compound of formula (XVIIIa) from an oxidation step. Such reactions are usually carried out in the presence of an oxidant, for example iodine, bromine, thionyl chloride, Bis(trifluoroacetoxy)iodobenzene; The reaction can be carried our in the presence of an acid or not, such as trifluoroacetic acid or acetic acid, optionally in the presence of a solvent, for example dichloroethane, dimethylsulfoxide, N,N-dimethylformamide, methanol, ethanol, toluene, dichloromethane, ethyl acetate or chlorobenzene. The reaction is carried out at a temperature of from 0° C. to 200° C., preferably from 25° C. to 100° C. Such transformations, including reaction conditions and suitable catalyst, are described in Journal of the Chemical Society, Perkin Transactions 1: Organic and Bio-Organic Chemistry (1972-1999) (1985), (1), 153-7 and Organic Letters (2006), 8(21), 4811-4813. Similarly, compounds of formula (I-I) wherein P is as defined for compounds (I) can be obtained from a compound of formula (XVIIIb) wherein $Z^1$ is arylsulfonyl- or arylthio-, by an oxidation step, are described in Journal of Organic Chemistry (1990), 55(13), 4156-62.

17) Compounds of formula (I) can be obtained from compound of formula (XVIIIc) wherein $Z^2$ is $C_1$-$C_8$alkoxy-. Such reactions are usually carried out in the presence of a copper (I) reagent, such copper-3-methylsalicylate. The reaction can be carried out in the presence of a solvent, for example dichloroethane, dimethylsulfoxide, N,N-dimethylformamide, methanol, ethanol, toluene, dichloromethane, ethyl acetate or chlorobenzene. The reaction is carried out at a temperature of from 0° C. to 200° C., preferably from 25° C. to 100° C., or under microwave heating conditions. Such transformations are described in Journal of the American Chemical Society (2011), 133, 6403-6410.

18) Alternatively, compounds of formula (I) can be obtained directly from a compound of formula (XVII) wherein $Z^1$ is hydrogen. Such reactions are usually carried out in the presence chloramines, formed in situ from ammonia and chlorine or sodium hypochlorite or hypochlorous acid, optionally in the presence of a solvent, for example dichloroethane, methanol, ethanol, toluene, dichloromethane or chlorobenzene. The reaction is carried out at a temperature of from −80° C. to 40° C., preferably below −40° C.

19) Alternatively, compounds of formula (I) can be obtained directly from a compound of formula (XVII) wherein $Z^1$ is halogen, cyano, arylsulfonyl- or arylthio-. Such reactions are usually carried out in the presence ammonia, optionally in the presence of a solvent, for example dichloroethane, tetrahydrofuran, methanol, ethanol, toluene, dichloromethane or chlorobenzene. The reaction is carried out at a temperature of from −80° C. to 80° C.

20) Alternatively, compounds of formula (I) can be obtained directly from a compound of formula (XVII) wherein $Z^1$ is aryl-$C_1$-$C_4$alkylene. Such reactions are usually carried out in two steps—The first one involves the treatment of a compound of formula (XVII) wherein $Z^1$ is aryl-$C_1$-$C_4$alkylene by a suitable oxidant, such as sulfuryl chloride or chlorine, in the presence of a solvent, for example dichloroethane, methanol, ethanol, toluene, dichloromethane or chlorobenzene, to provide a compound of formula (XVII) wherein $Z^1$ is chlorine. The second step then involves the treatment a compound of formula (XVII) wherein $Z^1$ is chlorine by an ammonia source, such as ammonia or ammonium bromide in the presence of a base, in the presence of a solvent, for example dichloroethane, methanol, ethanol, toluene, tetrahydrofuran, dichloromethane or chlorobenzene. Both steps are usually carried out at a temperature of from −80° C. to 80° C.

21) Alternatively, compounds of formula (I) can be obtained directly from a compound of formula (XVII) wherein $Z^1$ is hydrogen. Such reactions are usually carried out in the presence of a suitable nitrogen electrophile, such as Hydroxylamine-O-sulfonic acid. Such reactions are carried out in the presence of a base, for example an organic base, such as triethylamine or sodium acetate, or an inorganic base, such as sodium hydrogen carbonate, sodium hydroxide or potassium hydroxide optionally in the presence of a solvent, for example tetrahydrofuran, toluene, an alcohol, such as methanol or ethanol, or water, or mixtures thereof. The reaction is carried out at a temperature of from −80° C. to 80° C.

Scheme 8

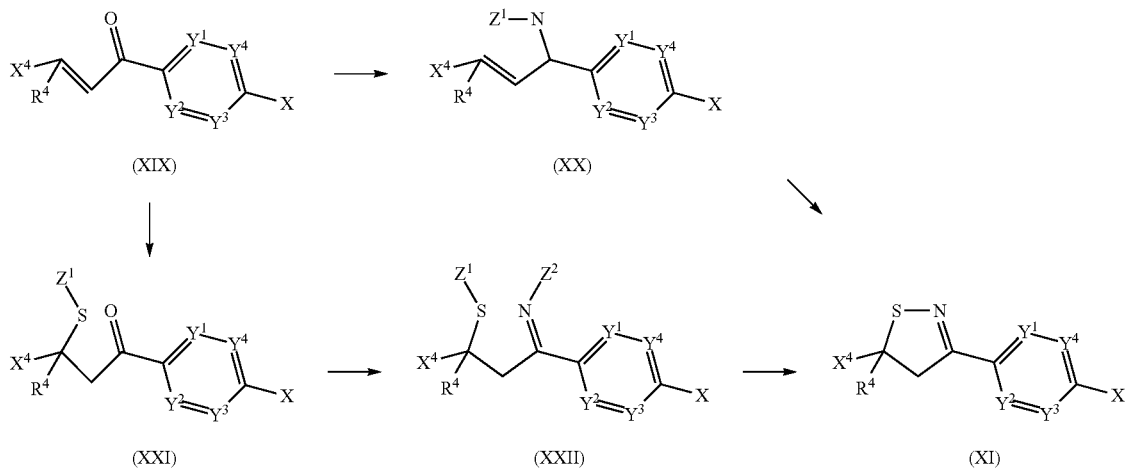

18) Similarly to what is described from 11) to 16), compounds of (XI) wherein X is a leaving group, for example a halogen, such as bromo can be obtained.

Scheme 9

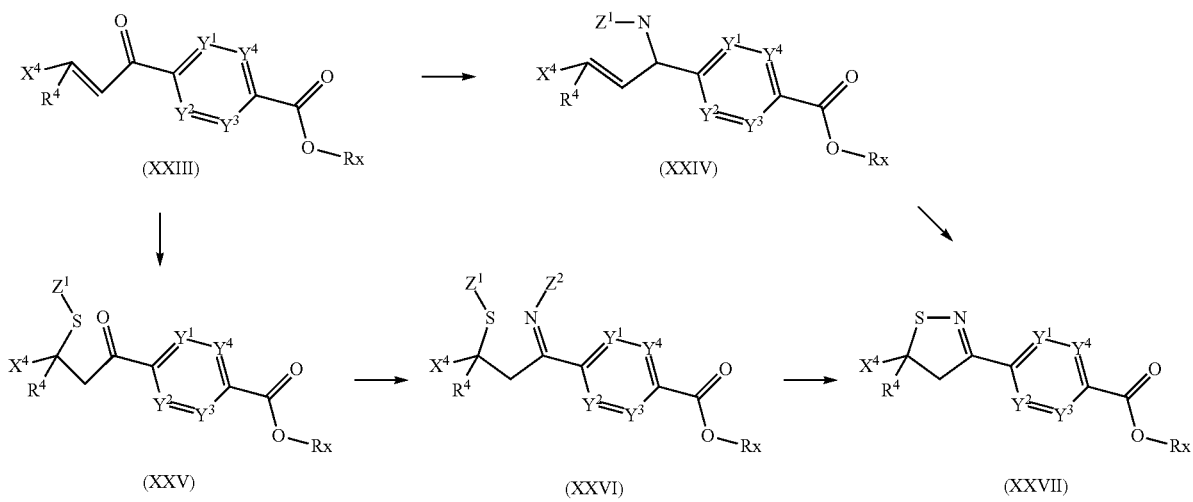

19)

Similarly to what is described from 11) to 16), compounds of formula (XXVII) wherein Rx is $C_1$-$C_{15}$alkoxy can be obtained. Unless otherwise indicated in the above descriptions reference to leaving groups includes leaving groups such as halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. the leaving group may be selected from $-N_2^+$ $Cl^-$, $-N_2^+$ $BF_4^-$, $-N_2^+$ $Br^-$, $-N_2^+$ $PF_6^-$) and phosphonate esters (e.g. $-OP(O)(OR)_2$, wherein R is methyl or ethyl).

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the compounds of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The compounds of the invention may be used for example on turf, ornamentals, such as flowers, shrubs, broad-leaved trees or evergreens, for example conifers, as well as for tree injection, pest management and the like. Compositions comprising the compound of formula I may be used on ornamental garden plants (e.g. flowers, shrubs, broad-leaved trees or evergreens), e.g. to control aphids, whitefly, scales, meelybug, beetles and caterpillars. Compositions comprising the compound of formula I may be used on garden plants (e.g. flowers, shrubs, broad-leaved trees or evergreens), on indoor plants (e.g. flowers and shrubs) and on indoor pest e.g. to control aphids, whitefly, scales, meelybug, beetles and caterpillars.

Furthermore, the compounds of the invention may be effective against harmful insects, without substantially imposing any harmful side effects to cultivated plants. Application of the compounds of the invention may increase the harvest yields, and may improve the quality of the harvested material. The compounds of the invention may have favourable properties with respect to amount applied, residue formulation, selectivity, toxicity, production methodology, high activity, wide spectrum of control, safety, control of resistant organisms, e.g. pests that are resistant to organic phosphorus agents and/or carbamate agents.

Examples of pest species which may be controlled by the compounds of formula (I) include: coleopterans, for example, *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus, Aulacophora femoralis;* lepidopterans, for example, *Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella;* hemipterans, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara* spp., *Trialeurodes vaporariorm, Psylla* spp.; thysanopterans, for example, *Thrips palmi, Franklinella occidental;* orthopterans, for example, *Blatella germanica, Periplaneta americana, Gryllotalpa Africana, Locusta migratoria migratoriodes;* isopterans, for example, *Reticulitermes speratus, Coptotermes formosanus;* dipterans, for example, *Musca domestica, Aedes aegypti, Hylemia platura, Culex pipiens, Anopheles sinensis, Culex tritaeniorhynchus, Liriomyza trifolii;* acari, for example, *Tetranychus cinnabarinus, Tetranychus urticae, Panonychus citri, Aculops pelekassi, Tarsonemus* spp.; nematodes, for example, *Meloidogyne incognita, Bursaphelenchus lignicolus Mamiya et Kiyohara, Aphelenchoides besseyi, Heterodera glycines, Pratylenchus* spp.

Examples of further pest species which may be controlled by the compounds of formula (I) include: from the order of the Anoplura (Phthiraptera), for example, *Damalinia* spp., *Haematopinus* spp., *Linognathus* spp., *Pediculus* spp., *Trichodectes* spp.; from the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;* from the class of the Bivalva, for example, *Dreissena* spp.; from the order of the Chilopoda, for example, *Geophilus* spp., *Scutigera* spp.; from the order of the Coleoptera, for example, *Acanthoscehdes obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.; from the order of the Collembola, for example, *Onychiurus armatus;* from the order of the Dermaptera, for example, *Forficula auricularia;* from the order of the Diplopoda, for example, *Blaniulus guttulatus;* from the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.; from the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*; ft may be furthermore possible to control protozoa, such as Eimeria; from the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.; from the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma pini*, *Aphis* spp., *Arboridia apicalis*, *Aspidiella* spp., *Aspidiotus* spp., *Atanus* spp., *Aulaconthum solani*, *Bemisia* spp., *Brachycaudus helichrysii*, *Brachycolus* spp., *Brevicoryne brassicae*, *Calligypona manginata*, *Carneocephala fulgida*, *Ceratovacuna lanigena*, *Cercopidae*, *Cenoplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeunodes* spp., *Diaphorina* spp., *Diaspis* spp., *Dorsalis* spp., *Drosicha* spp., *Dysaphis* spp., *Dysmicoccus* spp., *Empoasca* spp., *Eniosoma* spp., *Erythnoneuna* spp., *Euscelis bilobatus*, *Geococcus coffeae*, *Homalodisca coagulata*, *Hyaloptenus arundinis*, *Icerya* spp., *Idiocenus* spp., *Idioscopus* spp., *Laodelphax stniatellus*, *Lecanium* spp., *Lepidosaphes* spp., *Lipaphis erysimi*, *Macnosiphum* spp., *Mahanarva fimbniolata*, *Melanaphis sacchari*, *Metcalfiella* spp., *Metopolophium dinhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Onthezia pnaelonga*, *Panabemisia mynicae*, *Paratrioza* spp., *Panlatonia* spp., *Pemphigus* spp., *Peregrinus maidis*, *Phenacoccus* spp., *Phloeomyzus passeninii*, *Phorodon humuli*, *Phylloxera* spp., *Pinnaspis aspidistrae*, *Planococcus* spp., *Protopulvinania pyriformis*, *Pseudaulacaspis pentagona*, *Pseudococcus* spp., *Psylla* spp., *Ptenomalus* spp., *Pyrilla* spp., *Quadnaspidiotus* spp., *Quesada gigas*, *Rastrococcus* spp., *Rhopalosiphum* spp., *Saissetia* spp., *Scaphoides titanus*, *Schizaphis graminum*, *Selenaspidus anticulatus*, *Sogata* spp., *Sogatella furcifera*, *Sogatodes* spp., *Stictocephala festina*, *Tenalaphana malayensis*, *Tinocallis caryaefoliae*, *Tomaspis* spp., *Toxoptera* spp., *Tnialeunodes vaponanionum*, *Trioza* spp., *Typhlocyba* spp., *Unaspis* spp., *Viteus vitifolii*; from the order of the Hymenoptera, for example, *Dipnion* spp., *Hoplocampa* spp., *Lasius* spp., *Mono-monium pharaonis*, *Vespa* spp.; from the order of the Isopoda, for example, *Armadillidium vulgane*, *Oniscus asellus*, *Poncellio scaber*; from the order of the Isoptera, for example, *Reticulitermes* spp., *Odontotermes* spp.; from the order of the Lepidoptera, for example, *Acronicta major*, *Aedia leucomelas*, *Agnotis* spp., *Alabama angillacea*, *Anticansia* spp., *Banathna brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.; from the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*; from the order of the Siphonaptera, for example, *Ceratophyllus* spp., *Xenopsylla cheopis*. From the order of the Symphyla, for example, *Scutigerella immaculata*; from the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.; from the order of the Thysanura, for example, *Lepisma saccharina*. The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

In particular, the compounds of the invention may be used to control the following pest species:

*Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta_migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis (American dog tick), Ctenocephalides felis (cat flea), Liriomyza spp. (leafminer), Musca domestica (housefly), Aedes aegypti (mosquito), Anopheles spp. (mosquitoes), Culex spp. (mosquitoes), Lucillia spp. (blowflies), Blattella germanica (cockroach), Periplaneta americana (cockroach), Blatta orientalis (cockroach), termites of the Mastotermitidae (for example Mastotermes spp.), the Kalotermitidae (for example Neotermes spp.), the Rhinotermitidae (for example Coptotermes formosanus, Reticulitermes flavipes, R. speratu, R. virginicus, R. hesperus, and R. santonensis) and the Termitidae (for example Globitermes sulfureus), Solenopsis geminata (fire ant), Monomorium pharaonis (pharaoh's ant), Damalinia spp. and Linognathus spp. (biting and sucking lice), Meloidogyne spp. (root knot nematodes), Globodera spp. and Heterodera spp. (cyst nematodes), Pratylenchus spp. (lesion nematodes), Rhodopholus spp. (banana burrowing nematodes), Tylenchulus spp. (citrus nematodes), Haemonchus contortus (barber pole worm), Caenorhabditis elegans_(vinegar eelworm), Trichostrongylus spp. (gastro intestinal nematodes) and Deroceras reticulatum (slug).

The compound of formula I may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables, cucurbits and pulses (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used for pest control on various plants, including soybean, corn, sugarcane, alfalfa, brassicas, oilseed rape (e.g. canola), potatoes (including sweet potatoes), cotton, rice, coffee, citrus, almonds, fruiting vegetables, cucurbits and pulses (e.g. tomatoes, pepper, chili, eggplant, cucumber, squash etc.), tea, bulb vegetables (e.g. onion, leek etc.), grapes, pome fruit (e.g. apples, pears etc.), stone fruit (e.g. pears, plums etc.), and cereals.

The compounds of the invention may be used on soybean to control, for example, Elasmopalpus lignosellus, Diloboderus abderus, Diabrotica speciosa, Trialeurodes spp., Bemisia spp., aphids, Sternechus subsignatus, Formicidae, Agrotis ypsilon, Julus spp., Murgantia spp., Halyomorpha spp., Thyanta spp., Megascelis ssp., Procornitermes ssp., Gryllotalpidae, Nezara viridula, Piezodorus spp., Acrosternum spp., Neomegalotomus spp., Cerotoma trifurcata, Popillia japonica, Edessa spp., Liogenys fuscus, Euschistus heros, stalk borer, Scaptocoris castanea, phyllophaga spp., Migdolus spp., Pseudoplusia includens, Anticarsia gemmatalis, Epinotia spp., Rachiplusia spp., Spodoptera spp., Bemisia tabaci, Tetranychus spp., Agriotes spp., Euschistus spp. The compounds of the invention are preferably used on soybean to control Diloboderus abderus, Diabrotica speciosa, Trialeurodes spp., Bemisia spp., Nezara viridula, Piezodorus spp., Acrosternum spp., Cerotoma trifurcata, Popillia japonica, Euschistus heros, Scaptocoris castanea, phyllophaga spp., Migdolus spp., Agriotes spp., Euschistus spp.

The compounds of the invention may be used on corn to control, for example, Euschistus heros, Euschistus spp., Dichelops furcatus, Diloboderus abderus, Thyanta spp., Elasmopalpus lignosellus, Halyomorpha spp., Spodoptera frugiperda, Nezara viridula, Cerotoma trifurcata, Popillia japonica, Agrotis ypsilon, Diabrotica speciosa, aphids, Heteroptera, Procornitermes spp., Scaptocoris castanea, Formicidae, Julus ssp., Dalbulus maidis, Diabrotica virgifera, Diabrotica spp., Mocis latipes, Bemisia tabaci, heliothis spp., Tetranychus spp., thrips spp., phyllophaga spp., Migdolus spp., scaptocoris spp., Liogenys fuscus, Spodoptera spp., Ostrinia spp., Sesamia spp., wireworms, Agriotes spp., Halotydeus destructor. The compounds of the invention are preferably used on corn to control Euschistus heros, Euschistus spp., Dichelops furcatus, Diloboderus abderus, Nezara viridula, Cerotoma trifurcata, Popillia japonica, Diabrotica speciosa, Diabrotica virgifera, Diabrotica spp., Tetranychus spp., Thrips spp., Phyllophaga spp., Migdolus spp., Scaptocoris spp., Agriotes spp.

The compounds of the invention may be used on sugar cane to control, for example, Sphenophorus spp., termites, Migdolus spp., Diloboderus spp., Telchin licus, Diatrea saccharalis, Mahanarva spp., Mealybugs.

The compounds of the invention may be used on alfalfa to control, for example, Hypera brunneipennis, Hypera postica, Colias eurytheme, Collops spp., Empoasca solana, Epitrix spp., Geocoris spp., Lygus hesperus, Lygus lineolaris, Spissistilus spp., Spodoptera spp., Aphids, Trichoplusia ni. The compounds of the invention are preferably used on alfalfa to control Hypera brunneipennis, Hypera postica, Empoasca solana, Epitrix spp., Lygus hesperus, Lygus lineolaris, Trichoplusia ni.

The compounds of the invention may be used on brassicas to control, for example, Plutella xylostella, Pieris spp., Mamestra spp., Plusia spp., Trichoplusia ni, Phyllotreta spp., Spodoptera spp., Empoasca spp., thrips spp., Delia spp., Murgantia spp., Trialeurodes spp., Bemisia spp., Microtheca spp., Aphids. The compounds of the invention are preferably used on brassicas to control Plutella xylostella, Pieris spp., Plusia spp., Trichoplusia ni, Phyllotreta spp., Thrips spp.

The compounds of the invention may be used on oil seed rape, e.g. canola, to control, for example, Meligethes spp., Ceutorhynchus napi, Halotydeus destructor, Psylloides spp.

The compounds of the invention may be used on potatoes, including sweet potatoes, to control, for example, Empoasca spp., Leptinotarsa spp., Diabrotica speciosa, Phthorimaea spp., Paratrioza spp., Maladera matrida, Agriotes spp., Aphids, wireworms. The compounds of the invention are preferably used on potatoes, including sweet potatoes, to control Empoasca spp., Leptinotarsa spp., Diabrotica speciosa, Phthorimaea spp., Paratrioza spp., Agriotes spp.

The compounds of the invention may be used on cotton to control, for example, Anthonomus grandis, Pectinophora spp., heliothis spp., Spodoptera spp., Tetranychus spp., Empoasca spp., Thrips spp., Bemisia tabaci, Trialeurodes spp., Aphids, Lygus spp., phyllophaga spp., Scaptocoris spp., Austroasca viridigrisea, Creontiades spp., Nezara spp., Piezodorus spp., Halotydeus destructor, Oxycaraenus hyalinipennis, Dysdercus cingulatus. The compounds of the invention are preferably used on cotton to control Anthonomus grandis, Tetranychus spp., Empoasca spp., thrips spp., Lygus spp., phyllophaga spp., Scaptocoris spp.

The compounds of the invention may be used on rice to control, for example, Leptocorisa spp., Cnaphalocrosis spp., Chilo spp., Scirpophaga spp., Lissorhoptrus spp., Oebalus pugnax, Scotinophara spp., Nephotettix malayanus, Nephotettix nigropictus, Nephotettix parvus, Nephottetix virescens,

*Nephotettix* spp., Mealybugs, *Sogatella furcifera*, *Nilaparvata lugens*, *Orseolia* spp., *Cnaphalocrocis medinalis*, *Marasmia* spp., *Stenchaetothrips biformis*, *Thrips* spp., *Hydrellia philippina*, Grasshoppers, *Pomacea canaliculata*, *Scirpophaga innotata*, *Chilo suppressalis*, *Chilo auricilius*, *Chilo polychrysus*, *Sesamia inferens*, *Laodelphax striatellus*, *Nymphula depunctalis*, *Oulema oryzae*, Stinkbugs. The compounds of the invention are preferably used on rice to control *Leptocorisa* spp., *Lissorhoptrus* spp., *Oebalus pugnax*, *Nephotettix malayanus*, *Nephotettix nigropictus*, *Nephotettix parvus*, *Nephottetix virescens*, *Nephotettix* spp., *Sogatella furcifera*, *Stenchaetothrips biformis*, *Thrips* spp., *Hydrellia philippina*, Grasshoppers, *Pomacea canaliculata*, *Scirpophaga innotata*, *Chilo suppressalis*, *Chilo polychrysus*, *Oulema oryzae*.

The compounds of the invention may be used on coffee to control, for example, *Hypothenemus Hampei*, *Perileucoptera Coffeella*, *Tetranychus* spp., *Brevipalpus* spp., Mealybugs. The compounds of the invention are preferably used on coffee to control *Hypothenemus Hampei*, *Perileucoptera Coffeella*.

The compounds of the invention may be used on citrus to control, for example, *Panonychus citri*, *Phyllocoptruta oleivora*, *Brevipalpus* spp., *Diaphorina citri*, *Scirtothrips* spp., *Thrips* spp., *Unaspis* spp., *Ceratitis capitata*, *Phyllocnistis* spp., Aphids, Hardscales, Softscales, Mealybugs. The compounds of the invention are preferably used on citrus to control *Panonychus citri*, *Phyllocoptruta oleivora*, *Brevipalpus* spp., *Diaphorina citri*, *Scirtothrips* spp., thrips spp., *Phyllocnistis* spp.

The compounds of the invention may be used on almonds to control, for example, *Amyelois transitella*, *Tetranychus* spp.

The compounds of the invention may be used on fruiting vegetables, cucurbits and pulses, including tomatoes, pepper, chili, eggplant, cucumber, squash etc., to control, for example, *Thrips* spp., *Tetranychus* spp., *Polyphagotarsonemus* spp., *Aculops* spp., *Empoasca* spp., *Spodoptera* spp., *heliothis* spp., *Tuta absoluta*, *Liriomyza* spp., *Bemisia tabaci*, *Trialeurodes* spp., Aphids, *Paratrioza* spp., *Frankliniella occidentalis*, *Frankliniella* spp., *Anthonomus* spp., *Phyllotreta* spp., *Amrasca* spp., *Epilachna* spp., *Halyomorpha* spp., *Scirtothrips* spp., *Leucinodes* spp., *Neoleucinodes* spp. *Maruca* spp., Fruit flies, Stinkbugs, Lepidopteras, Coleopteras. The compounds of the invention are preferably used on fruiting vegetables, cucurbits and pulses, including tomatoes, pepper, chili, eggplant, cucumber, squash etc., to control *Thrips* spp., *Tetranychus* spp., *Polyphagotarsonemus* spp., *Aculops* spp., *Empoasca* spp., *Spodoptera* spp., *heliothis* spp., *Tuta absoluta*, *Liriomyza* spp., *Paratrioza* spp., *Frankliniella occidentalis*, *Frankliniella* spp., *Amrasca* spp., *Scirtothrips* spp., *Leucinodes* spp., *Neoleucinodes* spp.

The compounds of the invention may be used on tea to control, for example, *Pseudaulacaspis* spp., *Empoasca* spp., *Scirtothrips* spp., *Caloptilia theivora*, *Tetranychus* spp. The compounds of the invention are preferably used on tea to control *Empoasca* spp., *Scirtothrips* spp.

The compounds of the invention may be used on bulb vegetables, including onion, leek etc. to control, for example, *Thrips* spp., *Spodoptera* spp., *heliothis* spp. The compounds of the invention are preferably used on bulb vegetables, including onion, leek etc. to control *Thrips* spp.

The compounds of the invention may be used on grapes to control, for example, *Empoasca* spp., *Lobesia* spp., *Eupoecilia ambiguella*, *Frankliniella* spp., *Thrips* spp., *Tetranychus* spp., *Rhipiphorothrips Cruentatus*, *Eotetranychus Willamettei*, *Erythroneura Elegantula*, *Scaphoides* spp., *Scelodonta strigicollis*, Mealybugs. The compounds of the invention are preferably used on grapes to control *Frankliniella* spp., *Thrips* spp., *Tetranychus* spp., *Rhipiphorothrips Cruentatus*, *Scaphoides* spp.

The compounds of the invention may be used on pome fruit, including apples, pears etc., to control, for example, *Cacopsylla* spp., *Psylla* spp., *Panonychus ulmi*, *Cydia pomonella*, *Lepidopteras*, Aphids, Hardscales, Softscales. The compounds of the invention are preferably used on pome fruit, including apples, pears etc., to control *Cacopsylla* spp., *Psylla* spp., *Panonychus ulmi*.

The compounds of the invention may be used on stone fruit to control, for example, *Grapholita molesta*, *Scirtothrips* spp., *Thrips* spp., *Frankliniella* spp., *Tetranychus* spp., Aphids, Hardscales, Softscales, Mealybugs. The compounds of the invention are preferably used on stone fruit to control *Scirtothrips* spp., *Thrips* spp., *Frankliniella* spp., *Tetranychus* spp.

The compounds of the invention may be used on cereals to control, for example, Aphids, Stinkbugs, earthmites, *Eurygaster integriceps*, *Zabrus tenebrioides*, *Anisoplia austriaca*, *Chaetocnema aridula*, *Phyllotreta* spp., *Oulema melanopus*, *Oscinella* spp., *Delia* spp., *Mayetiola* spp., *Contarinia* spp., *Cephus* spp., *Steneotarsonemus* spp., *Apamea* spp.

In another embodiment compounds of formula I and mixtures of the invention may be used on rice to control *Baliothrips biformis* (Thrips), *Chilo* spp. (e.g. *Chilo polychrysus* (Dark headed striped borer), *Chilo suppressalis* (Rice stemborer), *Chilo indicus* (Paddy stem borer), *Chilo polychrysus* (Dark-headed rice borer), *Chilo suppressalis* (Stripe stem borer)), *Cnaphalocrocis medinalis* (Rice leaf folder), *Dicladispa armigera* (Hispa), *Hydrellia philipina* (Rice whorl-maggot), *Laodelphax* spp. (Smaller brown planthopper) (e.g. *Laodelphax striatellus*), *Lema oryzae* (Rice leafbeetle), *Leptocorsia acuta* (Rice bug), *Leptocorsia oratorius* (rice bug), *Lissorhoptrus oryzophilus* (rice water weevil), *Mythemina separata* (armyworm), *Nephottetix* spp. (Green leafhopper) (e.g. *Nephotettix cincticeps*, *Nephotettix malayanus*, *Nephotettix nigropictus*, *Nephotettix parvus*, *Nephottetix virescens*), *Nilaparvata lugens* (Brown Planthopper), *Nymphula depunctalis* (Rice caseworm), *Orseolia oryzae* (Rice Gall midge), *Oulema oryzae* (Rice leafbeetle), *Scirpophaga incertulas* (Yellow Stemborer), *Scirpophaga innotata* (White Stemborer), *Scotinophara coarctata* (Rice black bug), *Sogaella frucifera* (White-backed planthopper), *Steneotarsonemus spinki*.

The compounds of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, *Thrips*, Tip moths, Tussock moth larvae, Wasps, Broadmites, Brown softscales, California redscales (crawlers), Clover mites, Mealybugs, Pineneedlescales (crawlers), Spider mites, Whiteflies The compounds of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The compounds of formula (I) and mixture of the invention, in particular those in the tables above, may be used for soil applications, including as a seed application, to target at least the following: sucking pests such as aphids, *thrips*, brown plant hopper (e.g. on rice), sting bugs, white flies (e.g. on cotton and vegetables), mites; on soil pests such as corn root worm, wireworms, white grubs, *zabrus*, termites (e.g. on sugar cane, soy, pasture), maggots, cabbage root fly, red legged earth mite; on lepidoptera, such as *spodoptera*, cutworms, elasmoplpus, *plutella* (e.g. *brassica*), stem borers, leaf miners, flea beetle, *Sternechus*; on nematicides, such as *Heterodera glycines* (e.g. on soybean), *Pratylenchus* brachyurus (e.g. on corn), P. zeae (e.g. oncorn), *P. penetrans* (e.g. on corn), *Meloidogyne incognita* (e.g. on vegetables), *Heterodera schachtii* (e.g. on sugar beet), Rotylenchus reniformis (e.g. on cotton), *Heterodera avenae* (e.g. on cereals), *Pratylenchus* neglectus (e.g. on cereals), thornei (e.g. on cereals).

The compounds of formula (I) and mixture of the invention, in particular those in the tables above may be used for seed applications at least on the following: soil grubs for corn, soybeans, sugarcane: *Migdolus* spp; *Phyllophaga* spp.; *Diloboderus* spp; *Cyclocephala* spp; *Lyogenys fuscus*; sugarcane weevils: *Sphenophorus levis* & *Metamasius hemipterus*; termites for soybeans, sugarcane, pasture, others: *Heterotermes tenuis; Heterotermes longiceps; Cornitermes cumulans; Procornitermes triacifer; Neocapritermes opacus; Neocapritermes parvus*; corn root worms for corn and potatoes: *Diabrotica* spp., seed Maggot: *Delia platura*; soil stinkbugs: *Scaptocoris castanea*; wireworms: *Agriotes* spp; *Athous* spp *Hipnodes bicolor; Ctenicera destructor; Limonius canu; Limonius californicus*; rice water weevil: *Lissorhoptrus oryzophilus*; Red Legged earth mites: *Halotydeus destructor.*

The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

The compounds of the invention may be applied to plant parts. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

Compounds of formula I may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in superadditive "synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030, 295) or Cry1A105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (corn producing Cry1Ab), Agrisure®RW (corn producing mCry3A), Agrisure® Viptera (corn hybrids producing Vip3Aa); Agrisure300GT (corn hybrids producing Cry1Ab and mCry3A); YieldGard® (corn hybrids producing the Cry1Ab protein), YieldGard® Plus (corn hybrids producing Cry1Ab and Cry3Bb1), Genuity® SmartStax® (corn hybrids with Cry1A.105, Cry2Ab2, Cry1F, Cry34/35, Cry3Bb); Herculex® I (corn hybrids producing Cry1Fa) and Herculex®RW (corn hybrids producing Cry34Ab1, Cry35Ab1 and the enzyme Phosphinothricin-N-Acetyltransferase [PAT]); NuCOTN®33B (cotton cultivars producing Cry1Ac), Bollgard®I (cotton cultivars producing Cry1Ac), Bollgard®II (cotton cultivars producing Cry1Ac and Cry2Ab2) and VIPCOT® (cotton cultivars producing a Vip3Aa). Soybean Cyst Nematode resistance soybean (SCN®—Syngenta) and soybean with Aphid resistant trait (AMT®) are also of interest.

Further examples of such transgenic crops are:

1. Btl1 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Btl1 maize also transgenically expresses the enzyme PAT to achieve tolerance to the herbicide glufosinate ammonium.

2. Btl76 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Btl76 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4 D (e.g. Enlist®) (e.g. WO 2011066384), glyphosate (e.g. Roundup Ready®, Roundup Ready 2 Yield®), sulfonylurea (e.g. STS®), glufosinate (e.g. Liberty Link®, Ignite®), Dicamba (Monsanto), HPPD tolerance (e.g. isoxaflutole herbicide) (Bayer CropScience, Syngenta). Double or triple stacks of any of the traits described here are also of interest, including glyphosate and sulfonyl-urea tolerance ((e.g. Optimum GAT®), plants stacked with STS® and Roundup Ready® or plants stacked with STS® and Roundup Ready 2 Yield®), dicamba and glyphosate tolerance (Monsanto). Of particular interest are soybean plants carrying trains conferring resistance to 2.4 D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto).

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

Examples of cotton transgenic events include MON 531/757/1076 (Bollgard I®—Monsanto), MON1445 (Roundup ready cotton®—Monsanto), MON531×MON1445 (Bollgard I+RR®—Monsanto), MON15985 (Genuity Bollgard II cotton®—Monsanto), MON88913 (Genuity RR FLEX cotton®—Monsanto), MON15985×MON1445 (Genuity Bollgard II+RR FELX cotton®—Monsanto), MON15983×MON88913 (Genuity Bollgard II+RR FLEX cotton®—Monsanto), MON15985 (FibreMax Bollgard II Cotton®—Monsanto), LL25 (FibreMax LL cotton®—BCS Stoneville), GHB614 (FibreMax GlyTol cotton®—BCS Stoneville), LL25×MON15985 (FibreMax LL Bollgard II cotton®—BCS Stoneville/Monsanto), GHB614×LL25 (FibreMax LL GlyTol cotton®—BCS Stoneville), GHB614×LL25×MON15985 (FibreMax RR GlyTol Bollgard II cotton®—BCS Stoneville), MON88913×MON15985 (FibreMax LL GlyTol Bollgard II cotton®—Monsanto), MON88913 (FibreMax RR Flex cotton®—Monsanto), GHB119+T304-40 (Twinlink®—BCS Stoneville), GHB119+T304-40×LL25×GHB614 (Twinlink LL GT®—BCS Stoneville), 3006-210-23×281-24-236 (PhytoGen Widestrike Insect Protection®—Dow), 3006-210-23×281-24-236×MON88913 (PhytoGen Widestrike Insect Protection+RR FLEX—® Dow/Monsanto), 3006-210-23×281-24-236×MON1445 ((PhytoGen Widestrike Insect Protection+RR®—Dow/Monsanto), MON1445 (PhytoGen Roundup Ready®—Monsanto), MON88913 (PhytoGen Roundup Ready FLEX®—Monsanto), COT102×COT67B (Vipcot®—Syngenta), COT102×COT67B×MON88913 (Vipcot RR FLEX®—Syngenta/Monsanto), 281-24-236 (Dow), 3006-210-23 (Dow), COT102 (Syngenta), COT67B (Syngenta), T304-40 (BCS Stoneville).

Examples of Soy transgenic events include MON87701×MON89788 (Genuity Roundup ready 2 Yield soybeans®—Monsanto), MON89788 (Roundup Ready2Yield®, RR2Y®—Monsanto), MON87708 (Monsanto), 40-3-2 (Roundup Ready®, RR1®—Monsanto), MON87701 (Monsanto), DAS-68416 (Enlist Weed Control System®—Dow), DP356043 (Optimum GAT®—Pioneer), A5547-127 (LibertyLink soybean®—Bayercropscience), A2704-12 (Bayercropscience), GU262 (Bayercropscience), W62 W98 (Bayercropscience), CRV127 (Cultivance®—BASF/EMBRAPA) SYHT0H2 (WO2012/082548).

Examples of Maize transgenic events include T25 (LibertyLink®, LL®—Bayerscropscience), DHT-1 (Dow), TC1507 (Herculex I®—Dow), DAS59122-7 (Herculex RW®—Dow), TC1507+DAS59122-7—Herculex Xtra®—Dow), TC1507×DAS-59122-7×NK603 (Herculex Xtra+RR®—Dow), TC1507×DAS-59122-×MON88017×MON89034 (Genuity Smartstax corn®, Genuity Smartstax RIB complete®—Monsanto/Dow), MON89034×NK603 (Genuity VT double PRO®—Monsanto), MON89034+MON88017 (Genuity VT Triple PRO®—Monsanto), NK603 (Roundup Ready 2®, RR2®—Monsanto), MON810 (YieldGard BT®, Yieldgard cornborer®—Monsanto), MON810×NK603 (YieldGard cornborer RR Corn 2®—Monasnto), MON810×MON863 (YieldGard Plus®—Monsanto), MON863×MON810×NK603 (YieldGard Plus+RR Corn2®/YieldGard RR Maize®—Monsanto), MON863×NK603 (YieldGard Rotworm+RR Corn 2®—Monsanto), MON863 (YieldBard RW®—Monsanto), MON89034 (YieldGard RW®—Monsanto), MON88017 (YieldGard VT RW®Monsanto), MON810+MON88017 (YieldGard VT Triplet®—Monsanto), MON88017+MON89034 (YieldGard VT Triple Pro®—Monsanto), Btl1+MIR604+GA21 (Agrisure 3000®—Syngenta), Btl1+TC1507+MIR604+5307+GA21 (Syngenta), Btl1+TC1507+MIR604+DAS59122+GA21 (Agrisure 3122®—Syngenta), BT11 (Agrisure CB®—Syngenta), GA21—(Agrisure GT®—Syngenta), MIR604 (Agrisure RW®—Syngenta), Btl1+MIR162 (Agrisure TL VIP®—Syngenta), BT11+MIR162+GA21 (Agrisure Viptra 31100—Syngenta), BT11+MIR162+MIR604 (Agrisure TM 3100®—Syngenta), Event3272+BT11+MIR604+GA21 (Syngenta), BT11+MIR1692+MIR604+GA21 (Agrisure Viptera 3111®—Syngenta), BT11+MIR162+TC1507+GA21 (Agrisure Viptera 3220®—Syngenta), BT11+MIR162+TC1507+MIR604+5307+GA21 (Agrisure Viptera 3222®—Syngenta), MIR162 (Syngenta), BT11+GA21+MIR162+MIR604+5307 (Syngenta), 5307 (Syngenta).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of suitable pesticides include the following (where "Tx" means a compound of formula (I), and in particular a compound selected from Tables 1P to 120P and 1Q to 240Q which may result in a synergistic combination with the given active ingredient):

a) Pyrethroids, such as permethrin+Tx, cypermethrin+Tx, fenvalerate+Tx, esfenvalerate+Tx, deltamethrin+Tx, cyhalothrin+Tx (in particular lambda-cyhalothrin+Tx and gamma cyhalothrin+Tx), bifenthrin+Tx, fenpropathrin+Tx, cyfluthrin+Tx, tefluthrin+Tx, fish safe pyrethroids+Tx (for example ethofenprox+Tx), natural pyrethrin+Tx, tetramethrin+Tx, S-bioallethrin+Tx, fenfluthrin+Tx, pralethrin+Tx, acrinathirin+Tx, etofenprox+Tx or 5-benzyl-3-furylmethyl-(E)-(1R,3S)-2,2-dimethyl-3-(2-oxothiolan-3-ylidenemethyl)cyclopropane carboxylate+Tx;

b) Organophosphates, such as profenofos+Tx, sulprofos+Tx, acephate+Tx, methyl parathion+Tx, azinphos-methyl+Tx, demeton-s-methy+Tx 1, heptenophos+Tx, thiometon+Tx, fenamiphos+Tx, monocrotophos+Tx, profenofos+Tx, triazophos+Tx, methamidophos+Tx, dimethoate+Tx, phosphamidon+Tx, malathion+Tx, chlorpyrifos+Tx, phosalone+Tx, terbufos+Tx, fensulfothion+Tx, fonofos+Tx, phorate+Tx, phoxim+Tx, pirimiphos-methyl+Tx, pirimiphos-ethyl+Tx, fenitrothion+Tx, fosthiazate+Tx or diazinon+Tx;

c) Carbamates (including aryl carbamates), such as pirimicarb+Tx, triazamate+Tx, cloethocarb+Tx, carbofuran+Tx, furathiocarb+Tx, ethiofencarb+Tx, aldicarb+Tx, thiofurox+Tx, carbosulfan+Tx, bendiocarb+Tx, fenobucarb+Tx, propoxur+Tx, methomyl+Tx or oxamyl+Tx;

d) Benzoyl ureas, such as diflubenzuron+Tx, triflumuron+Tx, hexaflumuron+Tx, flufenoxuron+Tx, diafenthiuron+Tx, lufeneron+Tx, novaluron+Tx, noviflumuron+Tx or chlorfluazuron+Tx;
e) Organic tin compounds, such as cyhexatin+Tx, fenbutatin oxide+Tx or azocyclotin+Tx;
f) Pyrazoles, such as tebufenpyrad+Tx, tolfenpyrad+Tx, ethiprole+Tx, pyriprole+Tx, fipronil+Tx, and fenpyroximate+Tx;
g) Macrolides, such as avermectins or milbemycins, for example abamectin+Tx, emamectin benzoate+Tx, ivermectin+Tx, milbemycin+Tx, spinosad+Tx, azadirachtin+Tx, milbemectin+Tx, lepimectin+Tx or spinetoram+Tx;
h) Hormones+Tx or pheromones+Tx;
i) Organochlorine compounds, such as endosulfan+Tx (in particular alpha-endosulfan+Tx), benzene hexachloride+Tx, DDT+Tx, chlordane+Tx or dieldrin+Tx;
j) Amidines, such as chlordimeform+Tx or amitraz+Tx;
k) Fumigant agents, such as chloropicrin+Tx, dichloropropane+Tx, methyl bromide+Tx or metam+Tx;
l) Neonicotinoid compounds, such as imidacloprid+Tx, thiacloprid+Tx, acetamiprid+Tx, nitenpyram+Tx, dinotefuran+Tx, thiamethoxam+Tx, clothianidin+Tx, or nithiazine+Tx;
m) Diacylhydrazines+Tx, such as tebufenozide+Tx, chromafenozide+Tx or methoxyfenozide+Tx;
n) Diphenyl ethers, such as diofenolan+Tx or pyriproxifen+Tx;
o) Pyrazolines such as Indoxacarb+Tx or metaflumizone+Tx;
p) Ketoenols, such as Spirotetramat+Tx, spirodiclofen+Tx or spiromesifen+Tx;
q) Diamides, such as flubendiamide+Tx, chlorantraniliprole+Tx (Rynaxypyr®) or cyantraniliprole+Tx;
r) Essential oils such as Bugoil®—(PlantImpact); or
s) a compound selected from buprofezine+Tx, flonicamid+Tx, acequinocy+Tx 1, bifenazate+Tx, cyenopyrafen+Tx, cyflumetofen+Tx, etoxazole+Tx, flometoquin+Tx, fluacrypyrim+Tx, fluensulfone+Tx, flufenerim+Tx, flupyradifuone+Tx, harpin+Tx, iodomethane+Tx, dodecadienol+Tx, pyridaben+Tx, pyridalyl+Tx, pyrimidifen+Tx, flupyradifurone+Tx, 4-[(6-Chloro-pyridin-3-ylmethyl)-(2,2-difluoro-ethyl)-amino]-5H-furan-2-one (DE 102006015467), CAS: 915972-17-7+Tx (WO 2006129714; WO2011/147953; WO2011/147952), CAS: 26914-55-8 (WO 2007020986), chlorfenapyr+Tx, pymetrozine+Tx, sulfoxaflor+Tx and pyrifluquinazon+Tx.

In addition to the major chemical classes of pesticide listed above, other pesticides having particular targets may be employed in the composition, if appropriate for the intended utility of the composition. For instance, selective insecticides for particular crops, for example stemborer specific insecticide (combinations such as cartap+Tx) or hopper specific insecticides (combinations such as buprofezin+Tx) for use in rice may be employed. Alternatively insecticides or acaricides specific for particular insect species/stages may also be included in the compositions (for example acaricidal ovolarvicides, to give combinations such as clofentezine+Tx, flubenzimine+Tx, hexythiazox+Tx or tetradifon+Tx; acaricidal motilicides, to give combinations such as dicofol+Tx or propargite+Tx; acaricides, to give combinations such as bromopropylate+Tx or chlorobenzilate+Tx; or growth regulators, such as hydramethylnon+Tx, cyromazine+Tx, methoprene+Tx, chlorfluazuron+Tx or diflubenzuron+Tx).

Examples of fungicidal compounds and combinations which may be included in the composition of the invention are (E)-N-methyl-2-[2-(2,5-dimethylphenoxymethyl)phenyl]-2-methoxy-iminoacetamide (SSF-129)+Tx, 4-bromo-2-cyano-N,N-dimethyl-6-trifluoromethyl-benzimidazole-1-sulfonamide+Tx, α-[N-(3-chloro-2,6-xylyl)-2-methoxyacetamido]-γ-butyrolactone+Tx, 4-chloro-2-cyano-N,N-dimethyl-5-p-tolylimidazole-1-sulfonamide (IKF-916, cyamidazosulfamid)+Tx, 3-5-dichloro-N-(3-chloro-1-ethyl-1-methyl-2-oxopropyl)-4-methylbenzamide (RH-7281, zoxamide)+Tx, N-allyl-4,5,-dimethyl-2-trimethylsilylthiophene-3-carboxamide (MON65500)+Tx, N-(1-cyano-1,2-dimethylpropyl)-2-(2,4-dichlorophenoxy)-propionamide (AC382042)+Tx, N-(2-methoxy-5-pyridyl)-cyclopropane carboxamide+Tx, acibenzolar (CGA245704) (e.g. acibenzolar-S-methyl)+Tx, alanycarb+Tx, aldimorph+Tx, anilazine+Tx, azaconazole+Tx, azoxystrobin+Tx, benalaxyl+Tx, benomyl+Tx, benthiavalicarb+Tx, biloxazol+Tx, bitertanol+Tx, bixafen+Tx, blasticidin S+Tx, boscalid+Tx, bromuconazole+Tx, bupirimate+Tx, captafol+Tx, captan+Tx, carbendazim+Tx, carbendazim+Tx, chlorhydrate+Tx, carboxin+Tx, carpropamid+Tx, carvone+Tx, CGA41396+Tx, CGA41397+Tx, chinomethionate+Tx, chlorothalonil+Tx, chlorozolinate+Tx, clozylacon+Tx, copper containing compounds to give combinations such as copper oxychloride+Tx, copper oxyquinolate+Tx, copper sulfate+Tx, copper tallate+Tx and Bordeaux mixture+Tx, cyclufenamid+Tx, cymoxanil+Tx, cyproconazole+Tx, cyprodinil+Tx, debacarb+Tx, di-2-pyridyl disulfide 1,1'-dioxide+Tx, dichlofluanid+Tx, diclomezine+Tx, dicloran+Tx, diethofencarb+Tx, difenoconazole+Tx, difenzoquat+Tx, diflumetorim+Tx, O,O-di-iso-propyl-5-benzyl thiophosphate+Tx, dimefluazole+Tx, dimetconazole+Tx, dimethomorph+Tx, dimethirimol+Tx, diniconazole+Tx, dinocap+Tx, dithianon+Tx, dodecyl dimethyl ammonium chloride+Tx, dodemorph+Tx, dodine+Tx, doguadine+Tx, edifenphos+Tx, epoxiconazole+Tx, ethirimo+Tx 1, ethyl-(Z)—N-benzyl-N-([methyl(methyl-thioethylideneaminooxycarbonyl)amino]thio)-β-alaninate+Tx, etridiazole+Tx, famoxadone+Tx, fenamidone (RPA407213)+Tx, fenarimol+Tx, fenbuconazole+Tx, fenfuram+Tx, fenhexamid (KBR2738)+Tx, fenpiclonil+Tx, fenpropidin+Tx, fenpropimorph+Tx, fentin acetate+Tx, fentin hydroxide+Tx, ferbam+Tx, ferimzone+Tx, fluazinam+Tx, fludioxonil+Tx, flumetover+Tx, fluopyram+Tx, fluoxastrobin+Tx, fluoroimide+Tx, fluquinconazole+Tx, flusilazole+Tx, flutolanil+Tx, flutriafol+Tx, fluxapyroxad+Tx, folpet+Tx, fuberidazole+Tx, furalaxyl+Tx, furametpyr+Tx, guazatine, +Tx hexaconazole+Tx, hydroxyisoxazole+Tx, hymexazole+Tx, imazalil+Tx, imibenconazole+Tx, iminoctadine+Tx, iminoctadine triacetate+Tx, ipconazole+Tx, iprobenfos+Tx, iprodione+Tx, iprovalicarb (SZX0722)+Tx, isopropanyl butyl carbamate+Tx, isoprothiolane+Tx, isopyrazam+Tx, kasugamycin+Tx, kresoxim-methyl+Tx, LY186054+Tx, LY211795+Tx, LY248908+Tx, mancozeb+Tx, mandipropamid+Tx, maneb+Tx, mefenoxam+Tx, metalaxyl+Tx, mepanipyrim+Tx, mepronil+Tx, metalaxyl+Tx, metconazole+Tx, metiram+Tx, metiram-zinc+Tx, metominostrobin+Tx, myclobutanil+Tx, neoasozin+Tx, nickel dimethyldithiocarbamate+Tx, nitrothal-isopropyl+Tx, nuarimol+Tx, ofurace+Tx, organomercury compounds, +Tx oxadixyl+Tx, oxasulfuron+Tx, oxolinic acid+Tx, oxpoconazole+Tx, oxycarboxin+Tx, pefurazoate+Tx, penconazole+Tx, pencycuron+Tx, penflufen+Tx, penthiopyrad+Tx, phenazin oxide+Tx, phosetyl-Al+Tx, phosphorus acids+Tx, phthalide+Tx, picoxystrobin (ZA1963)+Tx, polyoxinD+Tx, polyram+Tx, probenazole+Tx, prochloraz+Tx, procymidone+Tx, propamocarb+Tx, propiconazole+Tx, propineb+Tx, propionic acid+Tx, prothioconazole+Tx, pyrazophos+Tx, pyrifenox+Tx, pyrimethanil+Tx, pyraclostrobin+Tx, pyroquilon+Tx, pyroxyfur+Tx, pyrroInitrin+Tx, quaternary ammonium compounds+Tx, quinomethionate+Tx, quinoxyfen+Tx, quintozene+Tx, sedaxane+Tx, sipconazole (F-155)+ Tx, sodium pentachlorophenate+Tx, spiroxamine+Tx, streptomycin+Tx, sulfur+Tx, tebuconazole+Tx, tecloftalam+Tx, tecnazene+Tx, tetraconazole+Tx, thiabendazole+Tx, thifluzamid+Tx, 2-(thiocyanomethylthio)benzothiazole+Tx, thiophanate-methyl+Tx, thiram+Tx, timibenconazole+Tx, tolclofos-methyl+Tx, tolylfluanid+Tx, triadimefon+Tx, triadimenol+Tx, triazbutil+Tx, triazoxide+Tx, tricyclazole+ Tx, tridemorph+Tx, trifloxystrobin (CGA279202)+Tx, triforine+Tx, triflumizole+Tx, triticonazole+Tx, validamycin A+Tx, vapam+Tx, vinclozolin+Tx, zineb+Tx and ziram+Tx, N-[9-(dichloromethylene)-1,2,3,4-tetrahydro-1,4-methanonaphthalen-5-yl]-3-(difluoromethyl)-1-methyl-1H-pyrazole-4-carboxamide [1072957-71-1]+Tx, 1-methyl-3-difluoromethyl-1H-pyrazole-4-carboxylic acid (2-dichloromethylene-3-ethyl-1-methyl-indan-4-yl)-amide+ Tx, and 1-methyl-3-difluoromethyl-4H-pyrazole-4-carboxylic acid [2-(2,4-dichloro-phenyl)-2-methoxy-1-methylethyl]-amide+Tx.

The active ingredients combinations described above comprising a compound selected of the invention, in particularly from Tables 1P to 90P and 1Q to 36Q and an active ingredient as described above are preferably combined in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

In addition, biological agents may be included in the composition of the invention e.g. *Bacillus* species such as *Bacillus firmus*+Tx, *Bacillus cereus*+Tx, *Bacillus subtilis*+Tx, and *Pasteuria* species such as *Pasteuria penetrans*+Tx and *Pasteuria nishizawae*+Tx. A suitable *Bacillus firmus* strain is strain CNCM I-1582 which is commercially available as BioNem™. A suitable *Bacillus cereus* strain is strain CNCM I-1562. Of both *Bacillus* strains more details can be found in U.S. Pat. No. 6,406,690. Other biological organisms that may be included in the compositions of the invention are bacteria such as *Streptomyces* spp. such as *S. avermitilis*, and fungi such as *Pochonia* spp. such as *P. chlamydosporia*+Tx. Also of interest are *Metarhizium* spp. such as *M. anisopliae*+Tx; *Pochonia* spp. such as *P. chlamydosporia*+Tx.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, Buprofezine pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp aizawai, kurstaki, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following (where "Tx" means a compound of formula (I), and in particular a compound selected from Tables 1P to 90P and 1Q to 36Q, which may result in a synergistic combination with the given active ingredient): imidacloprid+Tx, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, fipronil+Tx, ivermectin+Tx, omeprazole+Tx, tiamulin+Tx, benazepril+Tx, milbemycin+Tx, cyromazine+Tx, thiamethoxam+Tx, pyriprole+Tx, deltamethrin+Tx, cefquinome+Tx, florfenicol+Tx, buserelin+Tx, cefovecin+Tx, tulathromycin+Tx, ceftiour+Tx, selamectin+Tx, carprofen+Tx, metaflumizone+Tx, moxidectin+Tx, methoprene (including S-methoprene)+Tx, clorsulon+Tx, pyrantel+Tx, amitraz+Tx, triclabendazole+Tx, avermectin+Tx, abamectin+Tx, emamectin+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, fipronil+Tx, lufenuron+Tx, ecdysone+Tx or tebufenozide+Tx; more preferably, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx, pyrantel+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, lufenuron+Tx or ecdysone+Tx; even more preferably enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx or pyrantel+Tx.

Examples of ratios of the compound of formula I to any mixing partner described herein include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1 or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrates, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool), cultured fish, honeybees. By combating parasites, fatalities and performance reduction (in terms of meat, milk, wool, skins, eggs, etc.) are reduced, so that applying the compounds of the invention allows more economic and simple husbandry of animals.

By controlling these pests it is intended to reduce deaths and improve performance (in the case of meat, milk, wool, hides, eggs, honey and the like) and health of the host animal. Also, controlling parasites may help to prevent the transmittance of infectious agents, the term "controlling" referring to the veterinary field, meaning that the active compounds are effective in reducing the incidence of the respective parasite in an animal infected with such parasites to innocuous levels, e.g. the active compound is effective in killing the respective parasite, inhibiting its growth, or inhibiting its proliferation.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc. and protozoae, such as coccidia).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria.*

Of the above, the most common genera of nematodes infecting the animals referred to above are *Haemonchus, Trichostrongylus, Ostertagia, Nematodirus, Cooperia,*

*Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6$^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites, e.g. insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like. These include e.g. flies such as *Haematobia* (Lyperosia) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (Damalinia) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Examples of species of animal health pesets include those from the order of the Anoplurida, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus*; from the order of the Mallophagida and the suborders *Amblycerina* and *Ischnocerina*, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi*; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti*, *Aedes albopictus*, *Aedes taeniorhynchus*, *Anopheles gambiae*, *Anopheles maculipennis*, *Calliphora erythrocephala*, *Chrysozona pluvialis*, *Culex quinquefasciatus*, *Culex pipiens*, *Culex tarsalis*, *Fannia canicularis*, *Sarcophaga carnaria*, *Stomoxys calcitrans*, *Tipula paludosa*, *Lucilia cuprina*, *Lucilia sericata*, *Simulium reptans*, *Phlebotomus papatasi*, *Phlebotomus longipalpis*, *Odagmia ornata*, *Wilhelmia equina*, *Boophthora erythrocephala*, *Tabanus bromius*, *Tabanus spodopterus*, *Tabanus atratus*, *Tabanus sudeticus*, *Hybomitra ciurea*, *Chrysops caecutiens*, *Chrysops relictus*, *Haematopota pluvialis*, *Haematopota italica*, *Musca autumnalis*, *Musca domestica*, *Haematobia irritans irritans*, *Haematobia irritans exigua*, *Haematobia stimulans*, *Hydrotaea irritans*, *Hydrotaea albipuncta*, *Chrysomya chloropyga*, *Chrysomya bezziana*, *Oestrus ovis*, *Hypoderma bovis*, *Hypoderma lineatum*, *Przhevalskiana silenus*, *Dermatobia hominis*, *Melophagus ovinus*, *Lipoptena capreoli*, *Lipoptena cervi*, *Hippobosca variegata*, *Hippobosca equina*, *Gasterophilus intestinalis*, *Gasterophilus haemorroidalis*, *Gasterophilus inermis*, *Gasterophilus nasalis*, *Gasterophilus nigricornis*, *Gasterophilus pecorum*, *Braula coeca*; from the order of the Siphonapterida, for example *Pulex* spp., *Ctenocephalides* spp., *Tunga* spp., *Xenopsylla* spp., *Ceratophyllus* spp.; particular examples are: *Ctenocephalides canis*, *Ctenocephalides felis*, *Pulex irritans*, *Tunga penetrans*, *Xenopsylla cheopis*; from the order of the Heteropterida, for example *Cimex* spp., *Triatoma* spp., *Rhodnius* spp., *Panstrongylus* spp; from the order of the Blattarida, for example *Blatta orientalis*, *Periplaneta americana*, *Blattela germanica*, *Supella* spp. (e.g. *Suppella longipalpa*); from the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus* (Boophilus) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus*, *Argas reflexus*, *Ornithodorus moubata*, *Otobius megnini*, *Rhipicephalus* (Boophilus) *microplus*, *Rhipicephalus* (Boophilus) *decoloratus*, *Rhipicephalus* (Boophilus) *annulatus*, *Rhipicephalus* (Boophilus) *calceratus*, *Hyalomma anatolicum*, *Hyalomma aegypticum*, *Hyalomma marginatum*, *Hyalomma transiens*, *Rhipicephalus evertsi*, *Ixodes ricinus*, *Ixodes hexagonus*, *Ixodes canisuga*, *Ixodes pilosus*, *Ixodes rubicundus*, *Ixodes scapularis*, *Ixodes holocyclus*, *Haemaphysalis concinna*, *Haemaphysalis punctata*, *Haemaphysalis cinnabarina*, *Haemaphysalis otophila*, *Haemaphysalis leachi*, *Haemaphysalis longicorni*, *Dermacentor marginatus*, *Dermacentor reticulatus*, *Dermacentor pictus*, *Dermacentor albipictus*, *Dermacentor andersoni*, *Dermacentor variabilis*, *Hyalomma mauritanicum*, *Rhipicephalus sanguineus*, *Rhipicephalus bursa*, *Rhipicephalus appendiculatus*, *Rhipicephalus capensis*, *Rhipicephalus turanicus*, *Rhipicephalus zambeziensis*, *Amblyomma americanum*, *Amblyomma variegatum*, *Amblyomma maculatum*, *Amblyomma hebraeum*, *Amblyomma cajennense*, *Dermanyssus gallinae*, *Ornithonyssus bursa*, *Ornithonyssus sylviarum*, *Varroa jacobsoni*; from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri*, *Cheyletiella blakei*, *Demodex canis*, *Demodex bovis*, *Demodex ovis*, *Demodex caprae*, *Demodex equi*, *Demodex caballi*, *Demodex suis*, *Neotrombicula autumnalis*, *Neotrombicula desaleri*, *Neoschongastia xerothermobia*, *Trombicula akamushi*, *Otodectes cynotis*, *Notoedres cati*, *Sarcoptis canis*, *Sarcoptes bovis*, *Sarcoptes ovis*, *Sarcoptes rupicaprae* (*S. caprae*), *Sarcoptes equi*, *Sarcoptes suis*, *Psoroptes ovis*, *Psoroptes cuniculi*, *Psoroptes equi*, *Chorioptes bovis*, *Psoergates ovis*, *Pneumonyssoidic mange*, *Pneumonyssoides caninum*, *Acarapis woodi*; *Gasterophilus* spp., *Stomoxys* spp., *Trichodectes* spp., *Rhodnius* spp., *Ctenocephalides canis*, *Cimx lecturius*, *Ctenocephalides felis*, *Lucilia cuprina*; examples of acari include *Ornithodoros* spp., *Ixodes* spp., *Boophilus* spp.

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration; or by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection. The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry.

These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such as BHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly administration intervals (i.e. administering the compounds to the animal once every month).

The following Examples illustrate, but do not limit, the invention.

The following abbreviations were used in this section: DMF: dimethylformamide; THF: tetrahydrofuran; EtOAc: ethyl acetate; s=singlet; bs=broad singlet; d=doublet; dd=double doublet; dt=double triplet; t=triplet; tt=triple triplet, q=quartet, sept=septet; m=multiplet; Me=methyl; Et=ethyl; Pr=propyl; Bu=butyl; M.p.=melting point; RT=retention time, [M+H]$^+$=molecular mass of the molecular cation, [M−H]$^-$=molecular mass of the molecular anion.

The following abbreviations were used throughout this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; RT=retention time; MH$^+$=molecular cation.

The invention is now described by way of non-limiting Examples.

PREPARATION EXAMPLES

The following preparation examples describe synthesis of compounds of formula I and intermediates thereof.

Example 1

Preparation of tert-butyl 2-methyl-4-(2-oxo-1,3,4-oxathiazol-5-yl)benzoate

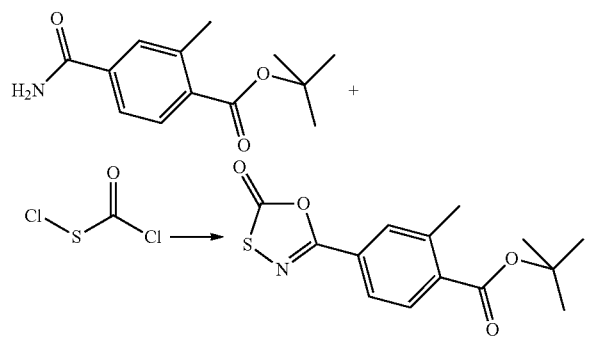

To a stirring solution of tert-butyl 4-carbamoyl-2-methyl-benzoate (10 g) in mixture of Toluene and Dioxane (3:1, 240 mL) was added potassium carbonate (5.88 g) then chlorocarbonylsulfenyl chloride (5.5 mL). The mixture was heated at 100° C. for 2 hours. The reaction mixture was allowed to cool to room temperature, filtered and the filtrate was evaporated under vacuo. The residue was purified by chromatography on silica gel (eluent: cyclohexane/ethyl acetate) to give tert-butyl 2-methyl-4-(2-oxo-1,3,4-oxathiazol-5-yl)benzoate (11.12 g) as a solid. $^1$H-NMR (CDCl$_3$, 400 MHz): δ=7.87-7.96 (m, 1 H), 7.79-7.87 (m, 2 H), 2.63 (s, 3 H), 1.56-1.64 ppm (m, 9 H).

Example 2

Preparation of tert-butyl 4-[5-(3,5-dichlorophenyl)-5-(trifluoromethyl)-4H-isothiazol-3-yl]-2-methyl-benzoate

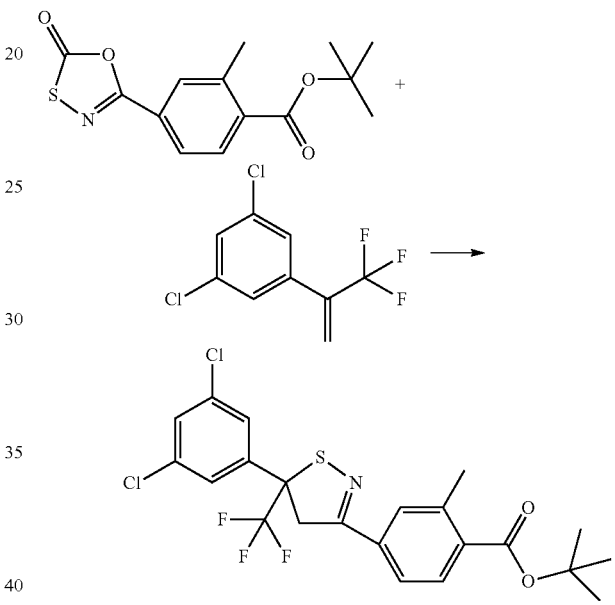

A solution of tert-butyl 2-methyl-4-(2-oxo-1,3,4-oxathiazol-5-yl)benzoate (50 mg) in 1,3-dichloro-5-[1-(trifluoromethyl)vinyl]benzene (5 mL, prepared according to WO 2005085216) was heated 190° C. during 10 minutes in a microwave. The residue was purified by chromatography on silica gel (eluent: cyclohexane/ethyl acetate) then on preparative HPLC to give tert-butyl 4-[5-(3,5-dichlorophenyl)-5-(trifluoromethyl)-4H-isothiazol-3-yl]-2-methyl-benzoate (18.5 mg) as a solid. $^1$H-NMR (CDCl$_3$, 400 MHz): δ=7.86 (d, 1 H), 7.54-7.64 (m, 2 H), 7.41 (t, 1 H), 7.31 (s, 2 H), 4.23 (d, 1 H), 3.88 (d, 1 H), 2.61 (s, 3 H), 1.61 ppm (s, 9 H).

Example 3

Preparation of 4-[5-(3,5-dichlorophenyl)-5-(trifluoromethyl)-4H-isothiazol-3-yl]-2-methyl-benzoic acid

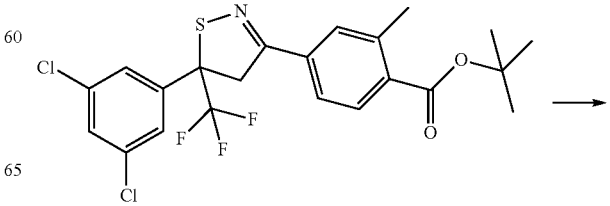

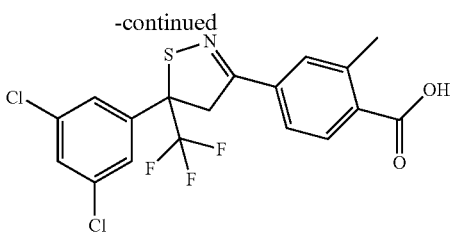

To a solution of tert-butyl 4-[5-(3,5-dichlorophenyl)-5-(trifluoromethyl)-4H-isothiazol-3-yl]-2-methyl-benzoate (164 mg) in dichloromethane (1.7 mL) was added trifluoroacetic acid (0.17 mL). The reaction mixture was stirred at room temperature for 6 hours then the solution was concentrated under vacuo. The residue was extracted with water and ethyl acetate. The organic extract was washed with water, dried over sodium sulfate and concentrated to give 4-[5-(3,5-dichlorophenyl)-5-(trifluoromethyl)-4H-isothiazol-3-yl]-2-methyl-benzoic acid (140 mg) as a white foam.

$^1$H-NMR (CDCl$_3$, 400 MHz): δ=8.11 (d, 1 H), 7.59-7.71 (m, 2 H), 7.42 (t, 1 H), 7.30-7.34 (m, 2 H), 4.25 (d, 1 H), 3.90 (d, 1 H), 2.71 ppm (s, 3 H).

Example 4

Preparation of 3-Benzylsulfanyl-1-(4-bromo-3-methyl-phenyl)-3-(3,5-dichloro-phenyl)-4,4,4-trifluoro-butan-1-one

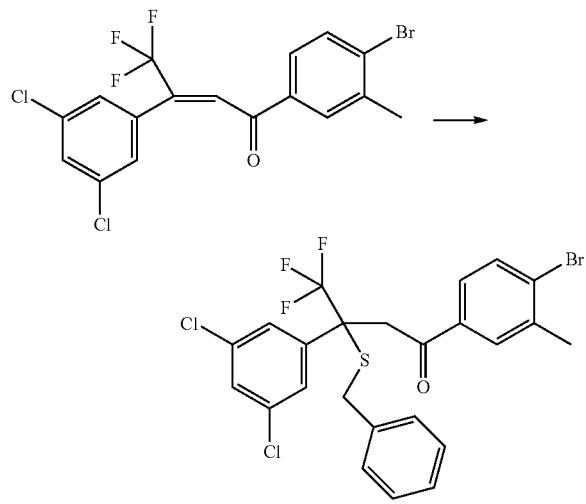

Benzylmercaptan (0.18 g) and a solution of sodium hydroxide (0.1 eq) were added to a solution of (E)-1-(4-Bromo-3-methyl-phenyl)-3-(3,5-dichloro-phenyl)-4,4,4-trifluoro-but-2-en-1-one (0.5 g) in tetrahydrofurane (11.4 mL). The solution was stirred at room temperature for 19 hours then heated at 80° C. for 4 hours. Then, more benzylmercaptan (0.5 mL) was added and the solution was stirred at 80° C. for 16 hours. More sodium hydroxide (20 mg) was added and after 90 minutes, the reaction was quenched by the addition of a saturated solution of sodium chloride, and then extracted with diethyl ether. The collected organic phases were dried over magnesium sulfate, filtered and the filtrate was evaporated under vacuo. The residue was purified by chromatography on silica gel (eluent: cyclohexane/ethyl acetate) to give 3-Benzylsulfanyl-1-(4-bromo-3-methyl-phenyl)-3-(3,5-dichloro-phenyl)-4,4,4-trifluoro-butan-1-one (276 mg).

$^1$H NMR (CDCl$_3$, 400 MHz): δ=7.65 (d, J=1.8 Hz, 1 H), 7.61 (d, J=8.1 Hz, 1 H), 7.52-7.55 (m, 2 H), 7.48 (dd, J=8.3, 2.0 Hz, 1 H), 7.34 (t, J=1.8 Hz, 1 H), 7.17-7.26 (m, 5 H), 3.87-3.94 (m, 1 H), 3.85 (d, J=11.7 Hz, 1 H), 3.69-3.79 (m, 1 H), 3.63 (d, J=11.4 Hz, 1 H), 2.44 (s, 3 H). $^{19}$F NMR (CDCl$_3$, 376 MHz): δ=−67.33 ppm Example 5

Preparation of tert-butyl 4-[3-benzylsulfanyl-3-(3,5-dichlorophenyl)-4,4,4-trifluoro-butanoyl]-2-methyl-benzoate

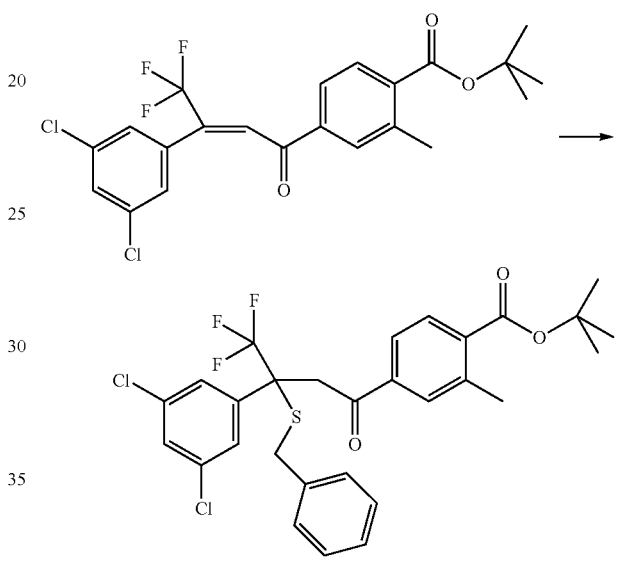

Benzylmercaptan (1.5 eq.) and 1-[3,5-bis(trifluoromethyl)phenyl]-3-[(1R,2R)-2-(dimethylamino)cyclohexyl]thiourea (0.01 eq.) were added to a solution of tert-butyl 4-[(E)-3-(3,5-dichlorophenyl)-4,4,4-trifluoro-but-2-enoyl]-2-methyl-benzoate (200 mg) in toluene (1.5 mL) at −40° C. The solution was stirred at −40° C. for 6 hours then at room temperature for 17 hours. The reaction was quenched by the addition of a saturated solution of sodium chloride, and then extracted with ethylacetate. The collected organic phases were dried over magnesium sulfate, filtered and the filtrate was evaporated under vacuo. The residue was purified by chromatography on silica gel (eluent: cyclohexane/ethyl acetate) to give tert-butyl 4-[3-benzylsulfanyl-3-(3,5-dichlorophenyl)-4,4,4-trifluoro-butanoyl]-2-methyl-benzoate (205 mg) as a mixture of two enantiomers.

Chiral HPLC analysis using a Waters UPLC—Hclass, DAD Detector Waters UPLC.
Column: Daicel CHIRALPAK® IB, 3 μm, 0.46 cm×10 cm
Mobile phase: Heptane/iPrOH 95/05
Flow rate: 1.0 ml/min
Detection: 254 nm
Sample concentration: 1 mg/mL in Hept/iPrOH 70/30
Injection: 4 μL
1$^{st}$ eluting isomer: rt=2.43 min, 14%
2$^{nd}$ eluting isomer: rt=2.95 min, 85%

$^1$H NMR (CHLOROFORM-d, 400 MHz): δ=7.83 (d, J=8.1 Hz, 1 H), 7.59-7.69 (m, 2 H), 7.51-7.57 (m, 2 H), 7.34 (t, J=1.8 Hz, 1 H), 7.14-7.29 (m, 5 H), 3.94 (d, J=16.9 Hz, 1

H), 3.84 (d, J=11.7 Hz, 1 H), 3.73-3.81 (m, 1 H), 3.64 (d, J=11.7 Hz, 1 H), 2.59 (s, 3 H), 1.61 ppm (s, 9 H).

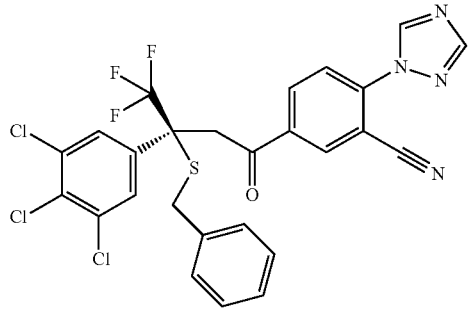 [SMILES: N#Cc1cc(C(=O)C[C@](SCc2ccccc2)(c2cc(Cl)c(Cl)c(Cl)c2)C(F)(F)F)ccc1-n1cncn1]

Similarly, 5-[(3S)-3-benzylsulfanyl-4,4,4-trifluoro-3-(3,4,5-trichlorophenyl)butanoyl]-2-(1,2,4-triazol-1-yl)benzonitrile could be prepared.

$^1$H NMR (CDCl$_3$, 400 MHz): δ=8.96 (s, 1 H), 8.23 (s, 1 H), 8.11-8.18 (m, 2 H), 7.95 (d, J=8.8 Hz, 1 H), 7.65 (s, 2 H), 7.15-7.26 (m, 5 H), 3.93 (d, J=12.5 Hz, 1 H), 3.89 (d, J=17.2 Hz, 1 H), 3.74 (d, J=16.9 Hz, 1 H), 3.69 ppm (d, J=12.5 Hz, 1 H)

19H NMR (CDCl$_3$, 376 MHz): δ=−67.03

Chiral HPLC analysis using a Waters UPLC (Alliance 2695)—Hclass, DAD Detector Waters UPLC (996).

Column: Daicel CHIRALPAK® IA, 3 µm, 0.46 cm×10 cm
Mobile phase: TBME/EtOH 98/02
Flow rate: 1 ml/min
Detection: 254 nm
Sample concentration: 1 mg/mL in TBM
Injection: 2 µL
1$^{st}$ eluting isomer: rt=2.52 min; 80.5%
2$^{nd}$ eluting isomer: rt=3.24 min; 19.5%

Example 6

Preparation of 1-(4-bromo-3-methyl-phenyl)-3-(3,5-dichlorophenyl)-4,4,4-trifluoro-3-sulfanyl-butan-1-one

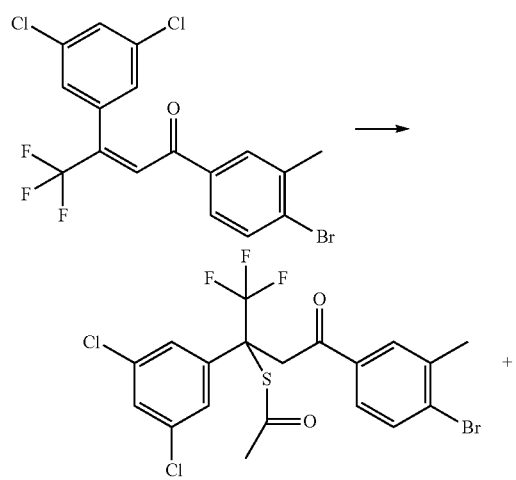

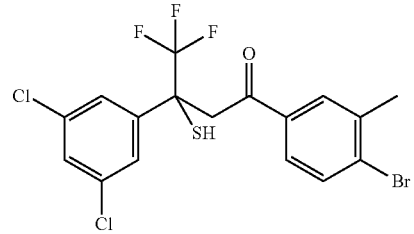

To (E)-1-(4-Bromo-3-methyl-phenyl)-3-(3,5-dichlorophenyl)-4,4,4-trifluoro-but-2-en-1-one (2 g) was added thioacetic acid (6 eq.) under argon. The solution was stirred at room temperature then 2 drops of triethylamine were added. The solution was stirred at room temperature for 4 days.

The mixture was then diluted with ethyl acetate, washed with brine, then water. The collected organic phases were dried over magnesium sulfate, filtered and the filtrate was evaporated under vacuo. The residue was purified by chromatography on silica gel (eluent: cyclohexane/dichloromethane) to give 1-(4-Bromo-3-methyl-phenyl)-3-(3,5-dichloro-phenyl)-4,4,4-trifluoro-3-mercapto-butan-1-one (382 mg).

$^1$H NMR (CDCl$_3$, 400 MHz): δ=7.77 (d, J=2.2 Hz, 1 H), 7.68 (d, J=8.4 Hz, 1 H), 7.58-7.63 (m, 1 H), 7.51-7.58 (m, 2 H), 7.35 (t, J=1.8 Hz, 1 H), 4.27 (d, J=18.7 Hz, 1 H), 3.94 (d, J=18.3 Hz, 1 H), 3.29 (s, 1H), 2.48 ppm (s, 3 H). $^{19}$F NMR (CDCl$_3$, 376 MHz): δ=−73.56 ppm Another fraction contained Thioacetic acid 3-(4-bromo-3-methyl-phenyl)-1-(3,5-dichloro-phenyl)-3-oxo-1-trifluoromethyl-propyl ester (782 mg). $^1$H NMR (CDCl$_3$, 400 MHz): δ=7.78-7.84 (m, 1 H), 7.62-7.69 (m, 2 H), 7.37 (s, 3 H), 5.16 (d, J=18.0 Hz, 1 H), 3.96 (d, J=18.3 Hz, 1 H), 2.48 (s, 3 H), 2.32 ppm (s, 3 H). $^{19}$F NMR (CDCl$_3$, 376 MHz): δ=−71.26 ppm Example 7

Preparation of 3-(4-Bromo-3-methyl-phenyl)-5-(3,5-dichloro-phenyl)-5-trifluoromethyl-4,5-dihydro-isothiazole

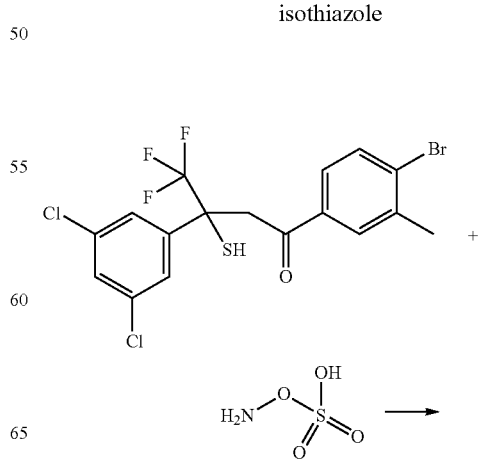

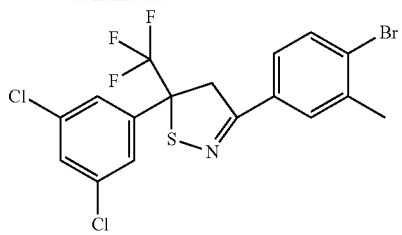

To a solution of 1-(4-Bromo-3-methyl-phenyl)-3-(3,5-dichloro-phenyl)-4,4,4-trifluoro-3-mercapto-butan-1-one (382 mg) in a solution of potassium hydroxide (162 mg in 8 mL of water) was added a solution of Hydroxylamine-O-sulfonic acid (2 equiv.) in a solution of potassium hydroxide (243 mg in 16 mL of water). After stirring at room temperature for 30 minutes, the mixture was diluted with ethyl acetate, and washed with brine. The collected organic phases were dried over magnesium sulfate, filtered and the filtrate was evaporated under vacuo. The residue was purified by chromatography on silica gel (eluent: cyclohexane/dichloromethane) to give 3-(4-Bromo-3-methyl-phenyl)-5-(3,5-dichloro-phenyl)-5-trifluoromethyl-4,5-dihydro-isothiazole (184 mg).

$^1$H NMR (CDCl$_3$, 400 MHz): δ=7.64 (d, J=1.8 Hz, 1 H), 7.60 (d, J=8.4 Hz, 1 H), 7.39-7.44 (m, 2 H), 7.28-7.33 (m, 2 H), 4.19 (d, J=17.6 Hz, 1 H), 3.86 (d, J=17.6 Hz, 1 H), 2.46 ppm (s, 3 H). $^{19}$F NMR (CDCl$_3$, 376 MHz): δ=−74.76 ppm

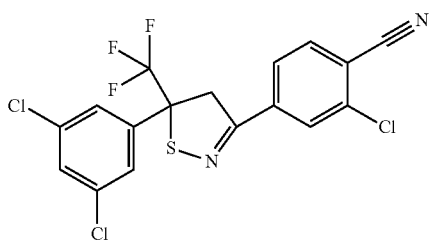 [SMILES: N#Cc1ccc(C2=NSC(c3cc(Cl)cc(Cl)c3)(C(F)(F)F)C2)cc1Cl]

Using the same sequence, 2-chloro-4-[5-(3,5-dichlorophenyl)-5-(trifluoromethyl)-4H-isothiazol-3-yl]benzonitrile could be obtained, starting from 2-chloro-4-[3-(3,5-dichlorophenyl)-4,4,4-trifluoro-but-2-enoyl]benzonitrile:

$^1$H NMR (CDCl$_3$, 400 MHz): δ=7.90 (t, J=0.9 Hz, 1 H), 7.74 (d, J=0.7 Hz, 2 H), 7.43 (t, J=1.8 Hz, 1 H), 7.29 (d, J=1.1 Hz, 2 H), 4.19 (d, J=17.6 Hz, 1 H), 3.86 (d, J=18.0 Hz, 1 H) ppm.

Example 8

Preparation of 4-[3-(3,5-Dichloro-phenyl)-4,4,4-trifluoro-3-mercapto-butyryl]-2-methyl-benzoic acid tert-butyl ester

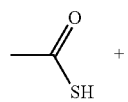 +

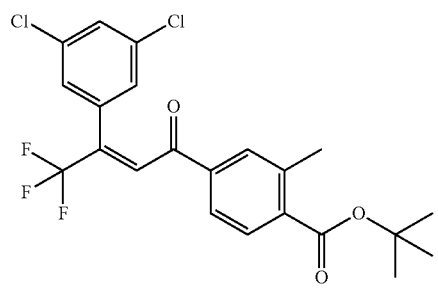

To 4-[(E)-3-(3,5-Dichloro-phenyl)-4,4,4-trifluoro-but-2-enoyl]-2-methyl-benzoic acid tert-butyl ester (25 g) was added thioacetic acid (6 eq.) and triethylamine (200 μL) The solution was stirred at room temperature 2 drops of triethylamine were added. After stirring at room temperature for 24 hours, the mixture was poured in a mixture of water and ethyl acetate, extracted with ethyl acetate and washed with brine. The collected organic phases were dried over magnesium sulfate, filtered and the filtrate was evaporated under vacuo. The residue was purified by chromatography on silica gel (eluent: cyclohexane/dichloromethane) to give 4-[3-(3,5-Dichloro-phenyl)-4,4,4-trifluoro-3-mercapto-butyryl]-2-methyl-benzoic acid tert-butyl ester (3.78 g) $^1$H NMR (CDCl$_3$, 400 MHz): δ=7.89 (d, J=8.8 Hz, 1 H), 7.72-7.79 (m, 2 H), 7.53-7.57 (m, 2 H), 7.35 (t, J=1.8 Hz, 1 H), 4.30 (d, J=18.3 Hz, 1 H), 3.97 (d, J=18.3 Hz, 1 H), 3.30 (s, 1 H), 2.59-2.65 (m, 3 H), 1.58-1.66 (m, 10 H), 1.56 ppm (s, 1 H).

$^{19}$F NMR (CDCl$_3$, 376 MHz): δ=−73.58 ppm.

Another collected fractions contained 4-[3-Acetylsulfanyl-3-(3,5-dichloro-phenyl)-4,4,4-trifluoro-butyryl]-2-methyl-benzoic acid tert-butyl ester (12.51 g).

$^1$H NMR (CDCl$_3$, 400 MHz): δ=7.84-7.91 (m, 1 H), 7.77-7.84 (m, 2 H), 7.38 (s, 3 H), 5.20 (d, J=18.3 Hz, 1 H), 4.00 (d, J=18.3 Hz, 1 H), 2.63 (s, 3 H), 2.28-2.36 (m, 3 H), 1.62 ppm (s, 9 H). $^{19}$F NMR (CDCl$_3$, 376 MHz): δ=−71.25 ppm

Example 9

Preparation of 4-[5-(3,5-Dichloro-phenyl)-5-trifluoromethyl-4,5-dihydro-isothiazol-3-yl]-2-methyl-benzoic acid tert-butyl ester

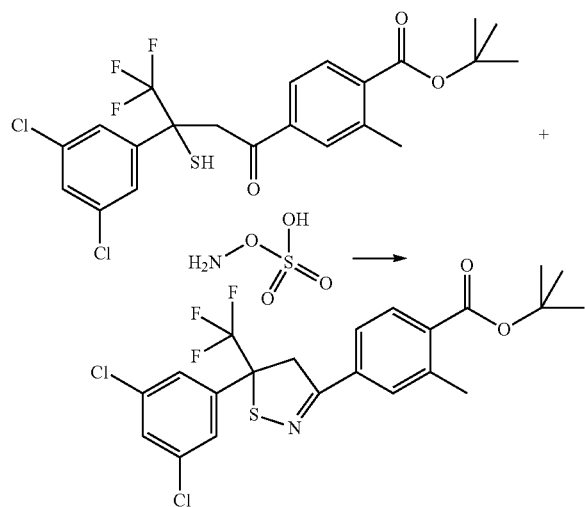

To a solution of 4-[3-(3,5-Dichloro-phenyl)-4,4,4-trifluoro-3-mercapto-butyryl]-2-methyl-benzoic acid tert-butyl ester (1.875 g) in tetrahydrofuran (6 mL) was added a solution of Hydroxylamine-O-sulfonic acid (2 equiv.) in a solution of potassium hydroxide (1.2 g in 75 mL of water). After stirring at room temperature for 30 minutes, the mixture was quenched with a solution of hydrochloric acid (1N), extracted with ethyl acetate and washed with brine. The collected organic phases were dried over magnesium sulfate, filtered and the filtrate was evaporated under vacuo. The residue was purified by chromatography on silica gel (eluent: cyclohexane/dichloromethane) to give 4-[5-(3,5-Dichloro-phenyl)-5-trifluoromethyl-4,5-dihydro-isothiazol-3-yl]-2-methyl-benzoic acid tert-butyl ester (881 mg)

$^1$H NMR (CDCl$_3$, 400 MHz): δ=7.86 (d, J=8.4 Hz, 1 H), 7.56-7.63 (m, 2 H), 7.41 (t, J=1.8 Hz, 1 H), 7.29-7.33 (m, 2 H), 4.22 (d, J=17.6 Hz, 1 H), 3.88 (d, J=18.0 Hz, 1 H), 2.62 (s, 3 H), 1.62 ppm (s, 10 H).

$^{19}$F NMR (CDCl$_3$, 376 MHz): δ=−74.73 ppm

Example 10

Preparation of 4-[5-(3,5-Dichloro-phenyl)-5-trifluoromethyl-4,5-dihydro-isothiazol-3-yl]-2-methyl-benzoic acid butyl ester

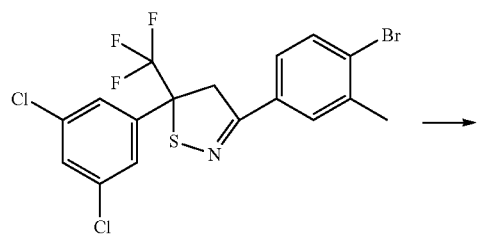

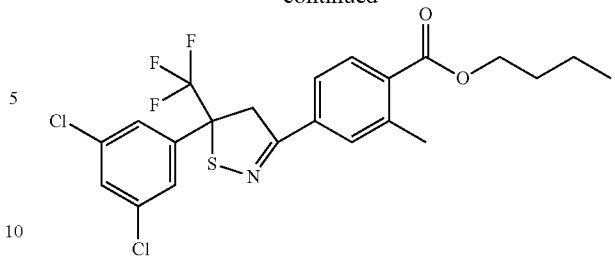

To a solution of 3-(4-Bromo-3-methyl-phenyl)-5-(3,5-dichloro-phenyl)-5-trifluoromethyl-4,5-dihydro-isothiazole (166 mg) in n-butanol (3 mL) was added palladium acetate (0.1 equiv.), butyl-1-adamantylphosphincataxium (0.3 equiv.) then tetramethylethylenediamine (TMEDA) (1 equiv.). The reactor was sealed and a carbon monoxide pressure (5 bars) was applied to the mixture. The reaction was stirred at 110° C. for 18 hours. The mixture was then filtered and the filtrate was evaporated under vacuo. The residue was purified by chromatography on silica gel (eluent: cyclohexane/ethyl acetate) to give 4-[5-(3,5-Dichloro-phenyl)-5-trifluoromethyl-4,5-dihydro-isothiazol-3-yl]-2-methyl-benzoic acid butyl ester (62 mg).

$^1$H NMR (CDCl$_3$, 400 MHz): δ=7.96 (d, J=8.1 Hz, 1 H), 7.59-7.64 (m, 2 H), 7.42 (t, J=1.8 Hz, 1 H), 7.31 (d, J=0.7 Hz, 2 H), 4.33 (t, J=6.6 Hz, 2 H), 4.23 (d, J=17.6 Hz, 1 H), 3.89 (d, J=17.6 Hz, 1 H), 2.65 (s, 3 H), 1.71-1.81 (m, 2 H), 1.35-1.63 (m, 2 H), 1.00 ppm (t, J=7.5 Hz, 3 H). $^{19}$F NMR (CDCl$_3$, 376 MHz): δ=−74.73 ppm

Example 11

Preparation of 4-[3-(3,5-Dichloro-phenyl)-4,4,4-trifluoro-3-mercapto-butyryl]-2-methyl-N-thietan-3-yl-benzamide

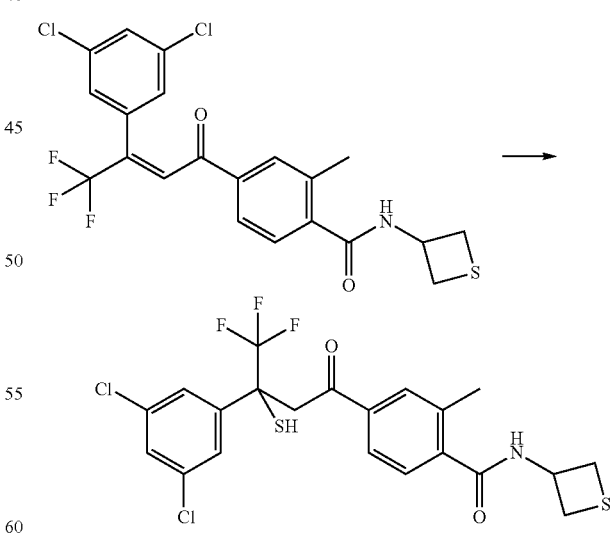

To 4-[(E)-3-(3,5-Dichloro-phenyl)-4,4,4-trifluoro-but-2-enoyl]-2-methyl-N-thietan-3-yl-benzamide (500 mg) was added thioacetic acid (6 eq.) and triethylamine (4 μL). The solution was stirred under argon at room temperature for 41 hours. To this mixture was added a minimum of dichloromethane and then isolute. The suspension was evaporated under vacuo. The residue was purified by chromatography on silica gel (eluent: cyclohexane/ethyl acetate) to give: 4-[3-(3,5-Dichloro-phenyl)-4,4,4-trifluoro-3-mercapto-butyryl]-2-methyl-N-thietan-3-yl-benzamide (493 mg).

¹H NMR (CDCl₃, 400 MHz): δ=7.69-7.81 (m, 2 H), 7.56 (s, 2 H), 7.44-7.51 (m, 1 H), 7.34-7.42 (m, 1H), 6.20 (d, J=8.1 Hz, 1 H), 5.44 (q, J=8.1 Hz, 1 H), 4.29 (d, J=18.3 Hz, 1 H), 3.96 (d, J=18.7 Hz, 1 H), 3.45-3.55 (m, 2 H), 3.35-3.45 (m, 2 H), 3.29 (s, 1 H), 2.51 ppm (s, 3 H) ¹⁹F NMR (CDCl₃, 376 MHz): δ=−73.55 ppm Example 12

Preparation of 2-Methyl-4-[4,4,4-trifluoro-3-mercapto-3-(3,4,5-trichloro-phenyl)-butyryl]-benzoic acid tert-butyl ester

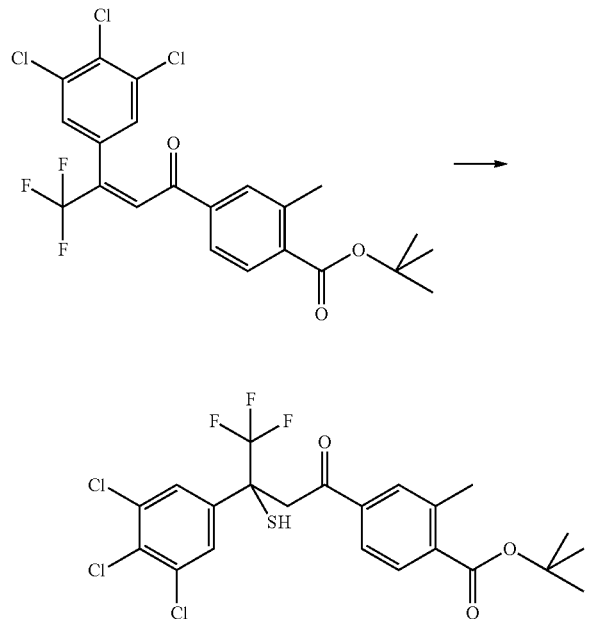

To 2-Methyl-4-[(E)-4,4,4-trifluoro-3-(3,4,5-trichloro-phenyl)-but-2-enoyl]-benzoic acid tert-butyl ester (1.29 g) was added thioacetic acid (6 eq.) and triethylamine (12 µL). The solution was stirred under argon at room temperature for 24 hours. More thioacetic acid (1 mL) and triethylamine (1 drop) were added and the solution was stirred under argon at room temperature for 72 hours. To this mixture was added a minimum of dichloromethane and then isolute. The suspension was evaporated under vacuo. The residue was purified by chromatography on silica gel (eluent: cyclohexane/dichloromethane) to give 2-Methyl-4-[4,4,4-trifluoro-3-mercapto-3-(3,4,5-trichloro-phenyl)-butyryl]-benzoic acid tert-butyl ester (573 mg).

¹H NMR (CDCl₃, 400 MHz): δ=7.89 (d, J=8.8 Hz, 1 H), 7.73-7.78 (m, 2 H), 7.69 (s, 2 H), 4.29 (d, J=18.3 Hz, 1 H), 3.99 (d, J=18.7 Hz, 1 H), 3.30 (s, 1 H), 2.63 (s, 3 H), 1.60-1.63 ppm (m, 9 H). ¹⁹F NMR (CDCl₃, 376 MHz): δ=−73.63 ppm Example 13

Preparation of 5-[3-(3,5-Dichloro-phenyl)-4,4,4-trifluoro-3-mercapto-butyryl]-2-[1,2,4]triazol-1-yl-benzonitrile

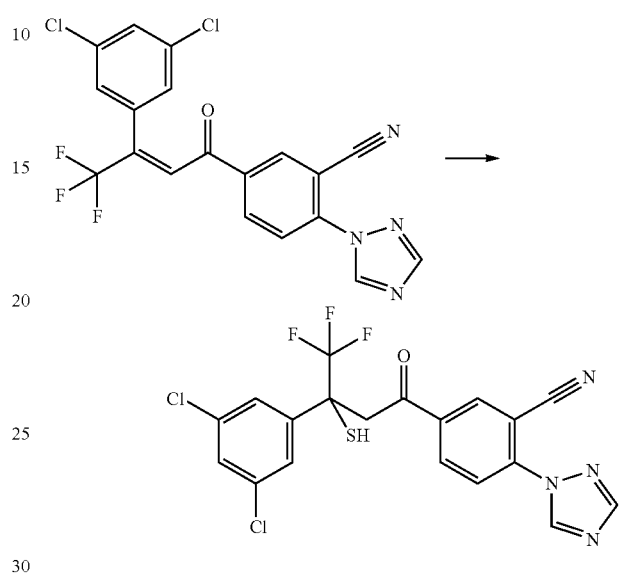

To 5-[(E)-3-(3,5-Dichloro-phenyl)-4,4,4-trifluoro-but-2-enoyl]-2-[1,2,4]triazol-1-yl-benzonitrile (100 mg) was added thioacetic acid (6 eq.) and triethylamine (4 µL). To dissolve the suspension more thioacetic acid (400 µL) was added. The solution was stirred under argon at room temperature for 20 hours. To this mixture was added a minimum of dichloromethane and then isolute. The suspension was evaporated under vacuo. The residue was purified by chromatography on silica gel (eluent: cyclohexane/dichloromethane) to give 5-[3-(3,5-Dichloro-phenyl)-4,4,4-trifluoro-3-mercapto-butyryl]-2-[1,2,4]triazol-1-yl-benzonitrile (108 mg).

¹H NMR (CDCl₃, 400 MHz): δ=8.99 (s, 1 H), 8.39 (d, J=1.8 Hz, 1 H), 8.30 (dd, J=8.8, 2.2 Hz, 1 H), 8.23-8.26 (m, 1 H), 8.05 (d, J=8.8 Hz, 1 H), 7.54-7.60 (m, 2 H), 7.37-7.41 (m, 1 H), 4.30 (d, J=18.3 Hz, 1H), 4.01 (d, J=18.3 Hz, 1 H), 3.22 ppm (s, 1 H). ¹⁹F NMR (CDCl₃, 376 MHz): δ=−73.52 ppm Example 14

Preparation of 4-[5-(3,5-Dichloro-phenyl)-5-trifluoromethyl-4,5-dihydro-isothiazol-3-yl]-2-methyl-N-thietan-3-yl-benzamide

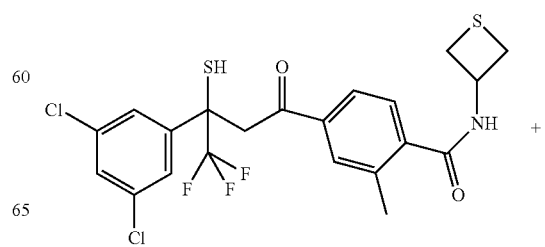

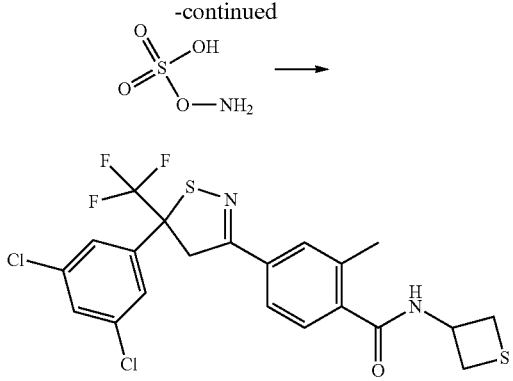

To a solution of 4-[3-(3,5-Dichloro-phenyl)-4,4,4-trifluoro-3-mercapto-butyryl]-2-methyl-N-thietan-3-yl-benzamide (493 mg) dissolved in a minimum amount of tetrahydrofuran then was added Hydroxylamine-O-sulfonic acid (2 equiv.). Then a solution of potassium hydroxide (5.6 equiv.) in water (19 mL) was added dropwise. After stirring at room temperature for 30 minutes, the mixture was quenched with a solution of hydrochloric acid (1N), extracted with ethyl acetate and washed with brine. The collected organic phases were dried over magnesium sulfate, filtered and the filtrate was evaporated under vacuo. The crude mixture was then redissolved in a minimum amount of tetrahydrofuran then was added Hydroxylamine-O-sulfonic acid (2 equiv.) Then a solution of potassium hydroxide (5.6 equiv.) in water (19 mL) was added dropwise. After stirring at room temperature for 30 minutes, the mixture was quenched with a solution of hydrochloric acid (1N), extracted with ethyl acetate and washed with brine. The collected organic phases were dried over magnesium sulfate, filtered and the filtrate was evaporated under vacuo. The residue was purified by chromatography on silica gel (eluent: cyclohexane/dichloromethane) to give 4-[5-(3,5-Dichloro-phenyl)-5-trifluoromethyl-4,5-dihydro-isothiazol-3-yl]-2-methyl-N-thietan-3-yl-benzamide (128 mg)

$^1$H NMR (CDCl$_3$, 400 MHz): δ=7.56-7.62 (m, 2 H), 7.37-7.43 (m, 2 H), 7.31 (s, 2 H), 6.30 (d, J=8.1 Hz, 1 H), 4.21 (d, J=17.6 Hz, 1 H), 3.87 (d, J=17.6 Hz, 1 H), 3.45-3.54 (m, 2 H), 3.36-3.44 (m, 2 H), 2.44-2.52 ppm (m, 3 H). $^{19}$F NMR (CDCl$_3$, 376 MHz): δ=−74.82 ppm Similarly, 5-[5-(3,5-dichlorophenyl)-5-(trifluoromethyl)-4,5-dihydro-isothiazol-3-yl]-2-(1,2,4-triazol-1-yl)benzonitrile (B1) can be obtained.

$^1$H NMR (CDCl$_3$, 400 MHz): δ=8.89 (s, 1 H), 8.18-8.24 (m, 2 H), 8.16 (dd, J=8.6, 2.0 Hz, 1 H), 7.92 (d, J=8.8 Hz, 1 H), 7.44 (t, J=1.8 Hz, 1 H), 7.31 (d, J=0.7 Hz, 2 H), 4.24 (d, J=17.6 Hz, 1 H), 3.92 ppm (d, J=17.6 Hz, 1 H). $^{19}$F NMR (CDCl$_3$, 376 MHz): δ=−74.88 ppm Similarly, tert-butyl 2-methyl-4-[5-(3,4,5-trichlorophenyl)-5-(trifluoromethyl)-4,5-dihydro-isothiazol-3-yl]benzoate can be obtained.

$^1$H NMR (CDCl$_3$, 400 MHz): δ=7.86 (d, J=8.4 Hz, 1 H), 7.54-7.63 (m, 2 H), 7.46 (s, 2 H), 4.22 (d, J=17.6 Hz, 1 H), 3.87 (d, J=17.6 Hz, 1 H), 2.61 (s, 3 H), 1.61 ppm (s, 9 H)

Example 15

Preparation of 2-Methyl-4-[4,4,4-trifluoro-3-mercapto-3-(3,4,5-trichloro-phenyl)-butyryl]-benzoic acid tert-butyl ester

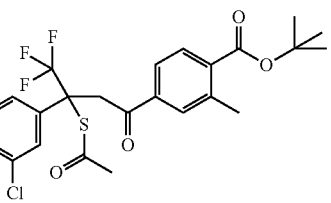

A solution of 4-[3-Acetylsulfanyl-4,4,4-trifluoro-3-(3,4,5-trichloro-phenyl)-butyryl]-2-methyl-benzoic acid tert-butyl ester (1.33 g) in aniline (13 mL) was stirred at room temperature for 3 hours. The mixture was quenched with a solution of hydrochloric acid (1N), extracted with ethyl acetate and washed with brine. The collected organic phases were dried over magnesium sulfate, filtered and the filtrate was evaporated under vacuo. The residue was purified by chromatography on silica gel (eluent: cyclohexane/dichloromethane) to give 2-Methyl-4-[4,4,4-trifluoro-3-mercapto-3-(3,4,5-trichloro-phenyl)-butyryl]-benzoic acid tert-butyl ester (950 mg).

$^1$H NMR (CDCl$_3$, 400 MHz): δ=7.89 (d, J=8.8 Hz, 1 H), 7.72-7.78 (m, 2 H), 7.69 (s, 2 H), 4.28 (d, J=18.7 Hz, 1 H), 3.98 (d, J=18.7 Hz, 1 H), 3.30 (s, 1 H), 2.63 (s, 3 H), 1.59-1.65 ppm (m, 9 H).

Example 16

Preparation of 2-chloro-4-[5-(3,5-dichlorophenyl)-5-(trifluoromethyl)-4H-isothiazol-3-yl]benzamide

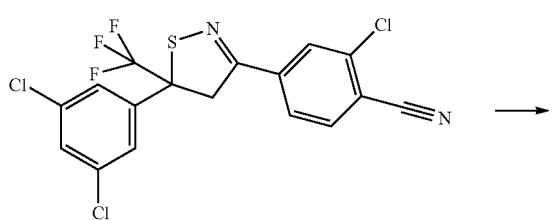

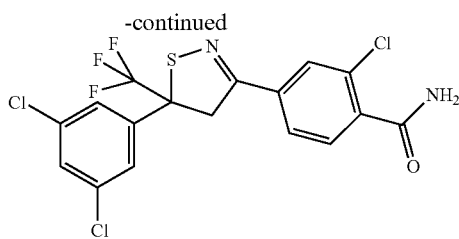

To a solution of 2-chloro-4-[5-(3,5-dichlorophenyl)-5-(trifluoromethyl)-4H-isothiazol-3-yl]benzonitrile (50 mg) in toluene (1 mL) were added acetaldehyde oxime (3 eq.) then indium trichloride (0.05 eq.). The mixture was stirred at 120° C. for 2 hours then it was allowed to cool to room temperature. The solution was diluted with ethyl acetate, then treated with ammonium hydroxide (2N). The mixture was washed two times with brine then the organic phase were collected and they were dried over magnesium sulfate, filtered and evaporated under vacuo to give 2-chloro-4-[5-(3,5-dichlorophenyl)-5-(trifluoromethyl)-4H-isothiazol-3-yl]benzamide (50 mg).

$^1$H NMR (CDCl$_3$, 400 MHz): δ=7.90 (d, J=8.1 Hz, 1 H), 7.84 (d, J=1.8 Hz, 1 H), 7.66-7.74 (m, 1 H), 7.37-7.46 (m, 1 H), 7.28-7.34 (m, 2 H), 6.40 (br. s., 1 H), 5.96 (br. s., 1 H), 4.19 (d, J=18.0 Hz, 1 H), 3.87 ppm (d, J=18.0 Hz, 1 H)

Example 17

Preparation of 2-chloro-4-[5-(3,5-dichlorophenyl)-5-(trifluoromethyl)-4H-isothiazol-3-yl]-N-[(E)-methoxyiminomethyl]benzamide (C3)

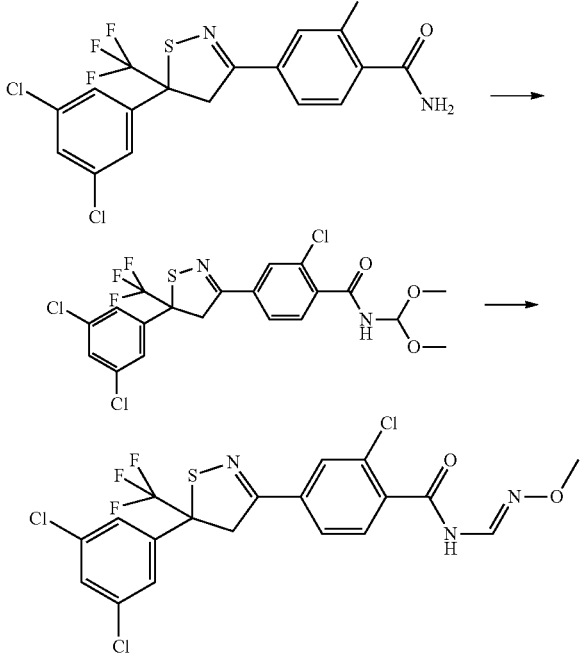

A solution of 2-chloro-4-[5-(3,5-dichlorophenyl)-5-(trifluoromethyl)-4H-isothiazol-3-yl]benzamide (50 mg) and N,N-Dimethylformamide dimethylacetal (1 mL) was refluxed under Argon for 30 min then the solution was concentrated in vacuo. The residue was dissolved in 1,4-dioxane (0.48 mL) and a solution of O-methylhydroxylamine hydrochloride (2.8 eq.) and sodium hydroxide (6 eq.) in water (0.43 mL) and acetic acid (0.43 mL) was added. The solution was stirred at rt for one hour. It was then quenched by addition of water and extracted with methyl tert-butyl ether. The combined organic extracts were washed with brine, dried over sodium sulfate and evaporated. Flash Chromatography eluting with Cyclohexane:EtOAc afforded 30 mg of the title compound.

$^1$H-NMR (CDCl$_3$, 400 MHz): δ=9.21 (d, J=9.5 Hz, 1 H), 7.93 (d, J=8.4 Hz, 1 H), 7.85-7.89 (m, 1 H), 7.81 (d, J=9.5 Hz, 1 H), 7.74 (dd, J=8.1, 1.5 Hz, 1 H), 7.43 (t, J=1.8 Hz, 1 H), 7.29-7.33 (m, 2 H), 4.20 (d, J=17.6 Hz, 1 H), 3.93 (s, 3 H), 3.88 ppm (d, J=17.6 Hz, 1 H)

Example 18

Preparation of 4-[5-(3,5-dichlorophenyl)-5-(trifluoromethyl)-4H-isothiazol-3-yl]-N-[(E)-ethoxyiminomethyl]-2-methyl-benzamide (C2)

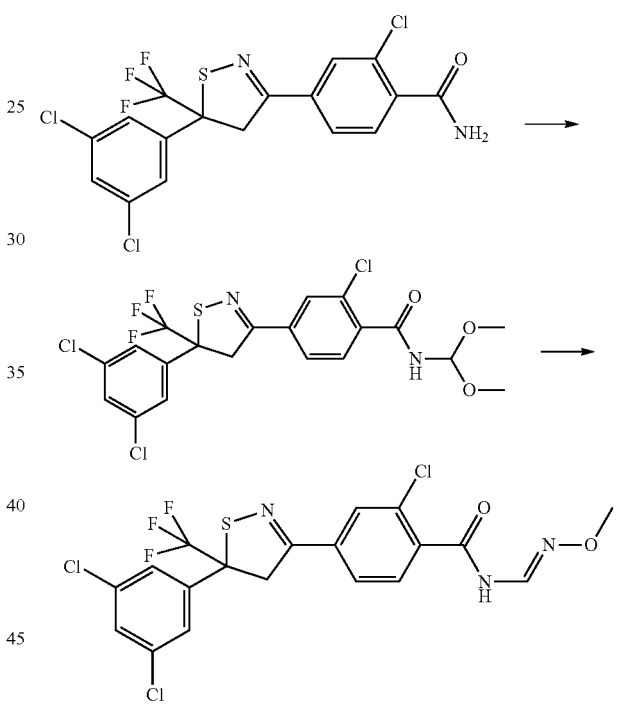

A solution of 4-[5-(3,5-dichlorophenyl)-5-(trifluoromethyl)-4H-isothiazol-3-yl]-2-methyl-benzamide (200 mg) and N,N-Dimethylformamide dimethylacetal (4 mL) was refluxed under Argon for one hour then the solution was concentrated in vacuo. The residue was dissolved in 1,4-dioxane (2 mL) and a solution of O-ethylhydroxylamine hydrochloride (2.8 eq.) and sodium hydroxide (6 eq.) in water (1.6 mL) and acetic acid (1.6 mL) was added. The solution was stirred at rt for 10 minutes. It was then quenched by addition of water and extracted with methyl tert-butyl ether. The combined organic extracts were washed with brine, dried over magnesium sulfate and evaporated. Flash Chromatography eluting with Cyclohexane:EtOAc afforded 237 mg of the title compound.

$^1$H-NMR (CDCl$_3$, 400 MHz): δ=8.52 (d, J=9.5 Hz, 1 H), 7.79 (d, J=9.2 Hz, 1 H), 7.67 (d, J=5.5 Hz, 2H), 7.56 (d, J=8.4 Hz, 1 H), 7.42 (t, J=1.7 Hz, 1 H), 7.31 (s, 2 H), 4.23 (d, J=17.6 Hz, 1 H), 4.16 (q, J=7.2 Hz, 2 H), 3.89 (d, J=18.0 Hz, 1 H), 2.56 (s, 3 H), 1.29 ppm (t, J=7.2 Hz, 3 H)

Example 19

Preparation of 4-[5-(3,5-dichlorophenyl)-5-(trifluoromethyl)-4H-isothiazol-3-yl]-N-[(E)-methoxyiminomethyl]-2-methyl-benzamide (C1)

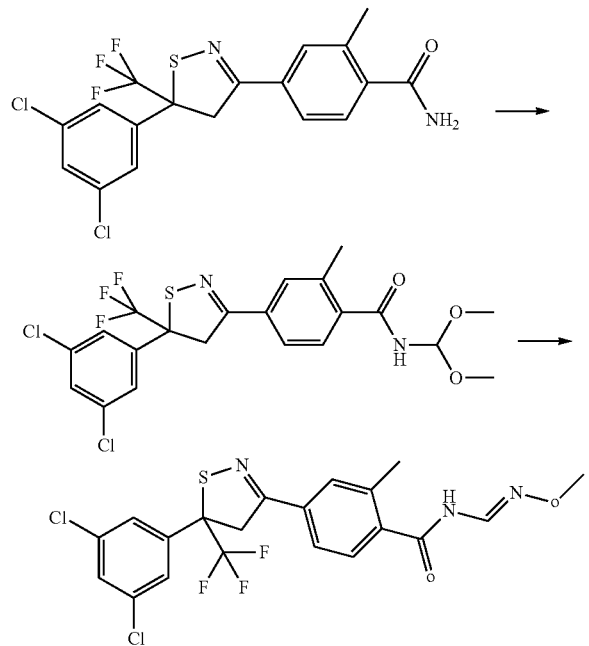

A solution of 4-[5-(3,5-dichlorophenyl)-5-(trifluoromethyl)-4H-isothiazol-3-yl]-2-methyl-benzamide (200 mg) and N,N-Dimethylformamide dimethylacetal (4 mL) was refluxed under argon for one hour then the solution was concentrated in vacuo. The residue was dissolved in 1,4-dioxane (2 mL) and a solution of O-methylhydroxylamine hydrochloride (2.8 eq.) and sodium hydroxide (6 eq.) in water (1.6 mL) and acetic acid (1.6 mL) was added. The solution was stirred at rt for 10 minutes. It was then quenched by addition of water and extracted with methyl tert-butyl ether. The combined organic extracts were washed with brine, dried over magnesium sulfate and evaporated. Flash Chromatography eluting with Cyclohexane:EtOAc afforded 243 mg of the title compound.

$^1$H-NMR (CDCl$_3$, 400 MHz) δ=8.50 (d, J=9.9 Hz, 1 H), 7.79 (d, J=9.5 Hz, 1 H), 7.63-7.71 (m, 2 H), 7.55 (d, J=8.4 Hz, 1 H), 7.42 (s, 1 H), 7.31 (s, 2 H), 4.22 (d, J=17.6 Hz, 1 H), 3.91 (s, 3 H), 3.83 (d, 1 H), 2.56 ppm (s, 3 H).

Example 20

Preparation of 4-[5-(3,5-dichlorophenyl)-5-(trifluoromethyl)-4H-isothiazol-3-yl]-2-methyl-benzamide

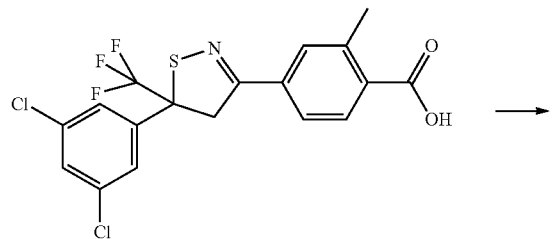

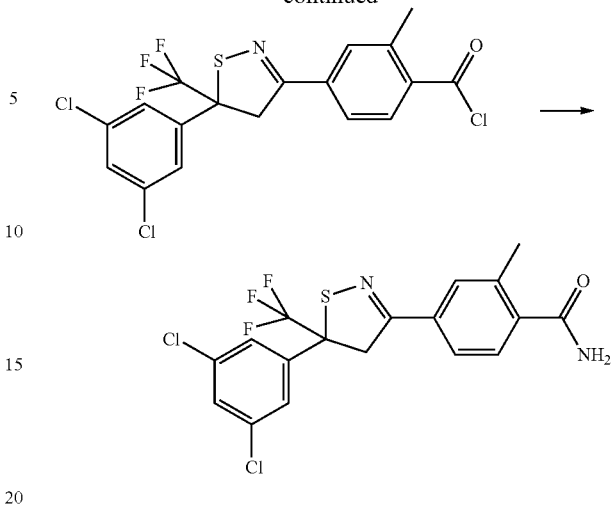

A solution of 4-[5-(3,5-dichlorophenyl)-5-(trifluoromethyl)-4H-isothiazol-3-yl]-2-methyl-benzoic acid (1.65 g) was suspended in dichloromethane (16 mL). A catalytic amount of N,N-dimethylformamide ("DMF") and oxalyl chloride (1.2 eq.) were added to the suspension. The reaction mixture was stirred at ambient temperature for 1.5 hour. The reaction mixture was concentrated and the residue dissolved in dry tetrahydrofuran (16 mL). To the solution was added a solution of ammonium hydroxide (8 mL, 25%). The reaction mixture was stirred at ambient temperature for two hours. It was then quenched by addition of water and extracted with ethyl acetate. The organic extract was washed with a saturated solution of sodium hydrogenocarbonate, dried over magnesium sulfate and concentrated in vacuo. The crude residue was triturated with tert-butylmethylether then the precipitate was filtered and dried under vacuo to give the title compound (841 mg) as a solid. $^1$H-NMR (CDCl$_3$, 400 MHz): δ=7.50-7.61 (m, 2 H), 7.39-7.50 (m, 1 H), 7.29-7.39 (m, 1 H), 7.14-7.27 (m, 2 H), 6.40 (br. s., 1 H), 6.05 (br. s., 1 H), 4.16 (m, J=17.4, 1 H), 3.74-3.91 (m, 1 H), 2.44-2.49 (m, 3 H).

Example 21

Compound A1: 4-[5-(3,5-dichlorophenyl)-5-(trifluoromethyl)-4H-isothiazol-3-yl]-N-(1,1-dioxothietan-3-yl)-2-methyl-benzamide

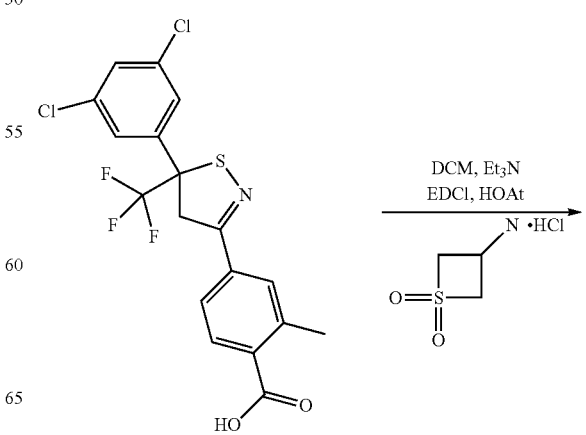

-continued

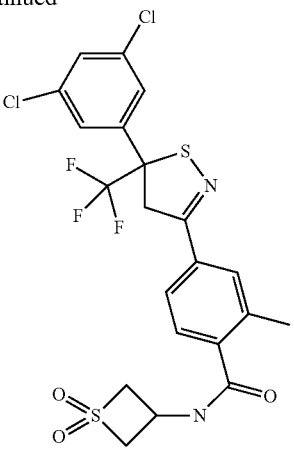

To a stirred solution of 4-[5-(3,5-dichlorophenyl)-5-(trifluoromethyl)-4H-isothiazol-3-yl]-2-methyl-benzoic acid (100 mg) in dichloromethane (3.8 mL) was added triethylamine (0.065 mL) at ambient temperature. The solution was stirred under argon and the hydrochloride salt of thietan-3-ylamine (44 mg) was added. To this solution, 1-hydroxyazabenzotriazole (35 mg) then 1-(3-Dimethylaminopropyl)-3-ethylcarbodiimide hydrochloride (50 mg) were added. The solution was stirred for 24 hours at ambient temperature. The residue was extracted with ethyl acetate and a saturated solution of ammonium chloride. The organic extract was washed with water, dried over sodium sulfate and concentrated under vacuo. The crude residue was purified by chromatography on silica gel (eluent: heptane/ethyl acetate) to give 4-[5-(3,5-dichlorophenyl)-5-(trifluoromethyl)-4H-isothiazol-3-yl]-N-(1,1-dioxothietan-3-yl)-2-methyl-benzamide (34 mg) as a white solid.

$^1$H-NMR (CDCl$_3$, 400 MHz): δ=7.60-7.69 (m, 2 H), 7.40-7.50 (m, 2 H), 7.30-7.33 (m, 2 H), 6.48 (d, 1H), 4.83-4.99 (m, 1 H), 4.56-4.71 (m, 2 H), 4.22 (d, 1 H), 3.99-4.07 (m, 2 H), 3.88 (d, 1 H), 2.51 ppm (s, 3 H).

Similarly, using the trifluoroacetate salt of 2-amino-N-(2,2,2-trifluoroethyl)acetamide as an amine, 4-[5-(3,5-dichlorophenyl)-5-(trifluoromethyl)-4H-isothiazol-3-yl]-2-methyl-N-[2-oxo-2-(2,2,2-trifluoroethylamino)ethyl]benzamide (compound A2) could be prepared. $^1$H-NMR (CDCl$_3$, 400 MHz): δ=7.63-7.69 (m, 1 H), 7.60 (d, 1 H), 7.48 (d, 1 H), 7.42 (t, 1 H), 7.29-7.34 (m, 2 H), 6.68 (br. s., 1H), 6.58 (s, 1 H), 4.16-4.26 (m, 3 H), 3.92-4.03 (m, 2 H), 3.88 (d, 1 H), 2.51 ppm (s, 3 H).

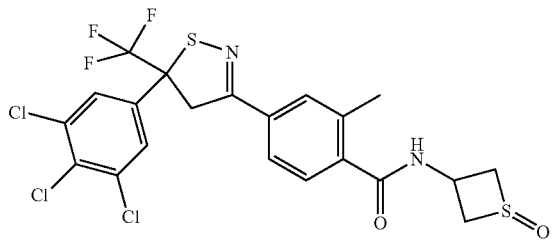 [SMILES: Cc1cc(C2=NSC(c3cc(Cl)c(Cl)c(Cl)c3)(C(F)(F)F)C2)ccc1C(=O)NC1CS(=O)C1]

Similarly, 2-methyl-N-(1-oxothietan-3-yl)-4-[5-(3,4,5-trichlorophenyl)-5-(trifluoromethyl)-4H-isothiazol-3-yl]benzamide (compound D3) could be prepared. $^1$H-NMR (DMSO-d$_6$, 400 MHz): δ=8.93 (d, J=7.3 Hz, 1 H), 7.81 (s, 2 H), 7.69-7.79 (m, 2 H), 7.48 (d, J=7.7 Hz, 1 H), 4.51-4.64 (m, 1 H), 4.30-4.47 (m, 2 H), 4.03-4.15 (m, 2 H), 3.15-3.29 (m, 2 H), 2.39 ppm (s, 3 H)

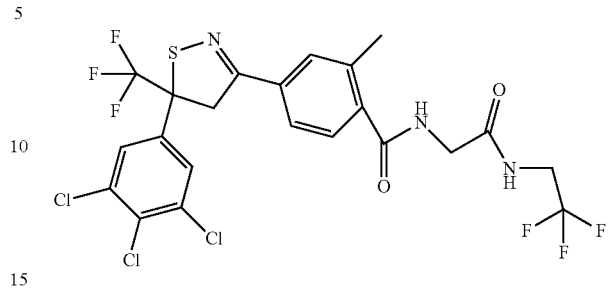

Similarly, 2-methyl-N-[2-oxo-2-(2,2,2-trifluoroethylamino)ethyl]-4-[5-(3,4,5-trichlorophenyl)-5-(trifluoromethyl)-4H-isothiazol-3-yl]benzamide (compound D1) could be prepared. $^1$H-NMR (CDCl$_3$, 400 MHz): δ=7.8-7.7 (m, 2 H), 7.52-7.46 (m, 3 H), 6.72 (m, 1 H), 6.61 (m, 1 H), 4.3-4.17 (m, 3 H), 4.05-3.82 (m, 3 H), 2.51 ppm (s, 3 H)

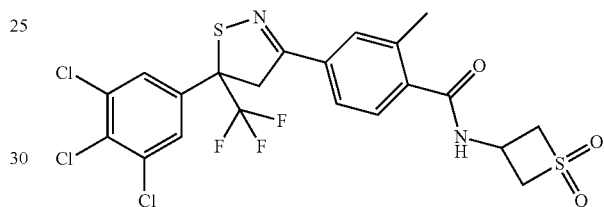

Similarly, N-(1,1-dioxothietan-3-yl)-2-methyl-4-[5-(3,4,5-trichlorophenyl)-5-(trifluoromethyl)-4H-isothiazol-3-yl]benzamide (compound D2) could be prepared. $^1$H-NMR (CDCl$_3$, 400 MHz): δ=7.7-7.6 (m, 2 H), 7.45-7.51 (m, 3 H), 6.51 (m, 1 H), 5.0-4.75 (m, 1 H), 4.7-4.6 (m, 2 H), 4.30-4.19 (m, 1 H), 4.1-4.0 (m, 2 H), 3.95-3.80 (m, 1 H), 2.52 ppm (s, 3 H)

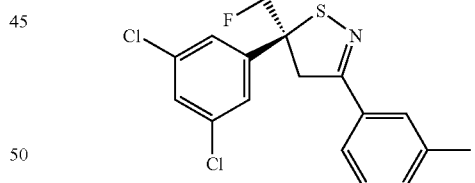

Similarly, 4-[(5S)-5-(3,5-dichlorophenyl)-5-(trifluoromethyl)-4H-isothiazol-3-yl]-N-[(4R)-2-ethyl-3-oxo-isoxazolidin-4-yl]-2-methyl-benzamide (compound A78) could be prepared. $^1$H-NMR (CDCl$_3$, 400 MHz): δ=7.64 (s, 1 H), 7.60 (d, J=8.1 Hz, 1 H), 7.51 (d, J=8.1 Hz, 1 H), 7.42 (t, J=1.7 Hz, 1 H), 7.29-7.34 (m, 2 H), 6.40 (d, J=3.7 Hz, 1 H), 4.94-5.06 (m, 1 H), 4.87 (dd, J=10.8, 3.9 Hz, 1 H), 4.22 (d, J=17.6 Hz, 1 H), 4.06 (dd, J=10.8, 8.6 Hz, 1 H), 3.88 (d, J=17.6 Hz, 1 H), 3.57-3.78 (m, 2 H), 2.52 (s, 3H), 1.20-1.32 ppm (m, 3 H).

Chiral HPLC analysis using a Waters UPLC—Hclass, DAD Detector Waters UPLC

Column: Daicel CHIRALPAK® IB, 3 μm, 0.46 cm×10 cm

Mobile phase: Heptane/iPrOH 80/20

Flow rate: 1.0 ml/min

Detection: 313

Sample concentration: 1 mg/mL in Hept/iPrOH 50/50

Injection: 2 μL $1^{st}$ eluting isomer: rt=4.23 min; 1.1%

$2^{nd}$ eluting isomer: rt=5.66 min; 98.9%

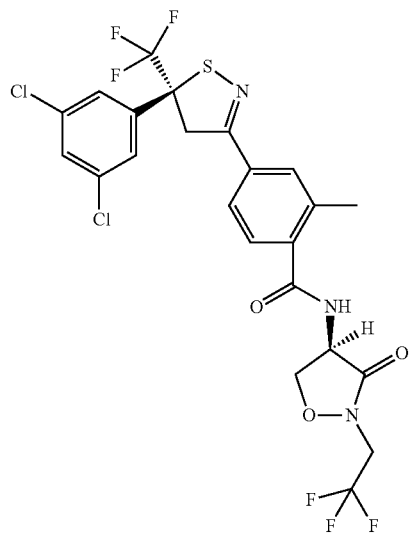 [SMILES: Cc1cc(C2=NS[C@@](c3cc(Cl)cc(Cl)c3)(C(F)(F)F)C2)ccc1C(=O)N[C@@H]1CON(CC(F)(F)F)C1=O]

Similarly, 4-[(5S)-5-(3,5-dichlorophenyl)-5-(trifluoromethyl)-4H-isothiazol-3-yl]-2-methyl-N-[(4R)-3-oxo-2-(2,2,2-trifluoroethyl)isoxazolidin-4-yl]benzamide (compound A79) could be prepared. $^1$H-NMR (CDCl$_3$, 400 MHz): δ=7.57-7.70 (m, 2 H), 7.51 (d, J=8.1 Hz, 1 H), 7.42 (t, J=1.8 Hz, 1 H), 7.29-7.34 (m, 2 H), 6.36 (d, J=4.0 Hz, 1 H), 5.00-5.09 (m, 1 H), 4.97 (dd, J=10.5, 4.6 Hz, 1 H), 4.06-4.33 (m, 4H), 3.88 (d, J=17.6 Hz, 1 H), 2.52 ppm (s, 3 H).

Chiral HPLC analysis using a Waters UPLC—Hclass, DAD Detector Waters UPLC

Column: Column: Daicel CHIRALPAK® IB, 3 μm, 0.46 cm×10 cm

Mobile phase: Heptane/iPrOH 80/20

Flow rate: 1.0 ml/min

Detection: 313

Sample concentration: 1 mg/mL in Hept/iPrOH 70/30

Injection: 4 μL $1^{st}$ eluting isomer: rt=4.19 min; 0.9%

$2^{nd}$ eluting isomer: rt=4.94 min; 99.1%

Example 22

Preparation of 4-bromo-2-methyl-benzoic acid tert-butyl ester

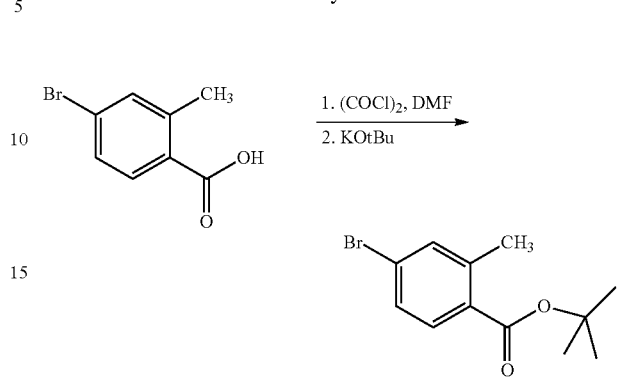

4-Bromo-2-methyl-benzoic acid (commercially available) (50 g) was suspended in dichloromethane (500 mL). A catalytic amount of N,N-dimethylformamide ("DMF") and oxalyl chloride (23 mL) were added to the suspension. The reaction mixture was stirred at ambient temperature for 3 hours. The reaction mixture was concentrated and the residue dissolved in dry tetrahydrofuran (800 mL). The solution was cooled to 2° C. and added to a solution of potassium tert-butoxide (39.2 g) in dry tetrahydrofuran (300 mL) dropwise at 5-10° C. The reaction mixture was stirred at ambient temperature for 30 minutes and then poured onto a mixture of ice and water. The mixture was extracted with ethyl acetate. The organic extract was washed with water, dried over sodium sulfate and concentrated to give 4-bromo-2-methyl-benzoic acid tert-butyl ester (65.3 g) as yellow oil.

$^1$H-NMR (CDCl$_3$, 400 MHz): δ=7.70 (d, 1 H), 7.40 (s, 1 H), 7.35 (d, 1 H), 2.58 (s, 3 H), 1.60 (s, 9 H).

Example 23

Preparation of tert-butyl 4-formyl-2-methyl-benzoate

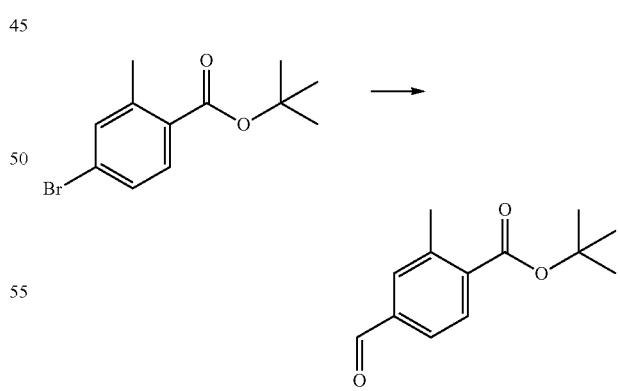

To a solution of 4-bromo-2-methyl-benzoic acid tert-butyl ester (500 g, 1.8 mol) in tetrahydrofuran (5 L) was added n-butyl lithium (1.6 M solution, 1.4 L, 2.2 mol) at such a rate that the reaction temperature is between −95° C. to −100° C. After completion of the addition, the reaction mixture was stirred for 30 min at −100° C. and monitored by quenching the reaction mixture with water and following the product by TLC. After complete conversion, DMF (170 ml, 2.2 mol) was added to the reaction mixture and after 15 min the reaction mixture was quenched with ammonium chloride (sat. solution, 5 L). The organic layers were separated at room temperature and the aqueous layer was extracted with ethyl acetate (3×2 L). The combined organic layer was washed with water (3×5 L), dried over sodium sulphate and concentrated to yield tert-butyl 4-formyl-2-methyl-benzoate (390 g, 96% isolated yield, 75-78% HPLC purity). The crude product was used as such without any further purification for the next step.
$^1$H-NMR (CDCl$_3$, 400 MHz): δ in ppm=1.59 (s, 9 H), 2.61 (s, 3 H), 7.71 (d, 2 H), 7.92 (d, 1 H), 10.01 (s, 1 H).

Example 24

Preparation of 4-tert-butoxycarbonyl-3-methyl-benzoic acid

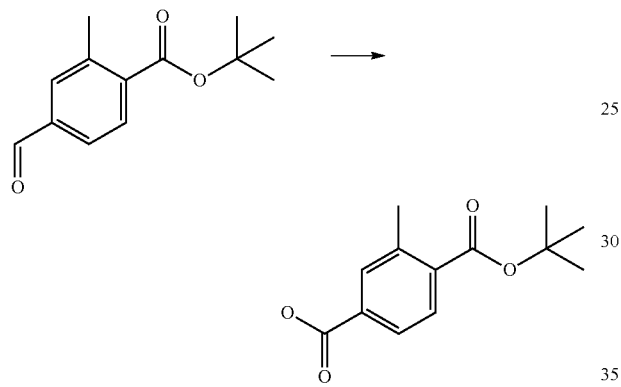

To a solution of tert-butyl 4-formyl-2-methyl-benzoate (390 g, ~78% purity, 1.8 mol) in DMF (2.0 L) was added oxone (270 g, 1.8 mol) over a period of 15 min at 10° C. After complete addition, the reaction mixture was warmed to room temperature and stirred for 12 h. After complete conversion of starting material, the reaction mixture was diluted with water at 10° C. The aqueous layer was extracted with ethyl acetate (2×5 L), washed with water (3×1 L) dried over sodium sulphate and concentrated to yield a crude residue (217 g). Pure 4-tert-butoxycarbonyl-3-methyl-benzoic acid (115 g) was obtained by column chromatography with ethyl acetate (6%) in hexane.
$^1$H-NMR (DMSO d$_6$, 400 MHz): δ in ppm=1.55 (s, 9 H), 2.51 (s, 3 H), 7.83 (m, 3 H), 13.11 (br, OH).

Example 25

Preparation of tert-butyl 4-carbamoyl-2-methyl-benzoate

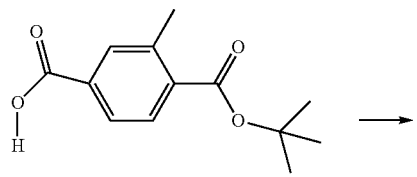

-continued

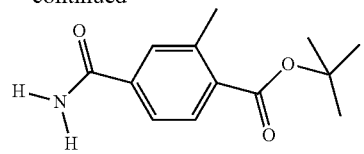

A solution of 4-tert-butoxycarbonyl-3-methyl-benzoic acid (40 g) was suspended in tetrahydrofuran (160 mL). This solution was cooled to −30 C then N-methyl morpholine (18.7 mL) followed by isobutylchloroformate (24.2 mL) were added. A white precipitate appeared. The solution was stirred for 8 hours then a solution of ammonium hydroxide (100 mL) was added. The reaction mixture was slowly allowed to warm to room temperature over 48 hours. Then water was added and the mixture was extracted with ethyl acetate. The organic extract was washed with water, dried over sodium sulfate and concentrated to give a solid which was further triturated with a mixture of dichloromethane/ethyl acetate, filtered, to give tert-butyl 4-carbamoyl-2-methyl-benzoate (29.9 g) as a white solid. $^1$H-NMR (CDCl$_3$, 400 MHz): 7.90 (d, 1 H), 7.72 (s, 1 H), 7.65 (d, 1 H), 2.63 (s, 3 H), 1.62 (s, 9 H).

Example 26

Preparation of 2-(1,2,4-triazol-1-yl)-5-[(5S)-5-(3,4,5-trichlorophenyl)-5-(trifluoromethyl)-4H-isothiazol-3-yl]benzonitrile (B2)

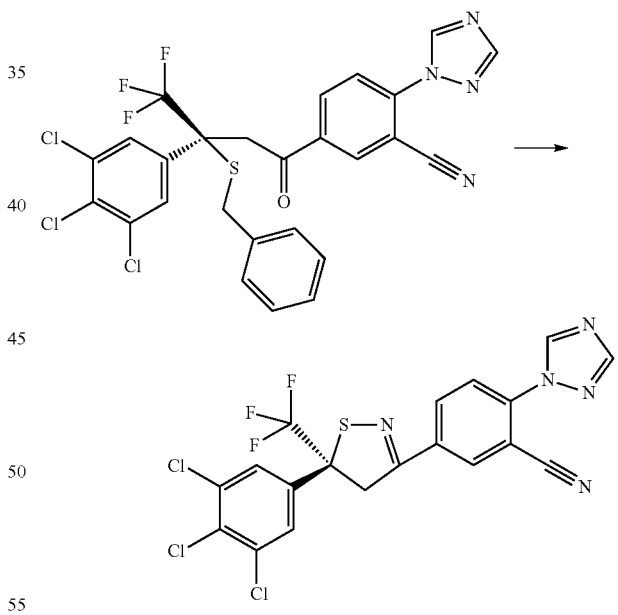

Sulfuryl chloride (5.97 mL) was slowly added to a solution of 5-[(3S)-3-benzylsulfanyl-4,4,4-trifluoro-3-(3,4,5-trichlorophenyl)butanoyl]-2-(1,2,4-triazol-1-yl)benzonitrile (40.54 g) in dichloromethane (264 mL) at 0° C. The mixture was stirred at room temperature for two hours.
The solvent was then evaporated, then tetrahydrofuran (264 mL) was added and slowly ammonia in ethanol (48.6 mL, 7N in ethanol) was added at 0° C. The reaction was stirred for another hour then a hydrochloric acid (2N) solution was added. The mixture was extracted with ethyl acetate. The organic phases were dried over magnesium sulfate and concentrated under vacuo. The crude residue was purified by chromatography on silica gel (eluent: cyclohexane/ethyl acetate) to give the desired compound as a mixture which was further purified using a preparative reverse phase HPLC to give with 2-(1,2,4-triazol-1-yl)-5-[(5S)-5-(3,4,5-trichlorophenyl)-5-(trifluoromethyl)-4H-isothiazol-3-yl]benzonitrile (4.056 g) as a white solid.

$^1$H NMR (CDCl$_3$, 400 MHz): δ=8.90 (s, 1 H), 8.17-8.27 (m, 2 H), 8.10-8.17 (m, 1 H), 7.92 (d, J=8.8 Hz, 1 H), 7.46 (s, 2 H), 4.24 (d, J=17.6 Hz, 1 H), 3.90 ppm (d, J=17.6 Hz, 1 H).
$^{19}$H NMR (CDCl$_3$, 376 MHz): δ=−74.61

Chiral HPLC analysis using a Waters UPLC (Alliance 2695)—Hclass, DAD Detector Waters UPLC (996).
Column: Daicel CHIRALPAK® IA, 3 μm, 0.46 cm×10 cm
Mobile phase: Hept/EtOH/DEA 80/20/0.1%
Flow rate: 1 ml/min
Detection: 325 nm
Sample concentration: 1 mg/mL in Heptan/iPrOH 50/50
Injection: 2 μL
1$^{st}$ eluting isomer: rt=6.17 min; 83.2%
2$^{nd}$ eluting isomer: rt=9.09 min; 16.8%

Similarly, tert-butyl 4-[(5S)-5-(3,5-dichlorophenyl)-5-(trifluoromethyl)-4H-isothiazol-3-yl]-2-methyl-benzoate could be obtained from tert-butyl 4-[(3S)-3-benzylsulfanyl-3-(3,5-dichlorophenyl)-4,4,4-trifluoro-butanoyl]-2-methyl-benzoate Chiral HPLC analysis using a Waters UPLC—Hclass, DAD Detector Waters UPLC
Column: Daicel CHIRALPAK® IA, 3 μm, 0.46 cm×10 cm
Mobile phase: Heptane/iPrOH 95/05
Flow rate: 1.0 ml/min
Detection: 318 nm
Sample concentration: 1 mg/mL in Hept/iPrOH 50/50
Injection: 2 μL
1$^{st}$ eluting isomer: rt=1.80 min; 98.6%
2$^{nd}$ eluting isomer: rt=2.33 min; 1.4%

Example 27

Method for Preparing Compounds of the Invention from a Carboxylic Acid

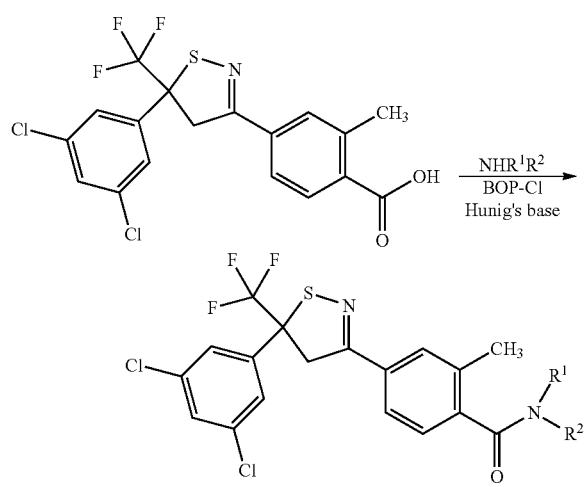

To a solution of the 4-[5-(3,5-dichlorophenyl)-5-(trifluoromethyl)-4H-isothiazol-3-yl]-2-methyl-benzoic acid (22 μmol) in dimethylacetamide (0.4 ml) was added successively a solution of an amine of formula HNR$^6$R$^7$ (26 μmol), for example thietan-3-ylamine (preparation described in, for example, WO 2007/080131) in the case of Compound No. A22 of Table A, in dimethylacetamide (0.11 ml), diisopropylethylamine (Hunig's Base) (0.030 ml), and a solution of bis(2-oxo-3-oxazolidinyl)phosphonic chloride ("BOP-Cl") (11.2 mg) in dimethylacetamide (0.02 ml). The reaction mixture was stirred at 80° C. for 16 hours. Then the reaction mixture was diluted with acetonitrile (0.6 ml) and a sample was used for LC-MS analysis. The remaining mixture was further diluted with acetonitrile/dimethylformamide (4:1) (0.8 ml) and purified by HPLC. This method was used to prepare a number of compounds (Compound Nos. A1 to A77 of Table A) in parallel.

TABLE A

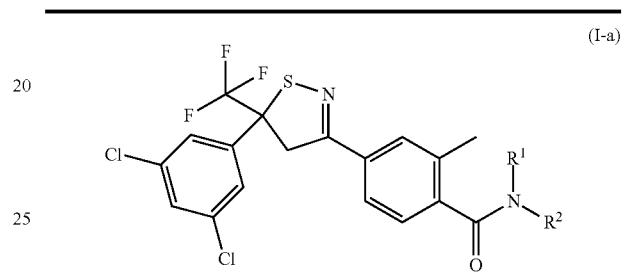

(I-a)

| Comp No. | R$^1$ | R$^2$ | RT (min) | [M + H]$^+$ |
|---|---|---|---|---|
| A01 | H | (2,2,2-Trifluoro-ethylcarbamoyl)-methyl | 1.97 | 572.23 |
| A02 | H | 1,1-Dioxo-thietan-3-yl | 1.91 | 537.14 |
| A03 | H | 2,2,2-Trifluoro-ethyl | 2.1 | 515.23 |
| A04 | H | ethyl | 2.02 | 461.23 |
| A05 | H | butyl | 2.18 | 489.27 |
| A06 | H | 1-methoxypropan-2-yl | 2.06 | 505.25 |
| A07 | H | 3,3,3-trifluoroprop-1-yl | 2.12 | 529.22 |
| A08 | H | butan-2-yl | 2.17 | 489.26 |
| A09 | H | tetrahydrofuran-2-ylmethyl | 2.04 | 517.24 |
| A10 | H | benzyl | 2.18 | 523.23 |
| A11 | H | (2-fluorophenyl)-methyl | 2.19 | 541.22 |
| A12 | H | 1-phenylethyl | 2.23 | 537.25 |
| A13 | H | (4-methoxyphenyl)-methyl | 2.16 | 553.25 |
| A14 | H | (6-chloro-3-pyridyl)methyl | 2.1 | 558.22 |
| A15 | H | 3-fluorophenyl | 2.27 | 527.24 |
| A16 | H | 2-pyridylmethyl | 1.9 | 524.24 |
| A17 | H | 2,5-dimethylpyrazol-3-yl | 2.01 | 527.25 |
| A18 | H | 4-methylthiazol-2-yl | 2.21 | 530.2 |
| A19 | H | 3-Methyl-thietan-3-yl | 2.19 | 519.22 |
| A20 | H | 2-methyl-1-methylsulfanyl-propan-2-yl | 2.28 | 535.27 |
| A21 | H | 1-Oxo-thietan-3-yl | 1.82 | 521.19 |
| A22 | H | Thietan-3-yl | 2.1 | 505.22 |
| A23 | H | (1R,2R,4S)-N-methylnorbornan-2-yl | 2.3 | 527.27 |
| A24 | H | Cyclobotuyl | 2.13 | 487.27 |
| A25 | H | N-methyl-2-methylsulfinyl-ethyl | 1.77 | 523.19 |
| A26 | H | 2-methylsulfanylethyl | 2.09 | 507.26 |
| A27 | H | tetrahydrothiophen-3-yl | 2.12 | 519.22 |
| A28 | H | thietan-3-ylmethyl | 2.14 | 519.33 |
| A29 | H | 3-(2,2,2-trifluoroethoxyimino) cyclobutyl | 2.2 | 598.32 |
| A30 | H | thietan-2-ylmethyl | 2.16 | 519.3 |
| A31 | H | (1,1-dioxothietan-2-yl)methyl | 1.93 | 551.31 |
| A32 | H | 2-(thietan-3-yl)ethyl | 2.18 | 533.35 |
| A33 | H | 2-(1,1-dioxothietan-3-yl)ethyl | 1.93 | 565.34 |
| A34 | H | 2-fluoroethyl | 2.01 | 479.29 |
| A35 | H | prop-2-ynyl | 2.03 | 471.32 |
| A36 | H | propanyl | 2.13 | 475.35 |
| A37 | H | 2-oxotetrahydrothiophen-3-yl | 2.07 | 533.27 |
| A38 | H | pyrimidin-2-yl | 1.95 | 511.12 |
| A39 | H | propan-2-yl | 2.13 | 475.34 |
| A40 | H | cyclobutylmethyl | 2.25 | 501.36 |
| A41 | H | 1-oxidopyridin-1-ium-4-yl | 1.82 | 526.32 |
| A42 | H | 2,2-difluoroethyl | 2.07 | 497.32 |
| A43 | H | cyano | 2.01 | 458.4 |

TABLE A-continued (I-a)

[Structure shown: isoxazoline/thiazoline compound with CF3, two Cl substituents on phenyl, and benzamide with R1, R2 substituents]

| Comp No. | R¹ | R² | RT (min) | [M + H]⁺ |
|---|---|---|---|---|
| A44 | H | 4,5-dihydrothiazol-2-yl | 2.02 | 518.31 |
| A45 | H | 1-cyanocyclopropyl | 2.03 | 498.32 |
| A46 | H | 2-methylpropan-1-yl | 2.21 | 489.35 |
| A47 | H | 4,6-dimethylpyrimidin-2-yl | 2.09 | 538.85 |
| A48 | H | pyrimidin-5-yl | 2 | 511.31 |
| A49 | H | 6-(diethylcarbamoyl)-2-pyridyl | 2.24 | 609.38 |
| A50 | H | indan-1-yl | 2.31 | 549.31 |
| A51 | H | 2-methoxyethyl | 2.01 | 491.33 |
| A52 | H | cyclopropyl | 2.05 | 473.34 |
| A53 | H | cyclopropylmethyl | 2.15 | 487.33 |
| A54 | H | 2-(1,3-dioxolan-2-yl)ethyl | 2.03 | 533.34 |
| A55 | H | 2,4-difluorophenyl | 2.28 | 545.35 |
| A56 | H | pyridin-2-yl | 2.19 | 510.31 |
| A57 | H | [4-(trifluoromethyl)phenyl]methyl | 2.31 | 591.29 |
| A58 | H | 4-(trifluoromethyl)phenyl | 2.39 | 577.33 |
| A59 | H | 4-fluorophenyl | 2.26 | 527.32 |
| A60 | H | 2-fluorophenyl | 2.28 | 527.32 |
| A61 | H | p-tolylmethyl | 2.28 | 537.38 |
| A62 | H | methyl | 1.96 | 447.32 |
| A63 | H | allyl | 2.09 | 473.33 |
| A64 | H | 4-methylphenyl | 2.32 | 523.35 |
| A65 | H | quinolin-8-yl | 2.54 | 560.35 |
| A66 | H | 4H-1,2,4-triazol-3-yl | 2.23 | 501.35 |
| A67 | H | cyclopentyl | 2.1 | 505.34 |
| A68 | H | 2-ethoxyethyl | 2.18 | 499.33 |
| A69 | H | cyclopent-3-en-1-yl | 1.73 | 550.34 |
| A70 | H | 1-(3-pyridyl)cyclopropyl | 2.08 | 517.36 |
| A71 | H | pentan-3-yl | 2.03 | 491.31 |
| A72 | H | cis-2-fluorocyclopropyl | 2.23 | 532.36 |
| A73 | H | (1E)-1-methoxyimino-2-methyl-propan-2-yl | 2.06 | 546.37 |
| A74 | H | 1-methoxypiperidin-4-yl | 2.02 | 560.39 |
| A75 | H | (1-methoxy-4-piperidyl)methyl | 2.17 | 507.3 |
| A76 | H | 2-chloroprop-2-en-1-yl | 2.05 | 500.3 |
| A77 | H | 3,3-dichloroprop-2-en-1-yl | 2.26 | 541.29 |

Corresponding LC/MS Method

| | |
|---|---|
| MS | ACQUITY SQD Mass Spectrometer from Waters (Single quadrupole mass) spectrometer<br>Ionisation method: Electrospray<br>Polarity: positive ions<br>Capillary (kV) 3.00, Cone (V) 20.00, Extractor (V) 3.00,<br>Source Temperature (° C.) 150,<br>Desolvation Temperature (° C.) 400, Cone Gas Flow (L/Hr) 60, Desolvation Gas Flow (L/Hr) 700<br>Mass range: 100 to 800 Da<br>DAD Wavelength range (nm): 210 to 400 |
| LC | Method Waters the ACQUITY UPLC with following HPLC gradient conditions<br>(Solvent A: Water/Methanol 9:1, 0.1% formic acid and Solvent B: Acetonitrile, 0.1% formic acid) |

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

BIOLOGICAL EXAMPLES

*Spodoptera littoralis* (Egyptian Cotton Leafworm):

Cotton leaf discs were placed on agar in a 24-well microtiter plate and sprayed with test solutions at an application rate of 200 ppm. After drying, the leaf discs were infested with 5 μl larvae. The samples were checked for mortality, feeding behavior, and growth regulation 3 days after treatment (DAT).

The following compound gave at least 80% control of *Spodoptera* littoralis: A01, A02, A03, A04, A05, A06, A07, A08, A09, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52, A53, A54, A55, A56, A57, A58, A59, A60, A61, A62, A63, A64, A67, A68, A69, A70, A71, A72, A73, A74, A75, A76, A77, A78, A79, B1, B2, C1, C2, C3, D1, D2, D3.

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compound gave at least 80% control of *Heliothis virescens*: A01, A02, A03, A04, A05, A06, A07, A08, A09, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A48, A49, A50, A51, A52, A53, A54, A55, A56, A57, A58, A59, A60, A61, A62, A63, A64, A66, A67, A68, A69, A70, A71, A72, A73, A74, A75, A76, A77, A78, A79, B1, B2, C1, C2, C3, D1, D2, D3.

*Plutella xylostella* (Diamond Back Moth):

24-well microtiter plate (MTP) with artificial diet was treated with test solutions at an application rate of 200 ppm (concentration in well 18 ppm) by pipetting. After drying, the MTPs were infested with L2 larvae (7-12 per well). After an incubation period of 6 days, samples were checked for larval mortality and growth regulation.

The following compound gave at least 80% control of *Plutella xylostella*: A01, A02, A03, A04, A05, A06, A07, A08, A09, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A48, A49, A50, A51, A52, A53, A54, A55, A56, A57, A58, A59, A60, A62, A63, A64, A67, A68, A69, A70, A71, A72, A73, A74, A75, A76, A77, A78, A79, B1, B2, C1, C2, C3, D1, D2, D3.

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTPs were infested with L2 larvae (6-10 per well). After an incubation period of 5 days, samples were checked for larval mortality and growth regulation.

The following compound gave at least 80% control of *Diabrotica balteata*: A01, A02, A03, A04, A05, A06, A07, A08, A09, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A42, A43, A44, A45, A46, A48, A49, A50, A51, A52, A53, A54, A55, A56, A57, A58, A59, A60, A61, A62, A63, A64, A66, A67, A68, A69, A70, A71, A72, A73, A74, A75, A76, A77, A78, A79, B1, B2, C1, C2, C3, D1, D2, D3.

*Thrips tabaci* (Onion *Thrips*):

Sunflower leaf discs were placed on agar in a 24-well microtiter plate and sprayed with test solutions at an application rate of 200 ppm. After drying, the leaf discs were infested with a *thrips* population of mixed ages. After an incubation period of 7 days, samples were checked for mortality.

The following compounds gave at least 80% control of *Thrips tabaci*: A01, A02, A03, A04, A05, A06, A07, A08, A09, A10, A11, A12, A13, A14, A15, A16, A17, A18, A19, A21, A22, A23, A24, A25, A26, A27, A28, A29, A30, A31, A32, A33, A34, A35, A36, A38, A39, A40, A42, A43, A45, A46, A48, A50, A51, A52, A53, A54, A55, A56, A58, A59, A60, A62, A63, A64, A67, A68, A69, A70, A71, A72, A73, A74, A75, A76, A77, A78, A79, B1, B2, C1, C2, C3, D1, D2, D3.

*Tetranychus urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compound gave at least 80% control of *Tetranychus urticae*: A01, A02, A03, A04, A05, A06, A07, A08, A09, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A42, A45, A46, A48, A49, A50, A51, A52, A53, A54, A55, A57, A59, A60, A62, A63, A66, A67, A68, A69, A70, A71, A72, A73, A74, A75, A76, A77, A78, A79, B1, B2, C1, C2, C3, D1, D2, D3.

Biological Examples Showing Increased Safety Profile:

*Spodoptera littoralis* (Egyptian Cotton Leafworm)

Cotton plants in the 5$^{th}$ leaf stage (around 5 weeks old) are treated in an automated turn table spray chamber. Plants are stored in the greenhouse length during the whole test period.

2, 16 and optionally 10 days after treatment 4 leaves from each sample are excised, placed into 14 cm plastic petri dishes on wet filter paper. The infestation of 10 L3-*Spodoptera littoralis* is made immediately afterwards. After an incubation period of 6 days the samples are checked for mortality.

Test Results:

| Compound | Application rate (in ppm) | Control after 2 days/% | Control after 16 days/% |
|---|---|---|---|
| Compound A12 | 12.5 | 30 | |
| Compound A24 | 12.5 | 100 | 0 |
| Compound D1 | 12.5 | 100 | 10 |
| Compound C1 | 12.5 | 100 | 5 |
| Compound C3 | 12.5 | 100 | 0 |
| Compound A45 | 12.5 | 75 | 0 |
| Compound A46 | 12.5 | 40 | 0 |
| Compound A53 | 12.5 | 85 | 0 |
| Compound A59 | 12.5 | 100 | 10 |
| Compound A76 | 12.5 | 65 | 0 |

Comparative Tests

In the following series of experiments the compounds of the invention are compared with the corresponding isoxazoline analogues from the prior art on *Spodoptera littoralis* (Egyptian cotton leafworm) performed as described in the method above.

Comparative Table 1

In this comparison it can be seen that the structures of the two compounds are identical apart from the replacement of the oxygen atom with a sulphur atom in the isoxazoline moiety.

| Compound 1-061 from EP1731512 | Compound A16 present invention |
|---|---|
| 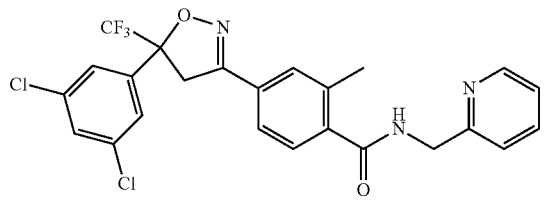 | 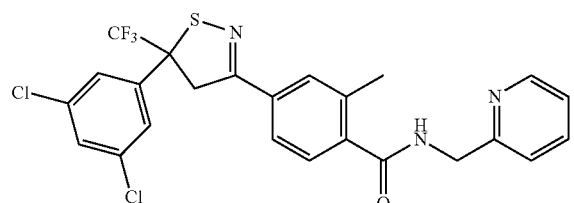 |

| Compound | Application rate/ppm | Control after 2 days/% | Control after 10 days/% | Control after 16 days/% |
|---|---|---|---|---|
| Compound 1-061 from EP1731512 | 12.5 | 100 | 100 | 100 |
| Compound A16 present invention | 12.5 | 100 | 25 | 10 |

Comparative Table 2
In this comparison it can be seen that the structures of the two compounds are identical apart from the replacement of the oxygen atom with a sulphur atom in the isoxazoline moiety.

Compound A10 from WO2009/080250

Compound A02 present invention

| Compound | Application rate/ppm | Control after 2 days/% | Control after 10 days/% | Control after 16 days/% |
|---|---|---|---|---|
| Compound A10 from WO2009/080250 | 12.5 | 100 | 100 | 100 |
| Compound A02 present invention | 12.5 | 100 | 35 | 5 |

Comparative Table 3
In this comparison it can be seen that the structures of the two compounds are identical apart from the replacement of the oxygen atom with a sulphur atom in the isoxazoline moiety.

Compound 3-086 from EP1731512

Compound A01 present invention

| Compound | Application rate/ppm | Control after 2 days/% | Control after 10 days/% | Control after 16 days/% |
|---|---|---|---|---|
| Compound 3-086 from EP1731512 | 12.5 | 100 | 100 | 100 |
| Compound A01 present invention | 12.5 | 100 | 60 | 10 |

CONCLUSIONS

Compounds that exhibit high control of pests at low application rates and that are readily bio-degradable are highly desirable for environmental safety reasons. The data shown above indicate that the compounds of the invention exhibit high pesticidal activity during the days immediately after application, with the activity significantly reduced after 10 to 16 days indicating that the compounds are bio-degrading. In contract, the close structural analogues from the prior art show little or no reduction in activity during the testing period, indicating that the compounds show no significant bio-degradation.

From the perspective of environmental safety the compounds of the invention are superior to those of the prior art and in addition retain a high level of pest control at low application rates. In the light of the structural similarities of the tested compounds, this significant difference in bio-degradability in favour of the compounds of the invention is completely unexpected and cannot be derived from what is known from the prior art.

The invention claimed is:
1. A compound of formula (I)

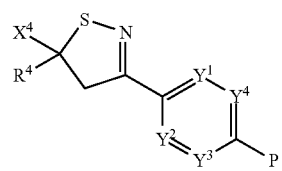

(I)

wherein

P is P0, heterocyclyl or heterocyclyl substituted by one to five Z;

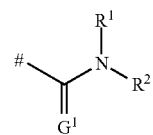

(P0)

$Y^1$, $Y^2$, $Y^3$ and $Y^4$ are independently of each other C—H, C—$R^5$, or nitrogen;

$G^1$ is oxygen or sulfur;

$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;

$R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene-wherein the aryl moiety is substituted by one to five $R^8$, heterocyclyl-$C_1$-$C_4$alkylene-or heterocyclyl-$C_1$-$C_4$alkylene- wherein the heterocyclyl moiety is substituted by one to five $R^8$, aryl-N($R^{20}$)- or aryl-N($R^{20}$)- wherein the aryl moiety is substituted by one to five $R^8$, heterocyclyl-N($R^{20}$)- or heterocyclyl-N($R^{20}$)- wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$alkylene, $C_1$-$C_8$alkylaminocarbonyl-, $C_1$-$C_8$haloalkylaminocarbonyl, $C_3$-$C_8$cycloalkyl-aminocarbonyl, $C_1$-$C_6$alkyl-O—N=CH— or $C_1$-$C_6$haloakly-O—N=CH—;

or $R^1$ and $R^2$ together represent group A

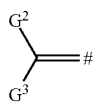

(A)

$G^2$ is O($R^{13}$), N($R^{14}$)($R^{15}$) or S($R^{16}$);

$G^3$ is N($R^{17}$)($R^{18}$) or S($R^{19}$);

$X^4$ is $C_1$-$C_8$haloalkyl;

$R^4$ is aryl or aryl substituted by one to five $R^9$, or heteroaryl or heteroaryl substituted by one to five $R^9$;

each $R^5$ is independently halogen, cyano, nitro, $C_2$-$C_8$alkenyl, $C_2$-$C_8$haloalkenyl, $C_2$-$C_8$alkynyl, $C_2$-$C_8$haloalkynyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-; or two $R^5$ on adjacent carbon atoms together form a —CH=CH—CH=CH— bridge;

each $R^6$ is independently halogen, cyano, nitro, hydroxy, amino, $C_1$-$C_8$alkylamino, ($C_1$-$C_8$alkyl)$_2$amino, $C_1$-$C_8$alkylcarbonylamino, $C_1$-$C_8$haloalkylcarbonylamino, $C_1$-$C_8$alkoxy-, $C_1$-$C_8$haloalkoxy-, aryloxy or aryloxy substituted by one to five $R^{10}$, aryloxy-$C_1$-$C_4$alkylene or aryloxy-$C_1$-$C_4$alkylene wherein the aryl moiety is substituted by one to five $R^{10}$, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, aryl-$C_1$-$C_4$alkylthio or aryl-$C_1$-$C_4$alkylthio wherein the aryl moiety is substituted by one to five $R^{10}$;

each $R^7$ is independently halogen, $C_1$-$C_8$alkyl, $C_2$-$C_8$alkenyl, $C_2$-$C_8$alkynyl, $C_1$-$C_8$alkyl-O—N=, $C_1$-$C_8$haloalkyl-O—N=; $C_1$-$C_8$alkoxy or $C_1$-$C_8$alkoxycarbonyl;

each $R^8$ is independently halogen, cyano, nitro, oxo, $C_1$-$C_8$alkyl, $C_1$-$C_8$haloalkyl, $C_1$-$C_8$cyanoalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkylene, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylaminosulfonyl, ($C_1$-$C_8$alkyl)$_2$aminosulfonyl-, $C_1$-$C_8$alkylcarbonyl-, $C_1$-$C_8$alkoxycarbonyl-, aryl or aryl substituted by one to five $R^{10}$, heterocyclyl or heterocyclyl substituted by one to five $R^{10}$, aryl-$C_1$-$C_4$alkylene or aryl-$C_1$-$C_4$alkylene wherein the aryl moiety is substituted by one to five $R^{10}$, heterocyclyl-$C_1$-$C_4$alkylene or heterocyclyl-$C_1$-$C_4$alkylene wherein the heterocyclyl moiety is substituted by one to five $R^{10}$, aryloxy or aryloxy substituted by one to five $R^{10}$, aryloxy-$C_1$-$C_4$alkylene or aryloxy-$C_1$-$C_4$alkylene wherein the aryl moiety is substituted by one to five $R^{10}$;

each $R^9$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{10}$, or heterocyclyl or heterocyclyl substituted by one to five $R^{10}$;

each $R^{10}$ is independently halogen, cyano, nitro, $C_1C_4$alkyl, $C_1C_4$haloalkyl, $C_1$-$C_4$alkoxy-, or $C_1C_4$haloalkoxy-;

each Z is independently halogen, $C_1$-$C_{12}$alkyl or $C_1$-$C_{12}$alkyl substituted by one to five $R^6$, nitro, $C_1$-$C_{12}$alkoxy or $C_1$-$C_{12}$alkoxy substituted by one to five $R^6$, cyano, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, hydroxyl or thiol;

$R^{13}$, $R^{16}$ and $R^{19}$ are independently $C_1$-$C_4$ alkyl;

$R^{14}$, $R^{15}$, $R^{17}$, and $R^{18}$ are independently hydrogen or $C_1$-$C_4$ alkyl;

$R^{20}$ is hydrogen or $C_1$-$C_4$ alkyl;

or a salt or N-oxide thereof.

2. A compound according to claim 1 wherein $Y^1$ is C—$R^{5b}$, C—H or nitrogen, $Y^2$ and $Y^3$ are independently C—H or nitrogen and $Y^4$ is C—$R^5$; wherein no more than two of $Y^1$, $Y^2$ and $Y^3$ are nitrogen and wherein $Y^2$ and $Y^3$ are not both nitrogen, and wherein $R^{5b}$ when present forms a —CH=CH—CH=CH— bridge with $R^5$.

3. A compound according to claim 1 wherein $G^1$ is oxygen.

4. A compound according to claim 1, wherein P is P0 or a heterocycle selected from H1 to H9

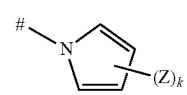

H1

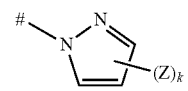

H2

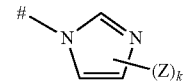

H3

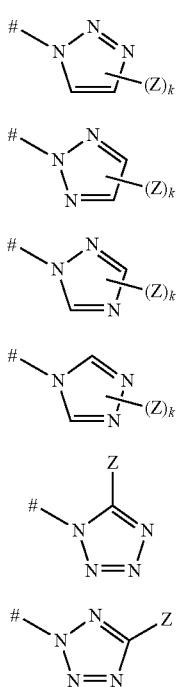

k is 0, 1 or 2.

5. A compound according to claim 1 wherein $R^1$ is hydrogen, methyl, ethyl, methylcarbonyl-, or methoxycarbonyl-.

6. A compound according to claim 1 wherein $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1

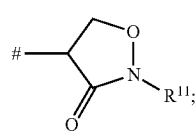

(C1)

$R^{11}$ is hydrogen, methyl, ethyl, propyl, isopropyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, benzyl, benzyl substituted by one to three $R^{12}$, or $R^{11}$ is pyridyl-methyl- or pyridyl-methyl- substituted by one to three $R^{12}$;

each $R^{12}$ is independently fluoro, chloro, bromo, trifluoromethyl, trifluoromethoxy, cyano or methoxy;

wherein each aryl group is a phenyl group and each heterocyclyl group is independently selected from pyridyl, pyridazinyl, pyrimidinyl, pyrazinyl, pyrrolyl, pyrazolyl, imidazolyl, triazolyl, tetrahydrothiophenyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxo-thietanyl, dioxo-thietanyl, pyrrolidinyl, tetrahydrofuranyl, [1,3]dioxolanyl, piperidinyl, piperazinyl, [1,4]dioxanyl, and morpholinyl, 2,3-dihydro-benzofuranyl, benzo[1,3]dioxolanyl, and 2,3-dihydro-benzo-[1,4]dioxinyl.

7. A compound according to claim 6 wherein $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, phenyl-$C_1$-$C_4$alkylene- or phenyl-$C_1$-$C_4$alkylene- wherein the phenyl moiety is substituted by one to five $R^8$, pyridyl-$C_1$-$C_4$alkylene- or pyridyl-$C_1$-$C_4$alkylene-wherein the pyridyl moiety is substituted by one to four $R^8$, oxetanyl or oxetanyl substituted by one to five $R^8$, thietanyl-$C_1$-$C_4$ alkylene or thietanyl-$C_1$-$C_4$ alkylene wherein the thietanyl moiety is substituted by one to five $R^8$, oxo-thietanyl-$C_1$-$C_4$ alkylene or oxo-thietanyl-$C_1$-$C_4$ alkylene wherein the oxo-thietanyl moiety is substituted by one to five $R^8$, dioxo-thietanyl-$C_1$-$C_4$ alkylene or dioxo-thietanyl-$C_1$-$C_4$ alkylene wherein the dioxo-thietanyl moiety is substituted by one to five $R^8$, thietanyl or thietanyl substituted by one to five $R^8$, oxo-thietanyl or oxo-thietanyl substituted by one to five $R^8$, dioxo-thietanyl or dioxo-thietanyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene or group C1

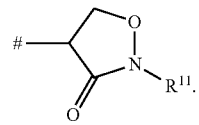

(C1)

8. A compound according to claim 1 wherein $X^4$ is chlorodifluoromethyl or trifluoromethyl.

9. A compound according to claim 1 wherein $R^4$ is aryl or aryl substituted by one to five $R^9$.

10. A compound according to claim 1, wherein the compound of formula I is a compound of formula Ic

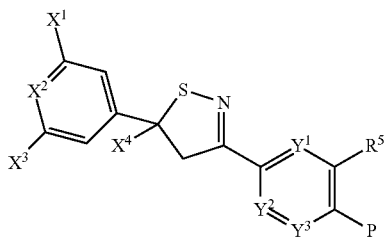

(Ic)

wherein
$Y^1$ is C—$R^{5b}$, CH or nitrogen;
$Y^2$ and $Y^3$ are independently CH or nitrogen;
wherein no more than two of $Y^1$, $Y^2$ and $Y^3$ are nitrogen and wherein $Y^2$ and $Y^3$ are not both nitrogen;
$R^5$ is hydrogen, halogen, cyano, nitro, $NH_2$, $C_1$-$C_2$alkyl, $C_1$-$C_2$haloalkyl, $C_3$-$C_5$cycloalkyl, $C_3$-$C_5$halocycloalkyl, $C_1$-$C_2$alkoxy or $C_1$-$C_2$haloalkoxy;
$R^{5b}$ when present together with $R^5$ forms a —CH=CH—CH=CH— bridge;
$X^2$ is C—$X^6$ or nitrogen;

$X^1$, $X^3$ and $X^6$ are independently hydrogen, halogen or trihalomethyl, wherein at least two of $X^1$, $X^3$ and $X^6$ are not hydrogen;

$X^4$ is trifluoromethyl, difluoromethyl or chlorodifluoromethyl.

11. A method of controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

12. An insecticidal, acaricidal, nematicidal or molluscicidal composition comprising an insecticidally, acaricidally, nematicidally or molluscicidally effective amount of a compound of formula (I) as defined in claim 1.

13. An insecticidal, acaricidal, nematicidal or molluscicidal composition according to claim 12 comprising at least one additional compound having biological activity.

14. A combination product comprising a pesticidally effective amount of a component A and a pesticidally effective amount of component B, wherein component A is a compound of formula (I) as defined in claim 1, and compound B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide.

* * * * *

UNITED STATES PATENT AND TRADEMARK OFFICE
CERTIFICATE OF CORRECTION

PATENT NO. : 9,078,444 B2  
APPLICATION NO. : 14/344123  
DATED : July 14, 2015  
INVENTOR(S) : Jerome Yves Cassayre et al.

Page 1 of 1

It is certified that error appears in the above-identified patent and that said Letters Patent is hereby corrected as shown below:

In the Claims

Claim 1, col. 316, line 28: replace "$C_1C_4$alkyl, $C_1C_4$haloalkyl," with "$C_1$-$C_4$alkyl, $C_1$-$C_4$haloalkyl";

Claim 1, col. 316, line 29: replace "$C_1C_4$ haloalkoxy-;" with "$C_1$-$C_4$ haloalkoxy-;".

Signed and Sealed this  
Twenty-ninth Day of December, 2015

Michelle K. Lee  
*Director of the United States Patent and Trademark Office*